US012492428B2

(12) United States Patent
Nygren

(10) Patent No.: US 12,492,428 B2
(45) Date of Patent: Dec. 9, 2025

(54) METHODS AND COMPOSITIONS FOR THE QUANTITATION OF MITOCHONDRIAL NUCLEIC ACID

(71) Applicant: Agena Bioscience, Inc., San Diego, CA (US)

(72) Inventor: Anders Olof Herman Nygren, San Diego, CA (US)

(73) Assignee: AGENA BIOSCIENCE, INC., San Diego, CA (US)

( * ) Notice: Subject to any disclaimer, the term of this patent is extended or adjusted under 35 U.S.C. 154(b) by 1187 days.

(21) Appl. No.: 16/983,528

(22) Filed: Aug. 3, 2020

(65) Prior Publication Data

US 2020/0385796 A1 Dec. 10, 2020

Related U.S. Application Data

(62) Division of application No. 15/268,058, filed on Sep. 16, 2016, now Pat. No. 10,774,375.

(60) Provisional application No. 62/220,749, filed on Sep. 18, 2015, provisional application No. 62/295,804, filed on Feb. 16, 2016.

(51) Int. Cl.

| | |
|---|---|
| ***C12Q 1/6851*** | (2018.01) |
| ***C12Q 1/6848*** | (2018.01) |
| ***C12Q 1/6858*** | (2018.01) |
| ***C12Q 1/686*** | (2018.01) |

(52) U.S. Cl.

CPC ......... *C12Q 1/6851* (2013.01); *C12Q 1/6848* (2013.01); *C12Q 1/6858* (2013.01); *C12Q 1/686* (2013.01); *C12Q 2535/122* (2013.01); *C12Q 2535/125* (2013.01); *C12Q 2600/156* (2013.01)

(58) Field of Classification Search

CPC .. C12Q 1/6848; C12Q 1/6851; C12Q 1/6858; C12Q 1/686; C12Q 2535/122; C12Q 2535/125; C12Q 2600/156

See application file for complete search history.

(56) References Cited

U.S. PATENT DOCUMENTS

| | | | |
|---|---|---|---|
| 6,344,322 | B1 | 2/2002 | Polyak et al. |
| 6,605,433 | B1 | 8/2003 | Fliss et al. |
| 6,750,021 | B2 | 6/2004 | Polyak et al. |
| 8,003,317 | B2 | 8/2011 | Beaulieu et al. |
| 8,349,566 | B2 | 1/2013 | Beaulieu et al. |
| 10,774,375 | B2 | 9/2020 | Nygren |
| 2005/0287533 | A1 | 12/2005 | Ehrich et al. |
| 2005/0287592 | A1 | 12/2005 | Kless |
| 2009/0026082 | A1 | 1/2009 | Rothberg et al. |
| 2009/0029377 | A1 | 1/2009 | Lo et al. |
| 2011/0091900 | A1 | 4/2011 | Williams et al. |
| 2013/0237428 | A1 | 9/2013 | Beaulieu et al. |
| 2016/0203260 | A1 | 7/2016 | Lo et al. |
| 2017/0101673 | A1 | 4/2017 | Nygren |

FOREIGN PATENT DOCUMENTS

| | | | |
|---|---|---|---|
| WO | 2008/117027 | A2 | 10/2008 |
| WO | 2009/046445 | A1 | 4/2009 |
| WO | 2010/004265 | A1 | 1/2010 |
| WO | 2017/049180 | A1 | 3/2017 |

OTHER PUBLICATIONS

Ding et al. (PLoS Genet., 2015, 11(7):e1005306) (Year: 2015).*

International Preliminary Report on Patentability mailed on Mar. 29, 2018 in International Patent Application No. PCT/US2016/052279, filed on Sep. 16, 2016, 9 pages.

International Search Report and Written Opinion mailed on Feb. 3, 2017 in International Patent Application No. PCT/US2016/052279, filed on Sep. 16, 2016, 12 pages.

Office Action dated Aug. 1, 2019 in U.S. Appl. No. 15/268,058, filed Sep. 16, 2016 and published as US 2017-0101673 on Apr. 13, 2017, 12 pages.

Office Action dated May 14, 2020 in U.S. Appl. No. 15/268,058, filed Sep. 16, 2016 and published as US 2017-0101673 on Apr. 13, 2017, 5 pages.

Beaucage et al., "Deoxynucleoside Phosphoramidites—A New Class of Key Intermediates for Deoxypolynucleotide Synthesis", Tetrahedron Letters, 1981, 22(20):1859-1862.

Cantsilieris et al., "Correlating Multiallelic Copy Number Polymorphisms with Disease Susceptibility", Human Mutation, Jan. 2013, 34(1):1-13.

Cote et al., "Changes in Mitochondrial DNA as a Marker of Nucleoside Toxicity in HIV-infected Patients", The New England Journal of Medicine, Mar. 14, 2002, 346(11):811-820.

Ellinger et al., "Circulating Mitochondrial DNA in Serum: A Universal Diagnostic Biomarker for Patients with Urological Malignancies", Urologic Oncology: seminars and Original Investigations, 2012, 30:509-515.

Fernandez-Jimenez et al., "Accuracy in Copy Number Calling by qPCR and PRT: A Matter of DNA", PLOS One, Dec. 2011, 6(12):7 pages.

Goidts et al., "Identification of Large-Scale Human-Specific Copy Number Differences by Inter-Species Array Comparative Genomic Hybridization", Human Genetics, 2006, 119:185-198.

(Continued)

*Primary Examiner* — Jeremy C Flinders

(74) *Attorney, Agent, or Firm* — LOZA & LOZA, LLP

(57) ABSTRACT

Provided herein are products and processes for the quantitation of mitochondrial nucleic acid in a sample from a subject. In certain aspects are multiplex methods for determining dosage of mitochondrial nucleic acid relative to genomic nucleic acid for a sample from a subject including amplifying sets of mitochondrial polynucleotides and genomic polynucleotides from nucleic acid for a sample under amplification conditions. In certain aspects are multiplex methods for determining dosage of mitochondrial nucleic acid relative to genomic nucleic acid for a sample from a subject including amplifying sets of mitochondrial polynucleotides and amplifying sets of nuclear polynucleotides from nucleic acid for a sample under amplification conditions.

18 Claims, 1 Drawing Sheet

Specification includes a Sequence Listing.

(56) References Cited

OTHER PUBLICATIONS

Harris et al., "Single-Molecule DNA Sequencing of a Viral Genome", Science, Apr. 4, 2008, 320:106-109.
Hosgood et al., "Mitochondrial DNA Copy Number and Lung Cancer Risk in a Prospective Cohort Study", Carcinogenesis, 2010, 31(5):847-849.
Jurinke et al., "MALDI-TOF Mass Spectrometry: A Versatile Tool for High-Performance DNA Analysis", Molecular Biotechnology, 2004, 26:147-164.
Kampira et al., "Peripheral Blood Mitochondrial DNA/Nuclear DNA (mtDNA/nDNA) Ratio as a Marker of Mitochondrial Toxicities of Stavudine Containing Antiretroviral Therapy in HIV-Infected Malawian Patients", Journal of Integrative Biology, 2014, 18(7):438-445.
Kim et al., "Role of Mitochondrial Dysfunction in Insulin Resistance", Circulation Research, Feb. 29, 2008, 102(4):401-414.
Malik et al., "Is Mitochondrial DNA Content a Potential Biomarker of Mitochondrial Dysfunction?", Mitochondrion, 2013, 13:481-492.
Margulies et al., "Genome Sequencing in Microfabricated High-density Picolitre Reactors", Nature, Sep. 15, 2005, 437:376-380.
Metzker, Michael L. "Sequencing Technologies—The Next Generation", Nature Review Genetics, Jan. 2010, 11:31-46.
Moudrianakis et al., "Base Sequence Determination in Nucleic Acids with the Electron Microscope, III. Chemistry and Microscopy of Guanine-Labeled DNA", Proceedings of the National Academy of Sciences, 1965, 53:564-571.
Needham-Vandevanter et al., "Characterization of an Adduct Between CC-1065 and a Defined Oligodeoxynucleotide Duplex", Nucleic Acids Research, 1984, 12(15):6159-6168.
Pearson et al., "High-Performance Anion-Exchange Chromatography of Oligonucleotides", Journal of Chromatography, 1983, 255:137-149.
Phillips et al., "Simultaneous Quantification of Mitochondrial DNA Copy Number and Deletion Ratio: A Multiplex Real-Time PCR Assay", Scientific Reports, Jan. 27, 2014, 4(3887):7 pages.
Pierce et al., "Comparison of the GenMark Diagnostics eSensor Respiratory Viral Panel to Real-Time PCR for Detection of Respiratory Viruses in Children", Journal of Clinical Microbiology, Nov. 2012, 50(11):3458-3465.
Pinto et al., "Mitochondrial Genome Changes and Neurodegenerative Diseases", Biochimica et Biophysica Acta, Aug. 2014, 1842(8):1198-1207.
Quispe-Tintaya et al., "Fast Mitochondrial DNA Isolation from Mammalian Cells for Next-Generation Sequencing", Biotechniques, Sep. 2013, 55(3):133-136.
Schon et al., "Human Mitochondrial DNA: Roles of Inherited and Somatic Mutations", Nature Reviews Genetics, Dec. 2012, 13:878-890.
Strauss William M. "Current Protocols in Molecular Biology", John Wiley & Sons, N.Y., 1993, 6.3.1-6.3.6.
Van Gisbergen et al., "How Do Changes in the mtDNA and Mitochondrial Dysfunction Influence Cancer and Cancer Therapy? Challenges, Opportunities and Models", Mutation Research, 2015, 764:16-30.
Veal et al., "Automated Design of Paralogue Ratio Test Assays for the Accurate and Rapid Typing of Copy Number Variation", Bioinformatics, 2013, 29(16):1997-2003.
Voelkerding et al., "Next-generation Sequencing: from Basic Research to Diagnostics", Clinical Chemistry, 2009, 55(4):641-658.
Walker et al., "Multiplex Paralogue Ratio Tests for Accurate Measurement of Multiallelic CNVs", Genomics, 2009, 93:98-103.

* cited by examiner

METHODS AND COMPOSITIONS FOR THE QUANTITATION OF MITOCHONDRIAL NUCLEIC ACID

RELATED APPLICATIONS

This patent application is a divisional of U.S. patent application Ser. No. 15/268,058, filed on Sep. 16, 2016, now U.S. Pat. No. 10,774,375, entitled METHODS AND COMPOSITIONS FOR THE QUANTITATION OF MITOCHONDRIAL NUCLEIC ACID, naming Anders Olof Herman Nygren as inventor; which claims the benefit of U.S. Provisional Patent Application No. 62/295,804, filed Feb. 16, 2016, entitled METHODS AND COMPOSITIONS FOR THE QUANTITATION OF MITOCHONDRIAL NUCLEIC ACID, naming Anders Olof Herman Nygren as inventor. U.S. patent application Ser. No. 15/268,058, filed on Sep. 16, 2016, entitled METHODS AND COMPOSITIONS FOR THE QUANTITATION OF MITOCHONDRIAL NUCLEIC ACID, naming Anders Olof Herman Nygren as inventor also claims the benefit of U.S. Provisional Application No. 62/220,749, filed Sep. 18, 2015, entitled METHODS AND COMPOSITIONS FOR THE QUANTITATION OF MITOCHONDRIAL NUCLEIC ACID, naming Anders Olof Herman Nygren as inventor. The subject matter of each of these applications is incorporated in its entirety by reference thereto, including texts, tables and drawings.

SEQUENCE LISTING

The instant application contains a Sequence Listing which has been submitted electronically in ASCII format and is hereby incorporated by reference in its entirety. Said ASCII copy, created on Dec. 16, 2016, is named AGB-7003-UT_SL.txt and is 332,274 bytes in size.

SUMMARY

Mitochondria are the energy center of the cell. Every cell has about 100 to 200 mitochondria and every mitochondria contains 1-10 copies of mitochondrial DNA. Qualitative changes in mitochondrial DNA (mtDNA), such as mutations and deletions, have been implicated in many diseases such as diabetes mellitus and cancer. Mitochondria are also vulnerable to oxidative stress.

Provided are methods and kits for determining dosage of mitochondrial nucleic acid relative to genomic nucleic acid.

Provided in certain aspects are multiplex methods for determining dosage of mitochondrial nucleic acid relative to genomic nucleic acid for a sample from a subject including: (a) amplifying sets of mitochondrial polynucleotides and genomic polynucleotides from nucleic acid for a sample under amplification conditions, wherein: (i) each set comprises a mitochondrial polynucleotide and a genomic polynucleotide; (ii) the mitochondrial polynucleotide and the genomic polynucleotide are native; (iii) the mitochondrial polynucleotide of a set differs from the mitochondrial polynucleotide of the other sets and the genomic polynucleotide of a set differs from the genomic polynucleotide of the other sets; (iv) the mitochondrial polynucleotide and the genomic polynucleotide of a set are defined by formula $^{5'}X—V—Y^{3'}$; (v) $^{5'}X—V—Y^{3'}$ represents a contiguous sequence of nucleotides present in the mitochondrial polynucleotide and the genomic polynucleotide; (vi) X and Y of the mitochondrial polynucleotide are identical to X and Y, respectively, of the genomic polynucleotide in each set; (vii) V is one or more nucleotide positions at which a nucleotide of the mitochondrial polynucleotide differs from the corresponding nucleotide of the genomic polynucleotide in a set; thereby providing a plurality of amplified sets each comprising amplicons corresponding to all or a portion of the mitochondrial polynucleotide and amplified genomic polynucleotide in the set; (b) comparing (i) the amplicons corresponding to the mitochondrial polynucleotide, to (ii) the amplicons corresponding to the genomic polynucleotide for each set, thereby generating a comparison; and (c) determining the relative dosage of mitochondrial nucleic acid to genomic nucleic acid in the sample based on the comparison.

Provided in other aspects, are kits including amplification primer pairs that comprise polynucleotides chosen from polynucleotides in Table 2 and Table 4, or portions thereof.

Provided in another aspect, is a multiplex method for determining dosage of extrachromosomal nucleic acid relative to genomic nucleic acid for a sample from a subject including: (a) amplifying sets of extrachromosomal polynucleotides and genomic polynucleotides from nucleic acid for a sample under amplification conditions, wherein: (i) each set comprises an extrachromosomal polynucleotide and a genomic polynucleotide; (ii) the extrachromosomal polynucleotide and the genomic polynucleotide are native; (iii) the extrachromosomal polynucleotide of a set differs from the extrachromosomal polynucleotide of the other sets and the genomic polynucleotide of a set differs from the genomic polynucleotide of the other sets; (iv) the extrachromosomal polynucleotide and the genomic polynucleotide of a set are defined by formula $^{5'}X—V—Y^{3'}$; (v) $^{5'}X—V—Y^{3'}$ represents a contiguous sequence of nucleotides present in the extrachromosomal polynucleotide and the genomic polynucleotide; (vi) X and Y of the extrachromosomal polynucleotide are identical to X and Y, respectively, of the genomic polynucleotide in each set; (vii) V is one or more nucleotide positions at which a nucleotide of the extrachromosomal polynucleotide differs from the corresponding nucleotide of the genomic polynucleotide in a set; thereby providing a plurality of amplified sets each comprising amplicons corresponding to all or a portion of the extrachromosomal polynucleotide and amplified genomic polynucleotide in the set; (b) comparing (i) the amplicons corresponding to the extrachromosomal polynucleotide, to (ii) the amplicons corresponding to the genomic polynucleotide for each set, thereby generating a comparison; and (c) determining the relative dosage of extrachromosomal nucleic acid to genomic nucleic acid in the sample based on the comparison.

Provided in another aspect, is a multiplex method for determining dosage of extrachromosomal nucleic acid relative to genomic nucleic acid for a sample from a subject including: (a) amplifying sets of extrachromosomal polynucleotides and genomic polynucleotides from nucleic acid for a sample under amplification conditions, wherein: (i) each set comprises an extrachromosomal polynucleotide and a genomic polynucleotide; (ii) the extrachromosomal polynucleotide and the genomic polynucleotide are native; (iii) the extrachromosomal polynucleotide of a set differs from the extrachromosomal polynucleotide of the other sets and the genomic polynucleotide of a set differs from the genomic polynucleotide of the other sets; (iv) the extrachromosomal polynucleotide and the genomic polynucleotide of a set are defined by formula $^{5'}X—V—Y^{3'}$; (v) the $^{5'}X—V—Y^{3'}$ represents a contiguous sequence of nucleotides present in the extrachromosomal polynucleotide and the genomic polynucleotide; (vi) X and Y of the extrachromosomal polynucleotide are identical to X and Y, respectively, of the genomic polynucleotide in each set; (vii) V is one or more nucleotide positions at which a nucleotide of the extrachromosomal polynucleotide differs from the corresponding nucleotide of the genomic polynucleotide in a set; thereby providing a plurality of amplified sets each comprising amplicons corresponding to all or a portion of the extrachromosomal polynucleotide and amplified genomic polynucleotide in the set; (b) comparing (i) the amplicons corresponding to the extrachromosomal polynucleotide, to (ii) the amplicons corresponding to the genomic polynucleotide for each set, thereby generating a comparison; and (c) determining the relative dosage of extrachromosomal nucleic acid to genomic nucleic acid in the sample based on the comparison.

Provided in another aspect, is a multiplex method for determining dosage of mitochondrial nucleic acid relative to nuclear nucleic acid for a sample from a subject, including: (a) contacting nucleic acid of a sample from a subject comprising nucleic acid of a first species comprising a nuclear genome and a mitochondrial genome with nucleic acid of a second species comprising nucleic acid of a nuclear genome and a mitochondrial genome for which the copy number of the mitochondrial genome and the copy number of the nuclear genome are known, wherein the nuclear genome of the first species has regions that are paralogous to regions of the nuclear genome of the second species and the mitochondrial genome of the first species has regions that are paralogous to regions of the mitochondrial genome of the second species; (b) amplifying sets of nuclear polynucleotides of paralogous regions of the nuclear genome of the first species and the nuclear genome of the second species and sets of mitochondrial polynucleotides of paralogous regions of the mitochondrial genome of the first species and the mitochondrial genome of the second species from the nucleic acid of (a) under amplification conditions, wherein: (i) each set comprises a polynucleotide of the nuclear genome of the first species and a polynucleotide of the nuclear genome of the second species or each set comprises a polynucleotide of the mitochondrial genome of the first species and a polynucleotide of the mitochondrial genome of the second species; (ii) the mitochondrial polynucleotides and the nuclear polynucleotides are native; (iii) the mitochondrial polynucleotides of a set differ from the mitochondrial polynucleotides of the other sets and the nuclear polynucleotides of a set differ from the nuclear polynucleotides of the other sets; (iv) the mitochondrial polynucleotides of a set and the nuclear polynucleotides of a set are defined by formula $^{5'}$J-V—K$^{3'}$; (v) $^{5'}$J-V—K$^{3'}$ represents a contiguous sequence of nucleotides present in the mitochondrial polynucleotides or in the nuclear polynucleotides; (vi) J and K of the mitochondrial polynucleotides of a set are identical and J and K of the nuclear polynucleotides of a set are identical; and (vii) V is one or more nucleotide positions at which a nucleotide of the mitochondrial polynucleotides of the first and second species of a set differ or V is one or more nucleotide positions at which a nucleotide of the nuclear polynucleotides of the first and second species of a set differ; thereby providing a plurality of amplified sets each comprising amplicons corresponding to all or a portion of the mitochondrial polynucleotides of a set or amplicons corresponding to all or a portion of the amplified nuclear polynucleotides of a set; (c) comparing the amplicons corresponding to the mitochondrial polynucleotide of the second species to the amplicons corresponding to mitochondrial polynucleotide of the first species in a set and comparing the amplicons corresponding to the nuclear polynucleotide of the second species to the amplicons corresponding to the nuclear polynucleotide of the first species in a set, thereby generating comparisons; and (d) determining the relative dosage of mitochondrial nucleic acid to the nuclear nucleic acid in the sample from the subject based on comparisons of (c) for all sets. In certain embodiments, the comparisons in (c) are a ratio of the amount of the amplicons corresponding to the polynucleotide of the mitochondrial genome of the second species to the amount of amplicons corresponding to polynucleotide of the mitochondrial genome of the first species in a set and a ratio of the amount of the amplicons corresponding to the polynucleotide of the nuclear genome of the second species to the amount of amplicons corresponding to the polynucleotide of the nuclear genome of the first species in a set, and determining the relative dosage of mitochondrial nucleic acid to nuclear nucleic acid in the sample from the subject in (d) is based on the ratios. In certain aspects, the first species is human. In some aspects, the second species is chimpanzee.

Provided in other aspects, are kits including amplification primer pairs that comprise polynucleotides chosen from polynucleotides in Table 7, or portions thereof.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

DETAILED DESCRIPTION

Figure 1A:
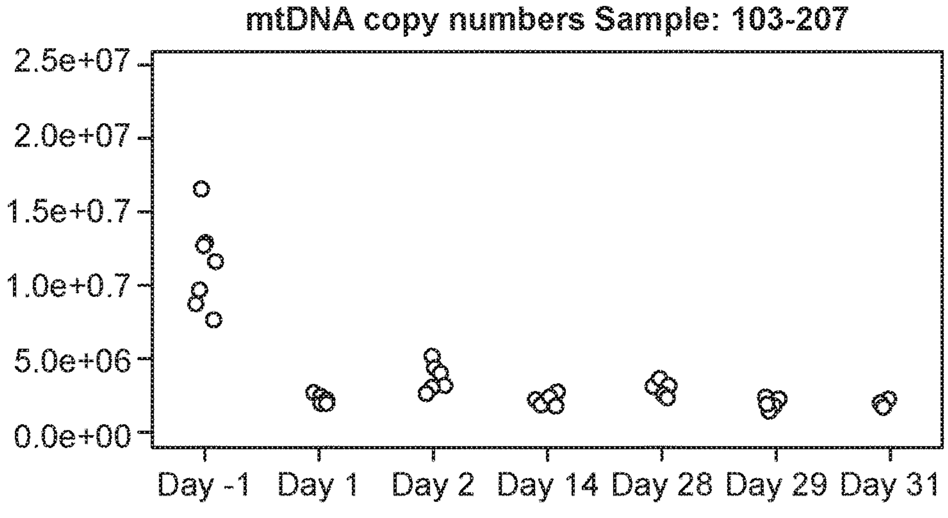
FIG. 1A-C show mitochondria copy numbers (FIG. 1A), nuclear copy numbers (FIG. 1B) mitochondrial vs nuclear ratios (FIG. 1C) calculated based on a multiplex assay targeting human and chimpanzee paralogs for a single subject over a period of time.

Certain of methods and kits provided herein enable the interrogation of both mitochondrial nucleic acid and genomic nucleic acid in a single reaction and do not require control samples or internal standards in order to compare amplicons representing these species. Certain methods and kits provided herein also do not require positive controls.

Certain of methods and kits provided herein enable the interrogation of both mitochondrial nucleic acid and nuclear (genomic) nucleic acid in a single reaction and utilize an internal standard that simulates the huge difference in copy number between the mitochondrial genome and the nuclear genome, as well as allowing for multiplex assays requiring little to no optimization. Certain methods and kits provided herein also utilize an internal standard.

The multiplex methods and kits provided herein by examining multiple regions of the mitochondrial DNA genome allow for both the determination of mitochondrial dosage and the detection of mitochondrial deletions in a single reaction. The examination of multiple locations of the mitochondrial genome also minimizes technical variability, allowing for a more accurate assessment of mitochondrial dosage.

Technology described herein can be utilized to assess a state of a cell, tissue, body function, medical condition (e.g., disease) or disorder, progression of a medical condition or disorder or treatment of a medical condition or disorder, for example. Certain embodiments of the technology are useful for (i) determining the likelihood a test subject has a medical condition or disorder or is pre-disposed to having a medical condition or disorder, (ii) determining the presence or absence of a progression of a medical condition or disorder in a test subject, (iii) determining the presence or absence of a response to a therapy administered to a test subject having the medical condition or disorder, (iv) determining whether a dosage of a therapeutic agent administered to a test subject should be increased, decreased or maintained; the like or combination of the foregoing. Various aspects and embodiments of the technology are described hereafter.

Nucleic Acid

Provided in part herein are methods for nucleic acid quantification. The terms "nucleic acid", "nucleic acid molecule" and "polynucleotide" may be used interchangeably throughout the disclosure. Non-limiting examples of nucleic acid include deoxyribonucleic acid (DNA, e.g., complementary DNA (cDNA), genomic DNA (gDNA) also referred to as nuclear DNA, mitochondrial DNA (mtDNA), episomal DNA, and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), DNA or RNA analogs (e.g., containing base analogs, sugar analogs and/or a non-native backbone and the like), RNA/DNA hybrids and polyamide nucleic acids (PNAs). A nucleic acid can be in single-stranded or double-stranded form, and unless otherwise limited, can encompass known analogs of natural nucleotides that can function in a similar manner as naturally occurring nucleotides.

A nucleic acid can be in any form useful for conducting processes herein (e.g., linear, circular, supercoiled, single-stranded, double-stranded and the like). A nucleic acid may be, or may be from, mitochondria, a plasmid, phage, virus, an episomal or extrachromosomal element, a chloroplast, a plastid, autonomously replicating sequence (ARS), centromere, artificial chromosome, chromosome, or other nucleic acid able to replicate or be replicated in vitro or in a host cell, a cell, a cell nucleus or cytoplasm of a cell, in certain embodiments. A nucleic acid in some embodiments can be from a single chromosome (e.g., a nucleic acid sample may be from one chromosome of a sample obtained from a diploid organism). The term also may include, as equivalents, derivatives, variants and analogs of RNA or DNA synthesized from nucleotide analogs, single-stranded (e.g., "sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base thymine is replaced with uracil. A nucleic acid may be prepared using a nucleic acid obtained from a subject.

Circulating Cell-Free Nucleic Acid

Nucleic acid can be circulating cell-free nucleic acid in certain embodiments. The terms "circulating cell-free nucleic acid," "extracellular nucleic acid" and "cell free nucleic acid" as used herein refer to nucleic acid isolated from a source having substantially no cells. Circulating cell-free nucleic acid (ccfNA, ccfDNA) can be present in and obtained from blood. Circulating cell-free nucleic acid often includes no detectable cells and may contain cellular elements or cellular remnants. Non-limiting examples of acellular sources for extracellular nucleic acid are blood, blood plasma, blood serum, cerebrospinal fluid, spinal fluid, and urine. Obtaining circulating cell-free nucleic acid includes obtaining a sample directly (e.g., collecting a sample, e.g., a test sample) or obtaining a sample from another who has collected a sample. Without being limited by theory, circulating cell-free nucleic acid may be a product of cell apoptosis and cell breakdown, which provides basis for extracellular nucleic acid often having a series of lengths across a spectrum (e.g., a "ladder").

Circulating cell-free nucleic acid can include different nucleic acid species, and therefore is referred to herein as "heterogeneous." For example, blood serum or plasma from a person having cancer can include nucleic acid from cancer cells and nucleic acid from non-cancer cells. In another non-limiting example, blood serum or plasma from a pregnant female can include maternal nucleic acid and fetal nucleic acid. In another non-limiting example, blood serum or plasma from a pregnant female can include maternal nucleic acid, placental nucleic acid and fetal nucleic acid. In another non-limiting example, blood serum or plasma can include nuclear or genomic nucleic acid and mitochondrial nucleic acid. At least two different nucleic acid species can exist in different amounts in circulating cell-free nucleic acid and sometimes are referred to as minority species and majority species. In certain instances, a minority species of nucleic acid is from an affected cell type (e.g., cancer cell, wasting cell, cell attacked by immune system). In some instances, a minority species of circulating cell-free nucleic acid sometimes is about 1% to about 40% of the overall nucleic acid (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40% of the nucleic acid is minority species nucleic acid). In circulating cell-free nucleic acid mitochondrial nucleic acid can be present in greater amounts than genomic or nuclear nucleic acid and can be considered the majority species. In some embodiments, a minority species of circulating cell-free nucleic acid is of a length of about 500 base pairs or less (e.g., about 80, 85, 90, 91, 92, 93, 94, 95, 96, 97, 98, 99 or 100% of minority species nucleic acid is of a length of about 500 base pairs or less). In some embodiments, a minority species of circulating cell-free nucleic acid is of a length of about 300 base pairs or less (e.g., about 80, 85, 90, 91, 92, 93, 94, 95, 96, 97, 98, 99 or 100% of minority species nucleic acid is of a length of about 300 base pairs or less). In some embodiments, a minority species of circulating cell-free nucleic acid is of a length of about 200 base pairs or less (e.g., about 80, 85, 90, 91, 92, 93, 94, 95, 96, 97, 98, 99 or 100% of minority species nucleic acid is of a length of about 200 base pairs or less). In some embodiments, a minority species of circulating cell-free nucleic acid is of a length of about 150 base pairs or less (e.g., about 80, 85, 90, 91, 92, 93, 94, 95, 96, 97, 98, 99 or 100% of minority species nucleic acid is of a length of about 150 base pairs or less). In some embodiments, the majority nucleic acid species of circulating cell-free nucleic acid (mitochondrial) is of a length that is less than the length of the minority nucleic acid species of circulating cell-free nucleic acid (nuclear or genomic). In some embodiments, the length of the majority nucleic acid species (mitochondrial) is about 50 base pairs and the length of the minority nucleic acid species (genomic or nuclear) is about 166 base pairs.

Cellular Nucleic Acid

Nucleic acid can be cellular nucleic acid in certain embodiments. The term "cellular nucleic acid" as used herein refers to nucleic acid isolated from a source having intact cells. Non-limiting examples of sources for cellular nucleic acid are blood cells, tissue cells, organ cells, tumor cells, hair cells, skin cells, and bone cells.

In some embodiments, nucleic acid is from peripheral blood mononuclear cells (PBMC). A PBMC is any blood cell having a round nucleus, such as, for example, lymphocytes, monocytes or macrophages. These cells can be extracted from whole blood, for example, using ficoll, a hydrophilic polysaccharide that separates layers of blood, with PBMCs forming a buffy coat under a layer of plasma. Additionally, PBMCs can be extracted from whole blood using a hypotonic lysis which preferentially lyses red blood cells and leaves PBMCs intact, and/or can be extracted using a differential centrifugation process known in the art.

Mitochondrial DNA can be extracted from whole blood using standard methods for DNA extraction from whole blood. Mitochondrial DNA can be enriched using a protocol as described in BioTechniques 55:133-136 (September 2013), hereby incorporated in its entirety by reference.

Using standard methods of DNA extraction both mitochondrial and nuclear DNA can be obtained from a sample. For example, standard DNA extraction kits can be used with buffy coat or buccal swaps for both mitochondrial and nuclear DNA and the corresponding kits when targeting circulating cell free DNA.

Nucleic Acid for Internal Standard

In some embodiments the copy number or genomic equivalents of the mitochondrial genome and the nuclear genome of nucleic acid of a second species is known or can be determined. The known equivalents of the mitochondrial genome and the nuclear genome for the nucleic acid of the second species serve as internal standards that can be used in conjunction with paralog assay results in determining the copy number of the mitochondrial genome and the copy number of the nuclear genome of the nucleic acid of the first species. The copy number of the mitochondrial nucleic acid and the copy number of the nuclear nucleic acid can be used to determine the mitochondrial/nuclear ratio for the nucleic acid of the sample from a subject (i.e., dosage). The exact amounts of mitochondrial and nuclear genomic equivalents or copy numbers for the nucleic acid of a second species (e.g., chimpanzee) that is utilized in an assay can be determined using methods such digital PCR. In some embodiments, the method is digital droplet PCR with a mitochondrial specific primer pair and a nuclear specific primer pair. In certain embodiments, ratios for mitochondrial to nuclear genomic equivalents for the internal standard species can be from approximately 500 to approximately 5000. A standard ratio for a chimpanzee is approximately 1200. As described below the nucleic acid for the internal standard is obtained from a genome (species) with regions in its mitochondrial and nuclear genome that are paralogs with regions of the mitochondrial and nuclear genome of the nucleic acid of the sample from a subject.

Samples

Nucleic acid in or from a suitable sample can be utilized in a method described herein. A mixture of nucleic acids can comprise two or more nucleic acid fragment species having different nucleotide sequences, different fragment lengths, different origins (e.g., genomic origin, mitochondrial vs nuclear (genomic) origin, fetal vs. maternal origin, cell or tissue origin, cancer vs. non-cancer origin, tumor vs. non-tumor origin, sample origin, subject origin, and the like), or combinations thereof. In some embodiments, nucleic acid is analyzed in situ (e.g., in a sample; in a subject), in vivo, ex vivo or in vitro.

Nucleic acid often is isolated from a sample obtained from a subject. A subject can be any living or non-living organism, including but not limited to a human, a non-human animal, a plant, a bacterium, a fungus or a protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be male or female.

Nucleic acid may be isolated from any type of suitable biological specimen or sample (e.g., a test sample). A sample or test sample can be any specimen that is isolated or obtained from a subject (e.g., a human subject, a pregnant female or a non-human subject). Non-limiting examples of specimens include fluid or tissue from a subject, including, without limitation, cerebrospinal fluid, spinal fluid, lavage fluid (e.g., bronchoalveolar, gastric, peritoneal, ductal, ear, arthroscopic), urine, feces, sputum, saliva, nasal mucous, prostate fluid, lavage, semen, lymphatic fluid, bile, tears, sweat, breast milk, breast fluid, biopsy sample (e.g., cancer biopsy), cell or tissue sample (e.g., from the liver, lung, spleen, pancreas, colon, skin, bladder, eye, brain, esophagus, head, neck, ovary, testes, prostate, the like or combination thereof). In some embodiments, a biological sample may be blood and sometimes a blood fraction (e.g., plasma or serum). As used herein, the term "blood" encompasses whole blood or any fractions of blood, such as serum and plasma as conventionally defined, for example. Blood or fractions thereof often comprise nucleosomes (e.g., maternal and/or fetal nucleosomes). Nucleosomes comprise nucleic acids and are sometimes cell-free or intracellular. Blood also comprises buffy coats. Buffy coats sometimes are isolated by utilizing a ficoll gradient. Buffy coats can comprise white blood cells (e.g., leukocytes, T-cells, B-cells, platelets, and the like). In some embodiments, buffy coats comprise maternal and/or fetal nucleic acid. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to or after preparation. A fluid or tissue sample from which nucleic acid is extracted may be acellular (e.g., cell-free). In some embodiments, a fluid or tissue sample may contain cellular elements or cellular remnants. In some embodiments cancer cells may be included in the sample.

Nucleic Acid Isolation and Processing

Nucleic acid can be isolated using any suitable technique. Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. High salt lysis procedures also are commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Tris, pH 8.0; 10 mM EDTA and 100 ug/ml Rnase A; a second solution can contain 0.2N NaOH and 1% SDS; and a third solution can contain 3M KOAc, pH 5.5. These procedures can be found in Current Protocols in Molecular Biology, John Wiley & Sons, N.Y., 6.3.1-6.3.6 (1989), incorporated herein in its entirety.

Nucleic acid may be isolated at a different time point as compared to another nucleic acid, where each of the samples is from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, cancer cell nucleic acid can be purified from a mixture comprising cancer cell and non-cancer cell nucleic acid. In certain examples, nucleosomes comprising small fragments of cancer cell nucleic acid can be purified from a mixture of larger nucleosome complexes comprising larger fragments of non-cancer nucleic acid.

Mitochondrial and Genomic (Nuclear) Nucleic Acid

Provided herein are methods to determine the dosage of mitochondrial nucleic acid relative to genomic (nuclear) nucleic acid in a sample. In some embodiments, the nucleic acid is DNA.

Mitochondrial/Genomic (Nuclear) Paralogs

In some embodiments, mitochondrial and genomic polynucleotides are analyzed in sets of polynucleotides. In some embodiments the mitochondrial polynucleotide and the genomic polynucleotide of a set are referred to as a mitochondrial/genomic (nuclear) paralog. A mitochondrial/genomic (nuclear) paralog is a region in the mitochondrial genome with a similar or nearly identical region in the nuclear genome. The paralogous sequence can be any size but must contain one or more regions that are identical in the mitochondrial genome and the nuclear genome and one or more nucleotides that are different in the mitochondria genome and the nuclear genome. In some embodiments, the paralogous sequence includes one or two base pair mismatches.

As used herein, the term "set" can refer to a mitochondrial polynucleotide and a corresponding genomic polynucleotide (paralogs) that have the following characteristics: (i) a set comprises a mitochondrial polynucleotide and a genomic polynucleotide; (ii) the mitochondrial polynucleotide and the genomic polynucleotide of a set are native; (iii) the mitochondrial polynucleotide is different from the genomic polynucleotide in a set; (iv) the mitochondrial polynucleotide and the genomic polynucleotide of a set are defined by formula $^{5'}X—V—Y^{3'}$ and (v) the mitochondrial polynucleotide of a set differs from the mitochondrial polynucleotide of the other sets and the genomic polynucleotide of a set differs from the genomic polynucleotide of the other sets.

The term "native" as used herein refers to the sequence of nucleotides as it is present in a mitochrondrial genome or nuclear genome and that has not been modified, altered or rearranged.

As used herein the term "multiplex" refers to the analysis of more than one set of a mitochondrial polynucleotide and a genomic polynucleotide in a single reaction. The polynucleotides represent distinct and different regions of the mitochondrial genome and distinct and different regions of the nuclear genome.

In some embodiments, $^{5'}X—V—Y^{3'}$ represents a contiguous sequence of nucleotides present in the mitochondrial polynucleotide and the genomic polynucleotide and X and Y of the mitochondrial polynucleotide are identical to X and Y, respectively, of the genomic polynucleotide in each set. V is one or more nucleotide positions at which a nucleotide of the mitochondrial polynucleotide differs from the corresponding nucleotide of the genomic polynucleotide in a set (e.g., a mismatch, single nucleotide polymorphisms (SNPs)). V can also be an insertion or a deletion. In certain embodiments, V is a single nucleotide position.

As used herein, the term "identical" refers to defined portions (specific length) of mitochondrial and genomic polynucleotides for which the nucleotide sequence does not differ at any position. $^{5'}X—V—Y^{3'}$ can be any length or number of nucleotides. In some embodiments, $^{5'}X—V—Y^{3}$ is about 30 to about 300 base pairs in length.

In some embodiments "dosage" is determined based on a comparison of mitochondrial nucleic acid (from mitochondrial genome) to genomic nucleic acid. In some embodiments "dosage" is a ratio of mitochondrial DNA to genomic DNA for a sample. In some embodiments "dosage" is a ratio of the amount of mitochondrial DNA to the amount of genomic DNA for a sample. In some embodiments, the comparison is a ratio of (i) the amount of the amplicons corresponding to the mitochondrial polynucleotide, to (ii) the amount of the amplicons corresponding to the genomic polynucleotide, in each set. A ratio could be either a comparison of the amount of the amplicons corresponding to the mitochondrial polynucleotide to the amount of the amplicons corresponding to the genomic polynucleotide or a comparison of the amount of the amplicons corresponding to the genomic polynucleotide to the amount of the amplicons corresponding to the mitochondrial polynucleotide. Sometimes dosage represents the copy number of mitochondrial DNA relative to the copy number of genomic DNA in a sample.

The term "amount" as used herein with respect to amplicons refers to any suitable measurement, including, but not limited to, copy number, weight (e.g., grams) and concentration (e.g., grams per unit volume (e.g., milliliter); molar units). In some embodiments, "amount" is determined based on analysis of a detectable parameter that correlates with amount; such as the quantification of a specific nucleotide at a defined position in a mitochondrial or a genomic polynucleotide (e.g., "V").

Mitochondrial/Mitochondrial Paralogs-Nuclear/Nuclear Paralogs

In some embodiments, mitochondrial polynucleotides of a first species present in a sample and mitochondrial polynucleotides of a second species provided as an internal standard are analyzed in sets of polynucleotides and nuclear polynucleotides of a first species present in a sample and nuclear polynucleotides of a second species provided as an internal standard are analyzed in sets of polynucleotides. In some embodiments, the mitochondrial polynucleotides of a set are referred to as a mitochondrial/mitochondrial paralog. In some embodiments, the nuclear polynucleotides of a set are referred to as a nuclear/nuclear paralog. A mitochondrial/mitochondrial paralog is a region in the mitochondrial genome of a first species with a similar or nearly identical region in the mitochondrial genome of a second species. A nuclear/nuclear paralog is a region in the nuclear genome of a first species with a similar or nearly identical region in the nuclear genome of a second species. The paralogous sequence can be any size but must contain one or more regions that are identical in the two mitochondrial genomes and one or more nucleotides that are different in the two mitochondrial genomes. For nuclear genomes, the paralogous sequence can be any size but must contain one or more regions that are identical in the two nuclear genomes and one or more nucleotides that are different in the two nuclear genomes. In some embodiments, the paralogous sequence includes one or two base pair mismatches.

The species of polynucleotides of a set can represent any two species where paralog regions occur in the mitochondrial genomes of the two species and where paralog regions occur in the nuclear genomes of the two species. In certain embodiments, the first species is human and second species is non-human. In some embodiments, the second species is chimpanzee. In certain embodiments, the nucleic acid of a sample from a subject is the first species and the nucleic acid providing an internal standard is the second species.

The term "set" can refer to a mitochondrial polynucleotide of a first species and a corresponding mitochondrial polynucleotide of a second species (paralogs) or can refer to a nuclear polynucleotide of a first species and a corresponding nuclear polynucleotide of a second species (paralogs) that have the following characteristics: (i) each set comprises a polynucleotide of the nuclear genome of the first species and a polynucleotide of the nuclear genome of the second species or each set comprises a polynucleotide of the mitochondrial genome of the first species and a polynucleotide of the mitochondrial genome of the second species; (ii) the mitochondrial polynucleotides and the nuclear polynucleotides are native; (iii) the mitochondrial polynucleotides of a set differ from the mitochondrial polynucleotides of the other sets and the nuclear polynucleotides of a set differ from the nuclear polynucleotides of the other sets; (iv) the mitochondrial polynucleotides of a set and the nuclear polynucleotides of a set are defined by formula $^{5'}$J-V—K$^{3'}$; (v) $^{5'}$J-V—K$^{3'}$ represents a contiguous sequence of nucleotides present in the mitochondrial polynucleotides or in the nuclear polynucleotides; (vi) J and K of the mitochondrial polynucleotides of a set are identical and J and K of the nuclear polynucleotides of a set are identical; and (vii) V is one or more nucleotide positions at which a nucleotide of the mitochondrial polynucleotides of the first and second species of a set differ or V is one or more nucleotide positions at which a nucleotide of the nuclear polynucleotides of the first and second species of a set differ.

The term "native" as used herein refers to the sequence of nucleotides as it is present in a mitochrondrial genome or nuclear genome and that has not been modified, altered or rearranged.

The term "multiplex" refers to the analysis of more than one set of a mitochondrial polynucleotide of a first species and a corresponding mitochondrial polynucleotide of a second species in a single reaction or more than one set of a nuclear polynucleotide of a first species and a corresponding nuclear polynucleotide of a second species in a single reaction. In some embodiments, the more than one set of mitochondrial polynucleotides and the more than one set of nuclear polynucleotides are in a single reaction. In some embodiments, the more than one set of mitochondrial polynucleotides and the more than one set of nuclear polynucleotides are in different reactions.

The mitochondrial polynucleotides of a set of a mitochondrial polynucleotide of a first species and a corresponding mitochondrial polynucleotide of a second species differs from the mitochondrial polynucleotides of other sets of mitochondrial polynucleotides. The nuclear polynucleotides of a set of a nuclear polynucleotide of a first species and a corresponding nuclear polynucleotide of a second species differs from the nuclear polynucleotides of other sets of nuclear polynucleotides. The polynucleotides represent distinct and different regions of the mitochondrial genomes and distinct and different regions of the nuclear genomes.

In some embodiments, $^{5'}$J-V—K$^{3'}$ represents a contiguous sequence of nucleotides present in the mitochondrial polynucleotides and J and K of the mitochondrial polynucleotides are identical in each set. In some embodiments, $^{5'}$J-V—K$^{3'}$ represents a contiguous sequence of nucleotides present in the nuclear polynucleotides and J and K of the nuclear polynucleotides are identical in each set. V is one or more nucleotide positions at which a nucleotide of the mitochondrial polynucleotides in a set differ or one or more nucleotide positions at which a nucleotide of the nuclear polynucleotides in a set differ. In some aspects V can be a mismatch or single nucleotide polymorphism (SNP). V can also be an insertion or a deletion. In certain embodiments, V is a single nucleotide position.

As used herein, the term "identical" refers to defined portions (specific length) of mitochondrial polynucleotides of a set or nuclear polynucleotides of a set for which the nucleotide sequences do not differ at any position.

$^{5'}$J-V—K$^{3'}$ can be any length or number of nucleotides. In some embodiments, $^{5'}$J-V—K$^{3'}$ is about 30 to about 300 base pairs in length.

In certain embodiments, a first species/second species paralog are analyzed together in an assay. In some embodiments, assays target nuclear paralogs. In some embodiments, assays target mitochondrial paralogs. In some embodiments, the first species/second species paralogs are human/chimpanzee paralogs. In some embodiments, an assay consists of a set of a mitochondrial polynucleotide of a first species and a corresponding mitochondrial polynucleotide of a second species that analyzed together. In some embodiments, an assay consists of set of a nuclear polynucleotide of a first species and a corresponding nuclear polynucleotide of a second species that are analyzed together. Certain ratios are based on the amounts of amplicons of a first and a second species determined in the assays that target mitochondrial paralogs. Certain ratios are based on the amounts of amplicons of a first and a second species determined in the assays that target nuclear paralogs.

In some embodiments "dosage" is determined based on a comparison of mitochondrial nucleic acid (from the mitochondrial genome) to nuclear nucleic acid (from the nuclear genome) for a first species. In some embodiments "dosage" is a ratio of mitochondrial DNA to nuclear DNA for a sample from a subject. In some embodiments "dosage" is a ratio of the amount of mitochondrial DNA to the amount of nuclear DNA for a sample from a subject. In some embodiments "dosage" is a ratio of the copy number of mitochondrial DNA to the copy number of nuclear DNA for a sample from a subject (e.g., first species or human). In some embodiments, the mitochondrial copy number for the nucleic acid of a first species can be derived based on the ratio of the amount of the mitochondrial polynucleotide of the first species and the amount of the mitochondrial polynucleotide of the second species as determined by assays targeting mitochondrial paralogs, in conjunction with the known value for the copy number of the mitochondrial nucleic acid (genome) of the second species. In some embodiments, the nuclear copy number for the nucleic acid of a first species can be derived based on the ratio of the amount of the nuclear polynucleotide of the first species and the amount of the nuclear polynucleotide of the second species as determined by assays targeting nuclear paralogs, in conjunction with the known value for the copy number of the nuclear nucleic acid (genome) of the second species.

In some embodiments, the subject is human and accordingly the nucleic acid of the first species is human and the nucleic acid of the second species is chimpanzee.

The term "amount" as used herein with respect to amplicons refers to any suitable measurement, including, but not limited to, copy number, weight (e.g., grams) and concentration (e.g., grams per unit volume (e.g., milliliter); molar units). In some embodiments, "amount" is determined based on analysis of a detectable parameter that correlates with amount; such as the quantification of a specific nucleotide at a defined position in a mitochondrial or a nuclear polynucleotide (e.g., "V").

Identification of Paralogs

The mitochondrial genome is a circular genome of about 16.5 Kb and contains 37 genes, 13 of which encode proteins. The mitochondrial genome can be is divided into short fragments of any length that is amenable to carrying out sequence comparison (e.g., 100 bp). Alignment techniques and sequence identity assessment methodology are known. Such analyses can be performed by using mathematical algorithms.

Mitochondrial/Genomic (Nuclear) Paralogs ($^{5'}$X—V—Y$^{3}$)

Fragments of the mitochondrial genome are aligned with and compared to regions of a human genome based on defined criteria, such as, but not limited to, the number of mismatches that are allowed in the sequence (e.g., 1 mismatch, 2 mismatches, 5 mismatches, 10 mismatches, 15 mismatches, 20 mismatches, 25 mismatches) to identify similar or nearly identical regions. From these regions, those regions that fulfil the criteria specified for ($^{5'}$X—V—Y$^{3'}$) and the other criteria that define a set, as discussed above, are selected. A sufficient number of regions are chosen from different locations in the mitochondrial genome in order to span the mitochondrial genome and to provide a sufficient number of measurements to minimize technical variability. In some embodiments, regions are chosen so that at least one region is located in specific mitochondrial genes of interest. In some embodiments the number of sets is about 2 sets to about 20 sets. In some embodiments the number of sets is about 2 sets to about 10 sets. In some embodiments the number of sets is 10 sets. In some embodiments the number of sets is a least 5 sets.

In some embodiments, sets of mitochondrial and genomic polynucleotides are described in Table 1.

Mitochondrial/Mitochondrial Paralogs-Nuclear/Nuclear Paralogs ($^{5'}$J-V—K$^{3}$)

Fragments of a mitochondrial genome of a first species are aligned with and compared to regions of a mitochondrial genome of a second species and fragments of a nuclear genome of a first species are aligned with and compared to regions of a nuclear genome of a second species based on defined criteria, such as, but not limited to, the number of mismatches that are allowed in the sequence (e.g., 1 mismatch, 2 mismatches, 5 mismatches, 10 mismatches, 15 mismatches, 20 mismatches, 25 mismatches) to identify similar or nearly identical regions. From these regions, those regions that fulfil the criteria specified for ($^{5'}$J-V—K$^{3'}$) and the other criteria that define a set, as discussed above, are selected. A sufficient number of regions are chosen from different locations in the mitochondrial genome in order to span the mitochondrial genome and to provide a sufficient number of measurements to minimize technical variability. In some embodiments, regions are chosen so that at least one region is located in specific mitochondrial genes of interest. A sufficient number of regions are chosen from different locations in the nuclear genome in order to provide a sufficient number of measurements to minimize technical variability. In some embodiments the number of sets of mitochondrial/mitochondrial paralogs and nuclear/nuclear paralogs are each about 2 sets to about 20 sets. In some embodiments, the number of sets of mitochondrial/mitochondrial paralogs and nuclear/nuclear paralogs are each about 2 sets to about 10 sets. In some embodiments, the number of sets is 10 sets. In some embodiments, the number of sets is a least 5 sets. In other embodiments, the number of sets of nuclear/nuclear paralogs is greater than the number of sets of mitochondrial/mitochondrial paralogs. For example, the number of sets of mitochondrial/mitochondrial paralogs and nuclear/nuclear paralogs are each about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475 or 500 sets, in some embodiments.

In some embodiments, sets of mitochondrial paralogs are described in Table 6.

Amplification

Often sets of mitochondrial polynucleotides and genomic polynucleotides from nucleic acid for a sample are amplified and then analyzed. Sometimes only a portion of a paralog $^{5'}$X—V—Y$^{3'}$ is amplified. In some embodiments, the length of an amplicon is about 30 base pairs to about 300 base pairs. An amplicon often includes at least a portion of X and Y regions and includes V. In some embodiments, an amplicon includes regions of a polynucleotide 5' of X and 3' of Y.

In some embodiments, sets of mitochondrial polynucleotides and sets of nuclear polynucleotides from nucleic acid for a sample and an added internal standard are amplified and then analyzed. Sometimes only a portion of a paralog $^{5'}$J-V—K$^{3'}$ is amplified. In some embodiments, the length of an amplicon is about 30 base pairs to about 300 base pairs. An amplicon often includes at least a portion of J and K regions and includes V.

Amplification primers are chosen as described below. In some embodiments, amplifying is by a polymerase chain reaction (PCR) process.

Amplification conditions are known and can be selected for a particular nucleic acid that will be amplified. Amplification conditions include certain reagents some of which can include, without limitation, nucleotides (e.g., nucleotide triphosphates), modified nucleotides, oligonucleotides (e.g., primer oligonucleotides for polymerase-based amplification and oligonucleotide building blocks for ligase-based amplification), one or more salts (e.g., magnesium-containing salt), one or more buffers, one or more polymerizing agents (e.g., ligase enzyme, polymerase enzyme), one or more nicking enzymes (e.g., an enzyme that cleaves one strand of a double-stranded nucleic acid) and one or more nucleases (e.g., exonuclease, endonuclease, RNase). Any polymerase suitable for amplification may be utilized, such as a polymerase with or without exonuclease activity, DNA polymerase and RNA polymerase, mutant forms of these enzymes, for example. Any ligase suitable for joining the 5' of one oligonucleotide to the 3' end of another oligonucleotide can be utilized. Amplification conditions also can include certain reaction conditions, such as isothermal or temperature cycle conditions. Methods for cycling temperature in an amplification process are known, such as by using a thermocycle device. The term “cycling” refers to amplification (e.g. an amplification reaction or extension reaction) utilizing a single amplification primer pair or multiple amplification primer pairs where temperature cycling is used. In some embodiments, about 25 PCR amplification cycles to about 45 PCR amplification cycles are performed in. Amplification conditions also can, in some embodiments, include an emulsion agent (e.g., oil) that can be utilized to form multiple reaction compartments within which single nucleic acid molecule species can be amplified. Amplification is sometimes an exponential product generating process and sometimes is a linear product generating process.

Any suitable amplification technique and amplification conditions can be selected for a particular nucleic acid for amplification. Known amplification processes include, without limitation, polymerase chain reaction (PCR), extension and ligation, ligation amplification (or ligase chain reaction (LCR)) and amplification methods based on the use of Q-beta replicase or template-dependent polymerase (see US Patent Publication Number US20050287592). Also useful are strand displacement amplification (SDA), thermophilic SDA, nucleic acid sequence based amplification (3SR or NASBA) and transcription-associated amplification (TAA). Reagents, apparatus and hardware for conducting amplification processes are commercially available, and amplification conditions are known and can be selected for the target nucleic acid at hand.

Amplification Primers

Primers useful for amplification of mitochondrial and genomic polynucleotides are provided. In some embodiments primers are used in sets, where a set contains at least a pair. In some embodiments a plurality of primer sets, each set comprising pair(s) of primers, may be used. The term “primer” as used herein refers to a nucleic acid that comprises a nucleotide sequence capable of hybridizing or annealing to a polynucleotide, at or near (e.g., adjacent to) a specific region of interest. A primer may be naturally occurring or synthetic. The term “specific” or “specificity”, as used herein, refers to the binding or hybridization of one molecule to another molecule, such as a primer for a polynucleotide. That is, “specific” or “specificity” refers to the recognition, contact, and formation of a stable complex between two molecules, as compared to substantially less recognition, contact, or complex formation of either of those two molecules with other molecules. As used herein, the term “anneal” refers to the formation of a stable complex between two molecules. The terms “primer”, “oligo”, or “oligonucleotide” may be used interchangeably throughout the document, when referring to primers.

A primer nucleic acid can be designed and synthesized using suitable processes, and may be of any length suitable for hybridizing to a nucleotide sequence of interest (e.g., where the nucleic acid is in liquid phase or bound to a solid support) and performing analysis processes described herein. Primers may be designed based upon a target nucleotide sequence. A primer in some embodiments may be about 10 to about 100 nucleotides, about 10 to about 70 nucleotides, about 10 to about 50 nucleotides, about 15 to about 30 nucleotides, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. A primer may be composed of naturally occurring and/or non-naturally occurring nucleotides (e.g., labeled nucleotides), or a mixture thereof. Primers suitable for use with embodiments described herein, may be synthesized and labeled using known techniques. Oligonucleotides (e.g., primers) may be chemically synthesized according to the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984. Purification of oligonucleotides can be effected by native acrylamide gel electrophoresis or by anion-exchange high-performance liquid chromatography (HPLC), for example, as described in Pearson and Regnier, J. Chrom., 255:137-149, 1983.

All or a portion of a primer nucleic acid sequence (naturally occurring or synthetic) may be substantially complementary to a target nucleic acid, in some embodiments. As referred to herein, “substantially complementary” with respect to sequences refers to nucleotide sequences that will hybridize with each other. The stringency of the hybridization conditions can be altered to tolerate varying amounts of sequence mismatch. Included are regions of counterpart, target and capture nucleotide sequences 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

Primers that are substantially complimentary to a target nucleic acid sequence are also substantially identical to the compliment of the target nucleic acid sequence. That is, primers are substantially identical to the anti-sense strand of the nucleic acid. As referred to herein, "substantially identical" with respect to sequences refers to nucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other. One test for determining whether two nucleotide sequences are substantially identical is to determine the percent of identical nucleotide sequences shared.

Amplification primer sequence, primer length and mismatches with the target nucleic acid are some of the parameters that affect amplification primer annealing to target nucleic acid sequences. By adjusting these parameters and others amplification primers can be designed that minimize annealing and accordingly inhibit elongation.

As used herein, the phrase "hybridizing" or grammatical variations thereof, refers to binding of a first nucleic acid molecule to a second nucleic acid molecule under nucleic acid synthesis conditions. Hybridizing can include instances where a first nucleic acid molecule binds to a second nucleic acid molecule, where the first and second nucleic acid molecules are complementary. As used herein, "specifically hybridizes" refers to preferential hybridization under nucleic acid synthesis conditions of a primer, to a nucleic acid molecule having a sequence complementary to the primer compared to hybridization to a nucleic acid molecule not having a complementary sequence. For example, specific hybridization includes the hybridization of a primer to a target nucleic acid sequence that is complementary to the primer.

A primer, in certain embodiments, may contain a modification such as inosines, abasic sites, locked nucleic acids, minor groove binders, duplex stabilizers (e.g., acridine, spermidine), Tm modifiers or any modifier that changes the binding properties of the primers or probes.

In some embodiments, amplification primers are designed to result in amplicons of about 30 base pairs to about 300 base pairs. In some embodiments, when the sample comprises circulating cell free nucleic acid, amplification primers are designed to result in amplicons greater than about 50 base pairs and less than about 166 pairs. Circulating cell free genomic nucleic acid (DNA) is less degraded (the mean is about 166 bp) than circulating cell free mitochondrial nucleic acid (DNA) (the mean is about 50 bp), Designing primers so amplicons are in the size range of greater than about 50 base pairs to less than about 166 base pairs results in amplification of a large portion of circulating cell free genomic nucleic acid and amplification of a smaller portion of the circulating cell free mitochondrial nucleic acid. This selective amplification can allow for the detection and quantitation of genomic nucleic acid in the same assay as mitochondrial nucleic acid. In some embodiments, the size of the amplicons is greater than about 60 bp and less than about 100 bp. In some embodiments, the size of the amplicons is greater than about 70 bp and less than about 100 bp.

In some embodiments, amplification primers are designed to amplify a paralog $^{5'}$X—V—Y$^{3'}$ and the mitochondrial polynucleotide and the genomic polynucleotide of a set are reproducibly amplified relative to each other by a single pair of amplification primers that hybridize to an internal polynucleotide within X and Y. One primer in the pair hybridizes to a polynucleotide within X and the other primer in the pair hybridizes to another polynucleotide within Y. The mitochondrial polynucleotide of a set is co-amplified with the genomic polynucleotide of a set using a single primer pair that binds to regions upstream and downstream of V. In some embodiments, mitochondrial and genomic polynucleotides are amplified under conditions that amplify each species at a "substantially reproducible level". In certain embodiments, a "substantially reproducible level" varies by about 1% or less. In some embodiments, a substantially reproducible level varies by 10%, 5%, 4%, 3%, 2%, 1.5%, 1%, 0.5%, 0.1%, 0.05%, 0.01%, 0.005% or 0.001%. Unbiased amplification of the mitochondrial and genomic polynucleotides of a set allows for a direct comparison of the amplicons in a single reaction and without the need for an internal standard. In some embodiments, determining the identity and quantity of the nucleotide at V is a good marker for relative copy number quantification.

In some embodiments, amplification primers are designed so the mitochondrial polynucleotide and the genomic polynucleotide of a set are amplified by different species specific pairs of amplification primers. The amplification primers are designed to hybridize to flanking polynucleotides that are 5' to X and 3' to Y. The flanking polynucleotides are different at one or more nucleotide positions between mitochondrial and genomic polynucleotides. The regions upstream and downstream of X and Y should have enough differences to allow for design of amplification primer pairs that are specific for mitochondrial polynucleotides or genomic polynucleotides. The mitochondrial polynucleotide amplification primers will not bind the genomic polynucleotide and vice versa. In some embodiments, methods employing amplification primers specific for mitochondrial polynucleotides can be used to reduce the amplification of the abundant mitochondrial polynucleotide relative to the amplification of the less abundant genomic polynucleotide. In some embodiments, the amplification primer that is specific for the mitochondrial polynucleotide is designed not to hybridize as well to amplification primer binding site (e.g., binding site contains nucleotide mismatches and/or nucleotides that have reduced hydrogen binding) as does the amplification primer that is specific for the genomic polynucleotide in a set. The amplicons corresponding to the mitochondrial polynucleotide are reduced with respect to the amplicons corresponding to the genomic polynucleotide in each set.

In some embodiments, the amplification primers that specifically hybridize to the mitochondrial polynucleotide are provided at a lower concentration than the concentration of the amplification primers that specifically hybridize to the genomic polynucleotide. The amplicons corresponding to the mitochondrial polynucleotide are reduced with respect to the amplicons corresponding to the genomic polynucleotide in each set. In some embodiments, the concentration of the amplification primers that specifically hybridize to the mitochondrial polynucleotide is about 2 times to about 30 times lower than the concentration of amplification primers that specifically hybridize to the genomic polynucleotide in a set. The concentration of the amplification primer for the mitochondrial polynucleotide relative to the concentration of the amplification primer for the genomic polynucleotide can be optimized to try to achieve equal signal strength based on the following scheme, for example.

| | Pool 1 | Pool 2 | Pool 3 | Pool 4 | Pool 5 | Pool 6 | Pool 7 | Pool 8 | Pool 9 | Pool 10 |
|---|---|---|---|---|---|---|---|---|---|---|
| gDNA primers | 100 nM | 100 nM | 100 nM | 100 nM | 100 nM | 100 nM | 100 nM | 100 nM | 100 nM | |
| mDNA primers | | 100 nM | 75 nM | 50 nM | 35 nM | 25 nM | 12.5 nM | 6.25 nM | 3.125 nM | 100 nM |

In some embodiments, the two approaches can be used together.

In some embodiments, amplification primers are designed to amplify a paralog $^{5'}X—V—Y^{3'}$ in which the mitochondrial polynucleotide and the genomic polynucleotide of such a set are amplified by an amplification primer that hybridizes to a polynucleotide within X and two different amplification primers that hybridize to flanking polynucleotides that are 3' to Y. The amplification primers that hybridize to X are the same for the mitochondrial and genomic polynucleotide, as X is identical for the mitochondrial and genomic polynucleotide. The amplification primers that hybridize to flanking polynucleotides 3' to Y are different for the mitochondrial and genomic polynucleotide. In some embodiments, amplification primers are designed to amplify a paralog $^{5'}X—V—Y^{3'}$ in which the mitochondrial polynucleotide and the genomic polynucleotide of such a set are amplified by an amplification primer that hybridizes to a polynucleotide within Y and two different amplification primers that hybridize to flanking polynucleotides that are 5' to X. The amplification primers that hybridize to Y are the same for the mitochondrial and genomic polynucleotide, as Y is identical for the mitochondrial and genomic polynucleotide. The amplification primers that hybridize to flanking polynucleotides 5' to X are different for the mitochondrial and genomic polynucleotide. Having at least one amplification primer for the mitochondrial and genomic polynucleotides that is different allows for an assay to be designed so the amplification of the mitochondrial polynucleotide of a set is reduced relative to the amplification of the genomic polynucleotide of the set. The concentration of the amplification primer specific for the mitochondrial polynucleotide can be made lower than the concentration of the amplification primer specific for the genomic polynucleotide. In some embodiments, the forward amplification primers specifically hybridize to and amplify either mitochondrial or genomic polynucleotides are at different concentrations relative to each other (e.g., 0.1 (mitochondrial) and 1.0 (genomic)) and the reverse amplification primer is universal and hybridizes and amplifies both species of polynucleotides (mitochondrial and genomic) is at the same relative concentration as the genomic specific forward amplification primer (e.g., 1.0). In some embodiments, the reverse amplification primers specifically hybridize to and amplify either mitochondrial or genomic polynucleotides are at different concentrations relative to each other (e.g., 0.1 (mitochondrial) and 1.0 (genomic)) and the forward amplification primer is universal and hybridizes and amplifies both species of polynucleotides (mitochondrial and genomic) is present at the same relative concentration as the genomic specific reverse amplification primer (e.g., 1.0). In some embodiments, the concentration of the amplification primer that specifically hybridizes to the mitochondrial polynucleotide is about 2 times to about 30 times lower than the concentration of the amplification primer that specifically hybridizes to the genomic polynucleotide in a set. Optimization of concentration of amplification primers is as described above. Forward and reverse amplification primers and their relative concentrations can be chosen based on the sequence of the polynucleotides that are to be amplified using known principles of PCR.

Alternatively, a primer binding site for the amplification primer specific for the mitochondrial polynucleotide can be selected so that the amplification primer for the mitochondrial polynucleotide does not hybridize to its primer binding site as well (e.g., binding site contains nucleotide mismatches and/or nucleotides that have reduced hydrogen binding) as the amplification primer specific for the genomic polynucleotide.

In some embodiments, the two approaches can be used together.

In some embodiments, amplification primers are designed so a paralog $^{5'}J\text{-}V—K^{3'}$ of the mitochondrial polynucleotides of a set or a paralog $^{5'}J\text{-}V—K^{3'}$ of the nuclear polynucleotides of a set are reproducibly amplified relative to each other by a single pair of amplification primers that hybridize to an internal polynucleotide within J and K. One primer in the pair hybridizes to a polynucleotide within J and the other primer in the pair hybridizes to another polynucleotide within K. The mitochondrial polynucleotides of a set are co-amplified using a single primer pair that binds to regions upstream and downstream of V. The nuclear polynucleotides of a set are co-amplified using a single primer pair that binds to regions upstream and downstream of V. In some embodiments, mitochondrial polynucleotides of a set are amplified under conditions that amplify each polynucleotide at a "substantially reproducible level". In some embodiments, nuclear polynucleotides of a set are amplified under conditions that amplify each polynucleotide at a "substantially reproducible level." In certain embodiments, a "substantially reproducible level" varies by about 1% or less. In some embodiments, a substantially reproducible level varies by 10%, 5%, 4%, 3%, 2%, 1.5%, 1%, 0.5%, 0.1%, 0.05%, 0.01%, 0.005% or 0.001%. Unbiased amplification of the mitochondrial polynucleotides of a set allow for a direct comparison of the amplicons in a single reaction. Unbiased amplification of nuclear polynucleotides of a set allow for a direct comparison of the amplicons in a single reaction. In some embodiments, determining the identity and quantity of the nucleotide at V is a good marker for relative copy number quantification.

Quantitation of Amplicons

In some embodiments, amplicons corresponding to the mitochondrial polynucleotide of a set and amplicons corresponding to the genomic polynucleotide of a set are quantified. In some embodiments amplicons are quantified by determining the amount of a nucleotide at V in the amplicons corresponding to the mitochondrial polynucleotide of a set and the amount of the nucleotide at V in the amplicons corresponding to the genomic polynucleotide of a set is determined. Based on the amount of a nucleotide at V in the amplicons corresponding to the mitochondrial polynucleotide of a set and the amount of the nucleotide at V in the amplicons corresponding to the genomic polynucleotide of a set a ratio of the amount of a mitochondrial polynucleotide relative to the amount of a genomic polynucleotide can be obtained and used to determine the dosage of mitochondrial nucleic acid relative to genomic nucleic acid.

In some embodiments, amplicons corresponding to the mitochondrial polynucleotides of a set are quantified and amplicons corresponding to the nuclear polynucleotides of a set are quantified. In some embodiments amplicons are quantified by determining the amount of a nucleotide at V in the amplicons corresponding to each of the mitochondrial polynucleotides of a set (e.g., first and second species, human and chimpanzee). In some embodiments amplicons are quantified by determining the amount of a nucleotide at V in the amplicons corresponding to each of the nuclear polynucleotides of a set (e.g., first and second species, human and chimpanzee).

Any suitable technology can be used to detect and/or quantify amplicons. Non-limiting examples of technologies that can be utilized to detect and/or quantify amplicons include primer extension assays, amplification (e.g., digital PCR, quantitative polymerase chain reaction (qPCR)), sequencing (e.g., nanopore sequencing, massive parallel sequencing), mass spectrometry, array hybridization (e.g., microarray hybridization; gene-chip analysis), flow cytometry, gel electrophoresis (e.g., capillary electrophoresis), cytofluorimetric analysis, fluorescence microscopy, confocal laser scanning microscopy, laser scanning cytometry, affinity chromatography, manual batch mode separation, electric field suspension, the like and combinations of the foregoing. Further detail is provided hereafter for certain amplicon detection and/or quantification technologies.

Primer Extension Reactions

In some embodiments, determining the amount of a nucleotide at V in the amplicons corresponding to the mitochondrial polynucleotide of a set and the amount of the nucleotide at V in the amplicons corresponding to the genomic polynucleotide of a set is by a primer extension reaction process. In some embodiments, determining the amount of a nucleotide at V in the amplicons corresponding to each of the mitochondrial polynucleotides of a set and the amount of the nucleotide at V in the amplicons corresponding to each of the nuclear polynucleotides of a set is by a primer extension reaction process. An extension reaction is conducted under extension conditions, and a variety of such conditions are known and selected for a particular application. Extension conditions can include certain reagents, including without limitation, one or more oligonucleotides, extension nucleotides (e.g., nucleotide triphosphates (dNTPs)), chain terminating reagents or nucleotides (e.g., one or more dideoxynucleotide triphosphates (ddNTPs) or acyclic terminators), one or more salts (e.g., magnesium-containing salt), one or more buffers (e.g., with beta-NAD, Triton X-100), and one or more polymerizing agents (e.g., DNA polymerase, RNA polymerase).

Extension can be conducted under isothermal conditions or under non-isothermal conditions (e.g., thermocycled conditions), in certain embodiments. One or more nucleic acid species can be extended in an extension reaction and one or more molecules of each nucleic acid species can be extended. A nucleic acid can be extended by one or more nucleotides, and in some embodiments, the extension product is about 10 nucleotides to about 10,000 nucleotides in length, about 10 to about 1000 nucleotides in length, about 10 to about 500 nucleotides in length, 10 to about 100 nucleotides in length, and sometimes about 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 nucleotides in length. Incorporation of a terminating nucleotide (e.g., ddNTP), the hybridization location, or other factors, can determine the length to which the oligonucleotide is extended. In certain embodiments, amplification and extension processes are carried out in the same detection procedure.

In some embodiments an extension reaction includes multiple temperature cycles repeated to amplify the amount of extension product in the reaction. In some embodiments the extension reaction is cycled 2 or more times. In some embodiments the extension reaction is cycled 10 or more times. In some embodiments the extension reaction is cycled about 10, 15, 20, 50, 55, 60, 65, 70, 75, 80, 85, 90, 95, 100, 200, 300, 400, 500 or 600 or more times. In some embodiments the extension reaction is cycled 20 to 50 times. In some embodiments the extension reaction is cycled 20 to 100 times. In some embodiments the extension reaction is cycled 20 to 300 times. In some embodiments the extension reaction is cycled 200 to 300 times. In certain embodiments, the extension reaction is cycled at least 50, 55, 60, 65, 70, 75, 80, 85, 90, 95 or 100 times.

Primer extension processes include methods such as iPLEX™ or homogeneous MassExtend® (hME) (see, for example, U.S. Published Patent Application No. 2013/0237428 A1, U.S. Pat. Nos. 8,349,566, and 8,003,317, the contents of which are incorporated in their entirety by reference herein), in which a mixture of minor nucleic acid species (e.g., mutant alleles) and major nucleic acid species (e.g., wild type alleles) are subjected to a polymerase chain reaction (PCR) amplification using a set of amplification primers, a polymerase and deoxynucleotides (dNTPs), thereby generating amplicons of the wild type and mutant species. After treatment with shrimp alkaline phosphatase (SAP) to dephosphorylate unincorporated dNTPs, the amplicon mixture is extended using extension primers (unextended primers or UEPs), a polymerase and a termination mix that includes chain terminating reagents (e.g., dideoxunucleotides or ddNTPs). The UEPs hybridize to the amplicons and are extended either up to the site of variance between the mutant and wild type species (i.e., extension stops at the mutation site where there is a difference in bases between the mutant and wild type species to generate single base extension products or SBEs, as in iPLEX™) or a few bases (e.g., 2-3 bases) past the site of variance (as in, for example, the hME method). The resulting extension products can then be processed (e.g., by desalting prior to mass spectrometry) and analyzed for the presence of the mutant alleles based on a difference in detection signal (e.g., mass) relative to the wild type allele.

The above-described iPLEX™ and homogeneous MassExtend® (hME) methods use an equimolar mixture of ddNTPs in the extension step for generating extension products corresponding to wild type and mutant species. Thus, in the iPLEX™ and homogeneous MassExtend® (hME) methods, all other factors being equal with the exception of the major nucleic acid species being present in a large excess relative to the minor nucleic acid species, the majority of the UEPs hybridize to the major nucleic acid species and are extended using the chain terminating reagent specific for the major nucleic acid species. Relatively few molecules of UEP are available for hybridization and extension of the minor nucleic acid species. This compromises the magnitude of the detection signal corresponding to the minor nucleic acid species, which is overshadowed by the predominant detection signal from the major nucleic acid species and may be subsumed by background noise.

In certain embodiments, the extension step uses a limiting concentration of chain terminating reagent specific for the mitochondrial polynucleotide, relative to the chain terminating reagent specific for the genomic polynucleotide. Amplicons are contacted with extension primers under extension conditions with chain terminating reagents. The chain terminating reagent that is specific for the amplicons corresponding to the mitochondrial polynucleotide is not specific for the amplicons corresponding to genomic polynucleotide and the chain terminating reagent specific for the amplicons corresponding to the genomic polynucleotide is not specific for the amplicons corresponding to mitochondrial polynucleotide. The extension primers are extended up to V, thereby generating chain terminated extension products corresponding to the mitochondrial polynucleotide or the genomic polynucleotide. The concentration of the chain terminating reagent specific for the mitochondrial polynucleotide is less than the concentration of the chain terminating reagent specific for the genomic polynucleotide.

In some embodiments, the ratio of the amount of extension product corresponding to the mitochondrial polynucleotides relative to the amount of extension product corresponding to the genomic polynucleotide is determined and the amount of mitochondrial nucleic acid relative to the amount of genomic nucleic acid in the sample is determined based on the ratio and based on the concentration of the chain terminating reagent specific for the mitochondrial polynucleotide relative to the concentration of the chain terminating reagent specific for genomic polynucleotide.

In certain embodiments, the concentration of the chain terminating reagent specific for a mitochondrial polynucleotide is between about 1% to about 20% of the concentration of the chain terminating reagent specific for a genomic polynucleotide. The concentration of the chain terminating reagent specific for a mitochondrial polynucleotide generally being between about 0.5% to less than about 20% of the concentration of the chain terminating reagent specific for a genomic polynucleotide, about 0.5% to less than about 15%, about 1% to about 15%, about 1% to about 10%, about 2% to about 10% or about 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of the concentration of the chain terminating reagent specific for a genomic polynucleotide.

In certain embodiments, the extension step uses an equimolar concentration of chain terminating reagents specific for each of the mitochondrial polynucleotides of a set or an equimolar concentration of chain terminating reagents specific for each of the nuclear polynucleotides of a set. Amplicons are contacted with extension primers under extension conditions with chain terminating reagents. The chain terminating reagent that is specific for the amplicons corresponding to the mitochondrial polynucleotide of the first species is not specific for the amplicons corresponding to the mitochondrial polynucleotide of the second species; and the chain terminating reagent specific for the amplicons corresponding to the nuclear polynucleotide of the first species is not specific for the amplicons corresponding to the nuclear polynucleotide of the second species. The primers are extended up to V, thereby generating chain terminated extension products corresponding to the mitochondrial polynucleotide of the first species, the mitochondrial polynucleotide of the second species, the nuclear polynucleotide of the first species and the nuclear polynucleotide of the second species.

In some embodiments, a ratio of the amount of extension product corresponding to the mitochondrial polynucleotide of the second species to the amount of extension product corresponding to the mitochondrial polynucleotide of the first species is determined. In some embodiments, a ratio of the amount of extension product corresponding to the nuclear polynucleotide of the second species to the amount of extension product corresponding to the nuclear polynucleotide of the first species and the amount of mitochondrial nucleic acid relative to the amount of nuclear nucleic acid in the sample is determined based on the ratios.

The term "up to" as used herein includes nucleotide position V.

In some embodiments, the chain terminating reagents are chain terminating nucleotides. In some embodiments, the chain terminating nucleotides independently are selected from among ddATP, ddGTP, ddCTP, ddTTP and ddUTP. In some embodiments, the chain terminating reagents comprise one or more acyclic terminators. In some embodiments, one or more of the chain terminating reagents comprises a detectable label. In some embodiments, the label is a fluorescent label or dye. In some embodiments, the label is a mass label and detection is by mass spectrometry.

Any suitable extension reaction can be selected and utilized. An extension reaction can be utilized, for example, to discriminate the nucleotide of a mitochondrial polynucleotide from the nucleotide of a genomic polynucleotide at V, to discriminate the nucleotide of a mitochondrial polynucleotide of a first species from the nucleotide of a mitochondrial polynucleotide of a second species at V or to discriminate the nucleotide of a nuclear polynucleotide of a first species from the nucleotide of a nuclear polynucleotide of a second species at V by the incorporation of deoxynucleotides and/or dideoxynucleotides to an extension oligonucleotide that hybridizes to a region adjacent to V in the amplicon. The primer often is extended with a polymerase. In some embodiments, the oligonucleotide is extended by only one deoxynucleotide or dideoxynucleotide complementary to the V site. In some embodiments, an oligonucleotide may be extended by dNTP incorporation and terminated by a ddNTP, or terminated by ddNTP incorporation without dNTP extension in certain embodiments. Extension may be carried out using unmodified extension oligonucleotides and unmodified dideoxynucleotides, unmodified extension oligonucleotides and biotinylated dideoxynucleotides, extension oligonucleotides containing a deoxyinosine and unmodified dideoxynucleotides, extension oligonucleotides containing a deoxyinosine and biotinylated dideoxynucleotides, extension by biotinylated dideoxynucleotides, or extension by biotinylated deoxynucleotide and/or unmodified dideoxynucleotides, in some embodiments.

The extension products corresponding to the mitochondrial polynucleotide and the genomic polynucleotide of a set, the mitochondrial polynucleotide of a first species and the mitochondrial polynucleotide of a second species of a set or the nuclear polynucleotide of a first species and the nuclear polynucleotide of a second species of a set that are obtained by the methods provided herein can be detected by a variety of methods. For example, the extension primers (UEPs) and/or the chain terminating reagents may be labeled with any type of chemical group or moiety that allows for detection of a signal and/or quantification of the signal including, but not limited to, mass labels, radioactive molecules, fluorescent molecules, antibodies, antibody fragments, haptens, carbohydrates, biotin, derivatives of biotin, phosphorescent moieties, luminescent moieties, electrochemiluminescent moieties, moieties that generate an electrochemical signal upon oxidation or reduction, e.g., complexes of iron, ruthenium or osmium (see, for example, eSensor technology used by Genmark Diagnostics, Inc. e.g., as described in Pierce et al., J. Clin. Micribiol., 50(11):3458-3465 (2012)), chromatic moieties, and moieties having a detectable electron spin resonance, electrical capacitance, dielectric constant or electrical conductivity, or any combination of labels thereof.

The labeled extension products corresponding to the mitochondrial polynucleotide and the genomic polynucleotide of a set, the mitochondrial polynucleotide of a first species and the mitochondrial polynucleotide of a second species of a set or the nuclear polynucleotide of a first species and the nuclear polynucleotide of a second species of a set can be analyzed by a variety of methods including, but not limited to, mass spectrometry, MALDI-TOF mass spectrometry, fluorescence detection, DNA sequencing gel, capillary electrophoresis on an automated DNA sequencing machine, microchannel electrophoresis, and other methods of sequencing, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry, measurement of current/electrochemical signal or by DNA hybridization techniques including Southern Blots, Slot Blots, Dot Blots, and DNA microarrays, wherein DNA fragments would be useful as both "probes" and "targets," ELISA, fluorimetry, Fluorescence Resonance Energy Transfer (FRET), SNP-IT, GeneChips, HuSNP, BeadArray, TaqMan assay, Invader assay, MassExtend®, or MassCleave® method.

In some embodiments, a chain terminating reagent or chain terminating nucleotide includes one detectable label. In some embodiments, a first chain terminating reagent or chain terminating nucleotide includes a detectable label that is different from the detectable label of a second chain terminating reagent or chain terminating nucleotide. In some embodiments, an extension composition includes one or more chain terminating reagents or chain terminating nucleotides where each chain terminating reagent or chain terminating nucleotide includes a different detectable label. In some embodiments, an extension composition includes one or more chain terminating reagents or chain terminating nucleotides where each contains the same detection label. In some embodiments, an extension composition includes a chain terminating reagent or chain terminating nucleotide and an extension nucleotide (e.g., dNTP) and one or more of the nucleotides (e.g. terminating nucleotides and/or extension nucleotides) includes a detection label. In some embodiments, the relative amount (frequency or copy number, e.g.) of a mitochondrial polynucleotide to that of a genomic polynucleotide can be determined by the proportions of their detection signals relative to the ratio of the concentration of the chain terminating reagents specific for the mitochondrial polynucleotide to the concentration of the chain terminating reagents specific for genomic polynucleotide, using a normalization coefficient. In some embodiments the amount (e.g. copy number, concentration, percentage) of mitochondrial polynucleotide is quantified by normalizing the ratio of the signal for the genomic polynucleotide to the signal for the mitochondrial polynucleotide, using a coefficient. This coefficient is inversely proportional to the fraction of concentration of the chain terminating reagent or nucleotide specific for the mitochondrial polynucleotide compared to the concentration of the chain terminating reagent or nucleotide specific for genomic polynucleotide (i.e., the lower the fraction of mitochondrial polynucleotide-specific chain terminating reagent relative to the chain terminating reagent specific for the genomic polynucleotide, the larger the coefficient).

In some embodiments, a normalization coefficient is not required as the ratio for a sample is either compared to a population or to samples obtained from the same subject over a period of time.

Mass Spectrometry

Mass spectrometry methods typically are used to determine the mass of a molecule. In some embodiments, mass spectrometry is used to detect and/or quantify the primer extension product based on its unique mass. The relative signal strength, e.g., mass peak on a spectra, for the nucleic acid nucleic acid can indicate the relative population of the species amongst other nucleic acids in the sample (see e.g., Jurinke et al. (2004) Mol. Biotechnol. 26, 147-164).

Mass spectrometry generally works by ionizing chemical compounds to generate charged molecules or molecule fragments and measuring their mass-to-charge ratios. A typical mass spectrometry procedure involves several steps, including (1) loading a sample onto a mass spectrometry instrument followed by vaporization, (2) ionization of the sample components by any one of a variety of methods (e.g., impacting with an electron beam), resulting in charged particles (ions), (3) separation of ions according to their mass-to-charge ratio in an analyzer by electromagnetic fields, (4) detection of ions (e.g., by a quantitative method), and (5) processing of ion signals into mass spectra.

Mass spectrometry methods are known, and include without limitation quadrupole mass spectrometry, ion trap mass spectrometry, time-of-flight mass spectrometry, gas chromatography mass spectrometry and tandem mass spectrometry can be used with a method described herein. Processes associated with mass spectrometry are generation of gas-phase ions derived from the sample, and measurement of ions. Movement of gas-phase ions can be precisely controlled using electromagnetic fields generated in the mass spectrometer, and movement of ions in these electromagnetic fields is proportional to the mass to charge ratio (m/z) of each ion, which forms the basis of measuring m/z and mass. Movement of ions in these electromagnetic fields allows for containment and focusing of the ions which accounts for high sensitivity of mass spectrometry. During the course of m/z measurement, ions are transmitted with high efficiency to particle detectors that record the arrival of these ions. The quantity of ions at each m/z is demonstrated by peaks on a graph where the x axis is m/z and the y axis is relative abundance. Different mass spectrometers have different levels of resolution (i.e., the ability to resolve peaks between ions closely related in mass). Resolution generally is defined as R=m/delta m, where m is the ion mass and delta m is the difference in mass between two peaks in a mass spectrum. For example, a mass spectrometer with a resolution of 1000 can resolve an ion with a m/z of 100.0 from an ion with a m/z of 100.1.

Certain mass spectrometry methods can utilize various combinations of ion sources and mass analyzers which allows for flexibility in designing customized detection protocols. In some embodiments, mass spectrometers can be programmed to transmit all ions from the ion source into the mass spectrometer either sequentially or at the same time. In some embodiments, a mass spectrometer can be programmed to select ions of a particular mass for transmission into the mass spectrometer while blocking other ions.

Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nano-spray and microspray or matrix-assisted laser desorption. Mass analyzers include, for example, a quadrupole mass filter, ion trap mass analyzer and time-of-flight mass analyzer.

An ion formation process generally is a starting point for mass spectrum analysis. Several ionization methods are available and the choice of ionization method depends on the sample used for analysis. For example, for the analysis of polypeptides a relatively gentle ionization procedure such as electrospray ionization (ESI) can be desirable. For ESI, a solution containing the sample is passed through a fine needle at high potential which creates a strong electrical field resulting in a fine spray of highly charged droplets that is directed into the mass spectrometer. Other ionization procedures include, for example, fast-atom bombardment (FAB) which uses a high-energy beam of neutral atoms to strike a solid sample causing desorption and ionization. Matrix-assisted laser desorption ionization (MALDI) is a method in which a laser pulse is used to strike a sample that has been crystallized in an UV-absorbing compound matrix (e.g., 2,5-dihydroxybenzoic acid, alpha-cyano-4-hydroxycinammic acid, 3-hydroxypicolinic acid (3-HPA), di-ammoniumcitrate (DAC) and combinations thereof). Other ionization procedures known in the art include, for example, plasma and glow discharge, plasma desorption ionization, resonance ionization, and secondary ionization.

A variety of mass analyzers are available that can be paired with different ion sources. Different mass analyzers have different advantages as known in the art and as described herein. The mass spectrometer and methods chosen for detection depends on the particular assay, for example, a more sensitive mass analyzer can be used when a small amount of ions are generated for detection. Several types of mass analyzers and mass spectrometry methods are described below. Ion mobility mass (IM) spectrometry is a gas-phase separation method. IM separates gas-phase ions based on their collision cross-section and can be coupled with time-of-flight (TOF) mass spectrometry. IM-MS methods are known in the art.

Quadrupole mass spectrometry utilizes a quadrupole mass filter or analyzer. This type of mass analyzer is composed of four rods arranged as two sets of two electrically connected rods. A combination of rf and dc voltages are applied to each pair of rods which produces fields that cause an oscillating movement of the ions as they move from the beginning of the mass filter to the end. The result of these fields is the production of a high-pass mass filter in one pair of rods and a low-pass filter in the other pair of rods. Overlap between the high-pass and low-pass filter leaves a defined m/z that can pass both filters and traverse the length of the quadrupole. This m/z is selected and remains stable in the quadrupole mass filter while all other m/z have unstable trajectories and do not remain in the mass filter. A mass spectrum results by ramping the applied fields such that an increasing m/z is selected to pass through the mass filter and reach the detector. In addition, quadrupoles can also be set up to contain and transmit ions of all m/z by applying a rf-only field. This allows quadrupoles to function as a lens or focusing system in regions of the mass spectrometer where ion transmission is needed without mass filtering.

A quadrupole mass analyzer, as well as the other mass analyzers described herein, can be programmed to analyze a defined m/z or mass range. Since the desired mass range of nucleic acid fragment is known, in some instances, a mass spectrometer can be programmed to transmit ions of the projected correct mass range while excluding ions of a higher or lower mass range. The ability to select a mass range can decrease the background noise in the assay and thus increase the signal-to-noise ratio. Thus, in some instances, a mass spectrometer can accomplish a separation step as well as detection and identification of certain mass-distinguishable nucleic acid fragments.

Ion trap mass spectrometry utilizes an ion trap mass analyzer. Typically, fields are applied such that ions of all m/z are initially trapped and oscillate in the mass analyzer. Ions enter the ion trap from the ion source through a focusing device such as an octapole lens system. Ion trapping takes place in the trapping region before excitation and ejection through an electrode to the detector. Mass analysis can be accomplished by sequentially applying voltages that increase the amplitude of the oscillations in a way that ejects ions of increasing m/z out of the trap and into the detector. In contrast to quadrupole mass spectrometry, all ions are retained in the fields of the mass analyzer except those with the selected m/z. Control of the number of ions can be accomplished by varying the time over which ions are injected into the trap.

Time-of-flight mass spectrometry utilizes a time-of-flight mass analyzer. Typically, an ion is first given a fixed amount of kinetic energy by acceleration in an electric field (generated by high voltage). Following acceleration, the ion enters a field-free or "drift" region where it travels at a velocity that is inversely proportional to its m/z. Therefore, ions with low m/z travel more rapidly than ions with high m/z. The time required for ions to travel the length of the field-free region is measured and used to calculate the m/z of the ion.

Gas chromatography mass spectrometry often can a target in real-time. The gas chromatography (GC) portion of the system separates the chemical mixture into pulses of analyte and the mass spectrometer (MS) identifies and quantifies the analyte.

Tandem mass spectrometry can utilize combinations of the mass analyzers described above. Tandem mass spectrometers can use a first mass analyzer to separate ions according to their m/z in order to isolate an ion of interest for further analysis. The isolated ion of interest is then broken into fragment ions (called collisionally activated dissociation or collisionally induced dissociation) and the fragment ions are analyzed by the second mass analyzer. These types of tandem mass spectrometer systems are called tandem in space systems because the two mass analyzers are separated in space, usually by a collision cell. Tandem mass spectrometer systems also include tandem in time systems where one mass analyzer is used, however the mass analyzer is used sequentially to isolate an ion, induce fragmentation, and then perform mass analysis.

Mass spectrometers in the tandem in space category have more than one mass analyzer. For example, a tandem quadrupole mass spectrometer system can have a first quadrupole mass filter, followed by a collision cell, followed by a second quadrupole mass filter and then the detector. Another arrangement is to use a quadrupole mass filter for the first mass analyzer and a time-of-flight mass analyzer for the second mass analyzer with a collision cell separating the two mass analyzers. Other tandem systems are known in the art including reflectron-time-of-flight, tandem sector and sector-quadrupole mass spectrometry.

Mass spectrometers in the tandem in time category have one mass analyzer that performs different functions at different times. For example, an ion trap mass spectrometer can be used to trap ions of all m/z. A series of rf scan functions are applied which ejects ions of all m/z from the trap except the m/z of ions of interest. After the m/z of interest has been isolated, an rf pulse is applied to produce collisions with gas molecules in the trap to induce fragmentation of the ions. Then the m/z values of the fragmented ions are measured by the mass analyzer. Ion cyclotron resonance instruments, also known as Fourier transform mass spectrometers, are an example of tandem-in-time systems.

Several types of tandem mass spectrometry experiments can be performed by controlling the ions that are selected in each stage of the experiment. The different types of experiments utilize different modes of operation, sometimes called "scans," of the mass analyzers. In a first example, called a mass spectrum scan, the first mass analyzer and the collision cell transmit all ions for mass analysis into the second mass analyzer. In a second example, called a product ion scan, the ions of interest are mass-selected in the first mass analyzer and then fragmented in the collision cell. The ions formed are then mass analyzed by scanning the second mass analyzer. In a third example, called a precursor ion scan, the first mass analyzer is scanned to sequentially transmit the mass analyzed ions into the collision cell for fragmentation. The second mass analyzer mass-selects the product ion of interest for transmission to the detector. Therefore, the detector signal is the result of all precursor ions that can be fragmented into a common product ion. Other experimental formats include neutral loss scans where a constant mass difference is accounted for in the mass scans.

For quantification, controls may be used which can provide a signal in relation to the amount of the nucleic acid fragment, for example, that is present or is introduced. A control to allow conversion of relative mass signals into absolute quantities can be accomplished by addition of a known quantity of a mass tag or mass label to each sample before detection of the nucleic acid fragments. Any mass tag that does not interfere with detection of the fragments can be used for normalizing the mass signal. Such standards typically have separation properties that are different from those of any of the molecular tags in the sample, and could have the same or different mass signatures.

A separation step sometimes can be used to remove salts, enzymes, or other buffer components from the nucleic acid sample. Several methods well known in the art, such as chromatography, gel electrophoresis, or precipitation, can be used to clean up the sample. For example, size exclusion chromatography or affinity chromatography can be used to remove salt from a sample. The choice of separation method can depend on the amount of a sample. For example, when small amounts of sample are available or a miniaturized apparatus is used, a micro-affinity chromatography separation step can be used. In addition, whether a separation step is desired, and the choice of separation method, can depend on the detection method used. Salts sometimes can absorb energy from the laser in matrix-assisted laser desorption/ionization and result in lower ionization efficiency. Thus, the efficiency of matrix-assisted laser desorption/ionization and electrospray ionization sometimes can be improved by removing salts from a sample.

Nanopores

In some embodiments, amplicons of mitochondrial and genomic (nuclear) polynucleotides are detected and/or quantified using a nanopore process. In some embodiments, determining the amount of a nucleotide at V in the amplicons corresponding to the mitochondrial polynucleotide of a set and the amount of the nucleotide at V in the amplicons corresponding to the genomic polynucleotide of a set is by using a nanopore process. In some embodiments, determining the amount of a nucleotide at V in the amplicons corresponding to the mitochondrial polynucleotide of the first species and the second species of a set and determining the amount of a nucleotide at V in the amplicons corresponding to the nuclear polynucleotide of the first species and the second species of a set is by a nanopore process.

A nanopore can be used to obtain nucleotide sequencing information for the amplicons. In some embodiments, amplicons are detected and/or quantified using a nanopore without obtaining nucleotide sequences. A nanopore is a small hole or channel, typically of the order of 1 nanometer in diameter. Certain transmembrane cellular proteins can act as nanopores (e.g., alpha-hemolysin). Nanopores can be synthesized (e.g., using a silicon platform). Immersion of a nanopore in a conducting fluid and application of a potential across it results in a slight electrical current due to conduction of ions through the nanopore. The amount of current which flows is sensitive to the size of the nanopore. As a nucleic acid fragment passes through a nanopore, the nucleic acid molecule obstructs the nanopore to a certain degree and generates a change to the current. In some embodiments, the duration of current change as the nucleic acid fragment passes through the nanopore can be measured.

In some embodiments, nanopore technology can be used in a method described herein for obtaining nucleotide sequence information for nucleic acid fragments. Nanopore sequencing is a single-molecule sequencing technology whereby a single nucleic acid molecule (e.g. DNA) is sequenced directly as it passes through a nanopore. As described above, immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree and generates characteristic changes to the current. The amount of current which can pass through the nanopore at any given moment therefore varies depending on whether the nanopore is blocked by an A, a C, a G, a T, or sometimes methyl-C. The change in the current through the nanopore as the DNA molecule passes through the nanopore represents a direct reading of the DNA sequence. In some embodiments, a nanopore can be used to identify individual DNA bases as they pass through the nanopore in the correct order (e.g., International Patent Application No. WO2010/004265).

There are a number of ways that nanopores can be used to sequence nucleic acid molecules. In some embodiments, an exonuclease enzyme, such as a deoxyribonuclease, is used. In this case, the exonuclease enzyme is used to sequentially detach nucleotides from a nucleic acid (e.g. DNA) molecule. The nucleotides are then detected and discriminated by the nanopore in order of their release, thus reading the sequence of the original strand. For such an embodiment, the exonuclease enzyme can be attached to the nanopore such that a proportion of the nucleotides released from the DNA molecule is capable of entering and interacting with the channel of the nanopore. The exonuclease can be attached to the nanopore structure at a site in close proximity to the part of the nanopore that forms the opening of the channel. In some embodiments, the exonuclease enzyme can be attached to the nanopore structure such that its nucleotide exit trajectory site is orientated towards the part of the nanopore that forms part of the opening.

In some embodiments, nanopore sequencing of nucleic acids involves the use of an enzyme that pushes or pulls the nucleic acid (e.g. DNA) molecule through the pore. In this case, the ionic current fluctuates as a nucleotide in the DNA molecule passes through the pore. The fluctuations in the current are indicative of the DNA sequence. For such an embodiment, the enzyme can be attached to the nanopore structure such that it is capable of pushing or pulling the target nucleic acid through the channel of a nanopore without interfering with the flow of ionic current through the pore. The enzyme can be attached to the nanopore structure at a site in close proximity to the part of the structure that forms part of the opening. The enzyme can be attached to the subunit, for example, such that its active site is orientated towards the part of the structure that forms part of the opening.

In some embodiments, nanopore sequencing of nucleic acids involves detection of polymerase bi-products in close proximity to a nanopore detector. In this case, nucleoside phosphates (nucleotides) are labeled so that a phosphate labeled species is released upon the addition of a polymerase to the nucleotide strand and the phosphate labeled species is detected by the pore. Typically, the phosphate species contains a specific label for each nucleotide. As nucleotides are sequentially added to the nucleic acid strand, the bi-products of the base addition are detected. The order that the phosphate labeled species are detected can be used to determine the sequence of the nucleic acid strand.

Probes

In some embodiments, amplicons are detected and/or quantified using one or more probes. In some embodiments, quantification comprises quantifying target nucleic acid (mitochondrial amplicon and/or genomic amplicon, mitochondrial amplicon of a first species, mitochondrial amplicon of a second species, nuclear amplicon of a first species, nuclear amplicon of a second species) specifically hybridized to the probe. In some embodiments, quantification comprises quantifying the probe in the hybridization product. In some embodiments, quantification comprises quantifying target nucleic acid specifically hybridized to the probe and quantifying the probe in the hybridization product. In some embodiments, quantification comprises quantifying the probe after dissociating from the hybridization product. Quantification of hybridization product, probe and/or nucleic acid target can comprise use of, for example, mass spectrometry, MASSARRAY and/or MASSEXTEND technology, as described herein.

In some embodiments, probes are designed such that they each hybridize to a nucleic acid of interest in a sample. For example, a probe may comprise a polynucleotide sequence that is complementary to a nucleic acid of interest or may comprise a series of monomers that can bind to a nucleic acid of interest. Probes may be any length suitable to hybridize (e.g., completely hybridize) to one or more nucleic acid fragments of interest. For example, probes may be of any length which spans or extends beyond the length of a nucleic acid fragment to which it hybridizes. Probes may be about 10 bp or more in length. For example, probes may be at least about 20, 30, 40, 50, 60, 70, 80, 100, 200, 300, 400, 500, 600, 700, 800, 900 or 1000 bp in length. In some embodiments, a detection and/or quantification method is used to detect and/or quantify probe-nucleic acid fragment duplexes.

Probes may be designed and synthesized according to methods known in the art and described herein for oligonucleotides (e.g., capture oligonucleotides). Probes also may include any of the properties known in the art and described herein for oligonucleotides. Probes herein may be designed such that they comprise nucleotides (e.g., adenine (A), thymine (T), cytosine (C), guanine (G) and uracil (U)), modified nucleotides (e.g., mass-modified nucleotides, pseudouridine, dihydrouridine, inosine (I), and 7-methylguanosine), synthetic nucleotides, degenerate bases (e.g., 6H,8H-3,4-dihydropyrimido[4,5-c][1,2]oxazin-7-one (P), 2-amino-6-methoxyaminopurine (K), N6-methoxyadenine (Z), and hypoxanthine (I)), universal bases and/or monomers other than nucleotides, modified nucleotides or synthetic nucleotides, mass tags or combinations thereof.

In some embodiments, probes are dissociated (i.e., separated) from their corresponding nucleic acid fragments. Probes may be separated from their corresponding nucleic acid fragments using any method known in the art, including, but not limited to, heat denaturation. Probes can be distinguished from corresponding nucleic acid fragments by a method known in the art or described herein for labeling and/or isolating a species of molecule in a mixture. For example, a probe and/or nucleic acid fragment may comprise a detectable property such that a probe is distinguishable from the nucleic acid to which it hybridizes. Non-limiting examples of detectable properties include mass properties, optical properties, electrical properties, magnetic properties, chemical properties, and time and/or speed through an opening of known size. In some embodiments, probes and sample nucleic acid fragments are physically separated from each other. Separation can be accomplished, for example, using capture ligands, such as biotin or other affinity ligands, and capture agents, such as avidin, streptavidin, an antibody, or a receptor. A probe or nucleic acid fragment can contain a capture ligand having specific binding activity for a capture agent. For example, fragments from a nucleic acid sample can be biotinylated or attached to an affinity ligand using methods well known in the art and separated away from the probes using a pull-down assay with steptavidin-coated beads, for example. In some embodiments, a capture ligand and capture agent or any other moiety (e.g., mass tag) can be used to add mass to the nucleic acid fragments such that they can be excluded from the mass range of the probes detected in a mass spectrometer. In some embodiments, mass is added to the probes, addition of a mass tag for example, to shift the mass range away from the mass range for the nucleic acid fragments. In some embodiments, a detection and/or quantification method is used to detect and/or quantify dissociated nucleic acid fragments. In some embodiments, detection and/or quantification method is used to detect and/or quantify dissociated probes.

Quantitative PCR

In certain embodiments quantitation of amplicons is by quantitative PCR (qPCR). In some embodiments, determining the amount of a nucleotide at V in the amplicons corresponding to the mitochondrial polynucleotide of a set and the amount of the nucleotide at V in the amplicons corresponding to the genomic polynucleotide of a set is by a process that comprises qPCR using the TAQman biochemistry with two fluorescent probes each specific for either the mitochondrial or genomic nucleotide at V.

In some embodiments, determining the amount of a nucleotide at V in the amplicons corresponding to the mitochondrial polynucleotide of the first species and the second species of a set is by a qPCR process comprising two fluorescent probes specific for the nucleotide at V of the mitochondrial polynucleotide of either the first or second species or a digital PCR process. In some embodiments, determining the amount of a nucleotide at V in the amplicons corresponding to the nuclear polynucleotide of the first species and the second species of a set is by a qPCR process comprising two fluorescent probes specific for the nucleotide at V of the nuclear polynucleotide of either the first or second species or a digital PCR process. In certain embodiments, the qPCR uses TAQman biochemistry.

Digital PCR

In some embodiments, amplicons are detected and/or quantified using digital PCR technology. Digital polymerase chain reaction (digital PCR or dPCR) can be used, for example, to directly identify and quantify nucleic acids in a sample. Digital PCR can be performed in an emulsion, in some embodiments. For example, individual nucleic acids are separated, e.g., in a microfluidic chamber device, and each nucleic acid is individually amplified by PCR. Nucleic acids can be separated such that there is no more than one nucleic acid per well. In some embodiments, different probes can be used to distinguish amplicons corresponding to the mitochondrial polynucleotide of a set and amplicons corresponding to the genomic polynucleotide of a set. In certain embodiments, different probes can be used to distinguish amplicons corresponding to the mitochondrial polynucleotide of the first species and the mitochondrial polynucleotide of the second species of a set or the nuclear polynucleotide of the first species and the nuclear polynucleotide of the second species of a set.

Nucleic acid Sequencing

In certain embodiments quantitation of amplicons is by sequencing amplicons of mitochondrial and genomic (nuclear) polynucleotides. In some embodiments, the sequencing process is massive parallel sequencing. In some embodiments, the amount of a nucleotide at V in the amplicons corresponding to the mitochondrial polynucleotide of a set and the amount of the nucleotide at V in the amplicons corresponding to the genomic polynucleotide of a set is determined by the amount of the nucleotide at V is by a massive parallel sequencing process. In some embodiments, the amount of a nucleotide at V in the amplicons corresponding to the mitochondrial polynucleotide of the first species and the second species of a set and/or the amount of a nucleotide at V in the amplicons corresponding to the nuclear polynucleotide of the first species and the second species of a set is determined by a massive parallel sequencing process. Sometimes the sequencing is by a sequencing by synthesis process. In some embodiments, a sequence tag or barcode is attached to one or more amplification primers in each amplification primer pair. The term "sequence tagging" refers to incorporating a recognizable and distinct sequence into a nucleic acid or population of nucleic acids.

In some embodiments, a full or substantially full sequence is obtained and sometimes a partial sequence is obtained. Sequencing, mapping and related analytical methods are known in the art (e.g., United States Patent Application Publication US2009/0029377, incorporated by reference). Certain aspects of such processes are described hereafter.

Certain sequencing technologies generate nucleotide sequence reads. As used herein, "reads" (i.e., "a read", "a sequence read") are short nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads).

In some embodiments the nominal, average, mean or absolute length of single-end reads sometimes is about 20 contiguous nucleotides to about 50 contiguous nucleotides, sometimes about 30 contiguous nucleotides to about 40 contiguous nucleotides, and sometimes about 35 contiguous nucleotides or about 36 contiguous nucleotides. In some embodiments, the nominal, average, mean or absolute length of single-end reads is about 20 to about 30 bases in length. In some embodiments, the nominal, average, mean or absolute length of single-end reads is about 24 to about 28 bases in length. In some embodiments, the nominal, average, mean or absolute length of single-end reads is about 21, 22, 23, 24, 25, 26, 27, 28 or about 29 bases in length.

In certain embodiments, the nominal, average, mean or absolute length of the paired-end reads sometimes is about 10 contiguous nucleotides to about 50 contiguous nucleotides (e.g., about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 nucleotides in length), sometimes is about 15 contiguous nucleotides to about 25 contiguous nucleotides, and sometimes is about 17 contiguous nucleotides, about 18 contiguous nucleotides, about 20 contiguous nucleotides, about 25 contiguous nucleotides, about 36 contiguous nucleotides or about 45 contiguous nucleotides.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from the blood of a pregnant female can be reads from a mixture of fetal and maternal nucleic acid. A mixture of relatively short reads can be transformed by processes described herein into a representation of a genomic nucleic acid present in the pregnant female and/or in the fetus. A mixture of relatively short reads can be transformed into a representation of a copy number variation (e.g., a maternal and/or fetal copy number variation), genetic variation or an aneuploidy, for example. Reads of a mixture of maternal and fetal nucleic acid can be transformed into a representation of a composite chromosome or a segment thereof comprising features of one or both maternal and fetal chromosomes. In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

Sequence reads can be mapped and the number of reads or sequence tags mapping to a specified nucleic acid region (e.g., a chromosome, a bin, a genomic section) are referred to as counts. In some embodiments, counts can be manipulated or transformed (e.g., normalized, combined, added, filtered, selected, averaged, derived as a mean, the like, or a combination thereof). In some embodiments, counts can be transformed to produce normalized counts.

Normalized counts for multiple genomic sections can be provided in a profile (e.g., a genomic profile, a chromosome profile, a profile of a segment of a chromosome). One or more different elevations in a profile also can be manipulated or transformed (e.g., counts associated with elevations can be normalized) and elevations can be adjusted.

In some embodiments, one nucleic acid sample from one individual is sequenced. In certain embodiments, nucleic acid samples from two or more biological samples, where each biological sample is from one individual or two or more individuals, are pooled and the pool is sequenced. In the latter embodiments, a nucleic acid sample from each biological sample often is identified by one or more unique identification tags.

In some embodiments, a fraction of the genome is sequenced, which sometimes is expressed in the amount of the genome covered by the determined nucleotide sequences (e.g., "fold" coverage less than 1). When a genome is sequenced with about 1-fold coverage, roughly 100% of the nucleotide sequence of the genome is represented by reads. A genome also can be sequenced with redundancy, where a given region of the genome can be covered by two or more reads or overlapping reads (e.g., "fold" coverage greater than 1). In some embodiments, a genome is sequenced with about 0.01-fold to about 100-fold coverage, about 0.2-fold to 20-fold coverage, or about 0.2-fold to about 1-fold coverage (e.g., about 0.02-, 0.03-, 0.04-, 0.05-, 0.06-, 0.07-, 0.08-, 0.09-, 0.1-, 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold coverage).

In certain embodiments, a subset of nucleic acid fragments is selected prior to sequencing. In certain embodiments, hybridization-based techniques (e.g., using oligonucleotide arrays) can be used to first select for nucleic acid sequences from certain regions of the mitochondrial and/or nuclear genome. In some embodiments, nucleic acid can be fractionated by size (e.g., by gel electrophoresis, size exclusion chromatography or by microfluidics-based approach). In some embodiments, a portion or subset of a pre-selected set of nucleic acid fragments is sequenced randomly. In some embodiments, the nucleic acid is amplified prior to sequencing. In some embodiments, a portion or subset of the nucleic acid is amplified prior to sequencing.

In some embodiments, a sequencing library is prepared prior to or during a sequencing process. Methods for preparing a sequencing library are known in the art and commercially available platforms may be used for certain applications. Certain commercially available library platforms may be compatible with certain nucleotide sequencing processes described herein. For example, one or more commercially available library platforms may be compatible with a sequencing by synthesis process. In some embodiments, a ligation-based library preparation method is used (e.g., ILLUMINA TRUSEQ, Illumina, San Diego California). Ligation-based library preparation methods typically use a methylated adaptor design which can incorporate an index sequence at the initial ligation step and often can be used to prepare samples for single-read sequencing, paired-end sequencing and multiplexed sequencing. In some embodiments, a transposon-based library preparation method is used (e.g., EPICENTRE NEXTERA, Illumina, Inc., California). Transposon-based methods typically use in vitro transposition to simultaneously fragment and tag DNA in a single-tube reaction (often allowing incorporation of platform-specific tags and optional barcodes), and prepare sequencer-ready libraries.

Any sequencing method suitable for conducting methods described herein can be utilized. In some embodiments, a high-throughput sequencing method is used. High-throughput sequencing methods generally involve clonally amplified DNA templates or single DNA molecules that are sequenced in a massively parallel fashion within a flow cell (e.g. as described in Metzker M Nature Rev 11:31-46 (2010); Volkerding et al. Clin Chem 55:641-658 (2009)). Such sequencing methods also can provide digital quantitative information, where each sequence read is a countable "sequence tag" or "count" representing an individual clonal DNA template, a single DNA molecule, bin or chromosome. Next generation sequencing techniques capable of sequencing DNA in a massively parallel fashion are collectively referred to herein as "massively parallel sequencing" (MPS). Certain MPS techniques include a sequencing-by-synthesis process. High-throughput sequencing technologies include, for example, sequencing-by-synthesis with reversible dye terminators, sequencing by oligonucleotide probe ligation, pyrosequencing and real time sequencing. Non-limiting examples of MPS include Massively Parallel Signature Sequencing (MPSS), Polony sequencing, Pyrosequencing, Illumina (Solexa) sequencing, SOLiD sequencing, Ion semiconductor sequencing, DNA nanoball sequencing, Helioscope single molecule sequencing, single molecule real time (SMRT) sequencing, nanopore sequencing, ION Torrent and RNA polymerase (RNAP) sequencing.

Systems utilized for high-throughput sequencing methods are commercially available and include, for example, the Roche 454 platform, the Applied Biosystems SOLID platform, the Helicos True Single Molecule DNA sequencing technology, the sequencing-by-hybridization platform from Affymetrix Inc., the single molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and nanopore sequencing also can be used in high-throughput sequencing approaches.

In some embodiments, first generation technology, such as, for example, Sanger sequencing including the automated Sanger sequencing, can be used in a method provided herein. Additional sequencing technologies that include the use of developing nucleic acid imaging technologies (e.g. transmission electron microscopy (TEM) and atomic force microscopy (AFM)), also are contemplated herein. Examples of various sequencing technologies are described below.

A nucleic acid sequencing technology that may be used in a method described herein is sequencing-by-synthesis and reversible terminator-based sequencing (e.g. Illumina's Genome Analyzer; Genome Analyzer II; HISEQ 2000; HISEQ 2500 (Illumina, San Diego CA)). With this technology, millions of nucleic acid (e.g. DNA) fragments can be sequenced in parallel. In one example of this type of sequencing technology, a flow cell is used which contains an optically transparent slide with 8 individual lanes on the surfaces of which are bound oligonucleotide anchors (e.g., adaptor primers). A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs.

In certain sequencing by synthesis procedures, for example, template DNA (e.g., circulating cell-free DNA (ccfDNA)) sometimes can be fragmented into lengths of several hundred base pairs in preparation for library generation. In some embodiments, library preparation can be performed without further fragmentation or size selection of the template DNA (e.g., ccfDNA). Sample isolation and library generation may be performed using automated methods and apparatus, in certain embodiments. Briefly, template DNA is end repaired by a fill-in reaction, exonuclease reaction or a combination of a fill-in reaction and exonuclease reaction. The resulting blunt-end repaired template DNA is extended by a single nucleotide, which is complementary to a single nucleotide overhang on the 3' end of an adapter primer, and often increases ligation efficiency. Any complementary nucleotides can be used for the extension/overhang nucleotides (e.g., A/T, C/G), however adenine frequently is used to extend the end-repaired DNA, and thymine often is used as the 3' end overhang nucleotide.

In certain sequencing by synthesis procedures, for example, adapter oligonucleotides are complementary to the flow-cell anchors, and sometimes are utilized to associate the modified template DNA (e.g., end-repaired and single nucleotide extended) with a solid support, such as the inside surface of a flow cell, for example. In some embodiments, the adapter also includes identifiers (i.e., indexing nucleotides, or "barcode" nucleotides (e.g., a unique sequence of nucleotides usable as an identifier to allow unambiguous identification of a sample and/or chromosome)), one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing). Identifiers or nucleotides contained in an adapter often are six or more nucleotides in length, and frequently are positioned in the adaptor such that the identifier nucleotides are the first nucleotides sequenced during the sequencing reaction. In certain embodiments, identifier nucleotides are associated with a sample but are sequenced in a separate sequencing reaction to avoid compromising the quality of sequence reads. Subsequently, the reads from the identifier sequencing and the DNA template sequencing are linked together and the reads de-multiplexed. After linking and de-multiplexing the sequence reads and/or identifiers can be further adjusted or processed as described herein.

In certain sequencing by synthesis procedures, utilization of identifiers allows multiplexing of sequence reactions in a flow cell lane, thereby allowing analysis of multiple samples per flow cell lane. The number of samples that can be analyzed in a given flow cell lane often is dependent on the number of unique identifiers utilized during library preparation and/or probe design. Non limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively). A method described herein can be performed using any number of unique identifiers (e.g., 4, 8, 12, 24, 48, 96, or more). The greater the number of unique identifiers, the greater the number of samples and/or chromosomes, for example, that can be multiplexed in a single flow cell lane. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell.

In certain sequencing by synthesis procedures, adapter-modified, single-stranded template DNA is added to the flow cell and immobilized by hybridization to the anchors under limiting-dilution conditions. In contrast to emulsion PCR, DNA templates are amplified in the flow cell by "bridge" amplification, which relies on captured DNA strands "arching" over and hybridizing to an adjacent anchor oligonucleotide. Multiple amplification cycles convert the single-molecule DNA template to a clonally amplified arching "cluster," with each cluster containing approximately 1000 clonal molecules. Approximately 1×10^9 separate clusters can be generated per flow cell. For sequencing, the clusters are denatured, and a subsequent chemical cleavage reaction and wash leave only forward strands for single-end sequencing. Sequencing of the forward strands is initiated by hybridizing a primer complementary to the adapter sequences, which is followed by addition of polymerase and a mixture of four differently colored fluorescent reversible dye terminators. The terminators are incorporated according to sequence complementarity in each strand in a clonal cluster. After incorporation, excess reagents are washed away, the clusters are optically interrogated, and the fluorescence is recorded. With successive chemical steps, the reversible dye terminators are unblocked, the fluorescent labels are cleaved and washed away, and the next sequencing cycle is performed. This iterative, sequencing-by-synthesis process sometimes requires approximately 2.5 days to generate read lengths of 36 bases. With 50×106 clusters per flow cell, the overall sequence output can be greater than 1 billion base pairs (Gb) per analytical run.

Another nucleic acid sequencing technology that may be used with a method described herein is 454 sequencing (Roche). 454 sequencing uses a large-scale parallel pyrosequencing system capable of sequencing about 400-600 megabases of DNA per run. The process typically involves two steps. In the first step, sample nucleic acid (e.g. DNA) is sometimes fractionated into smaller fragments (300-800 base pairs) and polished (made blunt at each end). Short adaptors are then ligated onto the ends of the fragments. These adaptors provide priming sequences for both amplification and sequencing of the sample-library fragments. One adaptor (Adaptor B) contains a 5'-biotin tag for immobilization of the DNA library onto streptavidin-coated beads. After nick repair, the non-biotinylated strand is released and used as a single-stranded template DNA (sstDNA) library. The sstDNA library is assessed for its quality and the optimal amount (DNA copies per bead) needed for emPCR is determined by titration. The sstDNA library is immobilized onto beads. The beads containing a library fragment carry a single sstDNA molecule. The bead-bound library is emulsified with the amplification reagents in a water-in-oil mixture. Each bead is captured within its own microreactor where PCR amplification occurs. This results in bead-immobilized, clonally amplified DNA fragments.

In the second step of 454 sequencing, single-stranded template DNA library beads are added to an incubation mix containing DNA polymerase and are layered with beads containing sulfurylase and luciferase onto a device containing pico-liter sized wells. Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing exploits the release of pyrophosphate (PPi) upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed (see, for example, Margulies, M. et al. Nature 437:376-380 (2005)).

Another nucleic acid sequencing technology that may be used in a method provided herein is Applied Biosystems' SOLiDTM technology. In SOLiDTM sequencing-by-ligation, a library of nucleic acid fragments is prepared from the sample and is used to prepare clonal bead populations. With this method, one species of nucleic acid fragment will be present on the surface of each bead (e.g. magnetic bead).

Sample nucleic acid (e.g. genomic DNA) is sheared into fragments, and adaptors are subsequently attached to the 5' and 3' ends of the fragments to generate a fragment library. The adapters are typically universal adapter sequences so that the starting sequence of every fragment is both known and identical. Emulsion PCR takes place in microreactors containing all the necessary reagents for PCR. The resulting PCR products attached to the beads are then covalently bound to a glass slide. Primers then hybridize to the adapter sequence within the library template. A set of four fluorescently labeled di-base probes compete for ligation to the sequencing primer. Specificity of the di-base probe is achieved by interrogating every 1st and 2nd base in each ligation reaction. Multiple cycles of ligation, detection and cleavage are performed with the number of cycles determining the eventual read length. Following a series of ligation cycles, the extension product is removed and the template is reset with a primer complementary to the n−1 position for a second round of ligation cycles. Often, five rounds of primer reset are completed for each sequence tag. Through the primer reset process, each base is interrogated in two independent ligation reactions by two different primers. For example, the base at read position 5 is assayed by primer number 2 in ligation cycle 2 and by primer number 3 in ligation cycle 1.

Another nucleic acid sequencing technology that may be used in a method described herein is Helicos True Single Molecule Sequencing (tSMS). In the tSMS technique, a polyA sequence is added to the 3' end of each nucleic acid (e.g. DNA) strand from the sample. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm2. The flow cell is then loaded into a sequencing apparatus and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step (see, for example, Harris T. D. et al., Science 320:106-109 (2008)).

Another nucleic acid sequencing technology that may be used in a method provided herein is the single molecule, real-time (SMRT™) sequencing technology of Pacific Biosciences. With this method, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is then repeated.

Another nucleic acid sequencing technology that may be used in a method described herein is ION TORRENT (Life Technologies) single molecule sequencing which pairs semiconductor technology with a simple sequencing chemistry to directly translate chemically encoded information (A, C, G, T) into digital information (0, 1) on a semiconductor chip. ION TORRENT uses a high-density array of micro-machined wells to perform nucleic acid sequencing in a massively parallel way. Each well holds a different DNA molecule. Beneath the wells is an ion-sensitive layer and beneath that an ion sensor. Typically, when a nucleotide is incorporated into a strand of DNA by a polymerase, a hydrogen ion is released as a byproduct. If a nucleotide, for example a C, is added to a DNA template and is then incorporated into a strand of DNA, a hydrogen ion will be released. The charge from that ion will change the pH of the solution, which can be detected by an ion sensor. A sequencer can call the base, going directly from chemical information to digital information. The sequencer then sequentially floods the chip with one nucleotide after another. If the next nucleotide that floods the chip is not a match, no voltage change will be recorded and no base will be called. If there are two identical bases on the DNA strand, the voltage will be double, and the chip will record two identical bases called. Because this is direct detection (i.e. detection without scanning, cameras or light), each nucleotide incorporation is recorded in seconds.

Another nucleic acid sequencing technology that may be used in a method described herein is the chemical-sensitive field effect transistor (CHEMFET) array. In one example of this sequencing technique, DNA molecules are placed into reaction chambers, and the template molecules can be hybridized to a sequencing primer bound to a polymerase. Incorporation of one or more triphosphates into a new nucleic acid strand at the 3' end of the sequencing primer can be detected by a change in current by a CHEMFET sensor. An array can have multiple CHEMFET sensors. In another example, single nucleic acids are attached to beads, and the nucleic acids can be amplified on the bead, and the individual beads can be transferred to individual reaction chambers on a CHEMFET array, with each chamber having a CHEMFET sensor, and the nucleic acids can be sequenced (see, for example, U.S. Patent Application Publication No. 2009/0026082).

Another nucleic acid sequencing technology that may be used in a method described herein is electron microscopy. In one example of this sequencing technique, individual nucleic acid (e.g. DNA) molecules are labeled using metallic labels that are distinguishable using an electron microscope. These molecules are then stretched on a flat surface and imaged using an electron microscope to measure sequences (see, for example, Moudrianakis E. N. and Beer M. Proc Natl Acad Sci USA. 1965 March; 53:564-71). In some embodiments, transmission electron microscopy (TEM) is used (e.g. Halcyon Molecular's TEM method). This method, termed Individual Molecule Placement Rapid Nano Transfer (IMPRNT), includes utilizing single atom resolution transmission electron microscope imaging of high-molecular weight (e.g. about 150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA (see, for example, International Patent Application No. WO 2009/046445).

Other sequencing methods that may be used to conduct methods herein include digital PCR and sequencing by hybridization. In sequencing by hybridization, the method involves contacting a plurality of polynucleotide sequences with a plurality of polynucleotide probes, where each of the plurality of polynucleotide probes can be optionally tethered to a substrate. The substrate can be a flat surface with an array of known nucleotide sequences, in some embodiments. The pattern of hybridization to the array can be used to determine the polynucleotide sequences present in the sample. In some embodiments, each probe is tethered to a bead, e.g., a magnetic bead or the like. Hybridization to the beads can be identified and used to identify the plurality of polynucleotide sequences within the sample.

In some embodiments, chromosome-specific sequencing is performed. In some embodiments, chromosome-specific sequencing is performed utilizing DANSR (digital analysis of selected regions). Digital analysis of selected regions enables simultaneous quantification of hundreds of loci by cfDNA-dependent catenation of two locus-specific oligonucleotides via an intervening 'bridge' oligo to form a PCR template. In some embodiments, chromosome-specific sequencing is performed by generating a library enriched in chromosome-specific sequences. In some embodiments, sequence reads are obtained only for a selected set of chromosomes. In some embodiments, sequence reads are obtained only for chromosomes 21, 18 and 13.

The length of the sequence read often is associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, the sequence reads are of a mean, median, mode or average length of about 4 bp to 900 bp long (e.g. about 5 bp, about 10 bp, about 15 bp, about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median, mode or average length of about 1,000 bp or more.

Distinguishable Labels and Release

As used herein, the terms "distinguishable labels" and "distinguishable tags" refer to types of labels or tags that can be distinguished from one another and used to identify the nucleic acid (e.g., amplicon or primer extension product) to which the tag is attached. A variety of types of labels and tags may be selected and used for multiplex methods provided herein. For example, oligonucleotides, amino acids, small organic molecules, light-emitting molecules, light-absorbing molecules, light-scattering molecules, luminescent molecules, isotopes, enzymes and the like may be used as distinguishable labels or tags. In certain embodiments, oligonucleotides, amino acids, and/or small molecule organic molecules of varying lengths, varying mass-to-charge ratios, varying electrophoretic mobility (e.g., capillary electrophoresis mobility) and/or varying mass also can be used as distinguishable labels or tags. Accordingly, a fluorophore, radioisotope, colormetric agent, light emitting agent, chemiluminescent agent, light scattering agent, and the like, may be used as a label. The choice of label may depend on the sensitivity required, ease of conjugation with a nucleic acid, stability requirements, and available instrumentation. The term "distinguishable feature," as used herein with respect to distinguishable labels and tags, refers to any feature of one label or tag that can be distinguished from another label or tag (e.g., mass and others described herein). In some embodiments, label composition of the distinguishable labels and tags can be selected and/or designed to result in optimal flight behavior in a mass spectrometer and to allow labels and tags to be distinguished at high multiplexing levels.

For methods used herein, a particular target (mitochondrial or genomic, nuclear)) nucleic acid species, amplicon species and/or extended oligonucleotide species often is paired with a distinguishable detectable label species, such that the detection of a particular label or tag species directly identifies the presence of and/or quantifies a particular target minor or nucleic acid species, amplicon species and/or extended oligonucleotide species in a particular composition. Accordingly, one distinguishable feature of a label species can be used, for example, to identify one target nucleic acid species in a composition, as that particular distinguishable feature corresponds to the particular target nucleic acid. Labels and tags may be attached to a nucleic acid (e.g., oligonucleotide) by any known methods and in any location (e.g., at the 5' of an oligonucleotide). Thus, reference to each particular label species as "specifically corresponding" to each particular target nucleic acid species, as used herein, refers to one label species being paired with one target species. When the presence of a label species is detected, then the presence of the target nucleic acid species associated with that label species thereby is detected and/or quantified, in certain embodiments.

The term "mass distinguishable label" as used herein refers to a label that is distinguished by mass as a feature. A variety of mass distinguishable labels can be selected and used, such as for example a compomer, amino acid and/or a concatemer. Different lengths and/or compositions of nucleotide strings (e.g., nucleic acids, compomers), amino acid strings (e.g., peptides, polypeptides, compomers) and/or concatemers can be distinguished by mass and be used as labels. Any number of units can be utilized in a mass distinguishable label, and upper and lower limits of such units depends in part on the mass window and resolution of the system used to detect and distinguish such labels. Thus, the length and composition of mass distinguishable labels can be selected based in part on the mass window and resolution of the detector used to detect and distinguish the labels.

The term "compomer" as used herein refers to the composition of a set of monomeric units and not the particular sequence of the monomeric units. For a nucleic acid, the term "compomer" refers to the base composition of the nucleic acid with the monomeric units being bases. The number of each type of base can be denoted by $B_n$ (i.e., $A_aC_cG_gT_t$, with $A_0C_0G_0T_0$ representing an "empty" compomer or a compomer containing no bases). A natural compomer is a compomer for which all component monomeric units (e.g., bases for nucleic acids and amino acids for polypeptides) are greater than or equal to zero. In certain embodiments, at least one of A, C, G or T equals 1 or more (e.g., $A_0C_0G_1T_0$, $A_1C_0G_1T_0$, $A_2C_1G_1T_2$, $A_3C_2G_1T_5$). For purposes of comparing sequences to determine sequence variations, in the methods provided herein, "unnatural" compomers containing negative numbers of monomeric units can be generated by an algorithm utilized to process data. For polypeptides, a compomer refers to the amino acid composition of a polypeptide fragment, with the number of each type of amino acid similarly denoted. A compomer species can correspond to multiple sequences. For example, the compomer $A_2G_3$ corresponds to the sequences AGGAG, GGGAA, AAGGG, GGAGA and others. In general, there is a unique compomer corresponding to a sequence, but more than one sequence can correspond to the same compomer. In certain embodiments, one compomer species is paired with (e.g., corresponds to) one target nucleic acid species, amplicon species and/or oligonucleotide species. Different compomer species have different base compositions, and distinguishable masses, in embodiments herein (e.g., $A_0C_0G_5T_0$ and $A_0C_5G_0T_0$ are different and mass-distinguishable compomer species). In some embodiments, a set of compomer species differ by base composition and have the same length. In certain embodiments, a set of compomer species differ by base compositions and length.

A nucleotide compomer used as a mass distinguishable label can be of any length for which all compomer species can be detectably distinguished, for example about 1 to 15, 5 to 20, 1 to 30, 5 to 35, 10 to 30, 15 to 30, 20 to 35, 25 to 35, 30 to 40, 35 to 45, 40 to 50, or 25 to 50, or sometimes about 55, 60, 65, 70, 75, 80, 85, 90, 85 or 100, nucleotides in length. A peptide or polypeptide compomer used as a mass distinguishable label can be of any length for which all compomer species can be detectably distinguished, for example about 1 to 20, 10 to 30, 20 to 40, 30 to 50, 40 to 60, 50 to 70, 60 to 80, 70 to 90, or 80 to 100 amino acids in length. As noted above, the limit to the number of units in a compomer often is limited by the mass window and resolution of the detection method used to distinguish the compomer species.

The terms "concatamer" and "concatemer" are used herein synonymously (collectively "concatemer"), and refer to a molecule that contains two or more units linked to one another (e.g., often linked in series; sometimes branched in certain embodiments). A concatemer sometimes is a nucleic acid and/or an artificial polymer in some embodiments. A concatemer can include the same type of units (e.g., a homoconcatemer) in some embodiments, and sometimes a concatemer can contain different types of units (e.g., a heteroconcatemer). A concatemer can contain any type of unit(s), including nucleotide units, amino acid units, small organic molecule units (e.g., trityl), particular nucleotide sequence units, particular amino acid sequence units, and the like. A homoconcatemer of three particular sequence units ABC is ABCABCABC, in an embodiment. A concatemer can contain any number of units so long as each concatemer species can be detectably distinguished from other species. For example, a trityl concatemer species can contain about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 trityl units, in some embodiments.

A distinguishable label can be released from a nucleic acid product (e.g., an extended oligonucleotide) in certain embodiments. The linkage between the distinguishable label and a nucleic acid can be of any type that can be transcribed and cleaved, cleaved and allow for detection of the released label or labels, thereby identifying and/or quantifying the nucleic acid product (e.g., U.S. patent application publication no. US20050287533A1, entitled "Target-Specific Compomers and Methods of Use," naming Ehrich et al.). Such linkages and methods for cleaving the linkages ("cleaving conditions") are known. In certain embodiments, a label can be separated from other portions of a molecule to which it is attached. In some embodiments, a label (e.g., a compomer) is cleaved from a larger string of nucleotides (e.g., extended oligonucleotides). Non-limiting examples of linkages include linkages that can be cleaved by a nuclease (e.g., ribonuclease, endonuclease); linkages that can be cleaved by a chemical; linkages that can be cleaved by physical treatment; and photocleavable linkers that can be cleaved by light (e.g., o-nitrobenzyl, 6-nitroveratryloxycarbonyl, 2-nitrobenzyl group). Photocleavable linkers provide an advantage when using a detection system that emits light (e.g., matrix-assisted laser desorption ionization (MALDI) mass spectrometry involves the laser emission of light), as cleavage and detection are combined and occur in a single step.

In certain embodiments, a label can be part of a larger unit, and can be separated from that unit prior to detection. For example, in certain embodiments, a label is a set of contiguous nucleotides in a larger nucleotide sequence, and the label is cleaved from the larger nucleotide sequence. In such embodiments, the label often is located at one terminus of the nucleotide sequence or the nucleic acid in which it resides. In some embodiments, the label, or a precursor thereof, resides in a transcription cassette that includes a promoter sequence operatively linked with the precursor sequence that encodes the label. In the latter embodiments, the promoter sometimes is a RNA polymerase-recruiting promoter that generates an RNA that includes or consists of the label. An RNA that includes a label can be cleaved to release the label prior to detection (e.g., with an RNase).

In certain embodiments, a distinguishable label or tag is not cleaved from an extended oligonucleotide, and in some embodiments, the distinguishable label or tag comprises a capture agent. In certain embodiments, detecting a distinguishable feature includes detecting the presence or absence of an extended oligonucleotide, and in some embodiments an extended oligonucleotide includes a capture agent.

Detection and Degree of Multiplexing

The term "detection" of a label as used herein refers to identification of a label species. Any suitable detection device can be used to distinguish label species in a sample. Detection devices suitable for detecting mass distinguishable labels, include, without limitation, certain mass spectrometers and gel electrophoresis devices. Examples of mass spectrometry formats include, without limitation, Matrix-Assisted Laser Desorption/Ionization Time-of-Flight (MALDI-TOF) Mass Spectrometry (MS), MALDI orthogonal TOF MS (OTOF MS; two dimensional), Laser Desorption Mass Spectrometry (LDMS), Electrospray (ES) MS, Ion Cyclotron Resonance (ICR) MS, and Fourier Transform MS. Methods described herein are readily applicable to mass spectrometry formats in which analyte is volatized and ionized ("ionization MS," e.g., MALDI-TOF MS, LDMS, ESMS, linear TOF, OTOF). Orthogonal ion extraction MALDI-TOF and axial MALDI-TOF can give rise to relatively high resolution, and thereby, relatively high levels of multiplexing. Detection devices suitable for detecting light-emitting, light absorbing and/or light-scattering labels, include, without limitation, certain light detectors and photodetectors (e.g., for fluorescence, chemiluminescence, absorbtion, and/or light scattering labels).

Multiplex Assay Design

The methods provided herein can be adapted to a multiplexed format to amplify and quantitate polynucleotides of a plurality of sets. Multiplexing can be performed in a single reaction vessel, compartment or container. In some embodiments, paralogs are chosen and assays are designed so that the nucleotide at V for the mitochondrial polynucleotides and genomic polynucleotides for a number of sets can be distinguished and quantified in a single reaction. The following are examples of multiplex reaction schemes and are not meant to be limiting. For example, paralogs with a combination of either C (mitochondrial) and T (genomic) or G (mitochondrial) and A (genomic) are selected. Single base extension reactions to probe C/A would be carried out in the forward direction and reactions to probe G/A in the reverse direction, i.e. at C/T. Thus enabling a plurality of sets to be examined in a single reaction vessel. This approach could be applied to sets of paralogs having C as the nucleotide at V for mitochondrial polynucleotides and A/G/T as the nucleotide at V for genomic polynucleotides. Another possible combination of sets of paralogs that could be plexed in a single reaction vessel has V as C/T, C/A, G/A, G/T, where C and G are mitochondrial and A and T are genomic. An alternative multiplex assay has paralog sets that share a common V nucleotide for the mitochondrial polynucleotides and have any of the other three nucleotides as the V nucleotide for genomic polynucleotides. Additional liberty in design can is obtained for any of the assays by allowing reverse design, i.e., probing a sequence on the opposite stand.

In some embodiments, mitochondrial paralogs are chosen and assays are designed for co-amplification of different sets of mitochondrial paralogs and so that the nucleotide at V for the mitochondrial polynucleotides of a number of sets can be distinguished and quantified in a single reaction. In some embodiments, nuclear paralogs are chosen and assays are designed for co-amplification of different sets of nuclear paralogs and so that the nucleotide at V for the nuclear polynucleotides for a number of sets can be distinguished and quantified in a single reaction. In certain embodiments, assays targeting nuclear paralogs and assays targeting mitochondrial paralogs can be performed in the same reaction. In certain embodiments, assays targeting nuclear paralogs are performed in a separate reaction from assays targeting mitochondrial paralogs (both amplification and single base extension). In some embodiments, amplification of nuclear paralogs and amplification of mitochondrial paralogs are carried out in separate reactions and then combined to carry out single base extension reactions.

Design methods for achieving resolved mass spectra with multiplexed assays can include primer and oligonucleotide design methods, relative concentrations of reagents such as chain terminating reagents, choice of detection labels and other reaction design methods. For primer and oligonucleotide design in multiplexed assays, the same general guidelines for primer design applies for uniplexed reactions, such as avoiding false priming and primer dimers, only more primers are involved for multiplex reactions. In addition, for analysis by mass spectrometry, analyte peaks in the mass spectra for one assay are sufficiently resolved from a product of any assay with which that assay is multiplexed, including pausing peaks and any other by-product peaks. Also, analyte peaks optimally fall within a user-specified mass window, for example, within a range of 5,000-8,500 Da. Extension oligonucleotides can be designed with respect to target sequences of a given V (e.g., SNP) strand, in some embodiments. In such embodiments, the length often is between limits that can be, for example, user-specified (e.g., 17 to 24 bases or 17-26 bases) and often do not contain bases that are uncertain in the target sequence. Hybridization strength sometimes is gauged by calculating the sequence-dependent melting (or hybridization/dissociation) temperature, $T_m$. A particular primer choice may be disallowed, or penalized relative to other choices of primers, because of its hairpin potential, false priming potential, primer-dimer potential, low complexity regions, and problematic subsequences such as GGGG. Methods and software for designing extension oligonucleotides (e.g., according to these criteria) are known, and include, for example, SpectroDESIGNER™ (Sequenom).

Mitochondrial Dosage

Mitochondrial/Genomic (Nuclear) Paralogs

In certain embodiments, the ratios for a plurality of sets are combined and the relative dosage of mitochondrial nucleic acid to genomic nucleic acid for the sample is determined based on the combined ratio. In some embodiments, the combined ratio is an average ratio or a median ratio. The term "average" as used herein is meant a value that is calculated by adding the value of the ratios for each of a number of sets and then dividing by the total number of sets.

The term "median" as used herein is meant a value for a ratio that is at the midpoint of the frequency distribution of observed values of the ratios for the sets examined, such that there is an equal probability of falling above or below it.

In some embodiments, the ratio of each set is compared to an average or median ratio based on the plurality of sets and an outlier or cluster that deviates from the average or median ratio is an indication of a mitochondrial deletion. In other embodiments, the ratio of a set representing one region of the mitochondrial genome is compared to the ratio of each of the other sets representing different regions of the mitochondrial genome and the presence of one or more deletions in the mitochondrial genome is determined based on a difference in the ratio for the one region compared with the ratios for one or more other regions of the mitochondrial genome.

Mitochondrial/Mitochondrial Paralogs-Nuclear/Nuclear Paralogs

In some embodiments, the ratios for a plurality of sets of mitochondrial polynucleotides are combined and the ratios for a plurality of sets of nuclear polynucleotides are combined and the mitochondrial/nuclear ratio for the sample is determined based on using the combined ratios. In some embodiments, the combined ratio is an average ratio or a median ratio. Variability can be minimized by using the results of multiple independent assays targeting nuclear paralogs and multiple independent assays targeting mitochondrial paralogs to derive Ratio X and Ratio Y.

In some embodiments, the ratio of a set of a mitochondrial paralog representing one region of the mitochondrial genome is compared to an average or median ratio based on the plurality of sets of mitochondrial paralogs and an outlier or cluster that deviates from the average or median ratio is an indication of a mitochondrial deletion.

In certain embodiments, the ratio of a set of a mitochondrial paralog representing one region of the mitochondrial genome is compared to the ratio of each of the other sets of a mitochondrial paralog representing different regions of the mitochondrial genome and the presence of one or more deletions in the mitochondrial genome is determined based on a difference in the ratio of the set representing the one region compared with the ratios for one or more sets representing other regions of the mitochondrial genome.

Baseline Mitochondrial Dosage

The number of mitochondria in a sample can exhibit differences based on the tissue of origin, the genetics of a subject, as well as fitness of the subject. In some embodiments, a baseline mitochondrial dosage is determined for an individual subject and/or population and the dosage determined for the sample is compared to or adjusted relative to the baseline dosage. For example, a baseline mitochondrial dosage for a subject can be based on a sample from the subject obtained at multiple points in time. A baseline mitochondrial dosage for a population can be determined for a sample from individuals that do not have or are not pre-disposed to having a disease, disorder or symptoms associated with an increase or decrease in the dosage of mitochondria nucleic acid or a deletion in the mitochondrial genome. The baseline mitochondrial dosage for a population can be used as the baseline for a subject when the subject and the population share one or more of the following exemplary characteristics: tissue of origin for which the mitochondria are examined, sex, ethnicity, age and activity level. Other relevant characteristics can be utilized depending on the subject and the population. If there are differences, such as tissue of origin, adjusts are made to normalize the samples.

Diseases and Disorders

An increase or decrease in mitochondrial dosage has be associated with a number of diseases, disorder, conditions and symptoms, including, but not limited to the following examples.

Neurodegenerative Disease

Non-limiting examples include: Parkinson's, Alzheimers, Friedreich's Ataxia, Amyotropic lateral sclerosis and Multiple sclerosis (MS).

Diseases Associated with nDNA Mutations that Cause mtDNA Stability

POLG associated diseases are most common (POLG is a gene that codes for the catalytic subunit of the mitochondrial DNA polymerase, called DNA polymerase gamma).

Non-limiting examples include: Opthalmoplegia, Alper's syndrome and Leigh's syndrome.

Diseases Associated with mtDNA Deletions/Mutations

Non-limiting examples include: Kearns-Sayre syndrome (KSS), Leber's heredity optic neuropathy (LHON), Mitochondiral encophalomyopathy, lactic acidosis, stroke like episodes (MELAS) and Myoclonic Epilepsy with Ragged Red Fibers (MERRF).

Cancer

Non-limiting examples include: gastric cancer, hepatocellular carcinoma (HCC), HPV associated cancer, breast cancer and Ewing's Sarcoma, pancreatic cancer, liver cancer, testicular cancer, prostate cancer, renal cell carcinoma (RCC), bladder cancer, and ovarian cancer.

Metabolic Disease

Non-limiting examples include: obesity, diabetes, prediabetes and diabetic retinopathy.

Cardiovascular Disease

Non-limiting examples include: diabetic cardiomyopathies and coronary heart disease.

Sepsis

Non-Limiting Examples Include: Sepsis Caused by Bacterial, Viral or Fungal Infection.

In some embodiments, the dosage of mitochondrial nucleic acid relative to genomic nucleic acid for the sample from the subject is used in determining the likelihood the subject has or is pre-disposed to having a disease, disorder or symptoms associated with an increase or decrease in the dosage of mitochondria nucleic acid or a deletion in the mitochondrial genome. In some embodiments, the disease or disorder is a neurodegenerative disease, a cancer, a disease or disorder associated with mitochondrial stability, a disease or disorder associated with a mitochondrial deletion, a metabolic disease or disorder, a cardiovascular disease or disorder, a disease or disorder associated with oxidative stress, a disease or disorder associated with infertility or a disease or disorder associated with sepsis.

In some embodiments, the disease, disorder or condition is Parkinson's disease, Alzheimers disease, Friedreich's Ataxia, Amyotropic lateral sclerosis, Multiple sclerosis (MS), POLG associated diseases, Opthalmoplegia, Alper's syndrome, Leigh's syndrome, Kearns-Sayre syndrome (KSS), Leber's heredity optic neuropathy (LHON), Mitochondiral encophalomyopathy, lactic acidosis, stroke like episodes (MELAS), Myoclonic Epilepsy with Ragged Red Fibers (MERRF), gastric cancer, hepatocellular carcinoma (HCC), HPV associated cancer, breast cancer, Ewing's Sarcoma, pancreatic cancer, liver cancer, testicular cancer, prostate cancer, renal cell carcinoma (RCC), bladder cancer, ovarian cancer, obesity, diabetes, pre-diabetes, diabetic retinopathy, diabetic cardiomyopathies coronary heart disease and sepsis.

In some embodiments, the dosage of mitochondrial nucleic acid relative to genomic nucleic acid for the sample from the subject can be used to monitor the efficacy of treatment of the subject for a disease, disorder or symptoms associated with an increase or decrease in the dosage of mitochondria nucleic acid or a deletion in the mitochondrial genome.

Kits

In some embodiments, provided are kits for carrying out methods described herein. Kits often comprise one or more containers that contain one or more components described herein. A kit comprises one or more components in any number of separate containers, packets, tubes, vials, multi-well plates and the like, or components may be combined in various combinations in such containers. One or more of the following components, for example, may be included in a kit: (i) one or more nucleotides (e.g., terminating nucleotides and/or non-terminating nucleotides); one or more of which can include a detection label; (ii) one or more oligonucleotides, one or more of which can include a detection label (e.g., amplification primers, one or more extension primers (UEPs)); (iii) one or more enzymes (e.g., a polymerase, endonuclease, restriction enzyme, etc.); (iv) one or more buffers and (vii) printed matter (e.g. directions, labels, etc). In some embodiments, a kit comprises amplification primer pairs that comprise polynucleotides chosen from polynucleotides in Table 2 and Table 4, or portions thereof. In some embodiments, a kit also comprises extension primers comprising polynucleotides chosen from polynucleotides in Table 2 and Table 4 or portions thereof.

In some embodiments, a kit comprises amplification primer pairs that comprise polynucleotides chosen from polynucleotides in Table 7, or portions thereof. In some embodiments, a kit also comprises extension primers comprising polynucleotides chosen from polynucleotides in Table 7 or portions thereof.

A kit sometimes is utilized in conjunction with a process, and can include instructions for performing one or more processes and/or a description of one or more compositions. A kit may be utilized to carry out a process described herein. Instructions and/or descriptions may be in tangible form (e.g., paper and the like) or electronic form (e.g., computer readable file on a tangle medium (e.g., compact disc) and the like) and may be included in a kit insert. A kit also may include a written description of an internet location that provides such instructions or descriptions.

EXAMPLES

The examples set forth below illustrate, and do not limit, the technology.

Example 1—Identification of Mitochondrial/Genomic (Nuclear) Paralogs

Mitochondrial/genomic (nuclear) paralogs were identified using a R-based algorithm. Utilizing the Biostrings library from the Bioconductor open source software for bioinformatics matched the sequences to the UCSC hg19 build. Bioconductor contains memory efficient string containers, string matching algorithms, and other utilities, for fast manipulation of large biological sequences or sets of sequences. When paralog regions were identified these were verified using the BLAST algorithm from NCBI.

An exemplary protocol is as follows:

1) The mitochondrial genome was split into shorter fragments (in the case here 100 bp) and given a name, here Seq-1 is the mitochondrial genome nt 1-100 and Seq-2 is nucleotides 101-200.
2) Each sequence was aligned against the human genome and a certain number of mismatches are allowed in this case 20 mismatches per sequence. Results are displayed in Table 1. Shown are sequence number, chromosome number, start of alignment, end of alignment, regions that are suitable for use as amplicons (potential amplification primer binding regions) and sequence. Dashes indicate matches in the nuclear sequence (genomic) and letter mismatches in the nuclear sequence (genomic).
3) Sequences that do not have a paralog (using the settings in 2) in the nuclear genome will only retrieve the mitochondrial match (Chr=M). Examples here are sequences Seq-3 to Seq-6a.
4) Sequences with multiplex alignments can be identified from sequences with only one or two nuclear alignments.
5) All sequence mismatches can be used for paralog detection (V) as long as the upstream/downstream regions X and Y and regions 5' to X and regions 3' to Y fit the strategy for amplification as described below.
6) For Co-amplification of mitochondrial and genomic polynucleotides with a single amplification primer pair—select a region V (denoted by "$" above the sequence) surrounded by regions X and Y (denoted by "*" above the sequence), where X and Y are identical in both the nuclear and mitochondrial genome. Examples are Seq-1 and Seq-41. Another example is sequence Seq-51 where perfect alignment is identified to chromosome 17 with a single mismatch but the alignments to chromosome 2 and 17 are different enough to enable amplification of chromosome 1 and M only. Amplification primers are designed to bind to a region within X and Y, for amplification of both mitochondrial and genomic polynucleotides. Amplicon produced with these amplification primers will include V. The nucleotide at V is analyzed to distinguish an amplicon of a mitochondrial polynucleotide from an amplicon of a genomic polynucleotide.
7) Amplification of mitochondrial polynucleotides with a mitochondrial specific amplification primer pair and amplification of genomic polynucleotides with a genomic specific amplification primer pair—select a region V (denoted by "$" above the sequence) surrounded by regions X and Y, where regions 5' to X and 3' to Y (denoted by "+" above the sequence) are not identical in both the genomic and mitochondrial genome. Example is sequence Seq-1. Mitochondrial specific amplification primers are designed to bind to a region outside of X and Y, region 5' to X and region 3' to Y. Genomic specific amplification primers are designed to bind to a region outside of X and Y, region 5' to X and region 3' to Y. Amplicon produced with these amplification primers will include V. The nucleotide at V is analyzed to distinguish an amplicon of a mitochondrial polynucleotide from an amplicon of a genomic polynucleotide.
8) Amplification with one amplification primer binding to both mitochondrial and genomic paralogs in region X and the other amplification primer being a pair of primers that binds to a region 3' to Y where one primer is mitochondrial specific and the other is genome specific—select a region V (denoted by "$" above the sequence) surrounded by regions X and Y (denoted by "*" above the sequence), where regions 5' to X and 3' to Y (denoted by "+" above the sequence) are not identical in both the genomic and mitochondrial genome. Regions will be selected that are hybrids from 6) and 7). Example is Seq-1 and Seq-95. One amplification primer is designed to bind to a region within X, for use in the amplification of a mitochondrial polynucleotide or a genomic polynucleotide. Two corresponding amplification primers, one specific for a mitochondrial polynucleotide and one specific for a genomic polynucleotide are designed to bind to a region '3 of Y that has one or more mismatches between mitochondrial and genomic polynucleotides of a set. Amplicon produced with these amplification primers will include V. The nucleotide at V is analyzed to distinguish an amplicon of a mitochondrial polynucleotide from an amplicon of a genomic polynucleotide.

TABLE 1

Mitochondria and Genomic (Nuclear) Paralogs

| Seq. No. | Chr | Start | End | Length | SEQ ID NO: | Sequence |
|---|---|---|---|---|---|---|
| | | | | | | +++++++++++++++++++++++ *********************** $$ ********************** ++++++++++ |
| Seq-1 | M | 1 | 100 | 100 | 1 | GATCACAGGTCTATCACCCTATTAACCACTCACGGGAGCTCTCCATGCATTTGGTATTTTCGTCTGGGGGGTGTGCACGCGATAGCATTGCGAGACGCTG |
| Seq-1 | 17 | 22020727 | 22020826 | 100 | 2 | -------G------T----------T--G-------------------------------AA----------------------------T--A------ |
| | | | | | | ++++++ |
| Seq-2 | M | 101 | 200 | 100 | 3 | GAGCCGGAGCACCCTATGTCGCAGTATCTGTCTTTGATTCCTGCCTCATTCTATTATTTATCGCACCTACGTTCAATATTACAGGCGAACATACCTACTA |
| Seq-2 | 17 | 22020827 | 22020926 | 100 | 4 | -CC--A-------------------G-------------------C---C-C------G---A-------A--------CC-------G--------TC- |
| Seq-3 | M | 201 | 300 | 100 | 5 | AAGTGTGTTAATTAATTAATGCTTGTAGGACATAATAATAACAATTGAATGTCTGCACAGCCGCTTTCCACACAGACATCATAACAAAAAATTTCCACCA |
| Seq-4 | M | 301 | 400 | 100 | 6 | AACCCCCCCTCCCCCGCTTCTGGCCACAGCACTTAAACACATCTCTGCCAAACCCCAAAAACAAAGAACCCTAACACCAGCCTAACCAGATTTCAAAT |
| Seq-5 | M | 401 | 500 | 100 | 7 | TTTATCTTTAGGCGGTATGCACTTTTAACAGTCACCCCCCAACTAACACATTATTTTCCCCTCCCACTCCCATACTACTAATCTCATCAATACAACCCCC |
| Seq-6 | M | 501 | 600 | 100 | 8 | GCCCATCCTACCCAGCACACACACACCGCTGCTAACCCCATACCCCGAACCAACCAAACCCCAAAGACACCCCCCACAGTTTATGTAGCTTACCTCCTCA |
| Seq-7 | M | 601 | 700 | 100 | 9 | AAGCAATACACTGAAAATGTTTAGACGGGCTCACATCACCCCATAAACAAATAGGTTTGGTCCTAGCCTTTCTATTAGCTCTTAGTAAGATTACACATGC |
| Seq-7 | 2 | 83048020 | 83048119 | 100 | 10 | ------G-------------C----T---TC----CA------------G-----C--------G------T-----C------T--------------G |
| Seq-7 | 2 | 117778792 | 117778891 | 100 | 11 | ------G-------------C---TT---TC----C-----G--G----G--------T-----G------T---------------------A------ |
| Seq-7 | 3 | 106617467 | 106617566 | 100 | 12 | ---A--GG-----------C-C---A-ATT----G-A--T---------C--------------G------T-G----T--------------T------ |
| Seq-7 | 4 | 117218921 | 117219020 | 100 | 13 | ------G-------------C----T--ATC-G--CA----T-------G-G------------G------T--C------------------------T |
| Seq-7 | 5 | 120366903 | 120367002 | 100 | 14 | -------G------------C-G--T----C----CTG--------------------CA----------------G-T------------------CT- |
| Seq-7 | 7 | 142373034 | 142373133 | 100 | 15 | ------G-------------C----T-----T-T-CAG-----------G-C--TC--------G------------A---------------------- |
| Seq-7 | 8 | 32868986 | 32869085 | 100 | 16 | ------G-----------A-C----T---TCTG--CA------------G----------C---GA-----T---------------------------- |
| Seq-7 | 9 | 33656634 | 33656733 | 100 | 17 | ------G-------------C----T-----T-T-CAG----G------G-C------------G------------A---------------------- |
| Seq-7 | 17 | 19501896 | 19501995 | 100 | 18 | ------G-------------C----T---TCTG--CAT-----------G---T----------G---------------T----------------C-- |
| Seq-7 | 17 | 22021387 | 22021486 | 100 | 19 | ------G-----------A-C----T----CT---CTG-------G-------------------------------A-------------------A-- |
| Seq-7 | 23 | 125865728 | 125865827 | 100 | 20 | ------G---------G---C--------TCTG--CA--AT--------------C--------G----------------------------------- |
| Seq-7 | 24 | 8234672 | 8234771 | 100 | 21 | ------G-------------C----T---TCT-G-CA-T-----------C---A---A----AG-------------A--C---------------A-- |
| Seq-8 | M | 701 | 800 | 100 | 22 | AAGCATCCCCGTTCCAGTGAGTTCACCCTCTAAATCACCACGATCAAAAGGGACAAGCATCAAGCACGCAGCAATGCAGCTCAAAACGCTTAGCCTAGCC |
| Seq-8 | 9 | 33656734 | 33656833 | 100 | 23 | ----------A-C-------AAGT------------TT------------AAGT---T--------T---CA---------------A---T---C---- |
| Seq-8 | 17 | 22021487 | 22021586 | 100 | 24 | -------G--ACC-TG----AA-A-----------T--A------------AGT---T------------TT-G-------------A---T-------- |
| | | | | | | ++++++++++++++++++++++ $ +++++++++++++++++++++ |
| Seq-9 | M | 801 | 900 | 100 | 25 | ACACCCCCACGGGAAACAGCAGTGATTAACCTTTAGCAATAAACGAAAGTTTAACTAAGCTATACTAACCCCAGGGTTGGTCAATTTCGTGCCAGCCACC |
| Seq-9 | 17 | 22021587 | 22021686 | 100 | 26 | --------------G-----------A-----------------------------G------------TTT---------T------A----------- |
| Seq-10 | M | 901 | 1000 | 100 | 27 | GCGGTCACACGATTAACCCAAGTCAATAGAAGCCGGCGTAAAGAGTGTTTTAGATCACCCCCTCCCCAATAAAGCTAAAACTCACCTGAGTTGTAAAAAA |
| Seq-11 | M | 1001 | 1100 | 100 | 28 | CTCCAGTTGACACAAAATAGACTACGAAAGTGGCTTTAACATATCTGAACACACAATAGCTAAGACCCAAACTGGGATTAGATACCCCACTATGCTTAGC |
| Seq-11 | 1 | 9634769 | 9634868 | 100 | 29 | -C-T--C---A-T------A----T---G----------T-CT------G---------------------T---------------------------- |
| Seq-11 | 4 | 56194364 | 56194463 | 100 | 30 | ------C-----T------A--------------------G---------------------------------------------G-------GGCTCA |
| Seq-11 | 5 | 123096916 | 123097015 | 100 | 31 | -C-T--C---A-T------A--------G----AA----T--T-----GG-------------------------------------------------- |
| Seq-11 | 7 | 142373430 | 142373529 | 100 | 32 | -C-GG-C---A-T------A----T---G-A--------T-CT-------G-----------------------------------------G------- |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-11 | 17 | 22021783 | 22021882 | 100 | 33 | -C-T------T-T----C-A-------------------T--T-------T---------G----TT-----------------------------C--- |
| Seq-12 | M | 1101 | 1200 | 100 | 34 | CCTAAACCTCAACAGTTAAATCAACAAAACTGCTCGCCAGAACACTACGAGCCACAGCTTAAAACTCAAAGGACCTGGCGGTGCTTCATATCCCTCTAGA |
| Seq-12 | 1 | 142792707 | 142792806 | 100 | 35 | T------TCA--T-----G-----A-------T---------------A---A---------------------T-----------T-----------A- |
| Seq-12 | 1 | 143344785 | 143344884 | 100 | 36 | T------TCG--T-----G-------------T---------------A---A---------------------T-----------T-----------A- |
| Seq-12 | 4 | 117219422 | 117219521 | 100 | 37 | -------TCT--T-----C--TG-G-----CAT--------GT-----A---A---------------------T-----------T------------- |
| Seq-12 | 5 | 123097016 | 123097115 | 100 | 38 | -------TC---T------------------AT--A------------A---A-T-------------------T-----------T------------- |
| Seq-12 | 7 | 142373530 | 142373629 | 100 | 39 | -------TC---T------------------AT--C------------A---A-T-------------------T----A------T------------- |
| Seq-12 | 9 | 33657133 | 33657232 | 100 | 40 | -------TC---T-------------G----AT--A------------A---A-T-------------------T-----------T------------- |
| Seq-12 | 17 | 19502389 | 19502488 | 100 | 41 | -------TCT--T-----C--T--------CAT--------GT-----A---A---------------------T----A------T------------- |
| Seq-12 | 17 | 22021883 | 22021982 | 100 | 42 | -------T---------------------------------------G----A-----------------------------------C----------- |
| Seq-12 | 21 | 9735630 | 9735729 | 100 | 43 | T------TCG--T-----G-------------T---------------A---A---------------------T-----------T-----------A- |
| Seq-12 | 24 | 13290257 | 13290356 | 100 | 44 | -------TCG--T-----G-------------T---------------A---A---------------------T-T---------T-C---------A- |
| Seq-13 | M | 1201 | 1300 | 100 | 45 | GGAGCCTGTTCTGTAATCGATAAACCCCGATCAACCTCACCACCTCTTGCTCAGCCTATATACCGCCATCTTCAGCAAACCCTGATGAAGGCTACAAAGT |
| Seq-13 | 1 | 142792807 | 142792906 | 100 | 46 | ------------A---------------A--TT-----------------C-------A-----C-------------------GAA-G-CTGCAG-GTA |
| Seq-13 | 1 | 143344885 | 143344984 | 100 | 47 | ----G-------A---------------A--TT-----------------C-------A-----T-------------------GAA-G-C-GCAG-GTA |
| Seq-13 | 7 | 142373630 | 142373729 | 100 | 48 | ------------A----G----------A--TT----------T--------------------AT-----------------AG-A--A-TC------- |
| Seq-13 | 9 | 33657233 | 33657332 | 100 | 49 | ------------A----G------A---A--TTG------------------------------A-TG---------------AGCA------G------ |
| Seq-13 | 17 | 22021983 | 22022082 | 100 | 50 | ------------A---------------A--TC-------------------A--C-----------------------------CA-----C------- |
| Seq-13 | 21 | 9735730 | 9735829 | 100 | 51 | ----G-------A---------------A--TT-----------------C-------A-----T-------------------GAA-G-C-GCAG-GTA |
| Seq-14 | M | 1301 | 1400 | 100 | 52 | AAGCGCAAGTACCCACGTAAAGACGTTAGGTCAAGGTGTAGCCCATGAGGTGGCAAGAAATGGGCTACATTTTCTACCCCAGAAAACTACGATAGCCCTT |
| Seq-14 | 7 | 142373730 | 142373829 | 100 | 53 | ----A------T-T--A----A--A-------------------------C--T-----------------------A--CAG---A-CTC-C-A----- |
| Seq-14 | 9 | 5092100 | 5092199 | 100 | 54 | ----A------AAT--A----A------------C-------T----------------------C--------------------TCT-ACG-CAA-C- |
| Seq-14 | 17 | 22022083 | 22022182 | 100 | 55 | ----A------T-T--A----A-T-------------------T------------------------------------------T-CTACA-TAA-CC |
| Seq-15 | M | 1401 | 1500 | 100 | 56 | ATGAAACTTAAGGGTCGAAGGTGGATTTAGCAGTAAACTGAGAGTAGAGTGCTTAGTTGAACAGGGCCCTGAAGCGCGTACACACCGCCCGTCACCCTCC |
| Seq-15 | 1 | 142793009 | 142793108 | 100 | 57 | ------TC------CTC----A----------A----T------C------T---A-----T-A----A------AT-C-----------A--------- |
| Seq-15 | 1 | 143345087 | 143345186 | 100 | 58 | ------TC------CTC----A----------A----T------C------T---A-----T-A----A------AT-C--------------------- |
| Seq-15 | 4 | 117219730 | 117219829 | 100 | 59 | ------TC------CTC----A--------T-------CA--C-C---------G------T-A----A------AT-C---------T-A--------- |
| Seq-15 | 5 | 123097321 | 123097420 | 100 | 60 | -------C------C-C----A---------------T-AG---C----------A-----T-A----A-A----AT-C------T---T---------- |
| Seq-15 | 9 | 33657434 | 33657533 | 100 | 61 | ------TC------CTC----A-------------C-T-A----C----------A-----TGA----A-A----A--C-----AT-------------- |
| Seq-15 | 17 | 19502693 | 19502792 | 100 | 62 | ----C-TC------CTC----A------G---------CA----C---------G------T-A----A------AT-C-----------A--------- |
| Seq-15 | 17 | 22022185 | 22022284 | 100 | 63 | -------C-G------C----A--------T------T-A---AC----------A-----T------A-A----A--C-------A---A--------- |
| Seq-15 | 21 | 9735932 | 9736031 | 100 | 64 | ------TC------CTC----A----------A----T------C------T---A-----T-A----A------AT-C--------------------- |
| Seq-15 | 24 | 13290559 | 13290658 | 100 | 65 | ------TC------CTC----A----------A----T------C------T---A-----T-A----A------A--C-----------T--------- |
| | | | | | | +++++++++++++++++++++ $$ +++++++++++++++++++ |
| Seq-16 | M | 1501 | 1600 | 100 | 66 | TCAAGTATACTTCAAAGGACATTTAACTAAAACCCCTACGCATTTATATAGAGGAGACAAGTCGTAACATGGTAAGTGTACTGGAAAGTGCACTTGGACG |
| Seq-16 | 9 | 33657536 | 33657635 | 100 | 67 | AA-TA-TACT--AG-GATTAG------------------TT-----------------------------------------A---------------T- |
| Seq-17 | M | 1601 | 1700 | 100 | 68 | AACCAGAGTGTAGCTTAACACAAAGCACCCAACTTACACTTAGGAGATTTCAACTTAACTTGACCGCTCTGAGCTAAACCTAGCCCCAAACCCACTCCAC |
| Seq-17 | 7 | 145694412 | 145694511 | 100 | 69 | --TA-T-AA-G--G------T------------------------------------------------------------------------------- |
| Seq-17 | 17 | 22022353 | 22022452 | 100 | 70 | -----AG-------------T---------TG-------C-G-----------T----T------A-C---------TT---------------ACTA-T |
| | | | | | | $$$$$$$$$$$$$$$$$$$$$$$$$$$ *************************** |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-18 | M | 1701 | 1800 | 100 | 71 | CTTACTACCAGACAACCTTAGCCAAACCATTTACCCAAATAAAGTATAGGCGATAGAAATTGAAACCTGGCGCAATAGATATAGTACCGCAAGGGAAAGA |
| Seq-18 | 17 | 22022453 | 22022552 | 100 | 72 | TC--------A-T-----C-A-T---A---------------------------------GAT-T-TC---A-------C---A------G-T------- |
| | | | | | | |
| Seq-19 | M | 1801 | 1900 | 100 | 73 | TGAAAAATTATAACCAAGCATAATATAGCAAGGACTAACCCCTATACCTTCTGCATAATGAATTAACTAGAAATAACTTTGCAAGGAGAGCCAAAGCTAA |
| Seq-19 | 7 | 142374229 | 142374328 | 100 | 74 | ATG----AGT--------A----A----------TAG----T------------G-------------------------A--CA----A-------C-- |
| Seq-19 | 17 | 22022553 | 22022652 | 100 | 75 | -------AC--------------AG----------A--------------------------------------------A---A----A-------C-- |
| | | | | | | |
| Seq-20 | M | 1901 | 2000 | 100 | 76 | GACCCCCGAAACCAGACGAGCTACCTAAGAACAGCTAAAAGAGCACACCCGTCTATGTAGCAAAATAGTGGGAAGATTTATAGGTAGAGGCGACAAACCT |
| Seq-20 | 2 | 117780085 | 117780184 | 100 | 77 | -T----T---------T--------C-----T-A--G----C--------AC------G-------------------G--GA----G--G-----G--- |
| Seq-20 | 3 | 40294119 | 40294218 | 100 | 78 | -T--------------T--A-----C----------G-----------T-AC------G------------------GC--GA----C--TC----G--- |
| Seq-20 | 7 | 142374329 | 142374428 | 100 | 79 | -G-----A-----------------C----------------A-------A---------T-----------G-----C--GA----T--T--T--G--- |
| Seq-20 | 9 | 33657935 | 33658034 | 100 | 80 | -G----TA-----------------C---------G--------------A---------T-----------G-----C--GA-C--CA-T--T-CG--- |
| Seq-20 | 14 | 84637760 | 84637859 | 100 | 81 | -T---------------AG------C-----T----------------T-AC--G---G-----------A-------C--GA----C-----T--GG-- |
| Seq-20 | 17 | 19503190 | 19503289 | 100 | 82 | -T-----A--------T--------C----------G-------------AC------G---------G---------C--GA----CA----T--G--- |
| Seq-20 | 17 | 22022653 | 22022752 | 100 | 83 | ------------------------------------G-------------A---------------------------C-----------T-----G--- |
| | | | | | | |
| Seq-21 | M | 2001 | 2100 | 100 | 84 | ACCGAGCCTGGTGATAGCTGGTTGTCCAAGATAGAATCTTAGTTCAACTTTAAATTTGCCCACAGAACCCTCTAAATCCCCTTGTAAATTTAACTGTTAG |
| Seq-21 | 3 | 160665516 | 160665615 | 100 | 85 | T--A-----------------------------------------------------A--T--------ACT---T------GTA--T--A-CTGT-AGT |
| Seq-21 | 23 | 142519115 | 142519214 | 100 | 86 | ---A---------------------------------TGA-A---------------A--T--------AC----TC-TAT-GT---G-----T------ |
| | | | | | | |
| Seq-22 | M | 2101 | 2200 | 100 | 87 | TCCAAAGAGGAACAGCTCTTTGGACACTAGGAAAAAACCTTGTAGAGAGAGTAAAAAATTTAACACCCATAGTAGGCCTAAAAGCAGCCACCAATTAAGA |
| Seq-22 | 17 | 22022852 | 22022951 | 100 | 88 | --T-------G----------A-------------------------------------A----TT---A---T------G---A---G-T--------- |
| | | | | | | |
| Seq-23 | M | 2201 | 2300 | 100 | 89 | AAGCGTTCAAGCTCAACACCCACTACCTAAAAAATCCCAAACATATAACTGAACTCCTCACACCCAATTGGACCAATCTATCACCCTATAGAAGAACTAA |
| | | | | | | |
| Seq-24 | M | 2301 | 2400 | 100 | 90 | TGTTAGTATAAGTAACATGAAAACATTCTCCTCCGCATAAGCCTGCGTCAGATCAAAACACTGAACTGACAATTAACAGCCCAATATCTACAATCAACCA |
| Seq-24 | 17 | 22023053 | 22023152 | 100 | 91 | -------------G-----C------------------------A-A-----C-----T---TC--------------------------T--AT--T-- |
| | | | | | | |
| | | | | | | +++++++++++++++++++++++++ |
| Seq-M | M | 2401 | 2500 | 100 | 92 | ACAAGTCATTATTACCCTCACTGTCAACCCAACACAGGCATGCTCATAAGGAAAGGTTAAAAAAAGTAAAAGGAACTCGGCAAACCTTACCCCGCCTGTT |
| Seq-M | 6 | 62283999 | 62284098 | 100 | 93 | -TG-AA-TG------T-CT-----T------------------C--C-------------------------------------T--------------- |
| Seq-M | 7 | 45291551 | 45291650 | 100 | 94 | ----AC-GG-GC-----AT-----T-------------------T---------------------------------------T--------------- |
| Seq-M | 7 | 142374830 | 142374929 | 100 | 95 | CA--T-T---------GAT-----T--T-----------------TA-G-A--G-T-A-------T------------------TT------T------- |
| Seq-M | 17 | 22023154 | 22023253 | 100 | 96 | TG--AC-----------A------T-------------------T-C-------------------------------A--G--T--------T------ |
| | | | | | | |
| Seq-26 | M | 2501 | 2600 | 100 | 97 | TACCAAAAACATCACCTCTAGCATCACCAGTATTAGAGGCACCGCCTGCCCAGTGACACATGTTTAACGGCCGCGGTACCCTAACCGTGCAAAGGTAGCA |
| Seq-26 | 2 | 117780688 | 117780787 | 100 | 98 | ------------------------T-A---------------T----A----------T-------------A-A---T---G--A-----C-------- |
| Seq-26 | 3 | 40294719 | 40294818 | 100 | 99 | ------------------------T-------------T---T---------------T-----C---A---------T---G----------------- |
| Seq-26 | 4 | 117220823 | 117220922 | 100 | 100 | ------------------------T------T------T---T--------G------T-----C-------AT----T---G----------------- |
| Seq-26 | 6 | 62284099 | 62284198 | 100 | 101 | ------------------------T---------------------------------T--------------T-------------------------- |
| Seq-26 | 7 | 45291651 | 45291750 | 100 | 102 | ------------------------T---------------------------------T-----G--T--------CTTT---CGTC-CT-GG--CT-TG |
| Seq-26 | 8 | 32870812 | 32870911 | 100 | 103 | ------------------------T-----------------T-----T---------T-----CG-T------A---T---G--T-------------- |
| Seq-26 | 8 | 77114212 | 77114311 | 100 | 104 | ------------------------T-----------------T----A---------TT-----C--T-----T----T---G----------------- |
| Seq-26 | 9 | 5093284 | 5093383 | 100 | 105 | ------------------------T-----------------T---------------T-----C----A--A-CA--T---G---T------------- |
| Seq-26 | 9 | 33658532 | 33658631 | 100 | 106 | ------------------------T-TT------------G-T---------------T-----C---A---A-A-------G-G--------------- |
| Seq-26 | 10 | 20035756 | 20035855 | 100 | 107 | ------------------------T----------A------T----T--------T-T-----C--T---T-T----T---G--T-------------- |
| Seq-26 | 10 | 57359526 | 573596M | 100 | 108 | ----------------C-------TG-T--------------T------T--------T--------G--TT------T---G-A-T------------- |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-26 | 14 | 84638370 | 84638469 | 100 | 109 | ------------------------T-----------------T---------------T-----C-----TG-T----T---G---------G-TAGCAT |
| Seq-26 | 17 | 19504108 | 19504207 | 100 | 110 | ------------------------T-----------------T---------------T-----C---------A---T---G---A--T--G-TAGCAT |
| Seq-26 | 17 | 22023254 | 22023353 | 100 | 111 | --T---------------------T-------C----------A--------------T--------T---T-----------------T---------- |
| Seq-26 | 23 | 62061037 | 62061136 | 100 | 112 | -------------------GA---A--T--------------TA--------------T-A-------A---A-A---T---G---A---T--------- |
| Seq-26 | 23 | 142519695 | 142519794 | 100 | 113 | ------------------------T--T----CC-------AT----A---------GT--------G---T------T-T-G---A------------C |
| | | | | | | |
| Seq-27 | M | 2601 | 2700 | 100 | 114 | TAATCACTTGTTCCTTAAATAGGGACCTGTATGAATGGCTCCACGAGGGTTCAGCTGTCTCTTACTTTTAACCAGTGAAATTGACCTGCCCGTGAAGAGG |
| Seq-27 | 3 | 40294819 | 40294918 | 100 | 115 | --------------C-----------T------------CAT-T--A------------------------T---------------ATT---------- |
| Seq-27 | 4 | 117220923 | 117221022 | 100 | 116 | -----G--------C-----------T-----------ACA---A--------------------------T---------------AT-T--------- |
| Seq-27 | 6 | 62284199 | 62284298 | 100 | 117 | -G------------------------T--------------G------T-------------------C-----C--C--C------------------- |
| Seq-27 | 7 | 142375029 | 142375128 | 100 | 118 | --------------------------T----------A-C---------------------------CC-----------C---------T--------- |
| Seq-27 | 8 | 32870912 | 32871011 | 100 | 119 | --------------C-----------T-A----------CA--T---------------------------T-------------G-AT--A----A--- |
| Seq-27 | 9 | 33658632 | 33658731 | 100 | 120 | --------------------------T-----------------T----------------------CC-----------C----------A----C--- |
| Seq-27 | 10 | 57359626 | 573597M | 100 | 121 | --------------C---G-------T------------CA---C------T----------------C------------------A--TA-------- |
| Seq-27 | 14 | 84638469 | 84638568 | 100 | 122 | --------------C-----------T---------A--CA---A------G-------------------T---------------AT--A-------- |
| Seq-27 | 17 | 22023354 | 22023453 | 100 | 123 | --------------------------T---C-------------------------------------C------------------------------- |
| Seq-27 | 23 | 62061137 | 62061236 | 100 | 124 | -----T--------CA----G--A--T-CC---------CT---A------T-AT----------G-----T---------------AT-T---G----- |
| Seq-27 | 23 | 142519795 | 142519894 | 100 | 125 | -----G--T-----CC-----------------------CA--A------CTGAT----------C----GT--A------------A---A-------- |
| | | | | | | |
| Seq-28 | M | 2701 | 2800 | 100 | 126 | CGGGCATGACACAGCAAGACGAGAAGACCCTATGGAGCTTTAATTTATTAATGCAAACAGTACCTAACAAACCCACAGGTCCTAAACTACCAAACCTGCA |
| Seq-28 | 6 | 62284299 | 62284398 | 100 | 127 | ---A---A-T---A---------------A----------C------CC----------AC---C--T--G--------CT----C-------------- |
| Seq-28 | 17 | 22023454 | 22023553 | 100 | 128 | ---A---A-T---A------------------A---------------G----------AG---A--T-GG---G----C------------G------G |
| | | | | | | |
| Seq-29 | M | 2801 | 2900 | 100 | 129 | TTAAAAATTTCGGTTGGGGCGACCTCGGAGCAGAACCCAACCTCCGAGCAGTACATGCTAAGACTTCACCAGTCAAAGCGAACTACTATACTCAATTGAT |
| Seq-29 | 6 | 62284399 | 62284498 | 100 | 130 | -------------C----------------T-T-----------------AC-T-----G-----------------A---GT---C-CGTA-------- |
| Seq-29 | 17 | 22023554 | 22023653 | 100 | 131 | -----C------------------------T-T----T------------AC-T-----G-----AT---------G-----TAT-C-C-TA-------C |
| | | | | | | |
| Seq-30 | M | 2901 | 3000 | 100 | 132 | CCAATAACTTGACCAACGGAACAAGTTACCCTAGGGATAACAGCGCAATCCTATTCTAGAGTCCATATCAACAATAGGGTTTACGACCTCGATGTTGGAT |
| Seq-30 | 2 | 117781085 | 117781184 | 100 | 133 | -----G-T-C--T----A---T----------------------T-----------------T------G------------------------------ |
| Seq-30 | 3 | 40295118 | 40295217 | 100 | 134 | -------T----T--------T--------T--------G-----------C--------A--AG---TG-------A------A--------------- |
| Seq-30 | 7 | 142375331 | 142375430 | 100 | 135 | -------T----T-------------------------------------------------------TG------------------------------ |
| Seq-30 | 8 | 32871202 | 32871301 | 100 | 136 | -------T----T---T----T------TG-------------T-----------------------G-G---------A-G--T---------C--A-- |
| Seq-30 | 9 | 33658934 | 33659033 | 100 | 137 | -------T----T---------------------A----------------------------------G------------------------------ |
| Seq-30 | 10 | 57360227 | 57360326 | 100 | 138 | -------T-CT-T----A-G-T----G---------T---G--T---------------CA-------------C--------------T---------- |
| Seq-30 | 13 | 57262611 | 57262710 | 100 | 139 | -----------TT---G----T-------T--------------A------------------------G---------------------G-----T-- |
| Seq-30 | 17 | 19504821 | 19504920 | 100 | 140 | -------T----T--------T----------------------A-----------------T------G-G---------------G------------ |
| Seq-30 | 17 | 22023654 | 22023753 | 100 | 141 | -------T--------------------------T--------TA--------------G-----C---G---G---CA--A------------------ |
| Seq-30 | 23 | 62061579 | 62061678 | 100 | 142 | -A-G--GT----G---T------C------T--------G---TA---------------A---G-----G---------G--T---T-----A------ |
| Seq-30 | 23 | 1425204M | 142520524 | 100 | 143 | -A----GT---------T--G---------------------A-A-G---------------------TG--T-------------T------------- |
| | | | | | | |
| Seq-31 | M | 3001 | 3100 | 100 | 144 | CAGGACATCCCGATGGTGCAGCCGCTATTAAAGGTTCGTTTGTTCAACGATTAAAGTCCTACGTGATCTGAGTTCAGACCGGAGTAATCCAGGTCGGTTT |
| Seq-31 | 2 | 117781185 | 117781284 | 100 | 145 | ----------AA------T----A-------G---T--C-------A-------------T-----------------TA------------C------ |
| Seq-31 | 4 | 93623185 | 93623284 | 100 | 146 | ----------TA------T---T-----C--G---T----------T--------------A---------------------C----------A---- |
| Seq-31 | 4 | 117221300 | 117221399 | 100 | 147 | G---------TA------T------------G------------T----G-------T---T------------------T--------------A---- |
| Seq-31 | 7 | 142375431 | 142375530 | 100 | 148 | ----------TA------T---T-----C--G-----A---------T-----------------G------------------C--G-------T-G-A |
| Seq-31 | 8 | 32871302 | 32871401 | 100 | 149 | ---------TTA---C--G------------GA---T----------------------------------A--------A--A-----------A---C |
| Seq-31 | 9 | 5093795 | 5093894 | 100 | 150 | ----------TA------T------------G-----A---A-----T-------------T---------T--------A-------------T----- |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-31 | 9 | 33659034 | 33659133 | 100 | 151 | ----------TA------T---T---G-C--G-----------C---T------------------------------------C----------T-G-A |
| Seq-31 | 10 | 57360328 | 57360427 | 100 | 152 | GG-ACATC-TAA------T------------G--A--A---------T------------T-------------------A---C---------T----- |
| Seq-31 | 14 | 84638867 | 84638966 | 100 | 153 | ------G---TA------T--------A---G---------------T---C----------A--------------------------------A---- |
| Seq-31 | 17 | 19504921 | 19505020 | 100 | 154 | ----------TA-------------------G---------------T-----G-A------A---------------T--------------------- |
| Seq-31 | 17 | 22023754 | 22023853 | 100 | 155 | -----------A-----------------------------------------G-------T--------------------------------T----- |
| Seq-31 | 24 | 8239395 | 8239494 | 100 | 156 | A-------G-TA------T----AG------G-A---T--------GT--------------A----T------------A------C------------ |
| Seq-32 | M | 3101 | 3200 | 100 | 157 | CTATCTACTTCAAATTCCTCCCTGTACGAAAGGACAAGAGAAATAAGGCCTACTTCACAAAGCGCCTTCCCCCGTAAATGATATCATCTCAACTTAGTAT |
| Seq-33 | M | 3201 | 3300 | 100 | 158 | TATACCCACACCCACCCAAGAACAGGGTTTGTTAAGATGGCAGAGCCCGGTAATCGCATAAAACTTAAAACTTTACAGTCAGAGGTTCAATTCCTCTTCT |
| Seq-33 | 2 | 117781387 | 117781486 | 100 | 159 | C--CA-ACACA-T-TT--------A-----------------------A-C---T-------T------------T-A----------G-C--------- |
| Seq-33 | 9 | 5093993 | 5094092 | 100 | 160 | G-A-T-AC---A------------------C----------G-----T--C---A---------G------------A---A--------C---C----- |
| Seq-33 | 17 | 22023955 | 22024054 | 100 | 161 | -G------------------------------------------C---A-C---T--------T-------------AC-----------CC-------- |
| Seq-34 | M | 3301 | 3400 | 100 | 162 | TAACAACATACCCATGGCCAACCTCCTACTCCTCATTGTACCCATTCTAATCGCAATGGCATTCCTAATGCTTACCGAACGAAAAATTCTAGGCTATATA |
| Seq-34 | 17 | 22024055 | 22024154 | 100 | 163 | ---------GT----AA-T-----T-----T--T--------T--C--------C-----------C-----A--T---T-------C--------C--G |
| Seq-35 | M | 3401 | 3500 | 100 | 164 | CAACTACGCAAAGGCCCCAACGTTGTAGGCCCCTACGGGCTACTACAACCCTTCGCTGACGCCATAAAACTCTTCACCAAAGAGCCCCTAAAACCCGCCA |
| Seq-35 | 4 | 93623586 | 93623685 | 100 | 165 | ------T-------AT----TA--T----------T--A---T-T-----A--T-----T--A--------T-----T------A-----------T-AT |
| Seq-35 | 8 | 32871692 | 32871791 | 100 | 166 | ------T-------A--T---A-------T-----T-----G--T-----AG---T---T--A--------T-----------A---T---GG---T-A- |
| Seq-35 | 17 | 22024155 | 22024254 | 100 | 167 | --------------G-----TA-------------T--A---T-------T--T--C--T--------------T--------AT--T--------T-A- |
| Seq-36 | M | 3501 | 3600 | 100 | 168 | CATCTACCATCACCCTCTACATCACCGCCCCGACCTTAGCTCTCACCATCGCTCTTCTACTATGAACCCCCCTCCCCATACCCAACCCCCTGGTCAACCT |
| Seq-36 | 17 | 22024255 | 22024354 | 100 | 169 | -G--A--TG-T--------------T-----A--------C---T-T--T--C--------------T--------T-----T--------A--T--T-- |
| Seq-37 | M | 3601 | 3700 | 100 | 170 | CAACCTAGGCCTCCTATTTATTCTAGCCACCTCTAGCCTAGCCGTTTACTCAATCCTCTGATCAGGGTGAGCATCAAACTCAAACTACGCCCTGATCGGC |
| Seq-37 | 9 | 5094368 | 5094467 | 100 | 171 | T--TA--------T----------------A--A--------A--C--T--C--T--A--------A-A------C--T-----T--T-TA--------- |
| Seq-37 | 17 | 19505863 | 19505962 | 100 | 172 | T--TA----------------A--------A--A-----------C-----T--T--A--------A--------T--T-----T--T--A--A------ |
| Seq-37 | 17 | 22024355 | 22024454 | 100 | 173 | T---T-------T-----C-----GT----A--C--------T--C-----T-----A--------A--------------------T------------ |
| Seq-38 | M | 3701 | 3800 | 100 | 174 | GCACTGCGAGCAGTAGCCCAAACAATCTCATATGAAGTCACCCTAGCCATCATTCTACTATCAACATTACTAATAAGTGGCTCCTTTAACCTCTCCACCC |
| Seq-38 | 17 | 22024455 | 22024554 | 100 | 175 | ---T-AT-------T-----------T-----C-----T--------T-----C---T----G-TCC--------------CAA--C--T----G----- |
| Seq-39 | M | 3801 | 3900 | 100 | 176 | TTATCACAACACAAGAACACCTCTGATTACTCCTGCCATCATGACCCTTGGCCATAATATGATTTATCTCCACACTAGCAGAGACCAACCGAACCCCCTT |
| Seq-39 | 9 | 5094564 | 5094663 | 100 | 177 | GC-------TG-C----TTA------CCG-----A--------------A------T----------T------------A-A--T------G----T-- |
| Seq-39 | 15 | 35688444 | 35688543 | 100 | 178 | ---------TG------TT------GCCG-----A-----------TC-------------------------G--G-----A--T----A-G----A-- |
| Seq-39 | 17 | 19506063 | 19506162 | 100 | 179 | -C---------------TT-------C-G-----A--------C-G-C-A-T--------A-------C-------------A--T------G----T-- |
| Seq-39 | 17 | 22024555 | 22024654 | 100 | 180 | -C--T-G-------------------C-------AA-----------C-A--T--------------T--------------A-----T---G-TG-T-- |
| Seq-40 | M | 3901 | 4000 | 100 | 181 | CGACCTTGCCGAAGGGGAGTCCGAACTAGTCTCAGGCTTCAACATCGAATACGCCGCAGGCCCCTTCGCCCTATTCTTCATAGCCGAATACACAAACATT |
| Seq-40 | 1 | 564450 | 564549 | 100 | 182 | TC-G-AA-GTC--A-------------------------------------------------------------------------------------- |
| Seq-40 | 17 | 22024655 | 22024754 | 100 | 183 | T------A-T-----A--A--A-----------------------T-----T--T--------A--------------T-------------T---T--C |
| | | | | | | *********************************** |
| Seq-41 | M | 4001 | 4100 | 100 | 184 | ATTATAATAAACACCCTCACCACTACAATCTTCCTAGGAACAACATATGACGCACTCTCCCCTGAACTCTACACAACATATTTTGTCACCAAGACCCTAC |
| Seq-41 | 1 | 564550 | 564649 | 100 | 185 | ------------------------------------------------A--------------------------------------------------- |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-42 | M | 4101 | 4200 | 100 | 186 | TTCTAACCTCCCTGTTCTTATGAATTCGAACAGCATACCCCCGATTCCGCTACGACCAACTCATACACCTCCTATGAAAAAACTTCCTACCACTCACCCT |
| Seq-42 | 1 | 564650 | 564749 | 100 | 187 | ----G----------------------------------------------------------------------------------------------- |
| Seq-42 | 2 | 131029682 | 131029781 | 100 | 188 | -CT----------A--T-----------------T--T----A----T----T--TT-----T-----T---T------------T--------T--A-- |
| Seq-42 | 7 | 57253751 | 57253850 | 100 | 189 | -CT----------A--T----------A---------T-----T---G-----A-T--------C-----------------T--T----T---T--A-- |
| Seq-42 | 17 | 19506363 | 19506462 | 100 | 190 | --------G-----A-T------------------------T--C-GT-----A------------T-T-------------------------T-AA-- |
| Seq-42 | 17 | 22024855 | 22024954 | 100 | 191 | -C--------T--A--T--------C----------------------A------T---------GT-T---T---------T---T-----T-T--A-- |
| Seq-43 | M | 4201 | 4300 | 100 | 192 | AGCATTACTTATATGATATGTCTCCATACCCATTACAATCTCCAGCATTCCCCCTCAAACCTAAGAAATATGTCTGATAAAAGAGTTACTTTGATAGAGT |
| Seq-43 | 1 | 564750 | 564849 | 100 | 193 | ---------------------------------------------------------------------------------------------------- |
| Seq-43 | 2 | 131029782 | 131029881 | 100 | 194 | ------CTG-G-------CA----A--------C-T------------C--A--C-----G-------C--------C------A---------C---A- |
| Seq-43 | 7 | 57253851 | 57253950 | 100 | 195 | ------CTG-------C--A----A--------CCT------------C--A-------TG---------C-G----C------A--------------- |
| Seq-43 | 13 | 36639618 | 36639717 | 100 | 196 | CTATA-TT-C---------A-T--A---T----C--------------C--A--C----TG----------------C------A--------------- |
| Seq-43 | 17 | 22024955 | 22025054 | 100 | 197 | ----C-------------CA----A---T--GC------T----A---------CT ---T----------------C--------G------------- |
| Seq-44 | M | 4301 | 4400 | 100 | 198 | AAATAATAGGAGCTTAAACCCCCTTATTTCTAGGACTATGAGAATCGAACCCATCCCTGAGAATCCAAAATTCTCCGTGCCACCTATCACACCCCATCCT |
| Seq-44 | 1 | 564850 | 564949 | 100 | 199 | ------------T-----T--------------------------------------------------------------------------------- |
| Seq-44 | 2 | 131029882 | 131029981 | 100 | 200 | ---C--C--AG-T-G---T--T-A---------------AG----T------------------------------A---T------------A-G---- |
| Seq-44 | 3 | 106620849 | 106620948 | 100 | 201 | ----T----AG-T----GT--T-------G---A-T---AG----------T-C---------------------T----T-----AT-----A------ |
| Seq-44 | 7 | 57253951 | 57254050 | 100 | 202 | ---C--C--AG-A--TC-A--T-----------A-----AG----T-------C-------------------C--A---T------------A-G---- |
| Seq-44 | 13 | 36639718 | 36639817 | 100 | 203 | -----G---AG-T--------T-----C-----A-----AG----T-----T-A----------------------A---T----G-------A------ |
| Seq-44 | 17 | 19506558 | 19506657 | 100 | 204 | ---------AG-T-A---T--T-----------A-----AG----T-----T-C------T---------------A----------T-----A------ |
| Seq-44 | 17 | 22025055 | 22025154 | 100 | 205 | ---------AG-T--G--T--T--------------C--AG----T-----T-------------------------------G-G--------T----- |
| Seq-45 | M | 4401 | 4500 | 100 | 206 | AAAGTAAGGTCAGCTAAATAAGCTATCGGGCCCATACCCCGAAAATGTTGGTTATACCCTTCCCGTACTAATTAATCCCCTGGCCCAACCCGTCATCTAC |
| Seq-45 | 1 | 564950 | 565049 | 100 | 207 | --------------------------------------------------------T------------------------------------------- |
| Seq-45 | 2 | 117782580 | 117782679 | 100 | 208 | -G----------C--------A-C---A-A---------T--------------C---------A--------------T----T----TTA-T--TACT |
| Seq-45 | 2 | 131029982 | 131030081 | 100 | 209 | ---------------------------A--------T---A-------------C-T-------A----------C-TAT-A--T--G-TTA-------- |
| Seq-45 | 7 | 57254051 | 57254150 | 100 | 210 | --G------------------------A--------------------------------------C--------C--ATAA-GT----TTA-T--T-TA |
| Seq-45 | 8 | 32872717 | 32872816 | 100 | 211 | -G----------------------G-T-------------A-------------C---------A-GGC----------T-A--T----TT--T--T-C- |
| Seq-45 | 10 | 20036681 | 20036780 | 100 | 212 | -G--C---------------------------------T-AC------A-----C------------------------T-A--T----TTAGT--T-CT |
| Seq-45 | 17 | 19506658 | 19506757 | 100 | 213 | ----------------------------------------A-----------C-----------A-------------AT-A--TTGG--TTA-TAT-TT |
| Seq-45 | 17 | 22025155 | 22025254 | 100 | 214 | GG-------------------------A------------A---------------T---------------C-----A-----------T--------- |
| Seq-45 | 24 | 8240212 | 8240311 | 100 | 215 | ---T-----------------------A---------A-TA---------------T-------AA-G----------AT-A-TT----TTA-T----C- |
| Seq-46 | M | 4501 | 4600 | 100 | 216 | TCTACCATCTTTGCAGGCACACTCATCACAGCGCTAAGCTCGCACTGATTTTTTACCTGAGTAGGCCTAGAAATAAACATGCTAGCTTTTATTCCAGTTC |
| Seq-46 | 1 | 565050 | 565149 | 100 | 217 | ---------------------------------------------------------------------------------------------------- |
| Seq-47 | M | 4601 | 4700 | 100 | 218 | TAACCAAAAAAATAAACCCTCGTTCCACAGAAGCTGCCATCAAGTATTTCCTCACGCAAGCAACCGCATCCATAATCCTTCTAATAGCTATCCTCTTCAA |
| Seq-47 | 1 | 565150 | 565249 | 100 | 219 | ---------------------------------------------------------------------------------------------------- |
| Seq-47 | 17 | 22025355 | 22025454 | 100 | 220 | ---TT--------------C--C--T------A----T-----A--C--T-----AT--------A----T--------CA---------------C--- |
| | | | | | | $ ****************************  |
| Seq-48 | M | 4701 | 4800 | 100 | 221 | CAATATACTCTCCGGACAATGAACCATAACCAATACTACCAATCAATACTCATCATTAATAATCATAATGGCTATAGCAATAAAACTAGGAATAGCCCCC |
| Seq-48 | 1 | 565250 | 565349 | 100 | 222 | ------------------------------------C--------------------------------------------------------------- |
| Seq-48 | 17 | 22025455 | 22025554 | 100 | 223 | ----G---------------------C------C--C-----CA---------------C--CA--CC---T---------------------------T |
| | | | | | | +++++++++ |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-49 | M | 4801 | 4900 | 100 | 224 | TTTCACTTCTGAGTCCCAGAGGTTACCCAAGGCACCCCTCTGACATCCGGCCTGCTTCTTCTCACATGACAAAAACTAGCCCCCATCTCAATCATATACC |
| Seq-49 | 1 | 565350 | 565449 | 100 | 225 | --------------------------------------------------------C------------------------------------------- |
| Seq-49 | 1 | 50482956 | 50483055 | 100 | 226 | ---------------------AGG--------A--TT----A-T---T---A-A-----C--T-------------------T-----G--T----TT- |
| Seq-49 | 2 | 117782984 | 117783083 | 100 | 227 | -----------------------A--------A-T-T--T-A-----T--TA-A---T-----------------------T-----G-----G-TT- |
| Seq-49 | 2 | 131030381 | 131030480 | 100 | 228 | --------------T-----A--A--------A--TT----A-----T---A-A-----C-----G-----------A----T--T-----TCA--T-A |
| Seq-49 | 8 | 32873109 | 32873208 | 100 | 229 | ------------------C--T-A-------AA---T----A-TT--T---A-A-----C---------------------T-----G--T--G-TT- |
| Seq-49 | 9 | 5095554 | 5095653 | 100 | 230 | ---------C----------A--A-----G--A--TT----A-TG--T---A-A-----C---------------------T--------T----TT- |
| Seq-49 | 17 | 22025555 | 22025654 | 100 | 231 | --C-GT-------------A--C--T-----A--------A-T----A----A----CC----------------T------T--T-----T-----T- |
| | | | | | | +++++++++++++++                          $                  ++++++++++++++++++++++++******* |
| Seq-50 | M | 4901 | 5000 | 100 | 232 | AAATCTCTCCCTCACTAAACGTAAGCCTTCTCCTCACTCTCTCAATCTTATCCATCATAGCAGGCAGTTGAGGTGGATTAAACCAAACCCAGCTACGCAA |
| Seq-50 | 1 | 565450 | 565549 | 100 | 233 | ----T---------T-----------------------T----------------G------------------------------A-------- |
| | | | | | | **********************                  $          ************************** |
| Seq-51 | M | 5001 | 5100 | 100 | 234 | AATCTTAGCATACTCCTCAATTACCCACATAGGATGAATAATAGCAGTTCTACCGTACAACCCTAACATAACCATTCTTAATTTAACTATTTATATTATC |
| Seq-51 | 1 | 565550 | 565649 | 100 | 235 | ------------------------------------------C--------------------------------------------------------- |
| Seq-51 | 2 | 212642076 | 212642175 | 100 | 236 | ----C----C-----------C--T--------T--------------A---ATT--TG----A-----T----C---A---C-G-T------CC----- |
| Seq-51 | 17 | 22025749 | 22025848 | 100 | 237 | ----C----------------C-----T-----C--------------A---G-A--------A-GT--C------T-C--CC---TC--C-----C--T |
| | | | | | | *********************                         $                         ******************** |
| Seq-52 | M | 5101 | 5200 | 100 | 238 | CTAACTACTACCGCATTCCTACTACTCAACTTAAACTCCAGCACCACGACCCTACTACTATCTCGCACCTGAAACAAGCTAACATGACTAACACCCTTAA |
| Seq-52 | 1 | 565650 | 565749 | 100 | 239 | -----------------------------------------------A---------------------------------------------------- |
| Seq-52 | 2 | 68487950 | 68488049 | 100 | 240 | -----A-----T---------GC------TC-G--T--A--------AG-----T-------C-A-G----------A---------T---T-T--A--- |
| Seq-52 | 17 | 22025849 | 22025948 | 100 | 241 | -----A--C---A-------GG----------G-----T-----T--A-----------G-GC-----T-----T--A-----C-------T----C--- |
| | | | | | | ************ |
| Seq-53 | M | 5201 | 5300 | 100 | 242 | TTCCATCCACCCTCCTCTCCCTAGGAGGCCTGCCCCCGCTAACCGGCTTTTTGCCCAAATGGGCCATTATCGAAGAATTCACAAAAAACAATAGCCTCAT |
| Seq-53 | 1 | 565750 | 565849 | 100 | 243 | ---------------------------------------------------------------------------------------------------- |
| Seq-53 | 17 | 22025949 | 22026048 | 100 | 244 | -C-----T-----A--A--A-----------T-----A-----T------C-A--------ATTT--C--T-----------------T--C-A------ |
| | | | | | | ************       $                              $              ********************* |
| Seq-54 | M | 5301 | 5400 | 100 | 245 | CATCCCCACCATCATAGCCACCATCACCCTCCTTAACCTCTACTTCTACCTACGCCTAATCTACTCCACCTCAATCACACTACTCCCCATATCTAACAAC |
| Seq-54 | 1 | 565850 | 565949 | 100 | 246 | --------------------T-----------------------------G--------------------------------T----------- |
| Seq-54 | 17 | 22026049 | 22026148 | 100 | 247 | T--------T-C--------TT--T--T---T-------A--T--T---A-----T----------TG-T-----T------T----------C------ |
| Seq-55 | M | 5401 | 5500 | 100 | 248 | GTAAAAATAAAATGACAGTTTGAACATACAAAACCCACCCCATTCCTCCCCACACTCATCGCCCTTACCACGCTACTCCTACCTATCTCCCCTTTTATAC |
| Seq-55 | 1 | 565950 | 566049 | 100 | 249 | --------------------------C-------------------------------------------A--G----------------------G- |
| Seq-55 | 17 | 22026149 | 22026248 | 100 | 250 | -----------------A------A--------T----A---C--T------------CT-T---------C--C--------A-----T--AC---C-- |
| Seq-56 | M | 5501 | 5600 | 100 | 251 | TAATAATCTTATAGAAATTTAGGTTAAATACAGACCAAGAGCCTTCAAAGCCCTCAGTAAGTTGCAATACTTAATTTCTGCAACAGCTAAGGACTGCAAA |
| Seq-56 | 1 | 566050 | 566149 | 100 | 252 | ---------------------------------------------------------------------------------------------------- |
| Seq-57 | M | 5601 | 5700 | 100 | 253 | ACCCCACTCTGCATCAACTGAACGCAAATCAGCCACTTTAATTAAGCTAAGCCCTTACTAGACCAATGGGACTTAAACCCACAAACACTTAGTTAACAGC |
| Seq-57 | 1 | 566150 | 566249 | 100 | 254 | ---------------------------------------------------------------------------------------------------- |
| Seq-57 | 2 | 131031172 | 131031271 | 100 | 255 | -TT-T------T-----T-------------AT----------------------------TTG-----------------G----T---A-------A |
| Seq-57 | 2 | 212642676 | 212642775 | 100 | 256 | --T-T-T---------GT-----------A-A------------------------------TGG---A-T-C---A----G--A-T-----------T |
| Seq-57 | 7 | 57255247 | 57255346 | 100 | 257 | --TGT-T----------T----T--------AT--------------------A-GG------TGT---------------TG--A-T----C-----C- |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-57 | 8 | 134767787 | 134767886 | 100 | 258 | --T-T-T----------T-----A------C-------------------------G-----TTCGCA-A-T-C-------TG--A-T------------ |
| Seq-57 | 9 | 5096353 | 5096452 | 100 | 259 | ----T-T-T-------GT-------------A-------------------T----G-----T-GG---A-T-C-----------A-T------------ |
| Seq-57 | 17 | 22026350 | 22026449 | 100 | 260 | ----T---T------T----------------------------------------G-----T----------------------A-T--G--------- |
| Seq-58 | M | 5701 | 5800 | 100 | 261 | TAAGCACCCTAATCAACTGGCTTCAATCTACTTCTCCCGCCGCCGGGAAAAAAGGCGGGAGAAGCCCCGGCAGGTTTGAAGCTGCTTCTTCGAATTTGCA |
| Seq-58 | 1 | 566250 | 566349 | 100 | 262 | ---------------------------------------------------------------------------------------------------- |
| | | | | | | *******************  $$$$$$$$$$$$$$$$$$$$    ************************************************** |
| Seq-59 | M | 5801 | 5900 | 100 | 263 | ATTCAATATGAAAATCACCTCGGAGCTGGTAAAAAGAGGCCTAACCCCTGTCTTTAGATTTACAGTCCAATGCTTCACTCAGCCATTTTACCTCACCCCC |
| Seq-59 | 1 | 566350 | 566449 | 100 | 264 | ---------------------A------------------T----------------------------------------------------------- |
| Seq-59 | 21 | 10492946 | 10493045 | 100 | 265 | ---------------------A------------------T--------------------------------------------------------AGA |
| Seq-60 | M | 5901 | 6000 | 100 | 266 | ACTGATGTTCGCCGACCGTTGACTATTCTCTACAAACCACAAAGACATTGGAACACTATACCTATTATTCGGCGCATGAGCTGGAGTCCTAGGCACAGCT |
| Seq-60 | 1 | 566450 | 566549 | 100 | 267 | ---------------------------------------------------------------------------------------------------- |
| Seq-60 | 17 | 22026634 | 22026733 | 100 | 268 | ---A---------A----C-----------A-----T--T-----T--C-----------TT----G--T--T---------------T-G--------C |
| Seq-61 | M | 6001 | 6100 | 100 | 269 | CTAAGCCTCCTTATTCGAGCCGAGCTGGGCCAGCCAGGCAACCTTCTAGGTAACGACCACATCTACAACGTTATCGTCACAGCCCATGCATTTGTAATAA |
| Seq-61 | 1 | 566550 | 566649 | 100 | 270 | -----------------------A---------------------------------------------------------------------------- |
| Seq-61 | 17 | 22026734 | 22026833 | 100 | 271 | T---------------AGA-T--A--A--T--A--T-----------------------------------C--------------CA----CT-C---- |
| Seq-62 | M | 6101 | 6200 | 100 | 272 | TCTTCTTCATAGTAATACCCATCATAATCGGAGGCTTTGGCAACTGACTAGTTCCCCTAATAATCGGTGCCCCCGATATGGCGTTTCCCCGCATAAACAA |
| Seq-62 | 1 | 566650 | 566749 | 100 | 273 | ---------------------------------------------------------------------------------------------------- |
| Seq-62 | 8 | 134768284 | 134768383 | 100 | 274 | -------T--G--------A--------T--G--T--C-------AG-----C--T--------T-----A-----------A--C-----G-----TT- |
| Seq-62 | 17 | 19508954 | 19509053 | 100 | 275 | -A-----T--G--------A--------T-----T--C--------G-----C--T--------T-----A---------A-A------T-G-----T-- |
| Seq-62 | 17 | 22026834 | 22026933 | 100 | 276 | ----T-----------GT-T--------T-----T--------T-----G--C-----G-----T--C-----T--C-----A------T--G----T-- |
| | | | | | | ++++++++++++++++++++++                    $                       +++++++++++++++++++++++++++++ |
| Seq-63 | M | 6201 | 6300 | 100 | 277 | CATAAGCTTCTGACTCTTACCTCCCTCTCTCCTACTCCTGCTCGCATCTGCTATAGTGGAGGCCGGAGCAGGAACAGGTTGAACAGTCTACCCTCCCTTA |
| Seq-63 | 1 | 566750 | 566849 | 100 | 278 | ---------------------C--------------------T-----------------------C--------------------------------G |
| | | | | | | *********************************************************         $$$$$$$$$$$$$$$$$$ |
| Seq-64 | M | 6301 | 6400 | 100 | 279 | GCAGGGAACTACTCCCACCCTGGAGCCTCCGTAGACCTAACCATCTTCTCCTTACACCTAGCAGGTGTCTCCTCTATCTTAGGGGCCATCAATTTCATCA |
| Seq-64 | 1 | 566850 | 566949 | 100 | 280 | ------------------------------------------------------------------A----------------A---------------- |
| Seq-64 | 17 | 22027034 | 22027133 | 100 | 281 | -----A-----T-----T--A-AG-----T--------------T------C-T--T--------------------TC----A--T--T---------- |
| Seq-65 | M | 6401 | 6500 | 100 | 282 | CAACAATTATCAATATAAAACCCCCTGCCATAACCCAATACCAAACGCCCCTCTTCGTCTGATCCGTCCTAATCACAGCAGTCCTACTTCTCCTATCTCT |
| Seq-65 | 1 | 566950 | 567049 | 100 | 283 | ----------T-----------------------------------------T------------------------------T---------------- |
| Seq-65 | 1 | 142791954 | 142792053 | 100 | 284 | -C------G-T--------------A-----GT-------T--C--A---------A------TA--------T--------T--T--A-----T-G--- |
| Seq-65 | 1 | 143344026 | 1433441M | 100 | 285 | -C------G-T--------------A-----GT-------T--C--A---------A------TA--------T--------T--T--A-----T-G--- |
| Seq-65 | 17 | 22027134 | 22027233 | 100 | 286 | -C--------T--C------------------TAT--------------------T--------T-----------G-----------C-----C--C-- |
| Seq-65 | 21 | 9734872 | 9734971 | 100 | 287 | -C------G-T--------------A-----GT-------T--C--A---------A------TA--------T--------T--T--A-----T-G--- |
| Seq-65 | 24 | 13289499 | 13289598 | 100 | 288 | -C------G-T--------------A-----GT-------T--C--A---------A---A--TA--------T--------T--T--A-----T-G--- |
| | | | | | | +++++++++++++                             $                          +++++++++++++++++++++++++++ |
| Seq-66 | M | 6501 | 6600 | 100 | 289 | CCCAGTCCTAGCTGCTGGCATCACTATACTACTAACAGACCGCAACCTCAACACCACCTTCTTCGACCCCGCCGGAGGAGGAGACCCCATTCTATACCAA |
| Seq-66 | 1 | 567050 | 567149 | 100 | 290 | ------------C-----------------------------T--------------------------A------------------------------ |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-67 | M | 6601 | 6700 | 100 | 291 | CACCTATTCTGATTTTTCGGTCACCCTGAAGTTTATATTCTTATCCTACCAGGCTTCGGAATAATCTCCCATATTGTAACTTACTACTCCGGAAAAAAAG |
| Seq-67 | 1 | 567150 | 567249 | 100 | 292 | -----------------------------------------C--------------------------------------------------G------A |
| Seq-67 | 7 | 57256299 | 57256398 | 100 | 293 | ---T----------C-CT--------C-----C-G---CT-C---------------A-G-----T--------CAC---A--------T---------- |
| Seq-67 | 9 | 5097351 | 5097450 | 100 | 294 | --TT----------C--T--------------------C-----T---T-------T--G--G---------G-C--G--G--T-----T--------G- |
| Seq-67 | 17 | 22027333 | 22027432 | 100 | 295 | --------T-----C--T--------------C--------C--------------T--------T--T--C--C---C-A--T--T--------G---- |
| Seq-67 | 23 | 15745953 | 15746052 | 100 | 296 | --TT-------------T--------CA----C-----C--------------T--------------------------A--T--T-----G-G--CTC |
| Seq-67 | 23 | 125605734 | 125605833 | 100 | 297 | -----------------T--C-----C--------------------G-----------------T---------------------------------- |
| | | | | | | |
| Seq-68 | M | 6701 | 6800 | 100 | 298 | AACCATTTGGATACATAGGTATGGTCTGAGCTATGATATCAATTGGCTTCCTAGGGTTTATCGTGTGAGCACACCATATATTTACAGTAGGAATAGACGT |
| Seq-68 | 1 | 567251 | 567350 | 100 | 299 | ---------------------------------------------------------------------------------------------------- |
| Seq-68 | 2 | 131032284 | 131032383 | 100 | 300 | ----------G--T--G--C--A--A-----C--A---------------T-------------A--G--C-----C--------------------T-- |
| Seq-68 | 2 | 167271100 | 167271199 | 100 | 301 | ----------G-----G--C--------G-----A------G----------G--A--C--T--------T--------G--C-----G---------A- |
| Seq-68 | 3 | 171252207 | 171252306 | 100 | 302 | -CGGG--C-----T--G-A---A--------C--------------T--------A-----T--A--G--C----CC----------------------- |
| Seq-68 | 7 | 57256399 | 57256498 | 100 | 303 | -G--------G-----G--C--A--G-----C--A---------------T----------T--A--G--T-----C----------------C-T-T-- |
| Seq-68 | 8 | 104102235 | 104102334 | 100 | 304 | ----------T--T-----A-----G-----CG------T------T--T-----C------A-A--G--T--T-G----------A----G------A- |
| Seq-68 | 9 | 5097451 | 5097550 | 100 | 305 | -G--------G--T--G--C--A--A-----C--A-----T---------T----------T--A----------------------------C----A- |
| Seq-68 | 11 | 73221764 | 73221863 | 100 | 306 | -------------T-----------------------------------------------T--------------------------------G----- |
| Seq-68 | 12 | 40680151 | 40680250 | 100 | 307 | ----------G--T--G-----A--G-A---C--AG-----G---C----T-G---------A-A--G-TC-----C--------------------T-- |
| Seq-68 | 17 | 22027433 | 22027532 | 100 | 308 | -------C--G-----------------G-----A--------------------------T--A-----C--T--------C--------G-----T-- |
| Seq-68 | 23 | 125605834 | 125605933 | 100 | 309 | -------C-----T--------------------A-----------T---T----------T--------------------------------G----- |
| | | | | | | |
| Seq-69 | M | 6801 | 6900 | 100 | 310 | AGACACACGAGCATATTTCACCTCCGCTACCATAATCATCGCTATCCCCACCGGCGTCAAAGTATTTAGCTGACTCGCCACACTCCACGGAAGCAATATG |
| Seq-69 | 1 | 567351 | 567450 | 100 | 311 | ---------------------------------------------------------------------------------------------------- |
| Seq-69 | 2 | 131032384 | 131032483 | 100 | 312 | ---T---T----------------T-----T-----T--T-----T--T--T--T--------C--------G--A--T-----T---A-C--T-G---C |
| Seq-69 | 3 | 171252307 | 171252406 | 100 | 313 | ---T--------C--C--------------T-----T-----C--T-----T-----------------T--G-----T--G-----------T--C-CC |
| Seq-69 | 17 | 51183076 | 51183175 | 100 | 314 | CTCATTGA-CTGC-GGGA---------------------------T--------------------------------T--------------------- |
| Seq-69 | 23 | 125605934 | 125606033 | 100 | 315 | ------------C--------------------------------T------A--------------------------T------T-------------- |
| | | | | | | |
| Seq-70 | M | 6901 | 7000 | 100 | 316 | AAATGATCTGCTGCAGTGCTCTGAGCCCTAGGATTCATCTTTCTTTTCACCGTAGGTGGCCTGACTGGCATTGTATTAGCAAACTCATCACTAGACATCG |
| Seq-70 | 1 | 567451 | 567550 | 100 | 317 | -----------------------------------T--T------------------------------------------------------------- |
| Seq-70 | 9 | 5097657 | 5097756 | 100 | 318 | ---------C-C---A--T-------------------------------A-----A--T--A-T---------C-----T--T-----------T--TA |
| Seq-70 | 17 | 22027633 | 22027732 | 100 | 319 | -----G--CA-C-----A-----------------------C-----T--A--G--------A--G-A------C---------------T--------- |
| Seq-70 | 17 | 51183176 | 51183275 | 100 | 320 | --------------G--------------G--------T-----C-----T-----C-----A------------------------------------- |
| Seq-70 | 23 | 125606034 | 125606133 | 100 | 321 | --G--------------A--------------G-----T-----C-----T-----------A--C--------C---------------T--------- |
| | | | | | | |
| Seq-71 | M | 7001 | 7100 | 100 | 322 | TACTACACGACACGTACTACGTTGTAGCTCACTTCCACTATGTCCTATCAATAGGAGCTGTATTTGCCATCATAGGAGGCTTCATTCACTGATTTCCCCT |
| Seq-71 | 1 | 567551 | 567650 | 100 | 323 | ----------------------------C----------------------------------------------------------------------- |
| Seq-71 | 2 | 203478989 | 203479088 | 100 | 324 | -CT----------A--T--T-------GC--T-----------------------C--G-----------------------TG-C--------C----C |
| Seq-71 | 2 | 212644050 | 212644149 | 100 | 325 | CCT----T-----A--T--T--------C--T--------------------------A---C-C-----T-----------TG-C--------CT--T- |
| Seq-71 | 7 | 57256697 | 57256796 | 100 | 326 | -TT----T-----A--T--T--------C--T-----T--A---T-------------C--------T--T-----------TG-C--------C----- |
| Seq-71 | 17 | 22027733 | 22027832 | 100 | 327 | -------T--T--A--T--T-----G--C-----T-----C--T-----------------G-CA--------G--G--------C------------T- |
| Seq-71 | 17 | 51183276 | 51183375 | 100 | 328 | -------------A--------C-----C-----------C-----------------------C-----------G----------------------- |
| Seq-71 | 23 | 125606134 | 125606233 | 100 | 329 | -------------A--------C--------------T--C-----------------------C-------C------T-------------------- |
| | | | | | | |
| | | | | | | ******************************* $ ******************************* |
| Seq-72 | M | 7101 | 7200 | 100 | 330 | ATTCTCAGGCTACACCCTAGACCAAACCTACGCCAAAATCCATTTCACTATCATATTCATCGGCGTAAATCTAACTTTCTTCCCACAACACTTTCTCGGC |
| Seq-72 | 1 | 567651 | 567750 | 100 | 331 | ----------------------------------------------G----------------------------------------------------- |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-72 | 17 | 22027833 | 22027932 | 100 | 332 | ---------------A--C-G----G-T--T--------T--C--TG-C--------TG-A--------------C--------G--G------------ |
| Seq-72 | 17 | 51183376 | 51183475 | 100 | 333 | ---------------------------------T------------G----------------------C--------------------------T--- |
| Seq-73 | M | 7201 | 7300 | 100 | 334 | CTATCCGGAATGCCCCGACGTTACTCGGACTACCCCGATGCATACACCACATGAAACATCCTATCATCTGTAGGCTCATTCATTTCTCTAACAGCAGTAA |
| Seq-73 | 1 | 567751 | 567850 | 100 | 335 | --------------------------------T-----------------------T------------------------------------------- |
| Seq-73 | 3 | 120440919 | 120441018 | 100 | 336 | T----T-----A------T----T--T-----------C-----T-----G-----T--TT----------------------C--CT------------ |
| Seq-73 | 7 | 57256899 | 57256998 | 100 | 337 | --------T-----T---T-------CA-T--T-------T---------------T--TA-T-----CAG---------T-----C------------- |
| Seq-73 | 7 | 67562742 | 67562841 | 100 | 338 | ------A-T-----TT----------C--T--T--T--------------------T--TA-C-----------------T--C--A-----------T- |
| Seq-73 | 17 | 22027933 | 22028032 | 100 | 339 | -----T-AG---T-----T----T--C-----------------T------G----T--TT----------------------C--C----A-------G |
| Seq-73 | 17 | 51183476 | 51183575 | 100 | 340 | -----T-----A--------------------------------------------T-----------------------------C------------- |
| Seq-73 | 23 | 125606333 | 125606432 | 100 | 341 | -----T-----A--------------------------------------------T-----------------------------C------------- |
| Seq-74 | M | 7301 | 7400 | 100 | 342 | TATTAATAATTTTCATGATTTGAGAAGCCTTCGCTTCGAAGCGAAAAGTCCTAATAGTAGAAGAACCCTCCATAAACCTGGAGTGACTATATGGATGCCC |
| Seq-74 | 1 | 567851 | 567950 | 100 | 343 | ----------------A----------------------------------------------------------------------------------- |
| Seq-74 | 17 | 22028033 | 22028132 | 100 | 344 | -GC-------------A-CC-----GA----------A------------------AAT--GC----T----CT-----A-----G--G--G-------- |
| Seq-74 | 17 | 51183576 | 51183675 | 100 | 345 | -------------------------------------A------------------A-----------------------------------------G- |
| Seq-75 | M | 7401 | 7500 | 100 | 346 | CCCACCCTACCACACATTCGAAGAACCCGTATACATAAAATCTAGACAAAAAAGGAAGGAATCGAACCCCCCAAAGCTGGTTTCAAGCCAACCCCATGGC |
| Seq-75 | 1 | 567951 | 568050 | 100 | 347 | ---------------------------------------------------------------------------------------------------- |
| Seq-75 | 3 | 120441119 | 120441218 | 100 | 348 | T-----------T--G--T--------A--C---------C------G---------------C-------T---A-----------------T---AA- |
| Seq-75 | 17 | 22028133 | 22028232 | 100 | 349 | T-----------T-----TA-------A--C---------C---------------------T-----T--T--G---------------G--T---AA- |
| Seq-76 | M | 7501 | 7600 | 100 | 350 | CTCCATGACTTTTTCAAAAAGGTATTAGAAAAACCATTTCATAACTTTGTCAAAGTTAAATTATAGGCTAAATCCTATATATCTTAATGGCACATGCAGC |
| Seq-76 | 1 | 568051 | 568150 | 100 | 351 | ---------------------A------------------------------------------------------------------------------ |
| Seq-76 | 2 | 131033079 | 131033178 | 100 | 352 | ---TG----C--C----T---A------TG---TT------------------------G-------T---GC-G----------------C---A---T |
| Seq-76 | 3 | 120441219 | 120441318 | 100 | 353 | ---T-------------C---A-----------TT------------------------G---C---T---GC---------------------C----- |
| Seq-76 | 7 | 57257199 | 57257298 | 100 | 354 | ---T-CA-G---C--G-T---A------T----TT------------------------G-------T---GC------------------C---C---T |
| Seq-76 | 9 | 5098255 | 5098354 | 100 | 355 | ---TG-------C--G-T---A------C---TT----A-G------------------G--------------------G----------T---C---T |
| Seq-76 | 11 | 39788483 | 39788582 | 100 | 356 | ---T------C-C--G-T---A------T----TT---AT-------------------T-------T--------G---G----------T---C---T |
| Seq-76 | 13 | 97349967 | 97350066 | 100 | 357 | ---T-----------G-T---A------T----TT-----C--------C---------G-----A-T----C---G--------------C---C---- |
| Seq-76 | 17 | 22028233 | 22028332 | 100 | 358 | -C-T-------------C---A------G-----T------------C-----------G---C---T----C--CG-----------------C----- |
| | | | | | | ************************* $ ********************** |
| Seq-77 | M | 7601 | 7700 | 100 | 359 | GCAAGTAGGTCTACAAGACGCTACTTCCCCTATCATAGAAGAGCTTATCACCTTTCATGATCACGCCCTCATAATCATTTTCCTTATCTGCTTCCTAGTC |
| Seq-77 | 1 | 568151 | 568250 | 100 | 360 | --------------------------------------------------T------------------------------------------------- |
| Seq-77 | 3 | 120441319 | 120441418 | 100 | 361 | C---C----C--T-----T--C--A--------A-C---------A---G----C------------A-T--------C-----AT--A----------T |
| Seq-77 | 17 | 22028333 | 22028432 | 100 | 362 | C--GC-------T--------C--A--------------------A---G----C-----------------------C--T------A----T-----T |
| Seq-78 | M | 7701 | 7800 | 100 | 363 | CTGTATGCCCTTTTCCTAACACTCACAACAAAACTAACTAATACTAACATCTCAGACGCTCAGGAAATAGAAACCGTCTGAACTATCCTGCCCGCCATCA |
| Seq-78 | 1 | 568251 | 568350 | 100 | 364 | -----C---------------------------------------------------------------------------------------------- |
| | | | | | | ********************* |
| Seq-79 | M | 7801 | 7900 | 100 | 365 | TCCTAGTCCTCATCGCCCTCCCATCCCTACGCATCCTTTACATAACAGACGAGGTCAACGATCCCTCCCTTACCATCAAATCAATTGGCCACCAATGGTA |
| Seq-79 | 1 | 568351 | 568450 | 100 | 366 | ----------T---------------------------------------------------------T----------------------T-------- |
| Seq-79 | 17 | 22028529 | 22028628 | 100 | 367 | ----------A--T-----T-----------T-----G---G-------T--AA----T--C--T--TT-------T--------C--A--------A-- |
| | | | | | | $ *********************** |
| Seq-80 | M | 7901 | 8000 | 100 | 368 | CTGAACCTACGAGTACACCGACTACGGCGGACTAATCTTCAACTCCTACATACTTCCCCCATTATTCCTAGAACCAGGCGACCTGCGACTCCTTGACGTT |

TABLE 1-continued

| Mitochondria and Genomic (Nuclear) Paralogs | | | | | | |
|---|---|---|---|---|---|---|
| Seq. No. | Chr | Start | End | Length | SEQ ID NO: | Sequence |
| Seq-80 | 1 | 568451 | 568550 | 100 | 369 | ------------A--------------------------------------------------------------------------------------- |
| Seq-80 | 17 | 22028629 | 22028728 | 100 | 370 | ---------T--A------A-T--T--A---T----T--------T--T--------A---C-----T----C---A-T-----T-----T---A-A--- |
| Seq-81 | M | 8001 | 8100 | 100 | 371 | GACAATCGAGTAGTACTCCCGATTGAAGCCCCCATTCGTATAATAATTACATCACAAGACGTCTTGCACTCATGAGCTGTCCCCACATTAGGCTTAAAAA |
| Seq-81 | 1 | 568551 | 568650 | 100 | 372 | -------------------------G---------------------------------------A---------------------------------- |
| Seq-81 | 17 | 22028729 | 22028828 | 100 | 373 | --T-----------C--T--A-----------TG---A-------------------------C-A---------A------------------------ |
| Seq-82 | M | 8101 | 8200 | 100 | 374 | CAGATGCAATTCCCGGACGTCTAAACCAAACCACTTTCACCGCTACACGACCGGGGGTATACTACGGTCAATGCTCTGAAATCTGTGGAGCAAACCACAG |
| Seq-82 | 1 | 568651 | 568750 | 100 | 375 | ----------------------------------------T-----------A--------------C-----------------------------GTT |
| Seq-82 | 1 | 8969862 | 8969961 | 100 | 376 | ----------C--------C--------------A--------C--------A--A-----------------G--A--------CA----T-G------ |
| Seq-82 | 17 | 22028829 | 22028928 | 100 | 377 | ------T---C--------C--------------A--------C-T------A--A--------------------A--------C-----TG----T-- |
| Seq-83 | M | 8201 | 8300 | 100 | 378 | TTTCATGCCCATCGTCCTAGAATTAATTCCCCTAAAAATCTTTGAAATAGGGCCCGTATTTACCCTATAGCACCCCCTCTACCCCCTCTAGAGCCCACTG |
| Seq-83 | 1 | 568749 | 568848 | 100 | 379 | ---T------------------------------------------------------------------------------------------------ |
| | | | | | | *************************** |
| Seq-84 | M | 8301 | 8400 | 100 | 380 | TAAAGCTAACTTAGCATTAACCTTTTAAGTTAAAGATTAAGAGAACCAACACCTCTTTACAGTGAAATGCCCCAACTAAATACTACCGTATGGCCCACCA |
| Seq-84 | 1 | 568849 | 568948 | 100 | 381 | --------------------------------------------------------------------------------------------A------- |
| Seq-84 | 2 | 88124395 | 88124494 | 100 | 382 | CCGCCGCCG-CGCA-------------------------------------------------------------------------------------- |
| Seq-84 | 17 | 22029031 | 22029130 | 100 | 383 | --G----G--CC------------------------C--------T-GCT-T-------------C-----T------G-C--C---A----A-----T- |
| | | | | | | $$$$$$$          ************************ |
| Seq-85 | M | 8401 | 8500 | 100 | 384 | TAATTACCCCCATACTCCTTACACTATTCCTCATCACCCAACTAAAAATATTAAACACAAACTACCACCTACCTCCCTCACCAAAGCCCATAAAAATAAA |
| Seq-85 | 1 | 568949 | 569048 | 100 | 385 | -------------------------------------------------------T-----T-------------------------------------- |
| Seq-85 | 2 | 88124495 | 88124594 | 100 | 386 | -----G----------T--------------------T--G--------------T-----T-----T-----C-------------------------- |
| Seq-86 | M | 8501 | 8600 | 100 | 387 | AAATTATAACAAACCCTGAGAACCAAAATGAACGAAAATCTGTTCGCTTCATTCATTGCCCCCACAATCCTAGGCCTACCCGCCGCAGTACTGATCATTC |
| Seq-86 | 1 | 569049 | 569148 | 100 | 388 | ---C-----------------------------------------A------------------------------------------------------ |
| Seq-86 | 2 | 88124595 | 88124694 | 100 | 389 | ---C----GT-----------------G----------------------------------------------T--G---------------------- |
| Seq-86 | 2 | 131034053 | 131034152 | 100 | 390 | ---AC-------C--T-------T---------A-----------A-C-----T--C-----A-----------GT-----A-A----C---A-----CT |
| Seq-86 | 6 | 92436501 | 92436600 | 100 | 391 | ----C-C--T-----------G-----------------T-A---A-----------A----------T-----------T--T-------CA-----C- |
| Seq-86 | 7 | 57234880 | 57234979 | 100 | 392 | ---AC-------C--T---C---T------------------C--A-C-----T-C------G--------C--TT-------A----C---A-----CT |
| Seq-86 | 17 | 22029231 | 22029330 | 100 | 393 | ---CC-C--T--T--T-T---GT---------------------TA----------------------T--------T--A--T-----G-CA---G--- |
| Seq-87 | M | 8601 | 8700 | 100 | 394 | TATTTCCCCCTCTATTGATCCCCACCTCCAAATATCTCATCAACAACCGACTAATCACCACCCAACAATGACTAATCAAACTAACCTCAAAACAAATGAT |
| Seq-87 | 1 | 569149 | 569248 | 100 | 395 | -------------------------------------------------------T---------------------C---------------------- |
| Seq-87 | 2 | 88124695 | 88124794 | 100 | 396 | ----------------------------------C--------------------T---------------------C---------------------- |
| Seq-87 | 6 | 92436601 | 92436700 | 100 | 397 | ----------CT--C--G-T--A-TT--------C------------T----------T------------------C----C-T--T---------A-- |
| Seq-88 | M | 8701 | 8800 | 100 | 398 | AGCCATACACAACACTAAAGGACGAACCTGATCTCTTATACTAGTATCCTTAATCATTTTTATTGCCACAACTAACCTCCTCGGACTCCTGCCTCACTCA |
| Seq-88 | 1 | 569249 | 569348 | 100 | 399 | ------------------G--------------------------------------------------------------------------------- |
| Seq-88 | 2 | 88124795 | 88124894 | 100 | 400 | ---------------------G-----------------------------------------------------T--T-----G-----A-GC-GAGGC |
| Seq-88 | 8 | 20408741 | 20408840 | 100 | 401 | -ATG-----T----T---G-----------G--C---------A-C---C----T---------------G----T-----T------T-A--C------ |
| Seq-88 | 17 | 22029431 | 22029530 | 100 | 402 | -A-A---A-T----T------------------C--C--G---A-----C----T--C--C-----T-----C--T--------G---T----C------ |
| Seq-89 | M | 8801 | 8900 | 100 | 403 | TTTACACCAACCACCCAACTATCTATAAACCTAGCCATGGCCATCCCCTTATGAGCGGGCGCAGTGATTATAGGCTTTCGCTCTAAGATTAAAAATGCCC |
| Seq-89 | 1 | 569349 | 569448 | 100 | 404 | ---------------------------------------------------------------------------------------------------- |
| Seq-89 | 2 | 131034350 | 131034449 | 100 | 405 | -----------T-------C---A-----T-----T-CA--A--------------A---A----A--C-C------C----T---A-C------CT--T |
| Seq-90 | M | 8901 | 9000 | 100 | 406 | TAGCCCACTTCTTACCACAAGGCACACCTACACCCCTTATCCCCATACTAGTTATTATCGAAACCATCAGCCTACTCATTCAACCAATAGCCCTGGCCGT |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-90 | 1 | 569449 | 569548 | 100 | 407 | -------------------------------------------T-------------------------------------------------------- |
| Seq-90 | 2 | 203480860 | 203480959 | 100 | 408 | ----T-----T-------------------T---A--------T--G-----G--C--T-----T--T------T------T------G--A-CA--T-- |
| Seq-90 | 7 | 57235280 | 57235379 | 100 | 409 | ----T------C----------------C-T--TA----C---T--------A--C---A------CT--T-----T-----------G--A--A--T-- |
| Seq-90 | 9 | 5099929 | 5100028 | 100 | 410 | -G--TGG---T-------------------TG--A--------T--------A--C--T--------T------T-T--------------AT-A--T-- |
| Seq-90 | 17 | 22029630 | 22029729 | 100 | 411 | -------TC----G--------------CT--------C--T--------A--------C--------------T-T--C--------------A---A- |
| | | | | | | ************************************************ $ ********************** |
| Seq-91 | M | 9001 | 9100 | 100 | 412 | ACGCCTAACCGCTAACATTACTGCAGGCCACCTACTCATGCACCTAATTGGAAGCGCCACCCTAGCAATATCAACCATTAACCTTCCCTCTACACTTATC |
| Seq-91 | 1 | 569549 | 569648 | 100 | 413 | ------------------------------------------------------------A--------------T------------------------ |
| Seq-92 | M | 9101 | 9200 | 100 | 414 | ATCTTCACAATTCTAATTCTACTGACTATCCTAGAAATCGCTGTCGCCTTAATCCAAGCCTACGTTTTCACACTTCTAGTAAGCCTCTACCTGCACGACA |
| Seq-92 | 1 | 569649 | 569748 | 100 | 415 | --------------------------------------------------------------------T------------------------------- |
| Seq-92 | 17 | 22029830 | 22029929 | 100 | 416 | ------------T-G---T-------G--T--C---------------C-G--T-T------T-----------C-----G-----------A--T---- |
| Seq-93 | M | 9201 | 9300 | 100 | 417 | ACACATAATGACCCACCAATCACATGCCTATCATATAGTAAAACCCAGCCCATGACCCCTAACAGGGGCCCTCTCAGCCCTCCTAATGACCTCCGGCCTA |
| Seq-93 | 1 | 569749 | 569848 | 100 | 418 | ------------------------------------------------------G--------------------------------------------- |
| Seq-93 | 2 | 120969296 | 120969395 | 100 | 419 | -------------------A----------C-G------C-----------C----GA--G-----A--T--------T--------A--A--T-----G |
| Seq-93 | 2 | 131034750 | 131034849 | 100 | 420 | -T-----------------A----CA--------T----C-----------T-----AT----------T--------T--------A--A----C---- |
| Seq-93 | 2 | 203481159 | 203481258 | 100 | 421 | ----------------T-TA----------C--------C-----------C-----A--------A--T------T-T--------A--A--T-----G |
| Seq-93 | 3 | 72632514 | 72632613 | 100 | 422 | -T-----------------A----C-----C--C-----T--G--------T--G--AT-------A--T-----------------A--A--T------ |
| Seq-93 | 9 | 5100229 | 5100328 | 100 | 423 | -------------------A-------T-GC--------C-----------C-----A-------AA--T--------T--A-----A--A--T-----G |
| Seq-93 | 9 | 94871288 | 94871387 | 100 | 424 | -T----------------GA----------C----G---TGT---T-----T-----A--------A--T-----G--T--------A--A--T------ |
| Seq-93 | 17 | 22029930 | 22030029 | 100 | 425 | -T--------G-T------------------C-------------------------T--------------T-----------------A--------- |
| | | | | | | +++++++++++++++++++++++ *************************** $ *********** |
| Seq-94 | M | 9301 | 9400 | 100 | 426 | GCCATGTGATTTCACTTCCACTCCATAACGCTCCTCATACTAGGCCTACTAACCAACACACTAACCATATACCAATGGTGGCGCGATGTAACACGAGAAA |
| Seq-94 | 1 | 569849 | 569948 | 100 | 427 | -------------------------C---C-----------------------------------------------A---------------------- |
| | | | | | | ************************ ++++++++++++++++++++++++++ |
| Seq-95 | M | 9401 | 9500 | 100 | 428 | GCACATACCAAGGCCACCACACACCACCTGTCCAAAAAGGCCTTCGATACGGGATAATCCTATTTATTACCTCAGAAGTTTTTTTCTTCGCAGGATTTTT |
| Seq-95 | 1 | 569949 | 570048 | 100 | 429 | ----------------------------------G----------------------------------------------------------------- |
| Seq-95 | 2 | 120969496 | 120969595 | 100 | 430 | -T----TT-----------T---A--GT---------------C-A---G--A-----T-------- -T-------A-A--C-----T--T--T--C-- |
| Seq-95 | 6 | 153988650 | 153988749 | 100 | 431 | ------T------------T---T--ATC---------------------A-A------T----CG--TT-----G--G-----T-C---T--C--C-- |
| Seq-95 | 7 | 57235773 | 57235872 | 100 | 432 | -T----TT-----------T---A--AT-------------A-CT----T--A---G-A----------T---------A--------T--T-------- |
| Seq-95 | 13 | 24340119 | 24340218 | 100 | 433 | -T----TT----A----------A--A-CA-------------CT----T--A-----------C----TT--------A-----------C-----C-- |
| Seq-95 | 17 | 22030130 | 22030229 | 100 | 434 | -T----------A----------GT---C----------T------G--T--A-----TT----C--C-T---------C-----------T-----C-- |
| Seq-95 | 17 | 61470777 | 61470876 | 100 | 435 | -T----------------G----AT------------------C-A------A-----GT-C--C----TT--------C-----------T-----C-- |
| Seq-96 | M | 9501 | 9600 | 100 | 436 | CTGAGCCTTTTACCACTCCAGCCTAGCCCCTACCCCCCAACTAGGAGGGCACTGGCCCCCAACAGGCATCACCCCGCTAAATCCCCTAGAAGTCCCACTC |
| Seq-96 | 1 | 570049 | 570148 | 100 | 437 | ---------------------------T--C--------------G--A--------------------------------------------------- |
| Seq-96 | 17 | 22030230 | 22030329 | 100 | 438 | ------A--C--------------------C-----T-----------A-----A-----------------T--A--C--C------------------ |
| | | | | | | ************ $ ******************** |
| Seq-97 | M | 9601 | 9700 | 100 | 439 | CTAAACACATCCGTATTACTCGCATCAGGAGTATCAATCACCTGAGCTCACCATAGTCTAATAGAAAACAACCGAAACCAAATAATTCAAGCACTGCTTA |
| Seq-97 | 1 | 570149 | 570248 | 100 | 440 | -----------------------------G---------------------------------------------------------------------- |
| Seq-97 | 2 | 131035150 | 131035249 | 100 | 441 | --G--------T--------T--------G--T-----T--T-----C--T--C--CA----------T--T-----A---G-------------A---T |
| Seq-97 | 7 | 57235973 | 57236072 | 100 | 442 | -CG--T-----T--------T--------G--T-----T--------C--T--C--C-----------T--T-----A-----------------A---- |
| Seq-97 | 7 | 57259246 | 57259345 | 100 | 443 | -CG--T-----T--------T--------G--T-----T--------C--T--C--C-----------T--T-----A-----------------A---- |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-97 | 17 | 22030330 | 22030429 | 100 | 444 | -----------T---C----------G-----T-----T--T--------------C--------G-----TT-T--T---GC------------A---- |
| Seq-98 | M | 9701 | 9800 | 100 | 445 | TTACAATTTTACTGGGTCTCTATTTTACCCTCCTACAAGCCTCAGAGTACTTCGAGTCTCCCTTCACCATTTCCGACGGCATCTACGGCTCAACATTTTT |
| Seq-99 | M | 9801 | 9900 | 100 | 446 | TGTAGCCACAGGCTTCCACGGACTTCACGTCATTATTGGCTCAACTTTCCTCACTATCTGCTTCATCCGCCAACTAATATTTCACTTTACATCCAAACAT |
| Seq-99 | 2 | 95567160 | 95567259 | 100 | 447 | -A----T--------T---A-------T-----------A----TA---------G-----C-TC--------T---A--AC-----------T-GT--- |
| Seq-99 | 2 | 120970252 | 120970351 | 100 | 448 | -A---T------T--T-----------T--T-----CA-A-----A--T------------C--C------C-T---A---C--------------C--C |
| Seq-99 | 2 | 131035350 | 131035449 | 100 | 449 | -A----T--------TT-T---------A----------A-----------T---------C-TC--T-----T---A--AC-------------GC--- |
| Seq-99 | 2 | 203481748 | 203481847 | 100 | 450 | -AC------------T--T---T----T--T--------A-----A--T------------C--C---A----T---A---C----C---------T--C |
| Seq-99 | 15 | 58442575 | 58442674 | 100 | 451 | -A-------------T--T---------A--------C-G-----A--T------------C--C--T---------A---------------T--C--C |
| Seq-99 | 17 | 22030530 | 22030629 | 100 | 452 | ------T--G-----------G--C-C------C-----T-----A-----T---G-T---C-T------------T--A---T------------GT-C |
| Seq-100 | M | 9901 | 10000 | 100 | 453 | CACTTTGGCTTCGAAGCCGCCGCCTGATACTGGCATTTTGTAGATGTGGTTTGACTATTTCTGTATGTCTCCATCTATTGATGAGGGTCTTACTCTTTTA |
| Seq-100 | 1 | 143245677 | 143245776 | 100 | 454 | -------C---T------A-T--------TCAA--C-----------A--A--------CT-------T--T--T-----------A------------- |
| Seq-100 | 2 | 95567260 | 95567359 | 100 | 455 | -------C---T----GT--T--------T--A--C--CA-------A--A--------CT-------T--T--T-----------A------------- |
| Seq-100 | 2 | 120970352 | 120970451 | 100 | 456 | -----------T--------T--------T--A--C--CA-------A--AG-------CT-A--C-----TT----C--------A--C---------- |
| Seq-100 | 2 | 131035450 | 131035549 | 100 | 457 | --T--------T------A----------T--A--C-A---------A--A--------CTCA---A-T--T-----C---------------------- |
| Seq-100 | 2 | 203481848 | 203481947 | 100 | 458 | -------C---T----TT------G----T--A--C-----------A--A--------CT-A--------T-----------------C---------- |
| Seq-100 | 4 | 49248466 | 49248565 | 100 | 459 | -------C---T--------T--------TC-A--C-----------A--A--------CT-------T--T--T-----------A------------- |
| Seq-100 | 6 | 143398978 | 143399077 | 100 | 460 | -----------T---------A-T-A---T-AA--C--G--------A--A--------CT-A--------T-----C--------A--C-----C---- |
| Seq-100 | 6 | 153989150 | 153989249 | 100 | 461 | T-T----AA--T------A-T-----G--------C--------CA-A--A--T-----C--A-----T--T--------------A------------- |
| Seq-100 | 7 | 57236273 | 57236372 | 100 | 462 | -----------T----A----A-------T--A--C-----------A--A--------CT-----A-T--T--T--C--------A------------- |
| Seq-100 | 7 | 57259547 | 57259646 | 100 | 463 | -----------T-------TG--------T--A--C-----------A--A--------CT-C---A-T--T--T--C--------A------------- |
| Seq-100 | 9 | 5107065 | 5107164 | 100 | 464 | -----------T------A-T-------GT--A--C-----------A--A--------CT-A--------T-----C--------A--C---------- |
| Seq-100 | 11 | 81262696 | 81262795 | 100 | 465 | -------A---T---------A-------T-A--GC--C-C----A-A------------T-A--CA----TG----C-----------C---------- |
| Seq-100 | 15 | 58442675 | 58442774 | 100 | 466 | -----------T--------T--------T--A--C--CA-----A-A--AA-------CT-A--------T-----C--------A--C---------- |
| Seq-100 | 17 | 22030630 | 22030729 | 100 | 467 | -----C--------------T--T--------A--C-----------A-----------C--A--------T-----C--G-----A------------- |
| | | | | | | ++++++++++++++++++ $$$$$$$$$$$$ +++++++++++++++++++ |
| Seq-101 | M | 10001 | 10100 | 100 | 468 | GTATAAATAGTACCGTTAACTTCCAATTAACTAGTTTTGACAACATTCAAAAAAGAGTAATAAACTTCGCCTTAATTTTAATAATCAACACCCTCCTAGC |
| Seq-101 | 17 | 22030730 | 22030829 | 100 | 469 | -----G-C------AC-G-------------------C--T----C--G----------------C-G--AC--GCCC---C-G---------------- |
| Seq-102 | M | 10101 | 10200 | 100 | 470 | CTTACTACTAATAATTATTACATTTTGACTACCACAACTCAACGGCTACATAGAAAAATCCACCCCTTACGAGTGCGGCTTCGACCCTATATCCCCCGCC |
| | | | | | | +++++++++ $$$$ +++++++++++++++++++++++++ |
| Seq-103 | M | 10201 | 10300 | 100 | 471 | CGCGTCCCTTTCTCCATAAAATTCTTCTTAGTAGCTATTACCTTCTTATTATTTGATCTAGAAATTGCCCTCCTTTTACCCCTACCATGAGCCCTACAAA |
| Seq-103 | 17 | 22030929 | 22031028 | 100 | 472 | ---A-T--C--------------------GA-T-----C-----T-------C---C--------------AT-AC----------G--------C---- |
| Seq-104 | M | 10301 | 10400 | 100 | 473 | CAACTAACCTGCCACTAATAGTTATGTCATCCCTCTTATTAATCATCATCCTAGCCCTAAGTCTGGCCTATGAGTGACTACAAAAAGGATTAGACTGAGC |
| Seq-105 | M | 10401 | 10500 | 100 | 474 | CGAATTGGTATATAGTTTAAACAAAACGAATGATTTCGACTCATTAAATTATGATAATCATATTTACCAAATGCCCCTCATTTACATAAATATTATACTA |
| Seq-106 | M | 10501 | 10600 | 100 | 475 | GCATTTACCATCTCACTTCTAGGAATACTAGTATATCGCTCACACCTCATATCCTCCCTACTATGCCTAGAAGGAATAATACTATCGCTGTTCATTATAG |
| Seq-106 | 6 | 92436907 | 92437006 | 100 | 476 | --------T---------T-G---------A-C--CT----------A-----------G---------------G-----G-----A--A----C---A |
| Seq-106 | 7 | 57260142 | 57260241 | 100 | 477 | ----A------A--------G--G---T--A-C---T-A--C-----G-----A----C-----------------------T----AT-A----C---A |
| Seq-106 | 17 | 22031232 | 22031331 | 100 | 478 | --------T-C------GT-----------A-C--------------A-CG---------------------G--G------T----T--A----CG--A |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-107 | M | 10601 | 10700 | 100 | 479 | CTACTCTCATAACCCTCAACACCCACTCCCTCTTAGCCAATATTGTGCCTATTGCCATACTAGTCTTTGCCGCCTGCGAAGCAGCGGTGGGCCTAGCCCT |
| Seq-107 | 23 | 125606708 | 125606807 | 100 | 480 | G-GTAA----------------------------------------A-----CA----------------T------A-G-----A--A----------- |
| Seq-108 | M | 10701 | 10800 | 100 | 481 | ACTAGTCTCAATCTCCAACACATATGGCCTAGACTACGTACATAACCTAAACCTACTCCAATGCTAAAACTAATCGTCCCAACAATTATATTACTACCAC |
| Seq-108 | 2 | 120971147 | 120971246 | 100 | 482 | ------T--------T-----------T-----T--------A------C--T----T----A------A-T--TA-T------------C-GT-----A |
| Seq-108 | 2 | 131036246 | 131036345 | 100 | 483 | ------T-----T---------------T--A----T--G-----------TT----T-G-C-G-----A-T---A-T------------C-G------A |
| Seq-108 | 7 | 57237053 | 57237152 | 100 | 484 | ------T--C-----------C---A----------T---T----------TT----T-G---------A-T--TA-T------------C-G------A |
| Seq-108 | 9 | 94873087 | 94873186 | 100 | 485 | C------------------G----A-----------T-----A--T-----TT-----------C----A-T--TA-T------------C-GT---A-T |
| Seq-108 | 15 | 58443461 | 58443560 | 100 | 486 | ------T-----------------CA-------T--T-----A--T-----TT----T-----------G-T--TA-T------------C-GT------ |
| Seq-108 | 17 | 22031432 | 22031531 | 100 | 487 | ------------T--T----G---C--T-----T--T---------T-----T----------T-----T----TA----T-----C---C----T---A |
| Seq-108 | 23 | 125606808 | 125606907 | 100 | 488 | ---------------T----------------------------------G------------------------A----------C------------- |
| | | | | | | ++++++++++++++++++++++ $ ++++++++++++++++++++++++++ |
| Seq-109 | M | 10801 | 10900 | 100 | 489 | TGACATGACTTTCCAAAAAGCACATAATTTGAATCAACACAACCACCCACAGCCTAATTATTAGCATCATCCCCCTACTATTTTTTAACCAAATCAACAA |
| Seq-109 | 23 | 125606908 | 125607007 | 100 | 490 | -A------T-C---------A--T----------------------T----------------------C------------------------------ |
| | | | | | | +++++++++++++++++++ $ $ |
| Seq-110 | M | 10901 | 11000 | 100 | 491 | CAACCTATTTAGCTGTTCCCCAACCTTTTCCTCCGACCCCCTAACAACCCCCCTCCTAATACTAACTACCTGACTCCTACCCCTCACAATCATGGCAAGC |
| Seq-110 | 23 | 125607008 | 125607107 | 100 | 492 | ------------C----T-T----C--------------------G-----------------------------T------------------------ |
| | | | | | | +++++++++++++++++++++++ |
| Seq-111 | M | 11001 | 11100 | 100 | 493 | CAACGCCACTTATCCAGCGAACCACTATCACGAAAAAAACTCTACCTCTCTATACTAATCTCCCTACAAATCTCCTTAATTATAACATTCACAGCCACAG |
| Seq-111 | 23 | 125607108 | 125607207 | 100 | 494 | --G------C------A------------------------------------G-----------C--------------------------------G- |
| Seq-112 | M | 11101 | 11200 | 100 | 495 | AACTAATCATATTTTATATCTTCTTCGAAACCACACTTATCCCCACCTTGGCTATCATCACCCGATGAGGCAACCAGCCAGAACGCCTGAACGCAGGCAC |
| Seq-112 | 2 | 131036647 | 131036746 | 100 | 496 | -------T-----------TC----T---G-T-----------------AAT---T--T-----C--G--------A------T----C--T---A---- |
| Seq-112 | 7 | 57260746 | 57260845 | 100 | 497 | -------T-----------TC----T---G-T-----------T-----AAT---G-------CC-----T-----A-----------C--T---A--T- |
| Seq-113 | M | 11201 | 11300 | 100 | 498 | ATACTTCCTATTCTACACCCTAGTAGGCTCCCTTCCCCTACTCATCGCACTAATTTACACTCACAACACCCTAGGCTCACTAAACATTCTACTACTCACT |
| Seq-114 | M | 11301 | 11400 | 100 | 499 | CTCACTGCCCAAGAACTATCAAACTCCTGAGCCAACAACTTAATATGACTAGCTTACACAATAGCTTTTATAGTAAAGATACCTCTTTACGGACTCCACT |
| Seq-115 | M | 11401 | 11500 | 100 | 500 | TATGACTCCCTAAAGCCCATGTCGAAGCCCCCATCGCTGGGTCAATAGTACTTGCCGCAGTACTCTTAAAACTAGGCGGCTATGGTATAATACGCCTCAC |
| Seq-115 | 2 | 120971832 | 120971931 | 100 | 501 | -G-----------------C--A--------T--T-AC--C--------------A-----T---C----G----------G----G-----T-G--T-- |
| Seq-115 | 2 | 131036946 | 131037045 | 100 | 502 | -------T--------------A---A----T--T---A-C-----G--------A----G----C-------------------C----C---A--T-A |
| Seq-115 | 6 | 153990666 | 153990765 | 100 | 503 | -G---------G-------C--A-----------T--C--C--------------A---------C-----TA---------C--A--G---T-G----- |
| Seq-115 | 7 | 57237751 | 57237850 | 100 | 504 | -------T-------T-----A--------T--T--A--C-------------AGA-----T---C------C----A----C--C------T-G--T-- |
| Seq-115 | 7 | 57261048 | 57261147 | 100 | 505 | -------T-------------AC-------T--T--A--C---------------A-----T---C------C----A-------C--------GG-T-- |
| Seq-115 | 9 | 5108562 | 5108661 | 100 | 506 | -G--------A----------A--------T--T--C--C----C----------A--G------C--------------GC-----------G--T-- |
| Seq-115 | 11 | 81264219 | 81264318 | 100 | 507 | ----------C-------GA-A-----T--T--T--C--C---G-----------A---------C----------A----GCA--------TAG--T-- |
| Seq-115 | 14 | 84639220 | 84639319 | 100 | 508 | ----------C-----T-C--A-------TT--T--CA-C---------------A---------C----G-----T-------A-------T-G--T-- |
| Seq-115 | 15 | 58443978 | 58444077 | 100 | 509 | ----------C-------C--G--------T--T-----C---------------A-AG------C----G-----T-----------T-----G--T-- |
| Seq-116 | M | 11501 | 11600 | 100 | 510 | ACTCATTCTCAACCCCCTGACAAAACACATAGCCTACCCCTTCCTTGTACTATCCCTATGAGGCATAATTATAACAAGCTCCATCTGCCTACGACAAACA |
| Seq-116 | 2 | 120971932 | 120972031 | 100 | 511 | C--T--C----G------A---G--T-T-----------A-----CA--T-------------A--GG----G--------T--T--T-----------C |
| Seq-116 | 9 | 94873853 | 94873952 | 100 | 512 | C-----C----G------A-T-G--T-T---T-------------CA--------T-------A---G-------------T--T--T---A-------T |
| Seq-116 | 11 | 81264319 | 81264418 | 100 | 513 | C--T--C----G------A---G----T---------------T-CA------T---------G---G-------------T-CT--T--G------G-C |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-117 | M | 11601 | 11700 | 100 | 514 | GACCTAAAATCGCTCATTGCATACTCTTCAATCAGCCACATAGCCCTCGTAGTAACAGCCATTCTCATCCAAACCCCCTGAAGCTTCACCGGCGCAGTCA |
| Seq-118 | M | 11701 | 11800 | 100 | 515 | TTCTCATAATCGCCCACGGACTCACATCCTCATTACTATTCTGCCTAGCAAACTCAAACTACGAACGCACTCACAGTCGCATCATAATCCTCTCTCAAGG |
| Seq-119 | M | 11801 | 11900 | 100 | 516 | ACTTCAAACTCTACTCCCACTAATAGCTTTTTGATGACTTCTAGCAAGCCTCGCTAACCTCGCCTTACCCCCCACTATTAACCTACTGGGAGAACTCTCT |
| Seq-119 | 2 | 120972232 | 120972331 | 100 | 517 | C-------TA--G--T-----------C-C-----------------AT---A-------T-----------T--C-----T---G-A---T------T- |
| Seq-119 | 2 | 156167597 | 156167696 | 100 | 518 | C-----------G--T-----------C-C-----------------AT---A-C-----T---C-------T--C-----T---AGA----------T- |
| Seq-119 | 7 | 57238151 | 57238250 | 100 | 519 | G--------A-----------------C------------AG-----AT--TAT------T--------------C-----T---A------------T- |
| Seq-119 | 7 | 57261448 | 57261547 | 100 | 520 | T--------A-------------C---C------------A------A---TA-------T--------------C-C---T---A-A----------T- |
| Seq-120 | M | 11901 | 12000 | 100 | 521 | GTGCTAGTAACCACGTTCTCCTGATCAAATATCACTCTCCTACTTACAGGACTCAACATACTAGTCACAGCCCTATACTCCCTCTACATATTTACCACAA |
| Seq-121 | M | 12001 | 12100 | 100 | 522 | CACAATGGGGCTCACTCACCCACCACATTAACAACATAAAACCCTCATTCACACGAGAAAACACCCTCATGTTCATACACCTATCCCCCATTCTCCTCCT |
| Seq-122 | M | 12101 | 12200 | 100 | 523 | ATCCCTCAACCCCGACATCATTACCGGGTTTTCCTCTTGTAAATATAGTTTAACCAAAACATCAGATTGTGAATCTGACAACAGAGGCTTACGACCCCTT |
| Seq-123 | M | 12201 | 12300 | 100 | 524 | ATTTACCGAGAAAGCTCACAAGAACTGCTAACTCATGCCCCCATGTCTAACAACATGGCTTTCTCAACTTTTAAAGGATAACAGCTATCCATTGGTCTTA |
| Seq-123 | 1 | 181391978 | 181392077 | 100 | 525 | G-C-----------TGT----------------------------C---G---------------------G-------T-G--TC----G--------- |
| Seq-123 | 2 | 83042710 | 83042809 | 100 | 526 | --C--TG-------TATGTG----------------T--T-----C---------------------------------G-G--TC---AG--------- |
| Seq-123 | 2 | 120972629 | 120972728 | 100 | 527 | --C----A-----TTA-G----G--A-------TG----------C------------------------------A--T-G--T-G--T---------- |
| Seq-123 | 2 | 131037731 | 131037830 | 100 | 528 | -------A------TGTG---------------------------C--G----T-------------------G-------G-------TG-------C- |
| Seq-123 | 2 | 156167996 | 156168095 | 100 | 529 | --C---A-------TATG------T------G------A--A---C--------------C-----------G------T-G--TC----T--------- |
| Seq-123 | 7 | 57238545 | 57238644 | 100 | 530 | ------T-------TATG-----------------------TG--C---------------------G--G--G-------G--------G--------- |
| Seq-123 | 7 | 57261844 | 57261943 | 100 | 531 | ------T-------TATG---------------------------C---------------------G--G--G-------G----------------C- |
| Seq-123 | 9 | 5109356 | 5109455 | 100 | 532 | --C----A------TATG---------------------------C-------T-------------------------TGG--TC----G----C---- |
| Seq-123 | 11 | 81265012 | 81265111 | 100 | 533 | --C----A-----TTATG-----------------C---------C------------------------------A--T-G--G--------------- |
| Seq-123 | 14 | 84640014 | 84640113 | 100 | 534 | --A-G--A------TATGT--------------------------C------------T-C------------------T-G--T--------------- |
| Seq-123 | 16 | 69392576 | 69392675 | 100 | 535 | --C --TG------TATCTG-C---------------T----------------------------------------CT-G--TC-----C---A---- |
| Seq-123 | 19 | 57433652 | 57433751 | 100 | 536 | --C-----------TATG---------G-------------A--A-A------T-----A-------------------T-G--T--A----------A- |
| Seq-124 | M | 12301 | 12400 | 100 | 537 | GGCCCCAAAAATTTTGGTGCAACTCCAAATAAAAGTAATAACCATGCACACTACTATAACCACCCTAACCCTGACTTCCCTAATTCCCCCCATCCTTACC |
| Seq-1M | M | 12401 | 12500 | 100 | 538 | ACCCTCGTTAACCCTAACAAAAAAAACTCATACCCCCATTATGTAAAATCCATTGTCGCATCCACCTTTATTATCAGTCTCTTCCCCACAACAATATTCA |
| Seq-126 | M | 12501 | 12600 | 100 | 539 | TGTGCCTAGACCAAGAAGTTATTATCTCGAACTGACACTGAGCCACAACCCAAACAACCCAGCTCTCCCTAAGCTTCAAACTAGACTACTTCTCCATAAT |
| Seq-126 | 14 | 84640221 | 84640320 | 100 | 540 | -A---AC------------C--------A--------T----TA-----A-----TCT-A-A-----A-------------C--------------C--- |
| Seq-127 | M | 12601 | 12700 | 100 | 541 | ATTCATCCCTGTAGCATTGTTCGTTACATGGTCCATCATAGAATTCTCACTGTGATATATAAACTCAGACCCAAACATTAATCAGTTCTTCAAATATCTA |
| Seq-127 | 2 | 83043109 | 83043208 | 100 | 542 | ---T-----C------C-A---A----C--A--T--TG--A--------A-A--------------------T----------CA--T---------T-- |
| Seq-127 | 7 | 57262230 | 57262329 | 100 | 543 | ---T-----A------C-A--T--C--C--A--T--T-G----------A-A--G--------A-----T--C-----------A--T---------T-- |
| Seq-127 | 11 | 81265410 | 81265509 | 100 | 544 | G--T-----A------G-A--T-----C--A--T--TG---------G-A-A-----C--------------T-----------A--T--------CT-- |
| Seq-127 | 15 | 58445062 | 58445161 | 100 | 545 | ---T-----A--G---C-A--T-----C--A--T--TG----G------A-A--------------------T--T-C------A--T---------T-- |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-128 | M | 12701 | 12800 | 100 | 546 | CTCATTTTCCTAATTACCATACTAATCTTAGTTACCGCTAACAACCTATTCCAACTGTTCATCGGCTGAGAGGGCGTAGGAATTATATCCTTCTTGCTCA |
| Seq-128 | 5 | 93903199 | 93903298 | 100 | 547 | --T----------C----------TC----C-----C----------T-----C-------------------------C--G--T---C-A---- |
| | | | | | | ++++++++++++++++++$$$$$$$$$$$$$$$$$$$$$$$$$ ++++++++++++++++++++ |
| Seq-129 | M | 12801 | 12900 | 100 | 548 | TCAGTTGATGATACGCCCGAGCAGATGCCAACACAGCAGCCATTCAAGCAGTCCTATACAACCGTATCGGCGATATCGGTTTCATCCTCGCCTTAGCATG |
| Seq-129 | 5 | 93903299 | 93903398 | 100 | 549 | --G-------G--T--T---A---------------------C-C----A---------------T-----C--T--C--------A---C------- |
| Seq-130 | M | 12901 | 13000 | 100 | 550 | ATTTATCCTACACTCCAACTCATGAGACCCACAACAAATAGCCCTTCTAAACGCTAATCCAAGCCTCACCCCACTACTAGGCCTCCTCCTAGCAGCAGCA |
| Seq-130 | 5 | 93903399 | 93903498 | 100 | 551 | ---CC---------------------A------G-----CT---C------A----C--TGA-T-T-TT----------TT-----T----------- |
| Seq-131 | M | 13001 | 13100 | 100 | 552 | GGCAAATCAGCCCAATTAGGTCTCCACCCCTGACTCCCCTCAGCCATAGAAGGCCCCACCCCAGTCTCAGCCCTACTCCACTCAAGCACTATAGTTGTAG |
| Seq-131 | 2 | 83043509 | 83043608 | 100 | 553 | --A--G-----T-----C--C-----TA-------T--A--CA---------T--A-------------------------C--------C---A--- |
| Seq-131 | 2 | 120973719 | 120973818 | 100 | 554 | --A--G-----TA----CAAC-----T----------A--C-------------A----------G-----G-------C------G--------- |
| Seq-131 | 2 | 131038518 | 131038617 | 100 | 555 | --A---A--------C-T--C------T---C---T--T--C-----G--------AG----T-------------------T--T-A-----C---G- |
| Seq-131 | 2 | 156168791 | 156168890 | 100 | 556 | --A--G-----T-----CA-------T-------T--A--T--TG--T-------A---G---------T----------T-------------C-- |
| Seq-131 | 3 | 106618267 | 106618366 | 100 | 557 | --A-------------T--C-----T--T-----T--A-----T----------A--A------A---TT--G-----T--T-----A---------- |
| Seq-131 | 5 | 93903499 | 93903598 | 100 | 558 | --A--------T----------T--T---------------------------T-----CA------------T---------C-C---------- |
| Seq-131 | 7 | 57239333 | 57239432 | 100 | 559 | --A--G-----T-----T--C---T---------CT--T--C-----G-----T--A-------------------------T---G--G--------- |
| Seq-131 | 7 | 57262633 | 57262732 | 100 | 560 | --A--G-----T-----T--C-------------T--T--CA----G--------A-------C-------G---------T--------------- |
| Seq-131 | 9 | 5110127 | 5110226 | 100 | 561 | --A--G-----TA----C--C-----T--------T--A--C-------------A-------C---------G--------C--------------- |
| Seq-131 | 10 | 2277871 | 2277970 | 100 | 562 | A--CTCAA-TAG--G--T----------------T-----G--T----------A--------T----------------C--------------G- |
| Seq-131 | 11 | 81265806 | 81265905 | 100 | 563 | --A--G-----T--G--CA-C-----T------T-T--A----------------AG-----------------G-----C---------------- |
| Seq-131 | 13 | 85096902 | 85097001 | 100 | 564 | A---G------T-----T------------A-----TG-----T-------C---AG-A--CA-----------------T-----A-----G---- |
| Seq-131 | 14 | 84640720 | 84640819 | 100 | 565 | --A--G-----T-----C--C-----T--------T--A-GC----------T-AA------AC------------------C---------------- |
| Seq-131 | 15 | 46633609 | 46633708 | 100 | 566 | --A--G-----T-----CA-C-----T--------T--A--------C--------A------------AT-----------C---G----------- |
| Seq-131 | 15 | 58445461 | 58445560 | 100 | 567 | --A--G-----T-----T--C--T--T--------T--T--CA-TG---------A--------T-----------------T--------------C |
| Seq-132 | M | 13101 | 13200 | 100 | 568 | CAGGAATCTTCTTACTCATCCGCTTCCACCCCCTAGCAGAAAATAGCCCACTAATCCAAACTCTAACACTATGCTTAGGCGCTATCACCACTCTGTTCGC |
| Seq-132 | 4 | 17063502 | 17063601 | 100 | 569 | -T---G-----C------------T------T-G--------C-A----AC--------TCT-C---------C-------C-C---T--C-----T-- |
| Seq-132 | 5 | 93903599 | 93903698 | 100 | 570 | -T--GG----TC------A------------T-----------A-----C------------C---------C-------C-C------C-------- |
| Seq-133 | M | 13201 | 13300 | 100 | 571 | AGCAGTCTGCGCCCTTACACAAAATGACATCAAAAAAATCGTAGCCTTCTCCACTTCAAGTCAACTAGGACTCATAATAGTTACAATCGGCATCAACCAA |
| Seq-133 | 2 | 131038717 | 131038816 | 100 | 572 | ----A----T--TT-A-----------T--TG------------AC-------C---------------C--T-G---ACC-----T-----T--T--- |
| Seq-133 | 4 | 17063602 | 17063701 | 100 | 573 | ---------T--T-----------C-------------T-----------------G--C-----------T---G----C-----T-----------G |
| Seq-133 | 5 | 93903699 | 93903798 | 100 | 574 | ---------T--T------------------------------------T--------C---T----------GG----C----------------- |
| Seq-133 | 7 | 57239533 | 57239632 | 100 | 575 | ----A-T--T--T--A----------TG-----C-----------A--------C---------------C--T-------CC-----G----AG--T--- |
| Seq-133 | 7 | 57262833 | 57262932 | 100 | 576 | ----A-T--T--T--A----------TT-----C-----------G--A-----C---------------C--T--------C----CT-----T--T--- |
| Seq-133 | 7 | 112012836 | 112012935 | 100 | 577 | ---GA-------T--G-----------T--TT--------A----G----T---C-----C--G--G--C--T---------C-----T-----T--T--- |
| Seq-133 | 9 | 5110327 | 5110426 | 100 | 578 | ----A-------T--A-----------T--TT--------A----A--------C---------G--G--C--T-CG-----C-----T-----T--T--G |
| Seq-133 | 13 | 85097102 | 85097201 | 100 | 579 | ----A-----A-T--A--------------AT-------T--G--A--T-T---C--G---T-------------------------T--T--T------ |
| Seq-133 | 13 | 96344942 | 96345041 | 100 | 580 | ----A----T--T--A-----------T-------C---G-----AC---------------------AC--T-C----C-C-----T-A---T--T--- |
| Seq-134 | M | 13301 | 13400 | 100 | 581 | CCACACCTAGCATTCCTGCACATCTGTACCCACGCCTTCTTCAAAGCCATACTATTTATGTGCTCCGGGTCCATCATCCACAACCTTAACAATGAACAAG |
| Seq-134 | 2 | 120974184 | 120974283 | 100 | 582 | -----------------T--------C-T---------T-AA-----T---T-------A--T--A--C-----T-----T-----C--TG--------- |
| Seq-134 | 2 | 131038817 | 131038916 | 100 | 583 | -----------------A--------C-----------T-------TT---T----------T--A--A-------------G---C---G--------- |
| Seq-134 | 2 | 202422542 | 202422641 | 100 | 584 | -----T--------T--C--T--------A--T--A-----------T--G--G-----A------A-A--------T--T--------TG----C--G- |
| Seq-134 | 5 | 93903799 | 93903898 | 100 | 585 | ---T-------------A--------------T--T---------------T-------A--------A-----T--T--T-----C------------- |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-134 | 7 | 57239633 | 57239732 | 100 | 586 | -----------------A-----T--C------A----T--T-----T---T-------AA-T--A--A-----------T-----C------A------ |
| Seq-134 | 7 | 57262933 | 57263032 | 100 | 587 | G----------------A--T-----C-----T-----T-CT-----T---T-------A--T--A--A-------C---T-----C---G--------- |
| Seq-134 | 9 | 5110427 | 5110526 | 100 | 588 | -----T-----------T-----G--C------A----T--T-----T---T-------A-----A--C--------------T--C--TG--------- |
| Seq-134 | 11 | 47345580 | 47345679 | 100 | 589 | ---T-T-----------A--------------T--------T--------------C--A--------A--T-----T--T-----C---------T--- |
| Seq-134 | 11 | 81266104 | 81266203 | 100 | 590 | -----T-----------T--------------T-----T--T-----T---TA------A--T--A--------------T--T--C--TG--------- |
| Seq-134 | 14 | 84641019 | 84641118 | 100 | 591 | -----------------T----------TT--T-----T--T-----T--GT-------A--T--A-A------------T-G---C--TG--------C |
| Seq-135 | M | 13401 | 13500 | 100 | 592 | ATATTCGAAAAATAGGAGGACTACTCAAAACCATACCTCTCACTTCAACCTCCCTCACCATTGGCAGCCTAGCATTAGCAGGAATACCTTTCCTCACAGG |
| Seq-135 | 5 | 93903899 | 93903998 | 100 | 593 | -C----------------------------TT-----C--------------------------------G---C-T--------G--C--------G-- |
| Seq-135 | 15 | 58445848 | 58445947 | 100 | 594 | -C--CT-----------------T----G--TC---TC--------CT-------T-T------------CA--C-TA----T--G-------------- |
| Seq-136 | M | 13501 | 13600 | 100 | 595 | TTTCTACTCCAAAGACCACATCATCGAAACCGCAAACATATCATACACAAACGCCTGAGCCCTATCTATTACTCTCATCGCTACCTCCCTGACAAGCGCC |
| Seq-136 | 2 | 120974384 | 120974483 | 100 | 596 | C--T-----T-------TT-----------------T-C---------C--------------T-----------T--T--C----TTT-A---GCT-T- |
| Seq-136 | 5 | 93903999 | 93904098 | 100 | 597 | C-----T----T-----T-------A----------T-----------C--------------------------------C--T-----A--------- |
| Seq-136 | 15 | 58445948 | 58446047 | 100 | 598 | C--T--T--T-------T---T--T-----T-------C---------C--------------T-----------T-----A--------A---GCT-T- |
| Seq-137 | M | 13601 | 13700 | 100 | 599 | TATAGCACTCGAATAATTCTTCTCACCCTAACAGGTCAACCTCGCTTCCCCACCCTTACTAACATTAACGAAAATAACCCCACCCTACTAAACCCCATTA |
| Seq-137 | 5 | 93904099 | 93904198 | 100 | 600 | A-------------------C--------------C--------T-----A-----A--C-----C--------C-----T-----G----G------C- |
| Seq-138 | M | 13701 | 13800 | 100 | 601 | AACGCCTGGCAGCCGGAAGCCTATTCGCAGGATTTCTCATTACTAACAACATTTCCCCCGCATCCCCCTTCCAAACAACAATCCCCCTCTACCTAAAACT |
| Seq-138 | 5 | 93904199 | 93904298 | 100 | 602 | -------AA--AT---------------------------C--C-G--------T----A-----AT-CC-----TG--------A--TC--T------- |
| | | | | | | +++++++++++++++++++              $                     $                       +++++++++++++++++++++ |
| Seq-139 | M | 13801 | 13900 | 100 | 603 | CACAGCCCTCGCTGTCACTTTCCTAGGACTTCTAACAGCCCTAGACCTCAACTACCTAACCAACAAACTTAAAATAAAATCCCCACTATGCACATTTTAT |
| Seq-139 | 5 | 93904299 | 93904398 | 100 | 604 | ---------A-GCA----C--------------G---------------------T-------------C---------AA------G--T------C-C |
| Seq-140 | M | 13901 | 14000 | 100 | 605 | TTCTCCAACATACTCGGATTCTACCCTAGCATCACACACCGCACAATCCCCTATCTAGGCCTTCTTACGAGCCAAAACCTGCCCCTACTCCTCCTAGACC |
| | | | | | | +++++++++++++++++++++                   $ |
| Seq-141 | M | 14001 | 14100 | 100 | 606 | TAACCTGACTAGAAAAGCTATTACCTAAAACAATTTCACAGCACCAAATCTCCACCTCCATCATCACCTCAACCCAAAAAGGCATAATTAAACTTTACTT |
| Seq-141 | 5 | 93904499 | 93904598 | 100 | 607 | ----T-----------A---A------------CC------T------C----G-------------------T--------------C----------- |
| | | | | | | +++++++++++++++++++++++          +++++++++++++++++++++++         $                               +++ |
| Seq-142 | M | 14101 | 14200 | 100 | 608 | CCTCTCTTTCTTCTTCCCACTCATCCTAACCCTACTCCTAATCACATAACCTATTCCCCCGAGCAATCTCAATTACAATATATACACCAACAAACAATGT |
| Seq-142 | 5 | 93904597 | 93904696 | 100 | 609 | TTC-------------------C----------C------------------G--A---------C-------------------------------G-- |
| | | | | | | +++++++++++++++++++++++++ |
| Seq-143 | M | 14201 | 14300 | 100 | 610 | TCAACCAGTAACCACTACTAATCAACGCCCATAATCATACAAAGCCCCGCACCAATAGGATCCTCCCGAATCAACCCTGACCCCTCTCCTTCATAAATT |
| Seq-143 | 2 | 131039713 | 131039812 | 100 | 611 | --------C------C--C-------A--T-----T---G-----A--------C-C--A---T--A----C--------G------A--C---A----- |
| Seq-143 | 5 | 93904697 | 93904796 | 100 | 612 | ------------T--C--C------T----G-----G--T-----------------------------------TG---G------C------------ |
| Seq-143 | 9 | 80580108 | 80580207 | 100 | 613 | --------C---T--C--C-------A--------T---T-----A---A----C-C--A------A-------------T------A--C---A---CC |
| Seq-143 | 23 | 5087007 | 5087106 | 100 | 614 | --------C---T--C----G-----AT-----------T-----A--------T----A------A--------------------A--A---A----C |
| Seq-144 | M | 14301 | 14400 | 100 | 615 | ATTCAGCTTCCTACACTATTAAAGTTTACCACAACCACCACCCCATCATACTCTTTCACCCACAGCACCAATCCTACCTCCATCGCTAACCCCACTAAAA |
| Seq-144 | 5 | 9 3904797 | 93904896 | 100 | 616 | -----A-----------------A--C-------T---------------T-T---T-----T-A---T--C--C--T--T--T-----T---------- |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-145 | M | 14401 | 14500 | 100 | 617 | CACTCACCAAGACCTCAACCCCTGACCCCCATGCCTCAGGATACTCCTCAATAGCCATCGCTGTAGTATATCCAAAGACAACCATCATTCCCCCTAAATA |
| Seq-145 | 5 | 93904897 | 93904996 | 100 | 618 | ----T-------------T------------------------------------T--T--------G--C-----A--------T--A----------- |
| Seq-145 | 7 | 57264010 | 57264109 | 100 | 619 | A-G-TC-T--A-------TA-T---T--T-----------G--T---------------A-C-C------------A-----------C-----C----- |
| Seq-145 | 7 | 153665815 | 153665914 | 100 | 620 | -----C-T--A--T----TG--------T--------C-TG--T----A---------------------A-----A-----T--------G-GC--C-- |
| Seq-145 | 17 | 22018556 | 22018655 | 100 | 621 | -------------T----TT-------------T------------------------T--CA-------------A---------G-A-------G--- |
| Seq-146 | M | 14501 | 14600 | 100 | 622 | AATTAAAAAAACTATTAAACCCATATAACCTCCCCCAAAATTCAGAATAATAACACACCCGACCACACCGCTAACAATCAGTACTAAACCCCCATAAATA |
| Seq-146 | 5 | 93904998 | 93905097 | 100 | 623 | -T----------C--------T---C-----------T----T-A------G-T-----A---------A---------AC------G------------ |
| Seq-146 | 17 | 22018657 | 22018756 | 100 | 624 | -T-A--------C------------------------T--------------------A--T-------A----T-----A-----T------------- |
| Seq-147 | M | 14601 | 14700 | 100 | 625 | GGAGAAGGCTTAGAAGAAAACCCCACAAACCCCATTACTAAACCCACACTCAACAGAAACAAAGCATACATCATTATTCTCGCACGGACTACAACCACGA |
| Seq-147 | 5 | 93905098 | 93905197 | 100 | 626 | ------------------------------------------A-------T----A---T--------TG------------------------------ |
| Seq-147 | 17 | 22018757 | 22018856 | 100 | 627 | --------T--------------T--------T---------G-------T--TGAT--T--------TG-G----A--C-A--T---T----------- |
| Seq-148 | M | 14701 | 14800 | 100 | 628 | CCAATGATATGAAAAACCATCGTTGTATTTCAACTACAAGAACACCAATGACCCCAATACGCAAAATTAACCCCCTAATAAAATTAATTAACCACTCATT |
| Seq-148 | 2 | 131040206 | 131040305 | 100 | 629 | -T-------A----------T--CA-----------T--------T-------AT------T----CA--T--A---------A-C-----TT-T---C- |
| Seq-148 | 5 | 93905198 | 93905297 | 100 | 630 | ---------------------------------------------T-----------C--------CC---T-GT------------------------- |
| Seq-148 | 15 | 58447112 | 58447211 | 100 | 631 | -T----G--------------A--------------T--------T-------AA----T---C--CGC---TG---------A-T----GT--T----- |
| Seq-148 | 17 | 22018857 | 22018956 | 100 | 632 | ------------G--------A--T------G----T--------------------C-T-T----C---T--A---G-----A----C---------C- |
| Seq-149 | M | 14801 | 14900 | 100 | 633 | CATCGACCTCCCCACCCCATCCAACATCTCCGCATGATGAAACTTCGGCTCACTCCTTGGCGCCTGCCTGATCCTCCAAATCACCACAGGACTATTCCTA |
| Seq-149 | 5 | 93905298 | 93905397 | 100 | 634 | T--T--T--------T-----T---------A-----------C----------T--------------A-C-A-T-----G-T---------------- |
| Seq-149 | 13 | 96346876 | 96346975 | 100 | 635 | T--T--T--------A--------------TA----------T--T--------T-----T------T-A--T-----G-C--T-------T----T--G |
| Seq-149 | 17 | 22018957 | 22019056 | 100 | 636 | T-----T------G-----------------AT------G------A---TG--T-----T------T-A-C---T-----T-TT--------------- |
| Seq-149 | 23 | 5087606 | 5087705 | 100 | 637 | ------T--------T-----T--T-----TAT----------C--T-------T------A-----T-AT----T-------T------G--------- |
| Seq-150 | M | 14901 | 15000 | 100 | 638 | GCCATACACTACTCACCAGACGCCTCAACCGCCTTTTCATCAATCGCCCACATCACTCGAGACGTAAATTATGGCTGAATCATCCGCTACCTTCACGCCA |
| Seq-150 | 5 | 93905398 | 93905497 | 100 | 639 | -----------A--------T--T-----------C--------------------CT----------CC----------------------C-----T- |
| Seq-150 | 17 | 22019057 | 22019156 | 100 | 640 | --T----G---------------------------C--C---G---T---------------T-----C-----------------------C--T---- |
| Seq-150 | 23 | 5087706 | 5087805 | 100 | 641 | ------------A--------A--A----T-----C--T-----G-----T--T-A------T--G--C-----------T----A---T--C---A-T- |
| Seq-151 | M | 15001 | 15100 | 100 | 642 | ATGGCGCCTCAATATTCTTTATCTGCCTCTTCCTACACATCGGGCGAGGCCTATATTACGGATCATTTCTCTACTCAGAAACCTGAAACATCGGCATTAT |
| Seq-151 | 2 | 156170798 | 156170897 | 100 | 643 | ----------------T--C-----------------TG-T--C------T----C--T---------A-A-T-CT------------T--T-ATT--T- |
| Seq-151 | 5 | 8619543 | 8619642 | 100 | 644 | -------T--C-----T--C------------T-------T--CT----TT----C--T---------ACA-TTCT------------T----------- |
| Seq-151 | 5 | 93905498 | 93905597 | 100 | 645 | -C--T--------------C-----------------------C------T----C--T--C-----C------CT---------------T--T----- |
| Seq-151 | 7 | 57241291 | 57241390 | 100 | 646 | -----C-T----C------C------------------G----CG-----T-------T--G-----CG-AC-T-T------A-------CT-------- |
| Seq-151 | 7 | 112014629 | 112014728 | 100 | 647 | ----T--T--------T--C------------T-------T--C-A---GT----C-----G-----A--A-T-C-------------T--T-------- |
| Seq-151 | 17 | 22019157 | 22019256 | 100 | 648 | ----------------T--C-----------------T--T--C--------G--C--T--C-T----------CT---------------T-----C-- |
| Seq-151 | 23 | 5087806 | 5087905 | 100 | 649 | ---A---T----C------C-----T------------T-TA-C------T-------T--C-----CA-A----T-----A---------T-A------ |
| Seq-151 | 23 | 125863340 | 125863439 | 100 | 650 | ----T-----------T--C------------T-------T--C-A----T----C--T--G-----C--A-TTCT------------T--T-------- |
| Seq-152 | M | 15101 | 15200 | 100 | 651 | CCTCCTGCTTGCAACTATAGCAACAGCCTTCATAGGCTATGTCCTCCCGTGAGGCCAAATATCATTCTGAGGGGCCACAGTAATTACAAACTTACTATCC |
| Seq-152 | 2 | 83045608 | 83045707 | 100 | 652 | ----T-A--CA-------G--------A-----------CC-G-----A--------G--------------T-----------------TC-------G |
| Seq-152 | 2 | 131040606 | 131040705 | 100 | 653 | T---T-----A----C-C---------G--T-----------G--T--A---------------C-------C----------CC------C--A----A |
| Seq-152 | 5 | 8619643 | 8619742 | 100 | 654 | ------A--CA-------G--------A-----------C--G-----A-A------G-----T--------CA-T------G-------TC-------A |
| Seq-152 | 5 | 93905598 | 93905697 | 100 | 655 | ----T-AT-CA----C--------------------------------A-------------TC--------A-----G--------G--TC--T-G--- |
| Seq-152 | 7 | 57241391 | 57241490 | 100 | 656 | ------A--CAT---C-C---------A--T-----------G--T--A--------G---C----------CA-T--------C------C-------A |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-152 | 7 | 57264700 | 57264799 | 100 | 657 | G-----A--CA----C-C---------A--T-----------T--T--A-----------------------C--T--C----CC------C-------A |
| Seq-152 | 7 | 112014729 | 112014828 | 100 | 658 | T-----AT-CA--------------A-A--------------G-----A----C------------------CA-T--------------T--------A |
| Seq-152 | 8 | 18707079 | 18707178 | 100 | 659 | ------A--CA-------G--------A-----------CA-G-----A--------G---------G----C--T--------------TC-------A |
| Seq-152 | 11 | 81267892 | 81267991 | 100 | 660 | ------C--CA---------T------A-------C------G----G------------------------T--T----------T----C--TCC--A |
| Seq-152 | 14 | 84643115 | 84643214 | 100 | 661 | -TA------CA------------A---A----C---A--CA-G-----A--------G--------------C--T---A----------TC-------A |
| Seq-152 | 23 | 5087906 | 5088005 | 100 | 662 | TG-------CA----C-----------A--T-----------A--T--A-----------------------C--T-----G--------TC-------A |
| Seq-152 | 23 | 125863441 | 125863540 | 100 | 663 | -TC-TACT-AA----------------A-----------C--G-----A-----------------------T--T--------------TC------TA |
| Seq-153 | M | 15201 | 15300 | 100 | 664 | GCCATCCCATACATTGGGACAGACCTAGTTCAATGAATCTGAGGAGGCTACTCAGTAGACAGTCCCACCCTCACACGATTCTTTACCTTTCACTTCATCT |
| Seq-153 | 5 | 93905698 | 93905797 | 100 | 665 | -----T--------C--A-----------C------G-------T--------------A--A--------------------------C--------TC |
| Seq-153 | 7 | 57264800 | 57264899 | 100 | 666 | -----------T-----A--T-----T--C---------G----T--A-TTC----T----AAG----T--T------------CG---C---------- |
| Seq-153 | 7 | 112014829 | 112014928 | 100 | 667 | -----------T-----A--T---T-T--A--------------G--A-T----T-T----AAG----------------T---G----C--T------- |
| Seq-153 | 15 | 58447613 | 58447712 | 100 | 668 | -----T--G--T-----A--T-----T--G--------------T--A-TT----------AAG-------T--------T---G----C--T--T---- |
| Seq-154 | M | 15301 | 15400 | 100 | 669 | TACCCTTCATTATTGCAGCCCTAGCAGCACTCCACCTCCTATTCTTGCACGAAACGGGATCAAACAACCCCCTAGGAATCACCTCCCATTCCGATAAAAT |
| Seq-154 | 5 | 93905798 | 93905897 | 100 | 670 | -G-----T------A-----T--A--A-C--A-----T------C-A-------TA-----------T---T----C---C-------------C----- |
| | | | | | | +++++++++++++++++++++ |
| Seq-155 | M | 15401 | 15500 | 100 | 671 | CACCTTCCACCCTTACTACACAATCAAAGACGCCCTCGGCTTACTTCTCTTCCTTCTCTCCTTAATGACATTAACACTATTCTCACCAGACCTCCTAGGC |
| Seq-155 | 5 | 93905898 | 93905997 | 100 | 672 | T--------T-------------C-------AT---A---C--T-C--T-----C---A--C--T-A---C--GT---------------------G--- |
| | | | | | | $ +++++++++++++++++++ |
| Seq-156 | M | 15501 | 15600 | 100 | 673 | GACCCAGACAATTATACCCTAGCCAACCCCTTAAACACCCCTCCCCACATCAAGCCCGAATGATATTTCCTATTCGCCTACACAATTCTCCGATCCGTCC |
| Seq-156 | 5 | 93905998 | 93906097 | 100 | 674 | -----------C--C-----GA-T------C----------A-----------A---------------------------G--------------A-T- |
| Seq-156 | 6 | 133471815 | 133471914 | 100 | 675 | -----------C------------------C----------A--------T--A--------T--C--T------------G----C--A--G---A-T- |
| Seq-157 | M | 15601 | 15700 | 100 | 676 | CTAACAAACTAGGAGGCGTCCTTGCCCTATTACTATCCATCCTCATCCTAGCAATAATCCCCATCCTCCATATATCCAAACAACAAAGCATAATATTTCG |
| Seq-157 | 5 | 93906098 | 93906197 | 100 | 677 | -C--T------------A-T--A-----TC-----------------------GC---T--T--A-----C----------------------------A |
| Seq-157 | 17 | 22019755 | 22019854 | 100 | 678 | -C-----------------A--G-----CC-------A---------------GC---T----CA--T--C--G------------------------CT- |
| | | | | | | +++++++++++++++++++ $ ++++++++++++++++++++++ |
| Seq-158 | M | 15701 | 15800 | 100 | 679 | CCCACTAAGCCAATCACTTTATTGACTCCTAGCCGCAGACCTCCTCATTCTAACCTGAATCGGAGGACAACCAGTAAGCTACCCTTTTACCATCATTGGA |
| Seq-158 | 5 | 93906198 | 93906297 | 100 | 680 | ----T---------TC--A------T--------A-------T--T-CC-----------T--------------G-A------C--C--T-C---C--- |

TABLE 1-continued

Mitochondria and Genomic (Nuclear) Paralogs

| Seq. No. | Chr | Start | End | Length | SEQ ID NO: | Sequence |
|---|---|---|---|---|---|---|
| Seq-159 | M | 15801 | 15900 | 100 | 681 | CAAGTAGCATCCGTACTATACTTCACAACAATCCTAATCCTAATACCAACTATCTCCCTAATTGAAAACAAAATACTCAAATGGGCCTGTCCTTGTAGTA |
| Seq-159 | 5 | 93906298 | 93906397 | 100 | 682 | --------------------------G-----TT-------C------G-C-C----TC---C-----T---------------A----C--C------- |
| Seq-160 | M | 15901 | 16000 | 100 | 683 | TAAACTAATACACCAGTCTTGTAAACCGGAGACGAAAACCTTTTTCCAAGGACAAATCAGAGAAAAAGTCTTTAACTCCACCATTAGCACCCAAAGCTAA |
| Seq-160 | 5 | 93906398 | 93906497 | 100 | 684 | -----C--------G-----------T---A-T---G--T-CC--------------------------AC--G---T------C--------------- |
| Seq-160 | 17 | 22020055 | 22020154 | 100 | 685 | -----C----T-TTG------------A--A-T-G-G--TC-C-C----------C-------------AC--G---T------C--------------- |
| Seq-161 | M | 16001 | 16100 | 100 | 686 | GATTCTAATTTAAACTATTCTCTGTTCTTTCATGGGGAAGCAGATTTGGGTACCACCCAAGTATTGACTCACCCATCAACAACCGCTATGTATTTCGTAC |
| Seq-162 | M | 16101 | 16200 | 100 | 687 | ATTACTGCCAGCCACCATGAATATTGTACGGTACCATAAATACTTGACCACCTGTAGTACATAAAAACCCAACCCACATCAAACCCCCCCCCCCCATGCT |
| Seq-163 | M | 16201 | 16300 | 100 | 688 | TACAAGCAAGTACAGCAATCAACCTTCAACTATCACACATCAACTGCAACTCCAAAGCCACCCCTCACCCACTAGGATACCAACAAACCTACCCACCCTT |
| Seq-164 | M | 16301 | 16400 | 100 | 689 | AACAGTACATAGTACATAAAGTCATTTACCGTACATAGCACATTACAGTCAAATCCCTTCTCGTCCCCATGGATGACCCCCCTCAGATAGGGGTCCCTTG |
| Seq-165 | M | 16401 | 16500 | 100 | 690 | ACCACCATCCTCCGTGAAATCAATATCCCGCACAAGAGTGCTACTCTCCTCGCTCCGGGCCCATAACACTTGGGGGTAGCTAAAGTGAACTGTATCCGAC |
| Seq-165 | 17 | 22020556 | 22020655 | 100 | 691 | TT----------T---------------T---G--------------T--T-A---A--T------T---------------T-A-------------G- |

Example 2—Amplification and Primer Extension

An exemplary protocol used in Examples 3 and 4 is provided.

PCR Amplification

PCR was performed in a 5 μL volume reaction using Agena Bioscience's iPLEX Pro PCR kit, consisting of 2 μL DNA template, 0.5 μL 10×PCR Buffer, 0.4 μL 25 mM MgCl2, 0.1 μL dNTP/dUTP mix, 0.125 μL Uracyl-N-Glycosylase (New England Biolabs®, Ipswich, MA, USA), 0.2 μL DNA polymerase. For a strategy using the same PCR primer for both mitochondrial and nuclear DNA a concentration of 100 nM was used. For a strategy of template specific primer combinations a set of different combinations was used (Table A). Finally for the hybrid strategy of one universal PCR forward primer and a template specific pair of reverse primers, 100 nM of the universal primer was used and the combinations in Table A was used for the reverse primers. Alternatively, a hybrid strategy can use one universal PCR reverse primer and a template specific pair of forward primers with 100 nM of the universal primer and the combinations in Table A was used for the forward primers. Thermal cycling consisted of an initial incubation at 30° C. for 10 minutes followed by denaturation at 94° C. for 2 minutes; 30 cycles of 94° C. for 30 seconds, 60° C. for 30 seconds, and 72° C. for 1 minute; followed by a final extension of 5 minutes at 72° C. Following PCR, the reactions were treated with a 2 μL SAP mastermix consisting of 0.5 U shrimp alkaline phosphatase (SAP) and 0.17 μL 10×SAP Buffer. Samples were incubated for 20 minutes at 37° C., followed by SAP enzyme denaturation for 10 minutes at 85° C. Thermal cycling and incubation were performed in a GeneAmp® PCR System 9700 (Thermo Fisher). All reagents used were obtained from Agena Bioscience unless otherwise stated.

TABLE A

| PCR primer combination sets | | | | | | | | | | |
|---|---|---|---|---|---|---|---|---|---|---|
| | Pool 1 | Pool 2 | Pool 3 | Pool 4 | Pool 5 | Pool 6 | Pool 7 | Pool 8 | Pool 9 | Pool 10 |
| gDNA primers | 100 nM | 100 nM | 100 nM | 100 nM | 100 nM | 100 nM | 100 nM | 100 nM | 100 nM | |
| mDNA primers | | 100 nM | 75 nM | 50 nM | 35 nM | 25 nM | 12.5 nM | 6.25 nM | 3.125 nM | 100 nM |

gDNA = nucleic DNA specific PCR primers, mDNA = mitochondrial specific PCR primers Single Base Extension Single base extension was performed by adding 2 μL of a master mix consisting of 0.2×iPLex Buffer, 0.2× Termination Mix, 5-15 μM extension primer mix, and 0.00615 U iPLEX® Pro enzyme. Reaction parameters consisted of an initial incubation at 94° C. for 30 seconds followed by 20 cycles at 94° C. for 5 seconds with five nested cycles of 52° C. for 5 seconds followed by 80° C. for 5 seconds. A final extension was performed at 72° C. for 3 minutes. Thermal cyling was performed in a GeneAmp PCR System 9700.

Maldi-TOF Analysis

After 41 ul of water addition and desalting by the addition of 15 mg Clean Resin, 15 nL of each extend mixture was transferred to a SpectroCHIP® II-G384 and Mass spectra were recorded using a MassARRAY System. Spectra were acquired using SpectroAcquire software (Agena Bioscience, San Diego). The software parameters were set to acquire 20 shots from each of 5 raster positions. The resulting mass spectra were summed and peak detection and intensity analysis performed using Typer 4 software (Agena Bioscience, San Diego).

Example 3—Amplification Using Species Specific Amplification Primers and iPLEX

Table 2: ADF1 Assay design using strategy of species specific PCR primers but same extension primer, please note that each PCR primer has a 10 bp tag to move them out of the MassARRAY window 3500-9000 m/z Table 3: The alignment showing each primer pair alignment and the sequence of the amplicons (–g=nuclear specific primers, –mt=mitochondrial specific primers)

TABLE 2

| Assay Design ADF1 Different PCR same UEP | | | | | | | | | | | |
|---|---|---|---|---|---|---|---|---|---|---|---|
| WELL | SNP_ID | 2nd-PCRP | SEQ ID NO: | 1st-PCRP | SEQ ID NO: | UEP_ DIR | UEP_ MASS | UEP_SEQ | SEQ ID NO: | EXT1_ CALL | EXT1_ MASS |
| W1 | MitoQ-001 | acgttggatgGGTCTATTACCCTATTAATCAG | 692 | acgttggatgTCTGGGGCCAGCGTTTCA | 693 | R | 5439.6 | GCGTGCAIACCCCCCAGA | 694 | G | 5686.8 |
| W1 | | acgttggatgAGGTCTATCACCCTATTAACCAC | 695 | acgttggatgTCCGGCTCCAGCGTCTCG | 696 | | 7891.2 | ACTGACAATTAACAGCCCAATATCTA | 699 | C | 8138.4 |
| W1 | MitoQ-024 | acgttggatgGCCTACATCAGACCAAAATACTTC | 697 | acgttggatgAACAGTGTGGGTAATAATGGTTTCA | 698 | F | | | | | |
| W1 | | acgttggatgCTGCGTCAGATCAAAACACTGA | 700 | acgttggatgGACAGTGAGGGTAATAATGACTTGT | 701 | | | | | | |
| W1 | MitoQ-050 | acgttggatgTCATATACCAAATTTCTCCCTCAT | 702 | acgttggatgGAGTATGCTAAGATTTTGCGTAGT | 703 | F | 5032.3 | AGCCTTCTCCTCACTCT | 704 | C | 5279.5 |
| W1 | | acgttggatgTCATATACCAAATCTCTCCCTCAC | 705 | acgttggatgGAGTATGCTAAGATTTTGCGTAGC | 706 | | | | | | |
| W1 | MitoQ-065 | acgttggatgCCTATCTCTCCCAGTCCTAGCC | 707 | acgttggatgGAATGGGGTCTCCTCCTCCGGCT | 708 | F | 6960.6 | ATCACTATACTACTAACAGACCG | 709 | C | 7207.7 |
| W1 | | acgttggatgCCTATCTCTCCCAGTCCTAGCT | 710 | acgttggatgAATGGGGTCTCCTCCTCCGGCG | 711 | | | | | | |
| W1 | MitoQ-073 | acgttggatgCTCCCTAAAAGCAGTAGTGC | 712 | acgttggatgCTACAGCCACTCTAGGTTAG | 713 | R | 6377.2 | TACTATTAGGACTTTTCGCTT | 714 | G | 6624.3 |
| W1 | | acgttggatgCATTCATTTCTCTAACAGCAGTAATAT | 715 | acgttggatgCATCCATATAGTCACTCCAGGTTTA | 716 | | | | | | |
| W1 | MitoQ-094 | acgttggatgGATTTCACTTCCACTCCACAACC | 717 | acgttggatgTCCCGTATCGAAGGCCTTTC | 718 | R | 5804.8 | ggCGTGTTACATCGCGCCA | 719 | G | 6052 |
| W1 | | acgttggatgGATTTCACTTCCACTCCATAACG | 720 | acgttggatgTCCCGTATCGAAGGCCTTTT | 721 | | | | | | |
| W1 | MitoQ-110 | acgttggatgTAGCTGCTCCCTATCCTTC | 722 | acgttggatgTTCGTTGGATAGGTGGCGC | 723 | F | 7504.9 | caCTCCTAATACTAACTACCTGACT | 724 | C | 7752.1 |
| W1 | | acgttggatgTAGCTGTTCCCCAACCTTT | 725 | acgttggatgTTCGCTGGATAAGTGGCGT | 726 | | | | | | |
| W1 | MitoQ-129 | acgttggatgCGGTTGATGGTATGCTCGAA | 727 | acgttggatgTGTAGGAGGAATCATGCTAGGGCT | 728 | F | 7330.8 | ggAAGCAITCCTATACAACCGTAT | 729 | C | 7578 |

TABLE 2-continued

Assay Design ADF1 Different PCR same UEP

| | | | | | | | | | | | | |
|---|---|---|---|---|---|---|---|---|---|---|---|---|
| W1 | | acgttggatgCAGTTGATGATACGCCCGAG | 730 | acgttggatgTGTAGGATAAATCATGCTAAGGCG | 731 | | | | | | | |
| W1 | MitoQ-139 | acgttggatgCACAGCCCTAGGCATCACC | 732 | acgttggatgGTGAAATGTACACAGTGGGTT | 733 | F | 5990.9 | CAGCCCTAGACCTCAACTAC | 734 | C | 6238.1 | |
| W1 | | acgttggatgCACAGCCCTCGCTGTCACT | 735 | acgttggatgATAAAATGTGCATAGTGGGGA | 736 | | | | | | | |
| W1 | MitoQ-156 | acgttggatgCCCAGACAACTACACCCTGACT | 737 | acgttggatgGCCTCCTAGTTTATTGGGAAT | 738 | R | 6518.3 | GAATAGGAAATATCATTCGGG | 739 | G | 6765.5 | |
| W1 | | acgttggatgCCCAGACAATTATACCCTAGCC | 740 | acgttggatgGCCTCCTAGTTTGTTAGGGAC | 741 | | | | | | | |

| WELL | SNP_ID | EXT1_SEQ | SEQ ID NO: | EXT2_CALL | EXT2_MASS | EXT2_SEQ_ | SEQ ID NO: | EXT3_CALL | EXT3_MASS | EXT3_SEQ | EXT4_CALL | EXT4_MASS | EXT4_SEQ |
|---|---|---|---|---|---|---|---|---|---|---|---|---|---|
| W1 | MitoQ-001 | GCGTGCAIACCCCCCAGAC | 742 | A | 5766.7 | GCGTGCAIACCCCCCAGAT | 743 | | | | | | |
| W1 | | | | | | | | | | | | | |
| W1 | MitoQ-024 | ACTGACAATTAACAGCCCAATATCTAC | 744 | T | 8218.3 | ACTGACAATTAACAGCCCAATATCTAT | 745 | | | | | | |
| W1 | | | | | | | | | | | | | |
| W1 | MitoQ-050 | AGCCTTCTCCTCACTCTC | 746 | T | 5359.4 | AGCCTTCTCCTCACTCTT | 747 | | | | | | |
| W1 | | | | | | | | | | | | | |
| W1 | MitoQ-065 | ATCACTATACTACTAACAGACCGC | 748 | T | 7287.7 | ATCACTATACTACTAACAGACCGT | 749 | | | | | | |
| W1 | | | | | | | | | | | | | |
| W1 | MitoQ-073 | TACTATTAGGACTTTTCGCTTC | 750 | A | 6704.3 | TACTATTAGGACTTTTCGCTTT | 751 | | | | | | |
| W1 | | | | | | | | | | | | | |
| W1 | MitoQ-094 | ggCGTGTTACATCGCGCCAC | 752 | A | 6131.9 | ggCGTGTTACATCGCGCCAT | 753 | | | | | | |
| W1 | | | | | | | | | | | | | |

TABLE 2-continued

| Assay Design ADF1 Different PCR same UEP | | | | | | | |
|---|---|---|---|---|---|---|---|
| W1 | MitoQ-110 | caCTCCTAATACTAACTACCTGACTC | 754 | T | 7832 | caCTCCTAATACTAACTACCTGACTT | 755 |
| W1 | | | | | | | |
| W1 | MitoQ-129 | ggAAGCAITCCTATACAACCGTATC | 756 | T | 7657.9 | ggAAGCAITCCTATACAACCGTATCT | 757 |
| W1 | | | | | | | |
| W1 | MitoQ-139 | CAGCCCTAGACCTCAACTACC | 758 | T | 6318 | CAGCCCTAGACCTCAACTACT | 759 |
| W1 | | | | | | | |
| W1 | MitoQ-156 | GAATAGGAAATATCATTCGGGC | 760 | A | 6845.4 | GAATAGGAAATATCATTCGGGT | 761 |

TABLE 3

| Alignment Using ADF1 | | | | | | | | | | | |
|---|---|---|---|---|---|---|---|---|---|---|---|
| Assay | Chr | Start | End | Length | Amplicon | SEQ ID NO: | UEP | SEQ ID NO: | Direction | Nucleotide | WTExtension |
| MitoQ-001-g | chr17 | 22020734 | 22020834 | 101 | GGTCTATTACCCTATTAATCAGTCACGGGAGCTCTCCATGCA TTTGGTATTTTAATCTGGGGGGTG TGCACGCGATAGCATTGTGAAACGCTGGCCCCAGA | 762 | TCTGGGGGGTNTGCACGC | 763 | Reverse | 22020789 | A |
| MitoQ-001-mt | chrM | 7 | 108 | 102 | AGGTCTATCACCCTATTAACCACTCACGGGAGCTCTCCATGCA TTTGGTATTTTCGTCTGGGGGG TGTGCACGCGATAGCATTGCGAGACGCTGGAGCCGGA | 764 | TCTGGGGGGTNTGCACGC | 765 | Reverse | 63 | G |
| MitoQ-024-g | chr17 | 22023093 | 22023178 | 86 | GCCTACATCAGACCAAAATACTTCACTGACAATTAACAGCCCAA TATCTATAAATAATCAATGAAACCATTATTACCCACACTGTT | 766 | ACTGACAATTAACAGCCCAATATCTA | 767 | Forward | 22023144 | T |
| MitoQ-024-mt | chrM | 2343 | 2425 | 83 | CTGCGTCAGATCAAAACACTGAACTGACAATTAACAGCCCAA TATCTACAATCAACCAACAAGTCATTATTACCCTCACTGTC | 768 | ACTGACAATTAACAGCCCAATATCTA | 769 | Forward | 2392 | C |
| MitoQ-050-g | chr1 | 565441 | 565564 | 124 | TCATATACCAAATTTCTCCCTCATTAAACGTAAGCCTTCTCCT CACTCTTTCAATCTTATCCATCATGGCAGGCAGTTGAGGTG GATTAAACCAAACCCAACTACGCAAAATCTTAGCATACTC | 770 | AGCCTTCTCCTCACTCT | 771 | Forward | 565491 | T |
| MitoQ-050-mt | chrM | 4892 | 5015 | 124 | TCATATACCAAATCTCTCCCTCACTAAACGTAAGCCTTCTCCTC ACTCTCTCAATCTTATCCATCATAGCAGGCAGTTGAGGTGGATT AAACCAAACCCAGCTACGCAAAATCTTAGCATACTC | 772 | AGCCTTCTCCTCACTCT | 773 | Forward | 4942 | C |
| MitoQ-065-g | chr1 | 567041 | 567141 | 101 | CCTATCTCTCCCAGTCCTAGCCGCTGGCATCACTATACTACTAA CAGACCGTAACCTCAACACCACC TTCTTCGACCCAGCCGGAGGAGGAGACCCCATTC | 774 | ATCACTATACTACTAACAGACCG | 775 | Forward | 567093 | T |
| MitoQ-065-mt | chrM | 6492 | 6591 | 100 | CCTATCTCTCCCAGTCCTAGCTGCTGGCATCACTATACTACTA ACAGACCGCAACCTCAACACCACCT TCTTCGACCCCGCCGGAGGAGGAGACCCCATT | 776 | ATCACTATACTACTAACAGACCG | 777 | Forward | 6544 | C |
| MitoQ-073-g | chr17 | 22028016 | 22028124 | 109 | CTCCCTAAAAGCAGTAGTGCTAATAATTTTCATAACCTGAGAG ACCTTCGCTTCAAAGCGAAAAGTC CTAATAAATGAGCAACCTTCCACTAACCTAGAGTGGCTGTAG | 778 | AAGCGAAAAGTCCTAATAGTA | 779 | Reverse | 22028071 | A |
| MitoQ-073-mt | chr1 | 567827 | 567947 | 121 | CATTCATTTCTCTAACAGCAGTAATATTAATAATTTTCATAATTT GAGAAGCCTTCGCTTCGAAGCGA AAAGTCCTAATAGTAGAAGAACCCTCCATAAACCTGGAGTGA CTATATGGATG | 780 | AAGCGAAAAGTCCTAATAGTA | 781 | Reverse | 567889 | G |
| MitoQ-073-mt | chrM | 7277 | 7397 | 121 | CATTCATTTCTCTAACAGCAGTAATATTAATAATTTTCATGATTT GAGAAGCCTTCGCTTCGAAGCGA AAAGTCCTAATAGTAGAAGAACCCTCCATAAACCTGGAGT GACTATATGGATG | 782 | AAGCGAAAAGTCCTAATAGTA | 783 | Reverse | 7339 | G |

TABLE 3-continued

Alignment Using ADF1

| Assay | Chr | Start | End | Length | Amplicon | SEQ ID NO: | UEP | SEQ ID NO: | Direction | Nucleotide | WTExtension |
|---|---|---|---|---|---|---|---|---|---|---|---|
| MitoQ-094-g | chr1 | 569856 | 570002 | 147 | GATTTCACTTCCACTCCACAACCCTCCTCATACTAGGCCTACT AACCAACACACTAACCATATACCA ATGATGGCGCGATGTAACACGAGAAAGCACATACCAAGGCC ACCACACACCACCTGTCCAGAAAG GCCTTCGATACGGGA | 784 | TGGCGCGATGTAACACG | 785 | Reverse | 569927 | A |
| MitoQ-094-mt | chrM | 9308 | 9454 | 147 | GATTTCACTTCCACTCCATAACGCTCCTCATACTAGGCCTACT AACCAACACACTAACCATATACCAAT GGTGGCGCGATGTAACACGAGAAAGCACATACCAAGGCCA CCACACACCACCTGTCCAAAAAGGC CTTCGATACGGGA | 786 | TGGCGCGATGTAACACG | 787 | Reverse | 9379 | G |
| MitoQ-110-g | chrX | 125607017 | 125607128 | 112 | TAGCTGCTCCCTATCCTTCTCCTCCGACCCCCTAACGACCCC CCTCCTAATACTAACTACCTGACTTCTA CCCCTCACAATCATGGCAAGCCAGCGCCACCTATCCAACGAA | 788 | CTCCTAATACTAACTACCTGACT | 789 | Forward | 125607084 | T |
| MitoQ-110-mt | chrM | 10910 | 11021 | 112 | TAGCTGTTCCCCAACCTTTTCCTCCGACCCCCTAACAACCCCC CTCCTAATACTAACTACCTGACTCCTA CCCCTCACAATCATGGCAAGCCAACGCCACTTATCCAGCGAA | 790 | CTCCTAATACTAACTACCTGACT | 791 | Forward | 10977 | C |
| MitoQ-129-g | chr5 | 93903300 | 93903410 | 111 | CGGTTGATGGTATGCTCGAACAGATGCCAACACAGCAGCCA TCCCAGCAATCCTATACAACCGTATT GGCGACATTGGCTTCATCCTAGCCCTAGCATGATTCCTCCTACA | 792 | AAGCANTCCTATACAACCGTAT | 793 | Forward | 93903367 | T |
| MitoQ-129-mt | chrM | 12802 | 12912 | 111 | CAGTTGATGATACGCCCGAGCAGATGCCAACACAGCAGCCA TTCAAGCAGTCCTATACAACCGTAT CGGCGATATCGGTTTCATCCTCGCCTTAGCATGATTTATCCTACA | 794 | AAGCANTCCTATACAACCGTAT | 795 | Forward | 12869 | C |
| MitoQ-139-g | chr5 | 93904299 | 93904398 | 100 | CACAGCCCTAGGCATCACCTTCCTAGGACTTCTGACAGCCCT AGACCTCAACTACTTAACCAACAAA CTCAAAATAAAAAACCCACTGTGTACATTTCAC | 796 | CAGCCCTAGACCTCAACTAC | 797 | Forward | 93904355 | T |
| MitoQ-139-mt | chrM | 13801 | 13900 | 100 | CACAGCCCTCGCTGTCACTTTCCTAGGACTTCTAACAGCCCTA GACCTCAACTACCTAACCAACAAA CTTAAAATAAAATCCCCACTATGCACATTTTAT | 798 | CAGCCCTAGACCTCAACTAC | 799 | Forward | 13857 | C |
| MitoQ-156-g | chr5 | 93906000 | 93906114 | 115 | CCCAGACAACTACACCCTGACTAACCCCCTAAACACCCCACC CCACATCAAACCCGAATGATATTTCC TATTCGCCTACGCAATTCTCCGATCCATTCCCAAT AAACTAGGAGGC | 800 | CCCGAATGATATTTCCTATTC | 801 | Reverse | 93906052 | A |
| MitoQ-156-mt | chrM | 15503 | 15617 | 115 | CCCAGACAATTATACCCTAGCCAACCCCTTAAACACC CCTCCCCACATCAAGCCCGAATGATATTTCC TATTCGCCTACACAATTCTCCGATCCGTCCCTAAC AAACTAGGAGGC | 802 | CCCGAATGATATTTCCTATTC | 803 | Reverse | 15555 | G |

Example 4—Amplification Using Same Amplification Primer and iPLEX

Table 4: ADF2 Assay design using strategy of universal PCR primers and the same extension primer, please note that each PCR primer has a 10 bp tag to move them out of the MassARRAY window 3500-9000 m/z Table 5: The alignment showing each primer pair aligning both on nuclear as well as mitochondrial DNA All samples are set up in 25 uL PCR reactions.

TABLE 4

Assay Design ADF2 Same PCR same UEP

| WELL | TERM | Forward PCR primer | Reverse PCR primer | SEQ ID NO: | 1st-PCRP | SEQ ID NO: 1 | Comment | AMP_ LEN | UP_ CONF | MP_ CONF | Tm (NN) | PcGC | PWARN | UEP_ DIR | UEP_ MASS |
|---|---|---|---|---|---|---|---|---|---|---|---|---|---|---|---|
| W1 | iPLEX | Mito-019 | ACGTTGGATGGATCTAAAACACTCTTTAC | 804 | ACGTTGGATGTCACACGATTAACCCAAGTC | 805 | new FP | 74 | 82.7 | 98.9 | 51.1 | 47.4 | h | R | 5757 |
| W1 | iPLEX | Mito-081 | ACGTTGGATGTTGTGTAGAGTTCAGGGGAG | 806 | ACGTTGGATGCTACAATCTTCCTAGGAACA | 807 | | 75 | 92.8 | 98.9 | 53.5 | 58.8 | g | R | 5307 |
| W1 | iPLEX | Mito-100 | ACGTTGGATGGAGGAGTATGCTAAGATTTT | 808 | ACGTTGGATGCAGTTGAGGTGGATTAAACC | 809 | | 75 | 90.2 | 98.9 | 45.7 | 35 | h | R | 6162 |
| W1 | iPLEX | Mito-108 | ACGTTGGATGCTACTCCACCTCAATCACAC | 810 | ACGTTGGATGCATTTTATTTTTACGTTGTTAGA | 811 | new RP | 75 | 84.3 | 98.9 | 46.6 | 50 | | F | 5324 |
| W1 | iPLEX | Mito-129 | ACGTTGGATGAGGCCATCAATTTCATCACA | 812 | ACGTTGGATGGGGTTATGGCAGGGGGTT | 813 | new FP and RP | 73 | 93.6 | 98.9 | 45.5 | 21.7 | G | F | 6950 |
| W1 | iPLEX | Mito-138 | ACGTTGGATGCCGGCGTCAAAGTATTTAGC | 814 | ACGTTGGATGATTTCATATTGCTTCCGTGG | 815 | | 75 | 95.2 | 98.9 | 46.6 | 44.4 | | F | 5490 |
| W1 | iPLEX | Mito-162 | ACGTTGGATGGCCTAATGTGGGGACAGC | 816 | ACGTTGGATGTAATAATTACATCACAAGAC | 817 | new FP | 74 | 90 | 98.9 | 49.7 | 58.8 | g | R | 5275 |
| W1 | iPLEX | Mito-172 | ACGTTGGATGCTTCATTCATTGCCCCCACA | 818 | ACGTTGGATGGAATGATCAGTACTGCGGCG | 819 | | 75 | 95.6 | 98.9 | 52.2 | 64.7 | h | F | 5100 |
| W1 | iPLEX | Mito-184 | ACGTTGGATGCGCCTTAATCCAAGCCTAC | 820 | ACGTTGGATGGCAGGTAGAGGCTTACTAGA | 821 | | 75 | 95.6 | 98.9 | 46.3 | 41.2 | | F | 5120 |
| W1 | iPLEX | Mito-204 | ACGTTGGATGGGGATATAGGGTCGAAGCCG | 822 | ACGTTGGATGGGCTACATAGAAAAATCCAC | 823 | new FP and RP | 74 | 93.7 | 98.9 | 53.7 | 52.6 | G | R | 5862 |

| Forward PCR primer | Reverse PCR primer | SEQ ID NO: | UEP_SEQ | SEQ ID NO: | EXT1_ CALL | EXT1_ MASS | EXT1_SEQ | SEQ ID NO: | EXT2_ CALL | EXT2_ MASS | EXT2_SEQ | SEQ ID NO: | EXT3_ CALL | EXT3_ MASS | EXT3_ SEQ | EXT4_ CALL | EXT4_ MASS | EXT4_ SEQ |
|---|---|---|---|---|---|---|---|---|---|---|---|---|---|---|---|---|---|---|
| Mito-019 | ACGTTGGATGGATCTAAAACACTCTTTAC | 824 | AAAACACTCTTTACGCCGG | 825 | G | 6004 | AAAACACTCTTTACGCCGGC | 826 | A | 6083.9 | AAAACACTCTTTACGCCGGT | 827 | | | | | | |
| Mito-081 | ACGTTGGATGTTGTGTAGAGTTCAGGGGAG | 828 | TTCAGGGGAGAGTGCGT | 829 | G | 5553.6 | TTCAGGGGAGAGTGCGTC | 830 | A | 5633.5 | TTCAGGGGAGAGTGCGTT | 831 | | | | | | |

TABLE 4-continued

| Assay Design ADF2 Same PCR same UEP | | | | | | | | | | | | |
|---|---|---|---|---|---|---|---|---|---|---|---|---|
| Mito-100 | ACGTTGGATGGAGGAGTATGCTAAGATTTT | 832 | TATGCTAAGATTTTGCGTAG | 833 | G | 6409.2 | TATGCTAAGATTTTGCGTAGC | 834 | A | 6489.1 | TATGCTAAGATTTTGCGTAGT | 835 |
| Mito-108 | ACGTTGGATGCTACTCCACCTCAATCACAC | 836 | CTCAATCACACTACTCCC | 837 | C | 5570.7 | CTCAATCACACTACTCCCC | 838 | T | 5650.6 | CTCAATCACACTACTCCCT | 839 |
| Mito-129 | ACGTTGGATGAGGCCATCAATTTCATCACA | 840 | ATCAATTTCATCACAACAATTAT | 841 | C | 7196.8 | ATCAATTTCATCACAACAATTATC | 842 | T | 7276.7 | ATCAATTTCATCACAACAATTATT | 843 |
| Mito-138 | ACGTTGGATGCCGGCGTCAAAGTATTTAGC | 844 | AGTATTTAGCTGACTCGC | 845 | C | 5736.8 | AGTATTTAGCTGACTCGCC | 846 | T | 5816.7 | AGTATTTAGCTGACTCGCT | 847 |
| Mito-162 | ACGTTGGATGGCCTAATGTGGGGACAGC | 848 | GGGACAGCTCATGAGTG | 849 | G | 5522.6 | GGGACAGCTCATGAGTGC | 850 | A | 5602.5 | GGGACAGCTCATGAGTGT | 851 |
| Mito-172 | ACGTTGGATGCTTCATTCATTGCCCCCACA | 852 | GCCCCCACAATCCTAGG | 853 | C | 5347.5 | GCCCCCACAATCCTAGGC | 854 | T | 5427.4 | GCCCCCACAATCCTAGGT | 855 |
| Mito-184 | ACGTTGGATGCGCCTTAATCCAAGCCTAC | 856 | ATCCAAGCCTACGTTTT | 857 | C | 5367.5 | ATCCAAGCCTACGTTTTC | 858 | T | 5447.4 | ATCCAAGCCTACGTTTTT | 859 |
| Mito-204 | ACGTTGGATGGGGATATAGGGTCGAAGCCG | 860 | ATATAGGGTCGAAGCCGCA | 861 | G | 6109 | ATATAGGGTCGAAGCCGCAC | 862 | A | 6188.9 | ATATAGGGTCGAAGCCGCAT | 863 |

TABLE 5

Alignment Using ADF2

| Assay | Chr | Start | End | Length | Amplicon | SEQ ID NO: | UEP | SEQ ID NO: |
|---|---|---|---|---|---|---|---|---|
| Mito-019 | chr5 | 79947581 | 79947633 | 53 | TGATCTAAAACACTCTTTACGCCGGTTT CTATTGACTTGGGTTAATCGTGTGA | 864 | AAAACACTCTTTACGCCGG | 865 |
| Mito-019 | chr11 | 10531450 | 10531502 | 53 | TGATCTAAAACACTCTTTATGCCGGTTT CTATTGACTTGGGTTAATCGTGTGA | 866 | AAAACACTCTTTACGCCGG | 867 |
| Mito-019 | chrM | 905 | 957 | 53 | TCACACGATTAACCCAAGTCAATAGAA GCCGGCGTAAAGAGTGTTTTAGATCA | 868 | CCGGCGTAAAGAGTGTTTT | 869 |
| Mito-081 | chr1 | 564572 | 564625 | 54 | CTACAATCTTCCTAGGAACAACATATAA CGCACTCTCCCCTGAACTCTACACAA | 870 | ACGCACTCTCCCCTGAA | 871 |
| Mito-081 | chrM | 4023 | 4076 | 54 | CTACAATCTTCCTAGGAACAACATATGA CGCACTCTCCCCTGAACTCTACACAA | 872 | ACGCACTCTCCCCTGAA | 873 |
| Mito-100 | chr1 | 565514 | 565567 | 54 | CAGTTGAGGTGGATTAAACCAAACCCA ACTACGCAAAATCTTAGCATACTCCTC | 874 | CTACGCAAAATCTTAGCATA | 875 |
| Mito-100 | chrM | 4965 | 5018 | 54 | CAGTTGAGGTGGATTAAACCAAACCCA GCTACGCAAAATCTTAGCATACTCCTC | 876 | CTACGCAAAATCTTAGCATA | 877 |
| Mito-108 | chr1 | 565910 | 565963 | 54 | CTACTCCACCTCAATCACACTACTCCCTA TATCTAACAACGTAAAAATAAAATG | 878 | CTCAATCACACTACTCCC | 879 |
| Mito-108 | chrM | 5361 | 5414 | 54 | CTACTCCACCTCAATCACACTACTCCCC ATATCTAACAACGTAAAAATAAAATG | 880 | CTCAATCACACTACTCCC | 881 |
| Mito-129 | chr1 | 566934 | 566985 | 52 | GCCATCAATTTCATCACAACAATTATTA ATATAAAACCCCCTGCCATAACCC | 882 | ATCAATTTCATCACAACAAT TAT | 883 |
| Mito-129 | chrM | 6385 | 6436 | 52 | GCCATCAATTTCATCACAACAATTATCA ATATAAAACCCCCTGCCATAACCC | 884 | ATCAATTTCATCACAACAAT TAT | 885 |
| Mito-138 | chr1 | 567401 | 567454 | 54 | CCGGCGTCAAAGTATTTAGCTGACTCG CCACACTCCACGGAAGCAATATGAAAT | 886 | AGTATTTAGCTGACTCGC | 887 |
| Mito-138 | chr17 | 51183126 | 51183179 | 54 | CCGGCGTCAAAGTATTTAGCTGACTCG CTACACTCCACGGAAGCAATATGAAAT | 888 | AGTATTTAGCTGACTCGC | 889 |
| Mito-138 | chrM | 6851 | 6904 | 54 | CCGGCGTCAAAGTATTTAGCTGACTCG CCACACTCCACGGAAGCAATATGAAAT | 890 | AGTATTTAGCTGACTCGC | 891 |
| Mito-162 | chr1 | 568591 | 568643 | 53 | TAATAATTACATCACAAGACGTCTTACA CTCATGAGCTGTCCCCACATTAGGC | 892 | CACTCATGAGCTGTCCC | 893 |
| Mito-162 | chr18 | 45379691 | 45379743 | 53 | GCCTAATGTGGGGACAGCTCATGAGTG TAAGACGTCTTGTGATGTAATTATTA | 894 | GGGACAGCTCATGAGTG | 895 |
| Mito-162 | chrM | 8041 | 8093 | 53 | TAATAATTACATCACAAGACGTCTTGCA CTCATGAGCTGTCCCCACATTAGGC | 896 | CACTCATGAGCTGTCCC | 897 |
| Mito-172 | chr1 | 569095 | 569148 | 54 | CTTCATTCATTGCCCCCACAATCCTAGG CCTACCCGCCGCAGTACTGATCATTC | 898 | GCCCCCACAATCCTAGG | 899 |
| Mito-172 | chr2 | 88124641 | 88124694 | 54 | CTTCATTCATTGCCCCCACAATCCTAGG TCTGCCCGCCGCAGTACTGATCATTC | 900 | GCCCCCACAATCCTAGG | 901 |
| Mito-172 | chrM | 8547 | 8600 | 54 | CTTCATTCATTGCCCCCACAATCCTAGG CCTACCCGCCGCAGTACTGATCATTC | 902 | GCCCCCACAATCCTAGG | 903 |
| Mito-184 | chr1 | 569689 | 569742 | 54 | CTGTCGCCTTAATCCAAGCCTACGTTTT TACACTTCTAGTAAGCCTCTACCTGC | 904 | ATCCAAGCCTACGTTTT | 905 |
| Mito-184 | chrM | 9141 | 9194 | 54 | CTGTCGCCTTAATCCAAGCCTACGTTTT CACACTTCTAGTAAGCCTCTACCTGC | 906 | ATCCAAGCCTACGTTTT | 907 |
| Mito-204 | chr17 | 42075087 | 42075139 | 53 | TACATAGAAAAATCCACCCCTTACGAAT GCGGCTTCGACCCTATATCCCCCGC | 908 | TGCGGCTTCGACCCTATAT | 909 |
| Mito-204 | chrM | 10147 | 10199 | 53 | TACATAGAAAAATCCACCCCTTACGAGT GCGGCTTCGACCCTATATCCCCCGC | 910 | TGCGGCTTCGACCCTATAT | 911 |

TABLE 5-continued

| Alignment Using ADF2 | | | |
|---|---|---|---|
| Assay | Direction | Nucleotide | WTExtension |
| Mito-019 | Forward | 79947607 | T |
| Mito-019 | Forward | 10531476 | T |
| Mito-019 | Reverse | 933 | G |
| Mito-081 | Reverse | 564599 | A |
| Mito-081 | Reverse | 4050 | G |
| Mito-100 | Reverse | 565542 | A |
| Mito-100 | Reverse | 4993 | G |
| Mito-108 | Forward | 565938 | T |
| Mito-108 | Forward | 5389 | C |
| Mito-129 | Forward | 566961 | T |
| Mito-129 | Forward | 6412 | C |
| Mito-138 | Forward | 567430 | C |
| Mito-138 | Forward | 51183155 | T |
| Mito-138 | Forward | 6880 | C |
| Mito-162 | Reverse | 568617 | A |
| Mito-162 | Forward | 45379719 | T |
| Mito-162 | Reverse | 8067 | G |
| Mito-172 | Forward | 569124 | C |
| Mito-172 | Forward | 88124670 | T |
| Mito-172 | Forward | 8576 | C |
| Mito-184 | Forward | 569718 | T |
| Mito-184 | Forward | 9170 | C |
| Mito-204 | Reverse | 42075114 | A |
| Mito-204 | Reverse | 10174 | G |

Example 5—Identification of Chimpanzee Mitochondrial/Human Mitochondrial Paralogs and Chimpanzee Nuclear/Human Nuclear Paralogs Chimpanzee mitochondrial/human mitochondrial paralogs were identified using a R-based algorithm. Utilizing the Biostrings library from the Bioconductor open source software aligned small fragments (50-100 bps) of the human (*Homo sapiens*) mitochondrial genome (UCSC hg19 build) against the chimpanzee (*Pan troglodytes*) mitochondrial genome (*P. troglodytes* 2013 assembly). Bioconductor contains memory efficient string containers, string matching algorithms, and other utilities, for fast manipulation of large biological sequences or sets of sequences. Similar nucleotide regions containing at least one mismatch were selected and assays were designed based on these regions. When paralog regions were identified these were verified using the BLAST algorithm from NCBI.

An exemplary protocol is as follows:

1. The mitochondrial genome was split into shorter fragments (in the case here 75 bp) and given a name, e.g., Seq-1 is the mitochondrial genome nt 1-75 and Seq-2 is nucleotides 76-150.
2. Each sequence was aligned against the chimpanzee mitochondrial genome and a certain number of mismatches are allowed in this case 15 mismatches per sequence. Results are displayed in Table 6. Shown are sequence number, direction of DNA (strand) match, start of alignment, end of alignment, length of alignment (Width) finally regions that are suitable for use as amplicons (potential amplification primer binding regions) and sequence. Dashes indicate matches in the sequences and letters mismatches in the sequences. The human mitochondria is labelled with hchrM and the chimpanzee is labelled chrM.
3. All sequence mismatches can be used for paralog detection (V) as long as the upstream/downstream regions J and K fit the strategy for amplification as described below.
4. For Co-amplification of chimpanzee and human mitochondrial polynucleotides with a single amplification primer pair—a region V surrounded by regions J and K, where V is different between the chimpanzee and human mitochondrial genomes and J and K are identical in both the chimpanzee and human mitochondrial genomes was selected. Amplification primers were designed to bind to a region within J and K, for amplification of both chimpanzee and human polynucleotides. Amplicons produced with these amplification primers include V. The nucleotide at V was analyzed to distinguish an amplicon of a chimpanzee mitochondrial polynucleotide from an amplicon of a human mitochondrial polynucleotide.

The human and chimpanzee nuclear genomes are 99% identical, therefore there are numerous suitable paralog regions. Suitable chimpanzee nuclear/human nuclear paralogs were determined in the same manner as mitochondrial paralogs, e.g., by blasting portions of the human genome against the chimpanzee genome.

TABLE 6

Chimpanzee and Human Mitochondrial Paralogs

| fragment | chr | strand | start | end | width | SEQ ID NO: | amplicon |
|---|---|---|---|---|---|---|---|
| Seq-1 | chrM | Sense | 15986 | 16060 | 75 | 912 | ----------------------------G----------CT------- ------------------------G-- |
| Seq-1 | hchrM | Sense | 1 | 75 | 75 | 913 | GATCACAGGTCTATCACCCTATTAACCACTCACGGGAGCTCTCCATGC ATTTGGTATTTTCGTCTGGGGGGTATG |
| Seq-2 | chrM | Sense | 16061 | 16135 | 75 | 914 | ------------------A-------CC-------------------- ----------------------C---T |
| Seq-2 | hchrM | Sense | 76 | 150 | 75 | 915 | CACGCGATAGCATTGCGAGACGCTGGAGCCGGAGCACCCTATGTCGCA GTATCTGTCTTTGATTCCTGCCTCATC |
| Seq-3 | chrM | Sense | 16136 | 16210 | 75 | 916 | G-------------------------------GAC-T-G-----C--- -----------G--------------- |
| Seq-3 | hchrM | Sense | 151 | 225 | 75 | 917 | CTATTATTTATCGCACCTACGTTCAATATTACAGGCGAACATACTTAC TAAAGTGTGTTAATTAATTAATGCTTG |
| Seq-4 | hchrM | Sense | 226 | 300 | 75 | 918 | TAGGACATAATAATAACAATTGAATGTCTGCACAGCCACTTTCCACAC AGACATCATAACAAAAAATTTCCACCA |
| Seq-5 | chrM | Sense | 16281 | 16355 | 75 | 919 | C--AAA---C---TTC-CC-C------------C-----A-------- -----------------------AG-- |
| Seq-5 | hchrM | Sense | 301 | 375 | 75 | 920 | AACCCCCCCTCCCCCGCTTCTGGCCACAGCACTTAAACACATCTCTGC CAAACCCCAAAAACAAAGAACCCTAAC |
| Seq-6 | chrM | Sense | 16356 | 16430 | 75 | 921 | G--------G-----C---------C------A--------------- -------------T---T-----TGCC |
| Seq-6 | hchrM | Sense | 376 | 450 | 75 | 922 | ACCAGCCTAACCAGATTTCAAATTTTATCTTTTGGCGGTATGCACTTT TAACAGTCACCCCCCAACTAACACATT |
| Seq-7 | hchrM | Sense | 451 | 525 | 75 | 923 | ATTTTCCCCTCCCACTCCCATACTACTAATCTCATCAATACAACCCCC GCCCATCCTACCCAGCACACACACACC |

TABLE 6-continued

| Chimpanzee and Human Mitochondrial Paralogs | | | | | | | |
|---|---|---|---|---|---|---|---|
| fragment | chr | strand | start | end | width | SEQ ID NO: | amplicon |
| Seq-8 | hchrM | Sense | 526 | 600 | 75 | 924 | GCTGCTAACCCCATACCCCGAACCAACCAAACCCCAAAGACACCCCCC<br>ACAGTTTATGTAGCTTACCTCCTCAAA |
| Seq-9 | chrM | Sense | 25 | 99 | 75 | 925 | --------------------C------T-T------------------<br>-C------------------------- |
| Seq-9 | hchrM | Sense | 601 | 675 | 75 | 926 | GCAATACACTGAAAATGTTTAGACGGGCTCACATCACCCCATAAACAA<br>ATAGGTTTGGTCCTAGCCTTTCTATTA |
| Seq-10 | hchrM | Sense | 676 | 750 | 75 | 927 | GCTCTTAGTAAGATTACACATGCAAGCATCCCCGTTCCAGTGAGTTCA<br>CCCTCTAAATCACCACGATCAAAAGGA |
| Seq-11 | chrM | Sense | 173 | 247 | 75 | 928 | -----T-----------------------------------------<br>--------------G-----------A |
| Seq-11 | hchrM | Sense | 751 | 825 | 75 | 929 | ACAAGCATCAAGCACGCAGCAATGCAGCTCAAAACGCTTAGCCTAGCC<br>ACACCCCCACGGGAAACAGCAGTGATT |
| Seq-12 | chrM | Sense | 248 | 322 | 75 | 930 | ---------------------------------C---------T----<br>-----------------T--------- |
| Seq-12 | hchrM | Sense | 826 | 900 | 75 | 931 | AACCTTTAGCAATAAACGAAAGTTTAACTAAGCTATACTAACCCCAGG<br>GTTGGTCAATTTCGTGCCAGCCACCGC |
| Seq-13 | chrM | Sense | 323 | 397 | 75 | 932 | -----T-----------------------A------------------<br>------------C-ATA--GCT-AAAT |
| Seq-13 | hchrM | Sense | 901 | 975 | 75 | 933 | GGTCACACGATTAACCCAAGTCAATAGAAGCCGGCGTAAAGAGTGTTT<br>TAGATCACCCCCTCCCCAATAAAGCTA |
| Seq-14 | chrM | Sense | 394 | 468 | 75 | 934 | ---T-------------------------C---T--------A-----<br>----------------C-------T-- |
| Seq-14 | hchrM | Sense | 976 | 1050 | 75 | 935 | AAACTCACCTGAGTTGTAAAAAACTCCAGTTGACACAAAATAGACTAC<br>GAAAGTGGCTTTAACATATCTGAACAC |
| Seq-15 | chrM | Sense | 469 | 543 | 75 | 936 | ------------------------------------------------<br>-------T-------------T----- |
| Seq-15 | hchrM | Sense | 1051 | 1125 | 75 | 937 | ACAATAGCTAAGACCCAAACTGGGATTAGATACCCCACTATGCTTAGC<br>CCTAAACCTCAACAGTTAAATCAACAA |
| Seq-16 | chrM | Sense | 544 | 618 | 75 | 938 | ------------------------------------------------<br>--------------------------- |
| Seq-16 | hchrM | Sense | 1126 | 1200 | 75 | 939 | AACTGCTCGCCAGAACACTACGAGCCACAGCTTAAAACTCAAAGGACC<br>TGGCGGTGCTTCATATCCCTCTAGAGG |
| Seq-17 | chrM | Sense | 619 | 693 | 75 | 940 | ---------------------------------------G--------<br>--------------------------- |
| Seq-17 | hchrM | Sense | 1201 | 1275 | 75 | 941 | AGCCTGTTCTGTAATCGATAAACCCCGATCAACCTCACCACCTCTTGC<br>TCAGCCTATATACCGCCATCTTCAGCA |
| Seq-18 | chrM | Sense | 694 | 768 | 75 | 942 | --------------T------------A--------------------<br>------------------T-------- |
| Seq-18 | hchrM | Sense | 1276 | 1350 | 75 | 943 | AACCCTGATGAAGGCTACAAAGTAAGCGCAAGTACCCACGTAAAGACG<br>TTAGGTCAAGGTGTAGCCCATGAGGTG |
| Seq-19 | chrM | Sense | 769 | 843 | 75 | 944 | ----------------------------------T-------A-----<br>-------C--------A---------- |
| Seq-19 | hchrM | Sense | 1351 | 1425 | 75 | 945 | GCAAGAAATGGGCTACATTTTCTACCCCAGAAAACTACGATAGCCCTT<br>ATGAAACTTAAGGGTCGAAGGTGGATT |
| Seq-20 | chrM | Sense | 844 | 918 | 75 | 946 | ------------------------------------------------<br>--------------------------- |
| Seq-20 | hchrM | Sense | 1426 | 1500 | 75 | 947 | TAGCAGTAAACTAAGAGTAGAGTGCTTAGTTGAACAGGGCCCTGAAGC<br>GCGTACACACCGCCCGTCACCCTCCTC |

TABLE 6-continued

Chimpanzee and Human Mitochondrial Paralogs

| fragment | chr | strand | start | end | width | SEQ ID NO: | amplicon |
|---|---|---|---|---|---|---|---|
| Seq-21 | hchrM | Sense | 1501 | 1575 | 75 | 948 | AAGTATACTTCAAAGGACATTTAACTAAAACCCCTACGCATTTATATAGAGGAGACAAGTCGTAACATGGTAAGT |
| Seq-22 | chrM | Sense | 995 | 1069 | 75 | 949 | -------------------------------------------T-------------------------------- |
| Seq-22 | hchrM | Sense | 1576 | 1650 | 75 | 950 | GTACTGGAAAGTGCACTTGGACGAACCAGAGTGTAGCTTAACACAAAGCACCCAACTTACACTTAGGAGATTTCA |
| Seq-23 | chrM | Sense | 1070 | 1144 | 75 | 951 | ---C---------A--------C------------------C-------C--------A---------A------ |
| Seq-23 | hchrM | Sense | 1651 | 1725 | 75 | 952 | ACTTAACTTGACCGCTCTGAGCTAAACCTAGCCCCAAACCCACTCCACCTTACTACCAGACAACCTTAGCCAAAC |
| Seq-24 | chrM | Sense | 1145 | 1219 | 75 | 953 | -----------------------------------T--A-C-----------C---------------------- |
| Seq-24 | hchrM | Sense | 1726 | 1800 | 75 | 954 | CATTTACCCAAATAAAGTATAGGCGATAGAAATTGAAACCTGGCGCAATAGATATAGTACCGCAAGGGAAAGATG |
| Seq-25 | chrM | Sense | 1220 | 1294 | 75 | 955 | ----------C------------C-----------------G------T-------------------------- |
| Seq-25 | hchrM | Sense | 1801 | 1875 | 75 | 956 | AAAAATTATAACCAAGCATAATATAGCAAGGACTAACCCCTATACCTTCTGCATAATGAATTAACTAGAAATAAC |
| Seq-26 | chrM | Sense | 1295 | 1369 | 75 | 957 | -------A----A-------------------------------------------------------------- |
| Seq-26 | hchrM | Sense | 1876 | 1950 | 75 | 958 | TTTGCAAGGAGAGCCAAAGCTAAGACCCCCGAAACCAGACGAGCTACCTAAGAACAGCTAAAAGAGCACACCCGT |
| Seq-27 | chrM | Sense | 1370 | 1444 | 75 | 959 | --------------------------------------------------------------------------- |
| Seq-27 | hchrM | Sense | 1951 | 2025 | 75 | 960 | CTATGTAGCAAAATAGTGGGAAGATTTATAGGTAGAGGCGACAAACCTACCGAGCCTGGTGATAGCTGGTTGTCC |
| Seq-28 | chrM | Sense | 1445 | 1519 | 75 | 961 | ------------------------------A--T---------------------------C------------- |
| Seq-28 | hchrM | Sense | 2026 | 2100 | 75 | 962 | AAGATAGAATCTTAGTTCAACTTTAAATTTGCCCACAGAACCCTCTAAATCCCCTTGTAAATTTAACTGTTAGTC |
| Seq-29 | chrM | Sense | 1520 | 1594 | 75 | 963 | -------------------A----------------------A-------------------------------- |
| Seq-29 | hchrM | Sense | 2101 | 2175 | 75 | 964 | CAAAGAGGAACAGCTCTTTGGACACTAGGAAAAAACCTTGTAGAGAGAGTAAAAAATTTAACACCCATAGTAGGC |
| Seq-30 | chrM | Sense | 1595 | 1669 | 75 | 965 | ----------------------------------------------A----T---G------------C---C-- |
| Seq-30 | hchrM | Sense | 2176 | 2250 | 75 | 966 | CTAAAAGCAGCCACCAATTAAGAAAGCGTTCAAGCTCAACACCCACTACCTAAAAAATCCCAAACATATAACTGA |
| Seq-31 | chrM | Sense | 1670 | 1744 | 75 | 967 | ------T----------------------T----C---------------------------------------- |
| Seq-31 | hchrM | Sense | 2251 | 2325 | 75 | 968 | ACTCCTCACACCCAATTGGACCAATCTATCACCCTATAGAAGAACTAATGTTAGTATAAGTAACATGAAAACATT |
| Seq-32 | chrM | Sense | 1745 | 1819 | 75 | 969 | -----------------A-A-----CC----T-T-A------------------T-------------------- |
| Seq-32 | hchrM | Sense | 2326 | 2400 | 75 | 970 | CTCCTCCGCATAAGCCTGCGTCAGATTAAAACACTGAACTGACAATTAACAGCCCAATATCTACAATCAACCAAC |
| Seq-33 | chrM | Sense | 1820 | 1894 | 75 | 971 | ---C-----------C-G----T------------------C--C------------------------------ |

TABLE 6-continued

Chimpanzee and Human Mitochondrial Paralogs

| fragment | chr | strand | start | end | width | SEQ ID NO: | amplicon |
|---|---|---|---|---|---|---|---|
| Seq-33 | hchrM | Sense | 2401 | 2475 | 75 | 972 | AAGTCATTATTACCCTCACTGTCAACCCAACACAGGCATGCTCATAAG GAAAGGTTAAAAAAAGTAAAAGGAACT |
| Seq-34 | chrM | Sense | 1895 | 1969 | 75 | 973 | ------------------------------------------------ T-------------------------G |
| Seq-34 | hchrM | Sense | 2476 | 2550 | 75 | 974 | CGGCAAATCTTACCCCGCCTGTTTACCAAAAACATCACCTCTAGCATC ACCAGTATTAGAGGCACCGCCTGCCCA |
| Seq-35 | chrM | Sense | 1970 | 2044 | 75 | 975 | ------T----------------------------------------- --------------------------T |
| Seq-35 | hchrM | Sense | 2551 | 2625 | 75 | 976 | GTGACACATGTTTAACGGCCGCGGTACCCTAACCGTGCAAAGGTAGCA TAATCACTTGTTCCTTAAATAGGGACC |
| Seq-36 | chrM | Sense | 2045 | 2119 | 75 | 977 | ------------------------T----------------C------ ------------A-------------- |
| Seq-36 | hchrM | Sense | 2626 | 2700 | 75 | 978 | TGTATGAATGGCTCCACGAGGGTTCAGCTGTCTCTTACTTTTAACCAG TGAAATTGACCTGCCCGTGAAGAGGCG |
| Seq-37 | chrM | Sense | 2120 | 2194 | 75 | 979 | ---------T-A-------------------------------C---- ---------A---T---------T--- |
| Seq-37 | hchrM | Sense | 2701 | 2775 | 75 | 980 | GGCATAACACAGCAAGACGAGAAGACCCTATGGAGCTTTAATTTATTA ATGCAAACAGTACCTAACAAACCCACA |
| Seq-38 | chrM | Sense | 2195 | 2269 | 75 | 981 | ------------TT---------------------------------- -------C-----------------A- |
| Seq-38 | hchrM | Sense | 2776 | 2850 | 75 | 982 | GGTCCTAAACTACCAAACCTGCATTAAAAATTTCGGTTGGGGCGACCT CGGAGCAGAACCCAACCTCCGAGCAGT |
| Seq-39 | chrM | Sense | 2270 | 2344 | 75 | 983 | ------------C-----------------T-----C-TC-------- -----G--------------------- |
| Seq-39 | hchrM | Sense | 2851 | 2925 | 75 | 984 | ACATGCTAAGACTTCACCAGTCAAAGCGAACTACTATACTCAATTGAT CCAATAACTTGACCAACGGAACAAGTT |
| Seq-40 | chrM | Sense | 2345 | 2419 | 75 | 985 | -----------------------------C------------------ --------------------------- |
| Seq-40 | hchrM | Sense | 2926 | 3000 | 75 | 986 | ACCCTAGGGATAACAGCGCAATCCTATTCTAGAGTCCATATCAACAAT AGGGTTTACGACCTCGATGTTGGATCA |
| Seq-41 | chrM | Sense | 2420 | 2494 | 75 | 987 | ------------------------------------------------ --------------------------- |
| Seq-41 | hchrM | Sense | 3001 | 3075 | 75 | 988 | GGACATCCCGATGGTGCAGCCGCTATTAAAGGTTCGTTTGTTCAACGA TTAAAGTCCTACGTGATCTGAGTTCAG |
| Seq-42 | hchrM | Sense | 3076 | 3150 | 75 | 989 | ACCGGAGTAATCCAGGTCGGTTTCTATCTACNTTCAAATTCCTCCCTG TACGAAAGGACAAGAGAAATAAGGCCT |
| Seq-43 | chrM | Sense | 2569 | 2643 | 75 | 990 | ---------------------AA----------T---------T---- CGCC--G--A--------T-------A |
| Seq-43 | hchrM | Sense | 3151 | 3225 | 75 | 991 | ACTTCACAAAGCGCCTTCCCCCGTAAATGATATCATCTCAACTTAGTA TTATACCCACACCCACCCAAGAACAGG |
| Seq-44 | chrM | Sense | 2644 | 2718 | 75 | 992 | ----------------------------T------------------- ---A----------------------- |
| Seq-44 | hchrM | Sense | 3226 | 3300 | 75 | 993 | GTTTGTTAAGATGGCAGAGCCCGGTAATCGCATAAAACTTAAAACTTT ACAGTCAGAGGTTCAATTCCTCTTCTT |
| Seq-45 | chrM | Sense | 2719 | 2793 | 75 | 994 | G------C-------A----------------------------C--- --------A--------------A--- |
| Seq-45 | hchrM | Sense | 3301 | 3375 | 75 | 995 | AACAACATACCCATGGCCAACCTCCTACTCCTCATTGTACCCATTCTA ATCGCAATGGCATTCCTAATGCTTACC |
| Seq-46 | chrM | Sense | 2794 | 2868 | 75 | 996 | --------------------C-----------------T------A-- -----T--T---------T----G--- |

TABLE 6-continued

Chimpanzee and Human Mitochondrial Paralogs

| fragment | chr | strand | start | end | width | SEQ ID NO: | amplicon |
|---|---|---|---|---|---|---|---|
| Seq-46 | hchrM | Sense | 3376 | 3450 | 75 | 997 | GAACGAAAAATTCTAGGCTATATACAACTACGCAAAGGCCCCAACGTT GTAGGCCCCTACGGGCTACTACAACCC |
| Seq-47 | chrM | Sense | 2869 | 2943 | 75 | 998 | --------------------------T-----A---T--------T-- --T--A-----T-------------- |
| Seq-47 | hchrM | Sense | 3451 | 3525 | 75 | 999 | TTCGCTGACGCCATAAAACTCTTCACCAAAGAGCCCCTAAAACCCGCC ACATCTACCATCACCCTCTACATCACC |
| Seq-48 | chrM | Sense | 2944 | 3018 | 75 | 1000 | -----A---C----C--------T--C--CT----------------- -----------------A-----T-T |
| Seq-48 | hchrM | Sense | 3526 | 3600 | 75 | 1001 | GCCCCGACCTTAGCTCTCACCATCGCTCTTCTACTATGAACCCCCCTC CCCATACCCAACCCCCTGGTCAACCTC |
| Seq-49 | chrM | Sense | 3019 | 3093 | 75 | 1002 | ---T---------------------------C--------------- --------------------------- |
| Seq-49 | hchrM | Sense | 3601 | 3675 | 75 | 1003 | AACCTAGGCCTCCTATTTATTCTAGCCACCTCTAGCCTAGCCGTTTAC TCAATCCTCTGATCAGGGTGAGCATCA |
| Seq-50 | chrM | Sense | 3094 | 3168 | 75 | 1004 | -----G---------T-A-----T-----A------------------ --------C--------T--------T |
| Seq-50 | hchrM | Sense | 3676 | 3750 | 75 | 1005 | AACTCAAACTACGCCCTGATCGGCGCACTGCGAGCAGTAGCCCAAACA ATCTCATATGAAGTCACCCTAGCCATC |
| Seq-51 | chrM | Sense | 3169 | 3243 | 75 | 1006 | --C-----G-----GC-------------------C--T-----T--- ---G-------------G--------- |
| Seq-51 | hchrM | Sense | 3751 | 3825 | 75 | 1007 | ATTCTACTATCAACATTACTAATAAGTGGCTCCTTTAACCTCTCCACC CTTATCACAACACAAGAACACCTCTGA |
| Seq-52 | chrM | Sense | 3244 | 3318 | 75 | 1008 | C--A--------A--------C----------------------T--- --------------------T------ |
| Seq-52 | hchrM | Sense | 3826 | 3900 | 75 | 1009 | TTACTCCTGCCATCATGACCCTTGGCCATAATATGATTTATCTCCACA CTAGCAGAGACCAACCGAACCCCCTTC |
| Seq-53 | chrM | Sense | 3319 | 3393 | 75 | 1010 | ------A-T-----A--A--T-----------------T--T----- G--T-------------T--------T |
| Seq-53 | hchrM | Sense | 3901 | 3975 | 75 | 1011 | GACCTTGCCGAAGGGGAGTCCGAACTAGTCTCAGGCTTCAACATCGAA TACGCCGCAGGCCCCTTCGCCCTATTC |
| Seq-54 | chrM | Sense | 3394 | 3468 | 75 | 1012 | ----------------T---------------------------TG-- ---------------G-------CA-T |
| Seq-54 | hchrM | Sense | 3976 | 4050 | 75 | 1013 | TTCATAGCCGAATACACAAACATTATTATAATAAACACCCTCACCACT ACAATCTTCCTAGGAACAACATATGAC |
| Seq-55 | chrM | Sense | 3469 | 3543 | 75 | 1014 | A-T-A------------------G-----------------AG-T--- ------------------C-------- |
| Seq-55 | hchrM | Sense | 4051 | 4125 | 75 | 1015 | GCACTCTCCCCTGAACTCTACACAACATATTTTGTCACCAAGACCCTA CTTCTAACCTCCCTGTTCTTATGAATT |
| Seq-56 | chrM | Sense | 3544 | 3618 | 75 | 1016 | -----------T--------T-----------G--------------- --------------------------- |
| Seq-56 | hchrM | Sense | 4126 | 4200 | 75 | 1017 | CGAACAGCATACCCCCGATTCCGCTACGACCAACTCATACACCTCCTA TGAAAAAACTTCCTACCACTCACCCTA |
| Seq-57 | chrM | Sense | 3619 | 3693 | 75 | 1018 | ----C---C--G------A------------C-------------- C-------------------------- |
| Seq-57 | hchrM | Sense | 4201 | 4275 | 75 | 1019 | GCATTACTTATATGATATGTCTCCATACCCATTACAATCTCCAGCATT CCCCCTCAAACCTAAGAAATATGTCTG |
| Seq-58 | chrM | Sense | 3694 | 3768 | 75 | 1020 | --------A--------------------------T-C---T----- ---------------A---------T |

TABLE 6-continued

| Chimpanzee and Human Mitochondrial Paralogs | | | | | | | |
|---|---|---|---|---|---|---|---|
| fragment | chr | strand | start | end | width | SEQ ID NO: | amplicon |
| Seq-58 | hchrM | Sense | 4276 | 4350 | 75 | 1021 | ATAAAAGAGTTACTTTGATAGAGTAAATAATAGGAGCTTAAACCCCCT<br>TATTTCTAGGACTATGAGAATCGAACC |
| Seq-59 | chrM | Sense | 3769 | 3843 | 75 | 1022 | ------------------------------------------------<br>--------------------------- |
| Seq-59 | hchrM | Sense | 4351 | 4425 | 75 | 1023 | CATCCCTGAGAATCCAAAATTCTCCGTGCCACCTATCACACCCCATCC<br>TAAAGTAAGGTCAGCTAAATAAGCTAT |
| Seq-60 | chrM | Sense | 3844 | 3918 | 75 | 1024 | ----------------------------C-------------------<br>-------A---------A--------- |
| Seq-60 | hchrM | Sense | 4426 | 4500 | 75 | 1025 | CGGGCCCATACCCCGAAAATGTTGGTTATACCCTTCCCGTACTAATTA<br>ATCCCCTGGCCCAACCCGTCATCTACT |
| Seq-61 | chrM | Sense | 3919 | 3993 | 75 | 1026 | --------C--A-------G-----T--------------A-------<br>----C---------------------- |
| Seq-61 | hchrM | Sense | 4501 | 4575 | 75 | 1027 | CTACCATCTTTGCAGGCACACTCATCACAGCGCTAAGCTCGCACTGAT<br>TTTTTACCTGAGTAGGCCTAGAAATAA |
| Seq-62 | chrM | Sense | 3994 | 4068 | 75 | 1028 | -T--A-----------C---A-C----------------G---C--C-<br>----------C--------A--C--T- |
| Seq-62 | hchrM | Sense | 4576 | 4650 | 75 | 1029 | ACATGCTAGCTTTTATTCCAGTTCTAACCAAAAAAATAAACCCTCGTT<br>CCACAGAAGCTGCCATCAAGTATTTCC |
| Seq-63 | chrM | Sense | 4069 | 4143 | 75 | 1030 | ----A--------T--G--------T--C--G-------------C--<br>---GC---------------------- |
| Seq-63 | hchrM | Sense | 4651 | 4725 | 75 | 1031 | TCACGCAAGCAACCGCATCCATAATCCTTCTAATAGCTATCCTCTTCA<br>ACAATATACTCTCCGGACAATGAACCA |
| Seq-64 | chrM | Sense | 4144 | 4218 | 75 | 1032 | -------------------------------------T--------A-<br>-G------------------------- |
| Seq-64 | hchrM | Sense | 4726 | 4800 | 75 | 1033 | TAACCAATACTACCAATCAATACTCATCATTAATAATCATAATAGCTA<br>TAGCAATAAAACTAGGAATAGCCCCCT |
| Seq-65 | chrM | Sense | 4219 | 4293 | 75 | 1034 | -------T-----T-----A-----------------C--A-T-----<br>----A--C--C---------------T |
| Seq-65 | hchrM | Sense | 4801 | 4875 | 75 | 1035 | TTCACTTCTGAGTCCCAGAGGTTACCCAAGGCACCCCTCTGACATCCG<br>GCCTGCTTCTTCTCACATGACAAAAAC |
| Seq-66 | chrM | Sense | 4294 | 4368 | 75 | 1036 | -------T--T-----T-------------CT-A------G-------<br>A------------C--T--------G- |
| Seq-66 | hchrM | Sense | 4876 | 4950 | 75 | 1037 | TAGCCCCCATCTCAATCATATACCAAATCTCTCCCTCACTAAACGTAA<br>GCCTTCTCCTCACTCTCTCAATCTTAT |
| Seq-67 | chrM | Sense | 4369 | 4443 | 75 | 1038 | ----T-----------C-----C---C-------------A-------<br>-----C----------------C---- |
| Seq-67 | hchrM | Sense | 4951 | 5025 | 75 | 1039 | CCATCATAGCAGGCAGTTGAGGTGGATTAAACCAAACCCAGCTACGCA<br>AAATCTTAGCATACTCCTCAATTACCC |
| Seq-68 | chrM | Sense | 4444 | 4518 | 75 | 1040 | -------C--------------C-----A--T----------------<br>-------------C-----C--C---- |
| Seq-68 | hchrM | Sense | 5026 | 5100 | 75 | 1041 | ACATAGGATGAATAATAGCAGTTCTACCGTACAACCCTAACATAACCA<br>TTCTTAATTTAACTATTTATATTATCC |
| Seq-69 | chrM | Sense | 4519 | 4593 | 75 | 1042 | ----------------T--G--------------------------A-<br>--------------------------- |
| Seq-69 | hchrM | Sense | 5101 | 5175 | 75 | 1043 | TAACTACTACCGCATTCCTACTACTCAACTTAAACTCCAGCACCACGA<br>CCCTACTACTATCTCGCACCTGAAACA |
| Seq-70 | chrM | Sense | 4594 | 4668 | 75 | 1044 | -----------T----T---C---------------------------<br>-------A-----A-----T-----C- |
| Seq-70 | hchrM | Sense | 5176 | 5250 | 75 | 1045 | AGCTAACATGACTAACACCCTTAATTCCATCCACCCTCCTCTCCCTAG<br>GAGGCCTGCCCCCGCTAACCGGCTTTT |

TABLE 6-continued

Chimpanzee and Human Mitochondrial Paralogs

| fragment | chr | strand | start | end | width | SEQ ID NO: | amplicon |
|---|---|---|---|---|---|---|---|
| Seq-71 | chrM | Sense | 4669 | 4743 | 75 | 1046 | -A--------A-TT--C--------------------T---------- ---------------------T----- |
| Seq-71 | hchrM | Sense | 5251 | 5325 | 75 | 1047 | TGCCCAAATGGGCCATTATCGAAGAATTCACAAAAAACAATAGCCTCA TCATCCCCACCATCATAGCCACCATCA |
| Seq-72 | chrM | Sense | 4744 | 4818 | 75 | 1048 | -T--------------T------------------------------- -T--------T-----------T---- |
| Seq-72 | hchrM | Sense | 5326 | 5400 | 75 | 1049 | CCCTCCTTAACCTCTACTTCTACCTACGCCTAATCTACTCCACCTCAA TCACACTACTCCCCATATCTAACAACG |
| Seq-73 | chrM | Sense | 4819 | 4893 | 75 | 1050 | ----------------A--C--------------------C------- -T---------A----------A--G- |
| Seq-73 | hchrM | Sense | 5401 | 5475 | 75 | 1051 | TAAAAATAAAATGACAGTTTGAACATACAAAACCCACCCCATTCCTCC CCACACTCATCGCCCTTACCACGCTAC |
| Seq-74 | chrM | Sense | 4894 | 4968 | 75 | 1052 | -T-----C--------C--C---------------------------- ---GC---------------------- |
| Seq-74 | hchrM | Sense | 5476 | 5550 | 75 | 1053 | TCCTACCTATCTCCCCTTTTATACTAATAATCTTATAGAAATTTAGGT TAAATACAGACCAAGAGCCTTCAAAGC |
| Seq-75 | chrM | Sense | 4969 | 5043 | 75 | 1054 | ------C-----A----------------C----A------------- --------------------------- |
| Seq-75 | hchrM | Sense | 5551 | 5625 | 75 | 1055 | CCTCAGTAAGTTGCAATACTTAATTTCTGTAACAGCTAAGGACTGCAA AACCCCACTCTGCATCAACTGAACGCA |
| Seq-76 | chrM | Sense | 5044 | 5118 | 75 | 1056 | ------------------------------------TT---------- -------------T------------- |
| Seq-76 | hchrM | Sense | 5626 | 5700 | 75 | 1057 | AATCAGCCACTTTAATTAAGCTAAGCCCTTACTAGACCAATGGGACTT AAACCCACAAACACTTAGTTAACAGCT |
| Seq-77 | chrM | Sense | 5119 | 5193 | 75 | 1058 | --A---------------------------------------AA-A-- --------------------------- |
| Seq-77 | hchrM | Sense | 5701 | 5775 | 75 | 1059 | AAGCACCCTAATCAACTGGCTTCAATCTACTTCTCCCGCCGCCGGGAA AAAAGGCGGGAGAAGCCCCGGCAGGTT |
| Seq-78 | chrM | Sense | 5194 | 5268 | 75 | 1060 | ---------------------------------------------A-- ----------------T---------- |
| Seq-78 | hchrM | Sense | 5776 | 5850 | 75 | 1061 | TGAAGCTGCTTCTTCGAATTTGCAATTCAATATGAAAATCACCTCGGA GCTGGTAAAAAGAGGCCTAACCCCTGT |
| Seq-79 | hchrM | Sense | 5851 | 5925 | 75 | 1062 | CTTTAGATTTACAGTCCAATGCTTCACTCAGCCATTTTACCTCACCCC CACTGATGTTCGCCGACCGTTGACTAT |
| Seq-80 | chrM | Sense | 5343 | 5417 | 75 | 1063 | -------------------T------------------C-------T- ----------------G--------C- |
| Seq-80 | hchrM | Sense | 5926 | 6000 | 75 | 1064 | TCTCTACAAACCACAAAGACATTGGAACACTATACCTATTATTCGGCG CATGAGCTGGAGTCCTAGGCACAGCTC |
| Seq-81 | chrM | Sense | 5418 | 5492 | 75 | 1065 | ----T-----------G--T--A--A-----A-----------C---- ---T---------------T--C---- |
| Seq-81 | hchrM | Sense | 6001 | 6075 | 75 | 1066 | TAAGCCTCCTTATTCGAGCCGAGCTGGGCCAGCCAGGCAACCTTCTAG GTAACGACCACATCTACAACGTTATCG |
| Seq-82 | chrM | Sense | 5493 | 5567 | 75 | 1067 | ----------------C-----------------------G--T--T- ----------------------G---- |
| Seq-82 | hchrM | Sense | 6076 | 6150 | 75 | 1068 | TCACAGCCCATGCATTTGTAATAATCTTCTTCATAGTAATACCCATCA TAATCGGAGGCTTTGGCAACTGACTAG |
| Seq-83 | chrM | Sense | 5568 | 5642 | 75 | 1069 | -----T-G-----T-----------C-----A--C------------- -------------G---C-G--C--T- |

TABLE 6-continued

| Chimpanzee and Human Mitochondrial Paralogs | | | | | | | |
|---|---|---|---|---|---|---|---|
| fragment | chr | strand | start | end | width | SEQ ID NO: | amplicon |
| Seq-83 | hchrM | Sense | 6151 | 6225 | 75 | 1070 | TTCCCCTAATAATCGGTGCCCCCGATATGGCGTTTCCCCGCATAAACA<br>ACATAAGCTTCTGACTCTTACCTCCCT |
| Seq-84 | chrM | Sense | 5643 | 5717 | 75 | 1071 | ----------T--A--T--------C-----A--A-----C--G----<br>--------------------------- |
| Seq-84 | hchrM | Sense | 6226 | 6300 | 75 | 1072 | CTCTCCTACTCCTGCTCGCATCTGCTATAGTGGAGGCCGGAGCAGGAA<br>CAGGTTGAACAGTCTACCCTCCCTTAG |
| Seq-85 | chrM | Sense | 5718 | 5792 | 75 | 1073 | -G--A--------G--T-------------------------------<br>-------T--G-----CA--------- |
| Seq-85 | hchrM | Sense | 6301 | 6375 | 75 | 1074 | CAGGGAACTACTCCCACCCTGGAGCCTCCGTAGACCTAACCATCTTCT<br>CCTTACACCTAGCAGGTGTCTCCTCTA |
| Seq-86 | chrM | Sense | 5793 | 5867 | 75 | 1075 | --C----A-----T--C-----------------T-----------T-<br>-------G--------------A---- |
| Seq-86 | hchrM | Sense | 6376 | 6450 | 75 | 1076 | TCTTAGGGGCCATCAATTTCATCACAACAATTATCAATATAAAACCCC<br>CTGCCATAACCCAATACCAAACGCCCC |
| Seq-87 | chrM | Sense | 5868 | 5942 | 75 | 1077 | --------------------------------T-------------C-<br>-------------------------C- |
| Seq-87 | hchrM | Sense | 6451 | 6525 | 75 | 1078 | TCTTCGTCTGATCCGTCCTAATCACAGCAGTCCTACTTCTCCTATCTC<br>TCCCAGTCCTAGCTGCTGGCATCACTA |
| Seq-88 | chrM | Sense | 5943 | 6017 | 75 | 1079 | -----T-G-----T--T-----------T--------------A----<br>-G-----------T--------T---- |
| Seq-88 | hchrM | Sense | 6526 | 6600 | 75 | 1080 | TACTACTAACAGACCGCAACCTCAACACCACCTTCTTCGACCCCGCCG<br>GAGGAGGAGACCCCATTCTATACCAAC |
| Seq-89 | chrM | Sense | 6018 | 6092 | 75 | 1081 | --T-------------T--C-----C----------------------<br>----------------T-----C---- |
| Seq-89 | hchrM | Sense | 6601 | 6675 | 75 | 1082 | ACCTATTCTGATTTTTCGGTCACCCTGAAGTTTATATTCTTATCCTAC<br>CAGGCTTCGGAATAATCTCCCATATTG |
| Seq-90 | chrM | Sense | 6093 | 6167 | 75 | 1083 | -------T-----------------------------T-----C----<br>-T--------A---------------- |
| Seq-90 | hchrM | Sense | 6676 | 6750 | 75 | 1084 | TAACTTACTACTCCGGAAAAAAAGAACCATTTGGATACATAGGTATGG<br>TCTGAGCTATGATATCAATTGGCTTCC |
| Seq-91 | chrM | Sense | 6168 | 6242 | 75 | 1085 | ----------------------------------------G-------<br>-------C-----C------------- |
| Seq-91 | hchrM | Sense | 6751 | 6825 | 75 | 1086 | TAGGGTTTATCGTGTGAGCACACCATATATTTACAGTAGGAATAGACG<br>TAGACACACGAGCATATTTCACCTCCG |
| Seq-92 | chrM | Sense | 6243 | 6317 | 75 | 1087 | -------------T-----T--T-----------------C-------<br>----T-----T---------------- |
| Seq-92 | hchrM | Sense | 6826 | 6900 | 75 | 1088 | CTACCATAATCATCGCTATCCCCACCGGCGTCAAAGTATTTAGCTGAC<br>TCGCCACACTCCACGGAAGCAATATGA |
| Seq-93 | chrM | Sense | 6318 | 6392 | 75 | 1089 | ----------C-----A--------------G--T--------C----<br>-------------A--C----------C |
| Seq-93 | hchrM | Sense | 6901 | 6975 | 75 | 1090 | AATGATCTGCTGCAGTGCTCTGAGCCCTAGGATTCATCTTTCTTTTCA<br>CCGTAGGTGGCCTGACTGGCATTGTAT |
| Seq-94 | chrM | Sense | 6393 | 6467 | 75 | 1091 | --------------T----------G-----------A--------C-<br>----------------C--T------- |
| Seq-94 | hchrM | Sense | 6976 | 7050 | 75 | 1092 | TAGCAAACTCATCACTAGACATCGTACTACACGACACGTACTACGTTG<br>TAGCCCACTTCCACTATGTCCTATCAA |
| Seq-95 | chrM | Sense | 6468 | 6542 | 75 | 1093 | -------------C-----------------------------C----<br>-------------T------------- |
| Seq-95 | hchrM | Sense | 7051 | 7125 | 75 | 1094 | TAGGAGCTGTATTTGCCATCATAGGAGGCTTCATTCACTGATTTCCCC<br>TATTCTCAGGCTACACCCTAGACCAAA |

TABLE 6-continued

Chimpanzee and Human Mitochondrial Paralogs

| fragment | chr | strand | start | end | width | SEQ ID NO: | amplicon |
|---|---|---|---|---|---|---|---|
| Seq-96 | chrM | Sense | 6543 | 6617 | 75 | 1095 | ----T-----------A--TG-C-----G-----T--------C---- -C-----------G-----C--T---- |
| Seq-96 | hchrM | Sense | 7126 | 7200 | 75 | 1096 | CCTACGCCAAAATCCATTTCACTATCATATTCATCGGCGTAAATCTAA CTTTCTTCCCACAACACTTTCTCGGCC |
| Seq-97 | chrM | Sense | 6618 | 6692 | 75 | 1097 | ----T--G---------------------------------------- -------TG----------C------- |
| Seq-97 | hchrM | Sense | 7201 | 7275 | 75 | 1098 | TATCCGGAATGCCCCGACGTTACTCGGACTACCCCGATGCATACACCA CATGAAACATCCTATCATCTGTAGGCT |
| Seq-98 | chrM | Sense | 6693 | 6767 | 75 | 1099 | ----T--C--C--G---------------------------------- -------T-----A--A---------- |
| Seq-98 | hchrM | Sense | 7276 | 7350 | 75 | 1100 | CATTCATTTCTCTAACAGCAGTAATATTAATAATTTTCATGATTTGAG AAGCCTTCGCTTCGAAGCGAAAAGTCC |
| Seq-99 | chrM | Sense | 6768 | 6842 | 75 | 1101 | -------------G------GC---------A---------------- --------------------------- |
| Seq-99 | hchrM | Sense | 7351 | 7425 | 75 | 1102 | TAATAGTAGAAGAACCCTCCATAAACCTGGAGTGACTATATGGATGCC CCCCACCCTACCACACATTCGAAGAAC |
| Seq-100 | chrM | Sense | 6843 | 6917 | 75 | 1103 | ---------------------------------------------T-- -------------------------A- |
| Seq-100 | hchrM | Sense | 7426 | 7500 | 75 | 1104 | CCGTATACATAAAATCTAGACAAAAAAGGAAGGAATCGAACCCCCCAA AGCTGGTTTCAAGCCAACCCCATGGCC |
| Seq-101 | chrM | Sense | 6918 | 6992 | 75 | 1105 | --------------------A------------T-------------- -------------C---T---CC--C |
| Seq-101 | hchrM | Sense | 7501 | 7575 | 75 | 1106 | TCCATGACTTTTTCAAAAAGGTATTAGAAAAACCATTTCATAACTTTG TCAAAGTTAAATTATAGGCTAAATCCT |
| Seq-102 | chrM | Sense | 6993 | 7067 | 75 | 1107 | G-----------------------------------------T----- ------------------A-----T-T |
| Seq-102 | hchrM | Sense | 7576 | 7650 | 75 | 1108 | ATATATCTTAATGGCACATGCAGCGCAAGTAGGTCTACAAGACGCTAC TTCCCCTATCATAGAAGAGCTTATCAC |
| Seq-103 | chrM | Sense | 7068 | 7142 | 75 | 1109 | ------C--C--T-----------T--C--T--C--------T----- ---A--C-------------------- |
| Seq-103 | hchrM | Sense | 7651 | 7725 | 75 | 1110 | CTTTCATGATCACGCCCTCATAATCATTTTCCTTATCTGCTTCCTAGT CCTGTATGCCCTTTTCCTAACACTCAC |
| Seq-104 | chrM | Sense | 7143 | 7217 | 75 | 1111 | --------------------GT--T--------C-------------- --------------------------- |
| Seq-104 | hchrM | Sense | 7726 | 7800 | 75 | 1112 | AACAAAACTAACTAATACTAACATCTCAGACGCTCAGGAAATAGAAAC CGTCTGAACTATCCTGCCCGCCATCAT |
| Seq-105 | chrM | Sense | 7218 | 7292 | 75 | 1113 | ---------T--T-----A--------G--T----------------- ------------C------T----T-- |
| Seq-105 | hchrM | Sense | 7801 | 7875 | 75 | 1114 | CCTAGTCCTCATCGCCCTCCCATCCCTACGCATCCTTTACATAACAGA CGAGGTCAACGATCCCTCCCTTACCAT |
| Seq-106 | chrM | Sense | 7293 | 7367 | 75 | 1115 | T--------C-----T-----A--T-----------A----------- ------G-------------------- |
| Seq-106 | hchrM | Sense | 7876 | 7950 | 75 | 1116 | CAAATCAATTGGCCACCAATGGTACTGAACCTACGAGTACACCGACTA CGGCGGACTAATCTTCAACTCCTACAT |
| Seq-107 | chrM | Sense | 7368 | 7442 | 75 | 1117 | ---C-----------T-----------T--T--A-------------- ---T--C-----G--C-----AG---- |
| Seq-107 | hchrM | Sense | 7951 | 8025 | 75 | 1118 | ACTTCCCCCATTATTCCTAGAACCAGGCGACCTGCGACTCCTTGACGT TGACAATCGAGTAGTACTCCCGATTGA |

TABLE 6-continued

Chimpanzee and Human Mitochondrial Paralogs

| fragment | chr | strand | start | end | width | SEQ ID NO: | amplicon |
|---|---|---|---|---|---|---|---|
| Seq-108 | chrM | Sense | 7443 | 7517 | 75 | 1119 | -------G-------------------------T--TC-A--------<br>------T------------C------- |
| Seq-108 | hchrM | Sense | 8026 | 8100 | 75 | 1120 | AGCCCCCATTCGTATAATAATTACATCACAAGACGTCTTGCACTCATG<br>AGCTGTCCCCACATTAGGCTTAAAAAC |
| Seq-109 | chrM | Sense | 7518 | 7592 | 75 | 1121 | ---C--------------C-----------------------C-----<br>---A--A-----------C-------- |
| Seq-109 | hchrM | Sense | 8101 | 8175 | 75 | 1122 | AGATGCAATTCCCGGACGTCTAAACCAAACCACTTTCACCGCTACACG<br>ACCGGGGGTATACTACGGTCAATGCTC |
| Seq-110 | chrM | Sense | 7593 | 7667 | 75 | 1123 | A--------------------------T--A-----------------<br>---C--T-------------------- |
| Seq-110 | hchrM | Sense | 8176 | 8250 | 75 | 1124 | TGAAATCTGTGGAGCAAACCACAGTTTCATGCCCATCGTCCTAGAATT<br>AATTCCCCTAAAAATCTTTGAAATAGG |
| Seq-111 | hchrM | Sense | 8251 | 8325 | 75 | 1125 | GCCCGTATTTACCCTATAGCACCCCCTCTACCCCCTCTAGAGCCCACT<br>GTAAAGCTAACTTAGCATTAACCTTTT |
| Seq-112 | chrM | Sense | 7744 | 7818 | 75 | 1126 | -----------------G---G--------------------------<br>---------CG-------A-------- |
| Seq-112 | hchrM | Sense | 8326 | 8400 | 75 | 1127 | AAGTTAAAGATTAAGAGAACCAACACCTCTTTACAGTGAAATGCCCCA<br>ACTAAATACTACCGTATGGCCCACCAT |
| Seq-113 | chrM | Sense | 7819 | 7893 | 75 | 1128 | ------------------G--------T---G----------------<br>------TT----T-----T-----C-- |
| Seq-113 | hchrM | Sense | 8401 | 8475 | 75 | 1129 | AATTACCCCCATACTCCTTACACTATTCCTCATCACCCAACTAAAAAT<br>ATTAAACACAAACTACCACCTACCTCC |
| Seq-114 | chrM | Sense | 7894 | 7968 | 75 | 1130 | ---------A-----------------C--C--T--------------<br>-----------------A--------- |
| Seq-114 | hchrM | Sense | 8476 | 8550 | 75 | 1131 | CTCACCAAAGCCCATAAAAATAAAAAATTATAACAAACCCTGAGAACC<br>AAAATGAACGAAAATCTGTTCGCTTCA |
| Seq-115 | chrM | Sense | 7969 | 8043 | 75 | 1132 | ---GC-------------------T----------------A------<br>-----C---------C--G-------T |
| Seq-115 | hchrM | Sense | 8551 | 8625 | 75 | 1133 | TTCATTGCCCCCACAATCCTAGGCCTACCCGCCGCAGTACTGATCATT<br>CTATTTCCCCCTCTATTGATCCCCACC |
| Seq-116 | chrM | Sense | 8044 | 8118 | 75 | 1134 | --T---C----------------------T------------------<br>--TC----G--------------A--- |
| Seq-116 | hchrM | Sense | 8626 | 8700 | 75 | 1135 | TCCAAATATCTCATCAACAACCGACTAATCACCACCCAACAATGACTA<br>ATCAAACTAACCTCAAAACAAATGATA |
| Seq-117 | chrM | Sense | 8119 | 8193 | 75 | 1136 | --T-------G------------------------C------------<br>---------------A-------C--T |
| Seq-117 | hchrM | Sense | 8701 | 8775 | 75 | 1137 | ACCATACACAACACTAAAGGACGAACCTGATCTCTTATACTAGTATCC<br>TTAATCATTTTTATTGCCACAACTAAC |
| Seq-118 | chrM | Sense | 8194 | 8268 | 75 | 1138 | --T--T--G--T--A--C--------C---------------------<br>-----------------T------C-- |
| Seq-118 | hchrM | Sense | 8776 | 8850 | 75 | 1139 | CTCCTCGGACTCCTGCCTCACTCATTTACACCAACCACCCAACTATCT<br>ATAAACCTAGCCATGGCCATCCCCTTA |
| Seq-119 | chrM | Sense | 8269 | 8343 | 75 | 1140 | -----A---G----AG-C-------------T-----C----------<br>-----------------G--------- |
| Seq-119 | hchrM | Sense | 8851 | 8925 | 75 | 1141 | TGAGCGGGCACAGTGATTATAGGCTTTCGCTCTAAGATTAAAAATGCC<br>CTAGCCCACTTCTTACCACAAGGCACA |
| Seq-120 | chrM | Sense | 8344 | 8418 | 75 | 1142 | -----------------------------C--------T--T------<br>------------------T-A------ |
| Seq-120 | hchrM | Sense | 8926 | 9000 | 75 | 1143 | CCTACACCCCTTATCCCCATACTAGTTATTATCGAAACCATCAGCCTA<br>CTCATTCAACCAATAGCCCTGGCCGTA |

TABLE 6-continued

Chimpanzee and Human Mitochondrial Paralogs

| fragment | chr | strand | start | end | width | SEQ ID NO: | amplicon |
|---|---|---|---|---|---|---|---|
| Seq-121 | chrM | Sense | 8419 | 8493 | 75 | 1144 | --T---------------------------------------------<br>-----------A------T-------T |
| Seq-121 | hchrM | Sense | 9001 | 9075 | 75 | 1145 | CGCCTAACCGCTAACATTACTGCAGGCCACCTACTCATGCACCTAATT<br>GGAAGCGCCACCCTAGCAATATCAACC |
| Seq-122 | chrM | Sense | 8494 | 8568 | 75 | 1146 | --C--T--A----A-G----C--T-----------------C------<br>-----T-----G-----C--------- |
| Seq-122 | hchrM | Sense | 9076 | 9150 | 75 | 1147 | ATTAACCTTCCCTCTACACTTATCATCTTCACAATTCTAATTCTACTG<br>ACTATCCTAGAAATCGCTGTCGCCTTA |
| Seq-123 | chrM | Sense | 8569 | 8643 | 75 | 1148 | -----------------T-----------G------------------<br>--------------------------- |
| Seq-123 | hchrM | Sense | 9151 | 9225 | 75 | 1149 | ATCCAAGCCTACGTTTTCACACTTCTAGTAAGCCTCTACCTGCACGAC<br>AACACATAATGACCCACCAATCACATG |
| Seq-124 | chrM | Sense | 8644 | 8718 | 75 | 1150 | ----C--C----------------------------------------<br>-G-----------A-----------G- |
| Seq-124 | hchrM | Sense | 9226 | 9300 | 75 | 1151 | CCTATCATATAGTAAAACCCAGCCCATGACCCCTAACAGGGGCCCTCT<br>CAGCCCTCCTAATGACCTCCGGCCTAG |
| Seq-125 | chrM | Sense | 8719 | 8793 | 75 | 1152 | ----A-----C------T------C---A--A----C-------T---<br>----T------T-G--------T---- |
| Seq-125 | hchrM | Sense | 9301 | 9375 | 75 | 1153 | CCATGTGATTTCACTTCCACTCCATAACGCTCCTCATACTAGGCCTAC<br>TAACCAACACACTAACCATATACCAAT |
| Seq-126 | chrM | Sense | 8794 | 8868 | 75 | 1154 | ----A--------T-T-------G------------------------<br>----C-----------T--C-----T- |
| Seq-126 | hchrM | Sense | 9376 | 9450 | 75 | 1155 | GATGGCGCGATGTAACACGAGAAAGCACATACCAAGGCCACCACACAC<br>CACCTGTCCAAAAAGGCCTTCGATACG |
| Seq-127 | chrM | Sense | 8869 | 8943 | 75 | 1156 | -------T--T--------------------------T----------<br>-T-----T--C---------------- |
| Seq-127 | hchrM | Sense | 9451 | 9525 | 75 | 1157 | GGATAATCCTATTTATTACCTCAGAAGTTTTTTTCTTCGCAGGATTTT<br>TCTGAGCCTTTTACCACTCCAGCCTAG |
| Seq-128 | chrM | Sense | 8944 | 9018 | 75 | 1158 | -------------GC-------A-----------------T--T----<br>-A------------------------- |
| Seq-128 | hchrM | Sense | 9526 | 9600 | 75 | 1159 | CCCCTACCCCCCAATTAGGAGGGCACTGGCCCCCAACAGGCATCACCC<br>CGCTAAATCCCCTAGAAGTCCCACTCC |
| Seq-129 | chrM | Sense | 9019 | 9093 | 75 | 1160 | ----------T------------------------------T--T C-<br>-T--C--CT----------T------- |
| Seq-129 | hchrM | Sense | 9601 | 9675 | 75 | 1161 | TAAACACATCCGTATTACTCGCATCAGGAGTATCAATCACCTGAGCTC<br>ACCATAGTCTAATAGAAAACAACCGAA |
| Seq-130 | chrM | Sense | 9094 | 9168 | 75 | 1162 | ----------------------------G---C----A-----T----<br>----------------------A--T- |
| Seq-130 | hchrM | Sense | 9676 | 9750 | 75 | 1163 | ACCAAATAATTCAAGCACTGCTTATTACAATTTTACTGGGTCTCTATT<br>TTACCCTCCTACAAGCCTCAGAGTACT |
| Seq-131 | chrM | Sense | 9169 | 9243 | 75 | 1164 | ----A--C--T--T-----------T--------------------C-<br>-------------------------C- |
| Seq-131 | hchrM | Sense | 9751 | 9825 | 75 | 1165 | TCGAGTCTCCCTTCACCATTTCCGACGGCATCTACGGCTCAACATTTT<br>TTGTAGCCACAGGCTTCCACGGACTTC |
| Seq-132 | chrM | Sense | 9244 | 9318 | 75 | 1166 | -------------A---------------------C------------<br>-------------C------------- |
| Seq-132 | hchrM | Sense | 9826 | 9900 | 75 | 1167 | ACGTCATTATTGGCTCAACTTTCCTCACTATCTGCTTCATCCGCCAAC<br>TAATATTTCACTTTACATCCAAACATC |

TABLE 6-continued

| Chimpanzee and Human Mitochondrial Paralogs | | | | | | | |
|---|---|---|---|---|---|---|---|
| fragment | chr | strand | start | end | width | SEQ ID NO: | amplicon |
| Seq-133 | chrM | Sense | 9319 | 9393 | 75 | 1168 | ----C-----TC-------------------A--C--C--------A-<br>-C-----------A--------T--T- |
| Seq-133 | hchrM | Sense | 9901 | 9975 | 75 | 1169 | ACTTTGGCTTCGAAGCCGCCGCCTGATACTGGCATTTTGTAGATGTGG<br>TTTGACTATTTCTGTATGTCTCCATCT |
| Seq-134 | chrM | Sense | 9394 | 9468 | 75 | 1170 | -C--------A-------------------G-----------------<br>--------------------------- |
| Seq-134 | hchrM | Sense | 9976 | 10050 | 75 | 1171 | ATTGATGAGGGTCTTACTCTTTTAGTATAAATAGTACCGTTAACTTCC<br>AATTAACTAGTTTTGACAACATTCAAA |
| Seq-135 | chrM | Sense | 9469 | 9543 | 75 | 1172 | ------------------T-C------------C---T-----T----<br>--C-------G--------C-----C- |
| Seq-135 | hchrM | Sense | 10051 | 10125 | 75 | 1173 | AAAGAGTAATAAACTTCGCCTTAATTTTAATAATCAACACCCTCCTAG<br>CCTTACTACTAATAATTATTACATTTT |
| Seq-136 | chrM | Sense | 9544 | 9618 | 75 | 1174 | -----------------A----------------T-----------A-<br>-T------------------------- |
| Seq-136 | hchrM | Sense | 10126 | 10200 | 75 | 1175 | GACTACCACAACTCAACGGCTACATAGAAAAATCCACCCCTTACGAGT<br>GCGGCTTCGACCCTATATCCCCCGCCC |
| Seq-137 | chrM | Sense | 9619 | 9693 | 75 | 1176 | -------C--------------T---C-------C--C------C---<br>-------C-----------------A- |
| Seq-137 | hchrM | Sense | 10201 | 10275 | 75 | 1177 | GCGTCCCTTTCTCCATAAAATTCTTCTTAGTAGCTATTACCTTCTTAT<br>TATTTGATCTAGAAATTGCCCTCCTTT |
| Seq-138 | chrM | Sense | 9694 | 9768 | 75 | 1178 | -G---T----T--------------GG-C-----A-----------C-<br>CA-----------------T-CT---- |
| Seq-138 | hchrM | Sense | 10276 | 10350 | 75 | 1179 | TACCCCTACCATGAGCCCTACAAACAACTAACCTGCCACTAATAGTTA<br>TGTCATCCCTCTTATTAATCATCATCC |
| Seq-139 | chrM | Sense | 9769 | 9843 | 75 | 1180 | ----------C--C-----C--A---T----------G----------<br>----------------------T---- |
| Seq-139 | hchrM | Sense | 10351 | 10425 | 75 | 1181 | TAGCCCTAAGTCTGGCCTATGAGTGACTACAAAAAGGATTAGACTGAA<br>CCGAATTGGTATATAGTTTAAACAAAA |
| Seq-140 | chrM | Sense | 9844 | 9918 | 75 | 1182 | ------------------------------------------------<br>----T-----T---------------- |
| Seq-140 | hchrM | Sense | 10426 | 10500 | 75 | 1183 | CGAATGATTTCGACTCATTAAATTATGATAATCATATTTACCAAATGC<br>CCCTCATTTACATAAATATTATACTAG |
| Seq-141 | chrM | Sense | 9919 | 9993 | 75 | 1184 | ----------------------------------------------A-<br>----T---------------------- |
| Seq-141 | hchrM | Sense | 10501 | 10575 | 75 | 1185 | CATTTACCATCTCACTTCTAGGAATACTAGTATATCGCTCACACCTCA<br>TATCCTCCCTACTATGCCTAGAAGGAA |
| Seq-142 | chrM | Sense | 9994 | 10068 | 75 | 1186 | ----------A--------C-----C--C--------------T--T-<br>----------------------A--C- |
| Seq-142 | hchrM | Sense | 10576 | 10650 | 75 | 1187 | TAATACTATCGCTGTTCATTATAGCTACTCTCATAACCCTCAACACCC<br>ACTCCCTCTTAGCCAATATTGTGCCTA |
| Seq-143 | chrM | Sense | 10069 | 10143 | 75 | 1188 | -CA----------------T--------------A--A--T-----A-<br>-------T--------T---------- |
| Seq-143 | hchrM | Sense | 10651 | 10725 | 75 | 1189 | TTGCCATACTAGTCTTTGCCGCCTGCGAAGCAGCGGTGGGCCTAGCCC<br>TACTAGTCTCAATCTCCAACACATATG |
| Seq-144 | chrM | Sense | 10144 | 10218 | 75 | 1190 | --T---------------------------------------------<br>-A----G-------------------- |
| Seq-144 | hchrM | Sense | 10726 | 10800 | 75 | 1191 | GCCTAGACTACGTACATAACCTAAACCTACTCCAATGCTAAAACTAAT<br>CGTCCCAACAATTATATTACTACCACT |
| Seq-145 | chrM | Sense | 10219 | 10293 | 75 | 1192 | A------T-C--T-------GT-----------------------T--<br>------------C----C---T--CT- |

TABLE 6-continued

| Chimpanzee and Human Mitochondrial Paralogs | | | | | | | |
|---|---|---|---|---|---|---|---|
| fragment | chr | strand | start | end | width | SEQ ID NO: | amplicon |
| Seq-145 | hchrM | Sense | 10801 | 10875 | 75 | 1193 | GACATGACTTTCCAAAAAACACATAATTTGAATCAACACAACCACCCA CAGCCTAATTATTAGCATCATCCCTCT |
| Seq-146 | chrM | Sense | 10294 | 10368 | 75 | 1194 | ------------------T-------------C----------TGC- ---C-----------T-------T-- |
| Seq-146 | hchrM | Sense | 10876 | 10950 | 75 | 1195 | ACTATTTTTTAACCAAATCAACAACAACCTATTTAGCTGTTCCCCAAC CTTTTCCTCCGACCCCCTAACAACCCC |
| Seq-147 | chrM | Sense | 10369 | 10443 | 75 | 1196 | ----------T-----G-T-----T----------------A----- ---G------C------AC-------- |
| Seq-147 | hchrM | Sense | 10951 | 11025 | 75 | 1197 | CCTCCTAATACTAACTACCTGACTCCTACCCCTCACAATCATGGCAAG CCAACGCCACTTATCCAGTGAACCACT |
| Seq-148 | chrM | Sense | 10444 | 10518 | 75 | 1198 | -----------------------C--G-----T-----C-------- ----------------T-G-------- |
| Seq-148 | hchrM | Sense | 11026 | 11100 | 75 | 1199 | ATCACGAAAAAAACTCTACCTCTCTATACTAATCTCCCTACAAATCTC CTTAATTATAACATTCACAGCCACAGA |
| Seq-149 | chrM | Sense | 10519 | 10593 | 75 | 1200 | G-----T--------------------------------------C- ------------------G--T----- |
| Seq-149 | hchrM | Sense | 11101 | 11175 | 75 | 1201 | ACTAATCATATTTTATATCTTCTTCGAAACCACACTTATCCCCACCTT GGCTATCATCACCCGATGAGGCAACCA |
| Seq-150 | chrM | Sense | 10594 | 10668 | 75 | 1202 | A-------------------T----------------T-------- ---------C----------------- |
| Seq-150 | hchrM | Sense | 11176 | 11250 | 75 | 1203 | GCCAGAACGCCTGAACGCAGGCACATACTTCCTATTCTACACCCTAGT AGGCTCCCTTCCCCTACTCATCGCACT |
| Seq-151 | chrM | Sense | 10669 | 10743 | 75 | 1204 | ---C--T--C----------------------T--C---T------- ---T--AA----------------A- |
| Seq-151 | hchrM | Sense | 11251 | 11325 | 75 | 1205 | AATTTACACTCACAACACCCTAGGCTCACTAAACATTCTACTACTCAC TCTCACTGCCCAAGAACTATCAAACTC |
| Seq-152 | chrM | Sense | 10744 | 10818 | 75 | 1206 | --------------------------G-----G--G-----C--G-- ---A-----C---------------C- |
| Seq-152 | hchrM | Sense | 11326 | 11400 | 75 | 1207 | CTGAGCCAACAACTTAATATGACTAGCTTACACAATAGCTTTTATAGT AAAGATACCTCTTTACGGACTCCACTT |
| Seq-153 | chrM | Sense | 10819 | 10893 | 75 | 1208 | -----------------------------T--T--C--------G-- ------T---------------T---- |
| Seq-153 | hchrM | Sense | 11401 | 11475 | 75 | 1209 | ATGACTCCCTAAAGCCCATGTCGAAGCCCCCATCGCTGGGTCAATAGT ACTTGCCGCAGTACTCTTAAAACTAGG |
| Seq-154 | chrM | Sense | 10894 | 10968 | 75 | 1210 | T--------C--------------------C-----------A----- ---T--------T--------CA-GT- |
| Seq-154 | hchrM | Sense | 11476 | 11550 | 75 | 1211 | CGGCTATGGTATAATACGCCTCACACTCATTCTCAACCCCCTGACAAA ACACATAGCCTACCCCTTCCTTGTACT |
| Seq-155 | chrM | Sense | 10969 | 11043 | 75 | 1212 | G---T-------T-----C--------------------G-------- -------------------------C- |
| Seq-155 | hchrM | Sense | 11551 | 11625 | 75 | 1213 | ATCCCTATGAGGCATAATTATAACAAGCTCCATCTGCCTACGACAAAC AGACCTAAAATCGCTCATTGCATACTC |
| Seq-156 | chrM | Sense | 11044 | 11118 | 75 | 1214 | ----G------------------------------------------- ----------------------A-T-- |
| Seq-156 | hchrM | Sense | 11626 | 11700 | 75 | 1215 | TTCAATCAGCCACATAGCCCTCGTAGTAACAGCCATTCTCATCCAAAC CCCCTGAAGCTTCACCGGCGCAGTCAT |
| Seq-157 | chrM | Sense | 11119 | 11193 | 75 | 1216 | C-----------------A---------------T---C--------- ---------T--T--------C----- |

TABLE 6-continued

Chimpanzee and Human Mitochondrial Paralogs

| fragment | chr | strand | start | end | width | SEQ ID NO: | amplicon |
|---|---|---|---|---|---|---|---|
| Seq-157 | hchrM | Sense | 11701 | 11775 | 75 | 1217 | TCTCATAATCGCCCACGGGCTTACATCCTCATTACTATTCTGCCTAGC AAACTCAAACTACGAACGCACTCACAG |
| Seq-158 | chrM | Sense | 11194 | 11268 | 75 | 1218 | ------------T-----C----------------------------- ---C-----------C--G-------- |
| Seq-158 | hchrM | Sense | 11776 | 11850 | 75 | 1219 | TCGCATCATAATCCTCTCTCAAGGACTTCAAACTCTACTCCCACTAAT AGCTTTTTGATGACTTCTAGCAAGCCT |
| Seq-159 | chrM | Sense | 11269 | 11343 | 75 | 1220 | -------------C-------T--C-----T--C--A--G-------- C------------T-A----------- |
| Seq-159 | hchrM | Sense | 11851 | 11925 | 75 | 1221 | CGCTAACCTCGCCTTACCCCCCACTATTAACCTACTGGGAGAACTCTC TGTGCTAGTAACCACGTTCTCCTGATC |
| Seq-160 | chrM | Sense | 11344 | 11418 | 75 | 1222 | -----C------------C------T-----------A---------- G--------------G----------- |
| Seq-160 | hchrM | Sense | 11926 | 12000 | 75 | 1223 | AAATATCACTCTCCTACTTACAGGACTCAACATACTAGTCACAGCCCT ATACTCCCTCTACATATTTACCACAAC |
| Seq-161 | chrM | Sense | 11419 | 11493 | 75 | 1224 | ------A-----------------------T-G------G-------- ---------------T-----A--TT- |
| Seq-161 | hchrM | Sense | 12001 | 12075 | 75 | 1225 | ACAATGGGGCTCACTCACCCACCACATTAACAACATAAAACCCTCATT CACACGAGAAAACACCCTCATGTTCAT |
| Seq-162 | chrM | Sense | 11494 | 11568 | 75 | 1226 | ---------------C-----T-----------T--T--T-----C-- T--A--CA----C-------------- |
| Seq-162 | hchrM | Sense | 12076 | 12150 | 75 | 1227 | ACACCTATCCCCCATTCTCCTCCTATCCCTCAACCCCGACATCATTAC CGGGTTTTCCTCTTGTAAATATAGTTT |
| Seq-163 | chrM | Sense | 11569 | 11643 | 75 | 1228 | --------------------------------------C--------- -----------------T-T------- |
| Seq-163 | hchrM | Sense | 12151 | 12225 | 75 | 1229 | AACCAAAACATCAGATTGTGAATCTGACAACAGAGGCTTACGACCCCT TATTTACCGAGAAAGCTCACAAGAACT |
| Seq-164 | chrM | Sense | 11644 | 11718 | 75 | 1230 | --------G-ATT------C---------------------------- ----------T---------------- |
| Seq-164 | hchrM | Sense | 12226 | 12300 | 75 | 1231 | GCTAACTCATGCCCCCATGTCTAACAACATGGCTTTCTCAACTTTTAA AGGATAACAGCTATCCATTGGTCTTAG |
| Seq-165 | chrM | Sense | 11719 | 11793 | 75 | 1232 | ---------------------------------------------T- TG----C---------T--G----A--- |
| Seq-165 | hchrM | Sense | 12301 | 12375 | 75 | 1233 | GCCCCAAAAATTTTGGTGCAACTCCAAATAAAAGTAATAACCATGCAC ACTACTATAACCACCCTAACCCTGACT |
| Seq-166 | chrM | Sense | 11794 | 11868 | 75 | 1234 | ---T----------------CGG-G-----A----------------- -----------------C--G------ |
| Seq-166 | hchrM | Sense | 12376 | 12450 | 75 | 1235 | TCCCTAATTCCCCCCATCCTTACCACCCTCGTTAACCCTAACAAAAAA AACTCATACCCCCATTATGTAAAATCC |
| Seq-167 | chrM | Sense | 11869 | 11943 | 75 | 1236 | ---A----------------C--T--C--T------------------ --A---------------AC------- |
| Seq-167 | hchrM | Sense | 12451 | 12525 | 75 | 1237 | ATTGTCGCATCCACCTTTATTATCAGTCTCTTCCCCACAACAATATTC ATGTGCCTAGACCAAGAAGTTATTATC |
| Seq-168 | chrM | Sense | 11944 | 12018 | 75 | 1238 | -----------------A-----------------A--------G--- --T-----------T----------C- |
| Seq-168 | hchrM | Sense | 12526 | 12600 | 75 | 1239 | TCGAACTGACACTGAGCCACAACCCAAACAACCCAGCTCTCCCTAAGC TTCAAACTAGACTACTTCTCCATAATA |
| Seq-169 | chrM | Sense | 12019 | 12093 | 75 | 1240 | --T-----C------C-------------A------------------ --A---------G----------C--- |
| Seq-169 | hchrM | Sense | 12601 | 12675 | 75 | 1241 | TTCATCCCTGTAGCATTGTTCGTTACATGGTCCATCATAGAATTCTCA CTGTGATATATAAACTCAGACCCAAAC |

TABLE 6-continued

Chimpanzee and Human Mitochondrial Paralogs

| fragment | chr | strand | start | end | width | SEQ ID NO: | amplicon |
|---|---|---|---|---|---|---|---|
| Seq-170 | chrM | Sense | 12094 | 12168 | 75 | 1242 | --C--C--A-----------CT----T--------------T---------C----C------------------ |
| Seq-170 | hchrM | Sense | 12676 | 12750 | 75 | 1243 | ATTAATCAGTTCTTCAAATATCTACTCATCTTCCTAATTACCATACTAATCTTAGTTACCGCTAACAACCTATTC |
| Seq-171 | chrM | Sense | 12169 | 12243 | 75 | 1244 | -----C--------------A--------------------TC-A-----T--C-----G---------A----- |
| Seq-171 | hchrM | Sense | 12751 | 12825 | 75 | 1245 | CAACTGTTCATCGGCTGAGAGGGCGTAGGAATTATATCCTTCTTGCTCATCAGTTGATGATACGCCCGAGCAGAT |
| Seq-172 | chrM | Sense | 12244 | 12318 | 75 | 1246 | -----------------C--------------T-----------T-----T-----TG----A---C-------- |
| Seq-172 | hchrM | Sense | 12826 | 12900 | 75 | 1247 | GCCAACACAGCAGCCATTCAAGCAATCCTATACAACCGTATCGGCGATATCGGTTTCATCCTCGCCTTAGCATGA |
| Seq-173 | chrM | Sense | 12319 | 12393 | 75 | 1248 | ---C----------------------T------------AT---C----GTA-----A--GA---T--T------ |
| Seq-173 | hchrM | Sense | 12901 | 12975 | 75 | 1249 | TTTATCCTACACTCCAACTCATGAGACCCACAACAAATAGCCCTTCTAAACGCTAATCCAAGCCTCACCCCACTA |
| Seq-174 | chrM | Sense | 12394 | 12468 | 75 | 1250 | ------T----------------------------T---C----C--T--------------------------- |
| Seq-174 | hchrM | Sense | 12976 | 13050 | 75 | 1251 | CTAGGCCTCCTCCTAGCAGCAGCAGGCAAATCAGCCCAATTAGGTCTCCACCCCTGACTCCCCTCAGCCATAGAA |
| Seq-175 | chrM | Sense | 12469 | 12543 | 75 | 1252 | -----T-----T--T-----------------------C-----C---------------C-------------- |
| Seq-175 | hchrM | Sense | 13051 | 13125 | 75 | 1253 | GGCCCCACCCCAGTCTCAGCCCTACTCCACTCAAGCACTATAGTTGTAGCAGGAATCTTCTTACTCATCCGCTTC |
| Seq-176 | chrM | Sense | 12544 | 12618 | 75 | 1254 | T-------------G----A------------------C--G------C----------------C--A------ |
| Seq-176 | hchrM | Sense | 13126 | 13200 | 75 | 1255 | CACCCCCTAGCAGAAAATAGCCCACTAATCCAAACTCTAACACTATGCTTAGGCGCTATCACCACTCTGTTCGCA |
| Seq-177 | chrM | Sense | 12619 | 12693 | 75 | 1256 | --------------C--------------------------G-----------------C--------------- |
| Seq-177 | hchrM | Sense | 13201 | 13275 | 75 | 1257 | GCAGTCTGCGCCCTTACACAAAATGACATCAAAAAAATCGTAGCCTTCTCCACTTCAAGTCAACTAGGACTCATA |
| Seq-178 | chrM | Sense | 12694 | 12768 | 75 | 1258 | --------------T--------------------------T--------C--------T--------------- |
| Seq-178 | hchrM | Sense | 13276 | 13350 | 75 | 1259 | ATAGTTACAATCGGCATCAACCAACCACACCTAGCATTCCTGCACATCTGTACCCACGCCTTCTTCAAAGCCATA |
| Seq-179 | chrM | Sense | 12769 | 12843 | 75 | 1260 | -----C--A--------A-----T--T--------C--T-----G-----C------------------T----- |
| Seq-179 | hchrM | Sense | 13351 | 13425 | 75 | 1261 | CTATTTATGTGCTCCGGGTCCATCATCCACAACCTTAACAATGAACAAGATATTCGAAAAATAGGAGGACTACTC |
| Seq-180 | chrM | Sense | 12844 | 12918 | 75 | 1262 | -----------C--------------------------G-----------------------C------------ |
| Seq-180 | hchrM | Sense | 13426 | 13500 | 75 | 1263 | AAAACCATACCTCTCACTTCAACCTCCCTCACCATTGGCAGCCTAGCATTAGCAGGAATACCTTTCCTCACAGGT |
| Seq-181 | chrM | Sense | 12919 | 12993 | 75 | 1264 | ----------------T---------------T------------------------------------------ |
| Seq-181 | hchrM | Sense | 13501 | 13575 | 75 | 1265 | TTCTACTCCAAAGACCACATCATCGAAACCGCAAACATATCATACACAAACGCCTGAGCCCTATCTATTACTCTC |

TABLE 6-continued

Chimpanzee and Human Mitochondrial Paralogs

| fragment | chr | strand | start | end | width | SEQ ID NO: | amplicon |
|---|---|---|---|---|---|---|---|
| Seq-182 | chrM | Sense | 12994 | 13068 | 75 | 1266 | -----C-----T-------------C-----C--------C--C--- -------------------------A |
| Seq-182 | hchrM | Sense | 13576 | 13650 | 75 | 1267 | ATCGCTACCTCCCTGACAAGCGCCTATAGCACTCGAATAATTCTTCTC ACCCTAACAGGTCAACCTCGCTTCCCC |
| Seq-183 | chrM | Sense | 13069 | 13143 | 75 | 1268 | -----C--C--------------C--------T--GT----T------ --------AA-CATT------T----T |
| Seq-183 | hchrM | Sense | 13651 | 13725 | 75 | 1269 | ACCCTTACTAACATTAACGAAAATAACCCCACCCTACTAAACCCCATT AAACGCCTGGCAGCCGGAAGCCTATTC |
| Seq-184 | hchrM | Sense | 13726 | 13800 | 75 | 1270 | GCAGGATTTCTCATTACTAACAACATTTCCCCCGCATCCCCCTTCCAA ACAACAATCCCCCTCTACCTAAAACTC |
| Seq-185 | chrM | Sense | 13219 | 13293 | 75 | 1271 | --------A-GC--T----C---------------------------- --T----------G---G--C------ |
| Seq-185 | hchrM | Sense | 13801 | 13875 | 75 | 1272 | ACAGCCCTCGCTGTCACTTTCCTAGGACTTCTAACAGCCCTAGACCTC AACTACCTAACCAACAAACTTAAAATA |
| Seq-186 | chrM | Sense | 13294 | 13368 | 75 | 1273 | -------------AT------C-C-----T--T--------------- ----A---T-T-------T-G------ |
| Seq-186 | hchrM | Sense | 13876 | 13950 | 75 | 1274 | AAATCCCCACTATGCACATTTTATTTCTCCAACATACTCGGATTCTAC CCTAGCATCACACACCGCACAATCCCC |
| Seq-187 | chrM | Sense | 13369 | 13443 | 75 | 1275 | -----------------A-----------A--------T--T------ --G-----------G--A--------- |
| Seq-187 | hchrM | Sense | 13951 | 14025 | 75 | 1276 | TATCTAGGCCTTCTTACGAGCCAAAACCTGCCCCTACTCCTCCTAGAC CTAACCTGACTAGAAAAGCTATTACCT |
| Seq-188 | chrM | Sense | 13444 | 13518 | 75 | 1277 | ---------------T-----------G-T-----T-C---------- -----------G--C--------T--- |
| Seq-188 | hchrM | Sense | 14026 | 14100 | 75 | 1278 | AAAACAATTTCACAGCACCAAATCTCCACCTCCATCATCACCTCAACC CAAAAAGGCATAATTAAACTTTACTTC |
| Seq-189 | chrM | Sense | 13519 | 13593 | 75 | 1279 | --------T--------T------T-----T----------------- ------------------------C-- |
| Seq-189 | hchrM | Sense | 14101 | 14175 | 75 | 1280 | CTCTCTTTCTTCTTCCCACTCATCCTAACCCTACTCCTAATCACATAA CCTATTCCCCCGAGCAATCTCAATTAC |
| Seq-190 | chrM | Sense | 13594 | 13668 | 75 | 1281 | ---G--------------------C--------------------C-- ---------------T--G-------- |
| Seq-190 | hchrM | Sense | 14176 | 14250 | 75 | 1282 | AATATATACACCAACAAACAATGTTCAACCAGTAACTACTACTAATCA ACGCCCATAATCATACAAAGCCCCCGC |
| Seq-191 | chrM | Sense | 13669 | 13743 | 75 | 1283 | -----------------------G-----G------C----------- ------A-----C--G--------A-- |
| Seq-191 | hchrM | Sense | 14251 | 14325 | 75 | 1284 | ACCAATAGGATCCTCCCGAATCAACCCTGACCCCTCTCCTTCATAAAT TATTCAGCTTCCTACACTATTAAAGTT |
| Seq-192 | chrM | Sense | 13744 | 13818 | 75 | 1285 | --------------T----------C----T-----T-A---T----- ------------C-GT--T-------- |
| Seq-192 | hchrM | Sense | 14326 | 14400 | 75 | 1286 | TACCACAACCACCACCCCATCATACTCTTTCACCCACAGCACCAATCC TACCTCCATCGCTAACCCCACTAAAAC |
| Seq-193 | chrM | Sense | 13819 | 13893 | 75 | 1287 | ---A-----A-------------------------------------- ---------A--C--------C----- |
| Seq-193 | hchrM | Sense | 14401 | 14475 | 75 | 1288 | ACTCACCAAGACCTCAACCCCTGACCCCCATGCCTCAGGATACTCCTC AATAGCCATCGCTGTAGTATATCCAAA |
| Seq-194 | chrM | Sense | 13894 | 13968 | 75 | 1289 | A--------T--------C-----------------C--------T-- -------------T------A---G-- |
| Seq-194 | hchrM | Sense | 14476 | 14550 | 75 | 1290 | GACAACCATCATTCCCCCTAAATAAATTAAAAAAACTATTAAACCCAT ATAACCTCCCCCAAAATTCAGAATAAT |

TABLE 6-continued

| Chimpanzee and Human Mitochondrial Paralogs | | | | | | | |
|---|---|---|---|---|---|---|---|
| fragment | chr | strand | start | end | width | SEQ ID NO: | amplicon |
| Seq-195 | chrM | Sense | 13969 | 14043 | 75 | 1291 | GG-------A--T-----A----------------------------G------------------------- |
| Seq-195 | hchrM | Sense | 14551 | 14625 | 75 | 1292 | AACACACCCGACCACACCGCTAACAATCAATACTAAACCCCCATAAATAGGAGAAGGCTTAGAAGAAAACCCCAC |
| Seq-196 | chrM | Sense | 14044 | 14118 | 75 | 1293 | ------T--C----T-----------T-A---T--------TG------------------------------ |
| Seq-196 | hchrM | Sense | 14626 | 14700 | 75 | 1294 | AAACCCCATTACTAAACCCACACTCAACAGAAACAAAGCATACATCATTATTCTCGCACGGACTACAACCACGAC |
| Seq-197 | chrM | Sense | 14119 | 14193 | 75 | 1295 | ------------------------------------------------------G-C--------T------A-- |
| Seq-197 | hchrM | Sense | 14701 | 14775 | 75 | 1296 | CAATGATATGAAAAACCATCGTTGTATTTCAACTACAAGAACACCAATGACCCCAATACGCAAAACTAACCCCCT |
| Seq-198 | chrM | Sense | 14194 | 14268 | 75 | 1297 | T-------------T--------T-----------------------T-----------G----------- |
| Seq-198 | hchrM | Sense | 14776 | 14850 | 75 | 1298 | AATAAAATTAATTAACCACTCATTCATCGACCTCCCCACCCCATCCAACATCTCCGCATGATGAAACTTCGGCTC |
| Seq-199 | chrM | Sense | 14269 | 14343 | 75 | 1299 | ---T--C-----------A-----T-----T---------T----------T--A-------------------- |
| Seq-199 | hchrM | Sense | 14851 | 14925 | 75 | 1300 | ACTCCTTGGCGCCTGCCTGATCCTCCAAATCACCACAGGACTATTCCTAGCCATGCACTACTCACCAGACGCCTC |
| Seq-200 | chrM | Sense | 14344 | 14418 | 75 | 1301 | ---------C--G--G--------------C-----------C-----T--G-------------C-----T-- |
| Seq-200 | hchrM | Sense | 14926 | 15000 | 75 | 1302 | AACCGCCTTTTCATCAATCGCCCACATCACTCGAGACGTAAATTATGGCTGAATCATCCGCTACCTTCACGCCAA |
| Seq-201 | chrM | Sense | 14419 | 14493 | 75 | 1303 | C-------------T-------------------------C-----T-----------C------------CT |
| Seq-201 | hchrM | Sense | 15001 | 15075 | 75 | 1304 | TGGCGCCTCAATATTCTTTATCTGCCTCTTCCTACACATCGGGCGAGGCCTATATTACGGATCATTTCTCTACTC |
| Seq-202 | chrM | Sense | 14494 | 14568 | 75 | 1305 | ---------------T-------------T----CA----C-------------T--G--------------A-- |
| Seq-202 | hchrM | Sense | 15076 | 15150 | 75 | 1306 | AGAAACCTGAAACATCGGCATTATCCTCCTGCTTGCAACTATAGCAACAGCCTTCATAGGCTATGTCCTCCCGTG |
| Seq-203 | chrM | Sense | 14569 | 14643 | 75 | 1307 | ------------C--------A------------------C----G-----T-----------C--A-------- |
| Seq-203 | hchrM | Sense | 15151 | 15225 | 75 | 1308 | AGGCCAAATATCATTCTGAGGGGCCACAGTAATTACAAACTTACTATCCGCCATCCCATACATTGGGACAGACCT |
| Seq-204 | chrM | Sense | 14644 | 14718 | 75 | 1309 | G--C--G---G------------------------C--T-----T-----------C-----C-----T |
| Seq-204 | hchrM | Sense | 15226 | 15300 | 75 | 1310 | AGTTCAATGAATCTGAGGAGGCTACTCAGTAGACAGTCCCACCCTCACACGATTCTTTACCTTTCACTTCATCTT |
| Seq-205 | chrM | Sense | 14719 | 14793 | 75 | 1311 | A--------C--CA--------A-------T--T-----------A--------A--------T----------- |
| Seq-205 | hchrM | Sense | 15301 | 15375 | 75 | 1312 | GCCCTTCATTATTGCAGCCCTAGCAACACTCCACCTCCTATTCTTGCACGAAACGGGATCAAACAACCCCCTAGG |
| Seq-206 | chrM | Sense | 14794 | 14868 | 75 | 1313 | ------------C-----C-----T-----------C-----------------TAT---T------T-C--T-- |
| Seq-206 | hchrM | Sense | 15376 | 15450 | 75 | 1314 | AATCACCTCCCATTCCGATAAAATCACCTTCCACCCTTACTACACAATCAAAGACGCCCTCGGCTTACTTCTCTT |

TABLE 6-continued

Chimpanzee and Human Mitochondrial Paralogs

| fragment | chr | strand | start | end | width | SEQ ID NO: | amplicon |
|---|---|---|---|---|---|---|---|
| Seq-207 | chrM | Sense | 14869 | 14943 | 75 | 1315 | ---C--TAT-C---------------------------G---------<br>---T--------C-----------T-- |
| Seq-207 | hchrM | Sense | 15451 | 15525 | 75 | 1316 | CCTTCTCTCCTTAATGACATTAACACTATTCTCACCAGACCTCCTAGG<br>CGACCCAGACAATTATACCCTAGCCAA |
| Seq-208 | chrM | Sense | 14944 | 15018 | 75 | 1317 | ----C----------A--------T--A-----G-----C--T-----<br>T----------C----------A---- |
| Seq-208 | hchrM | Sense | 15526 | 15600 | 75 | 1318 | CCCCTTAAACACCCCTCCCCACATCAAGCCCGAATGATATTTCCTATT<br>CGCCTACACAATTCTCCGATCCGTCCC |
| Seq-209 | chrM | Sense | 15019 | 15093 | 75 | 1319 | C---------------C-----------C-------T-----A-----<br>-A--GC------TG-------C-C--- |
| Seq-209 | hchrM | Sense | 15601 | 15675 | 75 | 1320 | TAACAAACTAGGAGGCGTCCTTGCCCTATTACTATCCATCCTCATCCT<br>AGCAATAATCCCCATCCTCCATATATC |
| Seq-210 | chrM | Sense | 15094 | 15168 | 75 | 1321 | -------------------------------------CTG-----C--<br>----------A-------------C-- |
| Seq-210 | hchrM | Sense | 15676 | 15750 | 75 | 1322 | CAAACAACAAAGCATAATATTTCGCCCACTAAGCCAATCACTTTATTG<br>ACTCCTAGCCGCAGACCTCCTCATTCT |
| Seq-211 | chrM | Sense | 15169 | 15243 | 75 | 1323 | ---------------------------------C--C-T--C---C--<br>----A-----------T--------- |
| Seq-211 | hchrM | Sense | 15751 | 15825 | 75 | 1324 | AACCTGAATCGGAGGACAACCAGTAAGCTACCCTTTTACCATCATTGG<br>ACAAGTAGCATCCGTACTATACTTCAC |
| Seq-212 | chrM | Sense | 15244 | 15318 | 75 | 1325 | -----------------------TCGC---T-----C-----------<br>---TG----AA----C----------- |
| Seq-212 | hchrM | Sense | 15826 | 15900 | 75 | 1326 | AACAATCCTAATCCTAATACCAACTATCTCCCTAATTGAAAACAAAAT<br>ACTCAAATGGGCCTGTCCTTGTAGTAT |
| Seq-213 | chrM | Sense | 15319 | 15393 | 75 | 1327 | -------------G---------------A-C------T--C------<br>--------------------AA----- |
| Seq-213 | hchrM | Sense | 15901 | 15975 | 75 | 1328 | AAACTAATACACCAGTCTTGTAAACCGGAGATGAAAACCTTTTTCCAA<br>GGACAAATCAGAGAAAAAGTCTTTAAC |
| Seq-214 | chrM | Sense | 15394 | 15468 | 75 | 1329 | -T------C---------------------------------------<br>------------------A----A--- |
| Seq-214 | hchrM | Sense | 15976 | 16050 | 75 | 1330 | TCCACCATTAGCACCCAAAGCTAAGATTCTAATTTAAACTATTCTCTG<br>TTCTTTCATGGGGAAGCAGATTTGGGT |
| Seq-215 | hchrM | Sense | 16051 | 16125 | 75 | 1331 | ACCACCCAAGTATTGACTCACCCATCAACAACCGCTATGTATTTCGTA<br>CATTACTGCCAGCCACCATGAATATTG |
| Seq-216 | hchrM | Sense | 16126 | 16200 | 75 | 1332 | TACGGTACCATAAATACTTGACCACCTGTAGTACATAAAAACCCAATC<br>CACATCAAAACCCCCTCCCCATGCTTA |
| Seq-217 | hchrM | Sense | 16201 | 16275 | 75 | 1333 | CAAGCAAGTACAGCAATCAACCCTCAACTATCACACATCAACTGCAAC<br>TCCAAAGCCACCCCTCACCCACTAGGA |
| Seq-218 | chrM | Sense | 15692 | 15766 | 75 | 1334 | --------G-----T-TC-----G----A------------C-A----<br>AC------------------------- |
| Seq-218 | hchrM | Sense | 16276 | 16350 | 75 | 1335 | TACCAACAAACCTACCCACCCTTAACAGTACATAGTACATAAAGCCAT<br>TTACCGTACATAGCACATTACAGTCAA |
| Seq-219 | chrM | Sense | 15767 | 15841 | 75 | 1336 | -C----C----C-----C-----CT--------------AA-------<br>GT------------------------- |
| Seq-219 | hchrM | Sense | 16351 | 16425 | 75 | 1337 | ATCCCTTCTCGTCCCCATGGATGACCCCCCTCAGATAGGGGTCCCTTG<br>ACCACCATCCTCCGTGAAATCAATATC |
| Seq-220 | chrM | Sense | 15840 | 15914 | 75 | 1338 | T-C-G--CA--A-TG-------------------------TC-----<br>--------------------------- |
| Seq-220 | hchrM | Sense | 16426 | 16500 | 75 | 1339 | CCGCACAAGAGTGCTACTCTCCTCGCTCCGGGCCCATAACACTTGGGG<br>GTAGCTAAAGTGAACTGTATCCGACAT |

TABLE 6-continued

Chimpanzee and Human Mitochondrial Paralogs

| fragment | chr | strand | start | end | width | SEQ ID NO: | amplicon |
|---|---|---|---|---|---|---|---|
| Seq-1 | chrM | Sense | 15986 | 16060 | 75 | 1340 | ----------------------------G----------CT-------<br>------------------------G-- |
| Seq-1 | hchrM | Sense | 1 | 75 | 75 | 1341 | GATCACAGGTCTATCACCCTATTAACCACTCACGGGAGCTCTCCATGC<br>ATTTGGTATTTTCGTCTGGGGGGTATG |

chrM = Chimpanzee mitochondrial DNA, hchrM = Homo Sapiens mitochondrial DNA, (-) = Alignment Match, Letter (ACGT) = Corresponding chimpanzee mismatch

Example 6—Amplification and Primer Extension of Chimpanzee Mitochondrial/Human Mitochondrial Paralogs and Chimpanzee Nuclear/Human Nuclear Paralogs All samples were set up in 25 ul PCR reactions.

For circulating cell free DNA three parallel reactions were run using a different amount of chimpanzee DNA in each reaction, as the DNA concentration of the liquid biopsy sample is not known. Reactions were evaluated based on dynamic range. For each sample 3 wells were used. Each well had a different chimpanzee DNA amount (1 ng, 0.5 ng, and 0.125 ng total input).

1. Three concentrations of chimpanzee DNA; 0.0625 ng/uL, 0.125 ng/uL, and 0.5 ng/ul were prepared. Estimation of the number of chimpanzee nuclear and mitochondrial genomic equivalents (copy number) were carried out using the Biorad QX200 digital droplet PCR.
2. PCR Mastermix was prepared.

| | Final Conc. | uL/rxn |
|---|---|---|
| RNAse-free Water | N/A | 3.375 |
| 10× PCR buffer with 20 mM MgCl2 | 1× (2 mM MgCl2) | 2.5 |
| MgCl2, 25 mM | 2 mM | 2 |
| dUTP/dNTP Mix, 25 mM | 500 uM | 0.5 |
| Primer Mix, 500 nM | 100 nM | 5 |
| UNG Enzyme (5 U/uL) | 0.125 U/uL | 0.625 |
| PCR Enzyme (5 U/uL) | 1 U/rxn | 1 |
| Mastermix Total | | 15 |
| ccfDNA | | 8 |
| Chimp DNA | | 2 |
| Total | | 25 |

PCR and single base extension primers are described in Table 7.

3. 8 uL ccfDNA & 2 uL Chimp DNA were added to wells of a 96-well plate.
4. 15 uL PCR Mix was added to each well.
5. Wells were mixed by vortexing the plate and spun down briefly.
6. Thermocycling was carried out using the following parameters.

| PCR Cycle | Cycling | Number of Cycles |
|---|---|---|
| Initial Incubation | 30° C. for 10:00 | 1 Cycle |
| Initial Denaturation | 95° C. for 2:00 | 1 Cycle |
| Cycled Template Denaturation | 95° C. for 0:30 | 45 Cycles |

-continued

| PCR Cycle | Cycling | Number of Cycles |
|---|---|---|
| Cycled Primer Annealing | 56° C. for 0:30 | |
| Cycled Primer Extension | 72° C. for 1:00 | |
| Final Extension | 72° C. for 5:00 | 1 Cycle |
| Hold | 4° C. for ∞ | |

7. Following completion of PCR, 5 uL from each well were transferred to a well of a new plate.
8. SAP Mastermix was prepared (see table below) and 2 uL SAP Mastermix was added to each reaction.

| SAP | Final Conc. | 7 uL rxn |
|---|---|---|
| Water | N/A | 1.53 |
| SAP Buffer | 10× | 0.17 |
| SAP Enzyme | 1.7 U/ul | 0.3 |

9. Thermocycling was carried out using the following parameters.

| SAP Cycle | Cycling Conditions | Number of Cycles |
|---|---|---|
| Initial Incubation | 37° C. for 40:00 | 1 Cycle |
| Cycled Template Denaturation | 85° C. for 5:00 | 1 Cycle |
| Hold | 4° C. for ∞ | |

10. Single base extension was performed. Extend Mastermix was prepared (see table below) and 2 uL EXT Mastermix was added to each reaction.

| EXT | Final Conc. | 9 uL rxn |
|---|---|---|
| Water | N/A | 0.619 |
| iPLEX Buffer Plus (10×) | 0.222× | 0.2 |
| iPLEX Termination Mix | 0.222× | 0.2 |
| Primer Mix | Various | 0.94 |
| Thermosequenase | 0.15 U/uL | 0.041 |

11. Thermocycling was carried out using the following parameters.

| PCR Cycle | Cycling Conditions | Number of Cycles |
|---|---|---|
| Initial Denaturation | 95° C. for 0:30 | 1 Cycle |
| Cycled Template Denaturation | 95° C. for 0:05 | |

-continued

| PCR Cycle | Cycling Conditions | Number of Cycles |
|---|---|---|
| Cycled Primer Annealing | 52° C. for 0:05 5 Cycles | 40 Cycles |
| Cycled Primer Extension | 80° C. for 0:05 | |
| Final Denaturation | 72° C. for 3:00 | |
| Hold | 4° C. | |

12. Following completion of PCR, reactions were processed on the CPM or Nanodispenser and MA4 analyzer. After 41 ul of water addition and desalting by the addition of 15 mg Clean Resin, 15 nL of each extend mixture was transferred to a SpectroCHIP® II-G384 and Mass spectra were recorded using a MassARRAY System. Spectra were acquired using SpectroAcquire software (Agena Bioscience, San Diego). The software parameters were set to acquire 20 shots from each of 5 raster positions. The resulting mass spectra were summed and peak detection and intensity analysis performed using Typer 4 software (Agena Bioscience, San Diego).

TABLE 7

PCR and Primer Extension Primers

| SNP_ ID | Forward PCRprimer | SEQ ID NO: | Reverse PCRprimer | SEQ ID NO: | UEP _DIR | UEP _MASS | UEP | SEQ ID NO: |
|---|---|---|---|---|---|---|---|---|
| chr1_ AtoC | ACGTTGGATGCAAG GCATGCCTGTATACT C | 1342 | ACGTTGGATGGTAA CAACGCAGAGCTCA GG | 1343 | R | 8457 | agGCCTGTATA CTCTCTCCTG TTATCCT | 1344 |
| chr10 _AtoC | ACGTTGGATGGAAG CTCCTCCTTGCTCTT C | 1345 | ACGTTGGATGGGAA AAACTAGAGAAAGA GC | 1346 | R | 7053 | ggCTGCTGCA GGGCTTTTATT TC | 1347 |
| chr12 _Cto G | ACGTTGGATGTAGA GGTGATACACTTACC G | 1348 | ACGTTGGATGGACC AAAGAAGTAAACACT G | 1349 | R | 5034 | CATTTCCCTC CAAACAC | 1350 |
| chr19 _Cto G | ACGTTGGATGCCTC CCGGCCACAGAGTG TG | 1351 | ACGTTGGATGGGAT GACAAAGATGCCAG GC | 1352 | F | 5944 | CCCGCCCTCC CTCAGAGCCA | 1353 |
| chr20 _TtoA | ACGTTGGATGAAGG GAACAGGAGTGAGT G | 1354 | ACGTTGGATGTCTTC CAGTCCCTGATCTG G | 1355 | R | 8364 | tTAATGCCAAC CATGGGATAG TGTGAG | 1356 |
| Mito- 01240 | ACGTTGGATGGGGT TTGCTGAAGATGGC GG | 1357 | ACGTTGGATGCTGC TCGCCAGAACACTA CG | 1358 | R | 7836 | GGCGGTATAT AGGCTGAGCA AGAGG | 1359 |
| Mito- 02522 | ACGTTGGATGGTCC CTATTTAAGGAACAA G | 1360 | ACGTTGGATGCTCG GCAAATCTTACCCC GC | 1361 | R | 7689 | gtCAGGCGGT GCCTCTAATA CTGGT | 1362 |
| Mito- 05747 | ACGTTGGATGGGTG ATTTTCATATTGAATT G | 1363 | ACGTTGGATGCACC CTAATCAACTGGCTT C | 1364 | R | 7278 | gaCGGGGCTT CTCCCGCCTT TTTT | 1365 |
| Mito- 07471 | ACGTTGGATGTTTTG AAAAAGTCATGGAG G | 1366 | ACGTTGGATGTGAC TATATGGATGCCCC CC | 1367 | R | 5185 | GGCTTGAAAC CAGCTTT | 1368 |
| Mito- 09066 | ACGTTGGATGGCAC ACCTACACCCCTTAT C | 1369 | ACGTTGGATGGTGG CGCTTCCAATTAGGT G | 1370 | F | 6294 | CTACTCATTCA ACCAATAGCC | 1371 |
| Mito- 10477 | ACGTTGGATGCTGA ACCGAATTGGTATAT AG | 1372 | ACGTTGGATGAGGT GTGAGCGATATACT AG | 1373 | F | 5394 | TATTTACCAAA TGCCCCT | 1374 |
| Mito- 13487 | ACGTTGGATGGTAAT AGATAGGGCTCAGG C | 1375 | ACGTTGGATGCTCA CTTCAACCTCCCTCA C | 1376 | R | 6833 | ctGAGTAGAAA CCTGTGAGGA A | 1377 |
| Mito- 16467 | ACGTTGGATGCACC ATCCTCCGTGAAATC | 1378 | ACGTTGGATGGGTT AATAGGGTGATAGA CC | 1379 | F | 5783 | gaGCTCCGGG CCCATAACA | 1380 |

| SNP_ID | Allele1 _MASS | Allele 1 | SEQ ID NO: | Allele2 _MASS | Allele 2 | SEQ ID NO: |
|---|---|---|---|---|---|---|
| chr1_AtoC | 8743.7 | agGCCTGTATACTCTCTCCT GTTATCCTG | 1381 | 8783.6 | agGCCTGTATACTCTCT CCTGTTATCCTT | 1382 |

TABLE 7-continued

| PCR and Primer Extension Primers | | | | | | |
|---|---|---|---|---|---|---|
| chr10_AtoC | 7339.8 | ggCTGCTGCAGGGCTTTTATTTCG | 1383 | 7379.7 | ggCTGCTGCAGGGCTTTTATTTCT | 1384 |
| chr12_CtoG | 5281.5 | CATTTCCCTCCAAACACC | 1385 | 5321.5 | CATTTCCCTCCAAACACG | 1386 |
| chr19_CtoG | 6191 | CCCGCCCTCCCTCAGAGCCAC | 1387 | 6231.1 | CCCGCCCTCCCTCAGAGCCAG | 1388 |
| chr20_TtoA | 8634.7 | tTAATGCCAACCATGGGATAGTGTGAGA | 1389 | 8690.5 | tTAATGCCAACCATGGGATAGTGTGAGT | 1390 |
| Mito-01240 | 8083.3 | GGCGGTATATAGGCTGAGCAAGAGGC | 1391 | 8163.2 | GGCGGTATATAGGCTGAGCAAGAGGT | 1392 |
| Mito-02522 | 7960.2 | gtCAGGCGGTGCCTCTAATACTGGTA | 1393 | 7976.2 | gtCAGGCGGTGCCTCTAATACTGGTG | 1394 |
| Mito-05747 | 7524.9 | gaCGGGGCTTCTCCCGCCTTTTTTC | 1395 | 7604.8 | gaCGGGGCTTCTCCCGCCTTTTTTT | 1396 |
| Mito-07471 | 5456.6 | GGCTTGAAACCAGCTTTA | 1397 | 5472.6 | GGCTTGAAACCAGCTTTG | 1398 |
| Mito-09066 | 6541.3 | CTACTCATTCAACCAATAGCCC | 1399 | 6621.2 | CTACTCATTCAACCAATAGCCT | 1400 |
| Mito-10477 | 5640.7 | TATTTACCAAATGCCCCTC | 1401 | 5720.6 | TATTTACCAAATGCCCCTT | 1402 |
| Mito-13487 | 7103.7 | ctGAGTAGAAACCTGTGAGGAAA | 1403 | 7119.7 | ctGAGTAGAAACCTGTGAGGAAG | 1404 |
| Mito-16467 | 6030 | gaGCTCCGGGCCCATAACAC | 1405 | 6109.9 | gaGCTCCGGGCCCATAACAT | 1406 |

Example 7 Quantification of the Mitochondrial/Nuclear Ratio Using a Multiplex Assay Targeting Human and Chimpanzee Paralogs Samples were obtained from a single subject over the course of 1 month. Samples were obtained prior to start of a treatment and additional samples were obtained at start, halfway and at the end of treatment. Circulating cell free DNA was extracted and subjected to co-amplification with a known amount of chimpanzee DNA. The DNA was subjected to multiplex amplification in a single reaction using a panel consisting of 7 mitochondrial and 5 nuclear amplicons. PCR and single base extension primers used are shown in Table 8.

TABLE 8

Assay Design MitoChimp

| WELL | TERM SNP_ID | 2nd-PCRP | SEQ ID NO: | 1st-PCRP | SEQ ID NO: | AMP_LEN | UP_CONF | MP_CONF | Tm(NN) | PcGC |
|---|---|---|---|---|---|---|---|---|---|---|
| W1 | iPLEXchr1_AtoC | ACGTTGGATGCAAGGCATGCCTGTATACTC | 1407 | ACGTTGGATGGTAACAACGCAGAGCTCAGG | 1408 | 141 | 94.5 | 98.2 | 55.3 | 46.2 |
| W1 | iPLEXchr10_AtoC | ACGTTGGATGGAAGCTCCTCCTTGCTCTTC | 1409 | ACGTTGGATGGGAAAAACTAGAGAAAGAGC | 1410 | 127 | 88.1 | 98.2 | 52.8 | 47.6 |
| W1 | iPLEXchr12_CtoG | ACGTTGGATGTAGAGGTGATACACTTACCG | 1411 | ACGTTGGATGGACCAAAGAAGTAAACACTG | 1412 | 133 | 88.6 | 98.2 | 45.4 | 47.1 |
| W1 | iPLEXchr19_CtoG | ACGTTGGATGCCTCCCGGCCACAGAGTGTG | 1413 | ACGTTGGATGGGATGACAAAGATGCCAGGC | 1414 | 122 | 88.5 | 98.2 | 64 | 75 |
| W1 | iPLEXchr20_TtoA | ACGTTGGATGAAGGGAACAGGAGTGAGTG | 1415 | ACGTTGGATGTCTTCCAGTCCCTGATCTGG | 1416 | 119 | 85.6 | 98.2 | 57.2 | 46.2 |

TABLE 8-continued

| Assay Design MitoChimp | | | | | | | | | | |
|---|---|---|---|---|---|---|---|---|---|---|
| W1 | iPLEXMito-01240 | ACGTTGGATGGGGTTTGCTGAAGATGGCGG | 1417 | ACGTTGGATGCTGCTCGCCAGAACACTACG | 1418 | 174 | 100 | 98.2 | 58.9 | 56 |
| W1 | iPLEXMito-02522 | ACGTTGGATGGTCCCTATTTAAGGAACAAG | 1419 | ACGTTGGATGCTCGGCAAATCTTACCCCGC | 1420 | 172 | 96.8 | 98.2 | 59 | 56.5 |
| W1 | iPLEXMito-05747 | ACGTTGGATGGGTGATTTTCATATTGAATTG | 1421 | ACGTTGGATGCACCCTAATCAACTGGCTTC | 1422 | 136 | 86.1 | 98.2 | 60.8 | 59.1 |
| W1 | iPLEXMito-07471 | ACGTTGGATGTTTTGAAAAAGTCATGGAGG | 1423 | ACGTTGGATGTGACTATATGGATGCCCCCC | 1424 | 156 | 93.6 | 98.2 | 48.3 | 47.1 |
| W1 | iPLEXMito-09066 | ACGTTGGATGGCACACCTACACCCCTTATC | 1425 | ACGTTGGATGGTGGCGCTTCCAATTAGGTG | 1426 | 160 | 98.7 | 98.2 | 48.7 | 42.9 |
| W1 | iPLEXMito-13487 | ACGTTGGATGGTAATAGATAGGGCTCAGGC | 1427 | ACGTTGGATGCTCACTTCAACCTCCCTCAC | 1428 | 154 | 97.3 | 98.2 | 49.1 | 45 |
| W1 | iPLEXMito-16467 | ACGTTGGATGCACCATCCTCCGTGAAATC | 1429 | ACGTTGGATGGGTTAATAGGGTGATAGACC | 1430 | 147 | 92.5 | 98.2 | 55.1 | 64.7 |

| SNP_ID | PWARN | UEP_DIR | UEP_MASS | UEP_SEQ | SEQ ID NO: | EXT1_CALL | EXT1_MASS | EXT1_SEQ | SEQ ID NO: | EXT2_CALL |
|---|---|---|---|---|---|---|---|---|---|---|
| chr1_AtoC | | R | 8457 | agGCCTGTATACTCTCTCCTGTTATCCT | 1431 | C | 8744 | agGCCTGTATACTCTCTCCTGTTATCCTG | 1432 | A |
| chr10_AtoC | | R | 7053 | ggCTGCTGCAGGGCTTTTATTTC | 1433 | C | 7340 | ggCTGCTGCAGGGCTTTTATTTCG | 1434 | A |
| chr12_CtoG | | R | 5034 | CATTTCCCTCCAAACAC | 1435 | G | 5282 | CATTTCCCTCCAAACACC | 1436 | C |
| chr19_CtoG | h | F | 5944 | CCCGCCCTCCCTCAGAGCCA | 1437 | C | 6191 | CCCGCCCTCCCTCAGAGCCAC | 1438 | G |
| chr20_TtoA | h | R | 8364 | tTAATGCCAACCATGGGATAGTGTGAG | 1439 | T | 8635 | tTAATGCCAACCATGGGATAGTGTGAGA | 1440 | A |
| Mito-01240 | | R | 7836 | GGCGGTATATAGGCTGAGCAAGAGG | 1441 | G | 8083 | GGCGGTATATAGGCTGAGCAAGAGGC | 1442 | A |
| Mito-02522 | | R | 7689 | gtCAGGCGGTGCCTCTAATACTGGT | 1443 | T | 7960 | gtCAGGCGGTGCCTCTAATACTGGTA | 1444 | C |
| Mito-05747 | g | R | 7278 | gaCGGGGCTTCTCCCGCCTTTTTT | 1445 | G | 7525 | gaCGGGGCTTCTCCCGCCTTTTTTC | 1446 | A |
| Mito-07471 | | R | 5185 | GGCTTGAAACCAGCTTT | 1447 | T | 5457 | GGCTTGAAACCAGCTTTA | 1448 | C |
| Mito-09066 | | F | 6294 | CTACTCATTCAACCAATAGCC | 1449 | C | 6541 | CTACTCATTCAACCAATAGCCC | 1450 | T |
| Mito-13487 | h | R | 6833 | ctGAGTAGAAACCTGTGAGGAA | 1451 | T | 7104 | ctGAGTAGAAACCTGTGAGGAAA | 1452 | C |
| Mito-16467 | h | F | 5783 | gaGCTCCGGGCCCATAACA | 1453 | C | 6030 | gaGCTCCGGGCCCATAACAC | 1454 | T |

TABLE 8-continued

| Assay Design MitoChimp | | | |
|---|---|---|---|
| SNP_ID | EXT2_ MASS | EXT2_SEQ | SEQ ID NO: |
| chr1_AtoC | 8784 | agGCCTGTATACTCTCTCCTGTTATCCTT | 1455 |
| chr10_AtoC | 7380 | ggCTGCTGCAGGGCTTTTATTTCT | 1456 |
| chr12_CtoG | 5322 | CATTTCCCTCCAAACACG | 1457 |
| chr19_CtoG | 6231 | CCCGCCCTCCCTCAGAGCCAG | 1458 |
| chr20_TtoA | 8691 | tTAATGCCAACCATGGGATAGTGTGAGT | 1459 |
| Mito-01240 | 8163 | GGCGGTATATAGGCTGAGCAAGAGGT | 1460 |
| Mito-02522 | 7976 | gtCAGGCGGTGCCTCTAATACTGGTG | 1461 |
| Mito-05747 | 7605 | gaCGGGGCTTCTCCCGCCTTTTTTT | 1462 |
| Mito-07471 | 5473 | GGCTTGAAACCAGCTTTG | 1463 |
| Mito-09066 | 6621 | CTACTCATTCAACCAATAGCCT | 1464 |
| Mito-13487 | 7120 | ctGAGTAGAAACCTGTGAGGAAG | 1465 |
| Mito-16467 | 6110 | gaGCTCCGGGCCCATAACAT | 1466 |

Figure 1B:
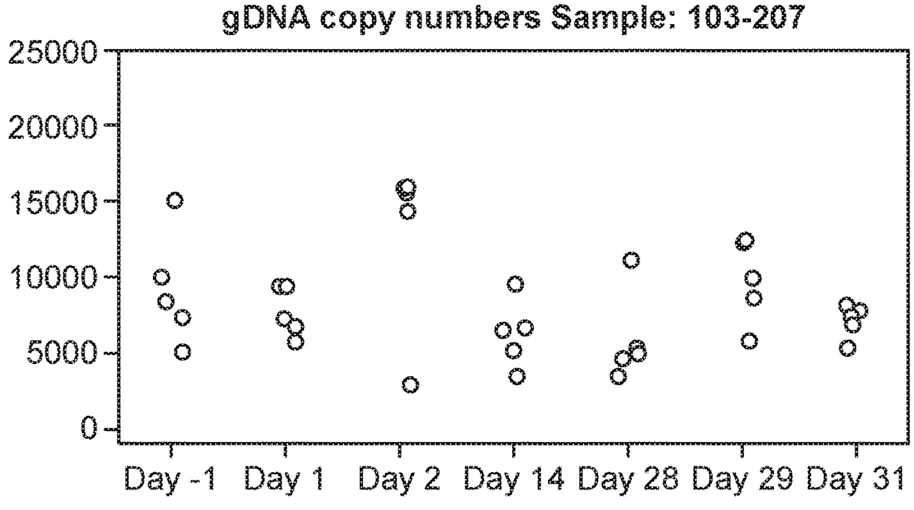
Figure 1C:
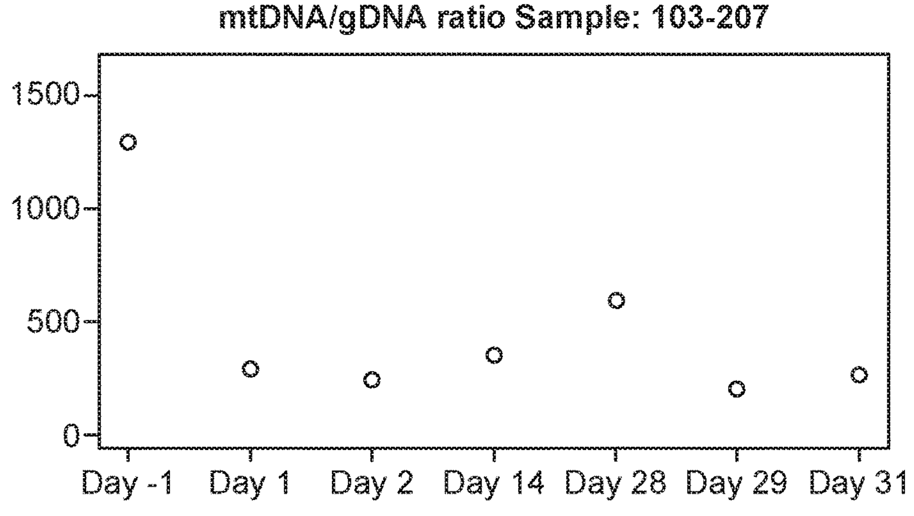

Mitochondria copy numbers (FIG. 1A) and nuclear copy numbers (FIG. 1B) were calculated and used for determining the mitochondrial vs nuclear ratio (FIG. 10) at each time point. In order to minimize variance a mean of the calculated nuclear and mitochondrial copy numbers were used to determine the ratio. As can be seen in the FIG. 1A there was spike in mitochondrial copy numbers at time point day −1 after which the mitochondrial copy numbers for the subject stabilized.

Example 8—Non-Limiting Examples of Embodiments

Provided hereafter are non-limiting examples of certain embodiments of the technology.

A1. A multiplex method for determining dosage of mitochondrial nucleic acid relative to genomic nucleic acid for a sample from a subject, comprising:

a. amplifying sets of mitochondrial polynucleotides and genomic polynucleotides from nucleic acid for a sample under amplification conditions, wherein: (i) each set comprises a mitochondrial polynucleotide and a genomic polynucleotide; (ii) the mitochondrial polynucleotide and the genomic polynucleotide are native; (iii) the mitochondrial polynucleotide of a set differs from the mitochondrial polynucleotide of the other sets and the genomic polynucleotide of a set differs from the genomic polynucleotide of the other sets; (iv) the mitochondrial polynucleotide and the genomic polynucleotide of a set are defined by formula $^{5'}$X—V—Y$^{3'}$; (v) $^{5'}$X—V—Y$^{3'}$ represents a contiguous sequence of nucleotides present in the mitochondrial polynucleotide and the genomic polynucleotide; (vi) X and Y of the mitochondrial polynucleotide are identical to X and Y, respectively, of the genomic polynucleotide in each set; (vii) V is one or more nucleotide positions at which a nucleotide of the mitochondrial polynucleotide differs from the corresponding nucleotide of the genomic polynucleotide in a set; thereby providing a plurality of amplified sets each comprising amplicons corresponding to all or a portion of the mitochondrial polynucleotide and amplified genomic polynucleotide in the set;

b. comparing (i) the amplicons corresponding to the mitochondrial polynucleotide, to (ii) the amplicons corresponding to the genomic polynucleotide for each set, thereby generating a comparison; and c. determining the relative dosage of mitochondrial nucleic acid to genomic nucleic acid in the sample based on the comparison.

A1.1. The method of embodiment A1, wherein the comparison in (b) is a ratio of (i) the amount of the amplicons corresponding to the mitochondrial polynucleotide, to (ii) the amount of the amplicons corresponding to the genomic polynucleotide, in each set and determining the relative dosage of mitochondrial nucleic acid to genomic nucleic acid in the sample in (c) is based on the ratio.

A2. The method of embodiment A1 or A1.1, wherein the nucleic acid for the sample is DNA.

A3. The method of any one of embodiments of A1 to A2, wherein amplifying is by a polymerase chain reaction (PCR) process.

A4. The method of any one of embodiments A1 to A3, wherein V is a single nucleotide position.

A5. The method of any one of embodiments A1 to A4, wherein $^{5'}$X—V—Y$^{3'}$ is about 30 base pairs to about 300 base pairs in length.

A6. The method of any one of embodiments A1 to A5, wherein the lengths of the amplicons are about 30 base pairs to about 300 base pairs.

A7. The method of any one of embodiments A1 to A6, wherein the plurality of amplified sets is about 2 sets to about 20 sets.

A8. The method of any one of embodiments A1 to A7, wherein the plurality of amplified sets is about 2 sets to about 10 sets.

A9. The method of any one of embodiments A1 to A6, wherein the plurality of amplified sets is at least 5 sets.

A10. The method of any one of embodiments A1 to A9, wherein the mitochondrial polynucleotide and/or the genomic polynucleotide of a set comprise polynucleotides or portions thereof chosen from Table 1.

A11. The method of any one of embodiments A1 to A10, wherein the mitochondrial polynucleotide and the genomic polynucleotide of a set are reproducibly amplified relative to each other by a single pair of amplification primers that hybridize to a polynucleotide within X and Y.

A12. The method of any one of embodiments A1 to A10, wherein the mitochondrial polynucleotide and the genomic polynucleotide of a set are amplified by different species specific pairs of amplification primers.

A13. The method of embodiment A12, wherein amplification primers hybridize to flanking polynucleotides that are 5' to X and 3' to Y and are different between mitochondrial and genomic polynucleotides at one or more nucleotide positions.

A13.1. The method of any one of embodiments A1 to A10, wherein the amplification is by an amplification primer that hybridizes to a polynucleotide within X for both species and two species specific amplification primers that hybridize 3' to Y.

A13.2. The method of any one of embodiments A1 to A10, wherein the amplification is by an amplification primer that hybridizes to a polynucleotide within Y for both species and two species specific amplification primers that hybridize 5' to X.

A14. The method of any one of embodiments A12 to A13.2, wherein the amplification primer or primers that are specific for the mitochondrial polynucleotide hybridize less efficiently than the amplification primer or primers that are specific for the genomic polynucleotide in a set, whereby the amplicons corresponding to the mitochondrial polynucleotide are reduced with respect to the amplicons corresponding to the genomic polynucleotide in each set.

A15. The method of any one of embodiments A12 to A14, wherein the amplification primer or primers that specifically hybridize to the mitochondrial polynucleotides are provided at a lower concentration than the concentration of the amplification primer or primers that specifically hybridize to genomic polynucleotides, whereby the amplicons corresponding to the mitochondrial polynucleotide are reduced with respect to the amplicons corresponding to the genomic polynucleotide in each set.

A15.1 The method of embodiment A13.1, wherein the amplification primer that hybridizes to a polynucleotide within X is at the same concentration as the species specific amplification primer that hybridizes 3' to Y for a genomic polynucleotide and the species specific amplification primer that hybridizes 3' to Y for a mitochondrial polynucleotide is at a lower concentration.

A15.2 The method of embodiment A13.2, wherein the amplification primer that hybridizes to a polynucleotide within Y is at the same concentration as the species specific amplification primer that hybridizes 5' to X for a genomic polynucleotide and the species specific amplification primer that hybridizes 5' to X for a mitochondrial polynucleotide is at a lower concentration.

A16. The method of embodiment A15, wherein the concentration of the amplification primer or primers that specifically hybridize to the mitochondrial polynucleotide is about 2× to about 30× less than the concentration of amplification primer or primers that specifically hybridize to the genomic polynucleotide in a set.

A17. The method of any one of embodiments A1 to A16, wherein the nucleic acid for the sample comprises circulating cell free nucleic acid (ccfDNA) and the size of the amplicons is greater than about 50 bp and less than about 166 bp.

A18. The method of embodiment A17, wherein the size of the amplicons is greater than about 60 bp and less than about 100 bp.

A19. The method of embodiment A18, wherein the size of the amplicons is greater than about 70 bp and less than about 100 bp.

A20. The method of any one of embodiments A1 to A19, wherein (b) comprises determining the amount of a nucleotide at V in the amplicons corresponding to the mitochondrial polynucleotide of a set and the amount of the nucleotide at V in the amplicons corresponding to the genomic polynucleotide of a set.

A21. The method of embodiment A20, wherein determining the amount of a nucleotide at V in the amplicons corresponding to the mitochondrial polynucleotide of a set and the amount of the nucleotide at V in the amplicons corresponding to the genomic polynucleotide of a set is by massive parallel sequencing process.

A22. The method of embodiment A21, wherein the sequencing is by a sequencing by synthesis process.

A23. The method of embodiments A21 or A22, wherein a sequence tag or barcode is attached to one or more primers in each amplification primer pair.

A24. The method of embodiment A20, wherein determining the amount of a nucleotide at V in the amplicons corresponding to the mitochondrial polynucleotide of a set and the amount of the nucleotide at V in the amplicons corresponding to the genomic polynucleotide of a set is by a nanopore process.

A25. The method of embodiment A20, wherein (b) comprises determining the amount of amplicons corresponding to the mitochondrial polynucleotide of a set and the amount of amplicons corresponding to the genomic polynucleotide of a set by a qPCR process comprising two fluorescent probes each specific for either the mitochondrial or genomic nucleotide at V or a digital PCR process.

A26. The method of embodiment A20, wherein (b) comprises contacting the amplicons with extension primers under extension conditions comprising chain terminating reagents, wherein:

(1) the chain terminating reagent that is specific for the amplicons corresponding to the mitochondrial polynucleotide is not specific for the amplicons corresponding to the genomic polynucleotide; and (2) the chain terminating reagent specific for the amplicons corresponding to the genomic polynucleotide is not specific for the amplicons corresponding to mitochondrial polynucleotide, whereby the primers are extended up to V, thereby generating chain terminated extension products corresponding to the mitochondrial polynucleotide and the genomic polynucleotide, respectively, wherein: (1) the concentration of each of the chain terminating reagents is known; and (2) the concentration of the chain terminating reagent specific for the mitochondrial polynucleotide is less than the concentration of the chain terminating reagent specific for the genomic polynucleotide.

A27. The method of embodiment A26, wherein (b) comprises determining a ratio of the amount of extension product corresponding to the mitochondrial polynucleotide to the amount of extension product corresponding to the genomic polynucleotide; and (c) comprises determining the amount of mitochondrial nucleic acid relative to the amount of genomic nucleic acid in the sample based on the ratio of (b).

A28. The method of any one of embodiments A1 to A27, wherein for the sets of a mitochondrial polynucleotides and a genomic polynucleotides (a) and (b) are performed in a single reaction vessel or a single reaction vessel compartment.

A29. The method of embodiment A26 or A27, wherein (a) and (b) are performed in at least two reaction vessels or at least two reaction vessel compartments and each reaction vessel or vessel compartment comprises at least two sets of mitochondrial and genomic polynucleotides.

A30. The method of any one of embodiments A26 to A29, wherein V is a single nucleotide position at which a nucleotide of the mitochondrial polynucleotide differs from the corresponding nucleotide of the genomic polynucleotide and the primers are extended up to the single nucleotide.

A31. The method of any one of embodiments A26 to A30, wherein the concentration of the chain terminating reagent specific for a mitochondrial polynucleotide is between about 1% to about 20% of the concentration of the chain terminating reagent specific for a genomic polynucleotide.

A32. The method of any one of embodiments A26 to A31, wherein the chain terminating reagents are chain terminating nucleotides.

A33. The method of embodiment A32, wherein the chain terminating nucleotides independently are selected from among ddATP, ddGTP, ddCTP, ddTTP and ddUTP.

A34. The method of any one of embodiments A26 to A33, wherein the chain terminating reagents comprise one or more acyclic terminators.

A35. The method of any one of embodiments A26 to A34, wherein one or more of the chain terminating reagents comprises a detectable label.

A36. The method of embodiment A35, wherein the label is a fluorescent label or dye.

A37. The method of embodiment A35, wherein the label is a mass label and detection is by mass spectrometry.

A38. The method of any one of embodiments A1-A37, comprising between about 25 to about 45 PCR amplification cycles in (a).

A39. The method of any one of embodiments A26 to A38, wherein the extension conditions in (b) comprise between about 20 to about 300 cycles.

A40. The method of any one of embodiments A1.1 to A39, wherein the ratios for a plurality of sets are combined and the relative dosage of mitochondrial nucleic acid to genomic nucleic acid for the sample is determined based on the combined ratio.

A41. The method of embodiment A40, wherein the combined ratio is an average ratio or a median ratio.

A42. The method of any one of embodiments A1.1 to A41, wherein the ratio of each set is compared to an average or median ratio based on the plurality of sets and an outlier or cluster that deviates from the average or median ratio is an indication of a mitochondrial deletion.

A42.1. The method of any one of embodiments A1.1 to A41, wherein the ratio of a set representing one region of the mitochondrial genome is compared to the ratio of each of the other sets representing different regions of the mitochondrial genome and the presence of one or more deletions in the mitochondrial genome is determined based on a difference in the ratio of the set representing the one region compared with the ratios for one or more sets representing other regions of the mitochondrial genome.

A43. The method of any one of embodiments A1 to A42, wherein a baseline value for the dosage of mitochondrial nucleic acid relative to genomic nucleic acid is determined for the subject or a population of subjects and the dosage of mitochondrial nucleic acid relative to genomic nucleic acid for the sample from the subject is compared to the baseline value.

A44. The method of any one of embodiments A1 to A43, wherein the dosage of mitochondrial nucleic acid relative to genomic nucleic acid for the sample from the subject is used in determining the likelihood the subject has or is pre-disposed to having a disease, disorder or symptoms associated with an increase or decrease in the dosage of mitochondria nucleic acid or a deletion in the mitochondrial genome.

A45. The method of embodiment A44, wherein the disease or disorder is a neurodegenerative disease, a cancer, a disease or disorder associated with mitochondrial stability, a disease or disorder associated with a mitochondrial deletion, a metabolic disease, a cardiovascular disease, a disease or disorder associated with oxidative stress, a disease or disorder associated with infertility or a disease or disorder associated with sepsis.

A45.1. The method of embodiment A44, wherein the disease or disorder is Parkinson's disease, Alzheimers disease, Friedreich's Ataxia, Amyotropic lateral sclerosis, Multiple sclerosis (MS), POLG associated diseases, Opthalmoplegia, Alper's syndrome, Leigh's syndrome, Kearns-Sayre syndrome (KSS), Leber's heredity optic neuropathy (LHON), Mitochondiral encophalomyopathy, lactic acidosis, stroke like episodes (MELAS), Myoclonic Epilepsy with Ragged Red Fibers (MERRF), gastric cancer, hepatocellular carcinoma (HCC) HPV related cancer, breast cancer, Ewing's Sarcoma, pancreatic cancer, liver cancer, testicular cancer, prostate cancer, renal cell carcinoma (RCC), bladder cancer, ovarian cancer, obesity, diabetes, pre-diabetes, diabetic retinopathy, diabetic cardiomyopathies, coronary heart disease and sepsis.

A45.2.2. The method of any one of embodiments A1 to A43, wherein the dosage of mitochondrial nucleic acid relative to genomic nucleic acid for the sample from the subject is used to monitor the efficacy of treatment of the subject for a disease, disorder or symptoms associated with an increase or decrease in the dosage of mitochondria nucleic acid or a deletion in the mitochondrial genome.

A46. The method of any one of embodiments A1 to A45, wherein the sample comprises circulating cell free nucleic acid.

A46.1. The method of embodiment A46, wherein the sample is chosen from blood plasma, blood serum, spinal fluid, cerebrospinal fluid and urine.

B1. A kit comprising amplification primer pairs that comprise polynucleotides chosen from polynucleotides of Table 2 and Table 4 or portions thereof.

B2. The kit of embodiment B1, further comprising extension primers that comprise polynucleotides chosen from polynucleotides of Table 2 and Table 4, or portions thereof.

C1. A multiplex method for determining dosage of extrachromosomal nucleic acid relative to genomic nucleic acid for a sample from a subject, comprising:

a. amplifying sets of extrachromosomal polynucleotides and genomic polynucleotides from nucleic acid for a sample under amplification conditions, wherein: (i) each set comprises an extrachromosomal polynucleotide and a genomic polynucleotide; (ii) the extrachromosomal polynucleotide and the genomic polynucleotide are native; (iii) the extrachromosomal polynucleotide of a set differs from the extrachromosomal polynucleotide of the other sets and the genomic polynucleotide of a set differs from the genomic polynucleotide of the other sets; (iv) the extrachromosomal polynucleotide and the genomic polynucleotide of a set are defined by formula $^{5'}$X—V—Y$^{3'}$; (v) the $^{5'}$X—V—Y$^{3'}$ represents a contiguous sequence of nucleotides present in the extrachromosomal polynucleotide and the genomic polynucleotide; (vi) X and Y of the extrachromosomal polynucleotide are identical to X and Y, respectively, of the genomic polynucleotide in each set; (vii) V is one or more nucleotide positions at which a nucleotide of the extrachromosomal polynucleotide differs from the corresponding nucleotide of the genomic polynucleotide in a set;

thereby providing a plurality of amplified sets each comprising amplicons corresponding to all or a portion of the extrachromosomal polynucleotide and amplified genomic polynucleotide in the set;

b. comparing (i) the amplicons corresponding to the extrachromosomal polynucleotide, to (ii) the amplicons corresponding to the genomic polynucleotide for each set, thereby generating a comparison; and c. determining the relative dosage of extrachromosomal nucleic acid to genomic nucleic acid in the sample based on the comparison.

D1. A multiplex method for determining dosage of mitochondrial nucleic acid relative to nuclear nucleic acid for a sample from a subject, comprising:

a. contacting nucleic acid of a sample from a subject comprising nucleic acid of a first species comprising a nuclear genome and a mitochondrial genome with nucleic acid of a second species comprising nucleic acid of a nuclear genome and a mitochondrial genome for which the copy number of the mitochondrial genome and the copy number of the nuclear genome are known, wherein the nuclear genome of the first species has regions that are paralogous to regions of the nuclear genome of the second species and the mitochondrial genome of the first species has regions that are paralogous to regions of the mitochondrial genome of the second species;

b. amplifying sets of nuclear polynucleotides of paralogous regions of the nuclear genome of the first species and the nuclear genome of the second species and sets of mitochondrial polynucleotides of paralogous regions of the mitochondrial genome of the first species and the mitochondrial genome of the second species from the nucleic acid of (a) under amplification conditions, wherein: (i) each set comprises a polynucleotide of the nuclear genome of the first species and a polynucleotide of the nuclear genome of the second species or each set comprises a polynucleotide of the mitochondrial genome of the first species and a polynucleotide of the mitochondrial genome of the second species; (ii) the mitochondrial polynucleotides and the nuclear polynucleotides are native; (iii) the mitochondrial polynucleotides of a set differ from the mitochondrial polynucleotides of the other sets and the nuclear polynucleotides of a set differ from the nuclear polynucleotides of the other sets; (iv) the mitochondrial polynucleotides of a set and the nuclear polynucleotides of a set are defined by formula $^{5'}$J-V—K$^{3'}$; (v) $^{5'}$J-V—K$^{3'}$ represents a contiguous sequence of nucleotides present in the mitochondrial polynucleotides or in the nuclear polynucleotides; (vi) J and K of the mitochondrial polynucleotides of a set are identical and J and K of the nuclear polynucleotides of a set are identical; and (vii) V is one or more nucleotide positions at which a nucleotide of the mitochondrial polynucleotides of the first and second species of a set differ or V is one or more nucleotide positions at which a nucleotide of the nuclear polynucleotides of the first and second species of a set differ; thereby providing a plurality of amplified sets each comprising amplicons corresponding to all or a portion of the mitochondrial polynucleotides of a set or amplicons corresponding to all or a portion of the amplified nuclear polynucleotides of a set;

c. comparing the amplicons corresponding to the mitochondrial polynucleotide of the second species to the amplicons corresponding to mitochondrial polynucleotide of the first species in a set and comparing the amplicons corresponding to the nuclear polynucleotide of the second species to the amplicons corresponding to the nuclear polynucleotide of the first species in a set, thereby generating comparisons; and d. determining the relative dosage of mitochondrial nucleic acid to the nuclear nucleic acid in the sample from the subject based on comparisons of (c) for all sets.

D1.1. The method of embodiment D1, wherein the comparisons in (c) are a ratio of the amount of the amplicons corresponding to the polynucleotide of the mitochondrial genome of the second species to the amount of amplicons corresponding to polynucleotide of the mitochondrial genome of the first species in a set and a ratio of the amount of the amplicons corresponding to the polynucleotide of the nuclear genome of the second species to the amount of amplicons corresponding to the polynucleotide of the nuclear genome of the first species in a set, and determining the relative dosage of mitochondrial nucleic acid to nuclear nucleic acid in the sample from the subject in (d) is based on the ratios.

D1.2 The method of embodiment D1 or D1.1, wherein the first species is human.

D1.3 The method of any one of embodiments D1 to D1.2, wherein the second species is chimpanzee.

D2. The method of any one of embodiments D1 or D1.3, wherein the nucleic acid for the sample is DNA.

D3. The method of any one of embodiments of D1 to D2, wherein amplifying is by a polymerase chain reaction (PCR) process.

D4. The method of any one of embodiments D1 to D3, wherein V is a single nucleotide position.

D5. The method of any one of embodiments D1 to D4, wherein $^{5'}J\text{-}V\text{—}K^{3'}$ is about 30 base pairs to about 300 base pairs in length.

D6. The method of any one of embodiments D1 to D5, wherein the lengths of the amplicons are about 30 base pairs to about 300 base pairs.

D7. The method of any one of embodiments D1 to D6, wherein the plurality of amplified sets of nuclear polynucleotides and the plurality of amplified sets of mitochondrial polynucleotides are each about 2 sets to about 20 sets.

D8. The method of any one of embodiments D1 to D7, wherein the plurality of amplified sets of nuclear polynucleotides and the plurality of amplified sets of mitochondrial polynucleotides are each about 5 sets to about 15 sets.

D9. The method of any one of embodiments D1 to D6, wherein the plurality of amplified sets of nuclear polynucleotides and the plurality of amplified sets of mitochondrial polynucleotides are each at least 5 sets.

D9.1 The method of any one of embodiments D1 to D9, wherein the mitochondrial polynucleotides are distributed throughout the mitochondrial genome.

D10. The method of any one of embodiments D1 to D9.1, wherein the mitochondrial polynucleotides of a set comprise polynucleotides or portions thereof chosen from Table 6.

D11. The method of any one of embodiments D1 to D10, wherein the mitochondrial polynucleotides of a set are reproducibly amplified relative to each other by a single pair of amplification primers that hybridize to a mitochondrial polynucleotide within J and K and the nuclear polynucleotides of a set are reproducibly amplified relative to each other by a single pair of amplification primers that hybridize to a nuclear polynucleotide within J and K.

D12. The method of any one of embodiments D1 to D11, wherein (c) comprises determining the amount of a nucleotide at V in the amplicons corresponding to the mitochondrial polynucleotide of the first species and the second species of a set and determining the amount of a nucleotide at V in the amplicons corresponding to the nuclear polynucleotide of the first species and the second species of a set.

D13. The method of embodiment D12, wherein determining the amount of a nucleotide at V in the amplicons corresponding to the mitochondrial polynucleotide of the first species and the second species of a set and determining the amount of a nucleotide at V in the amplicons corresponding to the nuclear polynucleotide of the first species and the second species of a set is by massive parallel sequencing process.

D14. The method of embodiment D13, wherein the sequencing is by a sequencing by synthesis process.

D15. The method of embodiments D13 or D14, wherein a sequence tag or barcode is attached to one or more primers in each amplification primer pair.

D16. The method of embodiment D12, wherein determining the amount of a nucleotide at V in the amplicons corresponding to the mitochondrial polynucleotide of the first species and the second species of a set and determining the amount of a nucleotide at V in the amplicons corresponding to the nuclear polynucleotide of the first species and the second species of a set is by a nanopore process.

D17. The method of embodiment D12, determining the amount of a nucleotide at V in the amplicons corresponding to the mitochondrial polynucleotide of the first species and the second species of a set is by a qPCR process comprising two fluorescent probes specific for the nucleotide at V of the mitochondrial polynucleotide of either the first or second species or a digital PCR process and determining the amount of a nucleotide at V in the amplicons corresponding to the nuclear polynucleotide of the first species and the second species of a set is by a qPCR process comprising two fluorescent probes specific for the nucleotide at V of the nuclear polynucleotide of either the first or second species or a digital PCR process.

D18. The method of embodiment D12, wherein (c) comprises contacting the amplicons with extension primers under extension conditions comprising chain terminating reagents, wherein:

(1) the chain terminating reagent that is specific for the amplicons corresponding to the mitochondrial polynucleotide of the first species is not specific for the amplicons corresponding to the mitochondrial polynucleotide of the second species; and (2) the chain terminating reagent specific for the amplicons corresponding to the nuclear polynucleotide of the first species is not specific for the amplicons corresponding to the nuclear polynucleotide of the second species, whereby the primers are extended up to V, thereby generating chain terminated extension products corresponding to the mitochondrial polynucleotide of the first species, the mitochondrial polynucleotide of the second species, the nuclear polynucleotide of the first species and the nuclear polynucleotide of the second species.

D19. The method of embodiment D18, wherein (c) comprises determining a ratio of the amount of extension product corresponding to the mitochondrial polynucleotide of the second species to the amount of extension product corresponding to the mitochondrial polynucleotide of the first species and determining a ratio of the amount of extension product corresponding to the nuclear polynucleotide of the second species to the amount of extension product corresponding to the nuclear polynucleotide of the first species; and (d) comprises determining the amount of mitochondrial nucleic acid relative to the amount of nuclear nucleic acid in the sample based on the ratios of (c).

D20. The method of any one of embodiments D1 to D19, wherein the sets of mitochondrial polynucleotides and the sets of nuclear polynucleotides are in a single reaction vessel or a single reaction vessel compartment.

D20.1 The method of any one of embodiments D1 to D19, wherein the sets of mitochondrial polynucleotides and the sets of nuclear polynucleotides are in different separate reaction vessels or reaction vessel compartments.

D21. The method of any one of embodiments D18 to D20, wherein V is a single nucleotide position at which a nucleotide of the mitochondrial polynucleotide of the first species differs from the corresponding nucleotide of the mitochondrial polynucleotide of the second species and the primers are extended up to the single nucleotide.

D22. The method of any one of embodiments D18 to D20, wherein V is a single nucleotide position at which a nucleotide of the nuclear polynucleotide of the first species differs from the corresponding nucleotide of the nuclear polynucleotide of the second species and the primers are extended up to the single nucleotide.

D23. The method of any one of embodiments D18 to D22, wherein the chain terminating reagents are chain terminating nucleotides.

D24. The method of embodiment D23, wherein the chain terminating nucleotides independently are selected from among ddATP, ddGTP, ddCTP, ddTTP and ddUTP.

D25. The method of any one of embodiments D18 to D24, wherein the chain terminating reagents comprise one or more acyclic terminators.

D26. The method of any one of embodiments D18 to D25, wherein one or more of the chain terminating reagents comprises a detectable label.

D27. The method of embodiment D26, wherein the label is a fluorescent label or dye.

D28. The method of embodiment D26, wherein the label is a mass label and detection is by mass spectrometry.

D29. The method of any one of embodiments D1-D28, comprising between about 25 to about 45 PCR amplification cycles in (b).

D30. The method of any one of embodiments D18 to D25, wherein the extension conditions in (c) comprise between about 20 to about 300 cycles.

D31. The method of any one of embodiments D1.1 to D30, wherein the ratios for a plurality of sets mitochondrial polynucleotides and a plurality of sets of nuclear polynucleotides are combined and the relative dosage of mitochondrial nucleic acid to nuclear nucleic acid for the sample is determined based on the combined ratio.

D32. The method of embodiment D31, wherein the combined ratio is an average ratio or a median ratio.

D33. The method of any one of embodiments D1.1 to D32, wherein the ratio of each set is compared to an average or median ratio based on the plurality of sets and an outlier or cluster that deviates from the average or median ratio is an indication of a mitochondrial deletion.

D34. The method of any one of embodiments D1.1 to D32, wherein the ratio of a set of a mitochondrial paralog representing one region of the mitochondrial genome is compared to the ratio of each of the other sets of a mitochondrial paralog representing different regions of the mitochondrial genome and the presence of one or more deletions in the mitochondrial genome is determined based on a difference in the ratio of the set representing the one region compared with the ratios for one or more sets representing other regions of the mitochondrial genome.

D35. The method of any one of embodiments D1 to D34, wherein a baseline value for the dosage of mitochondrial nucleic acid relative to nuclear nucleic acid is determined for the subject or a population of subjects and the dosage of mitochondrial nucleic acid relative to nuclear nucleic acid for the sample from the subject is compared to the baseline value.

D36. The method of any one of embodiments D1 to D35, wherein the dosage of mitochondrial nucleic acid relative to nuclear nucleic acid for the sample from the subject is used in determining the likelihood the subject has or is pre-disposed to having a disease, disorder or symptoms associated with an increase or decrease in the dosage of mitochondria nucleic acid or a deletion in the mitochondrial genome.

D37. The method of embodiment D36, wherein the disease or disorder is a neurodegenerative disease, a cancer, a disease or disorder associated with mitochondrial stability, a disease or disorder associated with a mitochondrial deletion, a metabolic disease, a cardiovascular disease, a disease or disorder associated with oxidative stress, a disease or disorder associated with infertility or a disease or disorder associated with sepsis.

D38. The method of embodiment D37, wherein the disease or disorder is Parkinson's disease, Alzheimers disease, Friedreich's Ataxia, Amyotropic lateral sclerosis, Multiple sclerosis (MS), POLG associated diseases, Opthalmoplegia, Alper's syndrome, Leigh's syndrome, Kearns-Sayre syndrome (KSS), Leber's heredity optic neuropathy (LHON), Mitochondiral encophalomyopathy, lactic acidosis, stroke like episodes (MELAS), Myoclonic Epilepsy with Ragged Red Fibers (MERRF), gastric cancer, hepatocellular carcinoma (HCC) HPV related cancer, breast cancer, Ewing's Sarcoma, pancreatic cancer, liver cancer, testicular cancer, prostate cancer, renal cell carcinoma (RCC), bladder cancer, ovarian cancer, obesity, diabetes, pre-diabetes, diabetic retinopathy, diabetic cardiomyopathies, coronary heart disease and sepsis.

D39. The method of any one of embodiments D1 to D38, wherein the dosage of mitochondrial nucleic acid relative to nuclear nucleic acid for the sample from the subject is used to monitor the efficacy of treatment of the subject for a disease, disorder or symptoms associated with an increase or decrease in the dosage of mitochondria nucleic acid or a deletion in the mitochondrial genome.

D40. The method of any one of embodiments D1 to D39, wherein the sample comprises circulating cell free nucleic acid.

D41. The method of embodiment D40, wherein the sample is chosen from blood plasma, blood serum, spinal fluid, cerebrospinal fluid and urine.

E1. A kit comprising amplification primer pairs that comprise polynucleotides chosen from polynucleotides of Table 7 or portions thereof.

E2. The kit of embodiment E1, further comprising extension primers that comprise polynucleotides chosen from polynucleotides of Table 7 or portions thereof.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term “a” or “an” can refer to one of or a plurality of the elements it modifies (e.g., “a reagent” can mean one or more reagents) unless it is contextually clear either one of the elements or more than one of the elements is described. The term “about” as used herein refers to a value within 10% of the underlying parameter (i.e., plus or minus 10%), and use of the term “about” at the beginning of a string of values modifies each of the values (i.e., “about 1, 2 and 3” is about 1, about 2 and about 3). For example, a weight of “about 100 grams” can include weights between 90 grams and 110 grams. Thus, it should be understood that although the present technology has been specifically disclosed by representative embodiments and optional features, modification and variation of the concepts herein disclosed may be resorted to by those skilled in the art, and such modifications and variations are considered within the scope of this technology.

Embodiments of the technology are set forth in the claim(s) that follow(s).

What is claimed is:

1. A multiplex method for determining dosage of mitochondrial nucleic acid relative to genomic nucleic acid for a sample from a subject, comprising:

a. amplifying sets of mitochondrial polynucleotides and genomic polynucleotides from nucleic acid of a sample under amplification conditions using amplification primers, wherein:

(i) each set comprises a mitochondrial polynucleotide and a genomic polynucleotide;

(ii) the mitochondrial polynucleotide and the genomic polynucleotide are native;

(iii) the mitochondrial polynucleotide of a set differs from the mitochondrial polynucleotide of the other sets and the genomic polynucleotide of a set differs from the genomic polynucleotide of the other sets;

(iv) the mitochondrial polynucleotide and the genomic polynucleotide of a set are defined by formula $^{5'}X—V—Y^{3'}$;

(v) $^{5'}X—V—Y^{3'}$ is about 30 to about 300 base pairs in length and represents a contiguous sequence of nucleotides present in the mitochondrial polynucleotide and the genomic polynucleotide;

(vi) X and Y of the mitochondrial polynucleotide are identical to X and Y, respectively, of the genomic polynucleotide in each set;

(vii) V is one or more nucleotide positions at which a nucleotide of the mitochondrial polynucleotide differs from the corresponding nucleotide of the genomic polynucleotide in a set; and (viii) the amplification primers are selected such that: (1) the mitochondrial polynucleotide and the genomic polynucleotide of a set are reproducibly amplified relative to each other by a single pair of amplification primers that hybridize to a polynucleotide within X and Y; (2) the mitochondrial polynucleotide and the genomic polynucleotide of a set are amplified by different pairs of amplification primers that hybridize to flanking polynucleotides that are 5' to X and 3' to Y, wherein one pair of the amplification primers is specific for the mitochondrial polynucleotide and the other pair of the amplification primers is specific for the genomic polynucleotide; (3) the mitochondrial polynucleotide and the genomic polynucleotide of a set are amplified by an amplification primer that hybridizes to a polynucleotide within X for both the mitochondrial polynucleotide and the genomic polynucleotide and two amplification primers, wherein one of the amplification primers is specific for the mitochondrial polynucleotide and the other is specific for the genomic polynucleotide and each of the two amplification primers hybridizes 3' to Y; or (4) the mitochondrial polynucleotide and the genomic polynucleotide of a set are amplified by an amplification primer that hybridizes to a polynucleotide within Y for both the mitochondrial polynucleotide and the genomic polynucleotide and two amplification primers, wherein one of the amplification primers is specific for the mitochondrial polynucleotide and the other is specific for the genomic polynucleotide and each of the two amplification primers hybridizes 5' to X, thereby providing a plurality of amplified sets each comprising amplicons corresponding to all of the mitochondrial polynucleotide and genomic polynucleotide in the set, or amplicons comprising V and at least a portion of each of the X and Y regions of the mitochondrial polynucleotide and genomic polynucleotide in the set;

b. comparing (i) the amplicons corresponding to the mitochondrial polynucleotide, to (ii) the amplicons corresponding to the genomic polynucleotide for each set, thereby generating a comparison; and c. determining the relative dosage of mitochondrial nucleic acid to genomic nucleic acid in the sample based on the comparison.

2. The method of claim 1, wherein the comparison in (b) is a ratio of (i) the amount of the amplicons corresponding to the mitochondrial polynucleotide, to (ii) the amount of the amplicons corresponding to the genomic polynucleotide, in each set and determining the relative dosage of mitochondrial nucleic acid to genomic nucleic acid in the sample in (c) is based on the ratio.

3. The method of claim 1, wherein V is a single nucleotide position.

4. The method of claim 1, wherein the lengths of the amplicons are about 30 base pairs to about 300 base pairs.

5. The method of claim 1, wherein the plurality of amplified sets is about 2 sets to about 20 sets, or about 2 sets to about 10 sets, or at least 5 sets.

6. The method of claim 1, wherein the mitochondrial polynucleotide and/or the genomic polynucleotide of a set comprise polynucleotides or portions thereof chosen from SEQ ID NOS: 1-691.

7. The method of claim 1, wherein the amplification primer or primers that are specific for the mitochondrial polynucleotide hybridize less efficiently than the amplification primer or primers that are specific for the genomic polynucleotide in a set, whereby the amplification of the mitochondrial polynucleotide is reduced relative to the amplification of the corresponding genomic polynucleotide in each set.

8. The method of claim 1, wherein the amplification primer or primers that are specific for the mitochondrial polynucleotide are provided at a lower concentration than the concentration of the amplification primer or primers that are specific for the genomic polynucleotide, whereby the amplification of the mitochondrial polynucleotide is reduced relative to the amplification of the corresponding genomic polynucleotide in each set.

9. The method of claim 1, wherein (b) comprises:

(1) determining the amount of a nucleotide at V in the amplicons corresponding to the mitochondrial polynucleotide of a set and the amount of a nucleotide at V in the amplicons corresponding to the genomic polynucleotide of a set; or (2) determining the amount of amplicons corresponding to the mitochondrial polynucleotide of a set and the amount of amplicons corresponding to the genomic polynucleotide of a set by a qPCR process comprising two fluorescent probes each specific for either the mitochondrial or genomic nucleotide at V or a digital PCR process.

10. The method of claim 9, wherein determining the amount of a nucleotide at V in the amplicons corresponding to the mitochondrial polynucleotide of a set and the amount of a nucleotide at V in the amplicons corresponding to the genomic polynucleotide of a set is by a massive parallel sequencing process or by a nanopore process.

11. The method of claim 9, wherein the comparison in (b) is a ratio of (i) the amount of the amplicons corresponding to the mitochondrial polynucleotide based on the amount of a nucleotide at V in the amplicons corresponding to the mitochondrial polynucleotide of a set, to (ii) the amount of the amplicons corresponding to the genomic polynucleotide based on the amount of a nucleotide at V in the amplicons corresponding to the genomic polynucleotide of a set, and determining the relative dosage of mitochondrial nucleic acid to genomic nucleic acid in the sample in (c) is based on the ratio.

12. The method of claim 1, wherein (b) comprises contacting the amplicons with extension primers under extension conditions comprising a chain terminating reagent that is specific for the amplicons corresponding to the mitochondrial polynucleotide and a chain terminating reagent that is specific for the amplicons corresponding to the genomic polynucleotide, wherein:

(1) the chain terminating reagent that is specific for the amplicons corresponding to the mitochondrial polynucleotide is not specific for the amplicons corresponding to the genomic polynucleotide;

(2) the chain terminating reagent that is specific for the amplicons corresponding to the genomic polynucleotide is not specific for the amplicons corresponding to the mitochondrial polynucleotide; and (3) the concentration of each of the chain terminating reagents is known and the concentration of the chain terminating reagent specific for the mitochondrial polynucleotide is less than the concentration of the chain terminating reagent specific for the genomic polynucleotide, whereby the primers are extended up to V, thereby generating chain terminated extension products corresponding to the mitochondrial polynucleotide and the genomic polynucleotide, respectively.

13. The method of claim 12, wherein (b) comprises determining a ratio of the amount of extension product corresponding to the mitochondrial polynucleotide to the amount of extension product corresponding to the genomic polynucleotide; and (c) comprises determining the amount of mitochondrial nucleic acid relative to the amount of genomic nucleic acid in the sample based on the ratio of (b).

14. The method of claim 12, wherein V is a single nucleotide position at which a nucleotide of the mitochondrial polynucleotide differs from the corresponding nucleotide of the genomic polynucleotide and the primers are extended up to the single nucleotide.

15. The method of claim 12, wherein the concentration of the chain terminating reagent specific for a mitochondrial polynucleotide is between about 1% to about 20% of the concentration of the chain terminating reagent specific for a genomic polynucleotide.

16. The method of claim 2, wherein the ratios for a plurality of sets are combined and the relative dosage of mitochondrial nucleic acid to genomic nucleic acid for the sample is determined based on the combined ratio.

17. The method of claim 16, wherein the combined ratio is an average ratio or a median ratio.

18. The method of claim 2, wherein:

(1) the ratio of each set is compared to an average or median ratio based on the plurality of sets and an outlier or cluster that deviates from the average or median ratio is an indication of a mitochondrial deletion; or (2) the ratio of a set representing one region of the mitochondrial genome is compared to the ratio of each of the other sets representing different regions of the mitochondrial genome and the presence of one or more deletions in the mitochondrial genome is determined based on a difference in the ratio of the set representing the one region compared with the ratios for one or more sets representing other regions of the mitochondrial genome.

* * * * *

SEQUENCE LISTING

```
<160> NUMBER OF SEQ ID NOS: 1466

<210> SEQ ID NO 1
<211> LENGTH: 100
<212> TYPE: DNA
<213> ORGANISM: Homo sapiens

<400> SEQUENCE: 1

gatcacaggt ctatcaccct attaaccact cacgggagct ctccatgcat ttggtatttt     60

cgtctggggg gtgtgcacgc gatagcattg cgagacgctg                          100


<210> SEQ ID NO 2
<211> LENGTH: 100
<212> TYPE: DNA
<213> ORGANISM: Homo sapiens

<400> SEQUENCE: 2

gatcacgggt ctattaccct attaatcagt cacgggagct ctccatgcat ttggtatttt     60

aatctggggg gtgtgcacgc gatagcattg tgaaacgctg                          100


<210> SEQ ID NO 3
<211> LENGTH: 100
<212> TYPE: DNA
<213> ORGANISM: Homo sapiens

<400> SEQUENCE: 3

gagccggagc accctatgtc gcagtatctg tctttgattc ctgcctcatt ctattattta     60

tcgcacctac gttcaatatt acaggcgaac atacctacta                          100


<210> SEQ ID NO 4
<211> LENGTH: 100
<212> TYPE: DNA
<213> ORGANISM: Homo sapiens

<400> SEQUENCE: 4

gccccagagc accctatgtc gcagtgtctg tctttgattc ctgccccatc ccattattga     60

tcacacctac attcaatatc ccaggcgagc atacctatca                          100


<210> SEQ ID NO 5
<211> LENGTH: 100
<212> TYPE: DNA
<213> ORGANISM: Homo sapiens

<400> SEQUENCE: 5

aagtgtgtta attaattaat gcttgtagga cataataata acaattgaat gtctgcacag     60

ccgctttcca cacagacatc ataacaaaaa atttccacca                          100
```

<210> SEQ ID NO 6
<211> LENGTH: 100
<212> TYPE: DNA
<213> ORGANISM: Homo sapiens

<400> SEQUENCE: 6
aacccccccc tccccccgct tctggccaca gcacttaaac acatctctgc caaaccccaa 60
aaacaaagaa ccctaacacc agcctaacca gatttcaaat 100

<210> SEQ ID NO 7
<211> LENGTH: 100
<212> TYPE: DNA
<213> ORGANISM: Homo sapiens

<400> SEQUENCE: 7
tttatcttta ggcggtatgc acttttaaca gtcacccccc aactaacaca ttattttccc 60
ctcccactcc catactacta atctcatcaa tacaaccccc 100

<210> SEQ ID NO 8
<211> LENGTH: 100
<212> TYPE: DNA
<213> ORGANISM: Homo sapiens

<400> SEQUENCE: 8
gcccatccta cccagcacac acacaccgct gctaacccca taccccgaac caaccaaacc 60
ccaaagacac cccccacagt ttatgtagct tacctcctca 100

<210> SEQ ID NO 9
<211> LENGTH: 100
<212> TYPE: DNA
<213> ORGANISM: Homo sapiens

<400> SEQUENCE: 9
aagcaataca ctgaaaatgt ttagacgggc tcacatcacc ccataaacaa ataggtttgg 60
tcctagcctt tctattagct cttagtaaga ttacacatgc 100

<210> SEQ ID NO 10
<211> LENGTH: 100
<212> TYPE: DNA
<213> ORGANISM: Homo sapiens

<400> SEQUENCE: 10
aagcaagaca ctgaaaatgt ctagatgggt ccacacaacc ccataaacag ataggcttgg 60
tcctggcctt tttattacct cttattaaga ttacacatgg 100

<210> SEQ ID NO 11
<211> LENGTH: 100
<212> TYPE: DNA
<213> ORGANISM: Homo sapiens

<400> SEQUENCE: 11
aagcaagaca ctgaaaatgt ctagttgggt ccacaccacc cgatgaacag ataggttttg 60
tcctggcctt tttattagct cttagtaaga ttaaacatgc 100

<210> SEQ ID NO 12
<211> LENGTH: 100
<212> TYPE: DNA
<213> ORGANISM: Homo sapiens

<400> SEQUENCE: 12
aagaaaggca ctgaaaatgc tcagaagatt tcacgtaact ccataaacac ataggtttgg 60
tcctggcctt tttgttagtt cttagtaaga ttatacatgc 100

<210> SEQ ID NO 13
<211> LENGTH: 100
<212> TYPE: DNA
<213> ORGANISM: Homo sapiens

<400> SEQUENCE: 13
aagcaagaca ctgaaaatgt ctagatggat ccgcacaacc ctataaacag agaggtttgg 60
tcctggcctt tttactagct cttagtaaga ttacacatgt 100

<210> SEQ ID NO 14
<211> LENGTH: 100
<212> TYPE: DNA
<213> ORGANISM: Homo sapiens

<400> SEQUENCE: 14
aagcaatgca ctgaaaatgt ctggatgggc ccacactgcc ccataaacaa ataggtttca 60
tcctagcctt tctattggtt cttagtaaga ttacacactc 100

<210> SEQ ID NO 15
<211> LENGTH: 100
<212> TYPE: DNA
<213> ORGANISM: Homo sapiens

<400> SEQUENCE: 15
aagcaagaca ctgaaaatgt ctagatgggc ttatacagcc ccataaacag acagtcttgg 60
tcctggcctt tctattaact cttagtaaga ttacacatgc 100

<210> SEQ ID NO 16
<211> LENGTH: 100
<212> TYPE: DNA
<213> ORGANISM: Homo sapiens

<400> SEQUENCE: 16
aagcaagaca ctgaaaatat ctagatgggt ctgcacaacc ccataaacag ataggtttgg 60
ccctgacctt tttattagct cttagtaaga ttacacatgc 100

<210> SEQ ID NO 17
<211> LENGTH: 100
<212> TYPE: DNA
<213> ORGANISM: Homo sapiens

<400> SEQUENCE: 17
aagcaagaca ctgaaaatgt ctagatgggc ttatacagcc ccgtaaacag acaggtttgg 60
tcctggcctt tctattaact cttagtaaga ttacacatgc 100

<210> SEQ ID NO 18
<211> LENGTH: 100
<212> TYPE: DNA
<213> ORGANISM: Homo sapiens

<400> SEQUENCE: 18
aagcaagaca ctgaaaatgt ctagatgggt ctgcacatcc ccataaacag atatgtttgg 60
tcctggcctt tctattagct tttagtaaga ttacacacgc 100

<210> SEQ ID NO 19
<211> LENGTH: 100

<212> TYPE: DNA
<213> ORGANISM: Homo sapiens

<400> SEQUENCE: 19
aagcaagaca ctgaaaatat ctagatgggc ctacactgcc ccatagacaa ataggtttgg 60
tcctagcctt tctattaact cttagtaaga ttacacaagc 100

<210> SEQ ID NO 20
<211> LENGTH: 100
<212> TYPE: DNA
<213> ORGANISM: Homo sapiens

<400> SEQUENCE: 20
aagcaagaca ctgaaagtgt ctagacgggt ctgcacaaca tcataaacaa ataggcttgg 60
tcctggcctt tctattagct cttagtaaga ttacacatgc 100

<210> SEQ ID NO 21
<211> LENGTH: 100
<212> TYPE: DNA
<213> ORGANISM: Homo sapiens

<400> SEQUENCE: 21
aagcaagaca ctgaaaatgt ctagatgggt ctagacaatc ccataaacaa acagatttag 60
tccaggcctt tctattagat cctagtaaga ttacacaagc 100

<210> SEQ ID NO 22
<211> LENGTH: 100
<212> TYPE: DNA
<213> ORGANISM: Homo sapiens

<400> SEQUENCE: 22
aagcatcccc gttccagtga gttcaccctc taaatcacca cgatcaaaag ggacaagcat 60
caagcacgca gcaatgcagc tcaaaacgct tagcctagcc 100

<210> SEQ ID NO 23
<211> LENGTH: 100
<212> TYPE: DNA
<213> ORGANISM: Homo sapiens

<400> SEQUENCE: 23
aagcatcccc atcccagtga aagtaccctc taaatcacct tgatcaaaag aagtaagtat 60
caagcatgca caaatgcagc tcaaaacact ttgcccagcc 100

<210> SEQ ID NO 24
<211> LENGTH: 100
<212> TYPE: DNA
<213> ORGANISM: Homo sapiens

<400> SEQUENCE: 24
aagcatcgcc accctggtga aataaccctc taaatcacta caatcaaaag gagtaagtat 60
caagcacgca ttagtgcagc tcaaaacact ttgcctagcc 100

<210> SEQ ID NO 25
<211> LENGTH: 100
<212> TYPE: DNA
<213> ORGANISM: Homo sapiens

<400> SEQUENCE: 25
acacccccac gggaaacagc agtgattaac ctttagcaat aaacgaaagt ttaactaagc 60
tatactaacc ccagggttgg tcaatttcgt gccagccacc 100

<210> SEQ ID NO 26
<211> LENGTH: 100
<212> TYPE: DNA
<213> ORGANISM: Homo sapiens

<400> SEQUENCE: 26
acacccccac gggagacagc agtgataaac ctttagcaat aaacgaaagt ttaactgagc 60
tatactaact ttagggttgg ttaatttcat gccagccacc 100

<210> SEQ ID NO 27
<211> LENGTH: 100
<212> TYPE: DNA
<213> ORGANISM: Homo sapiens

<400> SEQUENCE: 27
gcggtcacac gattaaccca agtcaataga agccggcgta aagagtgttt tagatcaccc 60
cctccccaat aaagctaaaa ctcacctgag ttgtaaaaaa 100

<210> SEQ ID NO 28
<211> LENGTH: 100
<212> TYPE: DNA
<213> ORGANISM: Homo sapiens

<400> SEQUENCE: 28
ctccagttga cacaaaatag actacgaaag tggctttaac atatctgaac acacaatagc 60
taagacccaa actgggatta gataccccac tatgcttagc 100

<210> SEQ ID NO 29
<211> LENGTH: 100
<212> TYPE: DNA
<213> ORGANISM: Homo sapiens

<400> SEQUENCE: 29
ccctagctga aataaaataa actatgaagg tggctttaat acttctgaag acacaatagc 60
taagacccaa attgggatta gataccccac tatgcttagc 100

<210> SEQ ID NO 30
<211> LENGTH: 100
<212> TYPE: DNA
<213> ORGANISM: Homo sapiens

<400> SEQUENCE: 30
ctccagctga cataaaataa actacgaaag tggctttaac gtatctgaac acacaatagc 60
taagacccaa actgggatta gataccgcac tatgggctca 100

<210> SEQ ID NO 31
<211> LENGTH: 100
<212> TYPE: DNA
<213> ORGANISM: Homo sapiens

<400> SEQUENCE: 31
ccctagctga aataaaataa actacgaagg tgaatttaat atttctgagg acacaatagc 60
taagacccaa actgggatta gataccccac tatgcttagc 100

<210> SEQ ID NO 32
<211> LENGTH: 100
<212> TYPE: DNA
<213> ORGANISM: Homo sapiens

<400> SEQUENCE: 32
cccgggctga aataaaataa actatgaagg aggctttaat acttctgaag acacaatagc 60
taagacccaa actgggatta gataccccac taggcttagc 100

<210> SEQ ID NO 33
<211> LENGTH: 100
<212> TYPE: DNA
<213> ORGANISM: Homo sapiens

<400> SEQUENCE: 33
ccctagttga tataaaacaa actacgaaag tggctttaat atttctgaat acacaatagc 60
gaagattcaa actgggatta gataccccac tatgctcagc 100

<210> SEQ ID NO 34
<211> LENGTH: 100
<212> TYPE: DNA
<213> ORGANISM: Homo sapiens

<400> SEQUENCE: 34
cctaaacctc aacagttaaa tcaacaaaac tgctcgccag aacactacga gccacagctt 60
aaaactcaaa ggacctggcg gtgcttcata tccctctaga 100

<210> SEQ ID NO 35
<211> LENGTH: 100
<212> TYPE: DNA
<213> ORGANISM: Homo sapiens

<400> SEQUENCE: 35
tctaaactca aatagttaga tcaaaaaaac tgttcgccag aacactacaa gcaacagctt 60
aaaactcaaa ggacttggcg gtgctttata tccctctaaa 100

<210> SEQ ID NO 36
<211> LENGTH: 100
<212> TYPE: DNA
<213> ORGANISM: Homo sapiens

<400> SEQUENCE: 36
tctaaactcg aatagttaga tcaacaaaac tgttcgccag aacactacaa gcaacagctt 60
aaaactcaaa ggacttggcg gtgctttata tccctctaaa 100

<210> SEQ ID NO 37
<211> LENGTH: 100
<212> TYPE: DNA
<213> ORGANISM: Homo sapiens

<400> SEQUENCE: 37
cctaaactct aatagttaca ttgagaaaac cattcgccag agtactacaa gcaacagctt 60
aaaactcaaa ggacttggcg gtgctttata tccctctaga 100

<210> SEQ ID NO 38
<211> LENGTH: 100
<212> TYPE: DNA
<213> ORGANISM: Homo sapiens

<400> SEQUENCE: 38
cctaaactcc aatagttaaa tcaacaaaac tattcaccag aacactacaa gcaatagctt 60
aaaactcaaa ggacttggcg gtgctttata tccctctaga 100

<210> SEQ ID NO 39
<211> LENGTH: 100
<212> TYPE: DNA
<213> ORGANISM: Homo sapiens

<400> SEQUENCE: 39
cctaaactcc aatagttaaa tcaacaaaac tattccccag aacactacaa gcaatagctt 60
aaaactcaaa ggacttggca gtgctttata tccctctaga 100

<210> SEQ ID NO 40
<211> LENGTH: 100
<212> TYPE: DNA
<213> ORGANISM: Homo sapiens

<400> SEQUENCE: 40
cctaaactcc aatagttaaa tcaacagaac tattcaccag aacactacaa gcaatagctt 60
aaaactcaaa ggacttggcg gtgctttata tccctctaga 100

<210> SEQ ID NO 41
<211> LENGTH: 100
<212> TYPE: DNA
<213> ORGANISM: Homo sapiens

<400> SEQUENCE: 41
cctaaactct aatagttaca ttaacaaaac cattcgccag agtactacaa gcaacagctt 60
aaaactcaaa ggacttggca gtgctttata tccctctaga 100

<210> SEQ ID NO 42
<211> LENGTH: 100
<212> TYPE: DNA
<213> ORGANISM: Homo sapiens

<400> SEQUENCE: 42
cctaaacttc aacagttaaa tcaacaaaac tgctcgccag aacactagga gcaacagctt 60
aaaactcaaa ggacctggcg gtgcttcaca tccctctaga 100

<210> SEQ ID NO 43
<211> LENGTH: 100
<212> TYPE: DNA
<213> ORGANISM: Homo sapiens

<400> SEQUENCE: 43
tctaaactcg aatagttaga tcaacaaaac tgttcgccag aacactacaa gcaacagctt 60
aaaactcaaa ggacttggcg gtgctttata tccctctaaa 100

<210> SEQ ID NO 44
<211> LENGTH: 100
<212> TYPE: DNA
<213> ORGANISM: Homo sapiens

<400> SEQUENCE: 44
cctaaactcg aatagttaga tcaacaaaac tgttcgccag aacactacaa gcaacagctt 60
aaaactcaaa ggactttgcg gtgctttaca tccctctaaa 100

<210> SEQ ID NO 45
<211> LENGTH: 100
<212> TYPE: DNA
<213> ORGANISM: Homo sapiens

<400> SEQUENCE: 45
ggagcctgtt ctgtaatcga taaaccccga tcaacctcac cacctcttgc tcagcctata 60
taccgccatc ttcagcaaac cctgatgaag gctacaaagt 100

<210> SEQ ID NO 46
<211> LENGTH: 100
<212> TYPE: DNA
<213> ORGANISM: Homo sapiens

<400> SEQUENCE: 46
ggagcctgtt ctataatcga taaaccccaa tttacctcac cacctcttgc ccagcctaaa 60
tacccccatc ttcagcaaac cctggaaagg ctgcagagta 100

<210> SEQ ID NO 47
<211> LENGTH: 100
<212> TYPE: DNA
<213> ORGANISM: Homo sapiens

<400> SEQUENCE: 47
ggaggctgtt ctataatcga taaaccccaa tttacctcac cacctcttgc ccagcctaaa 60
tacctccatc ttcagcaaac cctggaaagg ccgcagagta 100

<210> SEQ ID NO 48
<211> LENGTH: 100
<212> TYPE: DNA
<213> ORGANISM: Homo sapiens

<400> SEQUENCE: 48
ggagcctgtt ctataatgga taaaccccaa tttacctcac cacttcttgc tcagcctata 60
taccatcatc ttcagcaaac cctagtaaaa gtcacaaagt 100

<210> SEQ ID NO 49
<211> LENGTH: 100
<212> TYPE: DNA
<213> ORGANISM: Homo sapiens

<400> SEQUENCE: 49
ggagcctgtt ctataatgga taaaacccaa tttgcctcac cacctcttgc tcagcctata 60
taccactgtc ttcagcaaac cctagcaaag gctgcaaagt 100

<210> SEQ ID NO 50
<211> LENGTH: 100
<212> TYPE: DNA
<213> ORGANISM: Homo sapiens

<400> SEQUENCE: 50
ggagcctgtt ctataatcga taaaccccaa ttcacctcac cacctcttgc tcaacccata 60
taccgccatc ttcagcaaac cctgacaaag gccacaaagt 100

<210> SEQ ID NO 51
<211> LENGTH: 100
<212> TYPE: DNA
<213> ORGANISM: Homo sapiens

<400> SEQUENCE: 51
ggaggctgtt ctataatcga taaaccccaa tttacctcac cacctcttgc ccagcctaaa 60
tacctccatc ttcagcaaac cctggaaagg ccgcagagta 100

<210> SEQ ID NO 52

<211> LENGTH: 100
<212> TYPE: DNA
<213> ORGANISM: Homo sapiens

<400> SEQUENCE: 52
aagcgcaagt acccacgtaa agacgttagg tcaaggtgta gcccatgagg tggcaagaaa 60
tgggctacat tttctacccc agaaaactac gatagccctt 100

<210> SEQ ID NO 53
<211> LENGTH: 100
<212> TYPE: DNA
<213> ORGANISM: Homo sapiens

<400> SEQUENCE: 53
aagcacaagt atctacataa aaacattagg tcaaggtgta gcccatgagg cggtaagaaa 60
tgggctacat tttctacacc cagaaaatct cacaaccctt 100

<210> SEQ ID NO 54
<211> LENGTH: 100
<212> TYPE: DNA
<213> ORGANISM: Homo sapiens

<400> SEQUENCE: 54
aagcacaagt aaatacataa aaacgttagg tcaacgtgta gctcatgagg tggcaagaaa 60
tgggccacat tttctacccc agaaaatctc acgacaacct 100

<210> SEQ ID NO 55
<211> LENGTH: 100
<212> TYPE: DNA
<213> ORGANISM: Homo sapiens

<400> SEQUENCE: 55
aagcacaagt atctacataa aaatgttagg tcaaggtgta gcctatgagg tggcaagaaa 60
tgggctacat tttctacccc agaaaattct acaataaccc 100

<210> SEQ ID NO 56
<211> LENGTH: 100
<212> TYPE: DNA
<213> ORGANISM: Homo sapiens

<400> SEQUENCE: 56
atgaaactta agggtcgaag gtggatttag cagtaaactg agagtagagt gcttagttga 60
acagggccct gaagcgcgta cacaccgccc gtcaccctcc 100

<210> SEQ ID NO 57
<211> LENGTH: 100
<212> TYPE: DNA
<213> ORGANISM: Homo sapiens

<400> SEQUENCE: 57
atgaaatcta agggctcaag gaggatttag caataaattg agagcagagt gtttaattga 60
ataaggccat gaagcatgca cacaccgccc atcaccctcc 100

<210> SEQ ID NO 58
<211> LENGTH: 100
<212> TYPE: DNA
<213> ORGANISM: Homo sapiens

<400> SEQUENCE: 58
atgaaatcta agggctcaag gaggatttag caataaattg agagcagagt gtttaattga 60
ataaggccat gaagcatgca cacaccgccc gtcaccctcc 100

<210> SEQ ID NO 59
<211> LENGTH: 100
<212> TYPE: DNA
<213> ORGANISM: Homo sapiens

<400> SEQUENCE: 59
atgaaatcta agggctcaag gaggatttag tagtaaacca agcgcagagt gcttggttga 60
ataaggccat gaagcatgca cacaccgctc atcaccctcc 100

<210> SEQ ID NO 60
<211> LENGTH: 100
<212> TYPE: DNA
<213> ORGANISM: Homo sapiens

<400> SEQUENCE: 60
atgaaaccta agggcccaag gaggatttag cagtaaatta ggagcagagt gcttaattga 60
ataaggccat aaagcatgca cacactgcct gtcaccctcc 100

<210> SEQ ID NO 61
<211> LENGTH: 100
<212> TYPE: DNA
<213> ORGANISM: Homo sapiens

<400> SEQUENCE: 61
atgaaatcta agggctcaag gaggatttag cagtacatta agagcagagt gcttaattga 60
atgaggccat aaagcacgca cacaatgccc gtcaccctcc 100

<210> SEQ ID NO 62
<211> LENGTH: 100
<212> TYPE: DNA
<213> ORGANISM: Homo sapiens

<400> SEQUENCE: 62
atgacatcta agggctcaag gaggatttgg cagtaaacca agagcagagt gcttggttga 60
ataaggccat gaagcatgca cacaccgccc atcaccctcc 100

<210> SEQ ID NO 63
<211> LENGTH: 100
<212> TYPE: DNA
<213> ORGANISM: Homo sapiens

<400> SEQUENCE: 63
atgaaacctg agggtccaag gaggatttag tagtaaatta agaacagagt gcttaattga 60
atagggccat aaagcacgca cacaccaccc atcaccctcc 100

<210> SEQ ID NO 64
<211> LENGTH: 100
<212> TYPE: DNA
<213> ORGANISM: Homo sapiens

<400> SEQUENCE: 64
atgaaatcta agggctcaag gaggatttag caataaattg agagcagagt gtttaattga 60
ataaggccat gaagcatgca cacaccgccc gtcaccctcc 100

<210> SEQ ID NO 65
<211> LENGTH: 100
<212> TYPE: DNA

<213> ORGANISM: Homo sapiens

<400> SEQUENCE: 65
atgaaatcta agggctcaag gaggatttag caataaattg agagcagagt gtttaattga 60
ataaggccat gaagcacgca cacaccgccc ttcaccctcc 100

<210> SEQ ID NO 66
<211> LENGTH: 100
<212> TYPE: DNA
<213> ORGANISM: Homo sapiens

<400> SEQUENCE: 66
tcaagtatac ttcaaaggac atttaactaa aacccctacg catttatata gaggagacaa 60
gtcgtaacat ggtaagtgta ctggaaagtg cacttggacg 100

<210> SEQ ID NO 67
<211> LENGTH: 100
<212> TYPE: DNA
<213> ORGANISM: Homo sapiens

<400> SEQUENCE: 67
aaatattact ttagagatta gtttaactaa aacccctact tatttatata gaggagacaa 60
gtcgtaacat ggtaagtgta ctagaaagtg cacttggatg 100

<210> SEQ ID NO 68
<211> LENGTH: 100
<212> TYPE: DNA
<213> ORGANISM: Homo sapiens

<400> SEQUENCE: 68
aaccagagtg tagcttaaca caaagcaccc aacttacact taggagattt caacttaact 60
tgaccgctct gagctaaacc tagccccaaa cccactccac 100

<210> SEQ ID NO 69
<211> LENGTH: 100
<212> TYPE: DNA
<213> ORGANISM: Homo sapiens

<400> SEQUENCE: 69
aataataaag gaggttaaca taaagcaccc aacttacact taggagattt caacttaact 60
tgaccgctct gagctaaacc tagccccaaa cccactccac 100

<210> SEQ ID NO 70
<211> LENGTH: 100
<212> TYPE: DNA
<213> ORGANISM: Homo sapiens

<400> SEQUENCE: 70
aaccaaggtg tagcttaaca taaagcaccc tgcttacacc tgggagattt caatttaatt 60
tgaccaccct gagctaattc tagccccaaa cccaactaat 100

<210> SEQ ID NO 71
<211> LENGTH: 100
<212> TYPE: DNA
<213> ORGANISM: Homo sapiens

<400> SEQUENCE: 71
cttactacca gacaacctta gccaaaccat ttacccaaat aaagtatagg cgatagaaat 60
tgaaacctgg cgcaatagat atagtaccgc aagggaaaga 100

<210> SEQ ID NO 72
<211> LENGTH: 100
<212> TYPE: DNA
<213> ORGANISM: Homo sapiens

<400> SEQUENCE: 72
tctactacca aataacctca actaaaacat ttacccaaat aaagtatagg cgatagaaat 60
gatatctcgg cacaatagac ataataccgc gatggaaaga 100

<210> SEQ ID NO 73
<211> LENGTH: 100
<212> TYPE: DNA
<213> ORGANISM: Homo sapiens

<400> SEQUENCE: 73
tgaaaaatta taaccaagca taatatagca aggactaacc cctatacctt ctgcataatg 60
aattaactag aaataacttt gcaaggagag ccaaagctaa 100

<210> SEQ ID NO 74
<211> LENGTH: 100
<212> TYPE: DNA
<213> ORGANISM: Homo sapiens

<400> SEQUENCE: 74
atgaaaaagt taaccaagaa taaaatagca aggatagacc cttatacctt ctgcgtaatg 60
aattaactag aaataacttt acacagagaa ccaaagccaa 100

<210> SEQ ID NO 75
<211> LENGTH: 100
<212> TYPE: DNA
<213> ORGANISM: Homo sapiens

<400> SEQUENCE: 75
tgaaaaaaca taaccaagca taaagtagca aggacaaacc cctatacctt ctgcataatg 60
aattaactag aaataacttt acaaagagaa ccaaagccaa 100

<210> SEQ ID NO 76
<211> LENGTH: 100
<212> TYPE: DNA
<213> ORGANISM: Homo sapiens

<400> SEQUENCE: 76
gacccccgaa accagacgag ctacctaaga acagctaaaa gagcacaccc gtctatgtag 60
caaaatagtg ggaagattta taggtagagg cgacaaacct 100

<210> SEQ ID NO 77
<211> LENGTH: 100
<212> TYPE: DNA
<213> ORGANISM: Homo sapiens

<400> SEQUENCE: 77
gtcccctgaa accagatgag ctacccaaga ataactgaaa gcgcacaccc acctatgtgg 60
caaaatagtg ggaagattga tgagtagggg ggacaagcct 100

<210> SEQ ID NO 78
<211> LENGTH: 100
<212> TYPE: DNA
<213> ORGANISM: Homo sapiens

<400> SEQUENCE: 78
gtcccccgaa accagatgaa ctacccaaga acagctgaaa gagcacactc acctatgtgg 60
caaaatagtg ggaagatgca tgagtagcgg tcacaagcct 100

<210> SEQ ID NO 79
<211> LENGTH: 100
<212> TYPE: DNA
<213> ORGANISM: Homo sapiens

<400> SEQUENCE: 79
ggcccccaaa accagacgag ctacccaaga acagctaaaa gaacacaccc atctatgtag 60
taaaatagtg gggagattca tgagtagtgg tgataagcct 100

<210> SEQ ID NO 80
<211> LENGTH: 100
<212> TYPE: DNA
<213> ORGANISM: Homo sapiens

<400> SEQUENCE: 80
ggcccctaaa accagacgag ctacccaaga acagcgaaaa gagcacaccc atctatgtag 60
taaaatagtg gggagattca tgagcagcag tgatacgcct 100

<210> SEQ ID NO 81
<211> LENGTH: 100
<212> TYPE: DNA
<213> ORGANISM: Homo sapiens

<400> SEQUENCE: 81
gtcccccgaa accagacagg ctacccaaga atagctaaaa gagcacactc acctgtgtgg 60
caaaatagtg agaagattca tgagtagcgg tgacaaggct 100

<210> SEQ ID NO 82
<211> LENGTH: 100
<212> TYPE: DNA
<213> ORGANISM: Homo sapiens

<400> SEQUENCE: 82
gtcccccaaa accagatgag ctacccaaga acagctgaaa gagcacaccc acctatgtgg 60
caaaataggg ggaagattca tgagtagcag cgataagcct 100

<210> SEQ ID NO 83
<211> LENGTH: 100
<212> TYPE: DNA
<213> ORGANISM: Homo sapiens

<400> SEQUENCE: 83
gacccccgaa accagacgag ctacctaaga acagctgaaa gagcacaccc atctatgtag 60
caaaatagtg ggaagattca taggtagagg tgacaagcct 100

<210> SEQ ID NO 84
<211> LENGTH: 100
<212> TYPE: DNA
<213> ORGANISM: Homo sapiens

<400> SEQUENCE: 84
accgagcctg gtgatagctg gttgtccaag atagaatctt agttcaactt taaatttgcc 60
cacagaaccc tctaaatccc cttgtaaatt taactgttag 100

<210> SEQ ID NO 85
<211> LENGTH: 100
<212> TYPE: DNA
<213> ORGANISM: Homo sapiens

<400> SEQUENCE: 85
tccaagcctg gtgatagctg gttgtccaag atagaatctt agttcaactt taaatttacc 60
tacagaacca cttaattccc ctgtaaattt aactgttagt 100

<210> SEQ ID NO 86
<211> LENGTH: 100
<212> TYPE: DNA
<213> ORGANISM: Homo sapiens

<400> SEQUENCE: 86
accaagcctg gtgatagctg gttgtccaag atagaattga aattcaactt taaatttacc 60
tacagaacca cctaatccta ttgttaagtt taattgttag 100

<210> SEQ ID NO 87
<211> LENGTH: 100
<212> TYPE: DNA
<213> ORGANISM: Homo sapiens

<400> SEQUENCE: 87
tccaaagagg aacagctctt tggacactag gaaaaaacct tgtagagaga gtaaaaaatt 60
taacacccat agtaggccta aaagcagcca ccaattaaga 100

<210> SEQ ID NO 88
<211> LENGTH: 100
<212> TYPE: DNA
<213> ORGANISM: Homo sapiens

<400> SEQUENCE: 88
tctaaagagg gacagctctt tagacactag gaaaaaacct tgtagagaga gtaaaaaata 60
taacttccaa agttggccta gaagaagcga tcaattaaga 100

<210> SEQ ID NO 89
<211> LENGTH: 100
<212> TYPE: DNA
<213> ORGANISM: Homo sapiens

<400> SEQUENCE: 89
aagcgttcaa gctcaacacc cactacctaa aaaatcccaa acatataact gaactcctca 60
cacccaattg gaccaatcta tcaccctata gaagaactaa 100

<210> SEQ ID NO 90
<211> LENGTH: 100
<212> TYPE: DNA
<213> ORGANISM: Homo sapiens

<400> SEQUENCE: 90
tgttagtata agtaacatga aaacattctc ctccgcataa gcctgcgtca gatcaaaaca 60
ctgaactgac aattaacagc ccaatatcta caatcaacca 100

<210> SEQ ID NO 91
<211> LENGTH: 100
<212> TYPE: DNA
<213> ORGANISM: Homo sapiens

<400> SEQUENCE: 91
tgttagtata agtgacatgc aaacattctc ctccgcataa gcctacatca gaccaaaata 60
cttcactgac aattaacagc ccaatatcta taaataatca 100

<210> SEQ ID NO 92
<211> LENGTH: 100
<212> TYPE: DNA
<213> ORGANISM: Homo sapiens

<400> SEQUENCE: 92
acaagtcatt attaccctca ctgtcaaccc aacacaggca tgctcataag gaaaggttaa 60
aaaaagtaaa aggaactcgg caaaccttac cccgcctgtt 100

<210> SEQ ID NO 93
<211> LENGTH: 100
<212> TYPE: DNA
<213> ORGANISM: Homo sapiens

<400> SEQUENCE: 93
atgaaactgt attactccta ctgttaaccc aacacaggca tgcccacaag gaaaggttaa 60
aaaaagtaaa aggaactcgg caaatcttac cccgcctgtt 100

<210> SEQ ID NO 94
<211> LENGTH: 100
<212> TYPE: DNA
<213> ORGANISM: Homo sapiens

<400> SEQUENCE: 94
acaaaccggt gctacccata ctgttaaccc aacacaggca tgcttataag gaaaggttaa 60
aaaaagtaaa aggaactcgg caaatcttac cccgcctgtt 100

<210> SEQ ID NO 95
<211> LENGTH: 100
<212> TYPE: DNA
<213> ORGANISM: Homo sapiens

<400> SEQUENCE: 95
caaatttatt attaccgata ctgttaatcc aacacaggca tgctctaagg aaaggttaaa 60
aaaaattaaa aggaactcgg caaattttac cctgcctgtt 100

<210> SEQ ID NO 96
<211> LENGTH: 100
<212> TYPE: DNA
<213> ORGANISM: Homo sapiens

<400> SEQUENCE: 96
tgaaaccatt attacccaca ctgttaaccc aacacaggca tgcttacaag gaaaggttaa 60
aaaaagtaaa aggaactcag cgaatcttac ccctcctgtt 100

<210> SEQ ID NO 97
<211> LENGTH: 100
<212> TYPE: DNA
<213> ORGANISM: Homo sapiens

<400> SEQUENCE: 97
taccaaaaac atcacctcta gcatcaccag tattagaggc accgcctgcc cagtgacaca 60
tgtttaacgg ccgcggtacc ctaaccgtgc aaaggtagca 100

<210> SEQ ID NO 98
<211> LENGTH: 100

<212> TYPE: DNA
<213> ORGANISM: Homo sapiens

<400> SEQUENCE: 98
taccaaaaac atcacctcta gcattaacag tattagaggc actgcctacc cagtgacata 60
tgtttaacgg ccacagtatc ctgacagtgc acaggtagca 100

<210> SEQ ID NO 99
<211> LENGTH: 100
<212> TYPE: DNA
<213> ORGANISM: Homo sapiens

<400> SEQUENCE: 99
taccaaaaac atcacctcta gcattaccag tattagagtc actgcctgcc cagtgacata 60
tgttcaacag ccgcggtatc ctgaccgtgc aaaggtagca 100

<210> SEQ ID NO 100
<211> LENGTH: 100
<212> TYPE: DNA
<213> ORGANISM: Homo sapiens

<400> SEQUENCE: 100
taccaaaaac atcacctcta gcattaccag ttttagagtc actgcctgcc cggtgacata 60
tgttcaacgg ccatggtatc ctgaccgtgc aaaggtagca 100

<210> SEQ ID NO 101
<211> LENGTH: 100
<212> TYPE: DNA
<213> ORGANISM: Homo sapiens

<400> SEQUENCE: 101
taccaaaaac atcacctcta gcattaccag tattagaggc accgcctgcc cagtgacata 60
tgtttaacgg ccgtggtacc ctaaccgtgc aaaggtagca 100

<210> SEQ ID NO 102
<211> LENGTH: 100
<212> TYPE: DNA
<213> ORGANISM: Homo sapiens

<400> SEQUENCE: 102
taccaaaaac atcacctcta gcattaccag tattagaggc accgcctgcc cagtgacata 60
tgttgaatgg ccgcggcttt ctacgtctct aggggctgtg 100

<210> SEQ ID NO 103
<211> LENGTH: 100
<212> TYPE: DNA
<213> ORGANISM: Homo sapiens

<400> SEQUENCE: 103
taccaaaaac atcacctcta gcattaccag tattagaggc actgcctgtc cagtgacata 60
tgttcgatgg ccgcagtatc ctgactgtgc aaaggtagca 100

<210> SEQ ID NO 104
<211> LENGTH: 100
<212> TYPE: DNA
<213> ORGANISM: Homo sapiens

<400> SEQUENCE: 104
taccaaaaac atcacctcta gcattaccag tattagaggc actgcctacc cagtgactta 60
tgttcaatgg ccgtggtatc ctgaccgtgc aaaggtagca 100

<210> SEQ ID NO 105
<211> LENGTH: 100
<212> TYPE: DNA
<213> ORGANISM: Homo sapiens

<400> SEQUENCE: 105
taccaaaaac atcacctcta gcattaccag tattagaggc actgcctgcc cagtgacata 60
tgttcaacga ccaccatatc ctgaccttgc aaaggtaaca 100

<210> SEQ ID NO 106
<211> LENGTH: 100
<212> TYPE: DNA
<213> ORGANISM: Homo sapiens

<400> SEQUENCE: 106
taccaaaaac atcacctcta gcattattag tattagaggc gctgcctgcc cagtgacata 60
tgttcaacag ccacagtacc ctgagcgtgc aaaggtagca 100

<210> SEQ ID NO 107
<211> LENGTH: 100
<212> TYPE: DNA
<213> ORGANISM: Homo sapiens

<400> SEQUENCE: 107
taccaaaaac atcacctcta gcattaccag tattaaaggc actgccttcc cagtgatata 60
tgttcaatgg ctgtggtatc ctgactgtgc aaaggtagca 100

<210> SEQ ID NO 108
<211> LENGTH: 100
<212> TYPE: DNA
<213> ORGANISM: Homo sapiens

<400> SEQUENCE: 108
taccaaaaac atcaccccta gcattgctag tattagaggc actgcctgct cagtgacata 60
tgtttaaggg ttgcggtatc ctgaacttgc aaaggtagca 100

<210> SEQ ID NO 109
<211> LENGTH: 100
<212> TYPE: DNA
<213> ORGANISM: Homo sapiens

<400> SEQUENCE: 109
taccaaaaac atcacctcta gcattaccag tattagaggc actgcctgcc cagtgacata 60
tgttcaacgg tggtggtatc ctgaccgtgc aaggtagcat 100

<210> SEQ ID NO 110
<211> LENGTH: 100
<212> TYPE: DNA
<213> ORGANISM: Homo sapiens

<400> SEQUENCE: 110
taccaaaaac atcacctcta gcattaccag tattagaggc actgcctgcc cagtgacata 60
tgttcaacgg ccgcagtatc ctgaccatgt aaggtagcat 100

<210> SEQ ID NO 111
<211> LENGTH: 100
<212> TYPE: DNA
<213> ORGANISM: Homo sapiens

<400> SEQUENCE: 111
tatcaaaaac atcacctcta gcattaccag tactagaggc accacctgcc cagtgacata 60
tgtttaatgg ctgcggtacc ctaaccgtgt aaaggtagca 100

<210> SEQ ID NO 112
<211> LENGTH: 100
<212> TYPE: DNA
<213> ORGANISM: Homo sapiens

<400> SEQUENCE: 112
taccaaaaac atcacctctg acataactag tattagaggc actacctgcc cagtgacata 60
agtttaacag ccacagtatc ctgaccatgc taaggtagca 100

<210> SEQ ID NO 113
<211> LENGTH: 100
<212> TYPE: DNA
<213> ORGANISM: Homo sapiens

<400> SEQUENCE: 113
taccaaaaac atcacctcta gcattactag taccagaggc aatgcctacc cagtgacgta 60
tgtttaaggg ctgcggtatc ttgaccatgc aaaggtagcc 100

<210> SEQ ID NO 114
<211> LENGTH: 100
<212> TYPE: DNA
<213> ORGANISM: Homo sapiens

<400> SEQUENCE: 114
taatcacttg ttccttaaat agggacctgt atgaatggct ccacgagggt tcagctgtct 60
cttactttta accagtgaaa ttgacctgcc cgtgaagagg 100

<210> SEQ ID NO 115
<211> LENGTH: 100
<212> TYPE: DNA
<213> ORGANISM: Homo sapiens

<400> SEQUENCE: 115
taatcacttg ttccctaaat agggacttgt atgaatggcc atatgaaggt tcagctgtct 60
cttactttta atcagtgaaa ttgacctatt cgtgaagagg 100

<210> SEQ ID NO 116
<211> LENGTH: 100
<212> TYPE: DNA
<213> ORGANISM: Homo sapiens

<400> SEQUENCE: 116
taatcgcttg ttccctaaat agggacttgt atgaatggac acacaagggt tcagctgtct 60
cttactttta atcagtgaaa ttgacctatc tgtgaagagg 100

<210> SEQ ID NO 117
<211> LENGTH: 100
<212> TYPE: DNA
<213> ORGANISM: Homo sapiens

<400> SEQUENCE: 117
tgatcacttg ttccttaaat agggacttgt atgaatggct cgacgaggtt tcagctgtct 60
cttactttca accactgcaa ctgacctgcc cgtgaagagg 100

<210> SEQ ID NO 118
<211> LENGTH: 100
<212> TYPE: DNA
<213> ORGANISM: Homo sapiens

<400> SEQUENCE: 118
taatcacttg ttccttaaat agggacttgt atgaatgacc ccacgagggt tcagctgtct 60
cttacttcca accagtgaaa ctgacctgcc tgtgaagagg 100

<210> SEQ ID NO 119
<211> LENGTH: 100
<212> TYPE: DNA
<213> ORGANISM: Homo sapiens

<400> SEQUENCE: 119
taatcacttg ttccctaaat agggacttat atgaatggcc acatgagggt tcagctgtct 60
cttactttta atcagtgaaa ttgacgtatc catgaaaagg 100

<210> SEQ ID NO 120
<211> LENGTH: 100
<212> TYPE: DNA
<213> ORGANISM: Homo sapiens

<400> SEQUENCE: 120
taatcacttg ttccttaaat agggacttgt atgaatggct ccatgagggt tcagctgtct 60
cttacttcca accagtgaaa ctgacctgcc catgaacagg 100

<210> SEQ ID NO 121
<211> LENGTH: 100
<212> TYPE: DNA
<213> ORGANISM: Homo sapiens

<400> SEQUENCE: 121
taatcacttg ttccctaagt agggacttgt atgaatggcc acaccagggt ttagctgtct 60
cttactttca accagtgaaa ttgacctacc tatgaagagg 100

<210> SEQ ID NO 122
<211> LENGTH: 100
<212> TYPE: DNA
<213> ORGANISM: Homo sapiens

<400> SEQUENCE: 122
taatcacttg ttccctaaat agggacttgt atgaatagcc acacaagggt tgagctgtct 60
cttactttta atcagtgaaa ttgacctatc catgaagagg 100

<210> SEQ ID NO 123
<211> LENGTH: 100
<212> TYPE: DNA
<213> ORGANISM: Homo sapiens

<400> SEQUENCE: 123
taatcacttg ttccttaaat agggacttgt ctgaatggct ccacgagggt tcagctgtct 60
cttactttca accagtgaaa ttgacctgcc cgtgaagagg 100

<210> SEQ ID NO 124
<211> LENGTH: 100
<212> TYPE: DNA
<213> ORGANISM: Homo sapiens

<400> SEQUENCE: 124
taatcatttg ttcccaaaat gggaacttcc atgaatggcc tcacaagggt ttaattgtct 60
cttacgttta atcagtgaaa ttgacctatc tgtggagagg 100

<210> SEQ ID NO 125
<211> LENGTH: 100
<212> TYPE: DNA
<213> ORGANISM: Homo sapiens

<400> SEQUENCE: 125
taatcagttt ttccccaaat agggacctgt atgaatggcc acaagagggt ctgattgtct 60
cttaccttta gtcaatgaaa ttgacctacc catgaagagg 100

<210> SEQ ID NO 126
<211> LENGTH: 100
<212> TYPE: DNA
<213> ORGANISM: Homo sapiens

<400> SEQUENCE: 126
cgggcatgac acagcaagac gagaagaccc tatggagctt taatttatta atgcaaacag 60
tacctaacaa acccacaggt cctaaactac caaacctgca 100

<210> SEQ ID NO 127
<211> LENGTH: 100
<212> TYPE: DNA
<213> ORGANISM: Homo sapiens

<400> SEQUENCE: 127
cggacataat acaacaagac gagaagacca tatggagctt caatttacca atgcaaacaa 60
cacccaataa gcccacaggc tctaacctac caaacctgca 100

<210> SEQ ID NO 128
<211> LENGTH: 100
<212> TYPE: DNA
<213> ORGANISM: Homo sapiens

<400> SEQUENCE: 128
cggacataat acaacaagac gagaagaccc taaggagctt taatttatga atgcaaacaa 60
gaccaaatag gcccgcaggc cctaaactac cagacctgcg 100

<210> SEQ ID NO 129
<211> LENGTH: 100
<212> TYPE: DNA
<213> ORGANISM: Homo sapiens

<400> SEQUENCE: 129
ttaaaaattt cggttggggc gacctcggag cagaacccaa cctccgagca gtacatgcta 60
agacttcacc agtcaaagcg aactactata ctcaattgat 100

<210> SEQ ID NO 130
<211> LENGTH: 100
<212> TYPE: DNA
<213> ORGANISM: Homo sapiens

<400> SEQUENCE: 130
ttaaaaattt cggctggggc gacctcggag tataacccaa cctccgagca acatatgctg 60
agacttcacc agtcaaaacg agttaccacg tacaattgat 100

<210> SEQ ID NO 131

<211> LENGTH: 100
<212> TYPE: DNA
<213> ORGANISM: Homo sapiens

<400> SEQUENCE: 131
ttaaacattt cggttggggc gacctcggag tataacctaa cctccgagca acatatgctg 60
agactatacc agtcaaggcg aatatccaca tacaattgac 100

<210> SEQ ID NO 132
<211> LENGTH: 100
<212> TYPE: DNA
<213> ORGANISM: Homo sapiens

<400> SEQUENCE: 132
ccaataactt gaccaacgga acaagttacc ctagggataa cagcgcaatc ctattctaga 60
gtccatatca acaatagggt ttacgacctc gatgttggat 100

<210> SEQ ID NO 133
<211> LENGTH: 100
<212> TYPE: DNA
<213> ORGANISM: Homo sapiens

<400> SEQUENCE: 133
ccaatgattc gatcaacaga ataagttacc ctagggataa cagctcaatc ctattctaga 60
gttcatatcg acaatagggt ttacgacctc gatgttggat 100

<210> SEQ ID NO 134
<211> LENGTH: 100
<212> TYPE: DNA
<213> ORGANISM: Homo sapiens

<400> SEQUENCE: 134
ccaataattt gatcaacgga ataagttacc ttagggatag cagcgcaatc ccattctaga 60
atcagtattg acaatagagt ttacaacctc gatgttggat 100

<210> SEQ ID NO 135
<211> LENGTH: 100
<212> TYPE: DNA
<213> ORGANISM: Homo sapiens

<400> SEQUENCE: 135
ccaataattt gatcaacgga acaagttacc ctagggataa cagcgcaatc ctattctaga 60
gtccatattg acaatagggt ttacgacctc gatgttggat 100

<210> SEQ ID NO 136
<211> LENGTH: 100
<212> TYPE: DNA
<213> ORGANISM: Homo sapiens

<400> SEQUENCE: 136
ccaataattt gatcaatgga ataagttatg ctagggataa cagtgcaatc ctattctaga 60
gtccatagcg acaataggga tgactacctc gatgctgaat 100

<210> SEQ ID NO 137
<211> LENGTH: 100
<212> TYPE: DNA
<213> ORGANISM: Homo sapiens

<400> SEQUENCE: 137
ccaataattt gatcaacgga acaagttacc ctagagataa cagcgcaatc ctattctaga 60
gtccatatcg acaatagggt ttacgacctc gatgttggat 100

<210> SEQ ID NO 138
<211> LENGTH: 100
<212> TYPE: DNA
<213> ORGANISM: Homo sapiens

<400> SEQUENCE: 138
ccaataattc tatcaacagg ataagtgacc ctagggttaa gagtgcaatc ctattctagc 60
atccatatca acaacagggt ttacgacctt gatgttggat 100

<210> SEQ ID NO 139
<211> LENGTH: 100
<212> TYPE: DNA
<213> ORGANISM: Homo sapiens

<400> SEQUENCE: 139
ccaataactt gttcaaggga ataagttact ctagggataa cagcacaatc ctattctaga 60
gtccatatcg acaatagggt ttacgacctc ggtgttgtat 100

<210> SEQ ID NO 140
<211> LENGTH: 100
<212> TYPE: DNA
<213> ORGANISM: Homo sapiens

<400> SEQUENCE: 140
ccaataattt gatcaacgga ataagttacc ctagggataa cagcacaatc ctattctaga 60
gttcatatcg agaatagggt ttacgacgtc gatgttggat 100

<210> SEQ ID NO 141
<211> LENGTH: 100
<212> TYPE: DNA
<213> ORGANISM: Homo sapiens

<400> SEQUENCE: 141
ccaataattt gaccaacgga acaagttacc ctagtgataa cagtacaatc ctattctagg 60
gtccacatcg acagtagcat taacgacctc gatgttggat 100

<210> SEQ ID NO 142
<211> LENGTH: 100
<212> TYPE: DNA
<213> ORGANISM: Homo sapiens

<400> SEQUENCE: 142
caagtagttt gagcaatgga acacgttacc ttagggatag cagtacaatc ctattctaga 60
atccgtatca gcaatagggt gtatgacttc gatattggat 100

<210> SEQ ID NO 143
<211> LENGTH: 100
<212> TYPE: DNA
<213> ORGANISM: Homo sapiens

<400> SEQUENCE: 143
caaatagttt gaccaactga gcaagttacc ctagggataa caacacgatc ctattctaga 60
gtccatattg actatagggt ttacgatctc gatgttggat 100

<210> SEQ ID NO 144
<211> LENGTH: 100
<212> TYPE: DNA

<213> ORGANISM: Homo sapiens

<400> SEQUENCE: 144
caggacatcc cgatggtgca gccgctatta aaggttcgtt tgttcaacga ttaaagtcct 60
acgtgatctg agttcagacc ggagtaatcc aggtcggttt 100

<210> SEQ ID NO 145
<211> LENGTH: 100
<212> TYPE: DNA
<213> ORGANISM: Homo sapiens

<400> SEQUENCE: 145
caggacatcc aaatggtgta gccactatta agggtttgtc tgttcaaaga ttaaagtcct 60
atgtgatctg agttcagact agagtaatcc aggccggttt 100

<210> SEQ ID NO 146
<211> LENGTH: 100
<212> TYPE: DNA
<213> ORGANISM: Homo sapiens

<400> SEQUENCE: 146
caggacatcc taatggtgta gctgctatca agggtttgtt tgttcaatga ttaaagtcct 60
acatgatctg agttcagacc ggagcaatcc aggtcagttt 100

<210> SEQ ID NO 147
<211> LENGTH: 100
<212> TYPE: DNA
<213> ORGANISM: Homo sapiens

<400> SEQUENCE: 147
gaggacatcc taatggtgta gccgctatta agggttcgtt tgtttaacgg ttaaagttct 60
atgtgatctg agttcagacc tgagtaatcc aggtcagttt 100

<210> SEQ ID NO 148
<211> LENGTH: 100
<212> TYPE: DNA
<213> ORGANISM: Homo sapiens

<400> SEQUENCE: 148
caggacatcc taatggtgta gctgctatca agggttcatt tgttcaatga ttaaagtcct 60
acgtggtctg agttcagacc ggagcaagcc aggtctggta 100

<210> SEQ ID NO 149
<211> LENGTH: 100
<212> TYPE: DNA
<213> ORGANISM: Homo sapiens

<400> SEQUENCE: 149
caggacatct taatgctgga gccgctatta agagtttgtt tgttcaacga ttaaagtcct 60
acgtgatctg aattcagacc agaataatcc aggtcagttc 100

<210> SEQ ID NO 150
<211> LENGTH: 100
<212> TYPE: DNA
<213> ORGANISM: Homo sapiens

<400> SEQUENCE: 150
caggacatcc taatggtgta gccgctatta agggttcatt tattcaatga ttaaagtcct 60
atgtgatctg atttcagacc agagtaatcc aggttggttt 100

<210> SEQ ID NO 151
<211> LENGTH: 100
<212> TYPE: DNA
<213> ORGANISM: Homo sapiens

<400> SEQUENCE: 151
caggacatcc taatggtgta gctgctgtca agggttcgtt tgtccaatga ttaaagtcct 60
acgtgatctg agttcagacc ggagcaatcc aggtctggta 100

<210> SEQ ID NO 152
<211> LENGTH: 100
<212> TYPE: DNA
<213> ORGANISM: Homo sapiens

<400> SEQUENCE: 152
gggacatcct aaatggtgta gccgctatta agggatcatt tgttcaatga ttaaagtcct 60
tcgtgatctg agttcagacc agagcaatcc aggttggttt 100

<210> SEQ ID NO 153
<211> LENGTH: 100
<212> TYPE: DNA
<213> ORGANISM: Homo sapiens

<400> SEQUENCE: 153
caggacgtcc taatggtgta gccgctaata agggttcgtt tgttcaatga tcaaagtcct 60
acatgatctg agttcagacc ggagtaatcc aggtcagttt 100

<210> SEQ ID NO 154
<211> LENGTH: 100
<212> TYPE: DNA
<213> ORGANISM: Homo sapiens

<400> SEQUENCE: 154
caggacatcc taatggtgca gccgctatta agggttcgtt tgttcaatga ttagaatcct 60
acatgatctg agttcagatc ggagtaatcc aggtcggttt 100

<210> SEQ ID NO 155
<211> LENGTH: 100
<212> TYPE: DNA
<213> ORGANISM: Homo sapiens

<400> SEQUENCE: 155
caggacatcc caatggtgca gccgctatta aaggttcgtt tgttcaacga ttagagtcct 60
atgtgatctg agttcagacc ggagtaatcc aggttggttt 100

<210> SEQ ID NO 156
<211> LENGTH: 100
<212> TYPE: DNA
<213> ORGANISM: Homo sapiens

<400> SEQUENCE: 156
aaggacatgc taatggtgta gccagtatta aggattcttt tgttcagtga ttaaagtcct 60
acatgatttg agttcagacc agagtaaccc aggtcggttt 100

<210> SEQ ID NO 157
<211> LENGTH: 100
<212> TYPE: DNA
<213> ORGANISM: Homo sapiens

<400> SEQUENCE: 157
ctatctactt caaattcctc cctgtacgaa aggacaagag aaataaggcc tacttcacaa 60
agcgccttcc cccgtaaatg atatcatctc aacttagtat 100

<210> SEQ ID NO 158
<211> LENGTH: 100
<212> TYPE: DNA
<213> ORGANISM: Homo sapiens

<400> SEQUENCE: 158
tatacccaca cccacccaag aacagggttt gttaagatgg cagagcccgg taatcgcata 60
aaacttaaaa ctttacagtc agaggttcaa ttcctcttct 100

<210> SEQ ID NO 159
<211> LENGTH: 100
<212> TYPE: DNA
<213> ORGANISM: Homo sapiens

<400> SEQUENCE: 159
catcacacac actattcaag aacaaggttt gttaagatgg cagagcccag caattgcata 60
aatcttaaaa ctttataatc agaggttcga ctcctcttct 100

<210> SEQ ID NO 160
<211> LENGTH: 100
<212> TYPE: DNA
<213> ORGANISM: Homo sapiens

<400> SEQUENCE: 160
gaaatcacca cacacccaag aacagggttt cttaagatgg cggagcctgg caatagcata 60
aaacgtaaaa ctttacaatc aaaggttcaa ctccccttct 100

<210> SEQ ID NO 161
<211> LENGTH: 100
<212> TYPE: DNA
<213> ORGANISM: Homo sapiens

<400> SEQUENCE: 161
tgtacccaca cccacccaag aacagggttt gttaagatgg cagaccccag caattgcata 60
aaatttaaaa ctttacaacc agaggttcaa cccctcttct 100

<210> SEQ ID NO 162
<211> LENGTH: 100
<212> TYPE: DNA
<213> ORGANISM: Homo sapiens

<400> SEQUENCE: 162
taacaacata cccatggcca acctcctact cctcattgta cccattctaa tcgcaatggc 60
attcctaatg cttaccgaac gaaaaattct aggctatata 100

<210> SEQ ID NO 163
<211> LENGTH: 100
<212> TYPE: DNA
<213> ORGANISM: Homo sapiens

<400> SEQUENCE: 163
taacaacatg tccataacta accttctact tcttattgta cctatcctaa tcgccatggc 60
attcctcatg ctaactgaat gaaaaatcct aggctacatg 100

<210> SEQ ID NO 164
<211> LENGTH: 100
<212> TYPE: DNA
<213> ORGANISM: Homo sapiens

<400> SEQUENCE: 164
caactacgca aaggccccaa cgttgtaggc ccctacgggc tactacaacc cttcgctgac 60
gccataaaac tcttcaccaa agagccccta aaacccgcca 100

<210> SEQ ID NO 165
<211> LENGTH: 100
<212> TYPE: DNA
<213> ORGANISM: Homo sapiens

<400> SEQUENCE: 165
caactatgca aaggatccaa tattttaggc ccctatggac tatttcaacc atttgctgat 60
gcaataaaac ttttcactaa agagacccta aaaccctcat 100

<210> SEQ ID NO 166
<211> LENGTH: 100
<212> TYPE: DNA
<213> ORGANISM: Homo sapiens

<400> SEQUENCE: 166
caactatgca aaggacctaa cattgtaggt ccctatgggc tgcttcaacc agtcgttgat 60
gcaataaaac ttttcaccaa agaaccctta aggccctcaa 100

<210> SEQ ID NO 167
<211> LENGTH: 100
<212> TYPE: DNA
<213> ORGANISM: Homo sapiens

<400> SEQUENCE: 167
caactacgca aagggcccaa tattgtaggc ccctatggac tattacaacc ttttgccgat 60
gccataaaac tctttaccaa agaatcctta aaaccctcaa 100

<210> SEQ ID NO 168
<211> LENGTH: 100
<212> TYPE: DNA
<213> ORGANISM: Homo sapiens

<400> SEQUENCE: 168
catctaccat caccctctac atcaccgccc cgaccttagc tctcaccatc gctcttctac 60
tatgaacccc cctccccata cccaaccccc tggtcaacct 100

<210> SEQ ID NO 169
<211> LENGTH: 100
<212> TYPE: DNA
<213> ORGANISM: Homo sapiens

<400> SEQUENCE: 169
cgtcaactgt taccctctac atcactgccc caaccttagc cctctctatt gcccttctac 60
tatgaactcc cctccctata cctaaccccc tagttaatct 100

<210> SEQ ID NO 170
<211> LENGTH: 100
<212> TYPE: DNA
<213> ORGANISM: Homo sapiens

<400> SEQUENCE: 170
caacctaggc ctcctattta ttctagccac ctctagccta gccgtttact caatcctctg 60
atcagggtga gcatcaaact caaactacgc cctgatcggc 100

<210> SEQ ID NO 171
<211> LENGTH: 100
<212> TYPE: DNA
<213> ORGANISM: Homo sapiens

<400> SEQUENCE: 171
taatataggc ctcttattta ttctagccac atcaagccta gcagtctatt ccattctatg 60
atcaggataa gcatccaatt caaattatgt actgatcggc 100

<210> SEQ ID NO 172
<211> LENGTH: 100
<212> TYPE: DNA
<213> ORGANISM: Homo sapiens

<400> SEQUENCE: 172
taatataggc ctcctattta tactagccac atcaagccta gccgtctact ctattctatg 60
atcaggatga gcatctaatt caaattatgc actaatcggc 100

<210> SEQ ID NO 173
<211> LENGTH: 100
<212> TYPE: DNA
<213> ORGANISM: Homo sapiens

<400> SEQUENCE: 173
taacttaggc cttctattca ttctggctac atccagccta gctgtctact ctatcctatg 60
atcaggatga gcatcaaact caaactatgc cctgatcggc 100

<210> SEQ ID NO 174
<211> LENGTH: 100
<212> TYPE: DNA
<213> ORGANISM: Homo sapiens

<400> SEQUENCE: 174
gcactgcgag cagtagccca aacaatctca tatgaagtca ccctagccat cattctacta 60
tcaacattac taataagtgg ctcctttaac ctctccaccc 100

<210> SEQ ID NO 175
<211> LENGTH: 100
<212> TYPE: DNA
<213> ORGANISM: Homo sapiens

<400> SEQUENCE: 175
gcattatgag cagttgccca aacaatttca tacgaagtta ccctagctat catcctatta 60
tcgatcctac taataagtgg ccaattcaat ctctgcaccc 100

<210> SEQ ID NO 176
<211> LENGTH: 100
<212> TYPE: DNA
<213> ORGANISM: Homo sapiens

<400> SEQUENCE: 176
ttatcacaac acaagaacac ctctgattac tcctgccatc atgacccttg gccataatat 60
gatttatctc cacactagca gagaccaacc gaacccctt 100

<210> SEQ ID NO 177
<211> LENGTH: 100

<212> TYPE: DNA
<213> ORGANISM: Homo sapiens

<400> SEQUENCE: 177
gcatcacaat gccagaatta ctctgaccgc tcctaccatc atgaccctta gccatattat 60
gatttatttc cacactagca aaaactaacc gagccccttt 100

<210> SEQ ID NO 178
<211> LENGTH: 100
<212> TYPE: DNA
<213> ORGANISM: Homo sapiens

<400> SEQUENCE: 178
ttatcacaat gcaagaattc ctctggccgc tcctaccatc atgacctctg gccataatat 60
gatttatctc cacgctggca gaaactaacc aagccccatt 100

<210> SEQ ID NO 179
<211> LENGTH: 100
<212> TYPE: DNA
<213> ORGANISM: Homo sapiens

<400> SEQUENCE: 179
tcatcacaac acaagaattc ctctgactgc tcctaccatc atgccgccta gtcataatat 60
aatttatctc cccactagca gaaactaacc gagccccttt 100

<210> SEQ ID NO 180
<211> LENGTH: 100
<212> TYPE: DNA
<213> ORGANISM: Homo sapiens

<400> SEQUENCE: 180
tcattagaac acaagaacac ctctgactac tcctaacatc atgaccccta gctataatat 60
gatttatttc cacactagca gaaaccaatc gagctgcttt 100

<210> SEQ ID NO 181
<211> LENGTH: 100
<212> TYPE: DNA
<213> ORGANISM: Homo sapiens

<400> SEQUENCE: 181
cgaccttgcc gaaggggagt ccgaactagt ctcaggcttc aacatcgaat acgccgcagg 60
ccccttcgcc ctattcttca tagccgaata cacaaacatt 100

<210> SEQ ID NO 182
<211> LENGTH: 100
<212> TYPE: DNA
<213> ORGANISM: Homo sapiens

<400> SEQUENCE: 182
tcagcaaggt caaagggagt ccgaactagt ctcaggcttc aacatcgaat acgccgcagg 60
ccccttcgcc ctattcttca tagccgaata cacaaacatt 100

<210> SEQ ID NO 183
<211> LENGTH: 100
<212> TYPE: DNA
<213> ORGANISM: Homo sapiens

<400> SEQUENCE: 183
tgaccttact gaaggagaat cagaactagt ctcaggcttc aacattgaat atgctgcagg 60
cccattcgcc ctattcttta tagccgaata cataaatatc 100

<210> SEQ ID NO 184
<211> LENGTH: 100
<212> TYPE: DNA
<213> ORGANISM: Homo sapiens

<400> SEQUENCE: 184
attataataa acaccctcac cactacaatc ttcctaggaa caacatatga cgcactctcc 60
cctgaactct acacaacata ttttgtcacc aagaccctac 100

<210> SEQ ID NO 185
<211> LENGTH: 100
<212> TYPE: DNA
<213> ORGANISM: Homo sapiens

<400> SEQUENCE: 185
attataataa acaccctcac cactacaatc ttcctaggaa caacatataa cgcactctcc 60
cctgaactct acacaacata ttttgtcacc aagaccctac 100

<210> SEQ ID NO 186
<211> LENGTH: 100
<212> TYPE: DNA
<213> ORGANISM: Homo sapiens

<400> SEQUENCE: 186
ttctaacctc cctgttctta tgaattcgaa cagcataccc ccgattccgc tacgaccaac 60
tcatacacct cctatgaaaa aacttcctac cactcaccct 100

<210> SEQ ID NO 187
<211> LENGTH: 100
<212> TYPE: DNA
<213> ORGANISM: Homo sapiens

<400> SEQUENCE: 187
ttctgacctc cctgttctta tgaattcgaa cagcataccc ccgattccgc tacgaccaac 60
tcatacacct cctatgaaaa aacttcctac cactcaccct 100

<210> SEQ ID NO 188
<211> LENGTH: 100
<212> TYPE: DNA
<213> ORGANISM: Homo sapiens

<400> SEQUENCE: 188
tcttaacctc cctattttta tgaattcgaa cagcttatcc ccaattctgc tatgattaac 60
ttatacatct cttatgaaaa aactttctac cacttacact 100

<210> SEQ ID NO 189
<211> LENGTH: 100
<212> TYPE: DNA
<213> ORGANISM: Homo sapiens

<400> SEQUENCE: 189
tcttaacctc cctattttta tgaattcaaa cagcatatcc ccgtttcggc tacaatcaac 60
tcacacacct cctatgaaaa aattttctac tacttacact 100

<210> SEQ ID NO 190
<211> LENGTH: 100
<212> TYPE: DNA
<213> ORGANISM: Homo sapiens

<400> SEQUENCE: 190
ttctaaccgc cctgatttta tgaattcgaa cagcataccc ctgactgtgc tacaaccaac 60
tcatatatct cctatgaaaa aacttcctac cacttaaact 100

<210> SEQ ID NO 191
<211> LENGTH: 100
<212> TYPE: DNA
<213> ORGANISM: Homo sapiens

<400> SEQUENCE: 191
tcctaacctc tctattttta tgaatccgaa cagcataccc ccgattccac tacgatcaac 60
tcatgtatct cttatgaaaa aatttcttac catttacact 100

<210> SEQ ID NO 192
<211> LENGTH: 100
<212> TYPE: DNA
<213> ORGANISM: Homo sapiens

<400> SEQUENCE: 192
agcattactt atatgatatg tctccatacc cattacaatc tccagcattc cccctcaaac 60
ctaagaaata tgtctgataa aagagttact ttgatagagt 100

<210> SEQ ID NO 193
<211> LENGTH: 100
<212> TYPE: DNA
<213> ORGANISM: Homo sapiens

<400> SEQUENCE: 193
agcattactt atatgatatg tctccatacc cattacaatc tccagcattc cccctcaaac 60
ctaagaaata tgtctgataa aagagttact ttgatagagt 100

<210> SEQ ID NO 194
<211> LENGTH: 100
<212> TYPE: DNA
<213> ORGANISM: Homo sapiens

<400> SEQUENCE: 194
agcattctgt gtatgataca tctcaatacc catcataatc tccagcatcc caccccaaac 60
gtaagaaaca tgtctgacaa aagaattact ttgacagaat 100

<210> SEQ ID NO 195
<211> LENGTH: 100
<212> TYPE: DNA
<213> ORGANISM: Homo sapiens

<400> SEQUENCE: 195
agcattctgt atatgacata tctcaatacc catcctaatc tccagcatcc cacctcaaat 60
gtaagaaata cggctgacaa aagaattact ttgatagagt 100

<210> SEQ ID NO 196
<211> LENGTH: 100
<212> TYPE: DNA
<213> ORGANISM: Homo sapiens

<400> SEQUENCE: 196
ctatattttc atatgatata tttcaatatc catcacaatc tccagcatcc caccccaaat 60
gtaagaaata tgtctgacaa aagaattact ttgatagagt 100

<210> SEQ ID NO 197
<211> LENGTH: 100
<212> TYPE: DNA
<213> ORGANISM: Homo sapiens

<400> SEQUENCE: 197
agcactactt atatgataca tctcaatatc cgctacaatt tccaacattc ccccctaaac 60
ttaagaaata tgtctgacaa aagagtgact ttgatagagt 100

<210> SEQ ID NO 198
<211> LENGTH: 100
<212> TYPE: DNA
<213> ORGANISM: Homo sapiens

<400> SEQUENCE: 198
aaataatagg agcttaaacc cccttatttc taggactatg agaatcgaac ccatccctga 60
gaatccaaaa ttctccgtgc cacctatcac accccatcct 100

<210> SEQ ID NO 199
<211> LENGTH: 100
<212> TYPE: DNA
<213> ORGANISM: Homo sapiens

<400> SEQUENCE: 199
aaataatagg agtttaaatc cccttatttc taggactatg agaatcgaac ccatccctga 60
gaatccaaaa ttctccgtgc cacctatcac accccatcct 100

<210> SEQ ID NO 200
<211> LENGTH: 100
<212> TYPE: DNA
<213> ORGANISM: Homo sapiens

<400> SEQUENCE: 200
aaacaacaga ggttgaaatc ctcatatttc taggactata ggaattgaac ccatccctga 60
gaatccaaaa ttctccatgc tacctatcac accacgtcct 100

<210> SEQ ID NO 201
<211> LENGTH: 100
<212> TYPE: DNA
<213> ORGANISM: Homo sapiens

<400> SEQUENCE: 201
aaattataga ggtttaagtc ctcttatttg tagaattata ggaatcgaac ctacccctga 60
gaatccaaaa ttctctgtgc tacctaatac accacatcct 100

<210> SEQ ID NO 202
<211> LENGTH: 100
<212> TYPE: DNA
<213> ORGANISM: Homo sapiens

<400> SEQUENCE: 202
aaacaacaga ggatttcaac ctcttatttc tagaactata ggaattgaac ccacccctga 60
gaatccaaaa ttccccatgc tacctatcac accacgtcct 100

<210> SEQ ID NO 203
<211> LENGTH: 100
<212> TYPE: DNA
<213> ORGANISM: Homo sapiens

<400> SEQUENCE: 203
aaatagtaga ggtttaaacc ctcttatctc tagaactata ggaattgaac ctaaccctga 60
gaatccaaaa ttctccatgc tacctgtcac accacatcct 100

<210> SEQ ID NO 204
<211> LENGTH: 100
<212> TYPE: DNA
<213> ORGANISM: Homo sapiens

<400> SEQUENCE: 204
aaataataga ggttaaaatc ctcttatttc tagaactata ggaattgaac ctaccccctga 60 taatccaaaa ttctccatgc cacctattac accacatcct 100

<210> SEQ ID NO 205
<211> LENGTH: 100
<212> TYPE: DNA
<213> ORGANISM: Homo sapiens

<400> SEQUENCE: 205
aaataataga ggtttgaatc ctcttatttc taggaccata ggaattgaac ctatccctga 60
gaatccaaaa ttctccgtgc cacgtgtcac accctatcct 100

<210> SEQ ID NO 206
<211> LENGTH: 100
<212> TYPE: DNA
<213> ORGANISM: Homo sapiens

<400> SEQUENCE: 206
aaagtaaggt cagctaaata agctatcggg cccatacccc gaaaatgttg gttataccct 60
tcccgtacta attaatcccc tggcccaacc cgtcatctac 100

<210> SEQ ID NO 207
<211> LENGTH: 100
<212> TYPE: DNA
<213> ORGANISM: Homo sapiens

<400> SEQUENCE: 207
aaagtaaggt cagctaaata agctatcggg cccatacccc gaaaatgttg gttatatcct 60
tcccgtacta attaatcccc tggcccaacc cgtcatctac 100

<210> SEQ ID NO 208
<211> LENGTH: 100
<212> TYPE: DNA
<213> ORGANISM: Homo sapiens

<400> SEQUENCE: 208
agagtaaggt cacctaaata aaccatcaga cccataccct gaaaatgttg gttacaccct 60
tcccatacta attaatccct tggctcaact tattattact 100

<210> SEQ ID NO 209
<211> LENGTH: 100
<212> TYPE: DNA
<213> ORGANISM: Homo sapiens

<400> SEQUENCE: 209
aaagtaaggt cagctaaata agctatcagg cccatatccc aaaaatgttg gttacatcct 60
tcccatacta attaacctat tagctcagct tatcatctac 100

<210> SEQ ID NO 210

<211> LENGTH: 100
<212> TYPE: DNA
<213> ORGANISM: Homo sapiens

<400> SEQUENCE: 210
aaggtaaggt cagctaaata agctatcagg cccataccccc gaaaatgttg gttataccct 60
tcccgtccta attaacccat aaggtcaact tattatttta 100

<210> SEQ ID NO 211
<211> LENGTH: 100
<212> TYPE: DNA
<213> ORGANISM: Homo sapiens

<400> SEQUENCE: 211
agagtaaggt cagctaaata agctgttggg cccataccccc aaaaatgttg gttacaccct 60
tcccatggca attaatccct tagctcaact tgttatttcc 100

<210> SEQ ID NO 212
<211> LENGTH: 100
<212> TYPE: DNA
<213> ORGANISM: Homo sapiens

<400> SEQUENCE: 212
agagcaaggt cagctaaata agctatcggg cccatacctc acaaatgtag gttacaccct 60
tcccgtacta attaatccct tagctcaact tagtatttct 100

<210> SEQ ID NO 213
<211> LENGTH: 100
<212> TYPE: DNA
<213> ORGANISM: Homo sapiens

<400> SEQUENCE: 213
aaagtaaggt cagctaaata agctatcggg cccataccccc aaaaatgttg gtcataccct 60
tcccatacta attaatccat tagcttggcc ttactatttt 100

<210> SEQ ID NO 214
<211> LENGTH: 100
<212> TYPE: DNA
<213> ORGANISM: Homo sapiens

<400> SEQUENCE: 214
ggagtaaggt cagctaaata agctatcagg cccataccca gaaaatgttg gttatatcct 60
tcccgtacta atcaatccac tggcccaacc tgtcatctac 100

<210> SEQ ID NO 215
<211> LENGTH: 100
<212> TYPE: DNA
<213> ORGANISM: Homo sapiens

<400> SEQUENCE: 215
aaattaaggt cagctaaata agctatcagg cccatacact aaaaatgttg gttatatcct 60
tcccaaagta attaatccat tagttcaact tattatctcc 100

<210> SEQ ID NO 216
<211> LENGTH: 100
<212> TYPE: DNA
<213> ORGANISM: Homo sapiens

<400> SEQUENCE: 216
tctaccatct ttgcaggcac actcatcaca gcgctaagct cgcactgatt ttttacctga 60
gtaggcctag aaataaacat gctagctttt attccagttc 100

<210> SEQ ID NO 217
<211> LENGTH: 100
<212> TYPE: DNA
<213> ORGANISM: Homo sapiens

<400> SEQUENCE: 217
tctaccatct ttgcaggcac actcatcaca gcgctaagct cgcactgatt ttttacctga 60
gtaggcctag aaataaacat gctagctttt attccagttc 100

<210> SEQ ID NO 218
<211> LENGTH: 100
<212> TYPE: DNA
<213> ORGANISM: Homo sapiens

<400> SEQUENCE: 218
taaccaaaaa aataaaccct cgttccacag aagctgccat caagtatttc ctcacgcaag 60
caaccgcatc cataatcctt ctaatagcta tcctcttcaa 100

<210> SEQ ID NO 219
<211> LENGTH: 100
<212> TYPE: DNA
<213> ORGANISM: Homo sapiens

<400> SEQUENCE: 219
taaccaaaaa aataaaccct cgttccacag aagctgccat caagtatttc ctcacgcaag 60
caaccgcatc cataatcctt ctaatagcta tcctcttcaa 100

<210> SEQ ID NO 220
<211> LENGTH: 100
<212> TYPE: DNA
<213> ORGANISM: Homo sapiens

<400> SEQUENCE: 220
taattaaaaa aataaacccc cgctctacag aaactgctat caaatacttt ctcacataag 60
caaccacatc tataatcctc ataatagcta tcctctccaa 100

<210> SEQ ID NO 221
<211> LENGTH: 100
<212> TYPE: DNA
<213> ORGANISM: Homo sapiens

<400> SEQUENCE: 221
caatatactc tccggacaat gaaccataac caatactacc aatcaatact catcattaat 60
aatcataatg gctatagcaa taaaactagg aatagccccc 100

<210> SEQ ID NO 222
<211> LENGTH: 100
<212> TYPE: DNA
<213> ORGANISM: Homo sapiens

<400> SEQUENCE: 222
caatatactc tccggacaat gaaccataac caataccacc aatcaatact catcattaat 60
aatcataatg gctatagcaa taaaactagg aatagccccc 100

<210> SEQ ID NO 223
<211> LENGTH: 100
<212> TYPE: DNA

<213> ORGANISM: Homo sapiens

<400> SEQUENCE: 223
caatgtactc tccggacaat gaaccacaac caacaccacc aacaaatact catcattaat 60
aatcacaaca gccctagtaa taaaactagg aatagcccct 100

<210> SEQ ID NO 224
<211> LENGTH: 100
<212> TYPE: DNA
<213> ORGANISM: Homo sapiens

<400> SEQUENCE: 224
tttcacttct gagtcccaga ggttacccaa ggcacccctc tgacatccgg cctgcttctt 60
ctcacatgac aaaaactagc ccccatctca atcatatacc 100

<210> SEQ ID NO 225
<211> LENGTH: 100
<212> TYPE: DNA
<213> ORGANISM: Homo sapiens

<400> SEQUENCE: 225
tttcacttct gagtcccaga ggttacccaa ggcacccctc tgacatccgg cctgctcctt 60
ctcacatgac aaaaactagc ccccatctca atcatatacc 100

<210> SEQ ID NO 226
<211> LENGTH: 100
<212> TYPE: DNA
<213> ORGANISM: Homo sapiens

<400> SEQUENCE: 226
tttcacttct gagtcccaga gaggacccaa ggaacttctc taatatctgg catacttctc 60
cttacatgac aaaaactagc ccctatctcg attatatttc 100

<210> SEQ ID NO 227
<211> LENGTH: 100
<212> TYPE: DNA
<213> ORGANISM: Homo sapiens

<400> SEQUENCE: 227
tttcacttct gagtcccaga ggtaacccaa ggaatctctt taacatctgg tatacttttt 60
ctcacatgac aaaaactagc ccctatctcg atcatgtttc 100

<210> SEQ ID NO 228
<211> LENGTH: 100
<212> TYPE: DNA
<213> ORGANISM: Homo sapiens

<400> SEQUENCE: 228
tttcacttct gagttccaga agtaacccaa ggaacttctc taacatctgg catacttctc 60
ctcacgtgac aaaaactaac ccctatttca attcaattca 100

<210> SEQ ID NO 229
<211> LENGTH: 100
<212> TYPE: DNA
<213> ORGANISM: Homo sapiens

<400> SEQUENCE: 229
tttcacttct gagtcccaca gttaacccaa gaaacctctc taatttctgg catacttctc 60
ctcacatgac aaaaactagc ccctatctcg attatgtttc 100

<210> SEQ ID NO 230
<211> LENGTH: 100
<212> TYPE: DNA
<213> ORGANISM: Homo sapiens

<400> SEQUENCE: 230
tttcacttcc gagtcccaga agtaacccag ggaacttctc taatgtctgg catacttctc 60
ctcacatgac aaaaactagc ccctatctca attatatttc 100

<210> SEQ ID NO 231
<211> LENGTH: 100
<212> TYPE: DNA
<213> ORGANISM: Homo sapiens

<400> SEQUENCE: 231
ttccgtttct gagtcccaga agtcactcaa ggaacccctc taatatccag cctacttccc 60
ctcacatgac aaaaattagc ccctatttca attatatatc 100

<210> SEQ ID NO 232
<211> LENGTH: 100
<212> TYPE: DNA
<213> ORGANISM: Homo sapiens

<400> SEQUENCE: 232
aaatctctcc ctcactaaac gtaagccttc tcctcactct ctcaatctta tccatcatag 60
caggcagttg aggtggatta aaccaaaccc agctacgcaa 100

<210> SEQ ID NO 233
<211> LENGTH: 100
<212> TYPE: DNA
<213> ORGANISM: Homo sapiens

<400> SEQUENCE: 233
aaatttctcc ctcattaaac gtaagccttc tcctcactct ttcaatctta tccatcatgg 60
caggcagttg aggtggatta aaccaaaccc aactacgcaa 100

<210> SEQ ID NO 234
<211> LENGTH: 100
<212> TYPE: DNA
<213> ORGANISM: Homo sapiens

<400> SEQUENCE: 234
aatcttagca tactcctcaa ttacccacat aggatgaata atagcagttc taccgtacaa 60
ccctaacata accattctta atttaactat ttatattatc 100

<210> SEQ ID NO 235
<211> LENGTH: 100
<212> TYPE: DNA
<213> ORGANISM: Homo sapiens

<400> SEQUENCE: 235
aatcttagca tactcctcaa ttacccacat aggatgaata acagcagttc taccgtacaa 60
ccctaacata accattctta atttaactat ttatattatc 100

<210> SEQ ID NO 236
<211> LENGTH: 100
<212> TYPE: DNA
<213> ORGANISM: Homo sapiens

<400> SEQUENCE: 236
aatcctagcc tactcctcaa tcactcacat aggttgaata atagcagtac taatttatga 60
cccaaacatt accactctaa atctgattat ttaccttatc 100

<210> SEQ ID NO 237
<211> LENGTH: 100
<212> TYPE: DNA
<213> ORGANISM: Homo sapiens

<400> SEQUENCE: 237
aatcctagca tactcctcaa tcacccatat aggctgaata atagcagtac tagcatacaa 60
cccaagtatc accattttca acctaatcat ctatatcatt 100

<210> SEQ ID NO 238
<211> LENGTH: 100
<212> TYPE: DNA
<213> ORGANISM: Homo sapiens

<400> SEQUENCE: 238
ctaactacta ccgcattcct actactcaac ttaaactcca gcaccacgac cctactacta 60
tctcgcacct gaaacaagct aacatgacta acacccttaa 100

<210> SEQ ID NO 239
<211> LENGTH: 100
<212> TYPE: DNA
<213> ORGANISM: Homo sapiens

<400> SEQUENCE: 239
ctaactacta ccgcattcct actactcaac ttaaactcca gcaccacaac cctactacta 60
tctcgcacct gaaacaagct aacatgacta acacccttaa 100

<210> SEQ ID NO 240
<211> LENGTH: 100
<212> TYPE: DNA
<213> ORGANISM: Homo sapiens

<400> SEQUENCE: 240
ctaacaacta ctgcattcct agcactcaat ctgaattcaa gcaccacagc cctattacta 60
tcccacgcct gaaacaaact aacatgatta atatccataa 100

<210> SEQ ID NO 241
<211> LENGTH: 100
<212> TYPE: DNA
<213> ORGANISM: Homo sapiens

<400> SEQUENCE: 241
ctaacaacca ccacattcct ggtactcaac ttgaactcta gcactacaac cctactactg 60
tgccgcactt gaaataaact aacctgacta atacccctaa 100

<210> SEQ ID NO 242
<211> LENGTH: 100
<212> TYPE: DNA
<213> ORGANISM: Homo sapiens

<400> SEQUENCE: 242
ttccatccac cctcctctcc ctaggaggcc tgcccccgct aaccggcttt ttgcccaaat 60
gggccattat cgaagaattc acaaaaaaca atagcctcat 100

<210> SEQ ID NO 243
<211> LENGTH: 100
<212> TYPE: DNA
<213> ORGANISM: Homo sapiens

<400> SEQUENCE: 243
ttccatccac cctcctctcc ctaggaggcc tgcccccgct aaccggcttt ttgcccaaat 60
gggccattat cgaagaattc acaaaaaaca atagcctcat 100

<210> SEQ ID NO 244
<211> LENGTH: 100
<212> TYPE: DNA
<213> ORGANISM: Homo sapiens

<400> SEQUENCE: 244
tcccatctac cctactatca ctaggaggcc ttcccccact aactggcttt ctacccaaat 60
gatttatcat tgaagaattc acaaaaaata acaacctcat 100

<210> SEQ ID NO 245
<211> LENGTH: 100
<212> TYPE: DNA
<213> ORGANISM: Homo sapiens

<400> SEQUENCE: 245
catccccacc atcatagcca ccatcaccct ccttaacctc tacttctacc tacgcctaat 60
ctactccacc tcaatcacac tactccccat atctaacaac 100

<210> SEQ ID NO 246
<211> LENGTH: 100
<212> TYPE: DNA
<213> ORGANISM: Homo sapiens

<400> SEQUENCE: 246
catccccacc atcatagcca tcatcaccct ccttaacctc tacttctacc tgcgcctaat 60
ctactccacc tcaatcacac tactccctat atctaacaac 100

<210> SEQ ID NO 247
<211> LENGTH: 100
<212> TYPE: DNA
<213> ORGANISM: Homo sapiens

<400> SEQUENCE: 247
tatccccact accatagcca ttattactct ctttaaccta tatttttaca tacgcttaat 60
ctactctgct tcaattacac tattccccat atccaacaac 100

<210> SEQ ID NO 248
<211> LENGTH: 100
<212> TYPE: DNA
<213> ORGANISM: Homo sapiens

<400> SEQUENCE: 248
gtaaaaataa aatgacagtt tgaacataca aaacccaccc cattcctccc cacactcatc 60
gcccttacca cgctactcct acctatctcc ccttttatac 100

<210> SEQ ID NO 249
<211> LENGTH: 100
<212> TYPE: DNA
<213> ORGANISM: Homo sapiens

<400> SEQUENCE: 249
gtaaaaataa aatgacagtt tgaacacaca aaacccaccc cattcctccc cacactcatc 60
gcccttacca cactgctcct acctatctcc ccttttatgc 100

<210> SEQ ID NO 250
<211> LENGTH: 100
<212> TYPE: DNA
<213> ORGANISM: Homo sapiens

<400> SEQUENCE: 250
gtaaaaataa aatgacaatt tgaaaataca aaatccacac cactcttccc cacactcact 60
gtccttacca ccctcctcct accaatctct ccacttacac 100

<210> SEQ ID NO 251
<211> LENGTH: 100
<212> TYPE: DNA
<213> ORGANISM: Homo sapiens

<400> SEQUENCE: 251
taataatctt atagaaattt aggttaaata cagaccaaga gccttcaaag ccctcagtaa 60
gttgcaatac ttaatttctg caacagctaa ggactgcaaa 100

<210> SEQ ID NO 252
<211> LENGTH: 100
<212> TYPE: DNA
<213> ORGANISM: Homo sapiens

<400> SEQUENCE: 252
taataatctt atagaaattt aggttaaata cagaccaaga gccttcaaag ccctcagtaa 60
gttgcaatac ttaatttctg caacagctaa ggactgcaaa 100

<210> SEQ ID NO 253
<211> LENGTH: 100
<212> TYPE: DNA
<213> ORGANISM: Homo sapiens

<400> SEQUENCE: 253
accccactct gcatcaactg aacgcaaatc agccacttta attaagctaa gcccttacta 60
gaccaatggg acttaaaccc acaaacactt agttaacagc 100

<210> SEQ ID NO 254
<211> LENGTH: 100
<212> TYPE: DNA
<213> ORGANISM: Homo sapiens

<400> SEQUENCE: 254
accccactct gcatcaactg aacgcaaatc agccacttta attaagctaa gcccttacta 60
gaccaatggg acttaaaccc acaaacactt agttaacagc 100

<210> SEQ ID NO 255
<211> LENGTH: 100
<212> TYPE: DNA
<213> ORGANISM: Homo sapiens

<400> SEQUENCE: 255
attctactct gtatcaattg aacgcaaatc aatcacttta attaagctaa gcccttacta 60
gattgatggg acttaaaccc acgaacattt aattaacaga 100

<210> SEQ ID NO 256
<211> LENGTH: 100

<212> TYPE: DNA
<213> ORGANISM: Homo sapiens

<400> SEQUENCE: 256
actctattct gcatcagttg aacgcaaata aaccacttta attaagctaa gcccttacta 60
gactggtgga attcaaaacc acgaaaattt agttaacagt 100

<210> SEQ ID NO 257
<211> LENGTH: 100
<212> TYPE: DNA
<213> ORGANISM: Homo sapiens

<400> SEQUENCE: 257
actgtattct gcatcaattg aatgcaaatc aatcacttta attaagctaa gccatggcta 60
gactgttggg acttaaaccc atgaaaattt agctaacacc 100

<210> SEQ ID NO 258
<211> LENGTH: 100
<212> TYPE: DNA
<213> ORGANISM: Homo sapiens

<400> SEQUENCE: 258
actctattct gcatcaattg aacacaaatc cgccacttta attaagctaa gcccttgcta 60
gattcgcaga attcaaaccc atgaaaattt agttaacagc 100

<210> SEQ ID NO 259
<211> LENGTH: 100
<212> TYPE: DNA
<213> ORGANISM: Homo sapiens

<400> SEQUENCE: 259
actctattct gcatcagttg aacgcaaatc aaccacttta attaagctaa gtccttgcta 60
gatcggtgga attcaaaccc acaaaaattt agttaacagc 100

<210> SEQ ID NO 260
<211> LENGTH: 100
<212> TYPE: DNA
<213> ORGANISM: Homo sapiens

<400> SEQUENCE: 260
accctacttt gcatctactg aacgcaaatc agccacttta attaagctaa gcccttgcta 60
gatcaatggg acttaaaccc acaaaaattt ggttaacagc 100

<210> SEQ ID NO 261
<211> LENGTH: 100
<212> TYPE: DNA
<213> ORGANISM: Homo sapiens

<400> SEQUENCE: 261
taagcaccct aatcaactgg cttcaatcta cttctcccgc cgccgggaaa aaaggcggga 60
gaagccccgg caggtttgaa gctgcttctt cgaatttgca 100

<210> SEQ ID NO 262
<211> LENGTH: 100
<212> TYPE: DNA
<213> ORGANISM: Homo sapiens

<400> SEQUENCE: 262
taagcaccct aatcaactgg cttcaatcta cttctcccgc cgccgggaaa aaaggcggga 60
gaagccccgg caggtttgaa gctgcttctt cgaatttgca 100

<210> SEQ ID NO 263
<211> LENGTH: 100
<212> TYPE: DNA
<213> ORGANISM: Homo sapiens

<400> SEQUENCE: 263
attcaatatg aaaatcacct cggagctggt aaaaagaggc ctaacccctg tctttagatt 60
tacagtccaa tgcttcactc agccatttta cctcaccccc 100

<210> SEQ ID NO 264
<211> LENGTH: 100
<212> TYPE: DNA
<213> ORGANISM: Homo sapiens

<400> SEQUENCE: 264
attcaatatg aaaatcacct cagagctggt aaaaagaggc ttaacccctg tctttagatt 60
tacagtccaa tgcttcactc agccatttta cctcaccccc 100

<210> SEQ ID NO 265
<211> LENGTH: 100
<212> TYPE: DNA
<213> ORGANISM: Homo sapiens

<400> SEQUENCE: 265
attcaatatg aaaatcacct cagagctggt aaaaagaggc ttaacccctg tctttagatt 60
tacagtccaa tgcttcactc agccatttta cctcaccaga 100

<210> SEQ ID NO 266
<211> LENGTH: 100
<212> TYPE: DNA
<213> ORGANISM: Homo sapiens

<400> SEQUENCE: 266
actgatgttc gccgaccgtt gactattctc tacaaaccac aaagacattg gaacactata 60
cctattattc ggcgcatgag ctggagtcct aggcacagct 100

<210> SEQ ID NO 267
<211> LENGTH: 100
<212> TYPE: DNA
<213> ORGANISM: Homo sapiens

<400> SEQUENCE: 267
actgatgttc gccgaccgtt gactattctc tacaaaccac aaagacattg gaacactata 60
cctattattc ggcgcatgag ctggagtcct aggcacagct 100

<210> SEQ ID NO 268
<211> LENGTH: 100
<212> TYPE: DNA
<213> ORGANISM: Homo sapiens

<400> SEQUENCE: 268
actaatgttc gccaaccgct gactattctc aacaaatcat aaagatatcg gaacactata 60
tttattgttt ggtgcatgag ctggagtctt gggcacagcc 100

<210> SEQ ID NO 269
<211> LENGTH: 100
<212> TYPE: DNA
<213> ORGANISM: Homo sapiens

<400> SEQUENCE: 269
ctaagcctcc ttattcgagc cgagctgggc cagccaggca accttctagg taacgaccac 60
atctacaacg ttatcgtcac agcccatgca tttgtaataa 100

<210> SEQ ID NO 270
<211> LENGTH: 100
<212> TYPE: DNA
<213> ORGANISM: Homo sapiens

<400> SEQUENCE: 270
ctaagcctcc ttattcgagc cgaactgggc cagccaggca accttctagg taacgaccac 60
atctacaacg ttatcgtcac agcccatgca tttgtaataa 100

<210> SEQ ID NO 271
<211> LENGTH: 100
<212> TYPE: DNA
<213> ORGANISM: Homo sapiens

<400> SEQUENCE: 271
ttaagcctcc ttattcagac tgaactaggt caacctggca accttctagg taacgaccac 60
atctacaacg tcatcgtcac agcccacaca ttcttcataa 100

<210> SEQ ID NO 272
<211> LENGTH: 100
<212> TYPE: DNA
<213> ORGANISM: Homo sapiens

<400> SEQUENCE: 272
tcttcttcat agtaataccc atcataatcg gaggctttgg caactgacta gttcccctaa 60
taatcggtgc ccccgatatg gcgtttcccc gcataaacaa 100

<210> SEQ ID NO 273
<211> LENGTH: 100
<212> TYPE: DNA
<213> ORGANISM: Homo sapiens

<400> SEQUENCE: 273
tcttcttcat agtaataccc atcataatcg gaggctttgg caactgacta gttcccctaa 60
taatcggtgc ccccgatatg gcgtttcccc gcataaacaa 100

<210> SEQ ID NO 274
<211> LENGTH: 100
<212> TYPE: DNA
<213> ORGANISM: Homo sapiens

<400> SEQUENCE: 274
tcttctttat ggtaatacca atcataattg gggtttcgg caactagcta gtccctctaa 60
taattggtgc acccgatatg gcattccccc ggataaatta 100

<210> SEQ ID NO 275
<211> LENGTH: 100
<212> TYPE: DNA
<213> ORGANISM: Homo sapiens

<400> SEQUENCE: 275
tattctttat ggtaatacca atcataattg gaggtttcgg caactggcta gtccctctaa 60
taattggtgc acccgatatg acatttccct ggataaataa 100

<210> SEQ ID NO 276
<211> LENGTH: 100
<212> TYPE: DNA
<213> ORGANISM: Homo sapiens

<400> SEQUENCE: 276
tctttttcat agtaatgtct atcataattg gaggttttgg caattgactg gtccccctga 60
taattggcgc ccctgacatg gcatttccct gcgtaaataa 100

<210> SEQ ID NO 277
<211> LENGTH: 100
<212> TYPE: DNA
<213> ORGANISM: Homo sapiens

<400> SEQUENCE: 277
cataagcttc tgactcttac ctccctctct cctactcctg ctcgcatctg ctatagtgga 60
ggccggagca ggaacaggtt gaacagtcta ccctccctta 100

<210> SEQ ID NO 278
<211> LENGTH: 100
<212> TYPE: DNA
<213> ORGANISM: Homo sapiens

<400> SEQUENCE: 278
cataagcttc tgactcttac ccccctctct cctactcctg cttgcatctg ctatagtgga 60
ggccggcgca ggaacaggtt gaacagtcta ccctcccttg 100

<210> SEQ ID NO 279
<211> LENGTH: 100
<212> TYPE: DNA
<213> ORGANISM: Homo sapiens

<400> SEQUENCE: 279
gcagggaact actcccaccc tggagcctcc gtagacctaa ccatcttctc cttacaccta 60
gcaggtgtct cctctatctt aggggccatc aatttcatca 100

<210> SEQ ID NO 280
<211> LENGTH: 100
<212> TYPE: DNA
<213> ORGANISM: Homo sapiens

<400> SEQUENCE: 280
gcagggaact actcccaccc tggagcctcc gtagacctaa ccatcttctc cttacaccta 60
gcaggtatct cctctatctt aggagccatc aatttcatca 100

<210> SEQ ID NO 281
<211> LENGTH: 100
<212> TYPE: DNA
<213> ORGANISM: Homo sapiens

<400> SEQUENCE: 281
gcaggaaact attcccatcc agaggcctct gtagacctaa ccattttctc ccttcatcta 60
gcaggtgtct cctctattct aggagctatt aatttcatca 100

<210> SEQ ID NO 282
<211> LENGTH: 100
<212> TYPE: DNA
<213> ORGANISM: Homo sapiens

<400> SEQUENCE: 282
caacaattat caatataaaa ccccctgcca taacccaata ccaaacgccc ctcttcgtct 60
gatccgtcct aatcacagca gtcctacttc tcctatctct 100

<210> SEQ ID NO 283
<211> LENGTH: 100
<212> TYPE: DNA
<213> ORGANISM: Homo sapiens

<400> SEQUENCE: 283
caacaattat taatataaaa ccccctgcca taacccaata ccaaacgccc cttttcgtct 60
gatccgtcct aatcacagca gtcttacttc tcctatctct 100

<210> SEQ ID NO 284
<211> LENGTH: 100
<212> TYPE: DNA
<213> ORGANISM: Homo sapiens

<400> SEQUENCE: 284
ccacaattgt taatataaaa cccccagcca tgtcccaata tcacacaccc ctcttcatct 60
gattagtcct aattacagca gttcttctac tcctttgtct 100

<210> SEQ ID NO 285
<211> LENGTH: 100
<212> TYPE: DNA
<213> ORGANISM: Homo sapiens

<400> SEQUENCE: 285
ccacaattgt taatataaaa cccccagcca tgtcccaata tcacacaccc ctcttcatct 60
gattagtcct aattacagca gttcttctac tcctttgtct 100

<210> SEQ ID NO 286
<211> LENGTH: 100
<212> TYPE: DNA
<213> ORGANISM: Homo sapiens

<400> SEQUENCE: 286
ccacaattat taacataaaa ccccctgcca tatatcaata ccaaacgccc ctctttgtct 60
gatctgtcct aatcacggca gtcctactcc tcctctccct 100

<210> SEQ ID NO 287
<211> LENGTH: 100
<212> TYPE: DNA
<213> ORGANISM: Homo sapiens

<400> SEQUENCE: 287
ccacaattgt taatataaaa cccccagcca tgtcccaata tcacacaccc ctcttcatct 60
gattagtcct aattacagca gttcttctac tcctttgtct 100

<210> SEQ ID NO 288
<211> LENGTH: 100
<212> TYPE: DNA
<213> ORGANISM: Homo sapiens

<400> SEQUENCE: 288
ccacaattgt taatataaaa cccccagcca tgtcccaata tcacacaccc ctcttcatct 60
aattagtcct aattacagca gttcttctac tcctttgtct 100

<210> SEQ ID NO 289

<211> LENGTH: 100
<212> TYPE: DNA
<213> ORGANISM: Homo sapiens

<400> SEQUENCE: 289
cccagtccta gctgctggca tcactatact actaacagac cgcaacctca acaccacctt 60
cttcgacccc gccggaggag gagaccccat tctataccaa 100

<210> SEQ ID NO 290
<211> LENGTH: 100
<212> TYPE: DNA
<213> ORGANISM: Homo sapiens

<400> SEQUENCE: 290
cccagtccta gccgctggca tcactatact actaacagac cgtaacctca acaccacctt 60
cttcgaccca gccggaggag gagaccccat tctataccaa 100

<210> SEQ ID NO 291
<211> LENGTH: 100
<212> TYPE: DNA
<213> ORGANISM: Homo sapiens

<400> SEQUENCE: 291
cacctattct gatttttcgg tcaccctgaa gtttatattc ttatcctacc aggcttcgga 60
ataatctccc atattgtaac ttactactcc ggaaaaaaag 100

<210> SEQ ID NO 292
<211> LENGTH: 100
<212> TYPE: DNA
<213> ORGANISM: Homo sapiens

<400> SEQUENCE: 292
cacctattct gatttttcgg tcaccctgaa gtttatattc tcatcctacc aggcttcgga 60
ataatctccc atattgtaac ttactactcc gggaaaaaaa 100

<210> SEQ ID NO 293
<211> LENGTH: 100
<212> TYPE: DNA
<213> ORGANISM: Homo sapiens

<400> SEQUENCE: 293
cacttattct gattctctgg tcaccccgaa gtctgtatct tcatcctacc aggcttcagg 60
ataatttccc atatcacaac atactactct ggaaaaaaag 100

<210> SEQ ID NO 294
<211> LENGTH: 100
<212> TYPE: DNA
<213> ORGANISM: Homo sapiens

<400> SEQUENCE: 294
catttattct gattctttgg tcaccctgaa gtttatatcc ttattctatc aggctttggg 60
atgatctccc atgtcgtgac gtattactct ggaaaaaagg 100

<210> SEQ ID NO 295
<211> LENGTH: 100
<212> TYPE: DNA
<213> ORGANISM: Homo sapiens

<400> SEQUENCE: 295
cacctatttt gattctttgg tcaccctgaa gtctatattc tcatcctacc aggctttgga 60
ataatttctc acatcgtacc atattattcc ggaaagaaag 100

<210> SEQ ID NO 296
<211> LENGTH: 100
<212> TYPE: DNA
<213> ORGANISM: Homo sapiens

<400> SEQUENCE: 296
catttattct gattttttgg tcaccccaaa gtctatatcc ttatcctacc aggtttcgga 60
ataatctccc atattgtaac atattattcc gggagaactc 100

<210> SEQ ID NO 297
<211> LENGTH: 100
<212> TYPE: DNA
<213> ORGANISM: Homo sapiens

<400> SEQUENCE: 297
cacctattct gattttttgg ccaccccgaa gtttatattc ttatcctgcc aggcttcgga 60
ataatttccc atattgtaac ttactactcc ggaaaaaaag 100

<210> SEQ ID NO 298
<211> LENGTH: 100
<212> TYPE: DNA
<213> ORGANISM: Homo sapiens

<400> SEQUENCE: 298
aaccatttgg atacataggt atggtctgag ctatgatatc aattggcttc ctagggttta 60
tcgtgtgagc acaccatata tttacagtag gaatagacgt 100

<210> SEQ ID NO 299
<211> LENGTH: 100
<212> TYPE: DNA
<213> ORGANISM: Homo sapiens

<400> SEQUENCE: 299
aaccatttgg atacataggt atggtctgag ctatgatatc aattggcttc ctagggttta 60
tcgtgtgagc acaccatata tttacagtag gaatagacgt 100

<210> SEQ ID NO 300
<211> LENGTH: 100
<212> TYPE: DNA
<213> ORGANISM: Homo sapiens

<400> SEQUENCE: 300
aaccatttgg gtatatgggc atagtatgag ccataatatc aattggcttc ttagggttta 60
tcgtatgggc ccaccacata tttacagtag gaatagatgt 100

<210> SEQ ID NO 301
<211> LENGTH: 100
<212> TYPE: DNA
<213> ORGANISM: Homo sapiens

<400> SEQUENCE: 301
aaccatttgg gtacatgggc atggtctggg ctataatatc agttggcttc ctgggattca 60
ttgtgtgagc tcaccatatg ttcacagtgg gaatagacat 100

<210> SEQ ID NO 302
<211> LENGTH: 100
<212> TYPE: DNA

<213> ORGANISM: Homo sapiens

<400> SEQUENCE: 302
acgggttcgg atatatggat atagtctgag ccatgatatc aattggtttc ctaggattta 60
ttgtatgggc ccaccccata tttacagtag gaatagacgt 100

<210> SEQ ID NO 303
<211> LENGTH: 100
<212> TYPE: DNA
<213> ORGANISM: Homo sapiens

<400> SEQUENCE: 303
agccatttgg gtacatgggc atagtgtgag ccataatatc aattggcttc ttagggttta 60
ttgtatgggc tcaccacata tttacagtag gaacatatgt 100

<210> SEQ ID NO 304
<211> LENGTH: 100
<212> TYPE: DNA
<213> ORGANISM: Homo sapiens

<400> SEQUENCE: 304
aaccatttgg ttatatagga atggtgtgag ccgtgatatt aattggtttt ctaggcttta 60
tcatatgggc tcatcgtata tttacaatag ggatagacat 100

<210> SEQ ID NO 305
<211> LENGTH: 100
<212> TYPE: DNA
<213> ORGANISM: Homo sapiens

<400> SEQUENCE: 305
agccatttgg gtatatgggc atagtatgag ccataatatc tattggcttc ttagggttta 60
ttgtatgagc acaccatata tttacagtag gaacagacat 100

<210> SEQ ID NO 306
<211> LENGTH: 100
<212> TYPE: DNA
<213> ORGANISM: Homo sapiens

<400> SEQUENCE: 306
aaccatttgg atatataggt atggtctgag ctatgatatc aattggcttc ctagggttta 60
ttgtgtgagc acaccatata tttacagtag gaatggacgt 100

<210> SEQ ID NO 307
<211> LENGTH: 100
<212> TYPE: DNA
<213> ORGANISM: Homo sapiens

<400> SEQUENCE: 307
aaccatttgg gtatatgggt atagtgtaag ccatagtatc agttgccttc ttggggttta 60
tcatatgggt ccaccacata tttacagtag gaatagatgt 100

<210> SEQ ID NO 308
<211> LENGTH: 100
<212> TYPE: DNA
<213> ORGANISM: Homo sapiens

<400> SEQUENCE: 308
aaccattcgg gtacataggt atggtctggg ctataatatc aattggcttc ctagggttta 60
ttgtatgagc ccatcatata ttcacagtag ggatagatgt 100

<210> SEQ ID NO 309
<211> LENGTH: 100
<212> TYPE: DNA
<213> ORGANISM: Homo sapiens

<400> SEQUENCE: 309
aaccattcgg atatataggt atggtctgag ctataatatc aattggtttc ttagggttta 60
ttgtgtgagc acaccatata tttacagtag gaatggacgt 100

<210> SEQ ID NO 310
<211> LENGTH: 100
<212> TYPE: DNA
<213> ORGANISM: Homo sapiens

<400> SEQUENCE: 310
agacacacga gcatatttca cctccgctac cataatcatc gctatcccca ccggcgtcaa 60
agtatttagc tgactcgcca cactccacgg aagcaatatg 100

<210> SEQ ID NO 311
<211> LENGTH: 100
<212> TYPE: DNA
<213> ORGANISM: Homo sapiens

<400> SEQUENCE: 311
agacacacga gcatatttca cctccgctac cataatcatc gctatcccca ccggcgtcaa 60
agtatttagc tgactcgcca cactccacgg aagcaatatg 100

<210> SEQ ID NO 312
<211> LENGTH: 100
<212> TYPE: DNA
<213> ORGANISM: Homo sapiens

<400> SEQUENCE: 312
agatacatga gcatatttca cctctgctac tataattatt gctattccta ctggtgtcaa 60
agtctttagc tggctagcta cacttcacag cagtagtatc 100

<210> SEQ ID NO 313
<211> LENGTH: 100
<212> TYPE: DNA
<213> ORGANISM: Homo sapiens

<400> SEQUENCE: 313
agatacacga gcctacttca cctccgctac tataattatc gccattccca ctggcgtcaa 60
agtatttagt tggctcgcta cgctccacgg aagtaacacc 100

<210> SEQ ID NO 314
<211> LENGTH: 100
<212> TYPE: DNA
<213> ORGANISM: Homo sapiens

<400> SEQUENCE: 314
ctcattgagc tgctgggaca cctccgctac cataatcatc gctattccca ccggcgtcaa 60
agtatttagc tgactcgcta cactccacgg aagcaatatg 100

<210> SEQ ID NO 315
<211> LENGTH: 100
<212> TYPE: DNA
<213> ORGANISM: Homo sapiens

<400> SEQUENCE: 315
agacacacga gcctatttca cctccgctac cataatcatc gctattccca ccagcgtcaa 60
agtatttagc tgactcgcta cactctacgg aagcaatatg 100

<210> SEQ ID NO 316
<211> LENGTH: 100
<212> TYPE: DNA
<213> ORGANISM: Homo sapiens

<400> SEQUENCE: 316
aaatgatctg ctgcagtgct ctgagcccta ggattcatct ttcttttcac cgtaggtggc 60
ctgactggca ttgtattagc aaactcatca ctagacatcg 100

<210> SEQ ID NO 317
<211> LENGTH: 100
<212> TYPE: DNA
<213> ORGANISM: Homo sapiens

<400> SEQUENCE: 317
aaatgatctg ctgcagtgct ctgagcccta ggatttattt ttcttttcac cgtaggtggc 60
ctgactggca ttgtattagc aaactcatca ctagacatcg 100

<210> SEQ ID NO 318
<211> LENGTH: 100
<212> TYPE: DNA
<213> ORGANISM: Homo sapiens

<400> SEQUENCE: 318
aaatgatctc ccgcaatgtt ctgagcccta ggattcatct ttcttttcac agtaggaggt 60
ctaattggca ttgtactagc taattcatca ctagatatta 100

<210> SEQ ID NO 319
<211> LENGTH: 100
<212> TYPE: DNA
<213> ORGANISM: Homo sapiens

<400> SEQUENCE: 319
aaatggtcca ccgcagtact ctgagcccta ggattcatct tcctttttac agtgggtggc 60
ctaacggaca ttgtactagc aaactcatca ttagacatcg 100

<210> SEQ ID NO 320
<211> LENGTH: 100
<212> TYPE: DNA
<213> ORGANISM: Homo sapiens

<400> SEQUENCE: 320
aaatgatctg ctgcggtgct ctgagccctg ggattcattt ttctcttcac tgtaggcggc 60
ctaactggca ttgtattagc aaactcatca ctagacatcg 100

<210> SEQ ID NO 321
<211> LENGTH: 100
<212> TYPE: DNA
<213> ORGANISM: Homo sapiens

<400> SEQUENCE: 321
aagtgatctg ctgcagtact ctgagcccta gggttcattt ttctcttcac tgtaggtggc 60
ctaaccggca ttgtactagc aaactcatca ttagacatcg 100

<210> SEQ ID NO 322
<211> LENGTH: 100
<212> TYPE: DNA
<213> ORGANISM: Homo sapiens

<400> SEQUENCE: 322
tactacacga cacgtactac gttgtagctc acttccacta tgtcctatca ataggagctg 60
tatttgccat cataggaggc ttcattcact gatttcccct 100

<210> SEQ ID NO 323
<211> LENGTH: 100
<212> TYPE: DNA
<213> ORGANISM: Homo sapiens

<400> SEQUENCE: 323
tactacacga cacgtactac gttgtagccc acttccacta tgtcctatca ataggagctg 60
tatttgccat cataggaggc ttcattcact gatttcccct 100

<210> SEQ ID NO 324
<211> LENGTH: 100
<212> TYPE: DNA
<213> ORGANISM: Homo sapiens

<400> SEQUENCE: 324
tcttacacga cacatattat gttgtaggcc atttccacta tgtcctatca ataggcgcgg 60
tatttgccat cataggaggc tttgtccact gattcccccc 100

<210> SEQ ID NO 325
<211> LENGTH: 100
<212> TYPE: DNA
<213> ORGANISM: Homo sapiens

<400> SEQUENCE: 325
ccttacatga cacatattat gttgtagccc atttccacta tgtcctatca ataggagcag 60
tactcgccat tataggaggc tttgtccact gattctcctt 100

<210> SEQ ID NO 326
<211> LENGTH: 100
<212> TYPE: DNA
<213> ORGANISM: Homo sapiens

<400> SEQUENCE: 326
ttttacatga cacatattat gttgtagccc atttccatta agtcttatca ataggagccg 60
tatttgctat tataggaggc tttgtccact gattcccct 100

<210> SEQ ID NO 327
<211> LENGTH: 100
<212> TYPE: DNA
<213> ORGANISM: Homo sapiens

<400> SEQUENCE: 327
tactacatga tacatattat gttgtggccc actttcacta cgttctatca ataggagctg 60
tgttcaccat catgggggc ttcatccact gatttccctt 100

<210> SEQ ID NO 328
<211> LENGTH: 100
<212> TYPE: DNA
<213> ORGANISM: Homo sapiens

<400> SEQUENCE: 328
tactacacga cacatactac gtcgtagccc acttccacta cgtcctatca ataggagctg 60
tattcgccat catagggggc ttcattcact gatttcccct 100

<210> SEQ ID NO 329
<211> LENGTH: 100
<212> TYPE: DNA
<213> ORGANISM: Homo sapiens

<400> SEQUENCE: 329
tactacacga cacatactac gtcgtagctc acttccatta cgtcctatca ataggagctg 60
tattcgccat cacaggaggt ttcattcact gatttcccct 100

<210> SEQ ID NO 330
<211> LENGTH: 100
<212> TYPE: DNA
<213> ORGANISM: Homo sapiens

<400> SEQUENCE: 330
attctcaggc tacaccctag accaaaccta cgccaaaatc catttcacta tcatattcat 60
cggcgtaaat ctaactttct tcccacaaca ctttctcggc 100

<210> SEQ ID NO 331
<211> LENGTH: 100
<212> TYPE: DNA
<213> ORGANISM: Homo sapiens

<400> SEQUENCE: 331
attctcaggc tacaccctag accaaaccta cgccaaaatc catttcgcta tcatattcat 60
cggcgtaaat ctaactttct tcccacaaca ctttctcggc 100

<210> SEQ ID NO 332
<211> LENGTH: 100
<212> TYPE: DNA
<213> ORGANISM: Homo sapiens

<400> SEQUENCE: 332
attctcaggc tacacactcg gccaagctta tgccaaaatt cactttgcca tcatatttgt 60
aggcgtaaat ctaaccttct tcccgcagca ctttctcggc 100

<210> SEQ ID NO 333
<211> LENGTH: 100
<212> TYPE: DNA
<213> ORGANISM: Homo sapiens

<400> SEQUENCE: 333
attctcaggc tacaccctag accaaaccta cgctaaaatc catttcgcta tcatattcat 60
cggcgtaaac ctaactttct tcccacaaca ctttcttggc 100

<210> SEQ ID NO 334
<211> LENGTH: 100
<212> TYPE: DNA
<213> ORGANISM: Homo sapiens

<400> SEQUENCE: 334
ctatccggaa tgccccgacg ttactcggac taccccgatg catacaccac atgaaacatc 60
ctatcatctg taggctcatt catttctcta acagcagtaa 100

<210> SEQ ID NO 335
<211> LENGTH: 100

<212> TYPE: DNA
<213> ORGANISM: Homo sapiens

<400> SEQUENCE: 335
ctatccggaa tgccccgacg ttactcggac tatcccgatg catacaccac atgaaatatc 60
ctatcatctg taggctcatt catttctcta acagcagtaa 100

<210> SEQ ID NO 336
<211> LENGTH: 100
<212> TYPE: DNA
<213> ORGANISM: Homo sapiens

<400> SEQUENCE: 336
ttatctggaa taccccgatg ttattctgac taccccgacg catataccac gtgaaatatt 60
ttatcatctg taggctcatt catctcctta acagcagtaa 100

<210> SEQ ID NO 337
<211> LENGTH: 100
<212> TYPE: DNA
<213> ORGANISM: Homo sapiens

<400> SEQUENCE: 337
ctatccggta tgcctcgatg ttactccaat tatcccgatg tatacaccac atgaaatatt 60
atttcatcca gaggctcatt tatttcccta acagcagtaa 100

<210> SEQ ID NO 338
<211> LENGTH: 100
<212> TYPE: DNA
<213> ORGANISM: Homo sapiens

<400> SEQUENCE: 338
ctatccagta tgccttgacg ttactccgat tatcctgatg catacaccac atgaaatatt 60
atctcatctg taggctcatt tatctcacta acagcagtta 100

<210> SEQ ID NO 339
<211> LENGTH: 100
<212> TYPE: DNA
<213> ORGANISM: Homo sapiens

<400> SEQUENCE: 339
ctatctgaga tgtcccgatg ttattccgac taccccgatg catataccac aggaaatatt 60
ttatcatctg taggctcatt catctcccta aaagcagtag 100

<210> SEQ ID NO 340
<211> LENGTH: 100
<212> TYPE: DNA
<213> ORGANISM: Homo sapiens

<400> SEQUENCE: 340
ctatctggaa taccccgacg ttactcggac taccccgatg catacaccac atgaaatatc 60
ctatcatctg taggctcatt catttcccta acagcagtaa 100

<210> SEQ ID NO 341
<211> LENGTH: 100
<212> TYPE: DNA
<213> ORGANISM: Homo sapiens

<400> SEQUENCE: 341
ctatctggaa taccccgacg ttactcggac taccccgatg catacaccac atgaaatatc 60
ctatcatctg taggctcatt catttcccta acagcagtaa 100

<210> SEQ ID NO 342
<211> LENGTH: 100
<212> TYPE: DNA
<213> ORGANISM: Homo sapiens

<400> SEQUENCE: 342
tattaataat tttcatgatt tgagaagcct tcgcttcgaa gcgaaaagtc ctaatagtag 60
aagaaccctc cataaacctg gagtgactat atggatgccc 100

<210> SEQ ID NO 343
<211> LENGTH: 100
<212> TYPE: DNA
<213> ORGANISM: Homo sapiens

<400> SEQUENCE: 343
tattaataat tttcataatt tgagaagcct tcgcttcgaa gcgaaaagtc ctaatagtag 60
aagaaccctc cataaacctg gagtgactat atggatgccc 100

<210> SEQ ID NO 344
<211> LENGTH: 100
<212> TYPE: DNA
<213> ORGANISM: Homo sapiens

<400> SEQUENCE: 344
tgctaataat tttcataacc tgagagacct tcgcttcaaa gcgaaaagtc ctaataaatg 60
agcaaccttc cactaaccta gagtggctgt agggatgccc 100

<210> SEQ ID NO 345
<211> LENGTH: 100
<212> TYPE: DNA
<213> ORGANISM: Homo sapiens

<400> SEQUENCE: 345
tattaataat tttcatgatt tgagaagcct tcgcttcaaa gcgaaaagtc ctaataatag 60
aagaaccctc cataaacctg gagtgactat atggatgcgc 100

<210> SEQ ID NO 346
<211> LENGTH: 100
<212> TYPE: DNA
<213> ORGANISM: Homo sapiens

<400> SEQUENCE: 346
cccaccctac cacacattcg aagaacccgt atacataaaa tctagacaaa aaaggaagga 60
atcgaacccc ccaaagctgg tttcaagcca accccatggc 100

<210> SEQ ID NO 347
<211> LENGTH: 100
<212> TYPE: DNA
<213> ORGANISM: Homo sapiens

<400> SEQUENCE: 347
cccaccctac cacacattcg aagaacccgt atacataaaa tctagacaaa aaaggaagga 60
atcgaacccc ccaaagctgg tttcaagcca accccatggc 100

<210> SEQ ID NO 348
<211> LENGTH: 100
<212> TYPE: DNA
<213> ORGANISM: Homo sapiens

<400> SEQUENCE: 348
tccaccctac catacgtttg aagaaccagt ctacataaaa cctagacgaa aaaggaagga 60
atccaacccc ctaaaactgg tttcaagcca acctcataac 100

<210> SEQ ID NO 349
<211> LENGTH: 100
<212> TYPE: DNA
<213> ORGANISM: Homo sapiens

<400> SEQUENCE: 349
tccaccctac catacattta aagaaccagt ctacataaaa cctagacaaa aaaggaagga 60
attgaacctc ctaaggctgg tttcaagcca gcctcataac 100

<210> SEQ ID NO 350
<211> LENGTH: 100
<212> TYPE: DNA
<213> ORGANISM: Homo sapiens

<400> SEQUENCE: 350
ctccatgact ttttcaaaaa ggtattagaa aaaccatttc ataactttgt caaagttaaa 60
ttataggcta aatcctatat atcttaatgg cacatgcagc 100

<210> SEQ ID NO 351
<211> LENGTH: 100
<212> TYPE: DNA
<213> ORGANISM: Homo sapiens

<400> SEQUENCE: 351
ctccatgact ttttcaaaaa gatattagaa aaaccatttc ataactttgt caaagttaaa 60
ttataggcta aatcctatat atcttaatgg cacatgcagc 100

<210> SEQ ID NO 352
<211> LENGTH: 100
<212> TYPE: DNA
<213> ORGANISM: Homo sapiens

<400> SEQUENCE: 352
ctctgtgacc ttctcaataa gatattagtg aaattatttc ataactttgt caaagttaag 60
ttataggtta agccgtatat atcttaatgg cccatacagt 100

<210> SEQ ID NO 353
<211> LENGTH: 100
<212> TYPE: DNA
<213> ORGANISM: Homo sapiens

<400> SEQUENCE: 353
ctctatgact ttttcaacaa gatattagaa aaattatttc ataactttgt caaagttaag 60
ttacaggtta agtcccatat atcttaatgg cacacgcagc 100

<210> SEQ ID NO 354
<211> LENGTH: 100
<212> TYPE: DNA
<213> ORGANISM: Homo sapiens

<400> SEQUENCE: 354
ctctacaagt ttctcgataa gatattagta aaattatttc ataactttgt caaagttaag 60
ttataggtta agccctatat atcttaatgg cccatccagt 100

<210> SEQ ID NO 355
<211> LENGTH: 100
<212> TYPE: DNA
<213> ORGANISM: Homo sapiens

<400> SEQUENCE: 355
ctctgtgact ttctcgataa gatattagca aattcattac gtaactttgt caaagttaag 60
ttataggcta aatcctatat gtcttaatgg ctcatccagt 100

<210> SEQ ID NO 356
<211> LENGTH: 100
<212> TYPE: DNA
<213> ORGANISM: Homo sapiens

<400> SEQUENCE: 356
ctctatgact ctctcgataa gatattagta aaattattat ataactttgt caaagttaat 60
ttataggtta aatcctgtat gtcttaatgg ctcatccagt 100

<210> SEQ ID NO 357
<211> LENGTH: 100
<212> TYPE: DNA
<213> ORGANISM: Homo sapiens

<400> SEQUENCE: 357
ctctatgact ttttcgataa gatattagta aaattatttc ctaactttgc caaagttaag 60
ttataagtta aaccctgtat atcttaatgg cccatccagc 100

<210> SEQ ID NO 358
<211> LENGTH: 100
<212> TYPE: DNA
<213> ORGANISM: Homo sapiens

<400> SEQUENCE: 358
ccctatgact ttttcaacaa gatattagga aaactatttc ataacttcgt caaagttaag 60
ttacaggtta aaccccgtat atcttaatgg cacacgcagc 100

<210> SEQ ID NO 359
<211> LENGTH: 100
<212> TYPE: DNA
<213> ORGANISM: Homo sapiens

<400> SEQUENCE: 359
gcaagtaggt ctacaagacg ctacttcccc tatcatagaa gagcttatca cctttcatga 60
tcacgccctc ataatcattt tccttatctg cttcctagtc 100

<210> SEQ ID NO 360
<211> LENGTH: 100
<212> TYPE: DNA
<213> ORGANISM: Homo sapiens

<400> SEQUENCE: 360
gcaagtaggt ctacaagacg ctacttcccc tatcatagaa gagcttatca tctttcatga 60
tcacgccctc ataatcattt tccttatctg cttcctagtc 100

<210> SEQ ID NO 361
<211> LENGTH: 100
<212> TYPE: DNA
<213> ORGANISM: Homo sapiens

<400> SEQUENCE: 361
ccaactaggc cttcaagatg ccacatcccc tataacagaa gagctaatcg ccttccatga 60
tcacgccatt ataatcatct tcctattcag cttcctagtt 100

<210> SEQ ID NO 362
<211> LENGTH: 100
<212> TYPE: DNA
<213> ORGANISM: Homo sapiens

<400> SEQUENCE: 362
ccagctaggt cttcaagacg ccacatcccc tatcatagaa gagctaatcg ccttccatga 60
tcacgccctc ataatcatct ttcttatcag ctttctagtt 100

<210> SEQ ID NO 363
<211> LENGTH: 100
<212> TYPE: DNA
<213> ORGANISM: Homo sapiens

<400> SEQUENCE: 363
ctgtatgccc ttttcctaac actcacaaca aaactaacta atactaacat ctcagacgct 60
caggaaatag aaaccgtctg aactatcctg cccgccatca 100

<210> SEQ ID NO 364
<211> LENGTH: 100
<212> TYPE: DNA
<213> ORGANISM: Homo sapiens

<400> SEQUENCE: 364
ctgtacgccc ttttcctaac actcacaaca aaactaacta atactaacat ctcagacgct 60
caggaaatag aaaccgtctg aactatcctg cccgccatca 100

<210> SEQ ID NO 365
<211> LENGTH: 100
<212> TYPE: DNA
<213> ORGANISM: Homo sapiens

<400> SEQUENCE: 365
tcctagtcct catcgccctc ccatccctac gcatccttta cataacagac gaggtcaacg 60
atccctccct taccatcaaa tcaattggcc accaatggta 100

<210> SEQ ID NO 366
<211> LENGTH: 100
<212> TYPE: DNA
<213> ORGANISM: Homo sapiens

<400> SEQUENCE: 366
tcctagtcct tatcgccctc ccatccctac gcatccttta cataacagac gaggtcaacg 60
atccctcctt taccatcaaa tcaattggcc atcaatggta 100

<210> SEQ ID NO 367
<211> LENGTH: 100
<212> TYPE: DNA
<213> ORGANISM: Homo sapiens

<400> SEQUENCE: 367
tcctagtcct aattgccctt ccatccctac gtatcctgta cgtaacagat gaaatcaatg 60
acccttcttt taccattaaa tcaatcggac accaatgata 100

<210> SEQ ID NO 368

<211> LENGTH: 100
<212> TYPE: DNA
<213> ORGANISM: Homo sapiens

<400> SEQUENCE: 368
ctgaacctac gagtacaccg actacggcgg actaatcttc aactcctaca tacttccccc 60
attattccta gaaccaggcg acctgcgact ccttgacgtt 100

<210> SEQ ID NO 369
<211> LENGTH: 100
<212> TYPE: DNA
<213> ORGANISM: Homo sapiens

<400> SEQUENCE: 369
ctgaacctac gaatacaccg actacggcgg actaatcttc aactcctaca tacttccccc 60
attattccta gaaccaggcg acctgcgact ccttgacgtt 100

<210> SEQ ID NO 370
<211> LENGTH: 100
<212> TYPE: DNA
<213> ORGANISM: Homo sapiens

<400> SEQUENCE: 370
ctgaacctat gaatacacca attatggagg attaattttc aactcttata tacttccacc 60
actattctta gacccaagtg accttcgact tcttaaagtt 100

<210> SEQ ID NO 371
<211> LENGTH: 100
<212> TYPE: DNA
<213> ORGANISM: Homo sapiens

<400> SEQUENCE: 371
gacaatcgag tagtactccc gattgaagcc cccattcgta taataattac atcacaagac 60
gtcttgcact catgagctgt ccccacatta ggcttaaaaa 100

<210> SEQ ID NO 372
<211> LENGTH: 100
<212> TYPE: DNA
<213> ORGANISM: Homo sapiens

<400> SEQUENCE: 372
gacaatcgag tagtactccc ggttgaagcc cccattcgta taataattac atcacaagac 60
gtcttacact catgagctgt ccccacatta ggcttaaaaa 100

<210> SEQ ID NO 373
<211> LENGTH: 100
<212> TYPE: DNA
<213> ORGANISM: Homo sapiens

<400> SEQUENCE: 373
gataatcgag tagtccttcc aattgaagcc cctgttcata taataattac atcacaagac 60
gtcctacact catgaactgt ccccacatta ggcttaaaaa 100

<210> SEQ ID NO 374
<211> LENGTH: 100
<212> TYPE: DNA
<213> ORGANISM: Homo sapiens

<400> SEQUENCE: 374
cagatgcaat tcccggacgt ctaaaccaaa ccactttcac cgctacacga ccgggggtat 60
actacggtca atgctctgaa atctgtggag caaaccacag 100

<210> SEQ ID NO 375
<211> LENGTH: 100
<212> TYPE: DNA
<213> ORGANISM: Homo sapiens

<400> SEQUENCE: 375
cagatgcaat tcccggacgt ctaaaccaaa ccactttcac tgctacacga ccaggggtat 60
actacggcca atgctctgaa atctgtggag caaaccagtt 100

<210> SEQ ID NO 376
<211> LENGTH: 100
<212> TYPE: DNA
<213> ORGANISM: Homo sapiens

<400> SEQUENCE: 376
cagatgcaat ccccggacgc ctaaaccaaa ccacattcac cgccacacga ccaggagtat 60
actacggtca atggtcagaa atctgcagag ctagccacag 100

<210> SEQ ID NO 377
<211> LENGTH: 100
<212> TYPE: DNA
<213> ORGANISM: Homo sapiens

<400> SEQUENCE: 377
cagatgtaat ccccggacgc ctaaaccaaa ccacattcac cgccatacga ccaggagtat 60
actacggtca atgctcagaa atctgcggag ctgaccatag 100

<210> SEQ ID NO 378
<211> LENGTH: 100
<212> TYPE: DNA
<213> ORGANISM: Homo sapiens

<400> SEQUENCE: 378
tttcatgccc atcgtcctag aattaattcc cctaaaaatc tttgaaatag ggcccgtatt 60
taccctatag caccccctct accccctcta gagcccactg 100

<210> SEQ ID NO 379
<211> LENGTH: 100
<212> TYPE: DNA
<213> ORGANISM: Homo sapiens

<400> SEQUENCE: 379
ttttatgccc atcgtcctag aattaattcc cctaaaaatc tttgaaatag ggcccgtatt 60
taccctatag caccccctct accccctcta gagcccactg 100

<210> SEQ ID NO 380
<211> LENGTH: 100
<212> TYPE: DNA
<213> ORGANISM: Homo sapiens

<400> SEQUENCE: 380
taaagctaac ttagcattaa ccttttaagt taaagattaa gagaaccaac acctctttac 60
agtgaaatgc cccaactaaa tactaccgta tggcccacca 100

<210> SEQ ID NO 381
<211> LENGTH: 100
<212> TYPE: DNA

<213> ORGANISM: Homo sapiens

<400> SEQUENCE: 381
taaagctaac ttagcattaa ccttttaagt taaagattaa gagaaccaac acctctttac 60
agtgaaatgc cccaactaaa tactaccgta tgacccacca 100

<210> SEQ ID NO 382
<211> LENGTH: 100
<212> TYPE: DNA
<213> ORGANISM: Homo sapiens

<400> SEQUENCE: 382
ccgccgccgc cgcacattaa ccttttaagt taaagattaa gagaaccaac acctctttac 60
agtgaaatgc cccaactaaa tactaccgta tggcccacca 100

<210> SEQ ID NO 383
<211> LENGTH: 100
<212> TYPE: DNA
<213> ORGANISM: Homo sapiens

<400> SEQUENCE: 383
tagagctgac ccagcattaa ccttttaagt taaagactaa gagaatcgct atctctttac 60
agtgacatgc ctcaactaga caccaccata tgacccacta 100

<210> SEQ ID NO 384
<211> LENGTH: 100
<212> TYPE: DNA
<213> ORGANISM: Homo sapiens

<400> SEQUENCE: 384
taattacccc catactcctt acactattcc tcatcaccca actaaaaata ttaaacacaa 60
actaccacct acctccctca ccaaagccca taaaaataaa 100

<210> SEQ ID NO 385
<211> LENGTH: 100
<212> TYPE: DNA
<213> ORGANISM: Homo sapiens

<400> SEQUENCE: 385
taattacccc catactcctt acactattcc tcatcaccca actaaaaata ttaaatacaa 60
attaccacct acctccctca ccaaagccca taaaaataaa 100

<210> SEQ ID NO 386
<211> LENGTH: 100
<212> TYPE: DNA
<213> ORGANISM: Homo sapiens

<400> SEQUENCE: 386
taattgcccc catacttctt acactattcc tcatcactca gctaaaaata ttaaatacaa 60
attaccatct acccccctca ccaaagccca taaaaataaa 100

<210> SEQ ID NO 387
<211> LENGTH: 100
<212> TYPE: DNA
<213> ORGANISM: Homo sapiens

<400> SEQUENCE: 387
aaattataac aaaccctgag aaccaaaatg aacgaaaatc tgttcgcttc attcattgcc 60
cccacaatcc taggcctacc cgccgcagta ctgatcattc 100

<210> SEQ ID NO 388
<211> LENGTH: 100
<212> TYPE: DNA
<213> ORGANISM: Homo sapiens

<400> SEQUENCE: 388
aaactataac aaaccctgag aaccaaaatg aacgaaaatc tgttcacttc attcattgcc 60
cccacaatcc taggcctacc cgccgcagta ctgatcattc 100

<210> SEQ ID NO 389
<211> LENGTH: 100
<212> TYPE: DNA
<213> ORGANISM: Homo sapiens

<400> SEQUENCE: 389
aaactatagt aaaccctgag aaccaaagtg aacgaaaatc tgttcgcttc attcattgcc 60
cccacaatcc taggtctgcc cgccgcagta ctgatcattc 100

<210> SEQ ID NO 390
<211> LENGTH: 100
<212> TYPE: DNA
<213> ORGANISM: Homo sapiens

<400> SEQUENCE: 390
aaaacataac aacccttgag aactaaaatg aacaaaaatc tgttcacctc atttatcgcc 60
ccaacaatcc tagggttacc cacagcagca ctaatcatct 100

<210> SEQ ID NO 391
<211> LENGTH: 100
<212> TYPE: DNA
<213> ORGANISM: Homo sapiens

<400> SEQUENCE: 391
aaatcacaat aaaccctgag agccaaaatg aacgaaaatt tattcacttc attcattacc 60
cccacaattc taggcctacc tgctgcagta ccaatcatcc 100

<210> SEQ ID NO 392
<211> LENGTH: 100
<212> TYPE: DNA
<213> ORGANISM: Homo sapiens

<400> SEQUENCE: 392
aaaacataac aacccttgac aactaaaatg aacgaaaatc tgctcacctc atttactgcc 60
ccgacaatcc tcggtttacc cgcagcagca ctaatcatct 100

<210> SEQ ID NO 393
<211> LENGTH: 100
<212> TYPE: DNA
<213> ORGANISM: Homo sapiens

<400> SEQUENCE: 393
aaaccacaat aatcctttag agtcaaaatg aacgaaaatc tgtttacttc attcattgcc 60
cccacaattc taggccttcc agctgcagtg ccaatcgttc 100

<210> SEQ ID NO 394
<211> LENGTH: 100
<212> TYPE: DNA
<213> ORGANISM: Homo sapiens

<400> SEQUENCE: 394
tatttccccc tctattgatc cccacctcca aatatctcat caacaaccga ctaatcacca 60
cccaacaatg actaatcaaa ctaacctcaa aacaaatgat 100

<210> SEQ ID NO 395
<211> LENGTH: 100
<212> TYPE: DNA
<213> ORGANISM: Homo sapiens

<400> SEQUENCE: 395
tatttccccc tctattgatc cccacctcca aatatctcat caacaaccga ctaattacca 60
cccaacaatg actaatccaa ctaacctcaa aacaaatgat 100

<210> SEQ ID NO 396
<211> LENGTH: 100
<212> TYPE: DNA
<213> ORGANISM: Homo sapiens

<400> SEQUENCE: 396
tatttccccc tctattgatc cccacctcca aatacctcat caacaaccga ctaattacca 60
cccaacaatg actaatccaa ctaacctcaa aacaaatgat 100

<210> SEQ ID NO 397
<211> LENGTH: 100
<212> TYPE: DNA
<213> ORGANISM: Homo sapiens

<400> SEQUENCE: 397
tatttccccc cttactggtt ccaatttcca aatacctcat caacaactga ctaatcacta 60
cccaacaatg actaatccaa ctcatcttaa aacaaataat 100

<210> SEQ ID NO 398
<211> LENGTH: 100
<212> TYPE: DNA
<213> ORGANISM: Homo sapiens

<400> SEQUENCE: 398
agccatacac aacactaaag gacgaacctg atctcttata ctagtatcct taatcatttt 60
tattgccaca actaacctcc tcggactcct gcctcactca 100

<210> SEQ ID NO 399
<211> LENGTH: 100
<212> TYPE: DNA
<213> ORGANISM: Homo sapiens

<400> SEQUENCE: 399
agccatacac aacactaagg gacgaacctg atctcttata ctagtatcct taatcatttt 60
tattgccaca actaacctcc tcggactcct gcctcactca 100

<210> SEQ ID NO 400
<211> LENGTH: 100
<212> TYPE: DNA
<213> ORGANISM: Homo sapiens

<400> SEQUENCE: 400
agccatacac aacactaaag ggcgaacctg atctcttata ctagtatcct taatcatttt 60
tattgccaca actaatcttc tcgggctcct acgccgaggc 100

<210> SEQ ID NO 401
<211> LENGTH: 100
<212> TYPE: DNA
<213> ORGANISM: Homo sapiens

<400> SEQUENCE: 401
aatgatacat aacattaagg gacgaacctg gtcccttata ctaatctccc taattatttt 60
tattgccaca gctaatctcc ttggactctt accccactca 100

<210> SEQ ID NO 402
<211> LENGTH: 100
<212> TYPE: DNA
<213> ORGANISM: Homo sapiens

<400> SEQUENCE: 402
aacaataaat aacattaaag gacgaacctg atccctcatg ctaatatccc taattatctt 60
cattgctaca accaatctcc tcgggctctt gccccactca 100

<210> SEQ ID NO 403
<211> LENGTH: 100
<212> TYPE: DNA
<213> ORGANISM: Homo sapiens

<400> SEQUENCE: 403
tttacaccaa ccacccaact atctataaac ctagccatgg ccatcccctt atgagcgggc 60
gcagtgatta taggctttcg ctctaagatt aaaaatgccc 100

<210> SEQ ID NO 404
<211> LENGTH: 100
<212> TYPE: DNA
<213> ORGANISM: Homo sapiens

<400> SEQUENCE: 404
tttacaccaa ccacccaact atctataaac ctagccatgg ccatcccctt atgagcgggc 60
gcagtgatta taggctttcg ctctaagatt aaaaatgccc 100

<210> SEQ ID NO 405
<211> LENGTH: 100
<212> TYPE: DNA
<213> ORGANISM: Homo sapiens

<400> SEQUENCE: 405
tttacaccaa ctacccaacc atcaataaat ctagctacag caatcccctt atgagcaggc 60
acagtaatca caggcttccg ctttaaaact aaaaactcct 100

<210> SEQ ID NO 406
<211> LENGTH: 100
<212> TYPE: DNA
<213> ORGANISM: Homo sapiens

<400> SEQUENCE: 406
tagcccactt cttaccacaa ggcacaccta cacccottat ccccatacta gttattatcg 60
aaaccatcag cctactcatt caaccaatag ccctggccgt 100

<210> SEQ ID NO 407
<211> LENGTH: 100
<212> TYPE: DNA
<213> ORGANISM: Homo sapiens

<400> SEQUENCE: 407
tagcccactt cttaccacaa ggcacaccta caccccttat ccctatacta gttattatcg 60
aaaccatcag cctactcatt caaccaatag ccctggccgt 100

<210> SEQ ID NO 408
<211> LENGTH: 100
<212> TYPE: DNA
<213> ORGANISM: Homo sapiens

<400> SEQUENCE: 408
tagctcactt tttaccacaa ggcacaccta taccacttat ccctatgcta gtgatcattg 60
aaactattag cctattcatt taaccaatgg caccagctgt 100

<210> SEQ ID NO 409
<211> LENGTH: 100
<212> TYPE: DNA
<213> ORGANISM: Homo sapiens

<400> SEQUENCE: 409
tagctcactt cctaccacaa ggcacaccca tactacttac ccctatacta gtaatcatca 60
aaaccactag tctacttatt caaccaatgg cactagctgt 100

<210> SEQ ID NO 410
<211> LENGTH: 100
<212> TYPE: DNA
<213> ORGANISM: Homo sapiens

<400> SEQUENCE: 410
tggctggctt tttaccacaa ggcacaccta tgccacttat ccctatacta gtaatcattg 60
aaaccattag cctatttatt caaccaatag cattagctgt 100

<210> SEQ ID NO 411
<211> LENGTH: 100
<212> TYPE: DNA
<213> ORGANISM: Homo sapiens

<400> SEQUENCE: 411
tagcccatct cttgccacaa ggcacaccct cacccctcat tcccatacta attattatcc 60
aaaccatcag cctatttatc caaccaatag ccctagccat 100

<210> SEQ ID NO 412
<211> LENGTH: 100
<212> TYPE: DNA
<213> ORGANISM: Homo sapiens

<400> SEQUENCE: 412
acgcctaacc gctaacatta ctgcaggcca cctactcatg cacctaattg gaagcgccac 60
cctagcaata tcaaccatta accttccctc tacacttatc 100

<210> SEQ ID NO 413
<211> LENGTH: 100
<212> TYPE: DNA
<213> ORGANISM: Homo sapiens

<400> SEQUENCE: 413
acgcctaacc gctaacatta ctgcaggcca cctactcatg cacctaattg gaagcgccac 60
actagcaata tcaactatta accttccctc tacacttatc 100

<210> SEQ ID NO 414
<211> LENGTH: 100

<212> TYPE: DNA
<213> ORGANISM: Homo sapiens

<400> SEQUENCE: 414
atcttcacaa ttctaattct actgactatc ctagaaatcg ctgtcgcctt aatccaagcc 60
tacgttttca cacttctagt aagcctctac ctgcacgaca 100

<210> SEQ ID NO 415
<211> LENGTH: 100
<212> TYPE: DNA
<213> ORGANISM: Homo sapiens

<400> SEQUENCE: 415
atcttcacaa ttctaattct actgactatc ctagaaatcg ctgtcgcctt aatccaagcc 60 tacgtttta cacttctagt aagcctctac ctgcacgaca 100

<210> SEQ ID NO 416
<211> LENGTH: 100
<212> TYPE: DNA
<213> ORGANISM: Homo sapiens

<400> SEQUENCE: 416
atcttcacaa ttttgatttt actgacgatt ctcgaaatcg ctgtcgccct gattctagcc 60
tatgttttca cactcctagt gagcctctac ctacatgaca 100

<210> SEQ ID NO 417
<211> LENGTH: 100
<212> TYPE: DNA
<213> ORGANISM: Homo sapiens

<400> SEQUENCE: 417
acacataatg acccaccaat cacatgccta tcatatagta aaacccagcc catgacccct 60
aacaggggcc ctctcagccc tcctaatgac ctccggccta 100

<210> SEQ ID NO 418
<211> LENGTH: 100
<212> TYPE: DNA
<213> ORGANISM: Homo sapiens

<400> SEQUENCE: 418
acacataatg acccaccaat cacatgccta tcatatagta aaacccagcc catggcccct 60
aacaggggcc ctctcagccc tcctaatgac ctccggccta 100

<210> SEQ ID NO 419
<211> LENGTH: 100
<212> TYPE: DNA
<213> ORGANISM: Homo sapiens

<400> SEQUENCE: 419
acacataatg acccaccaaa cacatgccta ccgtatagtc aaacccagcc cctgacgact 60
gacaggagct ctctcagctc tcctaataac atctggcctg 100

<210> SEQ ID NO 420
<211> LENGTH: 100
<212> TYPE: DNA
<213> ORGANISM: Homo sapiens

<400> SEQUENCE: 420
atacataatg acccaccaaa cacacaccta tcatttagtc aaacccagcc cttgaccatt 60
aacaggggct ctctcagctc tcctaataac atccgcccta 100

<210> SEQ ID NO 421
<211> LENGTH: 100
<212> TYPE: DNA
<213> ORGANISM: Homo sapiens

<400> SEQUENCE: 421
acacataatg acccactata cacatgccta ccatatagtc aaacccagcc cctgaccact 60
aacaggagct ctctcatctc tcctaataac atctggcctg 100

<210> SEQ ID NO 422
<211> LENGTH: 100
<212> TYPE: DNA
<213> ORGANISM: Homo sapiens

<400> SEQUENCE: 422
atacataatg acccaccaaa cacacgccta ccacatagtt aagcccagcc cttggccatt 60
aacaggagct ctctcagccc tcctaataac atctggccta 100

<210> SEQ ID NO 423
<211> LENGTH: 100
<212> TYPE: DNA
<213> ORGANISM: Homo sapiens

<400> SEQUENCE: 423
acacataatg acccaccaaa cacatgcttg ccatatagtc aaacccagcc cctgaccact 60
aacagaagct ctctcagctc tactaataac atctggcctg 100

<210> SEQ ID NO 424
<211> LENGTH: 100
<212> TYPE: DNA
<213> ORGANISM: Homo sapiens

<400> SEQUENCE: 424
atacataatg acccaccaga cacatgccta ccatagagtt gtacctagcc cttgaccact 60
aacaggagct ctctcggctc tcctaataac atctggccta 100

<210> SEQ ID NO 425
<211> LENGTH: 100
<212> TYPE: DNA
<213> ORGANISM: Homo sapiens

<400> SEQUENCE: 425
atacataatg gctcaccaat cacatgccta tcacatagta aaacccagcc catgacctct 60
aacaggggcc ctttcagccc tcctaatgac atccggccta 100

<210> SEQ ID NO 426
<211> LENGTH: 100
<212> TYPE: DNA
<213> ORGANISM: Homo sapiens

<400> SEQUENCE: 426
gccatgtgat ttcacttcca ctccataacg ctcctcatac taggcctact aaccaacaca 60
ctaaccatat accaatggtg gcgcgatgta acacgagaaa 100

<210> SEQ ID NO 427
<211> LENGTH: 100
<212> TYPE: DNA
<213> ORGANISM: Homo sapiens

<400> SEQUENCE: 427
gccatgtgat ttcacttcca ctccacaacc ctcctcatac taggcctact aaccaacaca 60
ctaaccatat accaatgatg gcgcgatgta acacgagaaa 100

<210> SEQ ID NO 428
<211> LENGTH: 100
<212> TYPE: DNA
<213> ORGANISM: Homo sapiens

<400> SEQUENCE: 428
gcacatacca aggccaccac acaccacctg tccaaaaagg ccttcgatac gggataatcc 60
tatttattac ctcagaagtt tttttcttcg caggattttt 100

<210> SEQ ID NO 429
<211> LENGTH: 100
<212> TYPE: DNA
<213> ORGANISM: Homo sapiens

<400> SEQUENCE: 429
gcacatacca aggccaccac acaccacctg tccagaaagg ccttcgatac gggataatcc 60
tatttattac ctcagaagtt tttttcttcg caggattttt 100

<210> SEQ ID NO 430
<211> LENGTH: 100
<212> TYPE: DNA
<213> ORGANISM: Homo sapiens

<400> SEQUENCE: 430
gtacatttca aggccaccat acaacagttg tccaaaaagg cctccaatag ggaataattc 60
tatttattat ctcagaaata ttcttctttg ctggtttctt 100

<210> SEQ ID NO 431
<211> LENGTH: 100
<212> TYPE: DNA
<213> ORGANISM: Homo sapiens

<400> SEQUENCE: 431
gcacattcca aggccaccat acatcaatcg tccaaaaagg ccttcgatac agaataatct 60
tattcgttat ttcagaggtg tttttttccg ctggcttctt 100

<210> SEQ ID NO 432
<211> LENGTH: 100
<212> TYPE: DNA
<213> ORGANISM: Homo sapiens

<400> SEQUENCE: 432
gtacatttca aggccaccat acaacaattg tccaaaaagg catctgatat ggaatagtac 60
tatttattat ctcagaagta tttttctttg ctggattttt 100

<210> SEQ ID NO 433
<211> LENGTH: 100
<212> TYPE: DNA
<213> ORGANISM: Homo sapiens

<400> SEQUENCE: 433
gtacatttca agaccaccac acaacaacca tccaaaaagg cctctgatat ggaataatcc 60
tattcattat ttcagaagta tttttcttcg ccggattctt 100

<210> SEQ ID NO 434
<211> LENGTH: 100
<212> TYPE: DNA
<213> ORGANISM: Homo sapiens

<400> SEQUENCE: 434
gtacatacca agaccaccac acagtacccg tccaaaaagt ccttcggtat ggaataattt 60
tattcatcat ctcagaagtc tttttcttcg ctggattctt 100

<210> SEQ ID NO 435
<211> LENGTH: 100
<212> TYPE: DNA
<213> ORGANISM: Homo sapiens

<400> SEQUENCE: 435
gtacatacca aggccaccgc acaatacctg tccaaaaagg cctccaatac ggaataatgt 60
tcttcattat ttcagaagtc tttttcttcg ctggattctt 100

<210> SEQ ID NO 436
<211> LENGTH: 100
<212> TYPE: DNA
<213> ORGANISM: Homo sapiens

<400> SEQUENCE: 436
ctgagccttt taccactcca gcctagcccc taccccccaa ctaggagggc actggccccc 60
aacaggcatc accccgctaa atcccctaga agtcccactc 100

<210> SEQ ID NO 437
<211> LENGTH: 100
<212> TYPE: DNA
<213> ORGANISM: Homo sapiens

<400> SEQUENCE: 437
ctgagccttt taccactcca gcctagctcc caccccccaa ctaggggac actggccccc 60 aacaggcatc accccgctaa atcccctaga agtcccactc 100

<210> SEQ ID NO 438
<211> LENGTH: 100
<212> TYPE: DNA
<213> ORGANISM: Homo sapiens

<400> SEQUENCE: 438
ctgagcattc taccactcca gcctagcccc cacccctcaa ctaggaggac actgaccccc 60
aacaggcatc actccactca accccctaga agtcccactc 100

<210> SEQ ID NO 439
<211> LENGTH: 100
<212> TYPE: DNA
<213> ORGANISM: Homo sapiens

<400> SEQUENCE: 439
ctaaacacat ccgtattact cgcatcagga gtatcaatca cctgagctca ccatagtcta 60
atagaaaaca accgaaacca aataattcaa gcactgctta 100

<210> SEQ ID NO 440
<211> LENGTH: 100
<212> TYPE: DNA
<213> ORGANISM: Homo sapiens

<400> SEQUENCE: 440
ctaaacacat ccgtattact cgcatcaggg gtatcaatca cctgagctca ccatagtcta 60
atagaaaaca accgaaacca aataattcaa gcactgctta 100

<210> SEQ ID NO 441
<211> LENGTH: 100
<212> TYPE: DNA
<213> ORGANISM: Homo sapiens

<400> SEQUENCE: 441
ctgaacacat ctgtattact tgcatcaggg gtttcaatta cttgagccca tcacagcata 60
atagaaaata atcgaaaaca agtaattcaa gcactacttt 100

<210> SEQ ID NO 442
<211> LENGTH: 100
<212> TYPE: DNA
<213> ORGANISM: Homo sapiens

<400> SEQUENCE: 442
ccgaatacat ctgtattact tgcatcaggg gtttcaatta cctgagccca tcacagccta 60
atagaaaata atcgaaaaca aataattcaa gcactactta 100

<210> SEQ ID NO 443
<211> LENGTH: 100
<212> TYPE: DNA
<213> ORGANISM: Homo sapiens

<400> SEQUENCE: 443
ccgaatacat ctgtattact tgcatcaggg gtttcaatta cctgagccca tcacagccta 60
atagaaaata atcgaaaaca aataattcaa gcactactta 100

<210> SEQ ID NO 444
<211> LENGTH: 100
<212> TYPE: DNA
<213> ORGANISM: Homo sapiens

<400> SEQUENCE: 444
ctaaacacat ctgtactact cgcatcggga gtttcaatta cttgagctca ccatagccta 60
atagagaaca attgtaatca agcaattcaa gcactactta 100

<210> SEQ ID NO 445
<211> LENGTH: 100
<212> TYPE: DNA
<213> ORGANISM: Homo sapiens

<400> SEQUENCE: 445
ttacaatttt actgggtctc tattttaccc tcctacaagc ctcagagtac ttcgagtctc 60
ccttcaccat ttccgacggc atctacggct caacattttt 100

<210> SEQ ID NO 446
<211> LENGTH: 100
<212> TYPE: DNA
<213> ORGANISM: Homo sapiens

<400> SEQUENCE: 446
tgtagccaca ggcttccacg gacttcacgt cattattggc tcaactttcc tcactatctg 60
cttcatccgc caactaatat ttcactttac atccaaacat 100

<210> SEQ ID NO 447

<211> LENGTH: 100
<212> TYPE: DNA
<213> ORGANISM: Homo sapiens

<400> SEQUENCE: 447
tatagctaca ggctttcaca gacttcatgt cattattgga tcaatattcc tcactgtctg 60
ccttctccgc caattaaaat accactttac atctagtcat 100

<210> SEQ ID NO 448
<211> LENGTH: 100
<212> TYPE: DNA
<213> ORGANISM: Homo sapiens

<400> SEQUENCE: 448
tatagtcaca ggttttcacg gacttcatgt tattatcaga tcaacatttc tcactatctg 60
cctcctccgc ccattaaaat tccactttac atccaaccac 100

<210> SEQ ID NO 449
<211> LENGTH: 100
<212> TYPE: DNA
<213> ORGANISM: Homo sapiens

<400> SEQUENCE: 449
tatagctaca ggcttttatg gacttcacat cattattgga tcaactttcc ttactatctg 60
ccttctctgc caattaaaat accactttac atccagccat 100

<210> SEQ ID NO 450
<211> LENGTH: 100
<212> TYPE: DNA
<213> ORGANISM: Homo sapiens

<400> SEQUENCE: 450
tacagccaca ggctttcatg gatttcatgt tattattgga tcaacatttc tcactatctg 60
cctcctccac caattaaaat tccactctac atccaatcac 100

<210> SEQ ID NO 451
<211> LENGTH: 100
<212> TYPE: DNA
<213> ORGANISM: Homo sapiens

<400> SEQUENCE: 451
tatagccaca ggctttcatg gacttcacat cattattcgg tcaacatttc tcactatctg 60
cctcctctgc caactaaaat ttcactttac atctaaccac 100

<210> SEQ ID NO 452
<211> LENGTH: 100
<212> TYPE: DNA
<213> ORGANISM: Homo sapiens

<400> SEQUENCE: 452
tgtagctacg ggcttccacg ggctccccgt catcattggt tcaacattcc ttactgtttg 60
ccttatccgc caactattat atcattttac atccaagtac 100

<210> SEQ ID NO 453
<211> LENGTH: 100
<212> TYPE: DNA
<213> ORGANISM: Homo sapiens

<400> SEQUENCE: 453
cactttggct tcgaagccgc cgcctgatac tggcattttg tagatgtggt ttgactattt 60
ctgtatgtct ccatctattg atgagggtct tactctttta 100

<210> SEQ ID NO 454
<211> LENGTH: 100
<212> TYPE: DNA
<213> ORGANISM: Homo sapiens

<400> SEQUENCE: 454
cactttgcct ttgaagccac tgcctgatat caacactttg tagatgtagt atgactattc 60
ttgtatgttt ctatttattg atgaggatct tactctttta 100

<210> SEQ ID NO 455
<211> LENGTH: 100
<212> TYPE: DNA
<213> ORGANISM: Homo sapiens

<400> SEQUENCE: 455
cactttgcct ttgaaggtgc tgcctgatat tgacacttca tagatgtagt atgactattc 60
ttgtatgttt ctatttattg atgaggatct tactctttta 100

<210> SEQ ID NO 456
<211> LENGTH: 100
<212> TYPE: DNA
<213> ORGANISM: Homo sapiens

<400> SEQUENCE: 456
cactttggct ttgaagccgc tgcctgatat tgacacttca tagatgtagt aggactattc 60
ttatacgtct ctttctactg atgaggatcc tactctttta 100

<210> SEQ ID NO 457
<211> LENGTH: 100
<212> TYPE: DNA
<213> ORGANISM: Homo sapiens

<400> SEQUENCE: 457
cattttggct ttgaagccac cgcctgatat tgacactatg tagatgtagt atgactattc 60
tcatatattt ctatctactg atgagggtct tactctttta 100

<210> SEQ ID NO 458
<211> LENGTH: 100
<212> TYPE: DNA
<213> ORGANISM: Homo sapiens

<400> SEQUENCE: 458
cactttgcct ttgaagttgc cgccggatat tgacactttg tagatgtagt atgactattc 60
ttatatgtct ctatctattg atgagggtcc tactctttta 100

<210> SEQ ID NO 459
<211> LENGTH: 100
<212> TYPE: DNA
<213> ORGANISM: Homo sapiens

<400> SEQUENCE: 459
cactttgcct ttgaagccgc tgcctgatat cgacactttg tagatgtagt atgactattc 60
ttgtatgttt ctatttattg atgaggatct tactctttta 100

<210> SEQ ID NO 460
<211> LENGTH: 100
<212> TYPE: DNA

<213> ORGANISM: Homo sapiens

<400> SEQUENCE: 460
cactttggct ttgaagccgc cacttaatat taacacttgg tagatgtagt atgactattc 60
ttatatgtct ctatctactg atgaggatcc tactccttta 100

<210> SEQ ID NO 461
<211> LENGTH: 100
<212> TYPE: DNA
<213> ORGANISM: Homo sapiens

<400> SEQUENCE: 461
tattttgaat ttgaagccac tgcctggtac tggcactttg tagacatagt atgtctattc 60
ctatatgttt ctatctattg atgaggatct tactctttta 100

<210> SEQ ID NO 462
<211> LENGTH: 100
<212> TYPE: DNA
<213> ORGANISM: Homo sapiens

<400> SEQUENCE: 462
cactttggct ttgaagacgc cacctgatat tgacactttg tagatgtagt atgactattc 60
ttgtatattt ctatttactg atgaggatct tactctttta 100

<210> SEQ ID NO 463
<211> LENGTH: 100
<212> TYPE: DNA
<213> ORGANISM: Homo sapiens

<400> SEQUENCE: 463
cactttggct ttgaagccgt ggcctgatat tgacactttg tagatgtagt atgactattc 60
ttctatattt ctatttactg atgaggatct tactctttta 100

<210> SEQ ID NO 464
<211> LENGTH: 100
<212> TYPE: DNA
<213> ORGANISM: Homo sapiens

<400> SEQUENCE: 464
cactttggct ttgaagccac tgcctgatgt tgacactttg tagatgtagt atgactattc 60
ttatatgtct ctatctactg atgaggatcc tactctttta 100

<210> SEQ ID NO 465
<211> LENGTH: 100
<212> TYPE: DNA
<213> ORGANISM: Homo sapiens

<400> SEQUENCE: 465
cactttgact ttgaagccgc cacctgatat tagcgcttcg cagatgtagt atgactattt 60
ttatacatct ctgtctactg atgagggtcc tactctttta 100

<210> SEQ ID NO 466
<211> LENGTH: 100
<212> TYPE: DNA
<213> ORGANISM: Homo sapiens

<400> SEQUENCE: 466
cactttggct ttgaagccgc tgcctgatat tgacacttca tagatatagt aagactattc 60
ttatatgtct ctatctactg atgaggatcc tactctttta 100

<210> SEQ ID NO 467
<211> LENGTH: 100
<212> TYPE: DNA
<213> ORGANISM: Homo sapiens

<400> SEQUENCE: 467
cacttcggct tcgaagccgc tgcttgatac tgacactttg tagatgtagt ttgactattc 60
ctatatgtct ctatctactg gtgaggatct tactctttta 100

<210> SEQ ID NO 468
<211> LENGTH: 100
<212> TYPE: DNA
<213> ORGANISM: Homo sapiens

<400> SEQUENCE: 468
gtataaatag taccgttaac ttccaattaa ctagttttga caacattcaa aaaagagtaa 60
taaacttcgc cttaatttta ataatcaaca ccctcctagc 100

<210> SEQ ID NO 469
<211> LENGTH: 100
<212> TYPE: DNA
<213> ORGANISM: Homo sapiens

<400> SEQUENCE: 469
gtatagacag taccactgac ttccaattaa ctagtttcga taacactcga aaaagagtaa 60
taaacctggc actagcccta acagtcaaca ccctcctggc 100

<210> SEQ ID NO 470
<211> LENGTH: 100
<212> TYPE: DNA
<213> ORGANISM: Homo sapiens

<400> SEQUENCE: 470
cttactacta ataattatta cattttgact accacaactc aacggctaca tagaaaaatc 60
caccccttac gagtgcggct tcgaccctat atcccccgcc 100

<210> SEQ ID NO 471
<211> LENGTH: 100
<212> TYPE: DNA
<213> ORGANISM: Homo sapiens

<400> SEQUENCE: 471
cgcgtccctt tctccataaa attcttctta gtagctatta ccttcttatt atttgatcta 60
gaaattgccc tccttttacc cctaccatga gccctacaaa 100

<210> SEQ ID NO 472
<211> LENGTH: 100
<212> TYPE: DNA
<213> ORGANISM: Homo sapiens

<400> SEQUENCE: 472
cgcattccct tctccataaa attcttcttg attgctatca cctttttatt atctgaccta 60
gaaattgccc tattactacc cctaccgtga gccctccaaa 100

<210> SEQ ID NO 473
<211> LENGTH: 100
<212> TYPE: DNA
<213> ORGANISM: Homo sapiens

<400> SEQUENCE: 473
caactaacct gccactaata gttatgtcat ccctcttatt aatcatcatc ctagccctaa 60
gtctggccta tgagtgacta caaaaaggat tagactgagc 100

<210> SEQ ID NO 474
<211> LENGTH: 100
<212> TYPE: DNA
<213> ORGANISM: Homo sapiens

<400> SEQUENCE: 474
cgaattggta tatagtttaa acaaaacgaa tgatttcgac tcattaaatt atgataatca 60
tatttaccaa atgcccctca tttacataaa tattatacta 100

<210> SEQ ID NO 475
<211> LENGTH: 100
<212> TYPE: DNA
<213> ORGANISM: Homo sapiens

<400> SEQUENCE: 475
gcatttacca tctcacttct aggaatacta gtatatcgct cacacctcat atcctcccta 60
ctatgcctag aaggaataat actatcgctg ttcattatag 100

<210> SEQ ID NO 476
<211> LENGTH: 100
<212> TYPE: DNA
<213> ORGANISM: Homo sapiens

<400> SEQUENCE: 476
gcatttacta tctcactttt gggaatacta atctactgct cacacctaat atcctccctg 60
ctatgcctag aagggataat gctatcacta ttcatcataa 100

<210> SEQ ID NO 477
<211> LENGTH: 100
<212> TYPE: DNA
<213> ORGANISM: Homo sapiens

<400> SEQUENCE: 477
gcatatacca tatcacttct ggggatatta atctattgat cccacctgat atcatcccca 60
ctatgcctag aaggaataat attatcatta ttcatcataa 100

<210> SEQ ID NO 478
<211> LENGTH: 100
<212> TYPE: DNA
<213> ORGANISM: Homo sapiens

<400> SEQUENCE: 478
gcatttacta cctcactgtt aggaatacta atctatcgct cacacctaac gtcctcccta 60
ctatgcctag aggggataat attatctcta ttcatcgtaa 100

<210> SEQ ID NO 479
<211> LENGTH: 100
<212> TYPE: DNA
<213> ORGANISM: Homo sapiens

<400> SEQUENCE: 479
ctactctcat aaccctcaac acccactccc tcttagccaa tattgtgcct attgccatac 60
tagtctttgc cgcctgcgaa gcagcggtgg gcctagccct 100

<210> SEQ ID NO 480
<211> LENGTH: 100
<212> TYPE: DNA
<213> ORGANISM: Homo sapiens

<400> SEQUENCE: 480
gtgtaatcat aaccctcaac acccactccc tcttagccaa tattgtacct atcaccatac 60
tagtctttgc tgcctgcaag gcagcagtag gcctagccct 100

<210> SEQ ID NO 481
<211> LENGTH: 100
<212> TYPE: DNA
<213> ORGANISM: Homo sapiens

<400> SEQUENCE: 481
actagtctca atctccaaca catatggcct agactacgta cataacctaa acctactcca 60
atgctaaaac taatcgtccc aacaattata ttactaccac 100

<210> SEQ ID NO 482
<211> LENGTH: 100
<212> TYPE: DNA
<213> ORGANISM: Homo sapiens

<400> SEQUENCE: 482
actagtttca atctctaaca catatggtct agattacgta caaaacctac acttacttca 60
atactaaaaa ttattattcc aacaattata ctgttaccaa 100

<210> SEQ ID NO 483
<211> LENGTH: 100
<212> TYPE: DNA
<213> ORGANISM: Homo sapiens

<400> SEQUENCE: 483
actagtttca atttccaaca catatggctt aaactatgtg cataacctaa atttacttcg 60
acggtaaaaa ttatcattcc aacaattata ctgctaccaa 100

<210> SEQ ID NO 484
<211> LENGTH: 100
<212> TYPE: DNA
<213> ORGANISM: Homo sapiens

<400> SEQUENCE: 484
actagtttcc atctccaaca cctatagcct agactatgta tataacctaa atttacttcg 60
atgctaaaaa ttattattcc aacaattata ctgctaccaa 100

<210> SEQ ID NO 485
<211> LENGTH: 100
<212> TYPE: DNA
<213> ORGANISM: Homo sapiens

<400> SEQUENCE: 485
cctagtctca atctccaacg cataaggcct agactatgta caaaatctaa atttactcca 60
atgccaaaaa ttattattcc aacaattata ctgttacaat 100

<210> SEQ ID NO 486
<211> LENGTH: 100
<212> TYPE: DNA
<213> ORGANISM: Homo sapiens

<400> SEQUENCE: 486
actagtttca atctccaaca catacagcct agattatgta caaaatctaa atttacttca 60
atgctaaaag ttattattcc aacaattata ctgttaccac 100

<210> SEQ ID NO 487
<211> LENGTH: 100
<212> TYPE: DNA
<213> ORGANISM: Homo sapiens

<400> SEQUENCE: 487
actagtctca atttctaaca gatacggtct agattatgta cataacttaa acttactcca 60
atgttaaaat taattatccc tacaatcata ctacttccaa 100

<210> SEQ ID NO 488
<211> LENGTH: 100
<212> TYPE: DNA
<213> ORGANISM: Homo sapiens

<400> SEQUENCE: 488
actagtctca atctctaaca catatggcct agactacgta cataacctaa gcctactcca 60
atgctaaaac taatcatccc aacaatcata ttactaccac 100

<210> SEQ ID NO 489
<211> LENGTH: 100
<212> TYPE: DNA
<213> ORGANISM: Homo sapiens

<400> SEQUENCE: 489
tgacatgact ttccaaaaag cacataattt gaatcaacac aaccacccac agcctaatta 60
ttagcatcat ccccctacta ttttttaacc aaatcaacaa 100

<210> SEQ ID NO 490
<211> LENGTH: 100
<212> TYPE: DNA
<213> ORGANISM: Homo sapiens

<400> SEQUENCE: 490
taacatgatt ctccaaaaaa catataattt gaatcaacac aaccactcac agcctaatta 60
ttagcaccat ccccctacta ttttttaacc aaatcaacaa 100

<210> SEQ ID NO 491
<211> LENGTH: 100
<212> TYPE: DNA
<213> ORGANISM: Homo sapiens

<400> SEQUENCE: 491
caacctattt agctgttccc caaccttttc ctccgacccc ctaacaaccc ccctcctaat 60
actaactacc tgactcctac ccctcacaat catggcaagc 100

<210> SEQ ID NO 492
<211> LENGTH: 100
<212> TYPE: DNA
<213> ORGANISM: Homo sapiens

<400> SEQUENCE: 492
caacctattt agctgctccc tatccttctc ctccgacccc ctaacgaccc ccctcctaat 60
actaactacc tgacttctac ccctcacaat catggcaagc 100

<210> SEQ ID NO 493
<211> LENGTH: 100

<212> TYPE: DNA
<213> ORGANISM: Homo sapiens

<400> SEQUENCE: 493
caacgccact tatccagcga accactatca cgaaaaaaac tctacctctc tatactaatc 60
tccctacaaa tctccttaat tataacattc acagccacag 100

<210> SEQ ID NO 494
<211> LENGTH: 100
<212> TYPE: DNA
<213> ORGANISM: Homo sapiens

<400> SEQUENCE: 494
cagcgccacc tatccaacga accactatca cgaaaaaaac tctacctctc tatgctaatc 60
tccctccaaa tctccttaat tataacattc acagccacgg 100

<210> SEQ ID NO 495
<211> LENGTH: 100
<212> TYPE: DNA
<213> ORGANISM: Homo sapiens

<400> SEQUENCE: 495
aactaatcat attttatatc ttcttcgaaa ccacacttat ccccaccttg gctatcatca 60
cccgatgagg caaccagcca gaacgcctga acgcaggcac 100

<210> SEQ ID NO 496
<211> LENGTH: 100
<212> TYPE: DNA
<213> ORGANISM: Homo sapiens

<400> SEQUENCE: 496
aactaattat attttatatt ctctttgaag ctacacttat ccccacctta attattatta 60
cccgctgggg caaccaacca gaatgcctca atgcaagcac 100

<210> SEQ ID NO 497
<211> LENGTH: 100
<212> TYPE: DNA
<213> ORGANISM: Homo sapiens

<400> SEQUENCE: 497
aactaattat attttatatt ctctttgaag ctacacttat ccctacctta attatgatca 60
ccccctgagg taaccaacca gaacgcctca atgcaagctc 100

<210> SEQ ID NO 498
<211> LENGTH: 100
<212> TYPE: DNA
<213> ORGANISM: Homo sapiens

<400> SEQUENCE: 498
atacttccta ttctacaccc tagtaggctc ccttccccta ctcatcgcac taatttacac 60
tcacaacacc ctaggctcac taaacattct actactcact 100

<210> SEQ ID NO 499
<211> LENGTH: 100
<212> TYPE: DNA
<213> ORGANISM: Homo sapiens

<400> SEQUENCE: 499
ctcactgccc aagaactatc aaactcctga gccaacaact taatatgact agcttacaca 60
atagctttta tagtaaagat acctctttac ggactccact 100

<210> SEQ ID NO 500
<211> LENGTH: 100
<212> TYPE: DNA
<213> ORGANISM: Homo sapiens

<400> SEQUENCE: 500
tatgactccc taaagcccat gtcgaagccc ccatcgctgg gtcaatagta cttgccgcag 60
tactcttaaa actaggcggc tatggtataa tacgcctcac 100

<210> SEQ ID NO 501
<211> LENGTH: 100
<212> TYPE: DNA
<213> ORGANISM: Homo sapiens

<400> SEQUENCE: 501
tgtgactccc taaagcccac gtagaagccc ctattgacgg ctcaatagta cttgcagcag 60
ttctcctaaa gctaggcggc tgtggtgtaa tatggcttac 100

<210> SEQ ID NO 502
<211> LENGTH: 100
<212> TYPE: DNA
<213> ORGANISM: Homo sapiens

<400> SEQUENCE: 502
tatgacttcc taaagcccat gtagaaaccc ctattgctag ctcaatggta cttgcagcag 60
gactcctaaa actaggcggc tatggcataa cacgacttaa 100

<210> SEQ ID NO 503
<211> LENGTH: 100
<212> TYPE: DNA
<213> ORGANISM: Homo sapiens

<400> SEQUENCE: 503
tgtgactccc tgaagcccac gtagaagccc ccattgccgg ctcaatagta cttgcagcag 60
tactcctaaa ataaggcggc tacggaatga tatggctcac 100

<210> SEQ ID NO 504
<211> LENGTH: 100
<212> TYPE: DNA
<213> ORGANISM: Homo sapiens

<400> SEQUENCE: 504
tatgacttcc taaagctcat gtagaagccc ctattgcagg ctcaatagta cttagagcag 60
ttctcctaaa accaggcagc tacggcataa tatggcttac 100

<210> SEQ ID NO 505
<211> LENGTH: 100
<212> TYPE: DNA
<213> ORGANISM: Homo sapiens

<400> SEQUENCE: 505
tatgacttcc taaagcccat gtacaagccc ctattgcagg ctcaatagta cttgcagcag 60
ttctcctaaa accaggcagc tatggcataa tacgggttac 100

<210> SEQ ID NO 506
<211> LENGTH: 100
<212> TYPE: DNA
<213> ORGANISM: Homo sapiens

<400> SEQUENCE: 506
tgtgactccc aaaagcccat gtagaagccc ctattgccgg ctcaacagta cttgcagcgg 60
tactcctaaa actaggcggc tgcggtataa tacggcttac 100

<210> SEQ ID NO 507
<211> LENGTH: 100
<212> TYPE: DNA
<213> ORGANISM: Homo sapiens

<400> SEQUENCE: 507
tatgactccc caaagcccag atagaagctc ctattgccgg ctcagtagta cttgcagcag 60
tactcctaaa actaggaggc tgcagtataa tatagcttac 100

<210> SEQ ID NO 508
<211> LENGTH: 100
<212> TYPE: DNA
<213> ORGANISM: Homo sapiens

<400> SEQUENCE: 508
tatgactccc caaagcctac gtagaagccc ttattgccag ctcaatagta cttgcagcag 60
tactcctaaa gctaggtggc tatgatataa tatggcttac 100

<210> SEQ ID NO 509
<211> LENGTH: 100
<212> TYPE: DNA
<213> ORGANISM: Homo sapiens

<400> SEQUENCE: 509
tatgactccc caaagcccac gtggaagccc ctattgctgg ctcaatagta cttgcagagg 60
tactcctaaa gctaggtggc tatggtatta tacggcttac 100

<210> SEQ ID NO 510
<211> LENGTH: 100
<212> TYPE: DNA
<213> ORGANISM: Homo sapiens

<400> SEQUENCE: 510
actcattctc aaccccctga caaaacacat agcctacccc ttccttgtac tatccctatg 60
aggcataatt ataacaagct ccatctgcct acgacaaaca 100

<210> SEQ ID NO 511
<211> LENGTH: 100
<212> TYPE: DNA
<213> ORGANISM: Homo sapiens

<400> SEQUENCE: 511
ccttatcctc agccccctaa cagaatatat agcctaccca ttcctcatat tatccctatg 60
aggaatggtt atgacaagct ctatttgtct acgacaaacc 100

<210> SEQ ID NO 512
<211> LENGTH: 100
<212> TYPE: DNA
<213> ORGANISM: Homo sapiens

<400> SEQUENCE: 512
cctcatcctc agccccctaa tagaatatat atcctacccc ttcctcatac tatccttatg 60
aggaatagtt ataacaagct ctatttgtct aagacaaact 100

<210> SEQ ID NO 513
<211> LENGTH: 100
<212> TYPE: DNA
<213> ORGANISM: Homo sapiens

<400> SEQUENCE: 513
ccttatcctc agccccctaa cagaacatat agcctacccc ttcttcatac tattcctatg 60
agggatagtt ataacaagct ctacttgtct gcgacaagcc 100

<210> SEQ ID NO 514
<211> LENGTH: 100
<212> TYPE: DNA
<213> ORGANISM: Homo sapiens

<400> SEQUENCE: 514
gacctaaaat cgctcattgc atactcttca atcagccaca tagccctcgt agtaacagcc 60
attctcatcc aaacccccctg aagcttcacc ggcgcagtca 100

<210> SEQ ID NO 515
<211> LENGTH: 100
<212> TYPE: DNA
<213> ORGANISM: Homo sapiens

<400> SEQUENCE: 515
ttctcataat cgcccacgga ctcacatcct cattactatt ctgcctagca aactcaaact 60
acgaacgcac tcacagtcgc atcataatcc tctctcaagg 100

<210> SEQ ID NO 516
<211> LENGTH: 100
<212> TYPE: DNA
<213> ORGANISM: Homo sapiens

<400> SEQUENCE: 516
acttcaaact ctactcccac taatagcttt ttgatgactt ctagcaagcc tcgctaacct 60
cgccttaccc cccactatta acctactggg agaactctct 100

<210> SEQ ID NO 517
<211> LENGTH: 100
<212> TYPE: DNA
<213> ORGANISM: Homo sapiens

<400> SEQUENCE: 517
ccttcaaata ctgcttccac taatagcctc ttgatgactt ctagcaaatc tcactaacct 60
tgccttaccc cctaccatta atctagtagg ataactcttt 100

<210> SEQ ID NO 518
<211> LENGTH: 100
<212> TYPE: DNA
<213> ORGANISM: Homo sapiens

<400> SEQUENCE: 518
ccttcaaact ctgcttccac taatagcctc ttgatgactt ctagcaaatc tcaccaacct 60
tgccctaccc cctaccatta atctaagagg agaactcttt 100

<210> SEQ ID NO 519
<211> LENGTH: 100
<212> TYPE: DNA
<213> ORGANISM: Homo sapiens

<400> SEQUENCE: 519
gcttcaaaca ctactcccac taatagcctt ttgatgactt agagcaaatc ttattaacct 60
tgccttaccc cccaccatta atctaatggg agaactcttt 100

<210> SEQ ID NO 520
<211> LENGTH: 100
<212> TYPE: DNA
<213> ORGANISM: Homo sapiens

<400> SEQUENCE: 520
tcttcaaaca ctactcccac taacagcctt ttgatgactt atagcaaacc ttactaacct 60
tgccttaccc cccaccacta atctaatagg agaactcttt 100

<210> SEQ ID NO 521
<211> LENGTH: 100
<212> TYPE: DNA
<213> ORGANISM: Homo sapiens

<400> SEQUENCE: 521
gtgctagtaa ccacgttctc ctgatcaaat atcactctcc tacttacagg actcaacata 60
ctagtcacag ccctatactc cctctacata tttaccacaa 100

<210> SEQ ID NO 522
<211> LENGTH: 100
<212> TYPE: DNA
<213> ORGANISM: Homo sapiens

<400> SEQUENCE: 522
cacaatgggg ctcactcacc caccacatta acaacataaa accctcattc acacgagaaa 60
acaccctcat gttcatacac ctatccccca ttctcctcct 100

<210> SEQ ID NO 523
<211> LENGTH: 100
<212> TYPE: DNA
<213> ORGANISM: Homo sapiens

<400> SEQUENCE: 523
atccctcaac cccgacatca ttaccgggtt ttcctcttgt aaatatagtt taaccaaaac 60
atcagattgt gaatctgaca acagaggctt acgacccctt 100

<210> SEQ ID NO 524
<211> LENGTH: 100
<212> TYPE: DNA
<213> ORGANISM: Homo sapiens

<400> SEQUENCE: 524
atttaccgag aaagctcaca agaactgcta actcatgccc ccatgtctaa caacatggct 60
ttctcaactt ttaaaggata acagctatcc attggtctta 100

<210> SEQ ID NO 525
<211> LENGTH: 100
<212> TYPE: DNA
<213> ORGANISM: Homo sapiens

<400> SEQUENCE: 525
gtctaccgag aaagtgtaca agaactgcta actcatgccc ccatgcctag caacatggct 60
ttctcaactt tgaaaggatt agagtcatcc gttggtctta 100

<210> SEQ ID NO 526

<211> LENGTH: 100
<212> TYPE: DNA
<213> ORGANISM: Homo sapiens

<400> SEQUENCE: 526
atctatggag aaagtatgtg agaactgcta actcattcct ccatgcctaa caacatggct 60
ttctcaactt ttaaaggatg agagtcatca gttggtctta 100

<210> SEQ ID NO 527
<211> LENGTH: 100
<212> TYPE: DNA
<213> ORGANISM: Homo sapiens

<400> SEQUENCE: 527
atctaccaag aaattacgca aggacagcta acttgtgccc ccatgcctaa caacatggct 60
ttctcaactt ttaaagaatt agagttgtct attggtctta 100

<210> SEQ ID NO 528
<211> LENGTH: 100
<212> TYPE: DNA
<213> ORGANISM: Homo sapiens

<400> SEQUENCE: 528
atttaccaag aaagtgtgca agaactgcta actcatgccc ccatgcctga caatatggct 60
ttctcaactt ttagaggata agagctatct gttggtccta 100

<210> SEQ ID NO 529
<211> LENGTH: 100
<212> TYPE: DNA
<213> ORGANISM: Homo sapiens

<400> SEQUENCE: 529
atctacagag aaagtatgca agaattgcta agtcatgcac caatgcctaa caacatggct 60
ctctcaactt ttgaaggatt agagtcatcc tttggtctta 100

<210> SEQ ID NO 530
<211> LENGTH: 100
<212> TYPE: DNA
<213> ORGANISM: Homo sapiens

<400> SEQUENCE: 530
atttactgag aaagtatgca agaactgcta actcatgccc ctgtgcctaa caacatggct 60
ttctcaagtt gtagaggata agagctatcc gttggtctta 100

<210> SEQ ID NO 531
<211> LENGTH: 100
<212> TYPE: DNA
<213> ORGANISM: Homo sapiens

<400> SEQUENCE: 531
atttactgag aaagtatgca agaactgcta actcatgccc ccatgcctaa caacatggct 60
ttctcaagtt gtagaggata agagctatcc attggtctca 100

<210> SEQ ID NO 532
<211> LENGTH: 100
<212> TYPE: DNA
<213> ORGANISM: Homo sapiens

<400> SEQUENCE: 532
atctaccaag aaagtatgca agaactgcta actcatgccc ccatgcctaa caatatggct 60
ttctcaactt ttaaaggatt ggagtcatcc gttggcctta 100

<210> SEQ ID NO 533
<211> LENGTH: 100
<212> TYPE: DNA
<213> ORGANISM: Homo sapiens

<400> SEQUENCE: 533
atctaccaag aaattatgca agaactgcta actcacgccc ccatgcctaa caacatggct 60
ttctcaactt ttaaagaatt agaggtatcc attggtctta 100

<210> SEQ ID NO 534
<211> LENGTH: 100
<212> TYPE: DNA
<213> ORGANISM: Homo sapiens

<400> SEQUENCE: 534
atatgccaag aaagtatgta agaactgcta actcatgccc ccatgcctaa caacatggtt 60
ctctcaactt ttaaaggatt agagttatcc attggtctta 100

<210> SEQ ID NO 535
<211> LENGTH: 100
<212> TYPE: DNA
<213> ORGANISM: Homo sapiens

<400> SEQUENCE: 535
atctatggag aaagtatctg acaactgcta actcatgtcc ccatgtctaa caacatggct 60
ttctcaactt ttaaaggact agagtcatcc actggactta 100

<210> SEQ ID NO 536
<211> LENGTH: 100
<212> TYPE: DNA
<213> ORGANISM: Homo sapiens

<400> SEQUENCE: 536
atctaccgag aaagtatgca agaactggta actcatgccc caatatataa caatatggca 60
ttctcaactt ttaaaggatt agagttaacc attggtctaa 100

<210> SEQ ID NO 537
<211> LENGTH: 100
<212> TYPE: DNA
<213> ORGANISM: Homo sapiens

<400> SEQUENCE: 537
ggccccaaaa attttggtgc aactccaaat aaaagtaata accatgcaca ctactataac 60
caccctaacc ctgacttccc taattccccc catccttacc 100

<210> SEQ ID NO 538
<211> LENGTH: 100
<212> TYPE: DNA
<213> ORGANISM: Homo sapiens

<400> SEQUENCE: 538
accctcgtta accctaacaa aaaaaactca tacccccatt atgtaaaatc cattgtcgca 60
tccaccttta ttatcagtct cttccccaca acaatattca 100

<210> SEQ ID NO 539
<211> LENGTH: 100
<212> TYPE: DNA

<213> ORGANISM: Homo sapiens

<400> SEQUENCE: 539
tgtgcctaga ccaagaagtt attatctcga actgacactg agccacaacc caaacaaccc 60
agctctccct aagcttcaaa ctagactact tctccataat 100

<210> SEQ ID NO 540
<211> LENGTH: 100
<212> TYPE: DNA
<213> ORGANISM: Homo sapiens

<400> SEQUENCE: 540
tatgcacaga ccaagaagtc attatctcaa actgacattg agtaacaaca caaactctca 60
aactctcact aagcttcaaa ccagactact tctccacaat 100

<210> SEQ ID NO 541
<211> LENGTH: 100
<212> TYPE: DNA
<213> ORGANISM: Homo sapiens

<400> SEQUENCE: 541
attcatccct gtagcattgt tcgttacatg gtccatcata gaattctcac tgtgatatat 60
aaactcagac ccaaacatta atcagttctt caaatatcta 100

<210> SEQ ID NO 542
<211> LENGTH: 100
<212> TYPE: DNA
<213> ORGANISM: Homo sapiens

<400> SEQUENCE: 542
atttatcccc gtagcactat tcattacctg atctattgta aaattctcaa tatgatatat 60
aaactcagac cctaacatta atccattttt caaatattta 100

<210> SEQ ID NO 543
<211> LENGTH: 100
<212> TYPE: DNA
<213> ORGANISM: Homo sapiens

<400> SEQUENCE: 543
atttatccca gtagcactat ttgtcacctg atctattaga gaattctcaa tatggtatat 60
aaaatcagat cccaacatta atcaattttt caaatattta 100

<210> SEQ ID NO 544
<211> LENGTH: 100
<212> TYPE: DNA
<213> ORGANISM: Homo sapiens

<400> SEQUENCE: 544
gtttatccca gtagcagtat ttgttacctg atctattgta gaattctgaa tatgatacat 60
aaactcagac cctaacatta atcaattttt caaatactta 100

<210> SEQ ID NO 545
<211> LENGTH: 100
<212> TYPE: DNA
<213> ORGANISM: Homo sapiens

<400> SEQUENCE: 545
atttatccca gtggcactat ttgttacctg atctattgta gagttctcaa tatgatatat 60
aaactcagac cctaatacta atcaattttt caaatattta 100

<210> SEQ ID NO 546
<211> LENGTH: 100
<212> TYPE: DNA
<213> ORGANISM: Homo sapiens

<400> SEQUENCE: 546
ctcattttcc taattaccat actaatctta gttaccgcta acaacctatt ccaactgttc 60
atcggctgag agggcgtagg aattatatcc ttcttgctca 100

<210> SEQ ID NO 547
<211> LENGTH: 100
<212> TYPE: DNA
<213> ORGANISM: Homo sapiens

<400> SEQUENCE: 547
cttattttcc taatcaccat actaattcta gtcaccgcca acaacctatt tcaactcttc 60
atcggctgag agggcgtagg aatcatgtct ttcctactca 100

<210> SEQ ID NO 548
<211> LENGTH: 100
<212> TYPE: DNA
<213> ORGANISM: Homo sapiens

<400> SEQUENCE: 548
tcagttgatg atacgcccga gcagatgcca acacagcagc cattcaagca gtcctataca 60
accgtatcgg cgatatcggt ttcatcctcg ccttagcatg 100

<210> SEQ ID NO 549
<211> LENGTH: 100
<212> TYPE: DNA
<213> ORGANISM: Homo sapiens

<400> SEQUENCE: 549
tcggttgatg gtatgctcga acagatgcca acacagcagc catcccagca atcctataca 60
accgtattgg cgacattggc ttcatcctag ccctagcatg 100

<210> SEQ ID NO 550
<211> LENGTH: 100
<212> TYPE: DNA
<213> ORGANISM: Homo sapiens

<400> SEQUENCE: 550
atttatccta cactccaact catgagaccc acaacaaata gcccttctaa acgctaatcc 60
aagcctcacc ccactactag gcctcctcct agcagcagca 100

<210> SEQ ID NO 551
<211> LENGTH: 100
<212> TYPE: DNA
<213> ORGANISM: Homo sapiens

<400> SEQUENCE: 551
attcctccta cactccaact catgagaacc acaagaaata ctcctcctaa acactaaccc 60
tgactttatt ccactactag gtttcctctt agcagcagca 100

<210> SEQ ID NO 552
<211> LENGTH: 100
<212> TYPE: DNA
<213> ORGANISM: Homo sapiens

<400> SEQUENCE: 552
ggcaaatcag cccaattagg tctccacccc tgactcccct cagccataga aggccccacc 60
ccagtctcag ccctactcca ctcaagcact atagttgtag 100

<210> SEQ ID NO 553
<211> LENGTH: 100
<212> TYPE: DNA
<213> ORGANISM: Homo sapiens

<400> SEQUENCE: 553
ggaaagtcag ctcaattcgg cctccatacc tgacttccat ccaccataga aggtccaacc 60
ccagtctcag ccctactcca ctccagcact atcgttatag 100

<210> SEQ ID NO 554
<211> LENGTH: 100
<212> TYPE: DNA
<213> ORGANISM: Homo sapiens

<400> SEQUENCE: 554
ggaaagtcag ctaaattcaa cctccatccc tgactcccat ccgccataga aggcccaacc 60
ccagtctcgg ccctgctcca ctccagcact gtagttgtag 100

<210> SEQ ID NO 555
<211> LENGTH: 100
<212> TYPE: DNA
<213> ORGANISM: Homo sapiens

<400> SEQUENCE: 555
ggaaaaacag cccaacttgg cctccactcc tcacttcctt ccgccatgga aggcccagcc 60
cctgtctcag ccctactcca ctctagtaat atagctgtgg 100

<210> SEQ ID NO 556
<211> LENGTH: 100
<212> TYPE: DNA
<213> ORGANISM: Homo sapiens

<400> SEQUENCE: 556
ggaaagtcag ctcaattcag tctccatccc tgacttccat ctgctgtata aggcccaacc 60
gcagtctcag ctctactcca ctctagcact atagttgcag 100

<210> SEQ ID NO 557
<211> LENGTH: 100
<212> TYPE: DNA
<213> ORGANISM: Homo sapiens

<400> SEQUENCE: 557
ggaaaatcag cccaatttgg cctccatcct tgacttccat cagctataga aggcccaaca 60
ccagtcacag ttctgctcca ttctagcaca atagttgtag 100

<210> SEQ ID NO 558
<211> LENGTH: 100
<212> TYPE: DNA
<213> ORGANISM: Homo sapiens

<400> SEQUENCE: 558
ggaaaatcag ctcaattagg tcttcatccc tgactcccct cagccataga aggccctacc 60
cccatctcag ccctacttca ctcaagcccc atagttgtag 100

<210> SEQ ID NO 559
<211> LENGTH: 100
<212> TYPE: DNA
<213> ORGANISM: Homo sapiens

<400> SEQUENCE: 559
ggaaagtcag ctcaatttgg cctctacccc tgacctcctt ccgccatgga aggtccaacc 60
ccagtctcag ccctactcca ctctagcgct gtagttgtag 100

<210> SEQ ID NO 560
<211> LENGTH: 100
<212> TYPE: DNA
<213> ORGANISM: Homo sapiens

<400> SEQUENCE: 560
ggaaagtcag ctcaatttgg cctccacccc tgacttcctt ccaccatgga aggcccaacc 60
ccagcctcag ccgtactcca ctctagcact atagttgtag 100

<210> SEQ ID NO 561
<211> LENGTH: 100
<212> TYPE: DNA
<213> ORGANISM: Homo sapiens

<400> SEQUENCE: 561
ggaaagtcag ctaaattcgg cctccatccc tgacttccat ccgccataga aggcccaacc 60
ccagcctcag ccctgctcca ctccagcact atagttgtag 100

<210> SEQ ID NO 562
<211> LENGTH: 100
<212> TYPE: DNA
<213> ORGANISM: Homo sapiens

<400> SEQUENCE: 562
agcctcaaat agcagtttgg tctccacccc tgacttccct cggctataga aggcccaacc 60
ccagtttcag ccctactcca ctccagcact atagttgtgg 100

<210> SEQ ID NO 563
<211> LENGTH: 100
<212> TYPE: DNA
<213> ORGANISM: Homo sapiens

<400> SEQUENCE: 563
ggaaagtcag ctcagttcag cctccatccc tgatttccat cagccataga aggcccagcc 60
ccagtctcag ccctactgca ctccagcact atagttgtag 100

<210> SEQ ID NO 564
<211> LENGTH: 100
<212> TYPE: DNA
<213> ORGANISM: Homo sapiens

<400> SEQUENCE: 564
agcagatcag ctcaatttgg tctccacccc taactcctgt cagctataga agccccagca 60
cccatctcag ccctactcca ctctagcaca atagtggtag 100

<210> SEQ ID NO 565
<211> LENGTH: 100
<212> TYPE: DNA
<213> ORGANISM: Homo sapiens

<400> SEQUENCE: 565
ggaaagtcag ctcaattcgg cctccatccc tgacttccat gcgccataga aggtcaaacc 60
ccaacctcag ccctactcca ctccagcact atagttgtag 100

<210> SEQ ID NO 566
<211> LENGTH: 100
<212> TYPE: DNA
<213> ORGANISM: Homo sapiens

<400> SEQUENCE: 566
ggaaagtcag ctcaattcag cctccatccc tgacttccat cagccacaga aggcccaacc 60
ccagtctcag atctactcca ctccagcgct atagttgtag 100

<210> SEQ ID NO 567
<211> LENGTH: 100
<212> TYPE: DNA
<213> ORGANISM: Homo sapiens

<400> SEQUENCE: 567
ggaaagtcag ctcaatttgg ccttcatccc tgacttcctt ccactgtaga aggcccaacc 60
ccagtttcag ccctactcca ctctagcact atagttgtac 100

<210> SEQ ID NO 568
<211> LENGTH: 100
<212> TYPE: DNA
<213> ORGANISM: Homo sapiens

<400> SEQUENCE: 568
caggaatctt cttactcatc cgcttccacc ccctagcaga aaatagccca ctaatccaaa 60
ctctaacact atgcttaggc gctatcacca ctctgttcgc 100

<210> SEQ ID NO 569
<211> LENGTH: 100
<212> TYPE: DNA
<213> ORGANISM: Homo sapiens

<400> SEQUENCE: 569
ctggagtctt cctactcatc cgctttcacc ccttggcaga aaacaaccca acaatccaaa 60
tcttcacact atgcctaggc gccaccacta ccctgtttgc 100

<210> SEQ ID NO 570
<211> LENGTH: 100
<212> TYPE: DNA
<213> ORGANISM: Homo sapiens

<400> SEQUENCE: 570
ctggggtctt tctactcaac cgcttccacc ccttagcaga aaataaccca ccaatccaaa 60
ctctcacact atgcctaggc gccaccacca ccctgttcgc 100

<210> SEQ ID NO 571
<211> LENGTH: 100
<212> TYPE: DNA
<213> ORGANISM: Homo sapiens

<400> SEQUENCE: 571
agcagtctgc gcccttacac aaaatgacat caaaaaaatc gtagccttct ccacttcaag 60
tcaactagga ctcataatag ttacaatcgg catcaaccaa 100

<210> SEQ ID NO 572
<211> LENGTH: 100

<212> TYPE: DNA
<213> ORGANISM: Homo sapiens

<400> SEQUENCE: 572
agcaatctgt gctttaacac aaaatgatat tgaaaaaatc gtagcactct ccacctcaag 60
tcaactaggc cttagaataa ccacaattgg cattaatcaa 100

<210> SEQ ID NO 573
<211> LENGTH: 100
<212> TYPE: DNA
<213> ORGANISM: Homo sapiens

<400> SEQUENCE: 573
agcagtctgt gctcttacac aaaacgacat caaaaaaatt gtagccttct ccacttcgag 60
ccaactagga cttatagtag tcacaattgg catcaaccag 100

<210> SEQ ID NO 574
<211> LENGTH: 100
<212> TYPE: DNA
<213> ORGANISM: Homo sapiens

<400> SEQUENCE: 574
agcagtctgt gctcttacac aaaatgacat caaaaaaatc gtagccttct ctacttcaag 60
ccaattagga ctcatggtag tcacaatcgg catcaaccaa 100

<210> SEQ ID NO 575
<211> LENGTH: 100
<212> TYPE: DNA
<213> ORGANISM: Homo sapiens

<400> SEQUENCE: 575
agcaatttgt gctctaacac aaaatgtgat caacaaaatc gtagcattct ccacctcaag 60
tcaactaggc cttataatag ccacaatggg caagaatcaa 100

<210> SEQ ID NO 576
<211> LENGTH: 100
<212> TYPE: DNA
<213> ORGANISM: Homo sapiens

<400> SEQUENCE: 576
agcaatttgt gctctaacac aaaatgttat caacaaaatc gtagcgttat ccacctcaag 60
tcaactaggc cttataatag tcacaactgg cattaatcaa 100

<210> SEQ ID NO 577
<211> LENGTH: 100
<212> TYPE: DNA
<213> ORGANISM: Homo sapiens

<400> SEQUENCE: 577
agcgatctgc gctctgacac aaaatgatat ttaaaaaatc atagcgttct tcacctcaag 60
ccagctgggc cttataatag tcacaattgg cattaatcaa 100

<210> SEQ ID NO 578
<211> LENGTH: 100
<212> TYPE: DNA
<213> ORGANISM: Homo sapiens

<400> SEQUENCE: 578
agcaatctgc gctctaacac aaaatgatat ttaaaaaatc atagcattct ccacctcaag 60
tcagctgggc cttacgatag tcacaattgg cattaatcag 100

<210> SEQ ID NO 579
<211> LENGTH: 100
<212> TYPE: DNA
<213> ORGANISM: Homo sapiens

<400> SEQUENCE: 579
agcaatctgc actctaacac aaaatgacat ataaaaaatt gtggcatttt tcacctcgag 60
ttaactagga ctcataatag ttacaattgg tattaaccaa 100

<210> SEQ ID NO 580
<211> LENGTH: 100
<212> TYPE: DNA
<213> ORGANISM: Homo sapiens

<400> SEQUENCE: 580
agcaatctgt gctctaacac aaaatgatat caaaacaatg gtagcactct ccacttcaag 60
tcaactagac cttacaatac tcacaattga cattaatcaa 100

<210> SEQ ID NO 581
<211> LENGTH: 100
<212> TYPE: DNA
<213> ORGANISM: Homo sapiens

<400> SEQUENCE: 581
ccacacctag cattcctgca catctgtacc cacgccttct tcaaagccat actatttatg 60
tgctccgggt ccatcatcca caaccttaac aatgaacaag 100

<210> SEQ ID NO 582
<211> LENGTH: 100
<212> TYPE: DNA
<213> ORGANISM: Homo sapiens

<400> SEQUENCE: 582
ccacacctag cattccttca catctgcatc cacgcctttt aaaaagctat attatttata 60
tgttcaggct ccattatcca taacctcaat gatgaacaag 100

<210> SEQ ID NO 583
<211> LENGTH: 100
<212> TYPE: DNA
<213> ORGANISM: Homo sapiens

<400> SEQUENCE: 583
ccacacctag cattcctaca catctgcacc cacgcctttt tcaaagttat attatttatg 60
tgttcaggat ccatcatcca cagcctcaac gatgaacaag 100

<210> SEQ ID NO 584
<211> LENGTH: 100
<212> TYPE: DNA
<213> ORGANISM: Homo sapiens

<400> SEQUENCE: 584
ccacatctag catttctcca tatctgtaca catgcattct tcaaagctat gctgtttata 60
tgctccagat ccatcattca taaccttaat gatgaccagg 100

<210> SEQ ID NO 585
<211> LENGTH: 100
<212> TYPE: DNA
<213> ORGANISM: Homo sapiens

<400> SEQUENCE: 585
ccatacctag cattcctaca catctgtacc catgctttct tcaaagccat attatttata 60
tgctccggat ccattattca taacctcaac aatgaacaag 100

<210> SEQ ID NO 586
<211> LENGTH: 100
<212> TYPE: DNA
<213> ORGANISM: Homo sapiens

<400> SEQUENCE: 586
ccacacctag cattcctaca catttgcacc cacacctttt ttaaagctat attatttata 60
agttcaggat ccatcatcca taacctcaac aataaacaag 100

<210> SEQ ID NO 587
<211> LENGTH: 100
<212> TYPE: DNA
<213> ORGANISM: Homo sapiens

<400> SEQUENCE: 587
gcacacctag cattcctaca tatctgcacc catgcctttt ctaaagctat attatttata 60
tgttcaggat ccatcaccca taacctcaac gatgaacaag 100

<210> SEQ ID NO 588
<211> LENGTH: 100
<212> TYPE: DNA
<213> ORGANISM: Homo sapiens

<400> SEQUENCE: 588
ccacatctag cattccttca catgtgcacc cacacctttt ttaaagctat attatttata 60
tgctcaggct ccatcatcca caatctcaat gatgaacaag 100

<210> SEQ ID NO 589
<211> LENGTH: 100
<212> TYPE: DNA
<213> ORGANISM: Homo sapiens

<400> SEQUENCE: 589
ccatatctag cattcctaca catctgtacc catgccttct ttaaagccat actattcata 60
tgctccggat ctatcattca taacctcaac aatgaataag 100

<210> SEQ ID NO 590
<211> LENGTH: 100
<212> TYPE: DNA
<213> ORGANISM: Homo sapiens

<400> SEQUENCE: 590
ccacatctag cattccttca catctgtacc catgcctttt ttaaagctat ataatttata 60
tgttcagggt ccatcatcca taatctcaat gatgaacaag 100

<210> SEQ ID NO 591
<211> LENGTH: 100
<212> TYPE: DNA
<213> ORGANISM: Homo sapiens

<400> SEQUENCE: 591
ccacacctag cattccttca catctgtatt catgcctttt ttaaagctat gttatttata 60
tgttcagagt ccatcatcca tagcctcaat gatgaacaac 100

<210> SEQ ID NO 592
<211> LENGTH: 100
<212> TYPE: DNA
<213> ORGANISM: Homo sapiens

<400> SEQUENCE: 592
atattcgaaa aataggagga ctactcaaaa ccatacctct cacttcaacc tccctcacca 60
ttggcagcct agcattagca ggaatacctt tcctcacagg 100

<210> SEQ ID NO 593
<211> LENGTH: 100
<212> TYPE: DNA
<213> ORGANISM: Homo sapiens

<400> SEQUENCE: 593
acattcgaaa aataggagga ctactcaaaa ttatacccct cacttcaacc tccctcacca 60
ttggcagcct ggcacttgca ggaatgccct tcctcacggg 100

<210> SEQ ID NO 594
<211> LENGTH: 100
<212> TYPE: DNA
<213> ORGANISM: Homo sapiens

<400> SEQUENCE: 594
acatctgaaa aataggagga ctattcaaga ctctactcct cacttcctcc tcccttatca 60
ttggcagcct cacacttaca ggtatgcctt tcctcacagg 100

<210> SEQ ID NO 595
<211> LENGTH: 100
<212> TYPE: DNA
<213> ORGANISM: Homo sapiens

<400> SEQUENCE: 595
tttctactcc aaagaccaca tcatcgaaac cgcaaacata tcatacacaa acgcctgagc 60
cctatctatt actctcatcg ctacctccct gacaagcgcc 100

<210> SEQ ID NO 596
<211> LENGTH: 100
<212> TYPE: DNA
<213> ORGANISM: Homo sapiens

<400> SEQUENCE: 596
cttttactct aaagacctta tcatcgaaac cgcaaataca tcatacacca acgcctgagc 60
cctttctatt actcttattg ccaccttttt aacagctgtc 100

<210> SEQ ID NO 597
<211> LENGTH: 100
<212> TYPE: DNA
<213> ORGANISM: Homo sapiens

<400> SEQUENCE: 597
cttctattcc atagacctca tcatcaaaac cgcaaatata tcatacacca acgcctgagc 60
cctatctatt actctcatcg ccacttccct aacaagcgcc 100

<210> SEQ ID NO 598
<211> LENGTH: 100
<212> TYPE: DNA
<213> ORGANISM: Homo sapiens

<400> SEQUENCE: 598
cttttattct aaagacctca ttattgaaac tgcaaacaca tcatacacca acgcctgagc 60
cctttctatt actcttatcg caacctccct aacagctgtc 100

<210> SEQ ID NO 599
<211> LENGTH: 100
<212> TYPE: DNA
<213> ORGANISM: Homo sapiens

<400> SEQUENCE: 599
tatagcactc gaataattct tctcacccta acaggtcaac ctcgcttccc cacccttact 60
aacattaacg aaaataaccc caccctacta aaccccatta 100

<210> SEQ ID NO 600
<211> LENGTH: 100
<212> TYPE: DNA
<213> ORGANISM: Homo sapiens

<400> SEQUENCE: 600
aatagcactc gaataattct cctcacccta acaggccaac ctcgtttccc aaccctaacc 60
aacatcaacg aaaacaaccc taccctgcta agccccatca 100

<210> SEQ ID NO 601
<211> LENGTH: 100
<212> TYPE: DNA
<213> ORGANISM: Homo sapiens

<400> SEQUENCE: 601
aacgcctggc agccggaagc ctattcgcag gatttctcat tactaacaac atttccccg 60 catcccccctt ccaaacaaca atccccctct acctaaaact 100

<210> SEQ ID NO 602
<211> LENGTH: 100
<212> TYPE: DNA
<213> ORGANISM: Homo sapiens

<400> SEQUENCE: 602
aacgcctaac aatcggaagc ctattcgcag gatttctcat caccagcaac attttcccca 60
catccatccc ccaaatgaca atcccacttc acttaaaact 100

<210> SEQ ID NO 603
<211> LENGTH: 100
<212> TYPE: DNA
<213> ORGANISM: Homo sapiens

<400> SEQUENCE: 603
cacagccctc gctgtcactt tcctaggact tctaacagcc ctagacctca actacctaac 60
caacaaactt aaaataaaat ccccactatg cacattttat 100

<210> SEQ ID NO 604
<211> LENGTH: 100
<212> TYPE: DNA
<213> ORGANISM: Homo sapiens

<400> SEQUENCE: 604
cacagcccta ggcatcacct tcctaggact tctgacagcc ctagacctca actacttaac 60
caacaaactc aaaataaaaa acccactgtg tacatttcac 100

<210> SEQ ID NO 605

<211> LENGTH: 100
<212> TYPE: DNA
<213> ORGANISM: Homo sapiens

<400> SEQUENCE: 605
ttctccaaca tactcggatt ctaccctagc atcacacacc gcacaatccc ctatctaggc 60
cttcttacga gccaaaacct gcccctactc ctcctagacc 100

<210> SEQ ID NO 606
<211> LENGTH: 100
<212> TYPE: DNA
<213> ORGANISM: Homo sapiens

<400> SEQUENCE: 606
taacctgact agaaaagcta ttacctaaaa caatttcaca gcaccaaatc tccacctcca 60
tcatcacctc aacccaaaaa ggcataatta aactttactt 100

<210> SEQ ID NO 607
<211> LENGTH: 100
<212> TYPE: DNA
<213> ORGANISM: Homo sapiens

<400> SEQUENCE: 607
taacttgact agaaaaacta atacctaaaa caacctcaca gtaccaaacc tccgcctcca 60
tcatcacctc aactcaaaaa ggcataatca aactttactt 100

<210> SEQ ID NO 608
<211> LENGTH: 100
<212> TYPE: DNA
<213> ORGANISM: Homo sapiens

<400> SEQUENCE: 608
cctctctttc ttcttcccac tcatcctaac cctactccta atcacataac ctattccccc 60
gagcaatctc aattacaata tatacaccaa caaacaatgt 100

<210> SEQ ID NO 609
<211> LENGTH: 100
<212> TYPE: DNA
<213> ORGANISM: Homo sapiens

<400> SEQUENCE: 609
ttcctctttc ttcttcccac tcctcctaac cctcctccta atcacataac ctgttacccc 60
gagcactctc aattacaata tatacaccaa caaacaaggt 100

<210> SEQ ID NO 610
<211> LENGTH: 100
<212> TYPE: DNA
<213> ORGANISM: Homo sapiens

<400> SEQUENCE: 610
tcaaccagta accactacta atcaacgccc ataatcatac aaagccccccg caccaatagg 60 atcctcccga atcaaccctg acccctctcc ttcataaatt 100

<210> SEQ ID NO 611
<211> LENGTH: 100
<212> TYPE: DNA
<213> ORGANISM: Homo sapiens

<400> SEQUENCE: 611
tcaaccagca accaccacca atcaacactc ataattatag aaagcacccg cacccacaga 60
atcttcacga accaaccctg gcccctcacc ctcaaaaatt 100

<210> SEQ ID NO 612
<211> LENGTH: 100
<212> TYPE: DNA
<213> ORGANISM: Homo sapiens

<400> SEQUENCE: 612
tcaaccagta actaccacca atcaatgccc gtaatcgtat aaagcccccg caccaatagg 60
atcctcccga atcaatgctg gcccctcccc ttcataaatt 100

<210> SEQ ID NO 613
<211> LENGTH: 100
<212> TYPE: DNA
<213> ORGANISM: Homo sapiens

<400> SEQUENCE: 613
tcaaccagca actaccacca atcaacaccc ataattatat aaagcaccca cacccacaga 60
atcctcacga atcaaccctg tcccctcacc ctcaaaaacc 100

<210> SEQ ID NO 614
<211> LENGTH: 100
<212> TYPE: DNA
<213> ORGANISM: Homo sapiens

<400> SEQUENCE: 614
tcaaccagca actaccacta gtcaacatcc ataatcatat aaagcacccg cacctataga 60
atcctcacga atcaaccctg acccctcacc atcaaaaatc 100

<210> SEQ ID NO 615
<211> LENGTH: 100
<212> TYPE: DNA
<213> ORGANISM: Homo sapiens

<400> SEQUENCE: 615
attcagcttc ctacactatt aaagtttacc acaaccacca ccccatcata ctctttcacc 60
cacagcacca atcctacctc catcgctaac cccactaaaa 100

<210> SEQ ID NO 616
<211> LENGTH: 100
<212> TYPE: DNA
<213> ORGANISM: Homo sapiens

<400> SEQUENCE: 616
attcaacttc ctacactatt aaaattcacc acaatcacca ccccatcata tttttttacc 60
cataacacta accccacttc tattgctaat cccactaaaa 100

<210> SEQ ID NO 617
<211> LENGTH: 100
<212> TYPE: DNA
<213> ORGANISM: Homo sapiens

<400> SEQUENCE: 617
cactcaccaa gacctcaacc cctgaccccc atgcctcagg atactcctca atagccatcg 60
ctgtagtata tccaaagaca accatcattc cccctaaata 100

<210> SEQ ID NO 618
<211> LENGTH: 100
<212> TYPE: DNA

<213> ORGANISM: Homo sapiens

<400> SEQUENCE: 618
cacttaccaa gacctcaatc cctgaccccc atgcctcagg atactcctca atagctattg 60
ctgtagtgta cccaaaaaca accattatac cccctaaata 100

<210> SEQ ID NO 619
<211> LENGTH: 100
<212> TYPE: DNA
<213> ORGANISM: Homo sapiens

<400> SEQUENCE: 619
aagttcctaa aacctcaata cttgatcctc atgcctcagg gtattcctca atagccatca 60
ccgcagtata tccaaaaaca accatcatcc cccccaaata 100

<210> SEQ ID NO 620
<211> LENGTH: 100
<212> TYPE: DNA
<213> ORGANISM: Homo sapiens

<400> SEQUENCE: 620
cactccctaa aacttcaatg cctgaccctc atgcctccgt gtattcctaa atagccatcg 60
ctgtagtata accaaaaaca actatcattc cgcgcaacta 100

<210> SEQ ID NO 621
<211> LENGTH: 100
<212> TYPE: DNA
<213> ORGANISM: Homo sapiens

<400> SEQUENCE: 621
cactcaccaa gacttcaatt cctgaccccc atgtctcagg atactcctca atagccattg 60
ccatagtata tccaaaaaca accatcgtac cccctagata 100

<210> SEQ ID NO 622
<211> LENGTH: 100
<212> TYPE: DNA
<213> ORGANISM: Homo sapiens

<400> SEQUENCE: 622
aattaaaaaa actattaaac ccatataacc tcccccaaaa ttcagaataa taacacaccc 60
gaccacaccg ctaacaatca gtactaaacc cccataaata 100

<210> SEQ ID NO 623
<211> LENGTH: 100
<212> TYPE: DNA
<213> ORGANISM: Homo sapiens

<400> SEQUENCE: 623
atttaaaaaa accattaaac ctatacaacc tcccccataa tttaaaataa tgatacaccc 60
aaccacacca ctaacaatca acactaagcc cccataaata 100

<210> SEQ ID NO 624
<211> LENGTH: 100
<212> TYPE: DNA
<213> ORGANISM: Homo sapiens

<400> SEQUENCE: 624
attaaaaaaa accattaaac ccatataacc tcccccataa ttcagaataa taacacaccc 60
aactacacca ctaataatca atactatacc cccataaata 100

<210> SEQ ID NO 625
<211> LENGTH: 100
<212> TYPE: DNA
<213> ORGANISM: Homo sapiens

<400> SEQUENCE: 625
ggagaaggct tagaagaaaa ccccacaaac cccattacta aacccacact caacagaaac 60
aaagcataca tcattattct cgcacggact acaaccacga 100

<210> SEQ ID NO 626
<211> LENGTH: 100
<212> TYPE: DNA
<213> ORGANISM: Homo sapiens

<400> SEQUENCE: 626
ggagaaggct tagaagaaaa ccccacaaac cccattacta aaaccacact taacaaaaat 60
aaagcatatg tcattattct cgcacggact acaaccacga 100

<210> SEQ ID NO 627
<211> LENGTH: 100
<212> TYPE: DNA
<213> ORGANISM: Homo sapiens

<400> SEQUENCE: 627
ggagaaggtt tagaagaaaa ccctacaaac cctattacta aagccacact taatgataat 60
aaagcatatg tgattaatcc cacatggatt acaaccacga 100

<210> SEQ ID NO 628
<211> LENGTH: 100
<212> TYPE: DNA
<213> ORGANISM: Homo sapiens

<400> SEQUENCE: 628
ccaatgatat gaaaaaccat cgttgtattt caactacaag aacaccaatg accccaatac 60
gcaaaattaa ccccctaata aaattaatta accactcatt 100

<210> SEQ ID NO 629
<211> LENGTH: 100
<212> TYPE: DNA
<213> ORGANISM: Homo sapiens

<400> SEQUENCE: 629
ctaatgataa gaaaaaccat tgtcatattt caactataag aacactaatg accataatac 60
gtaaaacaaa tccactaata aaaatcatta attattcact 100

<210> SEQ ID NO 630
<211> LENGTH: 100
<212> TYPE: DNA
<213> ORGANISM: Homo sapiens

<400> SEQUENCE: 630
ccaatgatat gaaaaaccat cgttgtattt caactacaag aacactaatg accccaacac 60
gcaaaaccaa ctcgttaata aaattaatta accactcatt 100

<210> SEQ ID NO 631
<211> LENGTH: 100
<212> TYPE: DNA
<213> ORGANISM: Homo sapiens

<400> SEQUENCE: 631
ctaatggtat gaaaaaccat cattgtattt caactataag aacactaatg accaaaatat 60
gcacaacgca cctgctaata aaaattatta gtcattcatt 100

<210> SEQ ID NO 632
<211> LENGTH: 100
<212> TYPE: DNA
<213> ORGANISM: Homo sapiens

<400> SEQUENCE: 632
ccaatgatat gagaaaccat cattttattt cgactataag aacaccaatg accccaacat 60
gtaaaactaa tccactagta aaaataatca accactcact 100

<210> SEQ ID NO 633
<211> LENGTH: 100
<212> TYPE: DNA
<213> ORGANISM: Homo sapiens

<400> SEQUENCE: 633
catcgacctc cccaccccat ccaacatctc cgcatgatga aacttcggct cactccttgg 60
cgcctgcctg atcctccaaa tcaccacagg actattccta 100

<210> SEQ ID NO 634
<211> LENGTH: 100
<212> TYPE: DNA
<213> ORGANISM: Homo sapiens

<400> SEQUENCE: 634
tattgatctc cccactccat ctaacatctc cacatgatga aacctcggct cacttcttgg 60
cgcctgccta accattcaaa tgatcacagg actattccta 100

<210> SEQ ID NO 635
<211> LENGTH: 100
<212> TYPE: DNA
<213> ORGANISM: Homo sapiens

<400> SEQUENCE: 635
tattgatctc cccacaccat ccaacatctc tacatgatga aattttggct cacttcttgg 60
tgcctgctta attctccaga ccatcacagg attatttctg 100

<210> SEQ ID NO 636
<211> LENGTH: 100
<212> TYPE: DNA
<213> ORGANISM: Homo sapiens

<400> SEQUENCE: 636
tatcgatctc cccgccccat ccaacatctc catatgatgg aacttcagct tgcttcttgg 60
tgcctgctta acccttcaaa ttattacagg actattccta 100

<210> SEQ ID NO 637
<211> LENGTH: 100
<212> TYPE: DNA
<213> ORGANISM: Homo sapiens

<400> SEQUENCE: 637
catcgatctc cccactccat ctaatatctc tatatgatga aacctctgct cacttcttgg 60
cacctgctta ttccttcaaa tcatcacagg gctattccta 100

<210> SEQ ID NO 638
<211> LENGTH: 100
<212> TYPE: DNA
<213> ORGANISM: Homo sapiens

<400> SEQUENCE: 638
gccatacact actcaccaga cgcctcaacc gccttttcat caatcgccca catcactcga 60
gacgtaaatt atggctgaat catccgctac cttcacgcca 100

<210> SEQ ID NO 639
<211> LENGTH: 100
<212> TYPE: DNA
<213> ORGANISM: Homo sapiens

<400> SEQUENCE: 639
gccatacact aatcaccaga tgcttcaacc gccttctcat caatcgccca catcacctga 60
gacgtaaacc atggctgaat catccgctac ctccacgcta 100

<210> SEQ ID NO 640
<211> LENGTH: 100
<212> TYPE: DNA
<213> ORGANISM: Homo sapiens

<400> SEQUENCE: 640
gctatacgct actcaccaga cgcctcaacc gccttctcct cagtcgtcca catcactcga 60
gatgtaaact atggctgaat catccgctac ctccatgcca 100

<210> SEQ ID NO 641
<211> LENGTH: 100
<212> TYPE: DNA
<213> ORGANISM: Homo sapiens

<400> SEQUENCE: 641
gccatacact acacaccaga caccacaact gccttctctt caatggccca tattaatcga 60
gatgtgaact atggctgaat tatccactat ctccacacta 100

<210> SEQ ID NO 642
<211> LENGTH: 100
<212> TYPE: DNA
<213> ORGANISM: Homo sapiens

<400> SEQUENCE: 642
atggcgcctc aatattcttt atctgcctct tcctacacat cgggcgaggc ctatattacg 60
gatcatttct ctactcagaa acctgaaaca tcggcattat 100

<210> SEQ ID NO 643
<211> LENGTH: 100
<212> TYPE: DNA
<213> ORGANISM: Homo sapiens

<400> SEQUENCE: 643
atggcgcctc aatatttttc atctgcctct tcctacatgt tggccgaggc ttatactatg 60
gatcatttat attcctagaa acctgaaata ttgatttttt 100

<210> SEQ ID NO 644
<211> LENGTH: 100
<212> TYPE: DNA
<213> ORGANISM: Homo sapiens

<400> SEQUENCE: 644
atggcgcttc catatttttc atctgcctct tcttacacat tggctgaggt ttatactatg 60
gatcatttac atttctagaa acctgaaata tcggcattat 100

<210> SEQ ID NO 645
<211> LENGTH: 100
<212> TYPE: DNA
<213> ORGANISM: Homo sapiens

<400> SEQUENCE: 645
acggtgcctc aatattcttc atctgcctct tcctacacat cggccgaggc ttatactatg 60
gctcattcct ctacctagaa acctgaaaca ttggtattat 100

<210> SEQ ID NO 646
<211> LENGTH: 100
<212> TYPE: DNA
<213> ORGANISM: Homo sapiens

<400> SEQUENCE: 646
atggcccttc aacattcttc atctgcctct tcctacacgt cggcggaggc ttatattatg 60
ggtcattcgt acatttagaa acatgaaaca ctggcattat 100

<210> SEQ ID NO 647
<211> LENGTH: 100
<212> TYPE: DNA
<213> ORGANISM: Homo sapiens

<400> SEQUENCE: 647
atggtgcttc aatatttttc atctgcctct tcttacacat tggccaaggg ttatactacg 60
ggtcattact attcccagaa acctgaaata ttggcattat 100

<210> SEQ ID NO 648
<211> LENGTH: 100
<212> TYPE: DNA
<213> ORGANISM: Homo sapiens

<400> SEQUENCE: 648
atggcgcctc aatatttttc atctgcctct tcctacatat tggccgaggc ctgtactatg 60
gcttatttct ctacctagaa acctgaaaca ttggcatcat 100

<210> SEQ ID NO 649
<211> LENGTH: 100
<212> TYPE: DNA
<213> ORGANISM: Homo sapiens

<400> SEQUENCE: 649
atgacgcttc aacattcttc atctgtctct tcctacactt tagccgaggc ttatattatg 60
gctcattcat atacttagaa aactgaaaca ttgacattat 100

<210> SEQ ID NO 650
<211> LENGTH: 100
<212> TYPE: DNA
<213> ORGANISM: Homo sapiens

<400> SEQUENCE: 650
atggtgcctc aatatttttc atctgcctct tcttacacat tggccaaggc ttatactatg 60
ggtcattcct atttctagaa acctgaaata ttggcattat 100

<210> SEQ ID NO 651
<211> LENGTH: 100

<212> TYPE: DNA
<213> ORGANISM: Homo sapiens

<400> SEQUENCE: 651
cctcctgctt gcaactatag caacagcctt cataggctat gtcctcccgt gaggccaaat 60
atcattctga ggggccacag taattacaaa cttactatcc 100

<210> SEQ ID NO 652
<211> LENGTH: 100
<212> TYPE: DNA
<213> ORGANISM: Homo sapiens

<400> SEQUENCE: 652
cctcttactc acaactatgg caacagcatt cataggctac ctgctcccat gaggccagat 60
atcattctga ggtgccacag taattacaaa tctactatcg 100

<210> SEQ ID NO 653
<211> LENGTH: 100
<212> TYPE: DNA
<213> ORGANISM: Homo sapiens

<400> SEQUENCE: 653
tctcttgctt acaaccacag caacagcgtt tataggctat gtgcttccat gaggccaaat 60
atcactctga ggcgccacag taaccacaaa cctaatatca 100

<210> SEQ ID NO 654
<211> LENGTH: 100
<212> TYPE: DNA
<213> ORGANISM: Homo sapiens

<400> SEQUENCE: 654
cctcctactc acaactatgg caacagcatt cataggctac gtgctcccat aaggccagat 60
atctttctga ggcactacag tagttacaaa tctactatca 100

<210> SEQ ID NO 655
<211> LENGTH: 100
<212> TYPE: DNA
<213> ORGANISM: Homo sapiens

<400> SEQUENCE: 655
cctcttattc acaaccatag caacagcctt cataggctat gtcctcccat gaggccaaat 60
attcttctga ggagccacgg taattacgaa tctattgtcc 100

<210> SEQ ID NO 656
<211> LENGTH: 100
<212> TYPE: DNA
<213> ORGANISM: Homo sapiens

<400> SEQUENCE: 656
cctcctactc ataaccacag caacagcatt tataggctat gtgcttccat gaggccagat 60
accattctga ggcactacag taatcacaaa cctactatca 100

<210> SEQ ID NO 657
<211> LENGTH: 100
<212> TYPE: DNA
<213> ORGANISM: Homo sapiens

<400> SEQUENCE: 657
gctcctactc acaaccacag caacagcatt tataggctat gttcttccat gaggccaaat 60
atcattctga ggcgctaccg taaccacaaa cctactatca 100

<210> SEQ ID NO 658
<211> LENGTH: 100
<212> TYPE: DNA
<213> ORGANISM: Homo sapiens

<400> SEQUENCE: 658
tctcctattc acaactatag caacaacatt cataggctat gtgctcccat gagcccaaat 60
atcattctga ggcactacag taattacaaa tttactatca 100

<210> SEQ ID NO 659
<211> LENGTH: 100
<212> TYPE: DNA
<213> ORGANISM: Homo sapiens

<400> SEQUENCE: 659
cctcctactc acaactatgg caacagcatt cataggctac atgctcccat gaggccagat 60
atcattcgga ggcgctacag taattacaaa tctactatca 100

<210> SEQ ID NO 660
<211> LENGTH: 100
<212> TYPE: DNA
<213> ORGANISM: Homo sapiens

<400> SEQUENCE: 660
cctcctcctc acaactatag taacagcatt catagcctat gtgctccggt gaggccaaat 60
atcattctga ggtgctacag taattataaa cctatcctca 100

<210> SEQ ID NO 661
<211> LENGTH: 100
<212> TYPE: DNA
<213> ORGANISM: Homo sapiens

<400> SEQUENCE: 661
ctacctgctc acaactatag caaaagcatt cacaggatac atgctcccat gaggccagat 60
atcattctga ggcgctacaa taattacaaa tctactatca 100

<210> SEQ ID NO 662
<211> LENGTH: 100
<212> TYPE: DNA
<213> ORGANISM: Homo sapiens

<400> SEQUENCE: 662
tgtcctgctc acaaccatag caacagcatt tataggctat gtacttccat gaggccaaat 60
atcattctga ggcgctacag tgattacaaa tctactatca 100

<210> SEQ ID NO 663
<211> LENGTH: 100
<212> TYPE: DNA
<213> ORGANISM: Homo sapiens

<400> SEQUENCE: 663
ctcctactta acaactatag caacagcatt cataggctac gtgctcccat gaggccaaat 60
atcattctga ggtgctacag taattacaaa tctactatta 100

<210> SEQ ID NO 664
<211> LENGTH: 100
<212> TYPE: DNA
<213> ORGANISM: Homo sapiens

<400> SEQUENCE: 664
gccatcccat acattgggac agacctagtt caatgaatct gaggaggcta ctcagtagac 60
agtcccaccc tcacacgatt ctttaccttt cacttcatct 100

<210> SEQ ID NO 665
<211> LENGTH: 100
<212> TYPE: DNA
<213> ORGANISM: Homo sapiens

<400> SEQUENCE: 665
gccattccat acatcggaac agacctagtc caatgagtct gaggtggcta ctcagtagaa 60
agacccaccc tcacacgatt ctttaccttc cacttcattc 100

<210> SEQ ID NO 666
<211> LENGTH: 100
<212> TYPE: DNA
<213> ORGANISM: Homo sapiens

<400> SEQUENCE: 666
gccatcccat atattggaac tgaccttgtc caatgaatcg gaggtggatt tccagttgac 60
aaagccactc ttacacgatt cttcgccttc cacttcatct 100

<210> SEQ ID NO 667
<211> LENGTH: 100
<212> TYPE: DNA
<213> ORGANISM: Homo sapiens

<400> SEQUENCE: 667
gccatcccat atattggaac tgactttgta caatgaatct gagggggatt ctcatttgac 60
aaagccaccc tcacacgatt ttttgccttc catttcatct 100

<210> SEQ ID NO 668
<211> LENGTH: 100
<212> TYPE: DNA
<213> ORGANISM: Homo sapiens

<400> SEQUENCE: 668
gccattccgt atattggaac tgaccttgtg caatgaatct gaggtggatt ttcagtagac 60
aaagccaccc ttacacgatt ttttgccttc cattttatct 100

<210> SEQ ID NO 669
<211> LENGTH: 100
<212> TYPE: DNA
<213> ORGANISM: Homo sapiens

<400> SEQUENCE: 669 taccettcat tattgcagcc ctagcagcac tccacctcct attcttgcac gaaacgggat 60
caaacaaccc cctaggaatc acctcccatt ccgataaaat 100

<210> SEQ ID NO 670
<211> LENGTH: 100
<212> TYPE: DNA
<213> ORGANISM: Homo sapiens

<400> SEQUENCE: 670
tgccctttat tattacagcc ttaacaaccc tacaccttct attcctacac gaaataggat 60
caaacaatcc cttaggcatc cctcccatt ccgacaaaat 100

<210> SEQ ID NO 671
<211> LENGTH: 100
<212> TYPE: DNA
<213> ORGANISM: Homo sapiens

<400> SEQUENCE: 671
caccttccac ccttactaca caatcaaaga cgccctcggc ttacttctct tccttctctc 60
cttaatgaca ttaacactat tctcaccaga cctcctaggc 100

<210> SEQ ID NO 672
<211> LENGTH: 100
<212> TYPE: DNA
<213> ORGANISM: Homo sapiens

<400> SEQUENCE: 672
taccttccat ccttactaca caaccaaaga catcctaggc ctattccttt tcctcctcac 60
cctattaaca ctagtactat tctcaccaga cctcctgggc 100

<210> SEQ ID NO 673
<211> LENGTH: 100
<212> TYPE: DNA
<213> ORGANISM: Homo sapiens

<400> SEQUENCE: 673
gacccagaca attataccct agccaacccc ttaaacaccc ctccccacat caagcccgaa 60
tgatatttcc tattcgccta cacaattctc cgatccgtcc 100

<210> SEQ ID NO 674
<211> LENGTH: 100
<212> TYPE: DNA
<213> ORGANISM: Homo sapiens

<400> SEQUENCE: 674
gacccagaca actacaccct gactaacccc ctaaacaccc caccccacat caaacccgaa 60
tgatatttcc tattcgccta cgcaattctc cgatccattc 100

<210> SEQ ID NO 675
<211> LENGTH: 100
<212> TYPE: DNA
<213> ORGANISM: Homo sapiens

<400> SEQUENCE: 675
gacccagaca actataccct agccaacccc ctaaacaccc caccccacat taaacccgaa 60
tgttactttc tattcgccta cgcaatccta cggtccattc 100

<210> SEQ ID NO 676
<211> LENGTH: 100
<212> TYPE: DNA
<213> ORGANISM: Homo sapiens

<400> SEQUENCE: 676
ctaacaaact aggaggcgtc cttgccctat tactatccat cctcatccta gcaataatcc 60
ccatcctcca tatatccaaa caacaaagca taatatttcg 100

<210> SEQ ID NO 677
<211> LENGTH: 100
<212> TYPE: DNA
<213> ORGANISM: Homo sapiens

<400> SEQUENCE: 677
ccaataaact aggaggcatt ctagcccttc tactatccat cctcatccta gcagcaattc 60
ctatactcca catatccaaa caacaaagca taatatttca 100

<210> SEQ ID NO 678
<211> LENGTH: 100
<212> TYPE: DNA
<213> ORGANISM: Homo sapiens

<400> SEQUENCE: 678
ccaacaaact aggaggcgta ctggccctcc tactatcaat cctcatccta gcagcaattc 60
ccacacttca catgtccaaa caacaaagca taatattctg 100

<210> SEQ ID NO 679
<211> LENGTH: 100
<212> TYPE: DNA
<213> ORGANISM: Homo sapiens

<400> SEQUENCE: 679
cccactaagc caatcacttt attgactcct agccgcagac ctcctcattc taacctgaat 60
cggaggacaa ccagtaagct accctttac catcattgga 100

<210> SEQ ID NO 680
<211> LENGTH: 100
<212> TYPE: DNA
<213> ORGANISM: Homo sapiens

<400> SEQUENCE: 680
cccattaagc caattcctat attgattcct agccacagac cttcttaccc taacctgaat 60
tggaggacaa ccagtgaact acccccttcac taccatcgga 100

<210> SEQ ID NO 681
<211> LENGTH: 100
<212> TYPE: DNA
<213> ORGANISM: Homo sapiens

<400> SEQUENCE: 681
caagtagcat ccgtactata cttcacaaca atcctaatcc taataccaac tatctcccta 60
attgaaaaca aaatactcaa atgggcctgt ccttgtagta 100

<210> SEQ ID NO 682
<211> LENGTH: 100
<212> TYPE: DNA
<213> ORGANISM: Homo sapiens

<400> SEQUENCE: 682
caagtagcat ccgtactata cttcacgaca attttaatcc tcataccagc cacctcctca 60
atcgaaaata aaatactcaa atggacctgc ccctgtagta 100

<210> SEQ ID NO 683
<211> LENGTH: 100
<212> TYPE: DNA
<213> ORGANISM: Homo sapiens

<400> SEQUENCE: 683
taaactaata caccagtctt gtaaaccgga gacgaaaacc tttttccaag gacaaatcag 60
agaaaaagtc tttaactcca ccattagcac ccaaagctaa 100

<210> SEQ ID NO 684

<211> LENGTH: 100
<212> TYPE: DNA
<213> ORGANISM: Homo sapiens

<400> SEQUENCE: 684
taaaccaata caccggtctt gtaaactgga aatgaagact tccttccaag gacaaatcag 60
agaaaaagta cttgacttca ccatcagcac ccaaagctaa 100

<210> SEQ ID NO 685
<211> LENGTH: 100
<212> TYPE: DNA
<213> ORGANISM: Homo sapiens

<400> SEQUENCE: 685
taaaccaata tattggtctt gtaaaccaga aatggagact ctctcccaag gacaactcag 60
agaaaaagta cttgacttca ccatcagcac ccaaagctaa 100

<210> SEQ ID NO 686
<211> LENGTH: 100
<212> TYPE: DNA
<213> ORGANISM: Homo sapiens

<400> SEQUENCE: 686
gattctaatt taaactattc tctgttcttt catggggaag cagatttggg taccacccaa 60
gtattgactc acccatcaac aaccgctatg tatttcgtac 100

<210> SEQ ID NO 687
<211> LENGTH: 100
<212> TYPE: DNA
<213> ORGANISM: Homo sapiens

<400> SEQUENCE: 687
attactgcca gccaccatga atattgtacg gtaccataaa tacttgacca cctgtagtac 60
ataaaaaccc aacccacatc aaaccccccc cccccatgct 100

<210> SEQ ID NO 688
<211> LENGTH: 100
<212> TYPE: DNA
<213> ORGANISM: Homo sapiens

<400> SEQUENCE: 688
tacaagcaag tacagcaatc aaccttcaac tatcacacat caactgcaac tccaaagcca 60
cccctcaccc actaggatac caacaaacct acccaccctt 100

<210> SEQ ID NO 689
<211> LENGTH: 100
<212> TYPE: DNA
<213> ORGANISM: Homo sapiens

<400> SEQUENCE: 689
aacagtacat agtacataaa gtcatttacc gtacatagca cattacagtc aaatcccttc 60
tcgtccccat ggatgacccc cctcagatag gggtcccttg 100

<210> SEQ ID NO 690
<211> LENGTH: 100
<212> TYPE: DNA
<213> ORGANISM: Homo sapiens

<400> SEQUENCE: 690
accaccatcc tccgtgaaat caatatcccg cacaagagtg ctactctcct cgctccgggc 60
ccataacact tgggggtagc taaagtgaac tgtatccgac 100

<210> SEQ ID NO 691
<211> LENGTH: 100
<212> TYPE: DNA
<213> ORGANISM: Homo sapiens

<400> SEQUENCE: 691
ttcaccatcc tctgtgaaat caatatcctg cagaagagtg ctactcttct tgatccaggt 60
ccataatact tgggggtagc tataatgaac tgtatccggc 100

<210> SEQ ID NO 692
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 692
acgttggatg ggtctattac cctattaatc ag 32

<210> SEQ ID NO 693
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 693
acgttggatg tctggggcca gcgtttca 28

<210> SEQ ID NO 694
<211> LENGTH: 18
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (8)..(8)
<223> OTHER INFORMATION: Inosine

<400> SEQUENCE: 694
gcgtgcanac cccccaga 18

<210> SEQ ID NO 695
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 695
acgttggatg aggtctatca ccctattaac cac 33

<210> SEQ ID NO 696
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 696
acgttggatg tccggctcca gcgtctcg 28

<210> SEQ ID NO 697
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 697
acgttggatg gcctacatca gaccaaaata cttc 34

<210> SEQ ID NO 698
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 698
acgttggatg aacagtgtgg gtaataatgg tttca 35

<210> SEQ ID NO 699
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 699
actgacaatt aacagcccaa tatcta 26

<210> SEQ ID NO 700
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 700
acgttggatg ctgcgtcaga tcaaaacact ga 32

<210> SEQ ID NO 701
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 701
acgttggatg gacagtgagg gtaataatga cttgt 35

<210> SEQ ID NO 702
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 702
acgttggatg tcatatacca aatttctccc tcat 34

<210> SEQ ID NO 703
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 703
acgttggatg gagtatgcta agattttgcg tagt 34

<210> SEQ ID NO 704
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 704
agccttctcc tcactct 17

<210> SEQ ID NO 705
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 705
acgttggatg tcatatacca aatctctccc tcac 34

<210> SEQ ID NO 706
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 706
acgttggatg gagtatgcta agattttgcg tagc 34

<210> SEQ ID NO 707
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 707
acgttggatg cctatctctc ccagtcctag cc 32

<210> SEQ ID NO 708
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 708
acgttggatg gaatggggtc tcctcctccg gct 33

<210> SEQ ID NO 709
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 709
atcactatac tactaacaga ccg 23

<210> SEQ ID NO 710
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 710
acgttggatg cctatctctc ccagtcctag ct 32

<210> SEQ ID NO 711
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 711
acgttggatg aatggggtct cctcctccgg cg 32

<210> SEQ ID NO 712
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 712
acgttggatg ctccctaaaa gcagtagtgc 30

<210> SEQ ID NO 713
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 713
acgttggatg ctacagccac tctaggttag 30

<210> SEQ ID NO 714
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 714
tactattagg acttttcgct t 21

<210> SEQ ID NO 715
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 715
acgttggatg cattcatttc tctaacagca gtaatat 37

<210> SEQ ID NO 716
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 716
acgttggatg catccatata gtcactccag gttta 35

<210> SEQ ID NO 717
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 717
acgttggatg gatttcactt ccactccaca acc 33

<210> SEQ ID NO 718
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 718
acgttggatg tcccgtatcg aaggcctttc 30

<210> SEQ ID NO 719
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 719
ggcgtgttac atcgcgcca 19

<210> SEQ ID NO 720
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 720
acgttggatg gatttcactt ccactccata acg 33

<210> SEQ ID NO 721
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 721
acgttggatg tcccgtatcg aaggcctttt 30

<210> SEQ ID NO 722
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 722
acgttggatg tagctgctcc ctatccttc 29

<210> SEQ ID NO 723
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 723
acgttggatg ttcgttggat aggtggcgc 29

<210> SEQ ID NO 724
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 724
cactcctaat actaactacc tgact 25

<210> SEQ ID NO 725
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 725
acgttggatg tagctgttcc ccaaccttt 29

<210> SEQ ID NO 726
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 726
acgttggatg ttcgctggat aagtggcgt 29

<210> SEQ ID NO 727
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 727
acgttggatg cggttgatgg tatgctcgaa 30

<210> SEQ ID NO 728
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 728
acgttggatg tgtaggagga atcatgctag ggct 34

<210> SEQ ID NO 729
<211> LENGTH: 24
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (8)..(8)
<223> OTHER INFORMATION: Inosine

<400> SEQUENCE: 729
ggaagcantc ctatacaacc gtat 24

<210> SEQ ID NO 730
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 730
acgttggatg cagttgatga tacgcccgag 30

<210> SEQ ID NO 731
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 731
acgttggatg tgtaggataa atcatgctaa ggcg 34

<210> SEQ ID NO 732
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 732
acgttggatg cacagcccta ggcatcacc 29

<210> SEQ ID NO 733
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 733
acgttggatg gtgaaatgta cacagtgggt t 31

<210> SEQ ID NO 734
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 734
cagccctaga cctcaactac 20

<210> SEQ ID NO 735
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 735
acgttggatg cacagccctc gctgtcact 29

<210> SEQ ID NO 736
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 736
acgttggatg ataaaatgtg catagtgggg a 31

<210> SEQ ID NO 737
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 737
acgttggatg cccagacaac tacaccctga ct 32

<210> SEQ ID NO 738
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 738
acgttggatg gcctcctagt ttattgggaa t 31

<210> SEQ ID NO 739
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 739
gaataggaaa tatcattcgg g 21

<210> SEQ ID NO 740
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 740
acgttggatg cccagacaat tataccctag cc 32

<210> SEQ ID NO 741
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 741
acgttggatg gcctcctagt ttgttaggga c 31

<210> SEQ ID NO 742
<211> LENGTH: 19
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (8)..(8)
<223> OTHER INFORMATION: Inosine

<400> SEQUENCE: 742
gcgtgcanac cccccagac 19

<210> SEQ ID NO 743
<211> LENGTH: 19
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (8)..(8)
<223> OTHER INFORMATION: Inosine

<400> SEQUENCE: 743
gcgtgcanac cccccagat 19

<210> SEQ ID NO 744
<211> LENGTH: 27
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 744

actgacaatt aacagcccaa tatctac                                          27


<210> SEQ ID NO 745
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 745

actgacaatt aacagcccaa tatctat                                          27


<210> SEQ ID NO 746
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 746

agccttctcc tcactctc                                                    18


<210> SEQ ID NO 747
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 747

agccttctcc tcactctt                                                    18


<210> SEQ ID NO 748
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 748

atcactatac tactaacaga ccgc                                             24


<210> SEQ ID NO 749
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 749

atcactatac tactaacaga ccgt                                             24


<210> SEQ ID NO 750
<211> LENGTH: 22
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 750
tactattagg acttttcgct tc 22

<210> SEQ ID NO 751
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 751
tactattagg acttttcgct tt 22

<210> SEQ ID NO 752
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 752
ggcgtgttac atcgcgccac 20

<210> SEQ ID NO 753
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 753
ggcgtgttac atcgcgccat 20

<210> SEQ ID NO 754
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 754
cactcctaat actaactacc tgactc 26

<210> SEQ ID NO 755
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 755
cactcctaat actaactacc tgactt 26

<210> SEQ ID NO 756
<211> LENGTH: 25
<212> TYPE: DNA
<213> ORGANISM: Artificial Sequence
<220> FEATURE:

<223> OTHER INFORMATION: Description of Artificial Sequence: Synthetic
      primer
<220> FEATURE:
<221> NAME/KEY: modified_base
<222> LOCATION: (8)..(8)
<223> OTHER INFORMATION: Inosine

<400> SEQUENCE: 756
ggaagcantc ctatacaacc gtatc 25

<210> SEQ ID NO 757
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (8)..(8)
<223> OTHER INFORMATION: Inosine

<400> SEQUENCE: 757
ggaagcantc ctatacaacc gtatct 26

<210> SEQ ID NO 758
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 758
cagccctaga cctcaactac c 21

<210> SEQ ID NO 759
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 759
cagccctaga cctcaactac t 21

<210> SEQ ID NO 760
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 760
gaataggaaa tatcattcgg gc 22

<210> SEQ ID NO 761
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 761
gaataggaaa tatcattcgg gt 22

<210> SEQ ID NO 762
<211> LENGTH: 101
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 762
ggtctattac cctattaatc agtcacggga gctctccatg catttggtat tttaatctgg 60
ggggtgtgca cgcgatagca ttgtgaaacg ctggccccag a 101

<210> SEQ ID NO 763
<211> LENGTH: 18
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (11)..(11)
<223> OTHER INFORMATION: a, c, t, g, unknown or other

<400> SEQUENCE: 763
tctggggggt ntgcacgc 18

<210> SEQ ID NO 764
<211> LENGTH: 102
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 764
aggtctatca ccctattaac cactcacggg agctctccat gcatttggta ttttcgtctg 60
gggggtgtgc acgcgatagc attgcgagac gctggagccg ga 102

<210> SEQ ID NO 765
<211> LENGTH: 18
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (11)..(11)
<223> OTHER INFORMATION: a, c, t, g, unknown or other

<400> SEQUENCE: 765
tctggggggt ntgcacgc 18

<210> SEQ ID NO 766
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 766
gcctacatca gaccaaaata cttcactgac aattaacagc ccaatatcta taaataatca 60
atgaaaccat tattacccac actgtt 86

<210> SEQ ID NO 767
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 767
actgacaatt aacagcccaa tatcta 26

<210> SEQ ID NO 768
<211> LENGTH: 83
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 768
ctgcgtcaga tcaaaacact gaactgacaa ttaacagccc aatatctaca atcaaccaac 60
aagtcattat taccctcact gtc 83

<210> SEQ ID NO 769
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 769
actgacaatt aacagcccaa tatcta 26

<210> SEQ ID NO 770
<211> LENGTH: 124
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 770
tcatatacca aatttctccc tcattaaacg taagccttct cctcactctt tcaatcttat 60
ccatcatggc aggcagttga ggtggattaa accaaaccca actacgcaaa atcttagcat 120
actc 124

<210> SEQ ID NO 771
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 771
agccttctcc tcactct 17

<210> SEQ ID NO 772
<211> LENGTH: 124
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 772
tcatatacca aatctctccc tcactaaacg taagccttct cctcactctc tcaatcttat 60
ccatcatagc aggcagttga ggtggattaa accaaaccca gctacgcaaa atcttagcat 120
actc 124

<210> SEQ ID NO 773
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 773
agccttctcc tcactct 17

<210> SEQ ID NO 774
<211> LENGTH: 101
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 774
cctatctctc ccagtcctag ccgctggcat cactatacta ctaacagacc gtaacctcaa 60
caccaccttc ttcgacccag ccggaggagg agaccccatt c 101

<210> SEQ ID NO 775
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 775
atcactatac tactaacaga ccg 23

<210> SEQ ID NO 776
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 776
cctatctctc ccagtcctag ctgctggcat cactatacta ctaacagacc gcaacctcaa 60
caccaccttc ttcgaccccg ccggaggagg agaccccatt 100

<210> SEQ ID NO 777
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 777
atcactatac tactaacaga ccg 23

<210> SEQ ID NO 778
<211> LENGTH: 109
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 778
ctccctaaaa gcagtagtgc taataatttt cataacctga gagaccttcg cttcaaagcg 60
aaaagtccta ataaatgagc aaccttccac taacctagag tggctgtag 109

<210> SEQ ID NO 779
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 779
aagcgaaaag tcctaatagt a 21

<210> SEQ ID NO 780
<211> LENGTH: 121
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 780
cattcatttc tctaacagca gtaatattaa taattttcat aatttgagaa gccttcgctt 60
cgaagcgaaa agtcctaata gtagaagaac cctccataaa cctggagtga ctatatggat 120
g 121

<210> SEQ ID NO 781
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 781
aagcgaaaag tcctaatagt a 21

<210> SEQ ID NO 782
<211> LENGTH: 121
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 782
cattcatttc tctaacagca gtaatattaa taattttcat gatttgagaa gccttcgctt 60
cgaagcgaaa agtcctaata gtagaagaac cctccataaa cctggagtga ctatatggat 120
g 121

<210> SEQ ID NO 783
<211> LENGTH: 21
<212> TYPE: DNA

<213> ORGANISM: Artificial Sequence
<220> FEATURE:
<223> OTHER INFORMATION: Description of Artificial Sequence: Synthetic primer

<400> SEQUENCE: 783
aagcgaaaag tcctaatagt a 21

<210> SEQ ID NO 784
<211> LENGTH: 147
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 784
gatttcactt ccactccaca accctcctca tactaggcct actaaccaac acactaacca 60
tataccaatg atggcgcgat gtaacacgag aaagcacata ccaaggccac cacacaccac 120
ctgtccagaa aggccttcga tacggga 147

<210> SEQ ID NO 785
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 785
tggcgcgatg taacacg 17

<210> SEQ ID NO 786
<211> LENGTH: 147
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 786
gatttcactt ccactccata acgctcctca tactaggcct actaaccaac acactaacca 60
tataccaatg gtggcgcgat gtaacacgag aaagcacata ccaaggccac cacacaccac 120
ctgtccaaaa aggccttcga tacggga 147

<210> SEQ ID NO 787
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 787
tggcgcgatg taacacg 17

<210> SEQ ID NO 788
<211> LENGTH: 112
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 788
tagctgctcc ctatccttct cctccgaccc cctaacgacc cccctcctaa tactaactac 60
ctgacttcta cccctcacaa tcatggcaag ccagcgccac ctatccaacg aa 112

<210> SEQ ID NO 789
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 789
ctcctaatac taactacctg act 23

<210> SEQ ID NO 790
<211> LENGTH: 112
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 790
tagctgttcc ccaacctttt cctccgaccc cctaacaacc cccctcctaa tactaactac 60
ctgactccta cccctcacaa tcatggcaag ccaacgccac ttatccagcg aa 112

<210> SEQ ID NO 791
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 791
ctcctaatac taactacctg act 23

<210> SEQ ID NO 792
<211> LENGTH: 111
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 792
cggttgatgg tatgctcgaa cagatgccaa cacagcagcc atcccagcaa tcctatacaa 60
ccgtattggc gacattggct tcatcctagc cctagcatga ttcctcctac a 111

<210> SEQ ID NO 793
<211> LENGTH: 22
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (6)..(6)
<223> OTHER INFORMATION: a, c, t, g, unknown or other

<400> SEQUENCE: 793
aagcantcct atacaaccgt at 22

<210> SEQ ID NO 794
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 794
cagttgatga tacgcccgag cagatgccaa cacagcagcc attcaagcag tcctatacaa     60
ccgtatcggc gatatcggtt tcatcctcgc cttagcatga tttatcctac a             111

<210> SEQ ID NO 795
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: a, c, t, g, unknown or other

<400> SEQUENCE: 795
aagcantcct atacaaccgt at                                              22

<210> SEQ ID NO 796
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 796
cacagcccta ggcatcacct tcctaggact tctgacagcc ctagacctca actacttaac     60
caacaaactc aaaataaaaa acccactgtg tacatttcac                          100

<210> SEQ ID NO 797
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 797
cagccctaga cctcaactac                                                 20

<210> SEQ ID NO 798
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 798
cacagccctc gctgtcactt tcctaggact tctaacagcc ctagacctca actacctaac     60
caacaaactt aaaataaaat ccccactatg cacattttat                          100

<210> SEQ ID NO 799
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 799
cagccctaga cctcaactac 20

<210> SEQ ID NO 800
<211> LENGTH: 115
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 800
cccagacaac tacaccctga ctaaccccct aaacacccca ccccacatca aacccgaatg 60
atatttccta ttcgcctacg caattctccg atccattccc aataaactag gaggc 115

<210> SEQ ID NO 801
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 801
cccgaatgat atttcctatt c 21

<210> SEQ ID NO 802
<211> LENGTH: 115
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 802
cccagacaat tataccctag ccaacccctt aaacacccct ccccacatca agcccgaatg 60
atatttccta ttcgcctaca caattctccg atccgtccct aacaaactag gaggc 115

<210> SEQ ID NO 803
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 803
cccgaatgat atttcctatt c 21

<210> SEQ ID NO 804
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 804
acgttggatg gatctaaaac actctttac 29

<210> SEQ ID NO 805

<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 805
acgttggatg tcacacgatt aacccaagtc 30

<210> SEQ ID NO 806
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 806
acgttggatg ttgtgtagag ttcaggggag 30

<210> SEQ ID NO 807
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 807
acgttggatg ctacaatctt cctaggaaca 30

<210> SEQ ID NO 808
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 808
acgttggatg gaggagtatg ctaagatttt 30

<210> SEQ ID NO 809
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 809
acgttggatg cagttgaggt ggattaaacc 30

<210> SEQ ID NO 810
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 810
acgttggatg ctactccacc tcaatcacac 30

<210> SEQ ID NO 811
<211> LENGTH: 33

<212> TYPE: DNA
<213> ORGANISM: Artificial Sequence
<220> FEATURE:
<223> OTHER INFORMATION: Description of Artificial Sequence: Synthetic
primer

<400> SEQUENCE: 811
acgttggatg cattttattt ttacgttgtt aga 33

<210> SEQ ID NO 812
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 812
acgttggatg aggccatcaa tttcatcaca 30

<210> SEQ ID NO 813
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 813
acgttggatg gggttatggc agggggtt 28

<210> SEQ ID NO 814
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 814
acgttggatg ccggcgtcaa agtatttagc 30

<210> SEQ ID NO 815
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 815
acgttggatg atttcatatt gcttccgtgg 30

<210> SEQ ID NO 816
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 816
acgttggatg gcctaatgtg gggacagc 28

<210> SEQ ID NO 817
<211> LENGTH: 30
<212> TYPE: DNA

<213> ORGANISM: Artificial Sequence
<220> FEATURE:
<223> OTHER INFORMATION: Description of Artificial Sequence: Synthetic
primer

<400> SEQUENCE: 817
acgttggatg taataattac atcacaagac 30

<210> SEQ ID NO 818
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 818
acgttggatg cttcattcat tgcccccaca 30

<210> SEQ ID NO 819
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 819
acgttggatg gaatgatcag tactgcggcg 30

<210> SEQ ID NO 820
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 820
acgttggatg cgccttaatc caagcctac 29

<210> SEQ ID NO 821
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 821
acgttggatg gcaggtagag gcttactaga 30

<210> SEQ ID NO 822
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 822
acgttggatg gggatatagg gtcgaagccg 30

<210> SEQ ID NO 823
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 823
acgttggatg ggctacatag aaaaatccac 30

<210> SEQ ID NO 824
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 824
acgttggatg gatctaaaac actctttac 29

<210> SEQ ID NO 825
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 825
aaaacactct ttacgccgg 19

<210> SEQ ID NO 826
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 826
aaaacactct ttacgccggc 20

<210> SEQ ID NO 827
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 827
aaaacactct ttacgccggt 20

<210> SEQ ID NO 828
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 828
acgttggatg ttgtgtagag ttcaggggag 30

<210> SEQ ID NO 829
<211> LENGTH: 17
<212> TYPE: DNA
<213> ORGANISM: Artificial Sequence
<220> FEATURE:

<223> OTHER INFORMATION: Description of Artificial Sequence: Synthetic primer

<400> SEQUENCE: 829
ttcaggggag agtgcgt 17

<210> SEQ ID NO 830
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 830
ttcaggggag agtgcgtc 18

<210> SEQ ID NO 831
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 831
ttcaggggag agtgcgtt 18

<210> SEQ ID NO 832
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 832
acgttggatg gaggagtatg ctaagatttt 30

<210> SEQ ID NO 833
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 833
tatgctaaga ttttgcgtag 20

<210> SEQ ID NO 834
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 834
tatgctaaga ttttgcgtag c 21

<210> SEQ ID NO 835
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 835
tatgctaaga ttttgcgtag t 21

<210> SEQ ID NO 836
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 836
acgttggatg ctactccacc tcaatcacac 30

<210> SEQ ID NO 837
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 837
ctcaatcaca ctactccc 18

<210> SEQ ID NO 838
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 838
ctcaatcaca ctactcccc 19

<210> SEQ ID NO 839
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 839
ctcaatcaca ctactccct 19

<210> SEQ ID NO 840
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 840
acgttggatg aggccatcaa tttcatcaca 30

<210> SEQ ID NO 841
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 841
atcaatttca tcacaacaat tat 23

<210> SEQ ID NO 842
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 842
atcaatttca tcacaacaat tatc 24

<210> SEQ ID NO 843
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 843
atcaatttca tcacaacaat tatt 24

<210> SEQ ID NO 844
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 844
acgttggatg ccggcgtcaa agtatttagc 30

<210> SEQ ID NO 845
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 845
agtatttagc tgactcgc 18

<210> SEQ ID NO 846
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 846
agtatttagc tgactcgcc 19

<210> SEQ ID NO 847
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 847
agtatttagc tgactcgct 19

<210> SEQ ID NO 848
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 848
acgttggatg gcctaatgtg gggacagc 28

<210> SEQ ID NO 849
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 849
gggacagctc atgagtg 17

<210> SEQ ID NO 850
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 850
gggacagctc atgagtgc 18

<210> SEQ ID NO 851
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 851
gggacagctc atgagtgt 18

<210> SEQ ID NO 852
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 852
acgttggatg cttcattcat tgcccccaca 30

<210> SEQ ID NO 853
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 853
gcccccacaa tcctagg 17

<210> SEQ ID NO 854
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 854
gcccccacaa tcctaggc 18

<210> SEQ ID NO 855
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 855
gcccccacaa tcctaggt 18

<210> SEQ ID NO 856
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 856
acgttggatg cgccttaatc caagcctac 29

<210> SEQ ID NO 857
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 857
atccaagcct acgtttt 17

<210> SEQ ID NO 858
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 858
atccaagcct acgttttc 18

<210> SEQ ID NO 859
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 859
atccaagcct acgttttt 18

<210> SEQ ID NO 860
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 860
acgttggatg gggatatagg gtcgaagccg 30

<210> SEQ ID NO 861
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 861
atatagggtc gaagccgca 19

<210> SEQ ID NO 862
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 862
atatagggtc gaagccgcac 20

<210> SEQ ID NO 863
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 863
atatagggtc gaagccgcat 20

<210> SEQ ID NO 864
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 864
tgatctaaaa cactctttac gccggtttct attgacttgg gttaatcgtg tga 53

<210> SEQ ID NO 865
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 865
aaaacactct ttacgccgg 19

<210> SEQ ID NO 866
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 866
tgatctaaaa cactctttat gccggtttct attgacttgg gttaatcgtg tga 53

<210> SEQ ID NO 867
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 867
aaaacactct ttacgccgg 19

<210> SEQ ID NO 868
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 868
tcacacgatt aacccaagtc aatagaagcc ggcgtaaaga gtgttttaga tca 53

<210> SEQ ID NO 869
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 869
ccggcgtaaa gagtgtttt 19

<210> SEQ ID NO 870
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 870
ctacaatctt cctaggaaca acatataacg cactctcccc tgaactctac acaa 54

<210> SEQ ID NO 871
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 871
acgcactctc ccctgaa 17

<210> SEQ ID NO 872
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 872
ctacaatctt cctaggaaca acatatgacg cactctcccc tgaactctac acaa 54

<210> SEQ ID NO 873
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 873
acgcactctc ccctgaa 17

<210> SEQ ID NO 874
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 874
cagttgaggt ggattaaacc aaacccaact acgcaaaatc ttagcatact cctc 54

<210> SEQ ID NO 875
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 875
ctacgcaaaa tcttagcata 20

<210> SEQ ID NO 876
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 876
cagttgaggt ggattaaacc aaacccagct acgcaaaatc ttagcatact cctc 54

<210> SEQ ID NO 877
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 877
ctacgcaaaa tcttagcata 20

<210> SEQ ID NO 878
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 878
ctactccacc tcaatcacac tactccctat atctaacaac gtaaaaataa aatg 54

<210> SEQ ID NO 879
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 879
ctcaatcaca ctactccc 18

<210> SEQ ID NO 880
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 880
ctactccacc tcaatcacac tactccccat atctaacaac gtaaaaataa aatg 54

<210> SEQ ID NO 881
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 881
ctcaatcaca ctactccc 18

<210> SEQ ID NO 882
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 882
gccatcaatt tcatcacaac aattattaat ataaaacccc ctgccataac cc 52

<210> SEQ ID NO 883
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 883
atcaatttca tcacaacaat tat 23

<210> SEQ ID NO 884

<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 884
gccatcaatt tcatcacaac aattatcaat ataaaacccc ctgccataac cc 52

<210> SEQ ID NO 885
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 885
atcaatttca tcacaacaat tat 23

<210> SEQ ID NO 886
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 886
ccggcgtcaa agtatttagc tgactcgcca cactccacgg aagcaatatg aaat 54

<210> SEQ ID NO 887
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 887
agtatttagc tgactcgc 18

<210> SEQ ID NO 888
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 888
ccggcgtcaa agtatttagc tgactcgcta cactccacgg aagcaatatg aaat 54

<210> SEQ ID NO 889
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 889
agtatttagc tgactcgc 18

<210> SEQ ID NO 890
<211> LENGTH: 54

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 890
ccggcgtcaa agtatttagc tgactcgcca cactccacgg aagcaatatg aaat 54

<210> SEQ ID NO 891
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 891
agtatttagc tgactcgc 18

<210> SEQ ID NO 892
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 892
taataattac atcacaagac gtcttacact catgagctgt ccccacatta ggc 53

<210> SEQ ID NO 893
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 893
cactcatgag ctgtccc 17

<210> SEQ ID NO 894
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 894
gcctaatgtg gggacagctc atgagtgtaa gacgtcttgt gatgtaatta tta 53

<210> SEQ ID NO 895
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 895
gggacagctc atgagtg 17

<210> SEQ ID NO 896
<211> LENGTH: 53
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 896

taataattac atcacaagac gtcttgcact catgagctgt ccccacatta ggc           53


<210> SEQ ID NO 897
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 897

cactcatgag ctgtccc                                                   17


<210> SEQ ID NO 898
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 898

cttcattcat tgcccccaca atcctaggcc tacccgccgc agtactgatc attc          54


<210> SEQ ID NO 899
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 899

gcccccacaa tcctagg                                                   17


<210> SEQ ID NO 900
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 900

cttcattcat tgcccccaca atcctaggtc tgcccgccgc agtactgatc attc          54


<210> SEQ ID NO 901
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 901

gcccccacaa tcctagg                                                   17


<210> SEQ ID NO 902
<211> LENGTH: 54
<212> TYPE: DNA
<213> ORGANISM: Artificial Sequence
```

<220> FEATURE:
<223> OTHER INFORMATION: Description of Artificial Sequence: Synthetic
oligonucleotide

<400> SEQUENCE: 902
cttcattcat tgcccccaca atcctaggcc tacccgccgc agtactgatc attc 54

<210> SEQ ID NO 903
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 903
gcccccacaa tcctagg 17

<210> SEQ ID NO 904
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 904
ctgtcgcctt aatccaagcc tacgttttta cacttctagt aagcctctac ctgc 54

<210> SEQ ID NO 905
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 905
atccaagcct acgtttt 17

<210> SEQ ID NO 906
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 906
ctgtcgcctt aatccaagcc tacgttttca cacttctagt aagcctctac ctgc 54

<210> SEQ ID NO 907
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 907
atccaagcct acgtttt 17

<210> SEQ ID NO 908
<211> LENGTH: 53
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 908
tacatagaaa aatccacccc ttacgaatgc ggcttcgacc ctatatcccc cgc            53

<210> SEQ ID NO 909
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 909
tgcggcttcg accctatat                                                  19

<210> SEQ ID NO 910
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 910
tacatagaaa aatccacccc ttacgagtgc ggcttcgacc ctatatcccc cgc            53

<210> SEQ ID NO 911
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 911
tgcggcttcg accctatat                                                  19

<210> SEQ ID NO 912
<211> LENGTH: 75
<212> TYPE: DNA
<213> ORGANISM: Pan troglodytes

<400> SEQUENCE: 912
gatcacaggt ctatcaccct attaaccagt cacgggagcc ttccatgcat ttggtatttt     60
cgtctggggg gtgtg                                                      75

<210> SEQ ID NO 913
<211> LENGTH: 75
<212> TYPE: DNA
<213> ORGANISM: Homo sapiens

<400> SEQUENCE: 913
gatcacaggt ctatcaccct attaaccact cacgggagct ctccatgcat ttggtatttt     60
cgtctggggg gtatg                                                      75

<210> SEQ ID NO 914
<211> LENGTH: 75
<212> TYPE: DNA
<213> ORGANISM: Pan troglodytes

<400> SEQUENCE: 914
cacgcgatag cattgcgaaa cgctggcccc ggagcaccct atgtcgcagt atctgtcttt     60
gattcctgcc ccatt 75

<210> SEQ ID NO 915
<211> LENGTH: 75
<212> TYPE: DNA
<213> ORGANISM: Homo sapiens

<400> SEQUENCE: 915
cacgcgatag cattgcgaga cgctggagcc ggagcaccct atgtcgcagt atctgtcttt 60
gattcctgcc tcatc 75

<210> SEQ ID NO 916
<211> LENGTH: 75
<212> TYPE: DNA
<213> ORGANISM: Pan troglodytes

<400> SEQUENCE: 916
gtattattta tcgcacctac gttcaatatt acgacctagc atacctacta aagtgtgttg 60
attaattaat gcttg 75

<210> SEQ ID NO 917
<211> LENGTH: 75
<212> TYPE: DNA
<213> ORGANISM: Homo sapiens

<400> SEQUENCE: 917
ctattattta tcgcacctac gttcaatatt acaggcgaac atacttacta aagtgtgtta 60
attaattaat gcttg 75

<210> SEQ ID NO 918
<211> LENGTH: 75
<212> TYPE: DNA
<213> ORGANISM: Homo sapiens

<400> SEQUENCE: 918
taggacataa taataacaat tgaatgtctg cacagccact ttccacacag acatcataac 60
aaaaaatttc cacca 75

<210> SEQ ID NO 919
<211> LENGTH: 75
<212> TYPE: DNA
<213> ORGANISM: Pan troglodytes

<400> SEQUENCE: 919
cacaaacccc cccttccccc cggccacagc actcaaacaa atctctgcca aaccccaaaa 60
acaaagaacc cagac 75

<210> SEQ ID NO 920
<211> LENGTH: 75
<212> TYPE: DNA
<213> ORGANISM: Homo sapiens

<400> SEQUENCE: 920 aacccccccct cccccgcttc tggccacagc acttaaacac atctctgcca aaccccaaaa 60
acaaagaacc ctaac 75

<210> SEQ ID NO 921
<211> LENGTH: 75
<212> TYPE: DNA

<213> ORGANISM: Pan troglodytes

<400> SEQUENCE: 921
gccagcctag ccagacttca aatttcatct ttaggcggta tgcactttta acagtcaccc 60
ctcaattaac atgcc 75

<210> SEQ ID NO 922
<211> LENGTH: 75
<212> TYPE: DNA
<213> ORGANISM: Homo sapiens

<400> SEQUENCE: 922
accagcctaa ccagatttca aattttatct tttggcggta tgcactttta acagtcaccc 60
cccaactaac acatt 75

<210> SEQ ID NO 923
<211> LENGTH: 75
<212> TYPE: DNA
<213> ORGANISM: Homo sapiens

<400> SEQUENCE: 923
attttcccct cccactccca tactactaat ctcatcaata caacccccgc ccatcctacc 60
cagcacacac acacc 75

<210> SEQ ID NO 924
<211> LENGTH: 75
<212> TYPE: DNA
<213> ORGANISM: Homo sapiens

<400> SEQUENCE: 924
gctgctaacc ccataccccg aaccaaccaa accccaaaga cacccccac agtttatgta 60 gcttacctcc tcaaa 75

<210> SEQ ID NO 925
<211> LENGTH: 75
<212> TYPE: DNA
<213> ORGANISM: Pan troglodytes

<400> SEQUENCE: 925
gcaatacact gaaaatgttt cgacgggttt acatcacccc ataaacaaac aggtttggtc 60
ctagcctttc tatta 75

<210> SEQ ID NO 926
<211> LENGTH: 75
<212> TYPE: DNA
<213> ORGANISM: Homo sapiens

<400> SEQUENCE: 926
gcaatacact gaaaatgttt agacgggctc acatcacccc ataaacaaat aggtttggtc 60
ctagcctttc tatta 75

<210> SEQ ID NO 927
<211> LENGTH: 75
<212> TYPE: DNA
<213> ORGANISM: Homo sapiens

<400> SEQUENCE: 927
gctcttagta agattacaca tgcaagcatc cccgttccag tgagttcacc ctctaaatca 60
ccacgatcaa aagga 75

<210> SEQ ID NO 928
<211> LENGTH: 75
<212> TYPE: DNA
<213> ORGANISM: Pan troglodytes

<400> SEQUENCE: 928
acaagtatca agcacgcagc aatgcagctc aaaacgctta gcctagccac acccccacgg 60
gagacagcag tgata 75

<210> SEQ ID NO 929
<211> LENGTH: 75
<212> TYPE: DNA
<213> ORGANISM: Homo sapiens

<400> SEQUENCE: 929
acaagcatca agcacgcagc aatgcagctc aaaacgctta gcctagccac acccccacgg 60
gaaacagcag tgatt 75

<210> SEQ ID NO 930
<211> LENGTH: 75
<212> TYPE: DNA
<213> ORGANISM: Pan troglodytes

<400> SEQUENCE: 930
aacctttagc aataaacgaa agtttaacta agccatacta acctcagggt tggtcaattt 60
cgtgctagcc accgc 75

<210> SEQ ID NO 931
<211> LENGTH: 75
<212> TYPE: DNA
<213> ORGANISM: Homo sapiens

<400> SEQUENCE: 931
aacctttagc aataaacgaa agtttaacta agctatacta accccagggt tggtcaattt 60
cgtgccagcc accgc 75

<210> SEQ ID NO 932
<211> LENGTH: 75
<212> TYPE: DNA
<213> ORGANISM: Pan troglodytes

<400> SEQUENCE: 932
ggtcatacga ttaacccaag tcaatagaaa ccggcgtaaa gagtgtttta gatcaccccc 60
ccataaagct aaaat 75

<210> SEQ ID NO 933
<211> LENGTH: 75
<212> TYPE: DNA
<213> ORGANISM: Homo sapiens

<400> SEQUENCE: 933
ggtcacacga ttaacccaag tcaatagaag ccggcgtaaa gagtgtttta gatcaccccc 60
tccccaataa agcta 75

<210> SEQ ID NO 934
<211> LENGTH: 75
<212> TYPE: DNA
<213> ORGANISM: Pan troglodytes

<400> SEQUENCE: 934
aaattcacct gagttgtaaa aaactccagc tgatacaaaa taaactacga aagtggcttt 60
aacacatctg aatac 75

<210> SEQ ID NO 935
<211> LENGTH: 75
<212> TYPE: DNA
<213> ORGANISM: Homo sapiens

<400> SEQUENCE: 935
aaactcacct gagttgtaaa aaactccagt tgacacaaaa tagactacga aagtggcttt 60
aacatatctg aacac 75

<210> SEQ ID NO 936
<211> LENGTH: 75
<212> TYPE: DNA
<213> ORGANISM: Pan troglodytes

<400> SEQUENCE: 936
acaatagcta agacccaaac tgggattaga taccccacta tgcttagccc taaacttcaa 60
cagttaaatt aacaa 75

<210> SEQ ID NO 937
<211> LENGTH: 75
<212> TYPE: DNA
<213> ORGANISM: Homo sapiens

<400> SEQUENCE: 937
acaatagcta agacccaaac tgggattaga taccccacta tgcttagccc taaacctcaa 60
cagttaaatc aacaa 75

<210> SEQ ID NO 938
<211> LENGTH: 75
<212> TYPE: DNA
<213> ORGANISM: Pan troglodytes

<400> SEQUENCE: 938
aactgctcgc cagaacacta cgagccacag cttaaaactc aaaggacctg gcggtgcttc 60
atatccctct agagg 75

<210> SEQ ID NO 939
<211> LENGTH: 75
<212> TYPE: DNA
<213> ORGANISM: Homo sapiens

<400> SEQUENCE: 939
aactgctcgc cagaacacta cgagccacag cttaaaactc aaaggacctg gcggtgcttc 60
atatccctct agagg 75

<210> SEQ ID NO 940
<211> LENGTH: 75
<212> TYPE: DNA
<213> ORGANISM: Pan troglodytes

<400> SEQUENCE: 940
agcctgttct gtaatcgata aaccccgatc aacctcaccg cctcttgctc agcctatata 60
ccgccatctt cagca 75

<210> SEQ ID NO 941
<211> LENGTH: 75
<212> TYPE: DNA
<213> ORGANISM: Homo sapiens

<400> SEQUENCE: 941
agcctgttct gtaatcgata aaccccgatc aacctcacca cctcttgctc agcctatata 60
ccgccatctt cagca 75

<210> SEQ ID NO 942
<211> LENGTH: 75
<212> TYPE: DNA
<213> ORGANISM: Pan troglodytes

<400> SEQUENCE: 942
aaccctgatg aaggttacaa agtaagcaca agtacccacg taaagacgtt aggtcaaggt 60
gtagcctatg aggtg 75

<210> SEQ ID NO 943
<211> LENGTH: 75
<212> TYPE: DNA
<213> ORGANISM: Homo sapiens

<400> SEQUENCE: 943
aaccctgatg aaggctacaa agtaagcgca agtacccacg taaagacgtt aggtcaaggt 60
gtagcccatg aggtg 75

<210> SEQ ID NO 944
<211> LENGTH: 75
<212> TYPE: DNA
<213> ORGANISM: Pan troglodytes

<400> SEQUENCE: 944
gcaagaaatg ggctacattt tctaccccag aaaattacga taacccttat gaaacctaag 60
ggtcaaaggt ggatt 75

<210> SEQ ID NO 945
<211> LENGTH: 75
<212> TYPE: DNA
<213> ORGANISM: Homo sapiens

<400> SEQUENCE: 945
gcaagaaatg ggctacattt tctaccccag aaaactacga tagcccttat gaaacttaag 60
ggtcgaaggt ggatt 75

<210> SEQ ID NO 946
<211> LENGTH: 75
<212> TYPE: DNA
<213> ORGANISM: Pan troglodytes

<400> SEQUENCE: 946
tagcagtaaa ctaagagtag agtgcttagt tgaacagggc cctgaagcgc gtacacaccg 60
cccgtcaccc tcctc 75

<210> SEQ ID NO 947
<211> LENGTH: 75
<212> TYPE: DNA
<213> ORGANISM: Homo sapiens

<400> SEQUENCE: 947
tagcagtaaa ctaagagtag agtgcttagt tgaacagggc cctgaagcgc gtacacaccg 60
cccgtcaccc tcctc 75

<210> SEQ ID NO 948
<211> LENGTH: 75
<212> TYPE: DNA
<213> ORGANISM: Homo sapiens

<400> SEQUENCE: 948
aagtatactt caaaggacat ttaactaaaa cccctacgca tttatataga ggagacaagt 60
cgtaacatgg taagt 75

<210> SEQ ID NO 949
<211> LENGTH: 75
<212> TYPE: DNA
<213> ORGANISM: Pan troglodytes

<400> SEQUENCE: 949
gtactggaaa gtgcacttgg acgaaccaga gtgtagctta acataaagca cccaacttac 60
acttaggaga tttca 75

<210> SEQ ID NO 950
<211> LENGTH: 75
<212> TYPE: DNA
<213> ORGANISM: Homo sapiens

<400> SEQUENCE: 950
gtactggaaa gtgcacttgg acgaaccaga gtgtagctta acacaaagca cccaacttac 60
acttaggaga tttca 75

<210> SEQ ID NO 951
<211> LENGTH: 75
<212> TYPE: DNA
<213> ORGANISM: Pan troglodytes

<400> SEQUENCE: 951
actcaacttg accactctga gccaaaccta gccccaaacc ccctccaccc tactaccaaa 60
caaccttaac caaac 75

<210> SEQ ID NO 952
<211> LENGTH: 75
<212> TYPE: DNA
<213> ORGANISM: Homo sapiens

<400> SEQUENCE: 952
acttaacttg accgctctga gctaaaccta gccccaaacc cactccacct tactaccaga 60
caaccttagc caaac 75

<210> SEQ ID NO 953
<211> LENGTH: 75
<212> TYPE: DNA
<213> ORGANISM: Pan troglodytes

<400> SEQUENCE: 953
catttaccca aataaagtat aggcgataga aattgtaaac cggcgcaata gacatagtac 60
cgcaagggaa agatg 75

<210> SEQ ID NO 954
<211> LENGTH: 75

<212> TYPE: DNA
<213> ORGANISM: Homo sapiens

<400> SEQUENCE: 954
catttaccca aataaagtat aggcgataga aattgaaacc tggcgcaata gatatagtac 60
cgcaagggaa agatg 75

<210> SEQ ID NO 955
<211> LENGTH: 75
<212> TYPE: DNA
<213> ORGANISM: Pan troglodytes

<400> SEQUENCE: 955
aaaaattata cccaagcata atacagcaag gactaacccc tgtacctttt gcataatgaa 60
ttaactagaa ataac 75

<210> SEQ ID NO 956
<211> LENGTH: 75
<212> TYPE: DNA
<213> ORGANISM: Homo sapiens

<400> SEQUENCE: 956
aaaaattata accaagcata atatagcaag gactaacccc tataccttct gcataatgaa 60
ttaactagaa ataac 75

<210> SEQ ID NO 957
<211> LENGTH: 75
<212> TYPE: DNA
<213> ORGANISM: Pan troglodytes

<400> SEQUENCE: 957
tttgcaaaga gaaccaaagc taagaccccc gaaaccagac gagctaccta agaacagcta 60
aaagagcaca cccgt 75

<210> SEQ ID NO 958
<211> LENGTH: 75
<212> TYPE: DNA
<213> ORGANISM: Homo sapiens

<400> SEQUENCE: 958
tttgcaagga gagccaaagc taagaccccc gaaaccagac gagctaccta agaacagcta 60
aaagagcaca cccgt 75

<210> SEQ ID NO 959
<211> LENGTH: 75
<212> TYPE: DNA
<213> ORGANISM: Pan troglodytes

<400> SEQUENCE: 959
ctatgtagca aaatagtggg aagatttata ggtagaggcg acaaacctac cgagcctggt 60
gatagctggt tgtcc 75

<210> SEQ ID NO 960
<211> LENGTH: 75
<212> TYPE: DNA
<213> ORGANISM: Homo sapiens

<400> SEQUENCE: 960
ctatgtagca aaatagtggg aagatttata ggtagaggcg acaaacctac cgagcctggt 60
gatagctggt tgtcc 75

<210> SEQ ID NO 961
<211> LENGTH: 75
<212> TYPE: DNA
<213> ORGANISM: Pan troglodytes

<400> SEQUENCE: 961
aagatagaat cttagttcaa ctttaaattt acctacagaa ccctctaaat ccccttgtaa 60
acttaactgt tagtc 75

<210> SEQ ID NO 962
<211> LENGTH: 75
<212> TYPE: DNA
<213> ORGANISM: Homo sapiens

<400> SEQUENCE: 962
aagatagaat cttagttcaa ctttaaattt gcccacagaa ccctctaaat ccccttgtaa 60
atttaactgt tagtc 75

<210> SEQ ID NO 963
<211> LENGTH: 75
<212> TYPE: DNA
<213> ORGANISM: Pan troglodytes

<400> SEQUENCE: 963
caaagaggaa cagctcttta gacactagga aaaaaccttg taaagagagt aaaaaattta 60
acacccatag taggc 75

<210> SEQ ID NO 964
<211> LENGTH: 75
<212> TYPE: DNA
<213> ORGANISM: Homo sapiens

<400> SEQUENCE: 964
caaagaggaa cagctctttg gacactagga aaaaaccttg tagagagagt aaaaaattta 60
acacccatag taggc 75

<210> SEQ ID NO 965
<211> LENGTH: 75
<212> TYPE: DNA
<213> ORGANISM: Pan troglodytes

<400> SEQUENCE: 965
ctaaaagcag ccaccaatta agaaagcgtt caagctcaac acccacaacc ttaaagatcc 60
caaacataca accga 75

<210> SEQ ID NO 966
<211> LENGTH: 75
<212> TYPE: DNA
<213> ORGANISM: Homo sapiens

<400> SEQUENCE: 966
ctaaaagcag ccaccaatta agaaagcgtt caagctcaac acccactacc taaaaaatcc 60
caaacatata actga 75

<210> SEQ ID NO 967
<211> LENGTH: 75
<212> TYPE: DNA
<213> ORGANISM: Pan troglodytes

<400> SEQUENCE: 967
actccttaca cccaattgga ccaatctatt accccataga agaactaatg ttagtataag 60
taacatgaaa acatt 75

<210> SEQ ID NO 968
<211> LENGTH: 75
<212> TYPE: DNA
<213> ORGANISM: Homo sapiens

<400> SEQUENCE: 968
actcctcaca cccaattgga ccaatctatc accctataga agaactaatg ttagtataag 60
taacatgaaa acatt 75

<210> SEQ ID NO 969
<211> LENGTH: 75
<212> TYPE: DNA
<213> ORGANISM: Pan troglodytes

<400> SEQUENCE: 969
ctcctccgca taagcctaca tcagaccaaa atattaaact gacaattaac agcctaatat 60
ctacaatcaa ccaac 75

<210> SEQ ID NO 970
<211> LENGTH: 75
<212> TYPE: DNA
<213> ORGANISM: Homo sapiens

<400> SEQUENCE: 970
ctcctccgca taagcctgcg tcagattaaa acactgaact gacaattaac agcccaatat 60
ctacaatcaa ccaac 75

<210> SEQ ID NO 971
<211> LENGTH: 75
<212> TYPE: DNA
<213> ORGANISM: Pan troglodytes

<400> SEQUENCE: 971
aagccattat tacccccgct gttaacccaa cacaggcatg cccacaagga aaggttaaaa 60
aaagtaaaag gaact 75

<210> SEQ ID NO 972
<211> LENGTH: 75
<212> TYPE: DNA
<213> ORGANISM: Homo sapiens

<400> SEQUENCE: 972
aagtcattat taccctcact gtcaacccaa cacaggcatg ctcataagga aaggttaaaa 60
aaagtaaaag gaact 75

<210> SEQ ID NO 973
<211> LENGTH: 75
<212> TYPE: DNA
<213> ORGANISM: Pan troglodytes

<400> SEQUENCE: 973
cggcaaatct taccccgcct gtttaccaaa aacatcacct ctagcattac cagtattaga 60
ggcaccgcct gcccg 75

<210> SEQ ID NO 974
<211> LENGTH: 75
<212> TYPE: DNA
<213> ORGANISM: Homo sapiens

<400> SEQUENCE: 974
cggcaaatct taccccgcct gtttaccaaa aacatcacct ctagcatcac cagtattaga 60
ggcaccgcct gccca 75

<210> SEQ ID NO 975
<211> LENGTH: 75
<212> TYPE: DNA
<213> ORGANISM: Pan troglodytes

<400> SEQUENCE: 975
gtgacatatg tttaacggcc gcggtaccct aaccgtgcaa aggtagcata atcacttgtt 60
ccttaaatag ggact 75

<210> SEQ ID NO 976
<211> LENGTH: 75
<212> TYPE: DNA
<213> ORGANISM: Homo sapiens

<400> SEQUENCE: 976
gtgacacatg tttaacggcc gcggtaccct aaccgtgcaa aggtagcata atcacttgtt 60
ccttaaatag ggacc 75

<210> SEQ ID NO 977
<211> LENGTH: 75
<212> TYPE: DNA
<213> ORGANISM: Pan troglodytes

<400> SEQUENCE: 977
tgtatgaatg gctccacgag ggtttagctg tctcttactt tcaaccagtg aaattgacct 60
acccgtgaag aggcg 75

<210> SEQ ID NO 978
<211> LENGTH: 75
<212> TYPE: DNA
<213> ORGANISM: Homo sapiens

<400> SEQUENCE: 978
tgtatgaatg gctccacgag ggttcagctg tctcttactt ttaaccagtg aaattgacct 60
gcccgtgaag aggcg 75

<210> SEQ ID NO 979
<211> LENGTH: 75
<212> TYPE: DNA
<213> ORGANISM: Pan troglodytes

<400> SEQUENCE: 979
ggcataacat aacaagacga gaagacccta tggagcttta attcattaat gcaaacaata 60
cttaacaaac ctaca 75

<210> SEQ ID NO 980
<211> LENGTH: 75
<212> TYPE: DNA
<213> ORGANISM: Homo sapiens

<400> SEQUENCE: 980
ggcataacac agcaagacga gaagacccta tggagcttta atttattaat gcaaacagta 60
cctaacaaac ccaca 75

<210> SEQ ID NO 981
<211> LENGTH: 75
<212> TYPE: DNA
<213> ORGANISM: Pan troglodytes

<400> SEQUENCE: 981
ggtcctaaac tattaaacct gcattaaaaa tttcggttgg ggcgacctcg gagcacaacc 60
caacctccga gcaat 75

<210> SEQ ID NO 982
<211> LENGTH: 75
<212> TYPE: DNA
<213> ORGANISM: Homo sapiens

<400> SEQUENCE: 982
ggtcctaaac taccaaacct gcattaaaaa tttcggttgg ggcgacctcg gagcagaacc 60
caacctccga gcagt 75

<210> SEQ ID NO 983
<211> LENGTH: 75
<212> TYPE: DNA
<213> ORGANISM: Pan troglodytes

<400> SEQUENCE: 983
acatgctaag acctcaccag tcaaagcgaa ttactacatc caattgatcc aatgacttga 60
ccaacggaac aagtt 75

<210> SEQ ID NO 984
<211> LENGTH: 75
<212> TYPE: DNA
<213> ORGANISM: Homo sapiens

<400> SEQUENCE: 984
acatgctaag acttcaccag tcaaagcgaa ctactatact caattgatcc aataacttga 60
ccaacggaac aagtt 75

<210> SEQ ID NO 985
<211> LENGTH: 75
<212> TYPE: DNA
<213> ORGANISM: Pan troglodytes

<400> SEQUENCE: 985
accctaggga taacagcgca atcctattcc agagtccata tcaacaatag ggtttacgac 60
ctcgatgttg gatca 75

<210> SEQ ID NO 986
<211> LENGTH: 75
<212> TYPE: DNA
<213> ORGANISM: Homo sapiens

<400> SEQUENCE: 986
accctaggga taacagcgca atcctattct agagtccata tcaacaatag ggtttacgac 60
ctcgatgttg gatca 75

<210> SEQ ID NO 987

<211> LENGTH: 75
<212> TYPE: DNA
<213> ORGANISM: Pan troglodytes

<400> SEQUENCE: 987
ggacatcccg atggtgcagc cgctattaaa ggttcgtttg ttcaacgatt aaagtcctac 60
gtgatctgag ttcag 75

<210> SEQ ID NO 988
<211> LENGTH: 75
<212> TYPE: DNA
<213> ORGANISM: Homo sapiens

<400> SEQUENCE: 988
ggacatcccg atggtgcagc cgctattaaa ggttcgtttg ttcaacgatt aaagtcctac 60
gtgatctgag ttcag 75

<210> SEQ ID NO 989
<211> LENGTH: 75
<212> TYPE: DNA
<213> ORGANISM: Homo sapiens
<220> FEATURE:
<221> NAME/KEY: modified_base
<222> LOCATION: (32)..(32)
<223> OTHER INFORMATION: a, c, t, g, unknown or other

<400> SEQUENCE: 989
accggagtaa tccaggtcgg tttctatcta cnttcaaatt cctccctgta cgaaaggaca 60
agagaaataa ggcct 75

<210> SEQ ID NO 990
<211> LENGTH: 75
<212> TYPE: DNA
<213> ORGANISM: Pan troglodytes

<400> SEQUENCE: 990
acttcacaaa gcgccttccc caataaatga tattatctca atttagcgcc atgccaacac 60
ccactcaaga acaga 75

<210> SEQ ID NO 991
<211> LENGTH: 75
<212> TYPE: DNA
<213> ORGANISM: Homo sapiens

<400> SEQUENCE: 991
acttcacaaa gcgccttccc ccgtaaatga tatcatctca acttagtatt atacccacac 60
ccacccaaga acagg 75

<210> SEQ ID NO 992
<211> LENGTH: 75
<212> TYPE: DNA
<213> ORGANISM: Pan troglodytes

<400> SEQUENCE: 992
gtttgttaag atggcagagc ccggtaattg cataaaactt aaaactttac aatcagaggt 60
tcaattcctc ttctt 75

<210> SEQ ID NO 993
<211> LENGTH: 75
<212> TYPE: DNA
<213> ORGANISM: Homo sapiens

<400> SEQUENCE: 993
gtttgttaag atggcagagc ccggtaatcg cataaaactt aaaactttac agtcagaggt 60
tcaattcctc ttctt 75

<210> SEQ ID NO 994
<211> LENGTH: 75
<212> TYPE: DNA
<213> ORGANISM: Pan troglodytes

<400> SEQUENCE: 994
gacaacacac ccatgaccaa cctcctactc ctcattgtac ccatcctaat cgcaatagca 60
ttcctaatgc taacc 75

<210> SEQ ID NO 995
<211> LENGTH: 75
<212> TYPE: DNA
<213> ORGANISM: Homo sapiens

<400> SEQUENCE: 995
aacaacatac ccatggccaa cctcctactc ctcattgtac ccattctaat cgcaatggca 60
ttcctaatgc ttacc 75

<210> SEQ ID NO 996
<211> LENGTH: 75
<212> TYPE: DNA
<213> ORGANISM: Pan troglodytes

<400> SEQUENCE: 996
gaacgaaaaa ttctaggcta catacaacta cgcaaaggtc ccaacattgt aggtccttac 60
gggctattac agccc 75

<210> SEQ ID NO 997
<211> LENGTH: 75
<212> TYPE: DNA
<213> ORGANISM: Homo sapiens

<400> SEQUENCE: 997
gaacgaaaaa ttctaggcta tatacaacta cgcaaaggcc ccaacgttgt aggcccctac 60
gggctactac aaccc 75

<210> SEQ ID NO 998
<211> LENGTH: 75
<212> TYPE: DNA
<213> ORGANISM: Pan troglodytes

<400> SEQUENCE: 998
ttcgctgacg ccataaaact cttcactaaa gaacccttaa aaccctccac ttcaaccatt 60
accctctaca tcacc 75

<210> SEQ ID NO 999
<211> LENGTH: 75
<212> TYPE: DNA
<213> ORGANISM: Homo sapiens

<400> SEQUENCE: 999
ttcgctgacg ccataaaact cttcaccaaa gagcccctaa aacccgccac atctaccatc 60
accctctaca tcacc 75

<210> SEQ ID NO 1000
<211> LENGTH: 75
<212> TYPE: DNA
<213> ORGANISM: Pan troglodytes

<400> SEQUENCE: 1000
gccccaaccc tagccctcac cattgccctc ttactatgaa ccccctccc catacccaac 60 cccctagtca atctc 75

<210> SEQ ID NO 1001
<211> LENGTH: 75
<212> TYPE: DNA
<213> ORGANISM: Homo sapiens

<400> SEQUENCE: 1001
gccccgacct tagctctcac catcgctctt ctactatgaa ccccctccc catacccaac 60 cccctggtca acctc 75

<210> SEQ ID NO 1002
<211> LENGTH: 75
<212> TYPE: DNA
<213> ORGANISM: Pan troglodytes

<400> SEQUENCE: 1002
aacttaggcc tcctatttat tctagccacc tccagcctag ccgtttactc aatcctctga 60
tcagggtgag catca 75

<210> SEQ ID NO 1003
<211> LENGTH: 75
<212> TYPE: DNA
<213> ORGANISM: Homo sapiens

<400> SEQUENCE: 1003
aacctaggcc tcctatttat tctagccacc tctagcctag ccgtttactc aatcctctga 60
tcagggtgag catca 75

<210> SEQ ID NO 1004
<211> LENGTH: 75
<212> TYPE: DNA
<213> ORGANISM: Pan troglodytes

<400> SEQUENCE: 1004
aactcgaact acgccttaat cggtgcacta cgagcagtag cccaaacaat ctcatacgaa 60
gtcactctag ccatt 75

<210> SEQ ID NO 1005
<211> LENGTH: 75
<212> TYPE: DNA
<213> ORGANISM: Homo sapiens

<400> SEQUENCE: 1005
aactcaaact acgccctgat cggcgcactg cgagcagtag cccaaacaat ctcatatgaa 60
gtcaccctag ccatc 75

<210> SEQ ID NO 1006
<211> LENGTH: 75
<212> TYPE: DNA
<213> ORGANISM: Pan troglodytes

<400> SEQUENCE: 1006
atcctactgt caacgctact aataagtggc tcctttcaatc tctctaccct tgtcacaaca 60
caagagcacc tctga 75

<210> SEQ ID NO 1007
<211> LENGTH: 75
<212> TYPE: DNA
<213> ORGANISM: Homo sapiens

<400> SEQUENCE: 1007
attctactat caacattact aataagtggc tcctttaacc tctccaccct tatcacaaca 60
caagaacacc tctga 75

<210> SEQ ID NO 1008
<211> LENGTH: 75
<212> TYPE: DNA
<213> ORGANISM: Pan troglodytes

<400> SEQUENCE: 1008
ctaatcctgc caacatgacc cctggccata atatgattta tctctacact agcagagacc 60
aaccgaactc ccttc 75

<210> SEQ ID NO 1009
<211> LENGTH: 75
<212> TYPE: DNA
<213> ORGANISM: Homo sapiens

<400> SEQUENCE: 1009
ttactcctgc catcatgacc cttggccata atatgattta tctccacact agcagagacc 60
aaccgaaccc ccttc 75

<210> SEQ ID NO 1010
<211> LENGTH: 75
<212> TYPE: DNA
<213> ORGANISM: Pan troglodytes

<400> SEQUENCE: 1010
gaccttactg aaggagaatc tgaactagtc tcaggcttta atatcgagta tgccgcaggc 60
ccctttgccc tattt 75

<210> SEQ ID NO 1011
<211> LENGTH: 75
<212> TYPE: DNA
<213> ORGANISM: Homo sapiens

<400> SEQUENCE: 1011
gaccttgccg aaggggagtc cgaactagtc tcaggcttca acatcgaata cgccgcaggc 60
cccttcgccc tattc 75

<210> SEQ ID NO 1012
<211> LENGTH: 75
<212> TYPE: DNA
<213> ORGANISM: Pan troglodytes

<400> SEQUENCE: 1012
ttcatagccg aatacataaa cattattata ataaacaccc tcactgctac aatcttccta 60
ggagcaacat acaat 75

<210> SEQ ID NO 1013

<211> LENGTH: 75
<212> TYPE: DNA
<213> ORGANISM: Homo sapiens

<400> SEQUENCE: 1013
ttcatagccg aatacacaaa cattattata ataaacaccc tcaccactac aatcttccta 60
ggaacaacat atgac 75

<210> SEQ ID NO 1014
<211> LENGTH: 75
<212> TYPE: DNA
<213> ORGANISM: Pan troglodytes

<400> SEQUENCE: 1014
actcactccc ctgaactcta cacgacatat tttgtcacca aagctctact tctaacctcc 60
ctgttcctat gaatt 75

<210> SEQ ID NO 1015
<211> LENGTH: 75
<212> TYPE: DNA
<213> ORGANISM: Homo sapiens

<400> SEQUENCE: 1015
gcactctccc ctgaactcta cacaacatat tttgtcacca agaccctact tctaacctcc 60
ctgttcttat gaatt 75

<210> SEQ ID NO 1016
<211> LENGTH: 75
<212> TYPE: DNA
<213> ORGANISM: Pan troglodytes

<400> SEQUENCE: 1016
cgaacagcat atccccgatt tcgctacgac cagctcatac acctcctatg aaaaaacttc 60
ctaccactca cccta 75

<210> SEQ ID NO 1017
<211> LENGTH: 75
<212> TYPE: DNA
<213> ORGANISM: Homo sapiens

<400> SEQUENCE: 1017
cgaacagcat acccccgatt ccgctacgac caactcatac acctcctatg aaaaaacttc 60
ctaccactca cccta 75

<210> SEQ ID NO 1018
<211> LENGTH: 75
<212> TYPE: DNA
<213> ORGANISM: Pan troglodytes

<400> SEQUENCE: 1018
gcatcactca tgtgatatat ctccataccc actacaatct ccagcatccc ccctcaaacc 60
taagaaatat gtctg 75

<210> SEQ ID NO 1019
<211> LENGTH: 75
<212> TYPE: DNA
<213> ORGANISM: Homo sapiens

<400> SEQUENCE: 1019
gcattactta tatgatatgt ctccataccc attacaatct ccagcattcc ccctcaaacc 60
taagaaatat gtctg 75

<210> SEQ ID NO 1020
<211> LENGTH: 75
<212> TYPE: DNA
<213> ORGANISM: Pan troglodytes

<400> SEQUENCE: 1020
ataaaagaat tactttgata gagtaaataa taggagttca aatcccctta tttctaggac 60
tataagaatc gaact 75

<210> SEQ ID NO 1021
<211> LENGTH: 75
<212> TYPE: DNA
<213> ORGANISM: Homo sapiens

<400> SEQUENCE: 1021
ataaaagagt tactttgata gagtaaataa taggagctta aaccccctta tttctaggac 60
tatgagaatc gaacc 75

<210> SEQ ID NO 1022
<211> LENGTH: 75
<212> TYPE: DNA
<213> ORGANISM: Pan troglodytes

<400> SEQUENCE: 1022
catccctgag aatccaaaat tctccgtgcc acctatcaca ccccatccta aagtaaggtc 60
agctaaataa gctat 75

<210> SEQ ID NO 1023
<211> LENGTH: 75
<212> TYPE: DNA
<213> ORGANISM: Homo sapiens

<400> SEQUENCE: 1023
catccctgag aatccaaaat tctccgtgcc acctatcaca ccccatccta aagtaaggtc 60
agctaaataa gctat 75

<210> SEQ ID NO 1024
<211> LENGTH: 75
<212> TYPE: DNA
<213> ORGANISM: Pan troglodytes

<400> SEQUENCE: 1024
cgggcccata ccccgaaaat gttggttaca cccttcccgt actaattaat cccctagccc 60
aacccatcat ctact 75

<210> SEQ ID NO 1025
<211> LENGTH: 75
<212> TYPE: DNA
<213> ORGANISM: Homo sapiens

<400> SEQUENCE: 1025
cgggcccata ccccgaaaat gttggttata cccttcccgt actaattaat cccctggccc 60
aacccgtcat ctact 75

<210> SEQ ID NO 1026
<211> LENGTH: 75
<212> TYPE: DNA

<213> ORGANISM: Pan troglodytes

<400> SEQUENCE: 1026
ctaccatcct tacaggcacg ctcattacag cgctaagctc acactgattt ttcacctgag 60
taggcctaga aataa 75

<210> SEQ ID NO 1027
<211> LENGTH: 75
<212> TYPE: DNA
<213> ORGANISM: Homo sapiens

<400> SEQUENCE: 1027
ctaccatctt tgcaggcaca ctcatcacag cgctaagctc gcactgattt tttacctgag 60
taggcctaga aataa 75

<210> SEQ ID NO 1028
<211> LENGTH: 75
<212> TYPE: DNA
<213> ORGANISM: Pan troglodytes

<400> SEQUENCE: 1028
atatactagc ttttatccca atcctaacca aaaaaataag cccccgctcc acagaagccg 60
ccatcaaata ctttc 75

<210> SEQ ID NO 1029
<211> LENGTH: 75
<212> TYPE: DNA
<213> ORGANISM: Homo sapiens

<400> SEQUENCE: 1029
acatgctagc ttttattcca gttctaacca aaaaaataaa ccctcgttcc acagaagctg 60
ccatcaagta tttcc 75

<210> SEQ ID NO 1030
<211> LENGTH: 75
<212> TYPE: DNA
<213> ORGANISM: Pan troglodytes

<400> SEQUENCE: 1030
tcacacaagc aactgcgtcc ataattctcc tgatagctat cctctccaac agcatactct 60
ccggacaatg aacca 75

<210> SEQ ID NO 1031
<211> LENGTH: 75
<212> TYPE: DNA
<213> ORGANISM: Homo sapiens

<400> SEQUENCE: 1031
tcacgcaagc aaccgcatcc ataatccttc taatagctat cctcttcaac aatatactct 60
ccggacaatg aacca 75

<210> SEQ ID NO 1032
<211> LENGTH: 75
<212> TYPE: DNA
<213> ORGANISM: Pan troglodytes

<400> SEQUENCE: 1032
taaccaatac taccaatcaa tactcatcat taataattat aatagcaatg gcaataaaac 60
taggaatagc cccct 75

<210> SEQ ID NO 1033
<211> LENGTH: 75
<212> TYPE: DNA
<213> ORGANISM: Homo sapiens

<400> SEQUENCE: 1033
taaccaatac taccaatcaa tactcatcat taataatcat aatagctata gcaataaaac 60
taggaatagc cccct 75

<210> SEQ ID NO 1034
<211> LENGTH: 75
<212> TYPE: DNA
<213> ORGANISM: Pan troglodytes

<400> SEQUENCE: 1034
ttcacttttg agttccagaa gttacccaag gcacccccct aatatccggc ctactcctcc 60
tcacatgaca aaaat 75

<210> SEQ ID NO 1035
<211> LENGTH: 75
<212> TYPE: DNA
<213> ORGANISM: Homo sapiens

<400> SEQUENCE: 1035
ttcacttctg agtcccagag gttacccaag gcacccctct gacatccggc ctgcttcttc 60
tcacatgaca aaaac 75

<210> SEQ ID NO 1036
<211> LENGTH: 75
<212> TYPE: DNA
<213> ORGANISM: Pan troglodytes

<400> SEQUENCE: 1036
tagcccctat ttcaattata taccaaatct cctcatcact gaacgtaaac cttctcctca 60
ccctttcaat cttgt 75

<210> SEQ ID NO 1037
<211> LENGTH: 75
<212> TYPE: DNA
<213> ORGANISM: Homo sapiens

<400> SEQUENCE: 1037
tagcccccat ctcaatcata taccaaatct ctccctcact aaacgtaagc cttctcctca 60
ctctctcaat cttat 75

<210> SEQ ID NO 1038
<211> LENGTH: 75
<212> TYPE: DNA
<213> ORGANISM: Pan troglodytes

<400> SEQUENCE: 1038
ccattatagc aggcagctga ggcggactaa accaaaccca actacgcaaa atcctagcat 60
actcctcaat caccc 75

<210> SEQ ID NO 1039
<211> LENGTH: 75
<212> TYPE: DNA
<213> ORGANISM: Homo sapiens

<400> SEQUENCE: 1039
ccatcatagc aggcagttga ggtggattaa accaaaccca gctacgcaaa atcttagcat 60
actcctcaat taccc 75

<210> SEQ ID NO 1040
<211> LENGTH: 75
<212> TYPE: DNA
<213> ORGANISM: Pan troglodytes

<400> SEQUENCE: 1040
acataggctg aataatagca gtcctaccat ataaccctaa cataaccatt cttaatttaa 60
ccatttacat catcc 75

<210> SEQ ID NO 1041
<211> LENGTH: 75
<212> TYPE: DNA
<213> ORGANISM: Homo sapiens

<400> SEQUENCE: 1041
acataggatg aataatagca gttctaccgt acaaccctaa cataaccatt cttaatttaa 60
ctatttatat tatcc 75

<210> SEQ ID NO 1042
<211> LENGTH: 75
<212> TYPE: DNA
<213> ORGANISM: Pan troglodytes

<400> SEQUENCE: 1042
taactactac cgcatttctg ctactcaact taaactccag caccacaacc ctactactat 60
ctcgcacctg aaaca 75

<210> SEQ ID NO 1043
<211> LENGTH: 75
<212> TYPE: DNA
<213> ORGANISM: Homo sapiens

<400> SEQUENCE: 1043
taactactac cgcattccta ctactcaact taaactccag caccacgacc ctactactat 60
ctcgcacctg aaaca 75

<210> SEQ ID NO 1044
<211> LENGTH: 75
<212> TYPE: DNA
<213> ORGANISM: Pan troglodytes

<400> SEQUENCE: 1044
agctaacatg attaactccc ctaattccat ccaccctcct ctccctagga ggcctacccc 60
cactaactgg cttct 75

<210> SEQ ID NO 1045
<211> LENGTH: 75
<212> TYPE: DNA
<213> ORGANISM: Homo sapiens

<400> SEQUENCE: 1045
agctaacatg actaacaccc ttaattccat ccaccctcct ctccctagga ggcctgcccc 60
cgctaaccgg ctttt 75

<210> SEQ ID NO 1046
<211> LENGTH: 75
<212> TYPE: DNA
<213> ORGANISM: Pan troglodytes

<400> SEQUENCE: 1046
tacccaaatg agttatcatc gaagaattca caaaaaataa tagcctcatc atccccacca 60
tcatagccat catca 75

<210> SEQ ID NO 1047
<211> LENGTH: 75
<212> TYPE: DNA
<213> ORGANISM: Homo sapiens

<400> SEQUENCE: 1047
tgcccaaatg ggccattatc gaagaattca caaaaaacaa tagcctcatc atccccacca 60
tcatagccac catca 75

<210> SEQ ID NO 1048
<211> LENGTH: 75
<212> TYPE: DNA
<213> ORGANISM: Pan troglodytes

<400> SEQUENCE: 1048
ctctccttaa cctctatttc tacctacgcc taatctactc cacctcaatt acactacttc 60
ccatatctaa taacg 75

<210> SEQ ID NO 1049
<211> LENGTH: 75
<212> TYPE: DNA
<213> ORGANISM: Homo sapiens

<400> SEQUENCE: 1049
ccctccttaa cctctacttc tacctacgcc taatctactc cacctcaatc acactactcc 60
ccatatctaa caacg 75

<210> SEQ ID NO 1050
<211> LENGTH: 75
<212> TYPE: DNA
<213> ORGANISM: Pan troglodytes

<400> SEQUENCE: 1050
taaaaataaa atgacaattc gaacatacaa aacccacccc cttcctccct acactcatca 60
cccttaccac actgc 75

<210> SEQ ID NO 1051
<211> LENGTH: 75
<212> TYPE: DNA
<213> ORGANISM: Homo sapiens

<400> SEQUENCE: 1051
taaaaataaa atgacagttt gaacatacaa aacccacccc attcctcccc acactcatcg 60
cccttaccac gctac 75

<210> SEQ ID NO 1052
<211> LENGTH: 75
<212> TYPE: DNA
<213> ORGANISM: Pan troglodytes

<400> SEQUENCE: 1052
ttctacccat ctccccctte atactaataa tcttatagaa atttaggtta agcacagacc 60
aagagccttc aaagc 75

<210> SEQ ID NO 1053
<211> LENGTH: 75
<212> TYPE: DNA
<213> ORGANISM: Homo sapiens

<400> SEQUENCE: 1053
tcctacctat ctccccttt atactaataa tcttatagaa atttaggtta aatacagacc 60
aagagccttc aaagc 75

<210> SEQ ID NO 1054
<211> LENGTH: 75
<212> TYPE: DNA
<213> ORGANISM: Pan troglodytes

<400> SEQUENCE: 1054
cctcagcaag ttacaatact taatttctgc aacaactaag gactgcaaaa ccccactctg 60
catcaactga acgca 75

<210> SEQ ID NO 1055
<211> LENGTH: 75
<212> TYPE: DNA
<213> ORGANISM: Homo sapiens

<400> SEQUENCE: 1055
cctcagtaag ttgcaatact taatttctgt aacagctaag gactgcaaaa ccccactctg 60
catcaactga acgca 75

<210> SEQ ID NO 1056
<211> LENGTH: 75
<212> TYPE: DNA
<213> ORGANISM: Pan troglodytes

<400> SEQUENCE: 1056
aatcagccac tttaattaag ctaagccctt actagattaa tgggacttaa acccacaaac 60
atttagttaa cagct 75

<210> SEQ ID NO 1057
<211> LENGTH: 75
<212> TYPE: DNA
<213> ORGANISM: Homo sapiens

<400> SEQUENCE: 1057
aatcagccac tttaattaag ctaagccctt actagaccaa tgggacttaa acccacaaac 60
acttagttaa cagct 75

<210> SEQ ID NO 1058
<211> LENGTH: 75
<212> TYPE: DNA
<213> ORGANISM: Pan troglodytes

<400> SEQUENCE: 1058
aaacacccta atcaactggc ttcaatctac ttctcccgcc gcaagaaaaa aaggcgggag 60
aagccccggc aggtt 75

<210> SEQ ID NO 1059
<211> LENGTH: 75

<212> TYPE: DNA
<213> ORGANISM: Homo sapiens

<400> SEQUENCE: 1059
aagcacccta atcaactggc ttcaatctac ttctcccgcc gccgggaaaa aaggcgggag 60
aagccccggc aggtt 75

<210> SEQ ID NO 1060
<211> LENGTH: 75
<212> TYPE: DNA
<213> ORGANISM: Pan troglodytes

<400> SEQUENCE: 1060
tgaagctgct tcttcgaatt tgcaattcaa tatgaaaatc acctcagagc tggtaaaaag 60
aggcttaacc cctgt 75

<210> SEQ ID NO 1061
<211> LENGTH: 75
<212> TYPE: DNA
<213> ORGANISM: Homo sapiens

<400> SEQUENCE: 1061
tgaagctgct tcttcgaatt tgcaattcaa tatgaaaatc acctcggagc tggtaaaaag 60
aggcctaacc cctgt 75

<210> SEQ ID NO 1062
<211> LENGTH: 75
<212> TYPE: DNA
<213> ORGANISM: Homo sapiens

<400> SEQUENCE: 1062
ctttagattt acagtccaat gcttcactca gccattttac ctcaccccca ctgatgttcg 60
ccgaccgttg actat 75

<210> SEQ ID NO 1063
<211> LENGTH: 75
<212> TYPE: DNA
<213> ORGANISM: Pan troglodytes

<400> SEQUENCE: 1063
tctctacaaa ccacaaagat attggaacac tatacctact attcggtgca tgagctggag 60
tcctgggcac agccc 75

<210> SEQ ID NO 1064
<211> LENGTH: 75
<212> TYPE: DNA
<213> ORGANISM: Homo sapiens

<400> SEQUENCE: 1064
tctctacaaa ccacaaagac attggaacac tatacctatt attcggcgca tgagctggag 60
tcctaggcac agctc 75

<210> SEQ ID NO 1065
<211> LENGTH: 75
<212> TYPE: DNA
<213> ORGANISM: Pan troglodytes

<400> SEQUENCE: 1065
taagtctcct tattcgggct gaactaggcc aaccaggcaa cctcctaggt aatgaccaca 60
tctacaatgt catcg 75

<210> SEQ ID NO 1066
<211> LENGTH: 75
<212> TYPE: DNA
<213> ORGANISM: Homo sapiens

<400> SEQUENCE: 1066
taagcctcct tattcgagcc gagctgggcc agccaggcaa ccttctaggt aacgaccaca 60
tctacaacgt tatcg 75

<210> SEQ ID NO 1067
<211> LENGTH: 75
<212> TYPE: DNA
<213> ORGANISM: Pan troglodytes

<400> SEQUENCE: 1067
tcacagccca tgcattcgta ataatcttct tcatagtaat gcctattata atcggaggct 60
ttggcaactg gctag 75

<210> SEQ ID NO 1068
<211> LENGTH: 75
<212> TYPE: DNA
<213> ORGANISM: Homo sapiens

<400> SEQUENCE: 1068
tcacagccca tgcatttgta ataatcttct tcatagtaat acccatcata atcggaggct 60
ttggcaactg actag 75

<210> SEQ ID NO 1069
<211> LENGTH: 75
<212> TYPE: DNA
<213> ORGANISM: Pan troglodytes

<400> SEQUENCE: 1069
ttcccttgat aattggtgcc cccgacatgg cattcccccg cataaacaac ataagcttct 60
ggctcctgcc ccctt 75

<210> SEQ ID NO 1070
<211> LENGTH: 75
<212> TYPE: DNA
<213> ORGANISM: Homo sapiens

<400> SEQUENCE: 1070
ttcccctaat aatcggtgcc cccgatatgg cgtttccccg cataaacaac ataagcttct 60
gactcttacc tccct 75

<210> SEQ ID NO 1071
<211> LENGTH: 75
<212> TYPE: DNA
<213> ORGANISM: Pan troglodytes

<400> SEQUENCE: 1071
ctctcctact tctacttgca tctgccatag tagaagccgg cgcgggaaca ggttgaacag 60
tctaccctcc cttag 75

<210> SEQ ID NO 1072
<211> LENGTH: 75
<212> TYPE: DNA
<213> ORGANISM: Homo sapiens

<400> SEQUENCE: 1072
ctctcctact cctgctcgca tctgctatag tggaggccgg agcaggaaca ggttgaacag 60
tctaccctcc cttag 75

<210> SEQ ID NO 1073
<211> LENGTH: 75
<212> TYPE: DNA
<213> ORGANISM: Pan troglodytes

<400> SEQUENCE: 1073
cgggaaacta ctcgcatcct ggagcctccg tagacctaac catcttctcc ttacatctgg 60
caggcatctc ctcta 75

<210> SEQ ID NO 1074
<211> LENGTH: 75
<212> TYPE: DNA
<213> ORGANISM: Homo sapiens

<400> SEQUENCE: 1074
cagggaacta ctcccaccct ggagcctccg tagacctaac catcttctcc ttacacctag 60
caggtgtctc ctcta 75

<210> SEQ ID NO 1075
<211> LENGTH: 75
<212> TYPE: DNA
<213> ORGANISM: Pan troglodytes

<400> SEQUENCE: 1075
tcctaggagc cattaacttc atcacaacaa ttattaatat aaaacctcct gccatgaccc 60
aataccaaac acccc 75

<210> SEQ ID NO 1076
<211> LENGTH: 75
<212> TYPE: DNA
<213> ORGANISM: Homo sapiens

<400> SEQUENCE: 1076
tcttaggggc catcaatttc atcacaacaa ttatcaatat aaaacccccct gccataaccc 60 aataccaaac gcccc 75

<210> SEQ ID NO 1077
<211> LENGTH: 75
<212> TYPE: DNA
<213> ORGANISM: Pan troglodytes

<400> SEQUENCE: 1077
tcttcgtctg atccgtccta atcacagcag tcttacttct cctatccctc ccagtcctag 60
ctgctggcat cacca 75

<210> SEQ ID NO 1078
<211> LENGTH: 75
<212> TYPE: DNA
<213> ORGANISM: Homo sapiens

<400> SEQUENCE: 1078
tcttcgtctg atccgtccta atcacagcag tcctacttct cctatctctc ccagtcctag 60
ctgctggcat cacta 75

<210> SEQ ID NO 1079
<211> LENGTH: 75
<212> TYPE: DNA
<213> ORGANISM: Pan troglodytes

<400> SEQUENCE: 1079
tactattgac agatcgtaac ctcaacacta ccttcttcga cccagccggg ggaggagacc 60
ctattctata tcaac 75

<210> SEQ ID NO 1080
<211> LENGTH: 75
<212> TYPE: DNA
<213> ORGANISM: Homo sapiens

<400> SEQUENCE: 1080
tactactaac agaccgcaac ctcaacacca ccttcttcga ccccgccgga ggaggagacc 60
ccattctata ccaac 75

<210> SEQ ID NO 1081
<211> LENGTH: 75
<212> TYPE: DNA
<213> ORGANISM: Pan troglodytes

<400> SEQUENCE: 1081
acttattctg attttttggc caccccgaag tttatattct tatcctacca ggcttcggaa 60
taatttccca cattg 75

<210> SEQ ID NO 1082
<211> LENGTH: 75
<212> TYPE: DNA
<213> ORGANISM: Homo sapiens

<400> SEQUENCE: 1082
acctattctg atttttcggt caccctgaag tttatattct tatcctacca ggcttcggaa 60
taatctccca tattg 75

<210> SEQ ID NO 1083
<211> LENGTH: 75
<212> TYPE: DNA
<213> ORGANISM: Pan troglodytes

<400> SEQUENCE: 1083
taacttatta ctccggaaaa aaagaaccat ttggatatat aggcatggtt tgagctataa 60
tatcaattgg cttcc 75

<210> SEQ ID NO 1084
<211> LENGTH: 75
<212> TYPE: DNA
<213> ORGANISM: Homo sapiens

<400> SEQUENCE: 1084
taacttacta ctccggaaaa aaagaaccat ttggatacat aggtatggtc tgagctatga 60
tatcaattgg cttcc 75

<210> SEQ ID NO 1085
<211> LENGTH: 75
<212> TYPE: DNA
<213> ORGANISM: Pan troglodytes

<400> SEQUENCE: 1085
tagggtttat cgtgtgagca caccatatat ttacagtagg gatagacgta gacacccgag 60
cctatttcac ctccg 75

<210> SEQ ID NO 1086
<211> LENGTH: 75
<212> TYPE: DNA
<213> ORGANISM: Homo sapiens

<400> SEQUENCE: 1086
tagggtttat cgtgtgagca caccatatat ttacagtagg aatagacgta gacacacgag 60
catatttcac ctccg 75

<210> SEQ ID NO 1087
<211> LENGTH: 75
<212> TYPE: DNA
<213> ORGANISM: Pan troglodytes

<400> SEQUENCE: 1087
ctaccataat cattgctatt cctaccggcg tcaaagtatt cagctgactc gctacacttc 60
acggaagcaa tatga 75

<210> SEQ ID NO 1088
<211> LENGTH: 75
<212> TYPE: DNA
<213> ORGANISM: Homo sapiens

<400> SEQUENCE: 1088
ctaccataat catcgctatc cccaccggcg tcaaagtatt tagctgactc gccacactcc 60
acggaagcaa tatga 75

<210> SEQ ID NO 1089
<211> LENGTH: 75
<212> TYPE: DNA
<213> ORGANISM: Pan troglodytes

<400> SEQUENCE: 1089
aatgatctgc cgcagtactc tgagccctag ggtttatctt tctcttcacc gtaggtggcc 60
taaccggcat tgtac 75

<210> SEQ ID NO 1090
<211> LENGTH: 75
<212> TYPE: DNA
<213> ORGANISM: Homo sapiens

<400> SEQUENCE: 1090
aatgatctgc tgcagtgctc tgagccctag gattcatctt tcttttcacc gtaggtggcc 60
tgactggcat tgtat 75

<210> SEQ ID NO 1091
<211> LENGTH: 75
<212> TYPE: DNA
<213> ORGANISM: Pan troglodytes

<400> SEQUENCE: 1091
tagcaaactc atcattagac atcgtgctac acgacacata ctacgtcgta gcccacttcc 60
actacgttct atcaa 75

<210> SEQ ID NO 1092

<211> LENGTH: 75
<212> TYPE: DNA
<213> ORGANISM: Homo sapiens

<400> SEQUENCE: 1092
tagcaaactc atcactagac atcgtactac acgacacgta ctacgttgta gcccacttcc 60
actatgtcct atcaa 75

<210> SEQ ID NO 1093
<211> LENGTH: 75
<212> TYPE: DNA
<213> ORGANISM: Pan troglodytes

<400> SEQUENCE: 1093
taggagctgt attcgccatc ataggaggct tcattcactg attcccccta ttctcaggct 60
ataccctaga ccaaa 75

<210> SEQ ID NO 1094
<211> LENGTH: 75
<212> TYPE: DNA
<213> ORGANISM: Homo sapiens

<400> SEQUENCE: 1094
taggagctgt atttgccatc ataggaggct tcattcactg atttccccta ttctcaggct 60
acaccctaga ccaaa 75

<210> SEQ ID NO 1095
<211> LENGTH: 75
<212> TYPE: DNA
<213> ORGANISM: Pan troglodytes

<400> SEQUENCE: 1095
cctatgccaa aatccaattt gccatcatgt tcattggcgt aaacctaacc ttcttcccac 60
agcacttcct tggcc 75

<210> SEQ ID NO 1096
<211> LENGTH: 75
<212> TYPE: DNA
<213> ORGANISM: Homo sapiens

<400> SEQUENCE: 1096
cctacgccaa aatccatttc actatcatat tcatcggcgt aaatctaact ttcttcccac 60
aacactttct cggcc 75

<210> SEQ ID NO 1097
<211> LENGTH: 75
<212> TYPE: DNA
<213> ORGANISM: Pan troglodytes

<400> SEQUENCE: 1097
tatctgggat gccccgacgt tactcggact accccgatgc atacaccaca tgaaatgtcc 60
tatcatccgt aggct 75

<210> SEQ ID NO 1098
<211> LENGTH: 75
<212> TYPE: DNA
<213> ORGANISM: Homo sapiens

<400> SEQUENCE: 1098
tatccggaat gccccgacgt tactcggact accccgatgc atacaccaca tgaaacatcc 60
tatcatctgt aggct 75

<210> SEQ ID NO 1099
<211> LENGTH: 75
<212> TYPE: DNA
<213> ORGANISM: Pan troglodytes

<400> SEQUENCE: 1099
catttatctc cctgacagca gtaatattaa taattttcat gatttgagaa gcctttgctt 60
caaaacgaaa agtcc 75

<210> SEQ ID NO 1100
<211> LENGTH: 75
<212> TYPE: DNA
<213> ORGANISM: Homo sapiens

<400> SEQUENCE: 1100
cattcatttc tctaacagca gtaatattaa taattttcat gatttgagaa gccttcgctt 60
cgaagcgaaa agtcc 75

<210> SEQ ID NO 1101
<211> LENGTH: 75
<212> TYPE: DNA
<213> ORGANISM: Pan troglodytes

<400> SEQUENCE: 1101
taatagtaga agagccctcc gcaaacctgg aatgactata tggatgcccc ccaccctacc 60
acacattcga agaac 75

<210> SEQ ID NO 1102
<211> LENGTH: 75
<212> TYPE: DNA
<213> ORGANISM: Homo sapiens

<400> SEQUENCE: 1102
taatagtaga agaaccctcc ataaacctgg agtgactata tggatgcccc ccaccctacc 60
acacattcga agaac 75

<210> SEQ ID NO 1103
<211> LENGTH: 75
<212> TYPE: DNA
<213> ORGANISM: Pan troglodytes

<400> SEQUENCE: 1103
ccgtatacat aaaatctaga caaaaaagga aggaatcgaa ccccctaaag ctggtttcaa 60 gccaaccccca tgacc 75

<210> SEQ ID NO 1104
<211> LENGTH: 75
<212> TYPE: DNA
<213> ORGANISM: Homo sapiens

<400> SEQUENCE: 1104
ccgtatacat aaaatctaga caaaaaagga aggaatcgaa ccccccaaag ctggtttcaa 60
gccaacccca tggcc 75

<210> SEQ ID NO 1105
<211> LENGTH: 75
<212> TYPE: DNA

<213> ORGANISM: Pan troglodytes

<400> SEQUENCE: 1105
tccatgactt tttcaaaaag atattagaaa aactatttca taactttgtc aaagttaaat 60
tacaggttaa ccccc 75

<210> SEQ ID NO 1106
<211> LENGTH: 75
<212> TYPE: DNA
<213> ORGANISM: Homo sapiens

<400> SEQUENCE: 1106
tccatgactt tttcaaaaag gtattagaaa aaccatttca taactttgtc aaagttaaat 60
tataggctaa atcct 75

<210> SEQ ID NO 1107
<211> LENGTH: 75
<212> TYPE: DNA
<213> ORGANISM: Pan troglodytes

<400> SEQUENCE: 1107
gtatatctta atggcacatg cagcgcaagt aggtctacaa gatgctactt cccctatcat 60
agaagaactt attat 75

<210> SEQ ID NO 1108
<211> LENGTH: 75
<212> TYPE: DNA
<213> ORGANISM: Homo sapiens

<400> SEQUENCE: 1108
atatatctta atggcacatg cagcgcaagt aggtctacaa gacgctactt cccctatcat 60
agaagagctt atcac 75

<210> SEQ ID NO 1109
<211> LENGTH: 75
<212> TYPE: DNA
<213> ORGANISM: Pan troglodytes

<400> SEQUENCE: 1109
ctttcacgac catgccctca taattatctt tctcatctgc tttctagtcc tatacgccct 60
tttcctaaca ctcac 75

<210> SEQ ID NO 1110
<211> LENGTH: 75
<212> TYPE: DNA
<213> ORGANISM: Homo sapiens

<400> SEQUENCE: 1110
ctttcatgat cacgccctca taatcatttt ccttatctgc ttcctagtcc tgtatgccct 60
tttcctaaca ctcac 75

<210> SEQ ID NO 1111
<211> LENGTH: 75
<212> TYPE: DNA
<213> ORGANISM: Pan troglodytes

<400> SEQUENCE: 1111
aacaaaacta actaatacta gtatttcaga cgcccaggaa atagaaaccg tctgaactat 60
cctgcccgcc atcat 75

<210> SEQ ID NO 1112
<211> LENGTH: 75
<212> TYPE: DNA
<213> ORGANISM: Homo sapiens

<400> SEQUENCE: 1112
aacaaaacta actaatacta acatctcaga cgctcaggaa atagaaaccg tctgaactat 60
cctgcccgcc atcat 75

<210> SEQ ID NO 1113
<211> LENGTH: 75
<212> TYPE: DNA
<213> ORGANISM: Pan troglodytes

<400> SEQUENCE: 1113
cctagtcctt attgccctac catccctgcg tatcctttac ataacagacg aggtcaacga 60
cccctccttt actat 75

<210> SEQ ID NO 1114
<211> LENGTH: 75
<212> TYPE: DNA
<213> ORGANISM: Homo sapiens

<400> SEQUENCE: 1114
cctagtcctc atcgccctcc catccctacg catcctttac ataacagacg aggtcaacga 60
tccctccctt accat 75

<210> SEQ ID NO 1115
<211> LENGTH: 75
<212> TYPE: DNA
<213> ORGANISM: Pan troglodytes

<400> SEQUENCE: 1115
taaatcaatc ggccatcaat gatattgaac ctacgaatac accgactacg gcgggctaat 60
cttcaactcc tacat 75

<210> SEQ ID NO 1116
<211> LENGTH: 75
<212> TYPE: DNA
<213> ORGANISM: Homo sapiens

<400> SEQUENCE: 1116
caaatcaatt ggccaccaat ggtactgaac ctacgagtac accgactacg gcggactaat 60
cttcaactcc tacat 75

<210> SEQ ID NO 1117
<211> LENGTH: 75
<212> TYPE: DNA
<213> ORGANISM: Pan troglodytes

<400> SEQUENCE: 1117
actcccccca ttatttctag aaccaggtga tctacgactc cttgacgttg ataaccgagt 60
ggtcctccca gttga 75

<210> SEQ ID NO 1118
<211> LENGTH: 75
<212> TYPE: DNA
<213> ORGANISM: Homo sapiens

<400> SEQUENCE: 1118
acttccccca ttattcctag aaccaggcga cctgcgactc cttgacgttg acaatcgagt 60
agtactcccg attga 75

<210> SEQ ID NO 1119
<211> LENGTH: 75
<212> TYPE: DNA
<213> ORGANISM: Pan troglodytes

<400> SEQUENCE: 1119
agcccccgtt cgtataataa ttacatcaca agatgttcta cactcatgag ctgttcccac 60
attaggccta aaaac 75

<210> SEQ ID NO 1120
<211> LENGTH: 75
<212> TYPE: DNA
<213> ORGANISM: Homo sapiens

<400> SEQUENCE: 1120
agcccccatt cgtataataa ttacatcaca agacgtcttg cactcatgag ctgtccccac 60
attaggctta aaaac 75

<210> SEQ ID NO 1121
<211> LENGTH: 75
<212> TYPE: DNA
<213> ORGANISM: Pan troglodytes

<400> SEQUENCE: 1121
agacgcaatt cccggacgcc taaaccaaac cactttcacc gccacacgac caggagtata 60
ctacggccaa tgctc 75

<210> SEQ ID NO 1122
<211> LENGTH: 75
<212> TYPE: DNA
<213> ORGANISM: Homo sapiens

<400> SEQUENCE: 1122
agatgcaatt cccggacgtc taaaccaaac cactttcacc gctacacgac cgggggtata 60
ctacggtcaa tgctc 75

<210> SEQ ID NO 1123
<211> LENGTH: 75
<212> TYPE: DNA
<213> ORGANISM: Pan troglodytes

<400> SEQUENCE: 1123
agaaatctgt ggagcaaacc acagttttat acccatcgtc ctagaattaa tccctctaaa 60
aatctttgaa atagg 75

<210> SEQ ID NO 1124
<211> LENGTH: 75
<212> TYPE: DNA
<213> ORGANISM: Homo sapiens

<400> SEQUENCE: 1124
tgaaatctgt ggagcaaacc acagtttcat gcccatcgtc ctagaattaa ttcccctaaa 60
aatctttgaa atagg 75

<210> SEQ ID NO 1125
<211> LENGTH: 75
<212> TYPE: DNA
<213> ORGANISM: Homo sapiens

<400> SEQUENCE: 1125
gcccgtattt accctatagc accccctcta ccccctctag agcccactgt aaagctaact 60
tagcattaac ctttt 75

<210> SEQ ID NO 1126
<211> LENGTH: 75
<212> TYPE: DNA
<213> ORGANISM: Pan troglodytes

<400> SEQUENCE: 1126
aagttaaaga ttaagaggac cgacacctct ttacagtgaa atgccccaac taaataccgc 60
cgtatgaccc accat 75

<210> SEQ ID NO 1127
<211> LENGTH: 75
<212> TYPE: DNA
<213> ORGANISM: Homo sapiens

<400> SEQUENCE: 1127
aagttaaaga ttaagagaac caacacctct ttacagtgaa atgccccaac taaatactac 60
cgtatggccc accat 75

<210> SEQ ID NO 1128
<211> LENGTH: 75
<212> TYPE: DNA
<213> ORGANISM: Pan troglodytes

<400> SEQUENCE: 1128
aattaccccc atactcctga cactatttct cgtcacccaa ctaaaaatat taaattcaaa 60
ttaccatcta ccccc 75

<210> SEQ ID NO 1129
<211> LENGTH: 75
<212> TYPE: DNA
<213> ORGANISM: Homo sapiens

<400> SEQUENCE: 1129
aattaccccc atactcctta cactattcct catcacccaa ctaaaaatat taaacacaaa 60
ctaccaccta cctcc 75

<210> SEQ ID NO 1130
<211> LENGTH: 75
<212> TYPE: DNA
<213> ORGANISM: Pan troglodytes

<400> SEQUENCE: 1130
ctcaccaaaa cccataaaaa taaaaaacta caataaaccc tgagaaccaa aatgaacgaa 60
aatctattcg cttca 75

<210> SEQ ID NO 1131
<211> LENGTH: 75
<212> TYPE: DNA
<213> ORGANISM: Homo sapiens

<400> SEQUENCE: 1131
ctcaccaaag cccataaaaa taaaaaatta taacaaaccc tgagaaccaa aatgaacgaa 60
aatctgttcg cttca 75

<210> SEQ ID NO 1132
<211> LENGTH: 75
<212> TYPE: DNA
<213> ORGANISM: Pan troglodytes

<400> SEQUENCE: 1132
ttcgctgccc ccacaatcct aggcttaccc gccgcagtac taatcattct attcccccct 60
ctactggtcc ccact 75

<210> SEQ ID NO 1133
<211> LENGTH: 75
<212> TYPE: DNA
<213> ORGANISM: Homo sapiens

<400> SEQUENCE: 1133
ttcattgccc ccacaatcct aggcctaccc gccgcagtac tgatcattct atttcccct 60 ctattgatcc ccacc 75

<210> SEQ ID NO 1134
<211> LENGTH: 75
<212> TYPE: DNA
<213> ORGANISM: Pan troglodytes

<400> SEQUENCE: 1134
tctaaacatc tcatcaacaa ccgactaatt accacccaac aatgactaat tcaactgacc 60
tcaaaacaaa taata 75

<210> SEQ ID NO 1135
<211> LENGTH: 75
<212> TYPE: DNA
<213> ORGANISM: Homo sapiens

<400> SEQUENCE: 1135
tccaaatatc tcatcaacaa ccgactaatc accacccaac aatgactaat caaactaacc 60
tcaaaacaaa tgata 75

<210> SEQ ID NO 1136
<211> LENGTH: 75
<212> TYPE: DNA
<213> ORGANISM: Pan troglodytes

<400> SEQUENCE: 1136
actatacaca gcactaaagg acgaacctga tctctcatac tagtatcctt aatcattttt 60
attaccacaa ccaat 75

<210> SEQ ID NO 1137
<211> LENGTH: 75
<212> TYPE: DNA
<213> ORGANISM: Homo sapiens

<400> SEQUENCE: 1137
accatacaca acactaaagg acgaacctga tctcttatac tagtatcctt aatcattttt 60
attgccacaa ctaac 75

<210> SEQ ID NO 1138
<211> LENGTH: 75

<212> TYPE: DNA
<213> ORGANISM: Pan troglodytes

<400> SEQUENCE: 1138
cttcttgggc ttctacccca ctcattcaca ccaaccaccc aactatctat aaacctagcc 60
atggctatcc cccta 75

<210> SEQ ID NO 1139
<211> LENGTH: 75
<212> TYPE: DNA
<213> ORGANISM: Homo sapiens

<400> SEQUENCE: 1139
ctcctcggac tcctgcctca ctcatttaca ccaaccaccc aactatctat aaacctagcc 60
atggccatcc cctta 75

<210> SEQ ID NO 1140
<211> LENGTH: 75
<212> TYPE: DNA
<213> ORGANISM: Pan troglodytes

<400> SEQUENCE: 1140
tgagcaggcg cagtagtcat aggctttcgc tttaagacta aaaatgccct agcccacttc 60
ttaccgcaag gcaca 75

<210> SEQ ID NO 1141
<211> LENGTH: 75
<212> TYPE: DNA
<213> ORGANISM: Homo sapiens

<400> SEQUENCE: 1141
tgagcgggca cagtgattat aggctttcgc tctaagatta aaaatgccct agcccacttc 60
ttaccacaag gcaca 75

<210> SEQ ID NO 1142
<211> LENGTH: 75
<212> TYPE: DNA
<213> ORGANISM: Pan troglodytes

<400> SEQUENCE: 1142
cctacacccc ttatccccat actagttatc atcgaaacta ttagcctact cattcaacca 60
atagccttag ccgta 75

<210> SEQ ID NO 1143
<211> LENGTH: 75
<212> TYPE: DNA
<213> ORGANISM: Homo sapiens

<400> SEQUENCE: 1143
cctacacccc ttatccccat actagttatt atcgaaacca tcagcctact cattcaacca 60
atagccctgg ccgta 75

<210> SEQ ID NO 1144
<211> LENGTH: 75
<212> TYPE: DNA
<213> ORGANISM: Pan troglodytes

<400> SEQUENCE: 1144
cgtctaaccg ctaacattac tgcaggccac ctactcatgc acctaattgg aagcgccaca 60
ctagcattat caact 75

<210> SEQ ID NO 1145
<211> LENGTH: 75
<212> TYPE: DNA
<213> ORGANISM: Homo sapiens

<400> SEQUENCE: 1145
cgcctaaccg ctaacattac tgcaggccac ctactcatgc acctaattgg aagcgccacc 60
ctagcaatat caacc 75

<210> SEQ ID NO 1146
<211> LENGTH: 75
<212> TYPE: DNA
<213> ORGANISM: Pan troglodytes

<400> SEQUENCE: 1146
atcaatctac cctatgcact cattatcttc acaattctaa tcctactgac tattctagag 60
atcgccgtcg cctta 75

<210> SEQ ID NO 1147
<211> LENGTH: 75
<212> TYPE: DNA
<213> ORGANISM: Homo sapiens

<400> SEQUENCE: 1147
attaaccttc cctctacact tatcatcttc acaattctaa ttctactgac tatcctagaa 60
atcgctgtcg cctta 75

<210> SEQ ID NO 1148
<211> LENGTH: 75
<212> TYPE: DNA
<213> ORGANISM: Pan troglodytes

<400> SEQUENCE: 1148
atccaagcct acgtttttac acttctagtg agcctctacc tgcacgacaa cacataatga 60
cccaccaatc acatg 75

<210> SEQ ID NO 1149
<211> LENGTH: 75
<212> TYPE: DNA
<213> ORGANISM: Homo sapiens

<400> SEQUENCE: 1149
atccaagcct acgttttcac acttctagta agcctctacc tgcacgacaa cacataatga 60
cccaccaatc acatg 75

<210> SEQ ID NO 1150
<211> LENGTH: 75
<212> TYPE: DNA
<213> ORGANISM: Pan troglodytes

<400> SEQUENCE: 1150
cctaccacat agtaaaaccc agcccatgac ccctaacagg ggccctctcg gccctcctaa 60
taacctccgg cctgg 75

<210> SEQ ID NO 1151
<211> LENGTH: 75
<212> TYPE: DNA
<213> ORGANISM: Homo sapiens

<400> SEQUENCE: 1151
cctatcatat agtaaaaccc agcccatgac ccctaacagg ggccctctca gccctcctaa 60
tgacctccgg cctag 75

<210> SEQ ID NO 1152
<211> LENGTH: 75
<212> TYPE: DNA
<213> ORGANISM: Pan troglodytes

<400> SEQUENCE: 1152
ccatatgatt ccacttctac tccacaacac tactcacact aggcttacta actaacacat 60
tgaccatata tcaat 75

<210> SEQ ID NO 1153
<211> LENGTH: 75
<212> TYPE: DNA
<213> ORGANISM: Homo sapiens

<400> SEQUENCE: 1153
ccatgtgatt tcacttccac tccataacgc tcctcatact aggcctacta accaacacac 60
taaccatata ccaat 75

<210> SEQ ID NO 1154
<211> LENGTH: 75
<212> TYPE: DNA
<213> ORGANISM: Pan troglodytes

<400> SEQUENCE: 1154
gatgacgcga tgttatacga gaaggcacat accaaggcca ccacacacca cccgtccaaa 60
aaggtctccg atatg 75

<210> SEQ ID NO 1155
<211> LENGTH: 75
<212> TYPE: DNA
<213> ORGANISM: Homo sapiens

<400> SEQUENCE: 1155
gatggcgcga tgtaacacga gaaagcacat accaaggcca ccacacacca cctgtccaaa 60
aaggccttcg atacg 75

<210> SEQ ID NO 1156
<211> LENGTH: 75
<212> TYPE: DNA
<213> ORGANISM: Pan troglodytes

<400> SEQUENCE: 1156
ggataattct ttttattacc tcagaagttt ttttctttgc aggatttttt tgagctttct 60
accactccag cctag 75

<210> SEQ ID NO 1157
<211> LENGTH: 75
<212> TYPE: DNA
<213> ORGANISM: Homo sapiens

<400> SEQUENCE: 1157
ggataatcct atttattacc tcagaagttt ttttcttcgc aggatttttc tgagcctttt 60
accactccag cctag 75

<210> SEQ ID NO 1158
<211> LENGTH: 75
<212> TYPE: DNA
<213> ORGANISM: Pan troglodytes

<400> SEQUENCE: 1158
cccctacccc ccagctagga ggacactggc ccccaacagg tattacccca ctaaatcccc 60
tagaagtccc actcc 75

<210> SEQ ID NO 1159
<211> LENGTH: 75
<212> TYPE: DNA
<213> ORGANISM: Homo sapiens

<400> SEQUENCE: 1159
cccctacccc ccaattagga gggcactggc ccccaacagg catcaccccg ctaaatcccc 60
tagaagtccc actcc 75

<210> SEQ ID NO 1160
<211> LENGTH: 75
<212> TYPE: DNA
<213> ORGANISM: Pan troglodytes

<400> SEQUENCE: 1160
taaacacatc tgtattactc gcatcaggag tatcaattac ttgagcccat cacagcttaa 60
tagaaaataa ccgaa 75

<210> SEQ ID NO 1161
<211> LENGTH: 75
<212> TYPE: DNA
<213> ORGANISM: Homo sapiens

<400> SEQUENCE: 1161
taaacacatc cgtattactc gcatcaggag tatcaatcac ctgagctcac catagtctaa 60
tagaaaacaa ccgaa 75

<210> SEQ ID NO 1162
<211> LENGTH: 75
<212> TYPE: DNA
<213> ORGANISM: Pan troglodytes

<400> SEQUENCE: 1162
accaaataat tcaagcactg cttattacga ttctactagg tctttatttt accctcctac 60
aagcctcaga atatt 75

<210> SEQ ID NO 1163
<211> LENGTH: 75
<212> TYPE: DNA
<213> ORGANISM: Homo sapiens

<400> SEQUENCE: 1163
accaaataat tcaagcactg cttattacaa ttttactggg tctctatttt accctcctac 60
aagcctcaga gtact 75

<210> SEQ ID NO 1164
<211> LENGTH: 75
<212> TYPE: DNA
<213> ORGANISM: Pan troglodytes

<400> SEQUENCE: 1164
tcgaatcccc ttttaccatt tccgatggca tctacggctc aacattcttt gtagccacag 60
gcttccacgg actcc 75

<210> SEQ ID NO 1165
<211> LENGTH: 75
<212> TYPE: DNA
<213> ORGANISM: Homo sapiens

<400> SEQUENCE: 1165
tcgagtctcc cttcaccatt tccgacggca tctacggctc aacatttttt gtagccacag 60
gcttccacgg acttc 75

<210> SEQ ID NO 1166
<211> LENGTH: 75
<212> TYPE: DNA
<213> ORGANISM: Pan troglodytes

<400> SEQUENCE: 1166
acgtcattat tggatcaact ttcctcacta tctgcctcat ccgccaacta atatttcact 60
tcacatccaa acatc 75

<210> SEQ ID NO 1167
<211> LENGTH: 75
<212> TYPE: DNA
<213> ORGANISM: Homo sapiens

<400> SEQUENCE: 1167
acgtcattat tggctcaact ttcctcacta tctgcttcat ccgccaacta atatttcact 60
ttacatccaa acatc 75

<210> SEQ ID NO 1168
<211> LENGTH: 75
<212> TYPE: DNA
<213> ORGANISM: Pan troglodytes

<400> SEQUENCE: 1168
acttcggctt tcaagccgcc gcctgatact gacacttcgt agatgtagtc tgactatttc 60
tatatgtctc tattt 75

<210> SEQ ID NO 1169
<211> LENGTH: 75
<212> TYPE: DNA
<213> ORGANISM: Homo sapiens

<400> SEQUENCE: 1169
actttggctt cgaagccgcc gcctgatact ggcattttgt agatgtggtt tgactatttc 60
tgtatgtctc catct 75

<210> SEQ ID NO 1170
<211> LENGTH: 75
<212> TYPE: DNA
<213> ORGANISM: Pan troglodytes

<400> SEQUENCE: 1170
actgatgagg atcttactct tttagtataa gtagtaccgt taacttccaa ttaactagtt 60
ttgacaacat tcaaa 75

<210> SEQ ID NO 1171

<211> LENGTH: 75
<212> TYPE: DNA
<213> ORGANISM: Homo sapiens

<400> SEQUENCE: 1171
attgatgagg gtcttactct tttagtataa atagtaccgt taacttccaa ttaactagtt 60
ttgacaacat tcaaa 75

<210> SEQ ID NO 1172
<211> LENGTH: 75
<212> TYPE: DNA
<213> ORGANISM: Pan troglodytes

<400> SEQUENCE: 1172
aaagagtaat aaacttcgtc ctaattttaa taaccaatac ccttctagcc ctactactga 60
taattatcac attct 75

<210> SEQ ID NO 1173
<211> LENGTH: 75
<212> TYPE: DNA
<213> ORGANISM: Homo sapiens

<400> SEQUENCE: 1173
aaagagtaat aaacttcgcc ttaattttaa taatcaacac cctcctagcc ttactactaa 60
taattattac atttt 75

<210> SEQ ID NO 1174
<211> LENGTH: 75
<212> TYPE: DNA
<213> ORGANISM: Pan troglodytes

<400> SEQUENCE: 1174
gactaccaca actcaacagc tacatagaaa aatctacccc ttacgaatgt ggcttcgacc 60
ctatatcccc cgccc 75

<210> SEQ ID NO 1175
<211> LENGTH: 75
<212> TYPE: DNA
<213> ORGANISM: Homo sapiens

<400> SEQUENCE: 1175
gactaccaca actcaacggc tacatagaaa aatccacccc ttacgagtgc ggcttcgacc 60
ctatatcccc cgccc 75

<210> SEQ ID NO 1176
<211> LENGTH: 75
<212> TYPE: DNA
<213> ORGANISM: Pan troglodytes

<400> SEQUENCE: 1176
gcgtcccctt ctccataaaa tttttcctag tagccatcac cttcctatta tttgacctag 60
aaattgccct cctat 75

<210> SEQ ID NO 1177
<211> LENGTH: 75
<212> TYPE: DNA
<213> ORGANISM: Homo sapiens

<400> SEQUENCE: 1177
gcgtcccttt ctccataaaa ttcttcttag tagctattac cttcttatta tttgatctag 60
aaattgccct ccttt 75

<210> SEQ ID NO 1178
<211> LENGTH: 75
<212> TYPE: DNA
<213> ORGANISM: Pan troglodytes

<400> SEQUENCE: 1178
tgcccttacc ttgagcccta caaacggcca acctaccact aatagtcaca tcatccctct 60
tattaattac tatcc 75

<210> SEQ ID NO 1179
<211> LENGTH: 75
<212> TYPE: DNA
<213> ORGANISM: Homo sapiens

<400> SEQUENCE: 1179 taccctacc atgagcccta caaacaacta acctgccact aatagttatg tcatccctct 60
tattaatcat catcc 75

<210> SEQ ID NO 1180
<211> LENGTH: 75
<212> TYPE: DNA
<213> ORGANISM: Pan troglodytes

<400> SEQUENCE: 1180
tagccctaag cctcgcctac gaatgattac aaaaagggtt agactgaacc gaattggtat 60
atagtttaaa taaaa 75

<210> SEQ ID NO 1181
<211> LENGTH: 75
<212> TYPE: DNA
<213> ORGANISM: Homo sapiens

<400> SEQUENCE: 1181
tagccctaag tctggcctat gagtgactac aaaaaggatt agactgaacc gaattggtat 60
atagtttaaa caaaa 75

<210> SEQ ID NO 1182
<211> LENGTH: 75
<212> TYPE: DNA
<213> ORGANISM: Pan troglodytes

<400> SEQUENCE: 1182
cgaatgattt cgactcatta aattatgata atcatattta ccaaatgccc cttatttata 60
taaatattat actag 75

<210> SEQ ID NO 1183
<211> LENGTH: 75
<212> TYPE: DNA
<213> ORGANISM: Homo sapiens

<400> SEQUENCE: 1183
cgaatgattt cgactcatta aattatgata atcatattta ccaaatgccc ctcatttaca 60
taaatattat actag 75

<210> SEQ ID NO 1184
<211> LENGTH: 75
<212> TYPE: DNA

<213> ORGANISM: Pan troglodytes

<400> SEQUENCE: 1184
catttaccat ctcacttcta ggaatactag tatatcgctc acacctaata tcttccctac 60
tatgcctaga aggaa 75

<210> SEQ ID NO 1185
<211> LENGTH: 75
<212> TYPE: DNA
<213> ORGANISM: Homo sapiens

<400> SEQUENCE: 1185
catttaccat ctcacttcta ggaatactag tatatcgctc acacctcata tcctccctac 60
tatgcctaga aggaa 75

<210> SEQ ID NO 1186
<211> LENGTH: 75
<212> TYPE: DNA
<213> ORGANISM: Pan troglodytes

<400> SEQUENCE: 1186
taatactatc actgttcatc atagccaccc tcataaccct caatactcac tccctcttag 60
ccaatattgt accca 75

<210> SEQ ID NO 1187
<211> LENGTH: 75
<212> TYPE: DNA
<213> ORGANISM: Homo sapiens

<400> SEQUENCE: 1187
taatactatc gctgttcatt atagctactc tcataaccct caacacccac tccctcttag 60
ccaatattgt gccta 75

<210> SEQ ID NO 1188
<211> LENGTH: 75
<212> TYPE: DNA
<213> ORGANISM: Pan troglodytes

<400> SEQUENCE: 1188
tcaccatact agtctttgct gcctgcgaag cagcagtagg tctagcacta ctagtttcaa 60
tctctaacac atatg 75

<210> SEQ ID NO 1189
<211> LENGTH: 75
<212> TYPE: DNA
<213> ORGANISM: Homo sapiens

<400> SEQUENCE: 1189
ttgccatact agtctttgcc gcctgcgaag cagcggtggg cctagcccta ctagtctcaa 60
tctccaacac atatg 75

<210> SEQ ID NO 1190
<211> LENGTH: 75
<212> TYPE: DNA
<213> ORGANISM: Pan troglodytes

<400> SEQUENCE: 1190
gcttagacta cgtacataac ctaaacctac tccaatgcta aaactaatca tcccgacaat 60
tatattacta ccact 75

<210> SEQ ID NO 1191
<211> LENGTH: 75
<212> TYPE: DNA
<213> ORGANISM: Homo sapiens

<400> SEQUENCE: 1191
gcctagacta cgtacataac ctaaacctac tccaatgcta aaactaatcg tcccaacaat 60
tatattacta ccact 75

<210> SEQ ID NO 1192
<211> LENGTH: 75
<212> TYPE: DNA
<213> ORGANISM: Pan troglodytes

<400> SEQUENCE: 1192
aacatgattc tctaaaaaac gtataatttg aatcaacaca accactcaca gcctaattat 60
cagcaccatt ccctt 75

<210> SEQ ID NO 1193
<211> LENGTH: 75
<212> TYPE: DNA
<213> ORGANISM: Homo sapiens

<400> SEQUENCE: 1193
gacatgactt tccaaaaaac acataatttg aatcaacaca accacccaca gcctaattat 60
tagcatcatc cctct 75

<210> SEQ ID NO 1194
<211> LENGTH: 75
<212> TYPE: DNA
<213> ORGANISM: Pan troglodytes

<400> SEQUENCE: 1194
actatttttt aaccaaatta acaacaacct attcagctgt tccctgccct tctcctccga 60
ccccttaaca actcc 75

<210> SEQ ID NO 1195
<211> LENGTH: 75
<212> TYPE: DNA
<213> ORGANISM: Homo sapiens

<400> SEQUENCE: 1195
actatttttt aaccaaatca acaacaacct atttagctgt tccccaacct tttcctccga 60
ccccctaaca acccc 75

<210> SEQ ID NO 1196
<211> LENGTH: 75
<212> TYPE: DNA
<213> ORGANISM: Pan troglodytes

<400> SEQUENCE: 1196
cctcctaata ttaactgctt gacttctacc cctcacaatc atagcaagcc agcgccacct 60
atccaacgaa ccact 75

<210> SEQ ID NO 1197
<211> LENGTH: 75
<212> TYPE: DNA
<213> ORGANISM: Homo sapiens

<400> SEQUENCE: 1197
cctcctaata ctaactacct gactcctacc cctcacaatc atggcaagcc aacgccactt 60
atccagtgaa ccact 75

<210> SEQ ID NO 1198
<211> LENGTH: 75
<212> TYPE: DNA
<213> ORGANISM: Pan troglodytes

<400> SEQUENCE: 1198
atcacgaaaa aaactctacc tctccatgct aatttccctc caaatctcct taattataac 60
attctcggcc acaga 75

<210> SEQ ID NO 1199
<211> LENGTH: 75
<212> TYPE: DNA
<213> ORGANISM: Homo sapiens

<400> SEQUENCE: 1199
atcacgaaaa aaactctacc tctctatact aatctcccta caaatctcct taattataac 60
attcacagcc acaga 75

<210> SEQ ID NO 1200
<211> LENGTH: 75
<212> TYPE: DNA
<213> ORGANISM: Pan troglodytes

<400> SEQUENCE: 1200
gctaattata ttttatatct tcttcgaaac cacacttatc cccaccctgg ctatcatcac 60
ccgatggggt aacca 75

<210> SEQ ID NO 1201
<211> LENGTH: 75
<212> TYPE: DNA
<213> ORGANISM: Homo sapiens

<400> SEQUENCE: 1201
actaatcata ttttatatct tcttcgaaac cacacttatc cccaccttgg ctatcatcac 60
ccgatgaggc aacca 75

<210> SEQ ID NO 1202
<211> LENGTH: 75
<212> TYPE: DNA
<213> ORGANISM: Pan troglodytes

<400> SEQUENCE: 1202
accagaacgc ctgaacgcag gtacatactt cctattctat accctagtag gctccctccc 60
cctactcatc gcact 75

<210> SEQ ID NO 1203
<211> LENGTH: 75
<212> TYPE: DNA
<213> ORGANISM: Homo sapiens

<400> SEQUENCE: 1203
gccagaacgc ctgaacgcag gcacatactt cctattctac accctagtag gctcccttcc 60
cctactcatc gcact 75

<210> SEQ ID NO 1204
<211> LENGTH: 75
<212> TYPE: DNA
<213> ORGANISM: Pan troglodytes

<400> SEQUENCE: 1204
aatctatacc cacaacaccc taggctcact aaatatccta ttactcactc ttacaaccca 60
agaactatca aacac 75

<210> SEQ ID NO 1205
<211> LENGTH: 75
<212> TYPE: DNA
<213> ORGANISM: Homo sapiens

<400> SEQUENCE: 1205
aatttacact cacaacaccc taggctcact aaacattcta ctactcactc tcactgccca 60
agaactatca aactc 75

<210> SEQ ID NO 1206
<211> LENGTH: 75
<212> TYPE: DNA
<213> ORGANISM: Pan troglodytes

<400> SEQUENCE: 1206
ctgagccaac aacttaatat gactagcgta cacgatggct ttcatggtaa aaatacccct 60
ttacggactc cacct 75

<210> SEQ ID NO 1207
<211> LENGTH: 75
<212> TYPE: DNA
<213> ORGANISM: Homo sapiens

<400> SEQUENCE: 1207
ctgagccaac aacttaatat gactagctta cacaatagct tttatagtaa agatacctct 60
ttacggactc cactt 75

<210> SEQ ID NO 1208
<211> LENGTH: 75
<212> TYPE: DNA
<213> ORGANISM: Pan troglodytes

<400> SEQUENCE: 1208
atgactccct aaagcccatg tcgaagcccc tattgccggg tcaatggtac ttgctgcagt 60
actcttaaaa ttagg 75

<210> SEQ ID NO 1209
<211> LENGTH: 75
<212> TYPE: DNA
<213> ORGANISM: Homo sapiens

<400> SEQUENCE: 1209
atgactccct aaagcccatg tcgaagcccc catcgctggg tcaatagtac ttgccgcagt 60
actcttaaaa ctagg 75

<210> SEQ ID NO 1210
<211> LENGTH: 75
<212> TYPE: DNA
<213> ORGANISM: Pan troglodytes

<400> SEQUENCE: 1210
tggctatggc ataatacgcc tcacactcat cctcaacccc ctaacaaaac atatagccta 60
tcccttcctc atgtt 75

<210> SEQ ID NO 1211
<211> LENGTH: 75
<212> TYPE: DNA
<213> ORGANISM: Homo sapiens

<400> SEQUENCE: 1211
cggctatggt ataatacgcc tcacactcat tctcaacccc ctgacaaaac acatagccta 60
ccccttcctt gtact 75

<210> SEQ ID NO 1212
<211> LENGTH: 75
<212> TYPE: DNA
<213> ORGANISM: Pan troglodytes

<400> SEQUENCE: 1212
gtccttatga ggtataatca taacaagctc catctgcctg cgacaaacag acctaaaatc 60
gctcattgca taccc 75

<210> SEQ ID NO 1213
<211> LENGTH: 75
<212> TYPE: DNA
<213> ORGANISM: Homo sapiens

<400> SEQUENCE: 1213
atccctatga ggcataatta taacaagctc catctgccta cgacaaacag acctaaaatc 60
gctcattgca tactc 75

<210> SEQ ID NO 1214
<211> LENGTH: 75
<212> TYPE: DNA
<213> ORGANISM: Pan troglodytes

<400> SEQUENCE: 1214
ttcagtcagc cacatagccc tcgtagtaac agccattctc atccaaaccc cctgaagctt 60
caccggcgca attat 75

<210> SEQ ID NO 1215
<211> LENGTH: 75
<212> TYPE: DNA
<213> ORGANISM: Homo sapiens

<400> SEQUENCE: 1215
ttcaatcagc cacatagccc tcgtagtaac agccattctc atccaaaccc cctgaagctt 60
caccggcgca gtcat 75

<210> SEQ ID NO 1216
<211> LENGTH: 75
<212> TYPE: DNA
<213> ORGANISM: Pan troglodytes

<400> SEQUENCE: 1216
cctcataatc gcccacggac ttacatcctc attattatcc tgcctagcaa actcaaatta 60
tgaacgcacc cacag 75

<210> SEQ ID NO 1217
<211> LENGTH: 75

<212> TYPE: DNA
<213> ORGANISM: Homo sapiens

<400> SEQUENCE: 1217
tctcataatc gcccacgggc ttacatcctc attactattc tgcctagcaa actcaaacta 60
cgaacgcact cacag 75

<210> SEQ ID NO 1218
<211> LENGTH: 75
<212> TYPE: DNA
<213> ORGANISM: Pan troglodytes

<400> SEQUENCE: 1218
tcgcatcata attctctccc aaggacttca aactctactc ccactaatag ccttttgatg 60
actcctggca agcct 75

<210> SEQ ID NO 1219
<211> LENGTH: 75
<212> TYPE: DNA
<213> ORGANISM: Homo sapiens

<400> SEQUENCE: 1219
tcgcatcata atcctctctc aaggacttca aactctactc ccactaatag ctttttgatg 60
acttctagca agcct 75

<210> SEQ ID NO 1220
<211> LENGTH: 75
<212> TYPE: DNA
<213> ORGANISM: Pan troglodytes

<400> SEQUENCE: 1220
cgctaacctc gccctacccc ctaccattaa tctcctaggg gaactctccg tgctagtaac 60
ctcattctcc tgatc 75

<210> SEQ ID NO 1221
<211> LENGTH: 75
<212> TYPE: DNA
<213> ORGANISM: Homo sapiens

<400> SEQUENCE: 1221
cgctaacctc gccttacccc ccactattaa cctactggga gaactctctg tgctagtaac 60
cacgttctcc tgatc 75

<210> SEQ ID NO 1222
<211> LENGTH: 75
<212> TYPE: DNA
<213> ORGANISM: Pan troglodytes

<400> SEQUENCE: 1222
aaataccact ctcctactca caggattcaa catactaatc acagccctgt actccctcta 60
catgtttacc acaac 75

<210> SEQ ID NO 1223
<211> LENGTH: 75
<212> TYPE: DNA
<213> ORGANISM: Homo sapiens

<400> SEQUENCE: 1223
aaatatcact ctcctactta caggactcaa catactagtc acagccctat actccctcta 60
catatttacc acaac 75

<210> SEQ ID NO 1224
<211> LENGTH: 75
<212> TYPE: DNA
<213> ORGANISM: Pan troglodytes

<400> SEQUENCE: 1224
acaatgaggc tcactcaccc accacattaa tagcataaag ccctcattca cacgagaaaa 60
cactctcata ttttt 75

<210> SEQ ID NO 1225
<211> LENGTH: 75
<212> TYPE: DNA
<213> ORGANISM: Homo sapiens

<400> SEQUENCE: 1225
acaatggggc tcactcaccc accacattaa caacataaaa ccctcattca cacgagaaaa 60
caccctcatg ttcat 75

<210> SEQ ID NO 1226
<211> LENGTH: 75
<212> TYPE: DNA
<213> ORGANISM: Pan troglodytes

<400> SEQUENCE: 1226
acacctatcc cccatcctcc ttctatccct caatcctgat atcatcactg gattcacctc 60
ctgtaaatat agttt 75

<210> SEQ ID NO 1227
<211> LENGTH: 75
<212> TYPE: DNA
<213> ORGANISM: Homo sapiens

<400> SEQUENCE: 1227
acacctatcc cccattctcc tcctatccct caaccccgac atcattaccg ggttttcctc 60
ttgtaaatat agttt 75

<210> SEQ ID NO 1228
<211> LENGTH: 75
<212> TYPE: DNA
<213> ORGANISM: Pan troglodytes

<400> SEQUENCE: 1228
aaccaaaaca tcagattgtg aatctgacaa cagaggctca cgacccctta tttaccgaga 60
aagcttataa gaact 75

<210> SEQ ID NO 1229
<211> LENGTH: 75
<212> TYPE: DNA
<213> ORGANISM: Homo sapiens

<400> SEQUENCE: 1229
aaccaaaaca tcagattgtg aatctgacaa cagaggctta cgacccctta tttaccgaga 60
aagctcacaa gaact 75

<210> SEQ ID NO 1230
<211> LENGTH: 75
<212> TYPE: DNA
<213> ORGANISM: Pan troglodytes

<400> SEQUENCE: 1230
gctaactcgt attcccatgc ctaacaacat ggctttctca acttttaaag gataacagtt 60
atccattggt cttag 75

<210> SEQ ID NO 1231
<211> LENGTH: 75
<212> TYPE: DNA
<213> ORGANISM: Homo sapiens

<400> SEQUENCE: 1231
gctaactcat gcccccatgt ctaacaacat ggctttctca acttttaaag gataacagct 60
atccattggt cttag 75

<210> SEQ ID NO 1232
<211> LENGTH: 75
<212> TYPE: DNA
<213> ORGANISM: Pan troglodytes

<400> SEQUENCE: 1232
gccccaaaaa ttttggtgca actccaaata aaagtaataa ccatgtatgc taccataacc 60
accttagccc taact 75

<210> SEQ ID NO 1233
<211> LENGTH: 75
<212> TYPE: DNA
<213> ORGANISM: Homo sapiens

<400> SEQUENCE: 1233
gccccaaaaa ttttggtgca actccaaata aaagtaataa ccatgcacac tactataacc 60
accctaaccc tgact 75

<210> SEQ ID NO 1234
<211> LENGTH: 75
<212> TYPE: DNA
<213> ORGANISM: Pan troglodytes

<400> SEQUENCE: 1234
tccttaattc cccccatcct cggcgccctc attaacccta acaaaaaaaa ctcatacccc 60
cattacgtga aatcc 75

<210> SEQ ID NO 1235
<211> LENGTH: 75
<212> TYPE: DNA
<213> ORGANISM: Homo sapiens

<400> SEQUENCE: 1235
tccctaattc cccccatcct taccaccctc gttaacccta acaaaaaaaa ctcatacccc 60
cattatgtaa aatcc 75

<210> SEQ ID NO 1236
<211> LENGTH: 75
<212> TYPE: DNA
<213> ORGANISM: Pan troglodytes

<400> SEQUENCE: 1236
attatcgcat ccacctttat cattagcctt ttccccacaa caatattcat atgcctagac 60
caagaaacta ttatc 75

<210> SEQ ID NO 1237
<211> LENGTH: 75
<212> TYPE: DNA
<213> ORGANISM: Homo sapiens

<400> SEQUENCE: 1237
attgtcgcat ccacctttat tatcagtctc ttccccacaa caatattcat gtgcctagac 60
caagaagtta ttatc 75

<210> SEQ ID NO 1238
<211> LENGTH: 75
<212> TYPE: DNA
<213> ORGANISM: Pan troglodytes

<400> SEQUENCE: 1238
tcgaactgac actgagcaac aacccaaaca acccaactct ccctgagctt taaactagac 60
tatttctcca taaca 75

<210> SEQ ID NO 1239
<211> LENGTH: 75
<212> TYPE: DNA
<213> ORGANISM: Homo sapiens

<400> SEQUENCE: 1239
tcgaactgac actgagccac aacccaaaca acccagctct ccctaagctt caaactagac 60
tacttctcca taata 75

<210> SEQ ID NO 1240
<211> LENGTH: 75
<212> TYPE: DNA
<213> ORGANISM: Pan troglodytes

<400> SEQUENCE: 1240
tttatccccg tagcactgtt cgttacatga tccatcatag aattctcact atgatatata 60
gactcagacc ccaac 75

<210> SEQ ID NO 1241
<211> LENGTH: 75
<212> TYPE: DNA
<213> ORGANISM: Homo sapiens

<400> SEQUENCE: 1241
ttcatccctg tagcattgtt cgttacatgg tccatcatag aattctcact gtgatatata 60
aactcagacc caaac 75

<210> SEQ ID NO 1242
<211> LENGTH: 75
<212> TYPE: DNA
<213> ORGANISM: Pan troglodytes

<400> SEQUENCE: 1242
atcaaccaat tcttcaaata cttacttatc ttcctaatta ctatactaat cctagtcacc 60
gctaacaacc tattc 75

<210> SEQ ID NO 1243
<211> LENGTH: 75
<212> TYPE: DNA
<213> ORGANISM: Homo sapiens

<400> SEQUENCE: 1243
attaatcagt tcttcaaata tctactcatc ttcctaatta ccatactaat cttagttacc 60
gctaacaacc tattc 75

<210> SEQ ID NO 1244
<211> LENGTH: 75
<212> TYPE: DNA
<213> ORGANISM: Pan troglodytes

<400> SEQUENCE: 1244
caactcttca tcggctgaga aggcgtagga attatatcct ttctactcat tagctgatgg 60
tacgcccgaa cagat 75

<210> SEQ ID NO 1245
<211> LENGTH: 75
<212> TYPE: DNA
<213> ORGANISM: Homo sapiens

<400> SEQUENCE: 1245
caactgttca tcggctgaga gggcgtagga attatatcct tcttgctcat cagttgatga 60
tacgcccgag cagat 75

<210> SEQ ID NO 1246
<211> LENGTH: 75
<212> TYPE: DNA
<213> ORGANISM: Pan troglodytes

<400> SEQUENCE: 1246
gccaacacag cagccatcca agcaatccta tataaccgta tcggtgatat tggttttgtc 60
ctagccctag catga 75

<210> SEQ ID NO 1247
<211> LENGTH: 75
<212> TYPE: DNA
<213> ORGANISM: Homo sapiens

<400> SEQUENCE: 1247
gccaacacag cagccattca agcaatccta tacaaccgta tcggcgatat cggtttcatc 60
ctcgccttag catga 75

<210> SEQ ID NO 1248
<211> LENGTH: 75
<212> TYPE: DNA
<213> ORGANISM: Pan troglodytes

<400> SEQUENCE: 1248
tttctcctac actccaactc atgagatcca caacaaataa tcctcctaag tactaataca 60
gaccttactc cacta 75

<210> SEQ ID NO 1249
<211> LENGTH: 75
<212> TYPE: DNA
<213> ORGANISM: Homo sapiens

<400> SEQUENCE: 1249
tttatcctac actccaactc atgagaccca caacaaatag cccttctaaa cgctaatcca 60
agcctcaccc cacta 75

<210> SEQ ID NO 1250

<211> LENGTH: 75
<212> TYPE: DNA
<213> ORGANISM: Pan troglodytes

<400> SEQUENCE: 1250
ctaggcttcc tcctagcagc agcaggcaaa tcagctcaac taggccttca cccctgactc 60
ccctcagcca tagaa 75

<210> SEQ ID NO 1251
<211> LENGTH: 75
<212> TYPE: DNA
<213> ORGANISM: Homo sapiens

<400> SEQUENCE: 1251
ctaggcctcc tcctagcagc agcaggcaaa tcagcccaat taggtctcca cccctgactc 60
ccctcagcca tagaa 75

<210> SEQ ID NO 1252
<211> LENGTH: 75
<212> TYPE: DNA
<213> ORGANISM: Pan troglodytes

<400> SEQUENCE: 1252
ggccctaccc ctgtttcagc cctactccac tcaagcacca tagtcgtagc aggaatcttc 60
ctactcatcc gcttc 75

<210> SEQ ID NO 1253
<211> LENGTH: 75
<212> TYPE: DNA
<213> ORGANISM: Homo sapiens

<400> SEQUENCE: 1253
ggccccaccc cagtctcagc cctactccac tcaagcacta tagttgtagc aggaatcttc 60
ttactcatcc gcttc 75

<210> SEQ ID NO 1254
<211> LENGTH: 75
<212> TYPE: DNA
<213> ORGANISM: Pan troglodytes

<400> SEQUENCE: 1254
taccccctag cagagaataa cccactaatc caaactctca cgctatgcct aggcgctatc 60
accaccctat tcgca 75

<210> SEQ ID NO 1255
<211> LENGTH: 75
<212> TYPE: DNA
<213> ORGANISM: Homo sapiens

<400> SEQUENCE: 1255 cacccctag cagaaaatag cccactaatc caaactctaa cactatgctt aggcgctatc 60
accactctgt tcgca 75

<210> SEQ ID NO 1256
<211> LENGTH: 75
<212> TYPE: DNA
<213> ORGANISM: Pan troglodytes

<400> SEQUENCE: 1256
gcagtctgcg ccctcacaca aaatgacatc aaaaaaatcg tggccttctc cacttcaagc 60
caactaggac tcata 75

<210> SEQ ID NO 1257
<211> LENGTH: 75
<212> TYPE: DNA
<213> ORGANISM: Homo sapiens

<400> SEQUENCE: 1257
gcagtctgcg cccttacaca aaatgacatc aaaaaaatcg tagccttctc cacttcaagt 60
caactaggac tcata 75

<210> SEQ ID NO 1258
<211> LENGTH: 75
<212> TYPE: DNA
<213> ORGANISM: Pan troglodytes

<400> SEQUENCE: 1258
atagttacaa tcggtatcaa ccaaccacac ctagcattcc ttcacatctg cacccacgct 60
ttcttcaaag ccata 75

<210> SEQ ID NO 1259
<211> LENGTH: 75
<212> TYPE: DNA
<213> ORGANISM: Homo sapiens

<400> SEQUENCE: 1259
atagttacaa tcggcatcaa ccaaccacac ctagcattcc tgcacatctg tacccacgcc 60
ttcttcaaag ccata 75

<210> SEQ ID NO 1260
<211> LENGTH: 75
<212> TYPE: DNA
<213> ORGANISM: Pan troglodytes

<400> SEQUENCE: 1260
ctattcatat gctccggatc cattattcac aacctcaata atgagcaaga cattcgaaaa 60
ataggaggat tactc 75

<210> SEQ ID NO 1261
<211> LENGTH: 75
<212> TYPE: DNA
<213> ORGANISM: Homo sapiens

<400> SEQUENCE: 1261
ctatttatgt gctccgggtc catcatccac aaccttaaca atgaacaaga tattcgaaaa 60
ataggaggac tactc 75

<210> SEQ ID NO 1262
<211> LENGTH: 75
<212> TYPE: DNA
<213> ORGANISM: Pan troglodytes

<400> SEQUENCE: 1262
aaaaccatac ccctcacttc aacctccctc accattggga gcctagcatt agcaggaata 60
cccttcctca caggt 75

<210> SEQ ID NO 1263
<211> LENGTH: 75
<212> TYPE: DNA

<213> ORGANISM: Homo sapiens

<400> SEQUENCE: 1263
aaaaccatac ctctcacttc aacctccctc accattggca gcctagcatt agcaggaata 60
cctttcctca caggt 75

<210> SEQ ID NO 1264
<211> LENGTH: 75
<212> TYPE: DNA
<213> ORGANISM: Pan troglodytes

<400> SEQUENCE: 1264
ttctactcca aagacctcat catcgaaacc gctaacatat catacacaaa cgcctgagcc 60
ctatctatta ctctc 75

<210> SEQ ID NO 1265
<211> LENGTH: 75
<212> TYPE: DNA
<213> ORGANISM: Homo sapiens

<400> SEQUENCE: 1265
ttctactcca aagaccacat catcgaaacc gcaaacatat catacacaaa cgcctgagcc 60
ctatctatta ctctc 75

<210> SEQ ID NO 1266
<211> LENGTH: 75
<212> TYPE: DNA
<213> ORGANISM: Pan troglodytes

<400> SEQUENCE: 1266
atcgccacct ctctgacaag cgcctacagc acccgaataa tcctcctcac cctaacaggt 60
caacctcgct tccca 75

<210> SEQ ID NO 1267
<211> LENGTH: 75
<212> TYPE: DNA
<213> ORGANISM: Homo sapiens

<400> SEQUENCE: 1267
atcgctacct ccctgacaag cgcctatagc actcgaataa ttcttctcac cctaacaggt 60
caacctcgct tcccc 75

<210> SEQ ID NO 1268
<211> LENGTH: 75
<212> TYPE: DNA
<213> ORGANISM: Pan troglodytes

<400> SEQUENCE: 1268
accctcacca acattaacga aaacaacccc actctgttaa atcccattaa acgcctaacc 60
attggaagct tattt 75

<210> SEQ ID NO 1269
<211> LENGTH: 75
<212> TYPE: DNA
<213> ORGANISM: Homo sapiens

<400> SEQUENCE: 1269
acccttacta acattaacga aaataacccc accctactaa accccattaa acgcctggca 60
gccggaagcc tattc 75

<210> SEQ ID NO 1270
<211> LENGTH: 75
<212> TYPE: DNA
<213> ORGANISM: Homo sapiens

<400> SEQUENCE: 1270
gcaggatttc tcattactaa caacatttcc cccgcatccc ccttccaaac aacaatcccc 60
ctctacctaa aactc 75

<210> SEQ ID NO 1271
<211> LENGTH: 75
<212> TYPE: DNA
<213> ORGANISM: Pan troglodytes

<400> SEQUENCE: 1271
acagccctag gcgttacttc cctaggactt ctaacagccc tagacctcaa ttacctaacc 60
agcaagctca aaata 75

<210> SEQ ID NO 1272
<211> LENGTH: 75
<212> TYPE: DNA
<213> ORGANISM: Homo sapiens

<400> SEQUENCE: 1272
acagccctcg ctgtcacttt cctaggactt ctaacagccc tagacctcaa ctacctaacc 60
aacaaactta aaata 75

<210> SEQ ID NO 1273
<211> LENGTH: 75
<212> TYPE: DNA
<213> ORGANISM: Pan troglodytes

<400> SEQUENCE: 1273
aaatccccac tatatacatt tcacttctct aatatactcg gattctaccc taacattata 60
caccgctcga tcccc 75

<210> SEQ ID NO 1274
<211> LENGTH: 75
<212> TYPE: DNA
<213> ORGANISM: Homo sapiens

<400> SEQUENCE: 1274
aaatccccac tatgcacatt ttatttctcc aacatactcg gattctaccc tagcatcaca 60
caccgcacaa tcccc 75

<210> SEQ ID NO 1275
<211> LENGTH: 75
<212> TYPE: DNA
<213> ORGANISM: Pan troglodytes

<400> SEQUENCE: 1275
tatctaggcc ttcttacaag ccaaaaccta cccctacttc ttctagacct gacctgacta 60
gagaaactat tacct 75

<210> SEQ ID NO 1276
<211> LENGTH: 75
<212> TYPE: DNA
<213> ORGANISM: Homo sapiens

<400> SEQUENCE: 1276
tatctaggcc ttcttacgag ccaaaacctg cccctactcc tcctagacct aacctgacta 60
gaaaagctat tacct 75

<210> SEQ ID NO 1277
<211> LENGTH: 75
<212> TYPE: DNA
<213> ORGANISM: Pan troglodytes

<400> SEQUENCE: 1277
aaaacaattt cacagtacca aatctccgct tccattacca cctcaaccca aaaaggcatg 60
atcaaacttt atttc 75

<210> SEQ ID NO 1278
<211> LENGTH: 75
<212> TYPE: DNA
<213> ORGANISM: Homo sapiens

<400> SEQUENCE: 1278
aaaacaattt cacagcacca aatctccacc tccatcatca cctcaaccca aaaaggcata 60
attaaacttt acttc 75

<210> SEQ ID NO 1279
<211> LENGTH: 75
<212> TYPE: DNA
<213> ORGANISM: Pan troglodytes

<400> SEQUENCE: 1279
ctctcttttt tcttccctct catcttaacc ttactcctaa tcacataacc tattcccccg 60
agcaatctca atcac 75

<210> SEQ ID NO 1280
<211> LENGTH: 75
<212> TYPE: DNA
<213> ORGANISM: Homo sapiens

<400> SEQUENCE: 1280
ctctctttct tcttcccact catcctaacc ctactcctaa tcacataacc tattcccccg 60
agcaatctca attac 75

<210> SEQ ID NO 1281
<211> LENGTH: 75
<212> TYPE: DNA
<213> ORGANISM: Pan troglodytes

<400> SEQUENCE: 1281
aatgtataca ccaacaaaca atgtccaacc agtaactact actaaccaac gcccataatc 60
atataaggcc cccgc 75

<210> SEQ ID NO 1282
<211> LENGTH: 75
<212> TYPE: DNA
<213> ORGANISM: Homo sapiens

<400> SEQUENCE: 1282
aatatataca ccaacaaaca atgttcaacc agtaactact actaatcaac gcccataatc 60
atacaaagcc cccgc 75

<210> SEQ ID NO 1283
<211> LENGTH: 75
<212> TYPE: DNA
<213> ORGANISM: Pan troglodytes

<400> SEQUENCE: 1283
accaatagga tcctcccgaa tcagccctgg cccctcccct tcataaatta ttcaacttcc 60
cacgctatta aaatt 75

<210> SEQ ID NO 1284
<211> LENGTH: 75
<212> TYPE: DNA
<213> ORGANISM: Homo sapiens

<400> SEQUENCE: 1284
accaatagga tcctcccgaa tcaaccctga cccctctcct tcataaatta ttcagcttcc 60
tacactatta aagtt 75

<210> SEQ ID NO 1285
<211> LENGTH: 75
<212> TYPE: DNA
<213> ORGANISM: Pan troglodytes

<400> SEQUENCE: 1285
taccacaacc accatcccat catacccttt tacccataac actaatccta cctccatcgc 60
cagtcctact aaaac 75

<210> SEQ ID NO 1286
<211> LENGTH: 75
<212> TYPE: DNA
<213> ORGANISM: Homo sapiens

<400> SEQUENCE: 1286
taccacaacc accaccccat catactcttt cacccacagc accaatccta cctccatcgc 60
taaccccact aaaac 75

<210> SEQ ID NO 1287
<211> LENGTH: 75
<212> TYPE: DNA
<213> ORGANISM: Pan troglodytes

<400> SEQUENCE: 1287
actaaccaaa acctcaaccc ctgaccccca tgcctcagga tactcctcaa tagccatagc 60
cgtagtatac ccaaa 75

<210> SEQ ID NO 1288
<211> LENGTH: 75
<212> TYPE: DNA
<213> ORGANISM: Homo sapiens

<400> SEQUENCE: 1288
actcaccaag acctcaaccc ctgaccccca tgcctcagga tactcctcaa tagccatcgc 60
tgtagtatat ccaaa 75

<210> SEQ ID NO 1289
<211> LENGTH: 75
<212> TYPE: DNA
<213> ORGANISM: Pan troglodytes

<400> SEQUENCE: 1289
aacaaccatt attcccccca aataaattaa aaaaaccatt aaacctatat aacctccccc 60
ataattcaaa atgat 75

<210> SEQ ID NO 1290
<211> LENGTH: 75
<212> TYPE: DNA
<213> ORGANISM: Homo sapiens

<400> SEQUENCE: 1290
gacaaccatc attcccccta aataaattaa aaaaactatt aaacccatat aacctccccc 60
aaaattcaga ataat 75

<210> SEQ ID NO 1291
<211> LENGTH: 75
<212> TYPE: DNA
<213> ORGANISM: Pan troglodytes

<400> SEQUENCE: 1291
ggcacaccca actacaccac taacaatcaa tactaaaccc ccataaatgg gagaaggctt 60
agaagaaaac cccac 75

<210> SEQ ID NO 1292
<211> LENGTH: 75
<212> TYPE: DNA
<213> ORGANISM: Homo sapiens

<400> SEQUENCE: 1292
aacacacccg accacaccgc taacaatcaa tactaaaccc ccataaatag gagaaggctt 60
agaagaaaac cccac 75

<210> SEQ ID NO 1293
<211> LENGTH: 75
<212> TYPE: DNA
<213> ORGANISM: Pan troglodytes

<400> SEQUENCE: 1293
aaaccctatc actaaactca cactcaataa aaataaagca tatgtcatta ttctcgcacg 60
gactacaacc acgac 75

<210> SEQ ID NO 1294
<211> LENGTH: 75
<212> TYPE: DNA
<213> ORGANISM: Homo sapiens

<400> SEQUENCE: 1294
aaaccccatt actaaaccca cactcaacag aaacaaagca tacatcatta ttctcgcacg 60
gactacaacc acgac 75

<210> SEQ ID NO 1295
<211> LENGTH: 75
<212> TYPE: DNA
<213> ORGANISM: Pan troglodytes

<400> SEQUENCE: 1295
caatgatatg aaaaaccatc gttgtatttc aactacaaga acaccaatga ccccgacacg 60
caaaattaac ccact 75

<210> SEQ ID NO 1296
<211> LENGTH: 75

<212> TYPE: DNA
<213> ORGANISM: Homo sapiens

<400> SEQUENCE: 1296
caatgatatg aaaaaccatc gttgtatttc aactacaaga acaccaatga ccccaatacg 60
caaaactaac cccct 75

<210> SEQ ID NO 1297
<211> LENGTH: 75
<212> TYPE: DNA
<213> ORGANISM: Pan troglodytes

<400> SEQUENCE: 1297
aataaaatta attaatcact catttatcga cctccccacc ccatccaaca tttccgcatg 60
atggaacttc ggctc 75

<210> SEQ ID NO 1298
<211> LENGTH: 75
<212> TYPE: DNA
<213> ORGANISM: Homo sapiens

<400> SEQUENCE: 1298
aataaaatta attaaccact cattcatcga cctccccacc ccatccaaca tctccgcatg 60
atgaaacttc ggctc 75

<210> SEQ ID NO 1299
<211> LENGTH: 75
<212> TYPE: DNA
<213> ORGANISM: Pan troglodytes

<400> SEQUENCE: 1299
acttctcggc gcctgcctaa tccttcaaat taccacagga ttattcctag ctatacacta 60
ctcaccagac gcctc 75

<210> SEQ ID NO 1300
<211> LENGTH: 75
<212> TYPE: DNA
<213> ORGANISM: Homo sapiens

<400> SEQUENCE: 1300
actccttggc gcctgcctga tcctccaaat caccacagga ctattcctag ccatgcacta 60
ctcaccagac gcctc 75

<210> SEQ ID NO 1301
<211> LENGTH: 75
<212> TYPE: DNA
<213> ORGANISM: Pan troglodytes

<400> SEQUENCE: 1301
aaccgccttc tcgtcgatcg cccacatcac ccgagacgta aactatggtt ggatcatccg 60
ctacctccac gctaa 75

<210> SEQ ID NO 1302
<211> LENGTH: 75
<212> TYPE: DNA
<213> ORGANISM: Homo sapiens

<400> SEQUENCE: 1302
aaccgccttt tcatcaatcg cccacatcac tcgagacgta aattatggct gaatcatccg 60
ctaccttcac gccaa 75

<210> SEQ ID NO 1303
<211> LENGTH: 75
<212> TYPE: DNA
<213> ORGANISM: Pan troglodytes

<400> SEQUENCE: 1303
cggcgcctca atattttta tctgcctctt cctacacatc ggccgaggtc tatattacgg 60
ctcatttctc tacct 75

<210> SEQ ID NO 1304
<211> LENGTH: 75
<212> TYPE: DNA
<213> ORGANISM: Homo sapiens

<400> SEQUENCE: 1304
tggcgcctca atattcttta tctgcctctt cctacacatc gggcgaggcc tatattacgg 60
atcatttctc tactc 75

<210> SEQ ID NO 1305
<211> LENGTH: 75
<212> TYPE: DNA
<213> ORGANISM: Pan troglodytes

<400> SEQUENCE: 1305
agaaacctga aacattggca ttatcctctt gctcacaacc atagcaacag cctttatggg 60
ctatgtcctc ccatg 75

<210> SEQ ID NO 1306
<211> LENGTH: 75
<212> TYPE: DNA
<213> ORGANISM: Homo sapiens

<400> SEQUENCE: 1306
agaaacctga aacatcggca ttatcctcct gcttgcaact atagcaacag ccttcatagg 60
ctatgtcctc ccgtg 75

<210> SEQ ID NO 1307
<211> LENGTH: 75
<212> TYPE: DNA
<213> ORGANISM: Pan troglodytes

<400> SEQUENCE: 1307
aggccaaata tccttctgag gagccacagt aattacaaac ctactgtccg ctatcccata 60
catcggaaca gacct 75

<210> SEQ ID NO 1308
<211> LENGTH: 75
<212> TYPE: DNA
<213> ORGANISM: Homo sapiens

<400> SEQUENCE: 1308
aggccaaata tcattctgag gggccacagt aattacaaac ttactatccg ccatcccata 60
cattgggaca gacct 75

<210> SEQ ID NO 1309
<211> LENGTH: 75
<212> TYPE: DNA
<213> ORGANISM: Pan troglodytes

<400> SEQUENCE: 1309
ggtccagtga gtctgaggag gctactcagt agacagccct acccttacac gattcttcac 60
cttccacttt atctt 75

<210> SEQ ID NO 1310
<211> LENGTH: 75
<212> TYPE: DNA
<213> ORGANISM: Homo sapiens

<400> SEQUENCE: 1310
agttcaatga atctgaggag gctactcagt agacagtccc accctcacac gattctttac 60
ctttcacttc atctt 75

<210> SEQ ID NO 1311
<211> LENGTH: 75
<212> TYPE: DNA
<213> ORGANISM: Pan troglodytes

<400> SEQUENCE: 1311
acccttcatc atcacagccc taacaacact tcatctccta ttcttacacg aaacaggatc 60
aaataacccc ctagg 75

<210> SEQ ID NO 1312
<211> LENGTH: 75
<212> TYPE: DNA
<213> ORGANISM: Homo sapiens

<400> SEQUENCE: 1312
gcccttcatt attgcagccc tagcaacact ccacctccta ttcttgcacg aaacgggatc 60
aaacaacccc ctagg 75

<210> SEQ ID NO 1313
<211> LENGTH: 75
<212> TYPE: DNA
<213> ORGANISM: Pan troglodytes

<400> SEQUENCE: 1313
aatcacctcc cactccgaca aaattacctt ccacccctac tacacaatca aagatatcct 60
tggcttattc ctttt 75

<210> SEQ ID NO 1314
<211> LENGTH: 75
<212> TYPE: DNA
<213> ORGANISM: Homo sapiens

<400> SEQUENCE: 1314
aatcacctcc cattccgata aaatcacctt ccacccttac tacacaatca aagacgccct 60
cggcttactt ctctt 75

<210> SEQ ID NO 1315
<211> LENGTH: 75
<212> TYPE: DNA
<213> ORGANISM: Pan troglodytes

<400> SEQUENCE: 1315
cctccttatc ctaatgacat taacactatt ctcaccaggc ctcctaggcg atccagacaa 60
ctatacccta gctaa 75

<210> SEQ ID NO 1316
<211> LENGTH: 75
<212> TYPE: DNA
<213> ORGANISM: Homo sapiens

<400> SEQUENCE: 1316
ccttctctcc ttaatgacat taacactatt ctcaccagac ctcctaggcg acccagacaa 60
ttatacccta gccaa 75

<210> SEQ ID NO 1317
<211> LENGTH: 75
<212> TYPE: DNA
<213> ORGANISM: Pan troglodytes

<400> SEQUENCE: 1317
ccccctaaac accccacccc acattaaacc cgagtgatac tttctatttg cctacacaat 60
cctccgatcc atccc 75

<210> SEQ ID NO 1318
<211> LENGTH: 75
<212> TYPE: DNA
<213> ORGANISM: Homo sapiens

<400> SEQUENCE: 1318
ccccttaaac acccctcccc acatcaagcc cgaatgatat ttcctattcg cctacacaat 60
tctccgatcc gtccc 75

<210> SEQ ID NO 1319
<211> LENGTH: 75
<212> TYPE: DNA
<213> ORGANISM: Pan troglodytes

<400> SEQUENCE: 1319
caacaaacta ggaggcgtcc tcgccctact actatctatc ctaatcctaa cagcaatccc 60
tgtcctccac acatc 75

<210> SEQ ID NO 1320
<211> LENGTH: 75
<212> TYPE: DNA
<213> ORGANISM: Homo sapiens

<400> SEQUENCE: 1320
taacaaacta ggaggcgtcc ttgccctatt actatccatc ctcatcctag caataatccc 60
catcctccat atatc 75

<210> SEQ ID NO 1321
<211> LENGTH: 75
<212> TYPE: DNA
<213> ORGANISM: Pan troglodytes

<400> SEQUENCE: 1321
caaacaacaa agcataatat ttcgcccact aagccaactg ctttactgac tcctagccac 60
agacctcctc atcct 75

<210> SEQ ID NO 1322
<211> LENGTH: 75
<212> TYPE: DNA
<213> ORGANISM: Homo sapiens

<400> SEQUENCE: 1322
caaacaacaa agcataatat ttcgcccact aagccaatca ctttattgac tcctagccgc 60
agacctcctc attct 75

<210> SEQ ID NO 1323
<211> LENGTH: 75
<212> TYPE: DNA
<213> ORGANISM: Pan troglodytes

<400> SEQUENCE: 1323
aacctgaatc ggaggacaac cagtaagcta ccccttcatc accatcggac aaatagcatc 60
cgtattatac ttcac 75

<210> SEQ ID NO 1324
<211> LENGTH: 75
<212> TYPE: DNA
<213> ORGANISM: Homo sapiens

<400> SEQUENCE: 1324
aacctgaatc ggaggacaac cagtaagcta cccttttacc atcattggac aagtagcatc 60
cgtactatac ttcac 75

<210> SEQ ID NO 1325
<211> LENGTH: 75
<212> TYPE: DNA
<213> ORGANISM: Pan troglodytes

<400> SEQUENCE: 1325
aacaatccta atcctaatac caatcgcctc tctaatcgaa aacaaaatac ttgaatgaac 60
ctgcccttgt agtat 75

<210> SEQ ID NO 1326
<211> LENGTH: 75
<212> TYPE: DNA
<213> ORGANISM: Homo sapiens

<400> SEQUENCE: 1326
aacaatccta atcctaatac caactatctc cctaattgaa aacaaaatac tcaaatgggc 60
ctgtccttgt agtat 75

<210> SEQ ID NO 1327
<211> LENGTH: 75
<212> TYPE: DNA
<213> ORGANISM: Pan troglodytes

<400> SEQUENCE: 1327
aaactaatac accggtcttg taaaccggaa acgaaaactt tcttccaagg acaaatcaga 60
gaaaaagtaa ttaac 75

<210> SEQ ID NO 1328
<211> LENGTH: 75
<212> TYPE: DNA
<213> ORGANISM: Homo sapiens

<400> SEQUENCE: 1328
aaactaatac accagtcttg taaaccggag atgaaaacct ttttccaagg acaaatcaga 60
gaaaaagtct ttaac 75

<210> SEQ ID NO 1329

<211> LENGTH: 75
<212> TYPE: DNA
<213> ORGANISM: Pan troglodytes

<400> SEQUENCE: 1329
ttcaccatca gcacccaaag ctaagattct aatttaaact attctctgtt ctttcatggg 60
gaagcaaatt taggt 75

<210> SEQ ID NO 1330
<211> LENGTH: 75
<212> TYPE: DNA
<213> ORGANISM: Homo sapiens

<400> SEQUENCE: 1330
tccaccatta gcacccaaag ctaagattct aatttaaact attctctgtt ctttcatggg 60
gaagcagatt tgggt 75

<210> SEQ ID NO 1331
<211> LENGTH: 75
<212> TYPE: DNA
<213> ORGANISM: Homo sapiens

<400> SEQUENCE: 1331
accacccaag tattgactca cccatcaaca accgctatgt atttcgtaca ttactgccag 60
ccaccatgaa tattg 75

<210> SEQ ID NO 1332
<211> LENGTH: 75
<212> TYPE: DNA
<213> ORGANISM: Homo sapiens

<400> SEQUENCE: 1332
tacggtacca taaatacttg accacctgta gtacataaaa acccaatcca catcaaaacc 60
ccctccccat gctta 75

<210> SEQ ID NO 1333
<211> LENGTH: 75
<212> TYPE: DNA
<213> ORGANISM: Homo sapiens

<400> SEQUENCE: 1333
caagcaagta cagcaatcaa ccctcaacta tcacacatca actgcaactc caaagccacc 60
cctcacccac tagga 75

<210> SEQ ID NO 1334
<211> LENGTH: 75
<212> TYPE: DNA
<213> ORGANISM: Pan troglodytes

<400> SEQUENCE: 1334
taccaacaga cctatctccc cttgacagaa catagtacat acaaccatac accgtacata 60
gcacattaca gtcaa 75

<210> SEQ ID NO 1335
<211> LENGTH: 75
<212> TYPE: DNA
<213> ORGANISM: Homo sapiens

<400> SEQUENCE: 1335
taccaacaaa cctacccacc cttaacagta catagtacat aaagccattt accgtacata 60
gcacattaca gtcaa 75

<210> SEQ ID NO 1336
<211> LENGTH: 75
<212> TYPE: DNA
<213> ORGANISM: Pan troglodytes

<400> SEQUENCE: 1336
acccctcctc gcccccacgg atgctccccc tcagatagga atcccttggt caccatcctc 60
cgtgaaatca atatc 75

<210> SEQ ID NO 1337
<211> LENGTH: 75
<212> TYPE: DNA
<213> ORGANISM: Homo sapiens

<400> SEQUENCE: 1337
atcccttctc gtccccatgg atgacccccc tcagataggg gtcccttgac caccatcctc 60
cgtgaaatca atatc 75

<210> SEQ ID NO 1338
<211> LENGTH: 75
<212> TYPE: DNA
<213> ORGANISM: Pan troglodytes

<400> SEQUENCE: 1338
tcccgcacaa gagtgactct cctcgctccg ggcccataac atctgggggt agctaaagtg 60
aactgtatcc gacat 75

<210> SEQ ID NO 1339
<211> LENGTH: 75
<212> TYPE: DNA
<213> ORGANISM: Homo sapiens

<400> SEQUENCE: 1339
ccgcacaaga gtgctactct cctcgctccg ggcccataac acttgggggt agctaaagtg 60
aactgtatcc gacat 75

<210> SEQ ID NO 1340
<211> LENGTH: 75
<212> TYPE: DNA
<213> ORGANISM: Pan troglodytes

<400> SEQUENCE: 1340
gatcacaggt ctatcaccct attaaccagt cacgggagcc ttccatgcat ttggtatttt 60
cgtctggggg gtgtg 75

<210> SEQ ID NO 1341
<211> LENGTH: 75
<212> TYPE: DNA
<213> ORGANISM: Homo sapiens

<400> SEQUENCE: 1341
gatcacaggt ctatcaccct attaaccact cacgggagct ctccatgcat ttggtatttt 60
cgtctggggg gtatg 75

<210> SEQ ID NO 1342
<211> LENGTH: 30
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 1342

acgttggatg caaggcatgc ctgtatactc                                        30


<210> SEQ ID NO 1343
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1343

acgttggatg gtaacaacgc agagctcagg                                        30


<210> SEQ ID NO 1344
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1344

aggcctgtat actctctcct gttatcct                                          28


<210> SEQ ID NO 1345
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1345

acgttggatg gaagctcctc cttgctcttc                                        30


<210> SEQ ID NO 1346
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1346

acgttggatg ggaaaaacta gagaaagagc                                        30


<210> SEQ ID NO 1347
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1347

ggctgctgca gggcttttat ttc                                               23


<210> SEQ ID NO 1348
<211> LENGTH: 30
<212> TYPE: DNA
<213> ORGANISM: Artificial Sequence
```

<220> FEATURE:
<223> OTHER INFORMATION: Description of Artificial Sequence: Synthetic
primer

<400> SEQUENCE: 1348
acgttggatg tagaggtgat acacttaccg 30

<210> SEQ ID NO 1349
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1349
acgttggatg gaccaaagaa gtaaacactg 30

<210> SEQ ID NO 1350
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1350
catttccctc caaacac 17

<210> SEQ ID NO 1351
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1351
acgttggatg cctcccggcc acagagtgtg 30

<210> SEQ ID NO 1352
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1352
acgttggatg ggatgacaaa gatgccaggc 30

<210> SEQ ID NO 1353
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1353
cccgccctcc ctcagagcca 20

<210> SEQ ID NO 1354
<211> LENGTH: 29
<212> TYPE: DNA
<213> ORGANISM: Artificial Sequence
<220> FEATURE:

<223> OTHER INFORMATION: Description of Artificial Sequence: Synthetic primer

<400> SEQUENCE: 1354
acgttggatg aagggaacag gagtgagtg 29

<210> SEQ ID NO 1355
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1355
acgttggatg tcttccagtc cctgatctgg 30

<210> SEQ ID NO 1356
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 1356
ttaatgccaa ccatgggata gtgtgag 27

<210> SEQ ID NO 1357
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1357
acgttggatg gggtttgctg aagatggcgg 30

<210> SEQ ID NO 1358
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1358
acgttggatg ctgctcgcca gaacactacg 30

<210> SEQ ID NO 1359
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 1359
ggcggtatat aggctgagca agagg 25

<210> SEQ ID NO 1360
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1360
acgttggatg gtccctattt aaggaacaag 30

<210> SEQ ID NO 1361
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1361
acgttggatg ctcggcaaat cttaccccgc 30

<210> SEQ ID NO 1362
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 1362
gtcaggcggt gcctctaata ctggt 25

<210> SEQ ID NO 1363
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 1363
acgttggatg ggtgattttc atattgaatt g 31

<210> SEQ ID NO 1364
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1364
acgttggatg caccctaatc aactggcttc 30

<210> SEQ ID NO 1365
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 1365
gacggggctt ctcccgcctt tttt 24

<210> SEQ ID NO 1366
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1366
acgttggatg ttttgaaaaa gtcatggagg 30

<210> SEQ ID NO 1367
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1367
acgttggatg tgactatatg gatgcccccc 30

<210> SEQ ID NO 1368
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 1368
ggcttgaaac cagcttt 17

<210> SEQ ID NO 1369
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1369
acgttggatg gcacacctac accccttatc 30

<210> SEQ ID NO 1370
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1370
acgttggatg gtggcgcttc caattaggtg 30

<210> SEQ ID NO 1371
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1371
ctactcattc aaccaatagc c 21

<210> SEQ ID NO 1372
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 1372
acgttggatg ctgaaccgaa ttggtatata g 31

<210> SEQ ID NO 1373
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1373
acgttggatg aggtgtgagc gatatactag 30

<210> SEQ ID NO 1374
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1374
tatttaccaa atgcccct 18

<210> SEQ ID NO 1375
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1375
acgttggatg gtaatagata gggctcaggc 30

<210> SEQ ID NO 1376
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1376
acgttggatg ctcacttcaa cctccctcac 30

<210> SEQ ID NO 1377
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1377
ctgagtagaa acctgtgagg aa 22

<210> SEQ ID NO 1378
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1378
acgttggatg caccatcctc cgtgaaatc 29

<210> SEQ ID NO 1379
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1379
acgttggatg ggttaatagg gtgatagacc 30

<210> SEQ ID NO 1380
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 1380
gagctccggg cccataaca 19

<210> SEQ ID NO 1381
<211> LENGTH: 29
<212> TYPE: DNA
<213> ORGANISM: Pan troglodytes

<400> SEQUENCE: 1381
aggcctgtat actctctcct gttatcctg 29

<210> SEQ ID NO 1382
<211> LENGTH: 29
<212> TYPE: DNA
<213> ORGANISM: Pan troglodytes

<400> SEQUENCE: 1382
aggcctgtat actctctcct gttatcctt 29

<210> SEQ ID NO 1383
<211> LENGTH: 24
<212> TYPE: DNA
<213> ORGANISM: Pan troglodytes

<400> SEQUENCE: 1383
ggctgctgca gggcttttat ttcg 24

<210> SEQ ID NO 1384
<211> LENGTH: 24
<212> TYPE: DNA
<213> ORGANISM: Pan troglodytes

<400> SEQUENCE: 1384
ggctgctgca gggcttttat ttct 24

<210> SEQ ID NO 1385
<211> LENGTH: 18
<212> TYPE: DNA
<213> ORGANISM: Pan troglodytes

<400> SEQUENCE: 1385
catttccctc caaacacc 18

<210> SEQ ID NO 1386
<211> LENGTH: 18
<212> TYPE: DNA
<213> ORGANISM: Pan troglodytes

<400> SEQUENCE: 1386
catttccctc caaacacg 18

<210> SEQ ID NO 1387
<211> LENGTH: 21
<212> TYPE: DNA
<213> ORGANISM: Pan troglodytes

<400> SEQUENCE: 1387
cccgccctcc ctcagagcca c 21

<210> SEQ ID NO 1388
<211> LENGTH: 21
<212> TYPE: DNA
<213> ORGANISM: Pan troglodytes

<400> SEQUENCE: 1388
cccgccctcc ctcagagcca g 21

<210> SEQ ID NO 1389
<211> LENGTH: 28
<212> TYPE: DNA
<213> ORGANISM: Pan troglodytes

<400> SEQUENCE: 1389
ttaatgccaa ccatgggata gtgtgaga 28

<210> SEQ ID NO 1390
<211> LENGTH: 28
<212> TYPE: DNA
<213> ORGANISM: Pan troglodytes

<400> SEQUENCE: 1390
ttaatgccaa ccatgggata gtgtgagt 28

<210> SEQ ID NO 1391
<211> LENGTH: 26
<212> TYPE: DNA
<213> ORGANISM: Pan troglodytes

<400> SEQUENCE: 1391
ggcggtatat aggctgagca agaggc 26

<210> SEQ ID NO 1392
<211> LENGTH: 26
<212> TYPE: DNA
<213> ORGANISM: Pan troglodytes

<400> SEQUENCE: 1392
ggcggtatat aggctgagca agaggt 26

<210> SEQ ID NO 1393
<211> LENGTH: 26
<212> TYPE: DNA
<213> ORGANISM: Pan troglodytes

<400> SEQUENCE: 1393
gtcaggcggt gcctctaata ctggta 26

<210> SEQ ID NO 1394
<211> LENGTH: 26
<212> TYPE: DNA
<213> ORGANISM: Pan troglodytes

<400> SEQUENCE: 1394
gtcaggcggt gcctctaata ctggtg 26

<210> SEQ ID NO 1395
<211> LENGTH: 25
<212> TYPE: DNA
<213> ORGANISM: Pan troglodytes

<400> SEQUENCE: 1395
gacggggctt ctcccgcctt ttttc 25

<210> SEQ ID NO 1396
<211> LENGTH: 25
<212> TYPE: DNA
<213> ORGANISM: Pan troglodytes

<400> SEQUENCE: 1396
gacggggctt ctcccgcctt ttttt 25

<210> SEQ ID NO 1397
<211> LENGTH: 18
<212> TYPE: DNA
<213> ORGANISM: Pan troglodytes

<400> SEQUENCE: 1397
ggcttgaaac cagcttta 18

<210> SEQ ID NO 1398
<211> LENGTH: 18
<212> TYPE: DNA
<213> ORGANISM: Pan troglodytes

<400> SEQUENCE: 1398
ggcttgaaac cagctttg 18

<210> SEQ ID NO 1399
<211> LENGTH: 22
<212> TYPE: DNA
<213> ORGANISM: Pan troglodytes

<400> SEQUENCE: 1399
ctactcattc aaccaatagc cc 22

<210> SEQ ID NO 1400
<211> LENGTH: 22
<212> TYPE: DNA
<213> ORGANISM: Pan troglodytes

<400> SEQUENCE: 1400
ctactcattc aaccaatagc ct 22

<210> SEQ ID NO 1401
<211> LENGTH: 19
<212> TYPE: DNA
<213> ORGANISM: Pan troglodytes

<400> SEQUENCE: 1401
tatttaccaa atgcccctc 19

<210> SEQ ID NO 1402
<211> LENGTH: 19
<212> TYPE: DNA
<213> ORGANISM: Pan troglodytes

<400> SEQUENCE: 1402
tatttaccaa atgcccctt 19

<210> SEQ ID NO 1403
<211> LENGTH: 23
<212> TYPE: DNA
<213> ORGANISM: Pan troglodytes

<400> SEQUENCE: 1403
ctgagtagaa acctgtgagg aaa 23

<210> SEQ ID NO 1404
<211> LENGTH: 23
<212> TYPE: DNA
<213> ORGANISM: Pan troglodytes

<400> SEQUENCE: 1404
ctgagtagaa acctgtgagg aag 23

<210> SEQ ID NO 1405
<211> LENGTH: 20
<212> TYPE: DNA
<213> ORGANISM: Pan troglodytes

<400> SEQUENCE: 1405
gagctccggg cccataacac 20

<210> SEQ ID NO 1406
<211> LENGTH: 20
<212> TYPE: DNA
<213> ORGANISM: Pan troglodytes

<400> SEQUENCE: 1406
gagctccggg cccataacat 20

<210> SEQ ID NO 1407
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1407
acgttggatg caaggcatgc ctgtatactc 30

<210> SEQ ID NO 1408
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1408
acgttggatg gtaacaacgc agagctcagg 30

<210> SEQ ID NO 1409
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1409
acgttggatg gaagctcctc cttgctcttc 30

<210> SEQ ID NO 1410
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1410
acgttggatg ggaaaaacta gagaaagagc 30

<210> SEQ ID NO 1411
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1411
acgttggatg tagaggtgat acacttaccg 30

<210> SEQ ID NO 1412
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1412
acgttggatg gaccaaagaa gtaaacactg 30

<210> SEQ ID NO 1413
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1413
acgttggatg cctcccggcc acagagtgtg 30

<210> SEQ ID NO 1414
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1414
acgttggatg ggatgacaaa gatgccaggc 30

<210> SEQ ID NO 1415

<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 1415
acgttggatg aagggaacag gagtgagtg 29

<210> SEQ ID NO 1416
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1416
acgttggatg tcttccagtc cctgatctgg 30

<210> SEQ ID NO 1417
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1417
acgttggatg gggtttgctg aagatggcgg 30

<210> SEQ ID NO 1418
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1418
acgttggatg ctgctcgcca gaacactacg 30

<210> SEQ ID NO 1419
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1419
acgttggatg gtccctattt aaggaacaag 30

<210> SEQ ID NO 1420
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1420
acgttggatg ctcggcaaat cttaccccgc 30

<210> SEQ ID NO 1421
<211> LENGTH: 31

<212> TYPE: DNA
<213> ORGANISM: Artificial Sequence
<220> FEATURE:
<223> OTHER INFORMATION: Description of Artificial Sequence: Synthetic primer

<400> SEQUENCE: 1421
acgttggatg ggtgattttc atattgaatt g 31

<210> SEQ ID NO 1422
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1422
acgttggatg caccctaatc aactggcttc 30

<210> SEQ ID NO 1423
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1423
acgttggatg ttttgaaaaa gtcatggagg 30

<210> SEQ ID NO 1424
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1424
acgttggatg tgactatatg gatgcccccc 30

<210> SEQ ID NO 1425
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1425
acgttggatg gcacacctac accccttatc 30

<210> SEQ ID NO 1426
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1426
acgttggatg gtggcgcttc caattaggtg 30

<210> SEQ ID NO 1427
<211> LENGTH: 30
<212> TYPE: DNA

<213> ORGANISM: Artificial Sequence
<220> FEATURE:
<223> OTHER INFORMATION: Description of Artificial Sequence: Synthetic
primer

<400> SEQUENCE: 1427
acgttggatg gtaatagata gggctcaggc 30

<210> SEQ ID NO 1428
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1428
acgttggatg ctcacttcaa cctccctcac 30

<210> SEQ ID NO 1429
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1429
acgttggatg caccatcctc cgtgaaatc 29

<210> SEQ ID NO 1430
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1430
acgttggatg ggttaatagg gtgatagacc 30

<210> SEQ ID NO 1431
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1431
aggcctgtat actctctcct gttatcct 28

<210> SEQ ID NO 1432
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1432
aggcctgtat actctctcct gttatcctg 29

<210> SEQ ID NO 1433
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1433
ggctgctgca gggcttttat ttc 23

<210> SEQ ID NO 1434
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1434
ggctgctgca gggcttttat ttcg 24

<210> SEQ ID NO 1435
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1435
catttccctc caaacac 17

<210> SEQ ID NO 1436
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1436
catttccctc caaacacc 18

<210> SEQ ID NO 1437
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1437
cccgccctcc ctcagagcca 20

<210> SEQ ID NO 1438
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1438
cccgccctcc ctcagagcca c 21

<210> SEQ ID NO 1439
<211> LENGTH: 27
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 1439
ttaatgccaa ccatgggata gtgtgag 27

<210> SEQ ID NO 1440
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1440
ttaatgccaa ccatgggata gtgtgaga 28

<210> SEQ ID NO 1441
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1441
ggcggtatat aggctgagca agagg 25

<210> SEQ ID NO 1442
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1442
ggcggtatat aggctgagca agaggc 26

<210> SEQ ID NO 1443
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1443
gtcaggcggt gcctctaata ctggt 25

<210> SEQ ID NO 1444
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1444
gtcaggcggt gcctctaata ctggta 26

<210> SEQ ID NO 1445
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 1445
gacggggctt ctcccgcctt tttt 24

<210> SEQ ID NO 1446
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1446
gacggggctt ctcccgcctt ttttc 25

<210> SEQ ID NO 1447
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1447
ggcttgaaac cagcttt 17

<210> SEQ ID NO 1448
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1448
ggcttgaaac cagcttta 18

<210> SEQ ID NO 1449
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1449
ctactcattc aaccaatagc c 21

<210> SEQ ID NO 1450
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1450
ctactcattc aaccaatagc cc 22

<210> SEQ ID NO 1451
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1451
ctgagtagaa acctgtgagg aa 22

<210> SEQ ID NO 1452
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 1452
ctgagtagaa acctgtgagg aaa 23

<210> SEQ ID NO 1453
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 1453
gagctccggg cccataaca 19

<210> SEQ ID NO 1454
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1454
gagctccggg cccataacac 20

<210> SEQ ID NO 1455
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 1455
aggcctgtat actctctcct gttatcctt 29

<210> SEQ ID NO 1456
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 1456
ggctgctgca gggcttttat ttct 24

<210> SEQ ID NO 1457
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 1457
catttccctc caaacacg 18

<210> SEQ ID NO 1458
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1458
cccgccctcc ctcagagcca g 21

<210> SEQ ID NO 1459
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 1459
ttaatgccaa ccatgggata gtgtgagt 28

<210> SEQ ID NO 1460
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 1460
ggcggtatat aggctgagca agaggt 26

<210> SEQ ID NO 1461
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 1461
gtcaggcggt gcctctaata ctggtg 26

<210> SEQ ID NO 1462
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 1462
gacggggctt ctcccgcctt ttttt 25

<210> SEQ ID NO 1463
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 1463

-continued

```
ggcttgaaac cagctttg                                                18


<210> SEQ ID NO 1464
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1464

ctactcattc aaccaatagc ct                                           22


<210> SEQ ID NO 1465
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1465

ctgagtagaa acctgtgagg aag                                          23


<210> SEQ ID NO 1466
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1466

gagctccggg cccataacat                                              20
```